(12) United States Patent  (10) Patent No.: US 8,785,639 B2
Wishart et al.  (45) Date of Patent: Jul. 22, 2014

(54) SUBSTITUTED DIHYDROPYRAZOLO[3,4-D]PYRROLO[2,3-B]PYRIDINES AND METHODS OF USE THEREOF

(75) Inventors: Neil Wishart, Jefferson, MA (US);
Maria A. Argiriadi, Wayland, MA (US);
David J. Calderwood, Framingham, MA (US); Anna M. Ericsson, Shrewsbury, MA (US); Kristine E. Frank, Grayslake, IL (US); Dawn M. George, Charlton, MA (US); Eric R. Goedken, Worcester, MA (US); Michael Friedman, Brookline, MA (US);
Nathan S. Josephsohn, Boston, MA (US); Biqin C. Li, Northborough, MA (US); Michael J. Morytko, Framingham, MA (US); Jeffrey W. Voss, Holden, MA (US); Lu Wang, Northborough, MA (US); Eric C. Breinlinger, Charlton, MA (US); Kelly D. Mullen, Charlton, MA (US);
Gagandeep Somal, Ashland, MA (US);
Michael Z Hoemann, Shrewsbury, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 12/958,291

(22) Filed: Dec. 1, 2010

(65) Prior Publication Data
US 2011/0190489 A1  Aug. 4, 2011

Related U.S. Application Data

(60) Provisional application No. 61/265,591, filed on Dec. 1, 2009.

(51) Int. Cl.
*C07D 471/00* (2006.01)

(52) U.S. Cl.
USPC ............. 546/82; 544/126; 544/350; 544/353; 544/361; 546/112; 546/126; 546/152; 546/268.1; 548/303.1; 548/364.7; 548/469; 548/518; 548/560

(58) Field of Classification Search
USPC ............ 544/126, 350, 353, 361; 546/82, 112, 546/126, 152, 268.1; 548/303.1, 364.7, 548/469, 518, 560
See application file for complete search history.

(56) References Cited

U.S. PATENT DOCUMENTS

| | | | |
|---|---|---|---|
| 3,663,559 A | 5/1972 | Derijckere et al. |
| 3,929,992 A | 12/1975 | Sehgal et al. |
| 4,053,474 A | 10/1977 | Treuner et al. |
| 5,212,310 A | 5/1993 | Thurkauf et al. |
| 5,266,698 A | 11/1993 | Shaw et al. |
| 5,521,173 A | 5/1996 | Venkatesan et al. |
| 5,605,690 A | 2/1997 | Jacobs et al. |
| 5,693,801 A | 12/1997 | Shaw et al. |
| 5,733,905 A | 3/1998 | Albright et al. |
| 5,736,540 A | 4/1998 | Albright et al. |
| 5,753,648 A | 5/1998 | Albright et al. |
| 5,763,137 A | 6/1998 | Deprez et al. |
| 5,840,888 A | 11/1998 | Shaw et al. |
| 5,990,109 A | 11/1999 | Chen et al. |
| 6,090,382 A | 7/2000 | Salfeld et al. |
| 6,262,241 B1 | 7/2001 | Cook et al. |
| 6,653,471 B2 | 11/2003 | Yohannes et al. |
| 6,949,562 B2 | 9/2005 | Yohannes et al. |
| 7,169,926 B1 | 1/2007 | Burgess et al. |
| 7,593,820 B2 | 9/2009 | Wilks et al. |
| 7,772,231 B2 | 8/2010 | Sheppard et al. |
| 8,426,411 B2 | 4/2013 | Wishart et al. |
| 8,637,529 B2 | 1/2014 | Woller et al. |
| 2003/0078277 A1 | 4/2003 | Hibi et al. |
| 2004/0023992 A1 | 2/2004 | Das et al. |
| 2005/0176796 A1 | 8/2005 | D Alessio et al. |
| 2006/0183758 A1 | 8/2006 | Beard et al. |
| 2008/0070914 A1 | 3/2008 | Freyne et al. |
| 2009/0215724 A1 | 8/2009 | Dubois et al. |
| 2009/0215750 A1 | 8/2009 | Bamberg et al. |

(Continued)

FOREIGN PATENT DOCUMENTS

CA  2675288  *  7/2008
EP  0423805 B1  8/2000

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Jain, Sanjay et al., A Novel Synthesis of Di (I-Methylazacycloalkeno) [2,3-b:2',3'-d]Pyridines Through Annulation on Lactam Acetals; Tetrahedron Letters,1990 , pp. 131-134, vol. 31 No. 1.

(Continued)

*Primary Examiner* — Douglas M Willis
(74) *Attorney, Agent, or Firm* — McCarter & English, LLP; Elizabeth A. Hanley; Yu Lu

(57) ABSTRACT

The invention provides a compound of Formula (Ie),

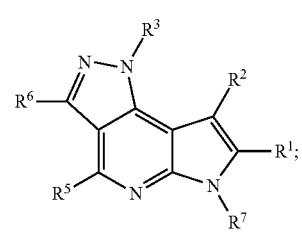

Formula (Ie)

pharmaceutically acceptable salts, or stereoisomers thereof wherein the variables are defined herein. The compounds of the invention are useful for treating immunological and oncological conditions.

9 Claims, No Drawings

(56) References Cited

U.S. PATENT DOCUMENTS

| | | |
|---|---|---|
| 2009/0215788 A1 | 8/2009 | Elworthy et al. |
| 2009/0264399 A1 | 10/2009 | Inoue et al. |
| 2009/0312338 A1 | 12/2009 | Wishart et al. |
| 2011/0021425 A1 | 1/2011 | Billedeau |
| 2011/0311474 A1 | 12/2011 | Wishart et al. |
| 2012/0034250 A1 | 2/2012 | Shirakami et al. |
| 2013/0072470 A1 | 3/2013 | Wishart et al. |
| 2013/0216497 A1 | 8/2013 | Wishart et al. |

FOREIGN PATENT DOCUMENTS

| | | |
|---|---|---|
| EP | 1097709 A2 | 5/2001 |
| GB | 716327 A | 10/1954 |
| WO | 91/10671 A1 | 7/1991 |
| WO | WO-92/16553 A1 | 10/1992 |
| WO | 92/22552 A1 | 12/1992 |
| WO | 93/22314 A1 | 11/1993 |
| WO | 94/05665 A1 | 3/1994 |
| WO | WO-94/11026 A2 | 5/1994 |
| WO | 94/19351 A1 | 9/1994 |
| WO | 96/09304 A1 | 3/1996 |
| WO | WO-99/45009 A1 | 9/1999 |
| WO | 03/031606 A2 | 4/2003 |
| WO | 2004/065378 A1 | 8/2004 |
| WO | 2005/110410 A2 | 11/2005 |
| WO | 2006/010567 A1 | 2/2006 |
| WO | 2006/074984 A1 | 7/2006 |
| WO | 2006/074985 A1 | 7/2006 |
| WO | 2006122137 A1 | 11/2006 |
| WO | 2007/022268 A2 | 2/2007 |
| WO | WO-2007/022268 A2 | 2/2007 |
| WO | 2007/035935 A1 | 3/2007 |
| WO | 2007/079164 A2 | 7/2007 |
| WO | WO-2007/077949 A1 | 7/2007 |
| WO | 2008/063287 A2 | 5/2008 |
| WO | 2008/084861 A1 | 7/2008 |
| WO | 2008/094602 A2 | 8/2008 |
| WO | 2008/112695 A2 | 9/2008 |
| WO | 2008121748 A2 | 10/2008 |
| WO | 2009/005675 A1 | 1/2009 |
| WO | 2009/152133 A1 | 12/2009 |
| WO | WO-2009/152133 A1 | 12/2009 |
| WO | 2010003133 A2 | 1/2010 |

OTHER PUBLICATIONS

Hisham A. ABD El-Nabi, 1-Aryl-2-Chloro-5-Methoxy-1H-3-Pyrrolecarbaldehyde As Synthons for Fused Heterocycles: Synthesis of Pyrazolo[3,4-D] Pyridine Derivatives, Journal of Chemical Research, May 2004, pp. 325-327, vol. 5.

Shashi Nayana et al., Comfa and Docking Studies on Triazolopyridine Oxazole Derivatives As P38 Map Kinase Inhibitors, European Journal of Medicinal Chemistry 43, pp. 1261-1269, 2008, Abstract; p. 1263-p. 1268.

U.S. Appl. No. 12/958,115, filed Dec. 1, 2010, Wishart et al.

Rochais et al., "Synthesis of new dipyrrolo- and furopyrrolopyazinones related to tripentones and their biological evaluation as potential kinases (CDKs1-5, GSK3) inhibitors," *Eur. J. Med. Chem.* (2009) 44:708-716.

U.S. Appl. No. 13/761,501, filed Feb. 7, 2013, Wishart et al.

Banker, et al., (1996), Modern Pharmaceuticals, p. 596.

Hauser, et al., Journal of Organic Chemistry (1961), 26, 451-5.

Mikhaleva, et al., Khimiya Geterotsiklicheskikh Soedinenii (1972),(12), 1696-9.

Wolff et al., "Burger's Medicinal Chemistry and Drug Discovery," 5th Ed. Part 1, p. 975-977 (1995).

Schram et al. (Journal of Heterocyclic Chemistry (1975) 12:(5); pp. 1021-1023.

Kempson, J. et al., "Synthesis, initial SAR and biological evaluation of 1.6-dihydroimidazo[4, 5-d]pyrrolo[2,3-b] pyridin-4-amine derived inhiibtors of IkB kinase", Bioorganic & Medicinal Chemistry Letters, 2009, vol. 19, pp. 2656-2649.

\* cited by examiner

SUBSTITUTED DIHYDROPYRAZOLO[3,4-D]PYRROLO[2,3-B]PYRIDINES AND METHODS OF USE THEREOF

CROSS REFERENCE TO RELATED APPLICATION

This application claims priority to U.S. Provisional Application Ser. No. 61/265,591 filed on Dec. 1, 2009, the contents of which are incorporated herein.

BACKGROUND OF THE INVENTION

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Jak1, Jak2, Jak3, Tyk2, KDR, Flt-3, CDK2, CDK4, TANK, Trk, FAK, Abl, Bcr-Abl, cMet, b-RAF, FGFR3, c-kit, PDGF-R, Syk, PKC kinases or Aurora kinases.

The protein kinases represent a large family of proteins that play a central role in the regulation of a wide variety of cellular processes and maintenance of cellular function. A partial, non-limiting, list of these kinases include: non-receptor tyrosine kinases such as the Janus kinase family (Jak1, Jak2, Jak3 and Tyk2); the fusion kinases, such as BCR-Abl, focal adhesion kinase (FAK), Fes, Lck and Syk; receptor tyrosine kinases such as platelet-derived growth factor receptor kinase (PDGF-R), the receptor kinase for stem cell factor, c-kit, the hepatocyte growth factor receptor, c-Met, and the fibroblast growth factor receptor, FGFR3; and serine/threonine kinases such as b-RAF, mitogen-activated protein kinases (e.g., MKK6) and SAPK2β. Aberrant kinase activity has been observed in many disease states including benign and malignant proliferative disorders as well as diseases resulting from inappropriate activation of the immune and nervous systems. The novel compounds of this invention inhibit the activity of one or more protein kinases and are, therefore, expected to be useful in the treatment of kinase-mediated diseases.

Spleen tyrosine kinase (Syk) (J. Bio. Chem, 1991, 266, 15790) is a non-receptor tyrosine kinase that plays a key role in immunoreceptor signaling in a host of inflammatory cells including B cells, mast cells, macrophages and neutrophils. Syk is related to zeta associated protein 70 (ZAP-70) but also demonstrates similarity with JAK, Src and Tec family kinases.

Syk plays a critical and specific role in B-cell receptor (BCR) signaling on auto-reactive B cells and in FcR signaling on mast cells, macrophages, osteoclasts and neutrophils. (see Immunology Today, 2002, 21(3), 148 and Current Opinion in Immunology 2002, 14(3), 341). Syk plays a key role in the activation mediated by Fc receptors of sentinel cells (mast cells and macrophages) and effector cells (neutrophils, basophils and eosinophils). The importance of Syk in rheumatoid arthritis is substantiated by data demonstrating the importance of Fc receptors (FcR) function and immune complexes in disease pathogenesis. Syk also mediates the activation of B cells through the BCR, which results in their expansion and the production of antispecific immunoglobulins. Therefore any disease that revolves around antibody-Fc receptor interactions may be modulated by Syk suppression. Thus a Syk inhibitor is likely to dampen both the initiation of the disease by blocking BCR signaling and the effector phase of the disease by blocking FcR signaling on macrophages, neutrophils and mast cells. Furthermore, blocking Syk would provide the added benefit of inhibiting osteoclast maturation and therefore attenuate bony erosions, joint destruction and generalized osteopenia associated with rheumatoid arthritis. Moreover Syk acts upstream close to the receptors at the initiation of complex signaling events and thus its inhibition influences all responses elicited by the activating agent. In mast cells for example, inhibition of Syk blocks the early release of a number of granule contents, as well as the subsequent production and secretion of lipid mediators and cytokines. Syk inhibitors can thus impart multiple beneficial effects as each of these mediators play distinct roles in the integrated inflammatory response.

Inhibiting Syk should impact several critical nodes of the inflammatory cascade resulting in an effective and rapid suppression of the deleterious responses. Inhibiting Syk may be useful in treating a host of inflammatory and allergic diseases—for example (but not limited to), rheumatoid arthritis (RA), systemic lupus erythematosus (SLE), multiple sclerosis (MS) and type I hypersensitivity reactions such as allergic rhinitis, allergic conjunctivitis, atopic dermatitis, allergic asthma and systemic anaphylaxis. For a review on targeting Syk as a treatment of autoimmune and allergic disorders, see Expert Opin. Invest. Drugs, 2004, 13(7), 743.

Taken together, Syk inhibitors provide a broad modality to treat a host of inflammatory diseases and immunological disorders.

SUMMARY OF THE INVENTION

In a first embodiment the invention provides a compound of formula

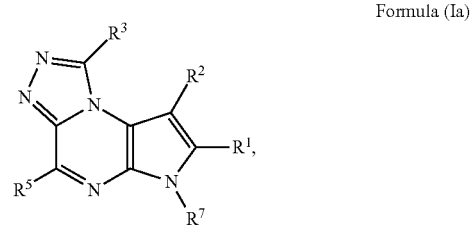

Formula (Ia)

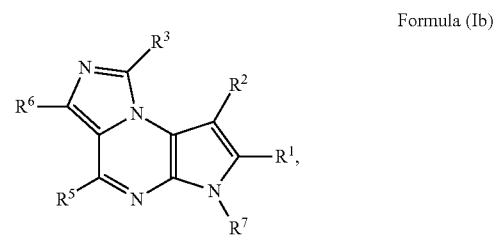

Formula (Ib)

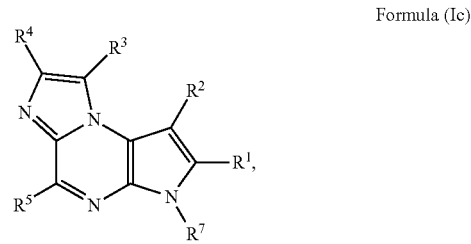

Formula (Ic)

Formula (Id)
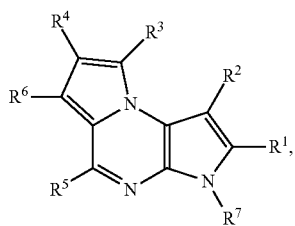

Formula (Ie)
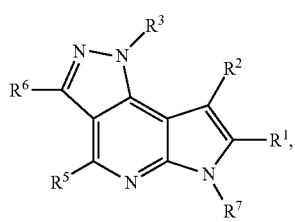

Formula (If)
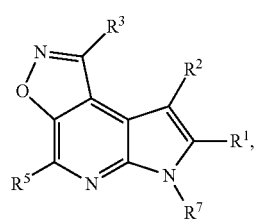

Formula (Ig)
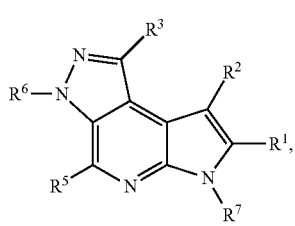

Formula (Ih)
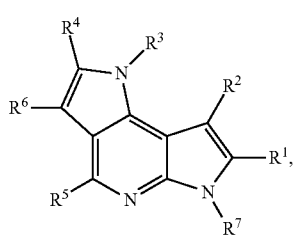

Formula (Ii)
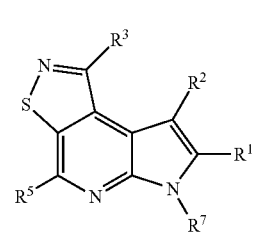

Formula (Ij)
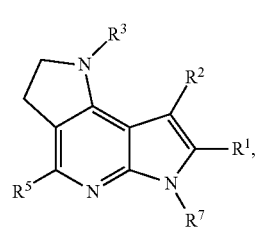

Formula (Ik)
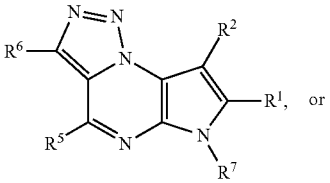, or

Formula (Il)
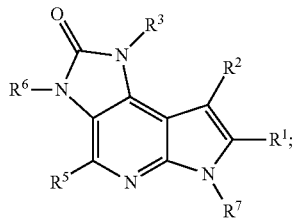;

pharmaceutically acceptable salts, pro-drugs, biologically active metabolites, stereoisomers and isomers thereof wherein $R^1$ is H, deuterium, halogen, $CF_3$, CN, $OR^a$, $N(R^a)(R^b)$, $OCF_3$, —C(O)—N($R^a$)($R^b$), —C(O)—$OR^a$, —C(O)-optionally substituted ($C_1$-$C_6$)alkyl, —C(O)-optionally substituted ($C_3$-$C_6$)cycloalkyl, —C(O)-optionally substituted ($C_6$-$C_{10}$) aryl, —C(O)-optionally substituted ($C_1$-$C_{10}$)heteroaryl, —C(O)-optionally substituted ($C_1$-$C_{10}$)heterocyclyl, —S-optionally substituted ($C_1$-$C_6$)alkyl, —S(O)-optionally substituted ($C_1$-$C_6$)alkyl, —S(O)$_2$-optionally substituted ($C_1$-$C_6$)alkyl, —S(O)$_2$N($R^a$)($R^b$), optionally substituted ($C_1$-$C_6$)alkyl, optionally substituted ($C_1$-$C_6$)alkoxy, optionally substituted ($C_2$-$C_6$)alkenyl, optionally substituted ($C_2$-$C_6$) alkynyl, optionally substituted ($C_3$-$C_{10}$)cycloalkyl, optionally substituted ($C_1$-$C_{10}$)heteroaryl, optionally substituted ($C_1$-$C_{10}$) heterocyclyl, or optionally substituted ($C_6$-$C_{10}$)aryl; or $R^1$ is —$Z^{101}$-$L^1$-$Z^{102}$ wherein $Z^{101}$ is optionally substituted ($C_1$-$C_6$)alkylene, optionally substituted ($C_1$-$C_{10}$)heteroarylene, optionally substituted ($C_1$-$C_{10}$)heterocyclylene, or optionally substituted ($C_6$-$C_{10}$)arylene;

$L^1$ is a bond, optionally substituted ($C_1$-$C_4$)alkylene, —$CH_2$C(O), —C(O)—, —C(O)$CH_2$—, —N($R^a$)—, —O—, -optionally substituted ($C_1$-$C_4$)alkylene-N($R^a$) C(O)—, -optionally substituted ($C_1$-$C_4$)alkylene-C(O)N($R^a$)—, —C(O)N($R^a$)—, —N($R^a$)C(O)—, —C(O)N($R^a$)S(O)$_2$—, —S(O)$_2$N($R^a$)C(O)—, —C(O)N($R^a$)-optionally substituted ($C_1$-$C_4$)alkylene-, —N($R^a$)C(O)-optionally substituted ($C_1$-$C_4$)alkylene-, —C(O)N($R^a$)-optionally substituted ($C_1$-$C_4$)alkylene-C(O), —N($R^a$) C(O)-optionally substituted ($C_1$-$C_4$)alkylene-C(O)—, —C(O)-optionally substituted ($C_1$-$C_4$)alkylene-N($R^a$)C (O)—, —C(O)-optionally substituted ($C_1$-$C_4$)alkylene-C(O)N($R^a$)—, -optionally substituted ($C_1$-$C_4$)alkylene-N($R^a$)C(O)—, —N($R^a$)C(O)-optionally substituted ($C_1$-$C_4$)alkylene, -optionally substituted ($C_1$-$C_4$)alkylene-N($R^a$)C(O)-optionally substituted ($C_1$-$C_4$)alkylene-, -optionally substituted ($C_1$-$C_4$)alkylene-C(O)N($R^a$)-optionally substituted ($C_1$-$C_4$)alkylene-, -optionally substituted ($C_1$-$C_4$)alkylene-N($R^a$)S(O)$_2$—, -optionally substituted ($C_1$-$C_4$)alkylene-S(O)$_2$N($R^a$)— N($R^a$)S(O)$_2$$CH_2$—, —S(O)$_2$N($R^a$)-optionally substituted ($C_1$-$C_4$)alkylene-, —C(O)N($R^a$)S(O)$_2$—, —S(O)$_2$N($R^a$)C(O)—, —S(O)$_2$—, —S(O)$_2$N($R^a$), —N($R^a$)S (O)$_2$—, —O—($C_1$-$C_4$)alkylene-, ($C_1$-$C_6$)alkylene-O—, —C(O)N($R^a$)—($C_1$-$C_6$)alkylene-C(O)—, or —C(O)—($C_1$-$C_6$)alkylene-N($R^a$)C(O)—;

$Z^{102}$ is H, —CN, —N($R^a$)($R^b$), —O$R^a$, optionally substituted ($C_1$-$C_6$)alkyl, optionally substituted ($C_1$-$C_4$)alkoxy, optionally substituted ($C_3$-$C_{10}$)cycloalkyl, optionally substituted ($C_6$-$C_{10}$)aryl, optionally substituted ($C_1$-$C_{10}$)heteroaryl, or optionally substituted ($C_1$-$C_{10}$)heterocyclyl, optionally substituted bridged ($C_5$-$C_{12}$)cycloalkyl, or optionally substituted bridged ($C_2$-$C_{10}$)heterocyclyl;

$R^2$ is H, deuterium, halogen, $CF_3$, CN, O$R^a$, N($R^a$)($R^b$), O$CF_3$, —C(O)-optionally substituted ($C_1$-$C_6$)alkyl, —C(O)-optionally substituted ($C_3$-$C_6$)cycloalkyl, —S-optionally substituted ($C_1$-$C_6$)alkyl, —S(O)$_2$-optionally substituted ($C_1$-$C_6$)alkyl, —S(O)$_2$N($R^a$)($R^b$), optionally substituted ($C_1$-$C_6$)alkoxy, —C(O)N($R^a$)($R^b$), —S(O)$_2$-optionally substituted ($C_1$-$C_6$)alkyl, optionally substituted ($C_1$-$C_6$)alkyl, optionally substituted ($C_2$-$C_6$)alkenyl, optionally substituted ($C_2$-$C_6$)alkynyl, optionally substituted ($C_3$-$C_{10}$)cycloalkyl, optionally substituted ($C_6$-$C_{10}$)aryl, optionally substituted ($C_1$-$C_{10}$)heteroaryl, or optionally substituted ($C_1$-$C_{10}$)heterocyclyl;

$R^3$ is H, deuterium, $CF_3$, CN, —C(O)O$R^a$, O$R^a$, O$CF_3$, N($R^a$)($R^b$), optionally substituted ($C_1$-$C_6$)alkyl, optionally substituted ($C_3$-$C_7$)cycloalkyl, optionally substituted ($C_1$-$C_{10}$)heteroaryl, optionally substituted ($C_1$-$C_{10}$) heterocyclyl, or optionally substituted ($C_6$-$C_{10}$)aryl;

or $R^3$ is -A-D-E-G, wherein:

A is a bond, —C(O)—, optionally substituted ($C_1$-$C_6$)alkylene, optionally substituted ($C_2$-$C_6$)alkenylene, optionally substituted ($C_2$-$C_6$)alkynylene, optionally substituted ($C_3$-$C_{12}$)cycloalkylene, optionally substituted ($C_2$-$C_6$)heterocyclylene, -optionally substituted ($C_1$-$C_6$)alkylene-N($R^a$)—, —$R^e$—C(O)N($R^a$)—$R^e$—, —$R^e$—N($R^a$)C(O)—$R^e$—, —$R^e$—O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

D is a bond, an optionally substituted ($C_1$-$C_8$)alkylene, optionally substituted bridged ($C_5$-$C_{12}$)cycloalkylene, optionally substituted ($C_3$-$C_{10}$)cycloalkylene, optionally substituted bridged ($C_5$-$C_{10}$)cycloalkenylene, optionally substituted ($C_3$-$C_{10}$)cycloalkenylene, optionally substituted ($C_6$-$C_{10}$)arylene, optionally substituted ($C_1$-$C_{10}$)heteroarylene, optionally substituted bridged ($C_2$-$C_{10}$)heterocyclylene or an optionally substituted ($C_2$-$C_{10}$)heterocyclylene;

E is a bond, —$R^e$—, —$R^e$—C(O)—$R^e$—, —$R^e$—C(O)C(O)—$R^e$—, —$R^e$—C(O)O—$R^e$—, —$R^e$—C(O)C(O)N($R^a$)—$R^e$—, —$R^e$—N($R^a$)—C(O)C(O)—$R^e$—, —$R^e$—C(O)N($R^a$)C(O)$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$—C(O)N($R^a$)$R^e$—, —$R^e$—OC(O)N($R^a$)—$R^e$—, —$R^e$—N($R^a$)C(O)O$R^e$—, —$R^e$—OC(O)—$R^e$—, —$R^e$—N($R^a$)C(O)N($R^b$)—$R^e$—, —$R^e$—N($R^a$)S(O)$_2$—$R^e$—, or —$R^e$—S(O)$_2$N($R^a$)$R^e$—; or E is

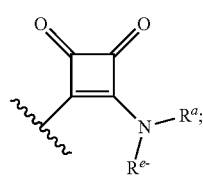

where in all cases, E is linked to either a carbon or a nitrogen atom in D;

G is H, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —OC(O)N($R^a$), —N($R^a$)C(O)N($R^b$)$_2$, —C(O—$R^a$)($R^b$)$_2$, —C(O)$R^a$, —$CF_3$, —O$CF_3$, —N($R^a$)S(O)$_2R^b$, —S(O)$_2$N($R^a$)($R^b$), —S(O)$_2$N($R^a$)C(O)$R^b$, an optionally substituted ($C_1$-$C_6$)alkyl, an optionally substituted ($C_2$-$C_6$)alkenyl, an optionally substituted ($C_2$-$C_6$)alkynyl, an optionally substituted ($C_3$-$C_{10}$)cycloalkyl, an optionally substituted ($C_1$-$C_{10}$)heteroaryl, an optionally substituted ($C_1$-$C_{10}$) heterocyclyl, an optionally substituted ($C_6$-$C_{10}$)aryl, an optionally substituted —($C_1$-$C_6$)alkyl-($C_3$-$C_{10}$)cycloalkyl, an optionally substituted —($C_1$-$C_6$)alkyl-($C_6$-$C_{10}$)aryl, an optionally substituted —($C_1$-$C_6$)alkyl-($C_1$-$C_{10}$)heteroaryl, or an optionally substituted —($C_1$-$C_6$)alkyl-($C_1$-$C_{10}$)heterocyclyl;

wherein in a moiety containing —N($R^a$)($R^b$), the nitrogen, $R^a$ and $R^b$ may form a ring such that —N($R^a$)($R^b$) represents an optionally substituted ($C_2$-$C_{10}$)heterocyclyl or an optionally substituted ($C_1$-$C_{10}$) heteroaryl linked through a nitrogen;

$R^4$ is H, deuterium, $CF_3$, CN, O$R^a$, O$CF_3$, N($R^a$)($R^b$), optionally substituted ($C_1$-$C_6$)alkyl, optionally substituted ($C_3$-$C_7$)cycloalkyl, optionally substituted ($C_1$-$C_{10}$)heteroaryl, optionally substituted ($C_1$-$C_{10}$) heterocyclyl, or optionally substituted ($C_6$-$C_{10}$)aryl;

or $R^4$ is -J-L-M-Q, wherein:

J is a bond, —C(O)—, optionally substituted ($C_1$-$C_6$)alkylene, optionally substituted ($C_2$-$C_6$)alkenylene, optionally substituted ($C_2$-$C_6$)alkynylene, optionally substituted ($C_3$-$C_{12}$)cycloalkylene, optionally substituted ($C_2$-$C_6$)heterocyclylene, -optionally substituted ($C_1$-$C_6$)alkylene-N($R^a$)—, —$R^e$—C(O)N($R^a$)—$R^e$—, —$R^e$—N($R^a$)C(O)—$R^e$—, —$R^e$—O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—;

L is an optionally substituted ($C_1$-$C_8$)alkylene, optionally substituted bridged ($C_5$-$C_{12}$)cycloalkylene, optionally substituted ($C_3$-$C_{10}$)cycloalkylene, optionally substituted bridged ($C_5$-$C_{10}$)cycloalkenylene, optionally substituted ($C_3$-$C_{10}$)cycloalkenylene, optionally substituted ($C_6$-$C_{10}$)arylene, optionally substituted ($C_1$-$C_{10}$)heteroarylene, optionally substituted bridged ($C_2$-$C_{10}$)heterocyclylene or an optionally substituted ($C_2$-$C_{10}$)heterocyclylene;

M is a bond, —$R^e$—, —$R^e$—C(O)—$R^e$—, —$R^e$—C(O)C(O)—$R^e$—, —$R^e$—C(O)O—$R^e$—, —$R^e$—C(O)C(O)N($R^a$)—$R^e$—, —$R^e$—N($R^a$)—C(O)C(O)—$R^e$—, —$R^e$—C(O)N($R^a$)C(O)$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$C(O)N($R^a$)$R^e$—, —$R^e$—OC(O)N($R^a$)—$R^e$—, —$R^e$—N($R^a$)C(O)O$R^e$—, —$R^e$—OC(O)—$R^e$, —$R^e$—N($R^a$)C(O)N($R^b$)—$R^e$—, —$R^e$—N($R^a$)S(O)$_2$—$R^e$—, or —$R^e$—S(O)$_2$N($R^a$)—$R^e$—; or M is

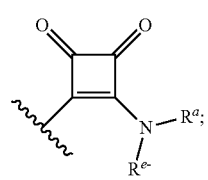

where in all cases, M is linked to either a carbon or a nitrogen atom in L;

Q is H, deuterium, —N($R^a$)($R^b$), halogen, —O$R^a$, —S$R^a$, —S(O)$R^a$, —S(O)$_2R^a$, —NO$_2$, —C(O)O$R^a$, —CN, —C(O)N($R^a$)($R^b$), —N($R^a$)C(O)$R^b$, —N($R^a$)C(O)O$R^b$, —OC(O)N($R^a$), —N($R^a$)C(O)N($R^b$)$_2$, —C(O—$R^a$)($R^b$)$_2$, —C(O)$R^a$, —CF$_3$, —OCF$_3$, —N($R^a$)S(O)$_2R^b$, —S(O)$_2$N($R^a$)($R^b$), —S(O)$_2$N($R^a$)C(O)$R^b$, an optionally substituted —(C$_1$-C$_6$)alkyl, an optionally substituted —(C$_2$-C$_6$)alkenyl, an optionally substituted —(C$_2$-C$_6$)alkynyl, an optionally substituted —(C$_3$-C$_{10}$)cycloalkyl, an optionally substituted —(C$_1$-C$_{10}$)heteroaryl, an optionally substituted —(C$_1$-C$_{10}$)heterocyclyl, an optionally substituted —(C$_6$-C$_{10}$)aryl, an optionally substituted —(C$_1$-C$_6$)alkyl-(C$_3$-C$_{10}$)cycloalkyl, an optionally substituted —(C$_1$-C$_6$)alkyl-(C$_6$-C$_{10}$)aryl, an optionally substituted —(C$_1$-C$_6$)alkyl-(C$_1$-C$_{10}$)heteroaryl, or an optionally substituted —(C$_1$-C$_6$)alkyl-(C$_1$-C$_{10}$)heterocyclyl;

wherein in a moiety containing —N($R^a$)($R^b$), the nitrogen, $R^a$ and $R^b$ may form a ring such that —N($R^a$)($R^b$) represents an optionally substituted (C$_2$-C$_{10}$)heterocyclyl or an optionally substituted (C$_1$-C$_{10}$) heteroaryl linked through a nitrogen;

$R^5$ is H, deuterium, N($R^a$)($R^b$), halogen, CN, CF$_3$, O$R^a$, optionally substituted (C$_1$-C$_6$)alkyl, OCF$_3$, —C(O)-optionally substituted (C$_1$-C$_6$)alkyl, —C(O)-optionally substituted (C$_3$-C$_6$)cycloalkyl, —S-optionally substituted (C$_1$-C$_6$)alkyl, —S(O)-optionally substituted (C$_1$-C$_6$)alkyl, —S(O)$_2$-optionally substituted (C$_1$-C$_6$)alkyl, —S(O)$_2$N($R^a$)($R^b$), optionally substituted (C$_1$-C$_6$)alkyl, or optionally substituted (C$_1$-C$_6$)alkoxy;

$R^6$ is H, deuterium, halogen, CF$_3$, CN, O$R^a$, N($R^a$)($R^b$), OCF$_3$, —C(O)—N($R^a$)($R^b$), —C(O)—O$R^a$, —C(O)-optionally substituted (C$_1$-C$_6$)alkyl, —C(O)-optionally substituted (C$_3$-C$_6$)cycloalkyl, —C(O)-optionally substituted (C$_6$-C$_{10}$)aryl, —C(O)-optionally substituted (C$_1$-C$_{10}$)heteroaryl, —C(O)-optionally substituted (C$_1$-C$_{10}$)heterocyclyl, —S-optionally substituted (C$_1$-C$_6$)alkyl, —S(O)-optionally substituted (C$_1$-C$_6$)alkyl, —S(O)$_2$-optionally substituted (C$_1$-C$_6$)alkyl, —S(O)$_2$N($R^a$)($R^b$), optionally substituted (C$_1$-C$_6$)alkyl, optionally substituted (C$_1$-C$_6$)alkoxy, optionally substituted (C$_2$-C$_6$)alkenyl, optionally substituted (C$_2$-C$_6$)alkynyl, optionally substituted (C$_3$-C$_{10}$)cycloalkyl, optionally substituted (C$_1$-C$_{10}$)heteroaryl, optionally substituted (C$_1$-C$_{10}$) heterocyclyl, or optionally substituted (C$_6$-C$_{10}$)aryl; or $R^6$ is —$Z^{201}$-$L^2$-$Z^{202}$ wherein $Z^{201}$ is optionally substituted (C$_1$-C$_6$)alkylene, optionally substituted (C$_1$-C$_{10}$)heteroarylene, optionally substituted (C$_1$-C$_{10}$)heterocyclylene, or optionally substituted (C$_6$-C$_{10}$)arylene;

$L^2$ is a bond, optionally substituted (C$_1$-C$_4$)alkylene, —CH$_2$C(O), —C(O)—, —C(O)CH$_2$—, —N($R^a$)—, —O—, -optionally substituted (C$_1$-C$_4$)alkylene-N($R^a$)C(O)—, -optionally substituted (C$_1$-C$_4$)alkylene-C(O)N($R^a$)—, —C(O)N($R^a$)—, —N($R^a$)C(O)—, —C(O)N($R^a$)-optionally substituted (C$_1$-C$_4$)alkylene-, —N($R^a$)C(O)-optionally substituted (C$_1$-C$_4$)alkylene-, -optionally substituted (C$_1$-C$_4$)alkylene-N($R^a$)C(O)-optionally substituted (C$_1$-C$_4$)alkylene-, -optionally substituted (C$_1$-C$_4$)alkylene-C(O)N($R^a$)-optionally substituted (C$_1$-C$_4$)alkylene-, -optionally substituted (C$_1$-C$_4$)alkylene-N($R^a$)S(O)$_2$—, -optionally substituted (C$_1$-C$_4$)alkylene-S(O)$_2$N($R^a$)—N($R^a$)S(O)$_2$CH$_2$—, —S(O)$_2$ N($R^a$)-optionally substituted (C$_1$-C$_4$)alkylene-, —S(O)$_2$—, —S(O)$_2$N($R^a$)—, —N($R^a$)S(O)$_2$—, —(C$_1$-C$_4$)alkylene-O—, or —O—(C$_1$-C$_4$)alkylene-;

$Z^{202}$ is H, —CN, —N($R^a$)($R^b$), —O$R^a$, optionally substituted (C$_1$-C$_6$)alkyl, optionally substituted (C$_1$-C$_4$)alkoxy, optionally substituted (C$_3$-C$_{10}$)cycloalkyl, optionally substituted (C$_6$-C$_{10}$)aryl, optionally substituted (C$_1$-C$_{10}$)heteroaryl, or optionally substituted (C$_1$-C$_{10}$)heterocyclyl, optionally substituted bridged (C$_5$-C$_{12}$)cycloalkyl, or optionally substituted bridged (C$_2$-C$_{10}$)heterocyclyl;

$R^7$ is H, optionally substituted-(CH$_2$)$_n$—P(=O)(O$R^a$), optionally substituted —(CH$_2$)$_n$—O—P(=O)(O$R^a$)(O$R^a$), optionally substituted-(CH$_2$)$_n$—P(=O)(O$R^a$)($R^a$), —CH=CH—P(=O)(O$R^a$)(O$R^a$);

$R^a$ and $R^b$ are each independently H, deuterium, an optionally substituted (C$_1$-C$_{10}$)alkyl, optionally substituted (C$_2$-C$_{10}$)alkenyl, optionally substituted (C$_2$-C$_{10}$)alkynyl, an optionally substituted (C$_1$-C$_{10}$)alkyl-O—(C$_1$-C$_{10}$)alkyl, optionally substituted (C$_3$-C$_{10}$)cycloalkyl, an optionally substituted (C$_6$-C$_{10}$)aryl, optionally substituted (C$_1$-C$_{10}$)heteroaryl, optionally substituted (C$_1$-C$_{10}$)heterocyclyl, optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, optionally substituted —(C$_1$-C$_6$)alkylene-(C$_1$-C$_{10}$)heteroaryl, or optionally substituted —(C$_1$-C$_6$)alkylene-(C$_1$-C$_{10}$)heterocyclyl;

$R^e$ for each occurrence is independently a bond, an optionally substituted (C$_1$-C$_{10}$)alkylene, an optionally substituted (C$_2$-C$_{10}$)alkenylene, an optionally substituted (C$_2$-C$_{10}$)alkynylene, an optionally substituted —(C$_1$-C$_{10}$)alkylene-O—(C$_1$-C$_{10}$)alkylene group, an optionally substituted (C$_3$-C$_{10}$) cycloalkylene, an optionally substituted (C$_6$-C$_{10}$)arylene, an optionally substituted (C$_1$-C$_{10}$)heteroarylene, or an optionally substituted (C$_1$-C$_{10}$)heterocyclylene; and n is 1, 2 or 3;

provided that $R^1$ and $R^6$ are not both H and when $R^6$ is H then $R^1$ is not H.

In a second embodiment the invention provides a compound according to the first embodiment wherein $R^1$ is H, halogen, CF$_3$, CN, OH, N($R^a$)($R^b$), OCF$_3$, —C(O)-optionally substituted (C$_1$-C$_6$)alkyl, —C(O)-optionally substituted (C$_3$-C$_6$)cycloalkyl, —S-optionally substituted (C$_1$-C$_6$)alkyl, —S(O)$_2$-optionally substituted (C$_1$-C$_6$) alkyl, —S(O)$_2$N($R^a$)($R^b$), optionally substituted (C$_1$-C$_6$) alkoxy, optionally substituted azaindolyl, optionally substituted azepinyl, optionally substituted azetidinyl, optionally substituted benz(b)thienyl, optionally substituted benzofuranyl, optionally substituted benzimidazolyl, optionally substituted benzoxazolyl, optionally substituted benzothiazolyl, optionally substituted benzothiadiazolyl, optionally substituted benzoxadiazolyl, optionally substituted 6,7-dihydro-5H-cyclopentapyrimidinyl, optionally substituted furanyl, optionally substituted imidazolyl, imidazopyridinyl, 5,6,7,8-tetrahydro-imidazo[1,2-c]pyrazinyl, 5,6,7,8-tetrahydro-imidazo[1,5-a]pyrazinyl, 5,6,7,8-tetrahydro[1,2,4]-triazolo[4,3-a]pyrazinyl, optionally substituted indazolyl, optionally substituted indolinyl, optionally substituted indolyl, optionally substituted isoindolinyl, optionally substituted isoxazolyl, optionally substituted isothiazolyl, optionally substituted morpholinyl, optionally substituted oxadiazolyl, optionally substituted oxazolyl, optionally substituted phenyl, optionally substituted piperazinyl, optionally substituted piperidinyl, optionally substituted purinyl, optionally substitute pyranyl, optionally substituted pyrazolyl, optionally substituted pyrazolo[3,4-d]pyrimidinyl, optionally substituted pyridinyl, optionally substituted pyrimidinyl, optionally substituted pyrrolidinyl, 6,7-dihydro-5H-pyrrolo[1,2-]imidazolyl, optionally substituted pyrrolyl, optionally substituted pyrrolo[3,2-c]pyrimidinyl, optionally substituted pyrrolo[2,3-d]pyrimidinyl, optionally substituted pyrrolo[2,3-b]pyridinyl, optionally substituted octahydropyrrolo[3,4-c]pyrrolyl, optionally substituted quinazolinyl, optionally substituted quinolinyl, optionally substituted quinucludinyl, optionally substituted quinoxalinyl, optionally substituted optionally substituted thiomorpholinyl, optionally substituted tetrahydropyranyl, optionally substituted tetrahydrofuranyl, optionally substituted tetrahydroindolyl, optionally substituted thiazolyl, optionally substituted thienyl, optionally substituted tetrazolyl, optionally substituted thiadiazolyl, optionally substituted [1,3,5]triazinyl, optionally substituted thiomorpholinyl, optionally substituted triazolyl, or optionally substituted tropanyl; or $R^1$ is $-Z^{101}-L^1-Z^{102}$ wherein $Z^{101}$ is H, optionally substituted $(C_1-C_6)$alkylene, optionally substituted $(C_1-C_{10})$heteroarylene, optionally substituted $(C_1-C_{10})$heterocylylene, or optionally substituted $(C_6-C_{10})$arylene;

$L^1$ is a bond, optionally substituted $(C_1-C_4)$alkylene, $-CH_2C(O)$, $-C(O)-$, $-C(O)CH_2-$, $-O-$, -optionally substituted $(C_1-C_4)$alkylene-$N(R^a)C(O)-$, -optionally substituted $(C_1-C_4)$alkylene-$C(O)N(R^a)-$, $-C(O)N(R^a)-$, $-N(R^a)C(O)-$, $-C(O)N(R^a)$-optionally substituted $(C_1-C_4)$alkylene-, $-N(R^a)C(O)$-optionally substituted $(C_1-C_4)$alkylene-, -optionally substituted $(C_1-C_4)$alkylene-$N(R^a)C(O)-$, -optionally substituted $(C_1-C_4)$alkylene-$N(R^a)C(O)$-optionally substituted $(C_1-C_4)$alkylene-, -optionally substituted $(C_1-C_4)$alkylene-$C(O)N(R^a)$-optionally substituted $(C_1-C_4)$alkylene-, -optionally substituted $(C_1-C_4)$alkylene-$N(R^a)S(O)_2-$, -optionally substituted $(C_1-C_4)$alkylene-$S(O)_2N(R^a)-$, $-N(R^a)S(O)_2CH_2-$, $-S(O)_2N(R^a)$-optionally substituted $(C_1-C_4)$alkylene-, $-S(O)_2-$, $-S(O)_2N(R^a)-$, $-N(R^a)S(O)_2-$ or $-O-(C_1-C_4)$alkylene-; and $Z^{102}$ is $-N(R^a)(R^b)$, -optionally substituted $(C_1-C_4)$alkyl, optionally substituted $(C_1-C_4)$alkoxy, optionally substituted $(C_1-C_{10})$heteroaryl, or optionally substituted $(C_1-C_{10})$heterocyclyl.

In a third embodiment the invention provides a compound according to any of the foregoing embodiments wherein $R^1$ is H, halogen, $CF_3$, CN, OH, $N(R^a)(R^b)$, $OCF_3$, $-C(O)$-optionally substituted $(C_1-C_6)$alkyl, $-C(O)$-optionally substituted $(C_3-C_6)$cycloalkyl, $-S$-optionally substituted $(C_1-C_6)$alkyl, $-S(O)_2$-optionally substituted $(C_1-C_6)$alkyl, $-S(O)_2N(R^a)(R^b)$, optionally substituted $(C_1-C_6)$alkoxy, optionally substituted benzofuranyl, optionally substituted benzo(b)thienyl, optionally substituted furanyl, optionally substituted imidazolyl, imidazopyridinyl, 5,6,7,8-tetrahydro-imidazo[1,2-c]pyrazinyl, 5,6,7,8-tetrahydro-imidazo[1,5-a]pyrazinyl, 5,6,7,8-tetrahydro[1,2,4]-triazolo[4,3-a]pyrazinyl, optionally substituted indazolyl, optionally substituted indolinyl, optionally substituted indolyl, optionally substituted isoxazolyl, optionally substituted oxadiazolyl, optionally substituted oxazolyl, optionally substituted phenyl, optionally substituted pyrazolyl, optionally substituted pyrazolo[3,4-d]pyrimidinyl, optionally substituted pyridinyl, optionally substituted pyrimidinyl, optionally substituted pyrrolyl, optionally substituted octahydropyrrolo[3,4-c]pyrrolyl, optionally substituted pyrrolo[2,3-c]pyridinyl, optionally substituted quinolinyl, optionally substituted thiazolyl, optionally substituted thienyl, or optionally substituted tetrazolyl; or $R^1$ is $-Z^{101}-L^1-Z^{102}$ wherein $Z^{101}$ is H, optionally substituted $(C_1-C_6)$alkylene, optionally substituted $(C_1-C_{10})$heteroarylene, optionally substituted $(C_1-C_{10})$heterocyclylene, or optionally substituted $(C_6-C_{10})$aryenel;

$L^1$ is a bond, optionally substituted $(C_1-C_4)$alkylene, $-CH_2C(O)$, $-C(O)-$, $-C(O)CH_2-$, $-N(R^a)-$, $-O-$, -optionally substituted $(C_1-C_4)$alkylene-$N(R^a)C(O)-$, -optionally substituted $(C_1-C_4)$alkylene-$C(O)N(R^a)-$, $-C(O)N(R^a)-$, $-N(R^a)C(O)-$, $-C(O)N(R^a)$-optionally substituted $(C_1-C_4)$alkylene-, $-N(R^a)C(O)$-optionally substituted $(C_1-C_4)$alkylene-, $-C(O)N(R^a)-$ optionally substituted $(C_1-C_4)$alkylene-$C(O)$, $-N(R^a)C(O)$-optionally substituted $(C_1-C_4)$alkylene-$C(O)-$, $-C(O)$-optionally substituted $(C_1-C_4)$alkylene-$N(R^a)C(O)-$, $-C(O)$-optionally substituted $(C_1-C_4)$alkylene-$C(O)N(R^a)-$, -optionally substituted $(C_1-C_4)$alkylene-$N(R^a)C(O)$-optionally substituted $(C_1-C_4)$alkylene-, -optionally substituted $(C_1-C_4)$alkylene-$C(O)N(R^a)$-optionally substituted $(C_1-C_4)$alkylene-, -optionally substituted $(C_1-C_4)$alkylene-$N(R^a)S(O)_2-$, -optionally substituted $(C_1-C_4)$alkylene-$S(O)_2N(R^a)-$, $-N(R^a)S(O)_2CH_2-$, $-S(O)_2N(R^a)$-optionally substituted $(C_1-C_4)$alkylene-, $-C(O)N(R^a)S(O)_2-$, $-S(O)_2N(R^a)C(O)-$, $-S(O)_2-$, $-S(O)_2N(R^a)-$, $-N(R^a)S(O)_2-$ or $-O-(C_1-C_4)$alkylene-; and $Z^{102}$ is, $-N(R^a)(R^b)$, -optionally substituted $(C_1-C_4)$alkyl, optionally substituted $(C_1-C_4)$alkoxy, optionally substituted $(C_1-C_{10})$heteroaryl, or optionally substituted $(C_1-C_{10})$heterocyclyl.

In a fourth embodiment the invention provides a compound according to any of the foregoing embodiments wherein $Z^{101}$ is optionally substituted indazolyl, optionally substituted indolyl, optionally substituted phenyl, optionally substituted pyrazolyl, or optionally substituted pyrrolyl.

In a fifth embodiment the invention provides a compound according to any of the foregoing embodiments wherein $Z^{102}$ is $-N(R^a)(R^b)$, -optionally substituted $(C_1-C_4)$alkyl, optionally substituted morpholinyl, optionally substituted piperazinyl, optionally substituted piperidinyl, optionally substituted pyrrolidinyl, In a sixth embodiment the invention provides a compound according to any of the foregoing embodiments wherein $R^2$ is H, halogen, $CF_3$, CN, $OR^a$, $N(R^a)(R^b)$, $OCF_3$, $-C(O)$-optionally substituted $(C_1-C_6)$alkyl, $-C(O)$-optionally substituted $(C_3-C_6)$cycloalkyl, $-S$-optionally substituted $(C_1-C_6)$alkyl, $-S(O)_2$-optionally substituted $(C_1-C_6)$alkyl, $-S(O)_2N(R^a)(R^b)$, optionally substituted $(C_1-C_6)$alkyl, optionally substituted $(C_1-C_6)$alkoxy, $-C(O)N(R^a)(R^b)$, optionally substituted $(C_1-C_6)$alkyl, optionally substituted $(C_2-C_6)$alkenyl, optionally substituted $(C_2-C_6)$alkynyl, optionally substituted $(C_3-C_{10})$cycloalkyl, optionally substituted azetidinyl, optionally substituted morpholinyl, optionally substituted piperazinyl, optionally substituted piperidinyl, optionally substitute pyranyl, optionally substituted pyrrolidinyl, optionally substituted optionally substituted thiomorpholinyl, optionally substituted tetrahydropyranyl, optionally substituted tetrahydrofuranyl, optionally substituted tetrahydroindolyl, optionally substituted tetrahydropyridinyl or optionally substituted tropanyl.

In a seventh embodiment the invention provides a compound according to any of the foregoing embodiments wherein $R^3$ is H, $CF_3$, $-C(O)OR^a$, $N(R^a)(R^b)$, optionally substituted $(C_1-C_6)$alkyl, optionally substituted $(C_3-C_6)$cycloalkyl, optionally substituted azepinyl, optionally substituted azetidinyl, optionally substituted dihydrobenzofuranyl, optionally substituted benzo[b]thienyl, optionally substituted isoquinolinyl, optionally substituted morpholinyl, optionally substituted phenyl, optionally substituted piperazinyl, optionally substituted piperidinyl, optionally substituted pyranyl, optionally substituted pyridinyl, optionally substituted pyrrolidinyl, optionally substituted thiomorpholinyl, optionally substituted tetrahydropyranyl, optionally substituted tetrahydrofuranyl, optionally substituted tetrahydroindolyl, or optionally substituted tropanyl.

In an eighth embodiment the invention provides a compound according to any of the foregoing embodiments wherein $R^3$ is -A-D-E-G, wherein:

A is a bond, —C(O)—, optionally substituted $(C_1-C_6)$alkylene, optionally substituted $(C_2-C_6)$alkenylene, optionally substituted $(C_2-C_6)$alkynylene, optionally substituted $(C_3-C_8)$cycloalkylene, optionally substituted azetidinyl, optionally substituted morpholinyl, optionally substituted piperazinyl, optionally substituted piperidinyl, optionally substitute pyranyl, substituted pyrrolidinyl, optionally substituted tetrahydropyranyl, optionally substituted tetrahydrofuranyl, optionally substituted tetrahydroindolyl, optionally substituted thiomorpholinyl, -optionally substituted $(C_1-C_6)$alkylene-N($R^a$)—, —$R^e$—C(O)N($R^a$)—$R^e$—, —$R^e$—N($R^a$)C(O)—$R^e$—, —O—$R^e$—, —N($R^a$)—$R^e$—, —S—$R^e$—, —S(O)$_2$—$R^e$—, —S(O)$R^e$—, —C(O—$R^a$)($R^b$)—$R^e$—, —S(O)$_2$N($R^a$)—$R^e$—, —N($R^a$)S(O)$_2$—$R^e$— or —N($R^a$)C(O)N($R^b$)—$R^e$—.

In a ninth embodiment the invention provides a compound according to any of the foregoing embodiments wherein $R^3$ is -A-D-E-G, wherein D is a bond, an optionally substituted $(C_1-C_8)$alkylene, optionally substituted adamantanylene, optionally substituted $(C_3-C_8)$cycloalkylene, optionally substituted $(C_3-C_{10})$cycloalkenylene, optionally substituted azaindolyl, optionally substituted azepanyl, optionally substituted azetidinyl, optionally substituted benzo(b)thienyl, optionally substituted benzofuranyl, optionally substituted benzimidazolyl, optionally substituted benzofuranyl, optionally substituted benzoxazolyl, optionally substituted benzothiazolyl, optionally substituted benzothiadiazolyl, optionally substituted benzoxadiazolyl, optionally substituted 6,7-dihydro-5H-cyclopentapyrimidinyl, optionally substituted furanyl, optionally substituted imidazolyl, imidazopyridinyl, optionally substituted indazolyl, optionally substituted indolinyl, optionally substituted indolyl, optionally substituted isoindolinyl, optionally substituted isoxazolyl, optionally substituted isothiazolyl, optionally substituted morpholinyl, optionally substituted oxadiazolyl, optionally substituted oxazolyl, optionally substituted phenylene, optionally substituted piperazinyl, optionally substituted piperidinyl, optionally substituted purinyl, optionally substitute pyranyl, optionally substituted pyrazolyl, optionally substituted pyrazolo[3,4-d]pyrimidinyl, optionally substituted pyridinyl, optionally substituted pyrimidinyl, optionally substituted pyrrolidinyl, 6,7-dihydro-5H-pyrrolo[1,2-a]imidazolyl, optionally substituted pyrrolyl, optionally substituted pyrrolo[2,3-d]pyrimidinyl, optionally substituted quinazolinyl, optionally substituted quinolinyl, optionally substituted quinucludinyl, optionally substituted quinoxalinyl, optionally substituted thiomorpholinyl, optionally substituted tetrahydropyranyl, optionally substituted tetrahydrofuranyl, optionally substituted tetrahydroindolyl, optionally substituted thiazolyl, optionally substituted thienyl, optionally substituted tetrazolyl, optionally substituted thiadiazolyl, optionally substituted [1,3,5]triazinyl, optionally substituted thiomorpholinyl, optionally substituted triazolyl, or optionally substituted tropanyl.

In a tenth embodiment the invention provides a compound according to any of the foregoing embodiments wherein $R^3$ is -A-D-E-G, wherein E is a bond, —$R^e$—, —$R^e$—C(O)—$R^e$—, —$R^e$—C(O)C(O)—$R^e$—, —$R^e$—C(O)O—$R^e$—, —$R^e$—C(O)N($R^a$)C(O)$R^e$—, —$R^e$—O—$R^e$—, —$R^e$—S(O)$_2$—$R^e$—, —$R^e$—S(O)—$R^e$—, —$R^e$—S—$R^e$—, —$R^e$—N($R^a$)—$R^e$—, —$R^e$—N($R^a$)C(O)—$R^e$—, —$R^e$C(O)N($R^a$)$R^e$—, —$R^e$—OC(O)N($R^a$)—$R^e$—, —$R^e$—N($R^a$)C(O)OR$^e$—, —$R^e$—N($R^a$)C(O)N($R^b$)—$R^e$—, —$R^e$—N($R^a$)S(O)$_2$—$R^e$—, or —$R^e$—S(O)$_2$N($R^a$)—$R^e$—; where in all cases, E is linked to either a carbon or a nitrogen atom in D.

In an eleventh embodiment the invention provides a compound according to any of the foregoing embodiments wherein E is a bond, $(C_1-C_6)$alkylene, —C(O)—, —CH$_2$—C(O)—, —C(O)CH$_2$—, —C(O)N($R^a$)C(O)—, —O—, —S(O)$_2$—, —S(O)—, —S—, —N($R^a$)—, —N($R^a$)C(O)—, —C(O)N($R^a$)—, —OC(O)N($R^a$)—, —N($R^a$)C(O)O—, —N($R^a$)C(O)N($R^b$)—, —N($R^a$)S(O)$_2$—, or —S(O)$_2$N($R^a$)—.

In a twelfth embodiment the invention provides a compound according to any of the foregoing embodiments wherein $R^3$ is -A-D-E-G, wherein G is H, deuterium, —N($R^a$)($R^b$), halogen, OR$^a$, —SR$^a$, —S(O)R$^a$, —S(O)$_2$R$^a$, —NO$_2$, —C(O)OR$^a$, —CN, —C(O)N($R^a$)($R^b$), —N($R^a$)C(O)R$^b$, —N($R^a$)C(O)OR$^b$, —OC(O)N($R^a$), —N($R^a$)C(O)N($R^b$)$_2$, —C(O—$R^a$)($R^b$)$_2$, —C(O)R$^a$, —CF$_3$, —OCF$_3$, —N($R^a$)S(O)$_2$R$^b$, —S(O)$_2$N($R^a$)($R^b$), —S(O)$_2$N($R^a$)C(O)R$^b$, an optionally substituted —$(C_1-C_6)$alkyl, an optionally substituted —$(C_2-C_6)$alkenyl, an optionally substituted —$(C_2-C_6)$alkynyl, an optionally substituted —$(C_3-C_8)$cycloalkyl, optionally substituted azaindolyl, optionally substituted azepinyl, optionally substituted azetidinyl, optionally substituted benzo(b)thienyl, optionally substituted benzofuranyl, optionally substituted benzimidazolyl, optionally substituted benzoxazolyl, optionally substituted benzothiazolyl, optionally substituted benzothiadiazolyl, optionally substituted benzoxadiazolyl, optionally substituted 6,7-dihydro-5H-cyclopentapyrimidinyl, optionally substituted furanyl, optionally substituted imidazolyl, optionally substituted imidazopyridinyl, optionally substituted indazolyl, optionally substituted indolinyl, optionally substituted indolyl, optionally substituted isoindolinyl, optionally substituted isoxazolyl, optionally substituted isothiazolyl, optionally substituted morpholinyl, optionally substituted oxadiazolyl, optionally substituted oxazolyl, optionally substituted phenyl, optionally substituted piperazinyl, optionally substituted piperidinyl, optionally substituted purinyl, optionally substitute pyranyl, optionally substituted pyrazolyl, optionally substituted pyrazolo[3,4-d]pyrimidinyl, optionally substituted pyridinyl, optionally substituted pyrimidinyl, optionally substituted pyrrolidinyl, 6,7-dihydro-5H-pyrrolo[1,2-a]imidazolyl, optionally substituted pyrrolyl, optionally substituted pyrrolo[2,3-d]pyrimidinyl, optionally substituted quinazolinyl, optionally substituted quinolinyl, optionally substituted quinucludinyl, optionally substituted quinoxalinyl, optionally substituted tetrahydropyranyl, optionally substituted tetrahydrofuranyl, optionally substituted tetrahydroindolyl, optionally substituted thiazolyl, optionally substituted thienyl, optionally substituted tetrazolyl, optionally substituted thiadiazolyl, optionally substituted [1,3,5]triazinyl, optionally substituted thiomorpholinyl, optionally substituted triazolyl, optionally substituted tropanyl, an optionally substituted —$(C_1-C_6)$alkyl-$(C_3-C_8)$cycloalkyl, an optionally substituted —$(C_1-C_6)$alkyl-phenyl, an optionally substituted —$(C_1-C_6)$alkyl-$(C_1-C_{10})$heteroaryl, or an optionally substituted —$(C_1-C_6)$alkyl-$(C_1-C_{10})$heterocyclyl.

In a thirteenth embodiment the invention provides a compound according to any of the foregoing embodiments wherein G is H, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —OC(O)N(R$^a$), —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted —(C$_1$-C$_6$)alkyl, an optionally substituted —(C$_2$-C$_6$)alkenyl, an optionally substituted —(C$_2$-C$_6$)alkynyl, an optionally substituted —(C$_3$-C$_8$)cycloalkyl, optionally substituted azetidinyl, optionally substituted furanyl, optionally substituted imidazolyl, optionally substituted indolyl, optionally substituted isoindolinyl, optionally substituted isoxazolyl, optionally substituted morpholinyl, optionally substituted phenyl, optionally substituted piperazinyl, optionally substituted piperidinyl, optionally substituted pyrazolyl, optionally substituted pyridinyl, optionally substituted pyrimidinyl, optionally substituted pyrrolidinyl, optionally substituted pyrrolyl, optionally substituted tetrahydropyranyl, optionally substituted tetrahydrofuranyl, optionally substituted thiazolyl, optionally substituted thienyl, optionally substituted tetrazolyl, optionally substituted thiadiazolyl, optionally substituted [1,3,5]triazinyl, optionally substituted thiomorpholinyl, optionally substituted triazolyl, an optionally substituted —(C$_1$-C$_6$)alkyl-(C$_3$-C$_8$)cycloalkyl, or an optionally substituted —(C$_1$-C$_6$)alkyl-phenyl.

In a fourteenth embodiment the invention provides a compound according to any of the foregoing embodiments wherein R$^4$ is H, CF$_3$, N(R$^a$)(R$^b$), optionally substituted (C$_1$-C$_6$)alkyl, optionally substituted (C$_3$-C$_6$)cycloalkyl, optionally substituted azaindolyl, optionally substituted azepinyl, optionally substituted azetidinyl, optionally substituted morpholinyl, optionally substituted phenyl, optionally substituted piperazinyl, optionally substituted piperidinyl, optionally substituted pyranyl, optionally substituted pyridinyl, optionally substituted pyrimidinyl, optionally substituted pyrrolidinyl, optionally substituted thiomorpholinyl, optionally substituted tetrahydropyranyl, optionally substituted tetrahydrofuranyl, optionally substituted tetrahydroindolyl, or optionally substituted tropanyl.

In a fifteenth embodiment the invention provides a compound according to any of the foregoing embodiments wherein R$^4$ is -J-L-M-Q, wherein:

J is a bond, —C(O)—, optionally substituted (C$_1$-C$_6$)alkylene, optionally substituted (C$_2$-C$_6$)alkenylene, optionally substituted (C$_2$-C$_6$)alkynylene, optionally substituted (C$_3$-C$_8$)cycloalkylene, optionally substituted azetidinyl, optionally substituted morpholinyl, optionally substituted piperazinyl, optionally substituted piperidinyl, optionally substitute pyranyl, optionally substituted pyrrolidinyl, optionally substituted tetrahydropyranyl, optionally substituted tetrahydrofuranyl, optionally substituted tetrahydroindolyl, -optionally substituted (C$_1$-C$_6$)alkylene-N(R$^a$)—, —R$^e$—C(O)N(R$^a$)—R$^e$—, —R$^e$—N(R$^a$)C(O)—R$^e$—, —O—R$^e$—, —N(R$^a$)—R$^e$—, —S—R$^e$—, —S(O)$_2$—R$^e$—, —S(O)R$^e$—, —C(O—R$^a$)(R$^b$)—R$^e$—, —S(O)$_2$N(R$^a$)—R$^e$—, —N(R$^a$)S(O)$_2$—R$^e$— or —N(R$^a$)C(O)N(R$^b$)—R$^e$—.

In a sixteenth embodiment the invention provides a compound according to any of the foregoing embodiments wherein R$^4$ is -J-L-M-Q, wherein L is a bond, an optionally substituted (C$_1$-C$_8$)alkylene, optionally substituted adamantanylene, optionally substituted (C$_3$-C$_8$)cycloalkylene, optionally substituted (C$_3$-C$_{10}$)cycloalkenylene, optionally substituted azaindolyl, optionally substituted azepinyl, optionally substituted azetidinyl, optionally substituted benzo(b)thienyl, optionally substituted benzofuranyl, optionally substituted benzimidazolyl, optionally substituted benzofuranyl, optionally substituted benzoxazolyl, optionally substituted benzothiazolyl, optionally substituted benzothiadiazolyl, optionally substituted benzoxadiazolyl, optionally substituted 6,7-dihydro-5H-cyclopentapyrimidinyl, optionally substituted furanyl, optionally substituted imidazolyl, imidazopyridinyl, optionally substituted indazolyl, optionally substituted indolinyl, optionally substituted indolyl, optionally substituted isoindolinyl, optionally substituted isoxazolyl, optionally substituted isothiazolyl, optionally substituted morpholinyl, optionally substituted oxadiazolyl, optionally substituted oxazolyl, optionally substituted phenylene, optionally substituted piperazinyl, optionally substituted piperidinyl, optionally substituted purinyl, optionally substitute pyranyl, optionally substituted pyrazolyl, optionally substituted pyrazolo[3,4-d]pyrimidinyl, optionally substituted pyridinyl, optionally substituted pyrimidinyl, optionally substituted pyrrolidinyl, 6,7-dihydro-5H-pyrrolo[1,2-a]imidazolyl, optionally substituted pyrrolyl, optionally substituted pyrrolo[2,3-d]pyrimidinyl, optionally substituted quinazolinyl, optionally substituted quinolinyl, optionally substituted quinucludinyl, optionally substituted quinoxalinyl, optionally substituted thiomorpholinyl, optionally substituted tetrahydropyranyl, optionally substituted tetrahydrofuranyl, optionally substituted tetrahydroindolyl, optionally substituted thiazolyl, optionally substituted thienyl, optionally substituted tetrazolyl, optionally substituted thiadiazolyl, optionally substituted [1,3,5]triazinyl, optionally substituted thiomorpholinyl, optionally substituted triazolyl, or optionally substituted tropanyl.

In a seventeenth embodiment the invention provides a compound according to any of the foregoing embodiments wherein R$^4$ is -J-L-M-Q, wherein M is a bond, —R$^e$—, —R$^e$—C(O)—R$^e$—, —R$^e$—C(O)C(O)—R$^e$—, —R$^e$—C(O)O—R$^e$—, —R$^e$—C(O)N(R$^a$)C(O)R$^e$—, —R$^e$—O—R$^e$—, —R$^e$—S(O)$_2$—R$^e$—, —R$^e$—S(O)—R$^e$—, —R$^e$—S—R$^e$—, —R$^e$—N(R$^a$)—R$^e$—, —R$^e$—N(R$^a$)C(O)—R$^e$—, —R$^e$C(O)N(R$^a$)R$^e$—, —R$^e$—OC(O)N(R$^a$)—R$^e$—, —R$^e$—N(R$^a$)C(O)OR$^e$—, —R$^e$—N(R$^a$)C(O)N(R$^b$)—R$^e$—, —R$^e$—N(R$^a$)S(O)$_2$—R$^e$—, or —R$^e$—S(O)$_2$N(R$^a$)—R$^e$—; where in all cases, M is linked to either a carbon or a nitrogen atom in L.

In an eighteenth embodiment the invention provides a compound according to any of the foregoing embodiments wherein M is a bond, (C$_1$-C$_6$)alkylene, —C(O)—, —CH$_2$—C(O)—, —C(O)CH$_2$—, —C(O)N(R$^a$)C(O)—, —O—, —S(O)$_2$—, —S(O)—, —S—, —N(R$^a$)—, —N(R$^a$)C(O)—, —C(O)N(R$^a$)—, —OC(O)N(R$^a$)—, —N(R$^a$)C(O)O—, —N(R$^a$)C(O)N(R$^b$)—, —N(R$^a$)S(O)$_2$—, or —S(O)$_2$N(R$^a$)—.

In a nineteenth embodiment the invention provides a compound according to any of the foregoing embodiments wherein R$^4$ is -J-L-M-Q, wherein Q is H, deuterium, —N(R$^a$)(R$^b$), halogen, —OR$^a$, —SR$^a$, —S(O)R$^a$, —S(O)$_2$R$^a$, —NO$_2$, —C(O)OR$^a$, —CN, —C(O)N(R$^a$)(R$^b$), —N(R$^a$)C(O)R$^b$, —N(R$^a$)C(O)OR$^b$, —OC(O)N(R$^a$), —N(R$^a$)C(O)N(R$^b$)$_2$, —C(O—R$^a$)(R$^b$)$_2$, —C(O)R$^a$, —CF$_3$, —OCF$_3$, —N(R$^a$)S(O)$_2$R$^b$, —S(O)$_2$N(R$^a$)(R$^b$), —S(O)$_2$N(R$^a$)C(O)R$^b$, an optionally substituted —(C$_1$-C$_6$)alkyl, an optionally substituted —(C$_2$-C$_6$)alkenyl, an optionally substituted —(C$_2$-C$_6$)alkynyl, an optionally substituted —(C$_3$-C$_8$)cycloalkyl, optionally substituted azaindolyl, optionally substituted azepinyl, optionally substituted azetidinyl, optionally substituted benzo(b)thienyl, optionally substituted benzofuranyl, optionally substituted benzimidazolyl, optionally substituted benzoxazolyl, optionally substituted benzothiazolyl, optionally substituted benzothiadiazolyl, optionally substituted benzoxadiazolyl, optionally substituted 6,7-dihydro-5H-cyclopentapyrimidinyl, optionally substituted furanyl, optionally substituted imidazolyl, optionally substituted imidazopyridinyl, optionally substituted indazolyl, optionally substituted indolinyl, optionally substituted indolyl, optionally substituted isoindolinyl, optionally substituted isoxazolyl, optionally substituted isothiazolyl, optionally substituted morpholinyl, optionally substituted oxadiazolyl, optionally substituted oxazolyl, optionally substituted phenyl, optionally substituted piperazinyl, optionally substituted piperidinyl, optionally substituted purinyl, optionally substitute pyranyl, optionally substituted pyrazolyl, optionally substituted pyrazolo[3,4-d]pyrimidinyl, optionally substituted pyridinyl, optionally substituted pyrimidinyl, optionally substituted pyrrolidinyl, 6,7-dihydro-5H-pyrrolo[1,2-a]imidazolyl, optionally substituted pyrrolyl, optionally substituted pyrrolo[2,3-d]pyrimidinyl, optionally substituted quinazolinyl, optionally substituted quinolinyl, optionally substituted quinucludinyl, optionally substituted quinoxalinyl, optionally substituted tetrahydropyranyl, optionally substituted tetrahydrofuranyl, optionally substituted tetrahydroindolyl, optionally substituted thiazolyl, optionally substituted thienyl, optionally substituted tetrazolyl, optionally substituted thiadiazolyl, optionally substituted [1,3,5]triazinyl, optionally substituted thiomorpholinyl, optionally substituted triazolyl, optionally substituted tropanyl, an optionally substituted —$(C_1$-$C_6)$alkyl-$(C_3$-$C_8)$cycloalkyl, an optionally substituted —$(C_1$-$C_6)$alkyl-phenyl, an optionally substituted —$(C_1$-$C_6)$alkyl-$(C_1$-$C_{10})$heteroaryl, or an optionally substituted —$(C_1$-$C_6)$alkyl-$(C_1$-$C_{10})$heterocyclyl.

In a twentieth embodiment the invention provides a compound according to any of the foregoing embodiments wherein Q is H, deuterium, —$N(R^a)(R^b)$, halogen, —$OR^a$, —$SR^a$, —$S(O)R^a$, —$S(O)_2R^a$, —$NO_2$, —$C(O)OR^a$, —CN, —$C(O)N(R^a)(R^b)$, —$N(R^a)C(O)R^b$, —$N(R^a)C(O)OR^b$, —$OC(O)N(R^a)$, —$N(R^a)C(O)N(R^b)_2$, —$C(O$—$R^a)(R^b)_2$, —$C(O)R^a$, —$CF_3$, —$OCF_3$, —$N(R^a)S(O)_2R^b$, —$S(O)_2N(R^a)(R^b)$, —$S(O)_2N(R^a)C(O)R^b$, an optionally substituted —$(C_1$-$C_6)$alkyl, an optionally substituted —$(C_2$-$C_6)$alkenyl, an optionally substituted —$(C_2$-$C_6)$alkynyl, an optionally substituted —$(C_3$-$C_8)$cycloalkyl, optionally substituted azetidinyl, optionally substituted furanyl, optionally substituted imidazolyl, optionally substituted indolyl, optionally substituted isoindolinyl, optionally substituted isoxazolyl, optionally substituted morpholinyl, optionally substituted phenyl, optionally substituted piperazinyl, optionally substituted piperidinyl, optionally substituted pyrazolyl, optionally substituted pyridinyl, optionally substituted pyrimidinyl, optionally substituted pyrrolidinyl, optionally substituted pyrrolyl, optionally substituted tetrahydropyranyl, optionally substituted tetrahydrofuranyl, optionally substituted thiazolyl, optionally substituted thienyl, optionally substituted tetrazolyl, optionally substituted thiadiazolyl, optionally substituted [1,3,5]triazinyl, optionally substituted thiomorpholinyl, optionally substituted triazolyl, an optionally substituted —$(C_1$-$C_6)$alkyl-$(C_3$-$C_8)$cycloalkyl, or an optionally substituted —$(C_1$-$C_6)$alkyl-phenyl.

In a twenty-first embodiment the invention provides a compound according to any of the foregoing embodiments wherein $R^6$ is optionally substituted $(C_1$-$C_6)$alkyl, optionally substituted $(C_2$-$C_6)$alkenyl, optionally substituted $(C_3$-$C_6)$cycloalkyl, optionally substituted dihydrobenzofuranyl, optionally substituted benzo(b)thienyl, optionally substituted furanyl, optionally substituted indolyl, optionally substituted isoquinolinyl, optionally substituted phenyl, optionally substituted piperidinyl, optionally substituted pyridinyl, optionally substituted pyrido[3,2-b]oxazin-3-(4H)-one, optionally substituted pyrimidinyl, optionally substituted pyrazolyl, optionally substituted quinolinyl, optionally substituted quinoxalinyl, optionally substituted tetrahydropyridinyl, or optionally substituted thienyl;

or $R^6$ is —$^{201}$-$L^2$-$Z^{202}$ wherein $Z^{201}$ is optionally substituted $(C_1$-$C_6)$alkylene, optionally substituted phenyl, optionally substituted piperidinyl, optionally substituted pyrazolyl, optionally substituted thienyl, or optionally substituted tetrhydropyridinyl;

$L^2$ is a bond, —$CH_2C(O)$—, —$C(O)CH_2$, —$C(O)$—, —$C(O)N(R^a)$—, —$N(R^a)C(O)$, —$S(O)_2$, optionally substituted $(C_1$-$C_6)$alkylene, -optionally substituted $(C_1$-$C_4)$alkylene-$S(O)_2N(R^a)$—, -optionally substituted $(C_1$-$C_4)$alkylene-$N(R^a)S(O)_2$—$S(O)_2N(R^a)$-optionally substituted $(C_1$-$C_4)$alkylene-, or —O—$(C_1$-$C_4)$alkylene-; and $Z^{202}$ is —CN, —$N(R^a)(R^b)$, —$OR^a$, optionally substituted $(C_1$-$C_6)$alkyl, optionally substituted $(C_3$-$C_6)$cycloalkyl, optionally substituted morpholinyl, optionally substituted oxetanyl, optionally substituted piperazinyl or optionally substituted piperidinyl.

In a twenty-second embodiment the invention provides a compound according to any of the foregoing embodiments wherein $R^1$ is optionally substituted $(C_1$-$C_4)$alkyl, optionally substituted benzofuranyl, 6,7-dihydro-5H-pyrrolo[1,2-a]imidazolyl, optionally substituted 2,3-dihydro-1H-pyrrolo[3,2-c]pyridine, optionally substituted indazolyl, optionally substituted indolyl, optionally substituted phenyl, optionally substituted pyrazolyl, optionally substituted pyridinyl, optionally substituted pyrrolo[2,3-b]pyrazinyl, optionally substituted pyrrolo[2,3-c]pyrazinyl, optionally substituted pyrrolyl, optionally substituted quinolinyl, optionally substituted quinoxalinyl or optionally substituted thienyl; or $R^1$ is —$Z^{101}$-$L^1$-$Z^{102}$ wherein $Z^{101}$ is optionally substituted indolyl, optionally substituted phenyl, optionally substituted pyrazolyl, or optionally substituted pyrrolyl;

$L^1$ is a bond, —$C(O)$—, —O—, —$S(O)_2$—, —$S(O)_2N(R^a)$—, —$N(R^a)S(O)_2$, -optionally substituted $(C_1$-$C_4)$alkylene, —$CH_2C(O)$—, —$C(O)CH_2$—, —$N(R^a)C(O)$—, —$N(R^a)C(O)$—, -optionally substituted $(C_1$-$C_4)$alkylene-$N(R^a)C(O)$—, —$N(R^a)C(O)$-optionally substituted $(C_1$-$C_4)$alkylene, —$N(R^a)S(O)_2$—, —$S(O)_2N(R^a)$—, -optionally substituted $(C_1$-$C_4)$alkylene-$N(R^a)C(O)$-optionally substituted $(C_1$-$C_4)$alkylene-, -optionally substituted $(C_1$-$C_4)$alkylene-$C(O)N(R^a)$-optionally substituted $(C_1$-$C_4)$alkylene-, —$C(O)N(R^a)S(O)_2$—, —$S(O)_2N(R^a)C(O)$—, —O—$(C_1$-$C_4)$alkylene-, —$(C_1$-$C_6)$alkylene-O—, —$C(O)N(R^a)$-optionally substituted $(C_1$-$C_4)$alkylene-, -optionally substituted $(C_1$-$C_4)$alkylene-$N(R^a)C(O)$—, —$C(O)N(R^a)$—$(C_1$-$C_6)$alkylene-$C(O)$—, or —$C(O)$—$(C_1$-$C_6)$alkylene-$N(R^a)C(O)$—; and $Z^{102}$ is —$N(R^a)(R^b)$, —$OR^a$, optionally substituted $(C_1$-$C_4)$alkyl, optionally substituted morpholinyl, optionally substituted piperadinyl, optionally substituted piperazinyl, or optionally substituted pyrrolidinyl.

In a twenty-third embodiment the invention provides a compound according to any of the foregoing embodiments wherein $R^2$ is H, —CN or optionally substituted $(C_1$-$C_4)$alkyl.

In a twenty-fourth embodiment the invention provides a compound according to any of the foregoing embodiments wherein $R^3$ is H, $CF_3$, —C(O)OH, $N(R^a)(R^b)$, optionally substituted $(C_1-C_4)$alkyl, optionally substituted $(C_3-C_6)$cycloalkyl, optionally substituted phenyl, optionally substituted piperazinyl, optionally substituted piperidinyl, optionally substituted pyridinyl, optionally substituted pyrimidinyl, optionally substituted pyrrolidinyl, optionally substituted quinolinyl, optionally substituted tetrahydropyranyl or $R^3$ is A-D-E-G wherein
A is a bond or optionally substituted $(C_1-C_4)$alkylene;
D is a bond, optionally substituted $(C_1-C_4)$alkylene, optionally substituted $(C_3-C_6)$cycloalkylene, optionally substituted indolyl, optionally substituted piperazinyl, optionally substituted piperidinyl, optionally substituted pyridinyl, optionally substituted pyrimidinyl, optionally substituted quinolinyl,
E is a bond, —$R^e$—, —$R^e$—C(O)—$R^e$—, —$R^e$—O—$R^e$—, —$R^e$—N($R^a$)C(O)—$R^e$—, —$R^e$C(O)N($R^a$)$R^e$—, —$R^e$—N($R^a$)S(O)$_2$—$R^e$—, or —$R^e$—S(O)$_2$N($R^a$)—$R^e$—
G is —N($R^a$)($R^b$), —O$R^a$, —CN, optionally substituted $(C_1-C_6)$alkyl, optionally substituted $(C_3-C_6)$cycloalkyl, optionally substituted diazepanyl, optionally substituted morpholinyl, optionally substituted piperazinyl, optionally substituted pyrrolidinyl;

In a twenty-fifth embodiment the invention provides a compound according to any of the foregoing embodiments wherein $R^6$ is H, optionally substituted $(C_1-C_6)$alkyl, optionally substituted $(C_2-C_6)$alkenyl, optionally substituted benzo[b]thiophenyl, optionally substituted dihyrobenzofuranyl, optionally substituted furanyl, optionally substituted indolyl, optionally substituted isoquinolinyl, optionally substituted phenyl, optionally substituted pyrazolyl, optionally substituted pyridinyl, optionally substituted pyrimidinyl, optionally substituted quinolinyl, optionally substituted quinoxalinyl, optionally substituted thienyl or optionally substituted tetrahydropyridinyl;

$R^6$ is —$Z^{201}$-$L^2$-$Z^{202}$ wherein
$Z^{201}$ is optionally substituted indolyl, optionally substituted phenyl, optionally substituted pyrazolyl, optionally substituted thienyl;
$L^2$ is a bond, optionally substituted $(C_1-C_4)$alkylene, —C(O)—, —C(O)N($R^a$)—, —N($R^a$)C(O)—, -optionally substituted $(C_1-C_4)$alkylene-N($R^a$)C(O)—, —C(O)N($R^a$)-optionally substituted $(C_1-C_4)$alkylene-, —S(O)$_2$—, —O—, —($C_1-C_4$)alkylene-O—, or —O—($C_1-C_4$)alkylene-
$Z^{202}$ is —N($R^a$)($R^b$), optionally substituted $(C_1-C_6)$alkyl, optionally substituted $(C_3-C_6)$cycloalkyl, optionally substituted morpholinyl, optionally substituted piperazinyl;

$R^6$ is H or optionally substituted quinoxalinyl.

In a twenty-sixth embodiment the invention provides a compound of Formula (Ia)

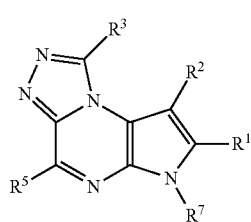

Formula (Ia)

pharmaceutically acceptable salts, pro-drugs, biologically active metabolites, stereoisomers and isomers thereof wherein $R^2$ is H, —CN, or optionally substituted $(C_1-C_4)$alkyl;

$R^1$ is optionally substituted indolyl or optionally substituted phenyl; or
$R^1$ is —$Z^{101}$-$L^1$-$Z^{102}$ wherein
$Z^{101}$ is optionally substituted indolyl or optionally substituted phenyl
$L^1$ is a bond, —C(O)N($R^a$)-optionally substituted $(C_1-C_4)$alkylene-, -optionally substituted $(C_1-C_4)$alkylene-N($R^a$)C(O)—, or —O—; and
$Z^{102}$ is optionally substituted $(C_1-C_4)$alkyl;
$R^2$ is H or optionally substituted $(C_1-C_4)$alkyl;
$R^3$ is optionally substituted $(C_1-C_4)$alkyl;
$R^5$ is H; and
$R^7$ is H.

In a twenty-seventh embodiment the invention provides a compound of Formula (Ib)

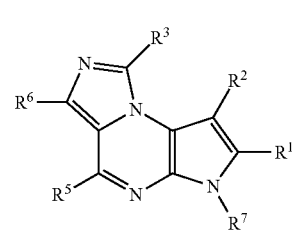

Formula (Ib)

pharmaceutically acceptable salts, pro-drugs, biologically active metabolites, stereoisomers and isomers thereof wherein $R^1$ is optionally substituted indolyl, optionally substituted pyrazolyl, optionally substituted phenyl; or
$R^1$ is —$Z^{101}$-$L^1$-$Z^{102}$ wherein
$Z^{101}$ is optionally substituted indolyl, optionally substituted phenyl, optionally substituted pyrazolyl
$L^1$ is a bond, —C(O)—, —O—, —S(O)$_2$—,
$Z^{102}$ is optionally substituted $(C_1-C_4)$alkyl;
$R^2$ is H, —CN, optionally substituted $(C_1-C_4)$alkyl,
$R^3$ is H, $CF_3$, —C(O)OH, $N(R^a)(R^b)$, optionally substituted $(C_1-C_4)$alkyl, optionally substituted $(C_3-C_6)$cycloalkyl, optionally substituted phenyl, optionally substituted piperazinyl, optionally substituted piperidinyl, optionally substituted pyridinyl, optionally substituted pyrimidinyl, optionally substituted pyrrolidinyl, optionally substituted quinolinyl, optionally substituted tetrahydropyranyl or
$R^3$ is A-D-E-G wherein
A is a bond or optionally substituted $(C_1-C_4)$alkylene;
D is a bond, optionally substituted $(C_1-C_4)$alkylene, optionally substituted $(C_3-C_6)$cycloalkylene, optionally substituted indolyl, optionally substituted piperazinyl, optionally substituted piperidinyl, optionally substituted pyridinyl, optionally substituted pyrimidinyl, optionally substituted quinolinyl,
E is a bond, —$R^e$—, —$R^e$—C(O)—$R^e$—, —$R^e$—O—$R^e$—, —$R^e$—N($R^a$)C(O)—$R^e$—, —$R^e$C(O)N($R^a$)$R^e$—, —$R^e$—N($R^a$)S(O)$_2$—$R^e$—, or —$R^e$—S(O)$_2$N($R^a$)—$R^e$—
G is —N($R^a$)($R^b$), —O$R^a$, —CN, optionally substituted $(C_1-C_6)$alkyl, optionally substituted $(C_3-C_6)$cycloalkyl, optionally substituted diazepanyl, optionally substituted morpholinyl, optionally substituted piperazinyl, optionally substituted pyrrolidinyl;

R⁵ is H

R⁶ is H, optionally substituted (C₁-C₆)alkyl, optionally substituted (C₂-C₆)alkenyl, optionally substituted benzo[b]thiophenyl, optionally substituted dihyrobenzofuranyl, optionally substituted furanyl, optionally substituted indolyl, optionally substituted isoquinolinyl, optionally substituted phenyl, optionally substituted pyrazolyl, optionally substituted pyridinyl, optionally substituted pyrimidinyl, optionally substituted quinolinyl, optionally substituted quinoxalinyl, optionally substituted thienyl or optionally substituted tetrahydropyridinyl;

R⁶ is —Z²⁰¹-L²-Z²⁰² wherein

Z²⁰¹ is optionally substituted indolyl, optionally substituted phenyl, optionally substituted pyrazolyl, optionally substituted thienyl;

L² is a bond, optionally substituted (C₁-C₄)alkylene, —C(O)—, —C(O)N(Rᵃ)—, —N(Rᵃ)C(O)—, -optionally substituted (C₁-C₄)alkylene-N(Rᵃ)C(O)—, —C(O)N(Rᵃ)-optionally substituted (C₁-C₄)alkylene-, —S(O)₂—, —O—, —(C₁-C₄)alkylene-O—, or —O—(C₁-C₄)alkylene-Z²⁰² is —N(Rᵃ)(Rᵇ), optionally substituted (C₁-C₆)alkyl, optionally substituted (C₃-C₆)cycloalkyl, optionally substituted morpholinyl, optionally substituted piperazinyl;

R⁷ is optionally substituted —(CH₂)ₙ—O—P(=O)(OR⁷)(OR⁷);

Rᵃ and Rᵇ are independently H or optionally substituted (C₁-C₄)alkyl;

Rᵉ is a bond, optionally substituted (C₁-C₄)alkyl; and n is 1.

In a twenty-eighth environment the invention provides a compound of Formula (Ic)

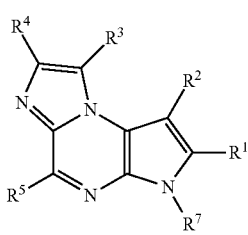

Formula (Ic)

pharmaceutically acceptable salts, pro-drugs, biologically active metabolites, stereoisomers and isomers thereof wherein R¹ is optionally substituted indolyl or optionally substituted phenyl; or R¹ is —Z¹⁰¹-L¹-Z¹⁰² wherein Z¹⁰¹ is optionally substituted indolyl or optionally substituted phenyl, L¹ is a bond, —O—;

Z¹⁰² is optionally substituted (C₁-C₄)alkyl;

R² is optionally substituted (C₁-C₄)alkyl

R³ is H, is optionally substituted (C₁-C₄)alkyl;

R⁴ is H,

R⁵ is H or optionally substituted (C₁-C₄)alkyl; and

R⁷ is H.

In a twenty-ninth embodiment the invention provides a compound of Formula (Id)

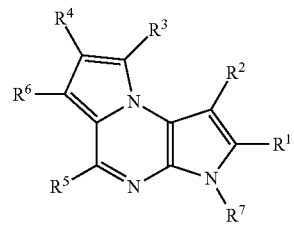

Formula (Id)

pharmaceutically acceptable salts, pro-drugs, biologically active metabolites, stereoisomers and isomers thereof wherein R¹ is optionally substituted phenyl; and R², R³, R⁴, R⁵, R⁶ and R⁷ are H.

In a thirtieth embodiment the invention provides a compound of Formula (Ie)

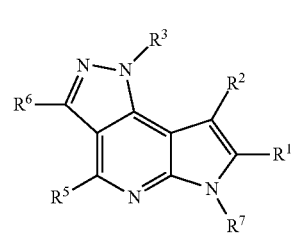

Formula (Ie)

pharmaceutically acceptable salts, pro-drugs, biologically active metabolites, stereoisomers and isomers thereof wherein R¹ is optionally substituted (C₁-C₄)alkyl, optionally substituted benzofuranyl, 6,7-dihydro-5H-pyrrolo[1,2-a]imidazolyl, optionally substituted 2,3-dihydro-1H-pyrrolo[3,2-c]pyridine, optionally substituted indazolyl, optionally substituted indolyl, optionally substituted phenyl, optionally substituted pyrazolyl, optionally substituted pyridinyl, optionally substituted pyrrolo[2,3-b]pyrazinyl, optionally substituted pyrrolo[2,3-c]pyrazinyl, optionally substituted pyrrolyl, optionally substituted quinolinyl, optionally substituted quinoxalinyl or optionally substituted thienyl;

R¹ is —Z¹⁰¹-L¹-Z¹⁰² wherein

Z¹⁰¹ is optionally substituted indolyl, optionally substituted phenyl, optionally substituted pyrazolyl, or optionally substituted pyrrolyl;

L¹ is a bond, —C(O)—, —O—, —S(O)₂—, —S(O)₂N(Rᵃ)—, —N(Rᵃ)S(O)₂, -optionally substituted (C₁-C₄)alkylene, —CH₂C(O)—, —C(O)CH₂—, —N(Rᵃ)C(O)—, —N(Rᵃ)C(O)—, -optionally substituted (C₁-C₄)alkylene-N(Rᵃ)C(O)—, —N(Rᵃ)C(O)-optionally substituted (C₁-C₄)alkylene, —N(Rᵃ)S(O)₂—, —S(O)₂N(Rᵃ)—, -optionally substituted (C₁-C₄)alkylene-N(Rᵃ)C(O)-optionally substituted (C₁-C₄)alkylene-, -optionally substituted (C₁-C₄)alkylene-C(O)N(Rᵃ)-optionally substituted (C₁-C₄)alkylene-, —C(O)N(Rᵃ)S(O)₂—, —S(O)₂N(Rᵃ)C(O)—, —O—(C₁-C₄)alkylene-, (C₁-C₆)alkylene-O—, —C(O)N(Rᵃ)—(C₁-C₆)alkylene-C(O)—, or —C(O)—(C₁-C₆)alkylene-N(Rᵃ)C(O)—; and Z¹⁰² is —N(Rᵃ)(Rᵇ), —ORᵃ, optionally substituted (C₁-C₄)alkyl, optionally substituted morpholinyl, optionally substituted piperadinyl, optionally substituted piperazinyl, or optionally substituted pyrrolidinyl;

R² is H, —CN, or optionally substituted (C₁-C₄)alkyl;

R³ is H or optionally substituted (C₁-C₄)alkyl;
R⁵ is H;
R⁶ is H or optionally substituted quinoxalinyl; or
R⁶ is —Z²⁰¹-L²-Z²⁰² wherein
Z²⁰¹ is optionally substituted phenyl;
L² is —C(O)N(Rᵃ)— or —N(Rᵃ)C(O)—;
Z²⁰² is optionally substituted (C₃-C₆)cycloalkyl; and
R⁷ is H.

In a thirty-first embodiment the invention provides a compound of Formula (If)

In another embodiment the invention is 1-cyclopropyl-7-(5-methoxy-1-methyl-1H-indol-3-yl)-6H-imidazo[1,5-a]pyrrolo[2,3-e]pyrazine.

In another embodiment the invention is 1-(cyclopropylmethyl)-7-(5-methoxy-1-methyl-1H-indol-3-yl)-6H-imidazo[1,5-a]pyrrolo[2,3-e]pyrazine.

In another embodiment the invention is 2-(4-(1-methyl-1,6-dihydropyrazolo[3,4-d]pyrrolo[2,3-b]pyridin-7-yl)phenyl)propan-2-ol.

In another embodiment the invention is 1-methyl-7-(1-methyl-1H-pyrazol-4-yl)-6H-imidazo[1,5-a]pyrrolo[2,3-e]pyrazine.

In another embodiment the invention is 7-(5-methoxy-1-methyl-1H-indol-3-yl)-1-(pyrrolidin-2-yl)-6H-imidazo[1,5-a]pyrrolo[2,3-e]pyrazine.

In another embodiment the invention is 7-(5-methoxy-1-methyl-1H-indol-3-yl)-1-(trifluoromethyl)-6H-imidazo[1,5-a]pyrrolo[2,3-e]pyrazine.

In another embodiment the invention is 4-(3-(1-methyl-1,6-dihydropyrazolo[3,4-d]pyrrolo[2,3-b]pyridin-7-yl)benzyl)morpholine;

In another embodiment the invention is (7-(5-methoxy-1-methyl-1H-indol-3-yl)-6H-imidazo[1,5-a]pyrrolo[2,3-e]pyrazin-1-yl)methanamine.

In another embodiment the invention is 7-(1-methyl-1H-pyrazol-4-yl)-1-phenyl-6H-imidazo[1,5-a]pyrrolo[2,3-e]pyrazine.

In another embodiment the invention is 7-(5-fluoro-1-methyl-1H-indol-3-yl)-1-methyl-1,6-dihydropyrazolo[3,4-d]pyrrolo[2,3-b]pyridine.

In another embodiment the invention is 7-(benzofuran-3-yl)-1-methyl-1,6-dihydropyrazolo[3,4-d]pyrrolo[2,3-b]pyridine.

In another embodiment the invention is 7-(5-methoxy-1H-indol-3-yl)-1-methyl-1,6-dihydropyrazolo[3,4-d]pyrrolo[2,3-b]pyridine.

In another embodiment the invention is 1-methyl-7-(1-methyl-1H-indol-3-yl)-1,6-dihydropyrazolo[3,4-d]pyrrolo[2,3-b]pyridine.

In another embodiment the invention is N-(3-(1-methyl-1,6-dihydropyrazolo[3,4-d]pyrrolo[2,3-b]pyridin-7-yl)benzyl)acetamide.

In another embodiment the invention is (R)-7-(5-methoxy-1-methyl-1H-indol-3-yl)-1-(pyrrolidin-3-yl)-6H-imidazo[1,5-a]pyrrolo[2,3-e]pyrazine.

In another embodiment the invention is N-methyl-3-(1-methyl-1,6-dihydropyrazolo[3,4-d]pyrrolo[2,3-b]pyridin-7-yl)benzamide.

In another embodiment the invention is 3-(1-methyl-1,6-dihydropyrazolo[3,4-d]pyrrolo[2,3-b]pyridin-7-yl)benzonitrile.

In another embodiment the invention is 7-(3-fluorophenyl)-1-methyl-1,6-dihydropyrazolo[3,4-d]pyrrolo[2,3-b]pyridine.

In another embodiment the invention is 2-(5-methoxy-3-(1-methyl-1,6-dihydropyrazolo[3,4-d]pyrrolo[2,3-b]pyridin-7-yl)-1H-indol-1-yl)-1-morpholinoethanone.

In another embodiment the invention is 2-(5-methoxy-3-(1-methyl-1,6-dihydropyrazolo[3,4-d]pyrrolo[2,3-b]pyridin-7-yl)-1H-indol-1-yl)acetic acid.

In another embodiment the invention is 4-(2-(5-methoxy-3-(1-methyl-1,6-dihydropyrazolo[3,4-d]pyrrolo[2,3-b]pyridin-7-yl)-1H-indol-1-yl)ethyl)morpholine.

In another embodiment the invention is 2-(5-methoxy-3-(1-methyl-1,6-dihydropyrazolo[3,4-d]pyrrolo[2,3-b]pyridin-7-yl)-1H-indol-1-yl)ethanol In another embodiment the invention is (3-(1-methyl-1,6-dihydropyrazolo[3,4-d]pyrrolo[2,3-b]pyridin-7-yl)phenyl)methanamine.

In another embodiment the invention is 2-(5-methoxy-3-(1-methyl-1,6-dihydropyrazolo[3,4-d]pyrrolo[2,3-b]pyridin-7-yl)-1H-indol-1-yl)-N,N-dimethylethanamine.

In another embodiment the invention is 2-(dimethylamino)-N-(3-(1-methyl-1,6-dihydropyrazolo[3,4-d]pyrrolo[2,3-b]pyridin-7-yl)benzyl)acetamide.

In another embodiment the invention is 3-(1-methyl-1,6-dihydropyrazolo[3,4-d]pyrrolo[2,3-b]pyridin-7-yl)-N-(2-morpholinoethyl)benzamide.

In another embodiment the invention is N-(3-methoxypropyl)-3-(1-methyl-1,6-dihydropyrazolo[3,4-d]pyrrolo[2,3-b]pyridin-7-yl)benzamide.

In another embodiment the invention is 3-methoxy-N-(3-(1-methyl-1,6-dihydropyrazolo[3,4-d]pyrrolo[2,3-b]pyridin-7-yl)benzyl)propanamide.

In another embodiment the invention is N-(3-(1-methyl-1,6-dihydropyrazolo[3,4-d]pyrrolo[2,3-b]pyridin-7-yl)benzyl)methanesulfonamide.

In another embodiment the invention is (3-(1-methyl-1,6-dihydropyrazolo[3,4-d]pyrrolo[2,3-b]pyridin-7-yl)phenyl)(pyrrolidin-1-yl)methanone.

In another embodiment the invention is 2-(5-methoxy-3-(1-methyl-1,6-dihydropyrazolo[3,4-d]pyrrolo[2,3-b]pyridin-7-yl)-1H-indol-1-yl)-1-(4-methylpiperazin-1-yl)ethanone.

In another embodiment the invention is N-(3-(1-methyl-1,6-dihydropyrazolo[3,4-d]pyrrolo[2,3-b]pyridin-7-yl)benzyl)-3-morpholinopropanamide.

In another embodiment the invention is 7-(6,7-dihydro-5H-pyrrolo[1,2-a]imidazol-3-yl)-1-methyl-1,6-dihydropyrazolo[3,4-d]pyrrolo[2,3-b]pyridine.

In another embodiment the invention is N-methyl-2-(3-(1-methyl-1,6-dihydropyrazolo[3,4-d]pyrrolo[2,3-b]pyridin-7-yl)phenyl)acetamide.

In another embodiment the invention is N-(3-hydroxy-2,2-dimethylpropyl)-2-(3-(1-methyl-1,6-dihydropyrazolo[3,4-d]pyrrolo[2,3-b]pyridin-7-yl)phenyl)acetamide.

In another embodiment the invention is N-(3-(1-methyl-1,6-dihydropyrazolo[3,4-d]pyrrolo[2,3-b]pyridin-7-yl)benzyl)pentanamide.

In another embodiment the invention is 1-(dimethylamino)-3-(5-methoxy-3-(1-methyl-1,6-dihydropyrazolo[3,4-d]pyrrolo[2,3-b]pyridin-7-yl)-1H-indol-1-yl)propan-2-ol.

In another embodiment the invention is N-(3-methoxypropyl)-2-(3-(1-methyl-1,6-dihydropyrazolo[3,4-d]pyrrolo[2,3-b]pyridin-7-yl)phenyl)acetamide.

In another embodiment the invention is 2-(3-(1-methyl-1,6-dihydropyrazolo[3,4-d]pyrrolo[2,3-b]pyridin-7-yl)phenyl)-N-(2-(4-methylpiperazin-1-yl)ethyl)acetamide.

In another embodiment the invention is 1-methyl-7-(pyridin-4-yl)-1,6-dihydropyrazolo[3,4-d]pyrrolo[2,3-b]pyridine.

In another embodiment the invention is 1-methyl-7-(pyridin-3-yl)-1,6-dihydropyrazolo[3,4-d]pyrrolo[2,3-b]pyridine.

In another embodiment the invention is 1-methyl-7-(1-methyl-1H-pyrazol-4-yl)-6H-pyrrolo[2,3-e][1,2,4]triazolo[4,3-a]pyrazine.

In another embodiment the invention is 2-(5-methoxy-3-(1-methyl-1,6-dihydropyrazolo[3,4-d]pyrrolo[2,3-b]pyridin-7-yl)-1H-indol-1-yl)-N,N-dimethylacetamide.

In another embodiment the invention is 2-(3-(1-methyl-1,6-dihydropyrazolo[3,4-d]pyrrolo[2,3-b]pyridin-7-yl)phenyl)-N-(2-morpholinoethyl)acetamide.

In another embodiment the invention is N,N-dimethyl-3-(1-methyl-1,6-dihydropyrazolo[3,4-d]pyrrolo[2,3-b]pyridin-7-yl)benzenesulfonamide.

In another embodiment the invention is 2-(4-(8-ethyl-1-methyl-1,6-dihydropyrazolo[3,4-d]pyrrolo[2,3-b]pyridin-7-yl)phenyl)propan-2-ol.

In another embodiment the invention is 8-ethyl-1-methyl-7-(3-(methylsulfonyl)phenyl)-1,6-dihydropyrazolo[3,4-d]pyrrolo[2,3-b]pyridine.

In another embodiment the invention is 2-(5-methoxy-3-(1-methyl-1,6-dihydropyrazolo[3,4-d]pyrrolo[2,3-b]pyridin-7-yl)-1H-indol-1-yl)-N-(2-methoxyethyl)acetamide.

In another embodiment the invention is N-(2-(dimethylamino)ethyl)-2-(3-(1-methyl-1,6-dihydropyrazolo[3,4-d]pyrrolo[2,3-b]pyridin-7-yl)phenyl)acetamide.

In another embodiment the invention is N-methyl-3-(1-methyl-1,6-dihydropyrazolo[3,4-d]pyrrolo[2,3-b]pyridin-7-yl)benzenesulfonamide.

In another embodiment the invention is 3-(1-methyl-1,6-dihydropyrazolo[3,4-d]pyrrolo[2,3-b]pyridin-7-yl)benzenesulfonamide.

In another embodiment the invention is N-(2-hydroxyethyl)-3-(1-methyl-1,6-dihydropyrazolo[3,4-d]pyrrolo[2,3-b]pyridin-7-yl)benzenesulfonamide.

In another embodiment the invention is 744-methoxyphenyl)-1-methyl-1,6-dihydropyrazolo[3,4-d]pyrrolo[2,3-b]pyridine.

In another embodiment the invention is 3-(5-methoxy-3-(1-methyl-1,6-dihydropyrazolo[3,4-d]pyrrolo[2,3-b]pyridin-7-yl)-1H-indol-1-yl)propane-1,2-diol.

In another embodiment the invention is N,N-dimethyl-2-(4-(1-methyl-1,6-dihydropyrazolo[3,4-d]pyrrolo[2,3-b]pyridin-7-yl)phenoxy)ethanamine.

In another embodiment the invention is 4-(2-(4-(1-methyl-1,6-dihydropyrazolo[3,4-d]pyrrolo[2,3-b]pyridin-7-yl)phenoxy)ethyl)morpholine.

In another embodiment the invention is 4-(3-(4-(1-methyl-1,6-dihydropyrazolo[3,4-d]pyrrolo[2,3-b]pyridin-7-yl)phenoxy)propyl)morpholine.

In another embodiment the invention is 2-(7-(5-methoxy-1-methyl-1H-indol-3-yl)-6H-imidazo[1,5-a]pyrrolo[2,3-e]pyrazin-1-yl)ethanamine.

In another embodiment the invention is 3-(7-(5-methoxy-1-methyl-1H-indol-3-yl)-6H-imidazo[1,5-a]pyrrolo[2,3-e]pyrazin-1-yl)propan-1-amine.

In another embodiment the invention is (1S,3R)-3-(7-(5-methoxy-1-methyl-1H-indol-3-yl)-6H-imidazo[1,5-a]pyrrolo[2,3-e]pyrazin-1-yl)cyclopentanamine.

In another embodiment the invention is 7-(5-methoxy-1-methyl-1H-indol-3-yl)-1-methyl-1,2,3,6-tetrahydrodipyrrolo[2,3-b:2',3'-d]pyridine.

In another embodiment the invention is 2-(4-(1-methyl-1,2,3,6-tetrahydrodipyrrolo[2,3-b:2',3'-d]pyridin-7-yl)phenyl)propan-2-ol.

In another embodiment the invention is 7-(3-(methylsulfonyl)phenyl)-1-(trifluoromethyl)-6H-imidazo[1,5-a]pyrrolo[2,3-e]pyrazine.

In another embodiment the invention is (R)-1-(3-(7-(5-methoxy-1-methyl-1H-indol-3-yl)-6H-imidazo[1,5-a]pyrrolo[2,3-e]pyrazin-1-yl)pyrrolidin-1-yl)ethanone.

In another embodiment the invention is 7-(5-methoxy-1-methyl-1H-indol-3-yl)-1-(2,2,2-trifluoroethyl)-6H-imidazo[1,5-a]pyrrolo[2,3-e]pyrazine.

In another embodiment the invention is 1-methyl-7-(3-(methylsulfonyl)phenyl)-6H-imidazo[1,5-a]pyrrolo[2,3-e]pyrazine.

In another embodiment the invention is 2,2,2-trifluoro-N-(3-(7-(3-(methylsulfonyl)phenyl)-6H-imidazo[1,5-a]pyrrolo[2,3-e]pyrazin-1-yl)propyl)acetamide.

In another embodiment the invention is 7-(5-methoxy-1-methyl-1H-indol-3-yl)-1-(tetrahydro-2H-pyran-3-yl)-6H-imidazo[1,5-a]pyrrolo[2,3-e]pyrazine.

In another embodiment the invention is N-(3-(7-(5-methoxy-1-methyl-1H-indol-3-yl)-6H-imidazo[1,5-a]pyrrolo[2,3-e]pyrazin-1-yl)propyl)acetamide.

In another embodiment the invention is 7-(5-methoxy-1-methyl-1H-indol-3-yl)-1-(tetrahydro-2H-pyran-4-yl)-6H-imidazo[1,5-a]pyrrolo[2,3-e]pyrazine.

In another embodiment the invention is (1S,3R)-3-(7-(3-(methylsulfonyl)phenyl)-6H-imidazo[1,5-a]pyrrolo[2,3-e]pyrazin-1-yl)cyclopentanamine.

In another embodiment the invention is 3-(7-(3-(methylsulfonyl)phenyl)-6H-imidazo[1,5-a]pyrrolo[2,3-e]pyrazin-1-yl)propan-1-amine In another embodiment the invention is 743-(methylsulfonyl)phenyl)-1-(tetrahydro-2H-pyran-3-yl)-6H-imidazo[1,5-a]pyrrolo[2,3-e]pyrazine.

In another embodiment the invention is 3-(7-(3-(methylsulfonyl)phenyl)-6H-imidazo[1,5-a]pyrrolo[2,3-e]pyrazin-1-yl)cyclopentanol.

In another embodiment the invention is N-((1S,3R)-3-(7-(3-(methylsulfonyl)phenyl)-6H-imidazo[1,5-a]pyrrolo[2,3-e]pyrazin-1-yl)cyclopentyl)acetamide.

In another embodiment the invention is 1-methyl-7-(quinolin-5-yl)-1,6-dihydropyrazolo[3,4-d]pyrrolo[2,3-b]pyridine.

In another embodiment the invention is 3-(1-methyl-6H-imidazo[1,5-a]pyrrolo[2,3-e]pyrazin-7-yl)-N-(2-morpholinoethyl)benzamide acetate.

In another embodiment the invention is 1-methyl-7-(quinolin-6-yl)-1,6-dihydropyrazolo[3,4-d]pyrrolo[2,3-b]pyridine.

In another embodiment the invention is 1-methyl-7-(quinoxalin-6-yl)-1,6-dihydropyrazolo[3,4-d]pyrrolo[2,3-b]pyridine.

In another embodiment the invention is N-(3-(7-(1-methyl-1H-pyrazol-4-yl)-6H-imidazo[1,5-a]pyrrolo[2,3-e]pyrazin-1-yl)propyl)acetamide.

In another embodiment the invention is 2-(4-(8-ethyl-1-methyl-6H-imidazo[1,5-a]pyrrolo[2,3-e]pyrazin-7-yl)phenyl)propan-2-ol.

In another embodiment the invention is 3-(8-ethyl-1-methyl-1,6-dihydropyrazolo[3,4-d]pyrrolo[2,3-b]pyridin-7-yl)-N-(2-morpholinoethyl)benzamide.

In another embodiment the invention is 7-(5-methoxy-1-methyl-1H-indol-3-yl)-N,N-dimethyl-6H-imidazo[1,5-a]pyrrolo[2,3-e]pyrazin-1-amine.

In another embodiment the invention is 3-(7-(5-methoxy-1-methyl-1H-indol-3-yl)-6H-imidazo[1,5-a]pyrrolo[2,3-e]pyrazin-1-yl)propan-1-ol.

In another embodiment the invention is 3-(7-(5-methoxy-1-methyl-1H-indol-3-yl)-6H-imidazo[1,5-a]pyrrolo[2,3-e]pyrazin-1-yl)propanenitrile.

In another embodiment the invention is 8-ethyl-1-methyl-7-(1-methyl-1H-indol-5-yl)-1,6-dihydropyrazolo[3,4-d]pyrrolo[2,3-b]pyridine.

In another embodiment the invention is 8-ethyl-1-methyl-7-(1-methyl-1H-indol-4-yl)-1,6-dihydropyrazolo[3,4-d]pyrrolo[2,3-b]pyridine.

In another embodiment the invention is 4-(4-(8-ethyl-1-methyl-1,6-dihydropyrazolo[3,4-d]pyrrolo[2,3-b]pyridin-7-yl)phenyl)morpholine.

In another embodiment the invention is 7-(1,3-dimethyl-1H-pyrazol-4-yl)-8-ethyl-1-methyl-1,6-dihydropyrazolo[3,4-d]pyrrolo[2,3-b]pyridine.

In another embodiment the invention is 7-(1,5-dimethyl-1H-pyrazol-4-yl)-8-ethyl-1-methyl-1,6-dihydropyrazolo[3,4-d]pyrrolo[2,3-b]pyridine.

In another embodiment the invention is 7-(5-methoxy-1-methyl-1H-indol-3-yl)-1-(3-methoxypropyl)-6H-imidazo[1,5-a]pyrrolo[2,3-e]pyrazine.

In another embodiment the invention is 8-ethyl-7-(5-methoxy-1-methyl-1H-indol-3-yl)-1-methyl-1,6-dihydropyrazolo[3,4-d]pyrrolo[2,3-b]pyridine.

In another embodiment the invention is 4-(8-ethyl-1-methyl-1,6-dihydropyrazolo[3,4-d]pyrrolo[2,3-b]pyridin-7-yl)-N-(2-morpholinoethyl)benzamide.

In another embodiment the invention is N-methyl-7-p-tolyl-6H-imidazo[1,5-a]pyrrolo[2,3-e]pyrazin-1-amine In another embodiment the invention is 3-(8-ethyl-1-methyl-1,6-dihydropyrazolo[3,4-d]pyrrolo[2,3-b]pyridin-7-yl)-N-propylbenzamide.

In another embodiment the invention is 2-(4-(8-ethyl-6H-imidazo[1,5-a]pyrrolo[2,3-e]pyrazin-7-yl)phenyl)propan-2-ol.

In another embodiment the invention is N,N-diethyl-3-(8-ethyl-1-methyl-1,6-dihydropyrazolo[3,4-d]pyrrolo[2,3-b]pyridin-7-yl)benzenesulfonamide.

In another embodiment the invention is N,N-dimethyl-7-p-tolyl-6H-imidazo[1,5-a]pyrrolo[2,3-e]pyrazin-1-amine.

In another embodiment the invention is 3-(1-methyl-1,6-dihydropyrazolo[3,4-d]pyrrolo[2,3-b]pyridin-7-yl)-N-(2-morpholinoethyl)benzenesulfonamide.

In another embodiment the invention is N42-methoxyethyl)-3-(1-methyl-1,6-dihydropyrazolo[3,4-d]pyrrolo[2,3-b]pyridin-7-yl)benzenesulfonamide.

In another embodiment the invention is 8-ethyl-7-(4-methoxyphenyl)-1-methyl-1,6-dihydropyrazolo[3,4-d]pyrrolo[2,3-b]pyridine.

In another embodiment the invention is 1-cyclohexyl-3-phenyl-6H-imidazo[1,5-a]pyrrolo[2,3-e]pyrazine.

In another embodiment the invention is (E)-3-(1-cyclohexyl-6H-imidazo[1,5-a]pyrrolo[2,3-e]pyrazin-3-yl)acrylic acid.

In another embodiment the invention is 7-(5-methoxy-1-methyl-1H-indol-3-yl)-1-(pyrrolidin-1-yl)-6H-imidazo[1,5-a]pyrrolo[2,3-e]pyrazine.

In another embodiment the invention is 1-(pyrrolidin-1-yl)-7-p-tolyl-6H-imidazo[1,5-a]pyrrolo[2,3-e]pyrazine.

In another embodiment the invention is 2-(4-(1-ethyl-3H-imidazo[1,2-a]pyrrolo[2,3-e]pyrazin-2-yl)phenyl)propan-2-ol.

In another embodiment the invention is 8-ethyl-1-methyl-7-(1-methyl-1H-pyrazol-4-yl)-1,6-dihydropyrazolo[3,4-d]pyrrolo[2,3-b]pyridine.

In another embodiment the invention is 2-(4-(8-ethyl-6H-pyrrolo[2,3-e][1,2,4]triazolo[4,3-a]pyrazin-7-yl)phenyl)propan-2-ol.

In another embodiment the invention is 2-(4-(8-ethyl-6H-pyrrolo[2,3-e][1,2,4]triazolo[4,3-a]pyrazin-7-yl)phenyl)propan-2-ol.

In another embodiment the invention is 4-(2-(4-(8-ethyl-1-methyl-$L^6$-dihydropyrazolo[3,4-d]pyrrolo[2,3-b]pyridin-7-yl)phenoxy)ethyl)morpholine.

In another embodiment the invention is 8-ethyl-7-(4-(2-methoxyethoxy)phenyl)-1-methyl-1,6-dihydropyrazolo[3,4-d]pyrrolo[2,3-b]pyridine.

In another embodiment the invention is 2-(4-(8-ethyl-1-methyl-1,6-dihydropyrazolo[3,4-d]pyrrolo[2,3-b]pyridin-7-yl)phenoxy)-N,N-dimethylethanamine.

In another embodiment the invention is 7-(5-methoxy-1-methyl-1H-indol-3-yl)-N-(2-methoxyethyl)-N-methyl-6H-imidazo[1,5-a]pyrrolo[2,3-e]pyrazin-1-amine.

In another embodiment the invention is 2-(4-(1-ethyl-3H-dipyrrolo[1,2-a:2',3'-e]pyrazin-2-yl)phenyl)propan-2-ol.

In another embodiment the invention is 1-methyl-7-(1-methyl-1H-indol-5-yl)-1,6-dihydropyrazolo[3,4-d]pyrrolo[2,3-b]pyridine.

In another embodiment the invention is 2-(4-(1-(dimethylamino)-8-ethyl-6H-imidazo[1,5-a]pyrrolo[2,3-e]pyrazin-7-yl)phenyl)propan-2-ol.

In another embodiment the invention is 2-(4-(8-ethyl-1-methyl-1,6-dihydropyrazolo[3,4-d]pyrrolo[2,3-b]pyridin-7-yl)phenyl)propan-2-amine.

In another embodiment the invention is 7-(2,4-dimethylphenyl)-1-methyl-1,6-dihydropyrazolo[3,4-d]pyrrolo[2,3-b]pyridine.

In another embodiment the invention is 7-(4-methoxyphenyl)-1,3-dimethyl-6H-imidazo[1,5-a]pyrrolo[2,3-e]pyrazine.

In another embodiment the invention is 7-(4-methoxyphenyl)-3-methyl-6H-imidazo[1,5-a]pyrrolo[2,3-e]pyrazine.

In another embodiment the invention is 1-cyclohexyl-3-(5-methoxy-1-methyl-1H-indol-3-yl)-6H-imidazo[1,5-a]pyrrolo[2,3-e]pyrazine.

In another embodiment the invention is 7-(4-methoxyphenyl)-1-methyl-6H-pyrrolo[2,3-e][1,2,4]triazolo[4,3-a]pyrazine.

In another embodiment the invention is 2-(4-(1-cyclohexyl-6H-imidazo[1,5-a]pyrrolo[2,3-e]pyrazin-3-yl)phenyl)propan-2-ol.

In another embodiment the invention is 1-cyclohexyl-3-(5-methoxy-1H-indol-3-yl)-6H-imidazo[1,5-a]pyrrolo[2,3-e]pyrazine.

In another embodiment the invention is 2-(4-(1-cyclohexyl-6H-imidazo[1,5-a]pyrrolo[2,3-e]pyrazin-3-yl)phenyl)propan-2-amine.

In another embodiment the invention is 7-(1-isopropyl-5-methoxy-1H-indol-3-yl)-1-methyl-1,6-dihydropyrazolo[3,4-d]pyrrolo[2,3-b]pyridine.

In another embodiment the invention is 7-(1-isopropyl-1H-indol-3-yl)-1-methyl-1,6-dihydropyrazolo[3,4-d]pyrrolo[2,3-b]pyridine.

In another embodiment the invention is 1-methyl-7-(1-methyl-1H-pyrrolo[3,2-c]pyridin-3-yl)-1,6-dihydropyrazolo[3,4-d]pyrrolo[2,3-b]pyridine.

In another embodiment the invention is 7-(5-methoxy-1-methyl-1H-indazol-3-yl)-1-methyl-1,6-dihydropyrazolo[3,4-d]pyrrolo[2,3-b]pyridine.

In another embodiment the invention is 2-(1-methyl-3-(1-methyl-1,6-dihydropyrazolo[3,4-d]pyrrolo[2,3-b]pyridin-7-yl)-1H-indol-5-yl)propan-2-ol.

In another embodiment the invention is 2-(5-methoxy-1-methyl-1H-indol-3-yl)-3H-imidazo[1,2-a]pyrrolo[2,3-e]pyrazine.

In another embodiment the invention is 1-methyl-7-(3-methyl-4-(4-methylpiperazin-1-yl)phenyl)-1,6-dihydropyrazolo[3,4-d]pyrrolo[2,3-b]pyridine.

In another embodiment the invention is 1-methyl-3-(1-methyl-1,6-dihydropyrazolo[3,4-d]pyrrolo[2,3-b]pyridin-7-yl)-N-(2-morpholino ethyl)-1H-indole-5-carboxamide.

In another embodiment the invention is N-(1-hydroxy-2-methylpropan-2-yl)-1-methyl-3-(1-methyl-1,6-dihydropyrazolo[3,4-d]pyrrolo[2,3-b]pyridin-7-yl)-1H-indole-5-carboxamide.

In another embodiment the invention is 2-(4-(8-ethyl-4-methyl-6H-imidazo[1,5-a]pyrrolo[2,3-e]pyrazin-7-yl)phenyl)propan-2-ol.

In another embodiment the invention is 6H-imidazo[1,5-a]pyrrolo[2,3-e]pyrazin-3-yl)phenyl)propan-2-ol.

In another embodiment the invention is 3-(4-methoxyphenyl)-1-methyl-6H-imidazo[1,5-a]pyrrolo[2,3-e]pyrazine.

In another embodiment the invention is 2-(7-(5-methoxy-1-methyl-1H-indol-3-yl)-6H-imidazo[1,5-a]pyrrolo[2,3-e]pyrazin-1-yl)propan-2-ol.

In another embodiment the invention is 1-methyl-3-(1-methyl-1,6-dihydropyrazolo[3,4-d]pyrrolo[2,3-b]pyridin-7-yl)-1H-indole-5-carboxylic acid.

In another embodiment the invention is N-(2-(4-(1-cyclohexyl-6H-imidazo[1,5-a]pyrrolo[2,3-e]pyrazin-3-yl)phenyl)propan-2-yl)acetamide.

In another embodiment the invention is N-(3-hydroxy-2,2-dimethylpropyl)-1-methyl-3-(1-methyl-1,6-dihydropyrazolo[3,4-d]pyrrolo[2,3-b]pyridin-7-yl)-1H-indole-5-carboxamide.

In another embodiment the invention is N-((1S,3R)-3-(3-(4-(2-hydroxypropan-2-yl)phenyl)-6H-imidazo[1,5-a]pyrrolo[2,3-e]pyrazin-1-yl)cyclopentyl)cyclopropanesulfonamide.

In another embodiment the invention is N-((1S,3R)-3-(3-(4-(prop-1-en-2-yl)phenyl)-6H-imidazo[1,5-a]pyrrolo[2,3-e]pyrazin-1-yl)cyclopentyl)cyclopropanesulfonamide.

In another embodiment the invention is 3-(5-methoxy-1-methyl-1H-indol-3-yl)-1-methyl-6H-imidazo[1,5-a]pyrrolo[2,3-e]pyrazine.

In another embodiment the invention is 7-(1,5-dimethyl-1H-indol-3-yl)-1-methyl-1,6-dihydropyrazolo[3,4-d]pyrrolo[2,3-b]pyridine.

In another embodiment the invention is 1-methyl-7-(1H-pyrrol-2-yl)-1,6-dihydropyrazolo[3,4-d]pyrrolo[2,3-b]pyridine.

In another embodiment the invention is 1,6-dihydropyrazolo[3,4-d]pyrrolo[2,3-b]pyridin-7-yl)-1H-pyrrol-1-yl)-1-(4-methylpiperazin-1-yl)ethanone.

In another embodiment the invention is N-(3-ethoxypropyl)-2-(2-(1-methyl-1,6-dihydropyrazolo[3,4-d]pyrrolo[2,3-b]pyridin-7-yl)-1H-pyrrol-1-yl)acetamide.

In another embodiment the invention is 2-(2-(1-methyl-1,6-dihydropyrazolo[3,4-d]pyrrolo[2,3-b]pyridin-7-yl)-1H-pyrrol-1-yl)-1-morpholinoethanone.

In another embodiment the invention is 1-cyclohexyl-3-p-tolyl-6H-imidazo[1,5-a]pyrrolo[2,3-e]pyrazine.

In another embodiment the invention is 7-(4-methoxyphenyl)-1-methyl-6H-imidazo[1,5-a]pyrrolo[2,3-e]pyrazine.

In another embodiment the invention is N-(2-hydroxyethyl)-1-methyl-3-(1-methyl-1,6-dihydropyrazolo[3,4-d]pyrrolo[2,3-b]pyridin-7-yl)-1H-indole-5-carboxamide.

In another embodiment the invention is N-((1S,3R)-3-(7-(5-methoxy-1-methyl-1H-indol-3-yl)-6H-imidazo[1,5-a]pyrrolo[2,3-e]pyrazin-1-yl)cyclopentyl)acetamide.

In another embodiment the invention is N-((1S,3R)-3-(7-(5-methoxy-1-methyl-1H-indol-3-yl)-6H-imidazo[1,5-a]pyrrolo[2,3-e]pyrazin-1-yl)cyclopentyl)cyclopropanesulfonamide.

In another embodiment the invention is 2-(2-(1-methyl-1,6-dihydropyrazolo[3,4-d]pyrrolo[2,3-b]pyridin-7-yl)-1H-pyrrol-1-yl)acetic acid.

In another embodiment the invention is 1-methyl-3-(quinolin-5-yl)-6H-imidazo[1,5-a]pyrrolo[2,3-e]pyrazine.

In another embodiment the invention is N-(2-(dimethylamino)ethyl)-1-methyl-3-(1-methyl-1,6-dihydropyrazolo[3,4-d]pyrrolo[2,3-b]pyridin-7-yl)-1H-indole-5-carboxamide.

In another embodiment the invention is (4-(hydroxymethyl)piperidin-1-yl)(1-methyl-3-(1-methyl-1,6-dihydropyrazolo[3,4-d]pyrrolo[2,3-b]pyridin-7-yl)-1H-indol-5-yl)methanone.

In another embodiment the invention is N,N,1-trimethyl-3-(1-methyl-1,6-dihydropyrazolo[3,4-d]pyrrolo[2,3-b]pyridin-7-yl)-1H-indole-5-carboxamide.

In another embodiment the invention is N-(3-hydroxy-2,2-dimethylpropyl)-N,1-dimethyl-3-(1-methyl-1,6-dihydropyrazolo[3,4-d]pyrrolo[2,3-b]pyridin-7-yl)-1H-indole-5-carboxamide.

In another embodiment the invention is 1-methyl-3-(7-methyl-1H-indol-4-yl)-6H-imidazo[1,5-a]pyrrolo[2,3-e]pyrazine.

In another embodiment the invention is 1-methyl-3-(1-methyl-1,6-dihydropyrazolo[3,4-d]pyrrolo[2,3-b]pyridin-7-yl)-1H-indole-6-carboxylic acid.

In another embodiment the invention is (R)-2-(4-(1-(piperidin-3-yl)-6H-imidazo[1,5-a]pyrrolo[2,3-e]pyrazin-3-yl)phenyl)propan-2-ol.

In another embodiment the invention is 4-(2-(1-methyl-3-(1-methyl-1,6-dihydropyrazolo[3,4-d]pyrrolo[2,3-b]pyridin-7-yl)-1H-indol-5-yloxy)ethyl)morpholine.

In another embodiment the invention is 1-methyl-3-(1-methyl-1,6-dihydropyrazolo[3,4-d]pyrrolo[2,3-b]pyridin-7-yl)-N-(2-(4-methylpiperazin-1-yl)-2-oxoethyl)-1H-indole-5-carboxamide.

In another embodiment the invention is N,N,1-trimethyl-3-(1-methyl-1,6-dihydropyrazolo[3,4-d]pyrrolo[2,3-b]pyridin-7-yl)-1H-indole-6-carboxamide.

In another embodiment the invention is N-(3-hydroxy-2,2-dimethylpropyl)-1-methyl-3-(1-methyl-1,6-dihydropyrazolo[3,4-d]pyrrolo[2,3-b]pyridin-7-yl)-1H-indole-6-carboxamide.

In another embodiment the invention is N-(1-hydroxy-2-methylpropan-2-yl)-1-methyl-3-(1-methyl-1,6-dihydropyrazolo[3,4-d]pyrrolo[2,3-b]pyridin-7-yl)-1H-indole-6-carboxamide.

In another embodiment the invention is 1-methyl-3-(1-methyl-1,6-dihydropyrazolo[3,4-d]pyrrolo[2,3-b]pyridin-7-yl)-N-(2-morpholinoethyl)-1H-indole-6-carboxamide.

In another embodiment the invention is 2-(4-(8-methyl-6H-pyrrolo[2,3-e][1,2,4]triazolo[4,3-a]pyrazin-7-yl)phenyl)propan-2-ol.

In another embodiment the invention is 1-cyclohexyl-3-(4-(methylsulfonyl)phenyl)-6H-imidazo[1,5-a]pyrrolo[2,3-e]pyrazine.

In another embodiment the invention is 2-(4-(1-(trifluoromethyl)-6H-imidazo[1,5-a]pyrrolo[2,3-e]pyrazin-3-yl)phenyl)propan-2-ol.

In another embodiment the invention is 2-(4-(1-(tetrahydro-2H-pyran-4-yl)-6H-imidazo[1,5-a]pyrrolo[2,3-e]pyrazin-3-yl)phenyl)propan-2-ol.

In another embodiment the invention is (S)-1-(3-(3-(4-(2-hydroxypropan-2-yl)phenyl)-6H-imidazo[1,5-a]pyrrolo[2,3-e]pyrazin-1-yl)piperidine-1-carbonyl)cyclopropanecarbonitrile.

In another embodiment the invention is 2-(4-(1-(dimethylamino)-6H-imidazo[1,5-a]pyrrolo[2,3-e]pyrazin-3-yl)phenyl)propan-2-ol.

In another embodiment the invention is 3-(1-methyl-6H-imidazo[1,5-a]pyrrolo[2,3-e]pyrazin-3-yl)-N-propylbenzamide.

In another embodiment the invention is 3-(4-(2-hydroxypropan-2-yl)phenyl)-1-(tetrahydro-2H-pyran-4-yl)-6H-imidazo[1,5-a]pyrrolo[2,3-e]pyrazine-8-carbonitrile.

In another embodiment the invention is 1-cyclohexyl-3-(3-methoxyphenyl)-6H-imidazo[1,5-a]pyrrolo[2,3-e]pyrazine.

In another embodiment the invention is 1-cyclohexyl-3-(4-fluorophenyl)-6H-imidazo[1,5-a]pyrrolo[2,3-e]pyrazine.

In another embodiment the invention is N-(3-(1-cyclohexyl-6H-imidazo[1,5-a]pyrrolo[2,3-e]pyrazin-3-yl)phenyl)acetamide.

In another embodiment the invention is 1-(3-(1-cyclohexyl-6H-imidazo[1,5-a]pyrrolo[2,3-e]pyrazin-3-yl)phenyl)ethanone.

In another embodiment the invention is 3-(benzo[b]thiophen-2-yl)-1-cyclohexyl-6H-imidazo[1,5-a]pyrrolo[2,3-e]pyrazine.

In another embodiment the invention is 1-cyclohexyl-3-(isoquinolin-4-yl)-6H-imidazo[1,5-a]pyrrolo[2,3-e]pyrazine.

In another embodiment the invention is N-(4-(1-cyclohexyl-6H-imidazo[1,5-a]pyrrolo[2,3-e]pyrazin-3-yl)phenyl)acetamide.

In another embodiment the invention is 1-cyclohexyl-3-(1-methyl-1H-indol-5-yl)-6H-imidazo[1,5-a]pyrrolo[2,3-e]pyrazine.

In another embodiment the invention is 1-cyclohexyl-3-(1-methyl-1H-pyrazol-4-yl)-6H-imidazo[1,5-a]pyrrolo[2,3-e]pyrazine.

In another embodiment the invention is 1-cyclohexyl-3-(quinolin-3-yl)-6H-imidazo[1,5-a]pyrrolo[2,3-e]pyrazine.

In another embodiment the invention is 3-(4-tert-butylphenyl)-1-cyclohexyl-6H-imidazo[1,5-a]pyrrolo[2,3-e]pyrazine.

In another embodiment the invention is 1-(4-(1-(pyrrolidine-1-carbonyl)-6H-imidazo[1,5-a]pyrrolo[2,3-e]pyrazin-7-yl)phenyl)ethanone.

In another embodiment the invention is 7-(4-acetylphenyl)-N-(2-(dimethylamino)ethyl)-6H-imidazo[1,5-a]pyrrolo[2,3-e]pyrazine-1-carboxamide.

In another embodiment the invention is 1-methyl-3-(1-methyl-1,6-dihydropyrazolo[3,4-d]pyrrolo[2,3-b]pyridin-7-yl)-N-(methylsulfonyl)-1H-indole-5-carboxamide.

In another embodiment the invention is 1-(4-(1,8-Dimethyl-6H-pyrrolo[2,3-e][1,2,4]triazolo[4,3-a]pyrazin-7-yl)phenyl)ethanone.

In another embodiment the invention is 2-(4-(8-ethyl-1-methyl-1,6-dihydropyrazolo[3,4-d]pyrrolo[2,3-b]pyridin-3-yl)phenyl)propan-2-ol.

In another embodiment the invention is 1-methyl-3-(4-(methylsulfonyl)phenyl)-6H-imidazo[1,5-a]pyrrolo[2,3-e]pyrazine.

In another embodiment the invention is 7-(5-methoxy-1-methyl-1H-pyrrolo[3,2-b]pyridin-3-yl)-1-methyl-1,6-dihydropyrazolo[3,4-d]pyrrolo[2,3-b]pyridine.

In another embodiment the invention is 1-methyl-7-(5-methyl-5H-pyrrolo[2,3-b]pyrazin-7-yl)-1,6-dihydropyrazolo[3,4-d]pyrrolo[2,3-b]pyridine.

In another embodiment the invention is 4-(1-methyl-6H-imidazo[1,5-a]pyrrolo[2,3-e]pyrazin-3-yl)-N-propylbenzamide.

In another embodiment the invention is N-(4-(1-cyclohexyl-6H-imidazo[1,5-a]pyrrolo[2,3-e]pyrazin-3-yl)phenyl)methanesulfonamide.

In another embodiment the invention is 1-methyl-3-(3-methyl-4-(4-methylpiperazin-1-yl)phenyl)-6H-imidazo[1,5-a]pyrrolo[2,3-e]pyrazine.

In another embodiment the invention is 2-(4-(1-cyclohexyl-6H-imidazo[1,5-a]pyrrolo[2,3-e]pyrazin-3-yl)phenyl)-2-methylpropanenitrile.

In another embodiment the invention is 4-(1-cyclohexyl-6H-imidazo[1,5-a]pyrrolo[2,3-e]pyrazin-3-yl)-N-methylbenzamide.

In another embodiment the invention is 1-cyclohexyl-3-(4-((4-methylpiperazin-1-yl)methyl)phenyl)-6H-imidazo[1,5-a]pyrrolo[2,3-e]pyrazine.

In another embodiment the invention is 4-(1-cyclohexyl-6H-imidazo[1,5-a]pyrrolo[2,3-e]pyrazin-3-yl)benzenesulfonamide.

In another embodiment the invention is 1-cyclohexyl-3-(pyrazin-2-yl)-6H-imidazo[1,5-a]pyrrolo[2,3-e]pyrazine.

In another embodiment the invention is 4-(1-cyclohexyl-6H-imidazo[1,5-a]pyrrolo[2,3-e]pyrazin-3-yl)-N-(2-methoxyethyl)benzamide.

In another embodiment the invention is N-(4-(1-cyclohexyl-6H-imidazo[1,5-a]pyrrolo[2,3-e]pyrazin-3-yl)benzyl)methanesulfonamide.

In another embodiment the invention is N-(4-(1-cyclohexyl-6H-imidazo[1,5-a]pyrrolo[2,3-e]pyrazin-3-yl)phenethyl)acetamide.

In another embodiment the invention is (1-(4-(1-cyclohexyl-6H-imidazo[1,5-a]pyrrolo[2,3-e]pyrazin-3-yl)phenyl)cyclopropyl)methanol.

In another embodiment the invention is 4-(2-(4-(1-methyl-6H-imidazo[1,5-a]pyrrolo[2,3-e]pyrazin-3-yl)phenoxy)ethyl)morpholine.

In another embodiment the invention is 2-(3-fluoro-4-(1-methyl-6H-imidazo[1,5-a]pyrrolo[2,3-e]pyrazin-3-yl)phenyl)propan-2-ol.

In another embodiment the invention is 3-(4-(2-methoxyethoxy)phenyl)-1-methyl-6H-imidazo[1,5-a]pyrrolo[2,3-e]pyrazine.

In another embodiment the invention is 1-methyl-3-(quinoxalin-5-yl)-6H-imidazo[1,5-a]pyrrolo[2,3-e]pyrazine.

In another embodiment the invention is 3-(8-methoxyquinolin-5-yl)-1-methyl-6H-imidazo[1,5-a]pyrrolo[2,3-e]pyrazine.

In another embodiment the invention is 2-(4-(1-methyl-6H-imidazo[1,5-a]pyrrolo[2,3-e]pyrazin-3-yl)phenoxy)acetic acid.

In another embodiment the invention is 3-(4-methoxy-2-methylphenyl)-1-methyl-6H-imidazo[1,5-a]pyrrolo[2,3-e]pyrazine.

In another embodiment the invention is 2-(4-(6H-imidazo[1,5-a]pyrrolo[2,3-e]pyrazin-3-yl)phenyl)propan-2-ol.

In another embodiment the invention is 3-(2,4-dimethoxyphenyl)-1-methyl-6H-imidazo[1,5-a]pyrrolo[2,3-e]pyrazine.

In another embodiment the invention is (5-methoxy-2-(1-methyl-6H-imidazo[1,5-a]pyrrolo[2,3-e]pyrazin-3-yl)phenyl)methanol.

In another embodiment the invention is 3-(2-fluoro-4-methoxyphenyl)-1-methyl-6H-imidazo[1,5-a]pyrrolo[2,3-e]pyrazine.

In another embodiment the invention is 3-(2-chloro-4-methoxyphenyl)-1-methyl-6H-imidazo[1,5-a]pyrrolo[2,3-e]pyrazine.

In another embodiment the invention is -methyl-6H-imidazo[1,5-a]pyrrolo[2,3-e]pyrazin-3-yl)phenyl)propan-2-ol.

In another embodiment the invention is 3-(4-methoxyphenyl)-1-methyl-1,6-dihydropyrazolo[3,4-d]pyrrolo[2,3-b]pyridine.

In another embodiment the invention is 2-(4-(1-cyclopropyl-6H-imidazo[1,5-a]pyrrolo[2,3-e]pyrazin-3-yl)phenyl)propan-2-ol.

In another embodiment the invention is 2-(3-methyl-4-(1-methyl-6H-imidazo[1,5-a]pyrrolo[2,3-e]pyrazin-3-yl)phenyl)propan-2-ol.

In another embodiment the invention is 2-(2-fluoro-4-(1-methyl-6H-imidazo[1,5-a]pyrrolo[2,3-e]pyrazin-3-yl)phenyl)propan-2-ol.

In another embodiment the invention is 2-methyl-2-(4-(1-methyl-6H-imidazo[1,5-a]pyrrolo[2,3-e]pyrazin-3-yl)phenyl)propan-1-ol.

In another embodiment the invention is 2-(4-(8-ethyl-6H-pyrrolo[2,3-e][1,2,3]triazolo[1,5-a]pyrazin-7-yl)phenyl)propan-2-ol.

In another embodiment the invention is (4-(1-methyl-6H-imidazo[1,5-a]pyrrolo[2,3-e]pyrazin-3-yl)phenyl)methanol.

In another embodiment the invention is 3-(4-methoxyphenyl)-6H-imidazo[1,5-a]pyrrolo[2,3-e]pyrazine.

In another embodiment the invention is 7-(5-methoxy-1-methyl-1H-pyrrolo[2,3-c]pyridin-3-yl)-1-methyl-1,6-dihydropyrazolo[3,4-d]pyrrolo[2,3-b]pyridine.

In another embodiment the invention is 3-(4-methoxyphenyl)-1-(4-methylpiperazin-1-yl)-6H-imidazo[1,5-a]pyrrolo[2,3-e]pyrazine.

In another embodiment the invention is 3-(4-methoxyphenyl)-1-(1-methylpiperidin-4-yl)-6H-imidazo[1,5-a]pyrrolo[2,3-e]pyrazine.

In another embodiment the invention is 7-(5-methoxy-1-methyl-1H-pyrrolo[2,3-b]pyridin-3-yl)-1-methyl-1,6-dihydropyrazolo[3,4-d]pyrrolo[2,3-b]pyridine.

In another embodiment the invention is 2-(4-(8-methyl-3H-imidazo[1,2-a]pyrrolo[2,3-e]pyrazin-2-yl)phenyl)propan-2-ol.

In another embodiment the invention is 3-(6-methoxypyridin-3-yl)-1-methyl-6H-imidazo[1,5-a]pyrrolo[2,3-e]pyrazine.

In another embodiment the invention is 1-methyl-3-(3-(methylsulfonyl)phenyl)-6H-imidazo[1,5-a]pyrrolo[2,3-e]pyrazine.

In another embodiment the invention is N-cyclopropyl-4-(1-methyl-6H-imidazo[1,5-a]pyrrolo[2,3-e]pyrazin-3-yl)benzenesulfonamide.

In another embodiment the invention is 1-methyl-3-(pyridin-3-yl)-6H-imidazo[1,5-a]pyrrolo[2,3-e]pyrazine.

In another embodiment the invention is 1-cyclopropyl-3-(4-methoxyphenyl)-6H-imidazo[1,5-a]pyrrolo[2,3-e]pyrazine.

In another embodiment the invention is 1-(2-methoxyethyl)-3-(4-methoxyphenyl)-6H-imidazo[1,5-a]pyrrolo[2,3-e]pyrazine.

In another embodiment the invention is 1-(3-(4-methoxyphenyl)-6H-imidazo[1,5-a]pyrrolo[2,3-e]pyrazin-1-yl)-N,N-dimethylmethanamine.

In another embodiment the invention is 3-(3,4-dimethoxyphenyl)-1-methyl-6H-imidazo[1,5-a]pyrrolo[2,3-e]pyrazine.

In another embodiment the invention is 3-(3-chloro-4-methoxyphenyl)-1-methyl-6H-imidazo[1,5-a]pyrrolo[2,3-e]pyrazine.

In another embodiment the invention is (7-(5-methoxy-1-methyl-1H-indol-3-yl)-1-methylpyrazolo[3,4-d]pyrrolo[2,3-b]pyridin-6(1H)-yl)methyl dihydrogen phosphate.

In another embodiment the invention is 3-(4-methoxy-3,5-dimethylphenyl)-1-methyl-6H-imidazo[1,5-a]pyrrolo[2,3-e]pyrazine.

In another embodiment the invention is N-methyl-4-(1-methyl-6H-imidazo[1,5-a]pyrrolo[2,3-e]pyrazin-3-yl)benzenesulfonamide.

In another embodiment the invention is 3-(2,3-dihydrobenzofuran-5-yl)-1-methyl-6H-imidazo[1,5-a]pyrrolo[2,3-e]pyrazine.

In another embodiment the invention is 3-(1-cyclohexyl-6H-imidazo[1,5-a]pyrrolo[2,3-e]pyrazin-3-yl)-N-(2-hydroxyethyl)benzenesulfonamide.

In another embodiment the invention is 4-(1-cyclohexyl-6H-imidazo[1,5-a]pyrrolo[2,3-e]pyrazin-3-yl)-N,N-dimethylbenzamide.

In another embodiment the invention is 1-cyclohexyl-3-(pyridin-4-yl)-6H-imidazo[1,5-a]pyrrolo[2,3-e]pyrazine.

In another embodiment the invention is 1-cyclohexyl-3-(furan-3-yl)-6H-imidazo[1,5-a]pyrrolo[2,3-e]pyrazine.

In another embodiment the invention is 1-cyclohexyl-3-(pyrimidin-5-yl)-6H-imidazo[1,5-a]pyrrolo[2,3-e]pyrazine.

In another embodiment the invention is 4-(1-cyclohexyl-6H-imidazo[1,5-a]pyrrolo[2,3-e]pyrazin-3-yl)-N-(2-(dimethylamino)ethyl)benzamide.

In another embodiment the invention is 1-cyclohexyl-3-m-tolyl-6H-imidazo[1,5-a]pyrrolo[2,3-e]pyrazine.

In another embodiment the invention is (4-(1-cyclohexyl-6H-imidazo[1,5-a]pyrrolo[2,3-e]pyrazin-3-yl)phenyl)(morpholino)methanone.

In another embodiment the invention is 3-(2-methoxypyrimidin-5-yl)-1-methyl-6H-imidazo[1,5-a]pyrrolo[2,3-e]pyrazine.

In another embodiment the invention is (1S,3R)-3-(3-(4-methoxyphenyl)-6H-imidazo[1,5-a]pyrrolo[2,3-e]pyrazin-1-yl)cyclopentanamine.

In another embodiment the invention is 4-(2-methyl-4-(1-methyl-6H-imidazo[1,5-cis-3-(3-(4-methoxyphenyl)-6H-imidazo[1,5-a]pyrrolo[2,3-e]pyrazin-1-yl)cyclohexanamine.

In another embodiment the invention is a]pyrrolo[2,3-e]pyrazin-3-yl)phenyl)morpholine.

In another embodiment the invention is N-(cis-3-(3-(4-methoxyphenyl)-6H-imidazo[1,5-a]pyrrolo[2,3-e]pyrazin-1-yl)cyclohexyl)acetamide.

In another embodiment the invention is 3-(4-methoxyphenyl)-1,6-dihydropyrazolo[3,4-d]pyrrolo[2,3-b]pyridine.

In another embodiment the invention is 2-(3-(4-methoxyphenyl)-6H-imidazo[1,5-a]pyrrolo[2,3-e]pyrazin-1-yl)-N,N-dimethylethanamine.

In another embodiment the invention is 3-(4-(methylsulfonyl)phenyl)-6H-imidazo[1,5-a]pyrrolo[2,3-e]pyrazine.

In another embodiment the invention is 1-isopropyl-3-(4-methoxyphenyl)-6H-imidazo[1,5-a]pyrrolo[2,3-e]pyrazine.

In another embodiment the invention is 3-(4-methoxyphenyl)-1-propyl-6H-imidazo[1,5-a]pyrrolo[2,3-e]pyrazine.

In another embodiment the invention is 7-(4-(2-hydroxypropan-2-yl)phenyl)-1-methyl-1,6-dihydropyrazolo[3,4-d]pyrrolo[2,3-b]pyridine-8-carbonitrile.

In another embodiment the invention is 2-methoxy-5-(1-methyl-6H-imidazo[1,5-a]pyrrolo[2,3-e]pyrazin-3-yl)-N-propylbenzamide.

In another embodiment the invention is 4-(1-cyclohexyl-6H-imidazo[1,5-a]pyrrolo[2,3-e]pyrazin-3-yl)-N,N-dimethylbenzenesulfonamide.

In another embodiment the invention is 1-cyclohexyl-3-(4-(isopropylsulfonyl)phenyl)-6H-imidazo[1,5-a]pyrrolo[2,3-e]pyrazine.

In another embodiment the invention is N,N-dimethyl-4-(1-methyl-6H-imidazo[1,5-a]pyrrolo[2,3-e]pyrazin-3-yl)benzenesulfonamide.

In another embodiment the invention is 3-(4-(isopropylsulfonyl)phenyl)-1-methyl-6H-imidazo[1,5-a]pyrrolo[2,3-e]pyrazine.

In another embodiment the invention is N-(2-(dimethylamino)ethyl)-2-methoxy-5-(1-methyl-6H-imidazo[1,5-a]pyrrolo[2,3-e]pyrazin-3-yl)benzamide.

In another embodiment the invention is 1-methyl-3-(4-(methylthio)phenyl)-1,6-dihydropyrazolo[3,4-d]pyrrolo[2,3-b]pyridine.

In another embodiment the invention is 3-(4-methoxyphenyl)-6H-imidazo[1,5-a]pyrrolo[2,3-e]pyrazine-1-carboxylic acid.

In another embodiment the invention is 1-methyl-6H-imidazo[1,5-a]pyrrolo[2,3-e]pyrazin-3-yl)phenyl)propan-2-ol.

In another embodiment the invention is (1-(4-(1-methyl-6H-imidazo[1,5-a]pyrrolo[2,3-e]pyrazin-3-yl)phenyl)cyclopropyl)methanol.

In another embodiment the invention is N-(2-hydroxyethyl)-2-methoxy-5-(1-methyl-6H-imidazo[1,5-a]pyrrolo[2,3-e]pyrazin-3-yl)benzamide.

In another embodiment the invention is 8-bromo-3-(4-methoxyphenyl)-1-methyl-1,6-dihydropyrazolo[3,4-d]pyrrolo[2,3-b]pyridine.

In another embodiment the invention is 1-cyclohexyl-3-(4-(methylsulfonyl)phenyl)-3,6-dihydroimidazo[4,5-d]pyrrolo[2,3-b]pyridin-2(1H)-one.

In another embodiment the invention is 1-methyl-3-(4-(4-methylpiperazin-1-ylsulfonyl)phenyl)-6H-imidazo[1,5-a]pyrrolo[2,3-e]pyrazine.

In another embodiment the invention is 2-(4-(6H-imidazo[1,5-a]pyrrolo[2,3-e]pyrazin-3-yl)phenyl)-2-methylpropan-1-ol.

In another embodiment the invention is 1,5-a]pyrrolo[2,3-e]pyrazin-3-yl)phenyl)methanol.

In another embodiment the invention is 2-(2-fluoro-4-(6H-imidazo[1,5-a]pyrrolo[2,3-e]pyrazin-3-yl)phenyl)propan-2-ol.

In another embodiment the invention is 5-a]pyrrolo[2,3-e]pyrazin-3-yl)-N-propylbenzamide.

In another embodiment the invention is 3-(5-methoxythiophen-2-yl)-1-methyl-6H-imidazo[1,5-a]pyrrolo[2,3-e]pyrazine.

In another embodiment the invention is 3-(4-(methylsulfonyl)phenyl)-6H-pyrrolo[2,3-e][1,2,3]triazolo[1,5-a]pyrazine.

In another embodiment the invention is 3-(4-methoxyphenyl)-6H-pyrrolo[2,3-e][1,2,3]triazolo[1,5-a]pyrazine.

In another embodiment the invention is 1-methyl-3-(4-(methylsulfonyl)phenyl)-1,6-dihydropyrazolo[3,4-d]pyrrolo[2,3-b]pyridine.

In another embodiment the invention is 3-(3,4-dimethoxyphenyl)-6H-imidazo[1,5-a]pyrrolo[2,3-e]pyrazine.

In another embodiment the invention is 3-(3-chloro-4-methoxyphenyl)-6H-imidazo[1,5-a]pyrrolo[2,3-e]pyrazine.

In another embodiment the invention is 3-(4-methoxy-3-methylphenyl)-6H-imidazo[1,5-a]pyrrolo[2,3-e]pyrazine.

In another embodiment the invention is 3-(4-methoxy-3-methylphenyl)-1-methyl-6H-imidazo[1,5-a]pyrrolo[2,3-e]pyrazine.

In another embodiment the invention is 3-(2-methoxypyridin-4-yl)-6H-imidazo[1,5-a]pyrrolo[2,3-e]pyrazine.

In another embodiment the invention is 1-(4-(6H-imidazo[1,5-a]pyrrolo[2,3-e]pyrazin-3-yl)pyridin-2-yl)ethanone.

In another embodiment the invention is (3-(4-methoxyphenyl)-6H-imidazo[1,5-a]pyrrolo[2,3-e]pyrazin-1-yl)methanol.

In another embodiment the invention is N-((3-(4-methoxyphenyl)-6H-imidazo[1,5-a]pyrrolo[2,3-e]pyrazin-1-yl)methyl)cyclopropanamine.

In another embodiment the invention is 1-(4-(1-methyl-1,6-dihydropyrazolo[3,4-d]pyrrolo[2,3-b]pyridin-3-yl)phenyl)ethanone.

In another embodiment the invention is (5-(1-methyl-6H-imidazo[1,5-a]pyrrolo[2,3-e]pyrazin-3-yl)pyridin-2-yl)methanol.

In another embodiment the invention is 2-methoxy-5-(1-methyl-6H-imidazo[1,5-a]pyrrolo[2,3-e]pyrazin-3-yl)benzamide.

In another embodiment the invention is 2-methoxy-5-(1-methyl-6H-imidazo[1,5-a]pyrrolo[2,3-e]pyrazin-3-yl)benzamide.

In another embodiment the invention is N-(2-hydroxyethyl)-3-(4-methoxyphenyl)-6H-imidazo[1,5-a]pyrrolo[2,3-e]pyrazine-1-carboxamide.

In another embodiment the invention is 2-(4-(1-methyl-1,6-dihydropyrazolo[3,4-d]pyrrolo[2,3-b]pyridin-3-yl)phenyl)propan-2-ol.

In another embodiment the invention is methyl 2-(4-(1-methyl-6H-imidazo[1,5-a]pyrrolo[2,3-e]pyrazin-3-yl)-1H-pyrazol-1-yl)acetate.

In another embodiment the invention is 3-(2-methylpyridin-4-yl)-6H-imidazo[1,5-a]pyrrolo[2,3-e]pyrazine.

In another embodiment the invention is 2-chloro-4-(1-methyl-6H-imidazo[1,5-a]pyrrolo[2,3-e]pyrazin-3-yl)-N-propylbenzamide.

In another embodiment the invention is 4-(4-(1-methyl-6H-imidazo[1,5-a]pyrrolo[2,3-e]pyrazin-3-yl)benzyl)morpholine.

In another embodiment the invention is 2-(2-chloro-4-(1-methyl-6H-imidazo[1,5-a]pyrrolo[2,3-e]pyrazin-3-yl)phenyl)propan-2-ol.

In another embodiment the invention is 3-(4-methoxyphenyl)-1-(piperazin-1-ylmethyl)-6H-imidazo[1,5-a]pyrrolo[2,3-e]pyrazine.

In another embodiment the invention is 2-methyl-1-(4-(1-methyl-6H-imidazo[1,5-a]pyrrolo[2,3-e]pyrazin-3-yl)-1H-pyrazol-1-yl)propan-2-ol.

In another embodiment the invention is 2-(3-(4-methoxyphenyl)pyrazolo[3,4-d]pyrrolo[2,3-b]pyridin-1(6H)-yl)ethanol.

In another embodiment the invention is 1-(5-(1-methyl-6H-imidazo[1,5-a]pyrrolo[2,3-e]pyrazin-3-yl)thiophen-2-yl)ethanone.

In another embodiment the invention is 2-(5-(1-methyl-6H-imidazo[1,5-a]pyrrolo[2,3-e]pyrazin-3-yl)thiophen-2-yl)propan-2-ol.

In another embodiment the invention is 2-((3-(4-methoxyphenyl)-6H-imidazo[1,5-a]pyrrolo[2,3-e]pyrazin-1-yl)methylamino)cyclohexanol.

In another embodiment the invention is (7-(5-methoxy-1-methyl-1H-indol-3-yl)-1-methyl-6H-imidazo[1,5-a]pyrrolo[2,3-e]pyrazin-6-yl)methyl dihydrogen phosphate.

In another embodiment the invention is N-(4-(1-methyl-6H-imidazo[1,5-a]pyrrolo[2,3-e]pyrazin-3-yl)benzyl)cyclopropanesulfonamide.

In another embodiment the invention is 3-(4-(pyrrolidin-3-yloxy)phenyl)-6H-imidazo[1,5-a]pyrrolo[2,3-e]pyrazine.

In another embodiment the invention is 4-(4-(1-methyl-6H-imidazo[1,5-a]pyrrolo[2,3-e]pyrazin-3-yl)phenyl)piperidin-4-ol.

In another embodiment the invention is 3-(4-methoxyphenyl)-1-methyl-1,6-dihydropyrazolo[3,4-d]pyrrolo[2,3-b]pyridine-8-carbonitrile.

In another embodiment the invention is 2-(4-(1-(piperazin-1-ylmethyl)-6H-imidazo[1,5-a]pyrrolo[2,3-e]pyrazin-3-yl)phenyl)propan-2-ol.

In another embodiment the invention is 2-(4-(1-((4-aminopiperidin-1-yl)methyl)-6H-imidazo[1,5-a]pyrrolo[2,3-e]pyrazin-3-yl)phenyl)propan-2-ol. (4-((3-(4-methoxyphenyl)-6H-imidazo[1,5-a]pyrrolo[2,3-e]pyrazin-1-yl)methyl)piperazin-2-yl)methanol.

In another embodiment the invention is 2-((3-(4-(methylsulfonyl)phenyl)-6H-imidazo[1,5-a]pyrrolo[2,3-e]pyrazin-1-yl)methyl)morpholine.

In another embodiment the invention is 2-(4-(1-(trans-3-aminocyclohexyl)-6H-imidazo[1,5-a]pyrrolo[2,3-e]pyrazin-3-yl)phenyl)propan-2-ol.

In another embodiment the invention is 3-(1,2,3,6-tetrahydropyridin-4-yl)-6H-imidazo[1,5-a]pyrrolo[2,3-e]pyrazine.

In another embodiment the invention is tert-butyl 4-hydroxy-4-(4-(1-methyl-6H-imidazo[1,5-a]pyrrolo[2,3-e]pyrazin-3-yl)phenyl)piperidine-1-carboxylate.

In another embodiment the invention is 2-(4-(1-(3-aminopropyl)-6H-imidazo[1,5-a]pyrrolo[2,3-e]pyrazin-3-yl)phenyl)propan-2-ol.

In another embodiment the invention is 2-(4-(1-(aminomethyl)-6H-imidazo[1,5-a]pyrrolo[2,3-e]pyrazin-3-yl)phenyl)propan-2-ol.

In another embodiment the invention is (S)-3-(4-(methylsulfonyl)phenyl)-1-(piperidin-3-yl)-6-tosyl-6H-imidazo[1,5-a]pyrrolo[2,3-e]pyrazine.

In another embodiment the invention is 1-(4-(6H-imidazo[1,5-a]pyrrolo[2,3-e]pyrazin-3-yl)-5,6-dihydropyridin-1(2H)-yl)ethanone.

In another embodiment the invention is tert-butyl 4-(1-methyl-6H-imidazo[1,5-a]pyrrolo[2,3-e]pyrazin-3-yl)-5,6-dihydropyridine-1(2H)-carboxylate.

In another embodiment the invention is 8-ethyl-3-(3-fluoro-4-methoxyphenyl)-1-methyl-1,6-dihydropyrazolo[3,4-d]pyrrolo[2,3-b]pyridine.

In another embodiment the invention is 8-ethyl-1-methyl-3-(quinoxalin-6-yl)-1,6-dihydropyrazolo[3,4-d]pyrrolo[2,3-b]pyridine.

In another embodiment the invention is 8-ethyl-3-(4-isopropoxyphenyl)-1-methyl-1,6-dihydropyrazolo[3,4-d]pyrrolo[2,3-b]pyridine.

In another embodiment the invention is N-cyclopropyl-4-(8-ethyl-1-methyl-1,6-dihydropyrazolo[3,4-d]pyrrolo[2,3-b]pyridin-3-yl)benzamide.

In another embodiment the invention is (4-(8-ethyl-1-methyl-1,6-dihydropyrazolo[3,4-d]pyrrolo[2,3-b]pyridin-3-yl)phenyl)methanol.

In another embodiment the invention is 4-(8-ethyl-1-methyl-1,6-dihydropyrazolo[3,4-d]pyrrolo[2,3-b]pyridin-3-yl)benzenesulfonamide.

In another embodiment the invention is 8-ethyl-1-methyl-3-(thiophen-3-yl)-1,6-dihydropyrazolo[3,4-d]pyrrolo[2,3-b]pyridine.

In another embodiment the invention is 8-ethyl-3-(4-methoxyphenyl)-1-methyl-1,6-dihydropyrazolo[3,4-d]pyrrolo[2,3-b]pyridine.

In another embodiment the invention is 8-ethyl-1-methyl-3-(pyridin-3-yl)-1,6-dihydropyrazolo[3,4-d]pyrrolo[2,3-b]pyridine.

In another embodiment the invention is 8-ethyl-1-methyl-3-(1-methyl-1H-pyrazol-4-yl)-1,6-dihydropyrazolo[3,4-d]pyrrolo[2,3-b]pyridine.

In another embodiment the invention is 8-ethyl-1-methyl-3-(3,4,5-trimethoxyphenyl)-1,6-dihydropyrazolo[3,4-d]pyrrolo[2,3-b]pyridine.

In another embodiment the invention is N-((3-(4-(2-hydroxypropan-2-yl)phenyl)-6H-imidazo[1,5-a]pyrrolo[2,3-e]pyrazin-1-yl)methyl)acetamide.

In another embodiment the invention is 3-hydroxy-1-(3-(3-(4-(methylsulfonyl)phenyl)-6H-imidazo[1,5-a]pyrrolo[2,3-e]pyrazin-1-yl)piperidin-1-yl)propan-1-one.

In another embodiment the invention is (1r,4r)-4-(3-(4-(methylsulfonyl)phenyl)-6H-imidazo[1,5-a]pyrrolo[2,3-e]pyrazin-1-yl)cyclohexanamine.

In another embodiment the invention is 1-(4-hydroxy-4-(4-(1-methyl-6H-imidazo[1,5-a]pyrrolo[2,3-e]pyrazin-3-yl)phenyl)piperidin-1-yl)ethanone.

In another embodiment the invention is 3-methoxy-1-(3-(3-(4-(methylsulfonyl)phenyl)-6H-imidazo[1,5-a]pyrrolo[2,3-e]pyrazin-1-yl)piperidin-1-yl)propan-1-one.

In another embodiment the invention is 2-(4-(1-(pyridin-3-yl)-6H-imidazo[1,5-a]pyrrolo[2,3-e]pyrazin-3-yl)phenyl)propan-2-ol.

In another embodiment the invention is 2-(4-(1-((3-methylpiperazin-1-yl)methyl)-6H-imidazo[1,5-a]pyrrolo[2,3-e]pyrazin-3-yl)phenyl)propan-2-ol.

In another embodiment the invention is 3-(3-(4-(2-hydroxypropan-2-yl)phenyl)-6H-imidazo[1,5-a]pyrrolo[2,3-e]pyrazin-1-yl)picolinonitrile.

In another embodiment the invention is 3-(4-hydroxy-4-(1-methyl-6H-imidazo[1,5-a]pyrrolo[2,3-e]pyrazin-3-yl)phenyl)piperidin-1-yl)-3-oxopropanenitrile.

In another embodiment the invention is 2-(4-(1-(2-(aminomethyl)phenyl)-6H-imidazo[1,5-a]pyrrolo[2,3-e]pyrazin-3-yl)phenyl)propan-2-ol.

In another embodiment the invention is 2-((3-(4-(methylsulfonyl)phenyl)-6H-imidazo[1,5-a]pyrrolo[2,3-e]pyrazin-1-yl)methoxy)ethanamine.

In another embodiment the invention is 4-(4-(6H-imidazo[1,5-a]pyrrolo[2,3-e]pyrazin-3-yl)phenyl)piperidin-4-ol.

In another embodiment the invention is (R)-3-hydroxy-1-(3-(3-(4-(2-hydroxypropan-2-yl)phenyl)-6H-imidazo[1,5-a]pyrrolo[2,3-e]pyrazin-1-yl)-4-methylpiperazin-1-yl)propan-1-one.

In another embodiment the invention is N,N-dimethyl-1-(1-(3-(4-(methylsulfonyl)phenyl)-6H-imidazo[1,5-a]pyrrolo[2,3-e]pyrazin-1-yl)pyrrolidin-3-yl)methanamine.

In another embodiment the invention is 2-(4-(1-(2-(aminomethyl)phenyl)-6H-imidazo[1,5-a]pyrrolo[2,3-e]pyrazin-3-yl)phenyl)propan-2-ol.

In another embodiment the invention is 2-(4-(1-(2-(hydroxymethyl)phenyl)-6H-imidazo[1,5-a]pyrrolo[2,3-e]pyrazin-3-yl)phenyl)propan-2-ol.

In another embodiment the invention is 2-(4-(1-((2-aminoethoxy)methyl)-6H-imidazo[1,5-a]pyrrolo[2,3-e]pyrazin-3-yl)phenyl)propan-2-ol.

In another embodiment the invention is N-((trans)-1-acetyl-5-(3-(4-(2-hydroxypropan-2-yl)phenyl)-6H-imidazo[1,5-a]pyrrolo[2,3-e]pyrazin-1-yl)pyrrolidin-3-yl)cyclopropanesulfonamide.

In another embodiment the invention is N-((3R,5R)-1-(cyclopropylsulfonyl)-5-(3-(4-(2-hydroxypropan-2-yl)phenyl)-6H-imidazo[1,5-a]pyrrolo[2,3-e]pyrazin-1-yl)pyrrolidin-3-yl)acetamide.

In another embodiment the invention is (R)-2-(4-(1-(pyrrolidin-3-yl)-6H-imidazo[1,5-a]pyrrolo[2,3-e]pyrazin-3-yl)phenyl)propan-2-ol.

In another embodiment the invention is 2-(4-(1-(2-methylpyridin-3-yl)-6H-imidazo[1,5-a]pyrrolo[2,3-e]pyrazin-3-yl)phenyl)propan-2-ol.

In another embodiment the invention is 2-(4-(1-((4-methylpiperazin-1-yl)methyl)-6H-imidazo[1,5-a]pyrrolo[2,3-e]pyrazin-3-yl)phenyl)propan-2-ol.

In another embodiment the invention is 2-(4-(1-((4-methylpiperazin-1-yl)methyl)-6H-imidazo[1,5-a]pyrrolo[2,3-e]pyrazin-3-yl)phenyl)propan-2-ol.

In another embodiment the invention is 2-(4-(1-(3-(aminomethyl)pyrrolidin-1-yl)-6H-imidazo[1,5-a]pyrrolo[2,3-e]pyrazin-3-yl)phenyl)propan-2-ol.

In another embodiment the invention is 2-(4-(1-((1,4-diazepan-1-yl)methyl)-6H-imidazo[1,5-a]pyrrolo[2,3-e]pyrazin-3-yl)phenyl)propan-2-ol.

In another embodiment the invention is 2-(4-(1-(piperidin-4-ylmethyl)-6H-imidazo[1,5-a]pyrrolo[2,3-e]pyrazin-3-yl)phenyl)propan-2-ol 2-(4-(1-(2-(hydroxymethyl)pyridin-3-yl)-6H-imidazo[1,5-a]pyrrolo[2,3-e]pyrazin-3-yl)phenyl)propan-2-ol.

In another embodiment the invention is 2-(5-(1-methyl-6H-imidazo[1,5-a]pyrrolo[2,3-e]pyrazin-3-yl)pyridin-2-yl)propan-2-ol.

In another embodiment the invention is 2-(4-(1-(3-amino-3-methylbutyl)-6H-imidazo[1,5-a]pyrrolo[2,3-e]pyrazin-3-yl)phenyl)propan-2-ol.

In another embodiment the invention is 1-(2-(3-(4-(2-hydroxypropan-2-yl)phenyl)-6H-imidazo[1,5-a]pyrrolo[2,3-e]pyrazin-1-yl)pyrrolidin-1-yl)ethanone.

In another embodiment the invention is 1-(2-(3-(4-(2-hydroxypropan-2-yl)phenyl)-6H-imidazo[1,5-a]pyrrolo[2,3-e]pyrazin-1-yl)pyrrolidin-1-yl)ethanone.

In another embodiment the invention is 2-(4-(7-bromo-1-methyl-6H-imidazo[1,5-a]pyrrolo[2,3-e]pyrazin-3-yl)phenyl)propan-2-ol.

In another embodiment the invention is 3-(4-methoxyphenyl)-8-(1,2,3,6-tetrahydropyridin-4-yl)-6H-imidazo[1,5-a]pyrrolo[2,3-e]pyrazine.

In another embodiment the invention is 2-(4-(1-((1R,2R)-2-(aminomethyl)cyclohexyl)-6H-imidazo[1,5-a]pyrrolo[2,3-e]pyrazin-3-yl)phenyl)propan-2-ol.

In another embodiment the invention is 2-(4-(8-bromo-1-methyl-6H-imidazo[1,5-a]pyrrolo[2,3-e]pyrazin-3-yl)phenyl)propan-2-ol.

In another embodiment the invention is 2-(4-(8-(1,2,3,6-tetrahydropyridin-4-yl)-6H-imidazo[1,5-a]pyrrolo[2,3-e]pyrazin-3-yl)phenyl)propan-2-ol.

In another embodiment the invention is 3-(4-(2-hydroxypropan-2-yl)phenyl)-1-methyl-6H-imidazo[1,5-a]pyrrolo[2,3-e]pyrazine-8-carbonitrile.

In another embodiment the invention is 2-hydroxy-N-((3-(4-(2-hydroxypropan-2-yl)phenyl)-6H-imidazo[1,5-a]pyrrolo[2,3-e]pyrazin-1-yl)methyl)acetamide.

In another embodiment the invention is 3-(4-(1-methyl-6H-imidazo[1,5-a]pyrrolo[2,3-e]pyrazin-3-yl)phenyl)oxetan-3-ol.

In another embodiment the invention is 2-(4-(8-(hydroxymethyl)-6H-imidazo[1,5-a]pyrrolo[2,3-e]pyrazin-3-yl)phenyl)propan-2-ol.

In another embodiment the invention is (S)-1-(2-(3-(4-(2-hydroxypropan-2-yl)phenyl)-6H-imidazo[1,5-a]pyrrolo[2,3-e]pyrazin-1-yl)pyrrolidin-1-yl)ethanone.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and serine/threonine kinases as a result of their substrate specificity.

Spleen Tyrosine Kinase (Syk) is a 72 kDa non-receptor protein tyrosine kinase that functions as a key signaling regulator in most hematopoietic cells. Its closest homolog is zeta-associated protein 70 (ZAP-70). Like Zap70, full-length Syk carries two N-terminal SH2 domains. These domains allow Syk to bind di-phosphorylated immunoreceptor tyrosine-based activation motifs (ITAMS) on the intercellular portion of a variety of receptors involved in immune regulation. Upon activation and recruitment to immunoreceptors, Syk phosphorylates a variety of cellular proteins including Linker for Activator of T-cells (LAT), B-cell Linker (BLNK), Vav, Bruton's Tyrosine Kinase, Gab, Bcap, SH2-domain containing Leukocyte Protein-76 (SLP-76) and Phospholipase Cγ.

In B-cells, Syk is essentially involved in B-cell Receptor (BCR) signal initiation, leading to development and survival of B lymphocytes in both bone marrow and periphery (Cheng et al. 1995, *Nature* 378:3003; Turner et al. 1995 *Nature* 378:298). It is activated by the Src-family kinase Lyn after Syk binds to doubly phosphorylated ITAMs on Igα/β chains on the BCR. The downstream effects of BCR engagement include $Ca^{2+}$ flux, mitogen-activated protein (MAP) kinase activation & Akt activation. Signaling through the BCR is critical for development and survival of B lymphocytes in both bone marrow and periphery.

In mast cells and basophils, Syk is a critical component of FcεR1 signaling where downstream effects of activation include degranulation, release of cytokines such a tumor necrosis factor α and interleukin-6 and release of lipid mediators such as LTC4 (Costello et al. 1996 *Oncogene* 13:2595). Similar Syk-dependent signaling is driven by IgG-antigen crosslinking via Fcγ receptors in macrophages, neutrophils & dendritic cells (Kiefer et al. 1998 *Mol Cell Biol* 18: 4209; Sedlik et al. 2003 *J Immun* 170:846). In macrophages, Syk activity is believed to regulate phagocytosis of opsonized foreign (and self) antigens via the FcγR, and Syk is important for antigen presentation from and maturation of dendritic cells. A role for Syk has been proposed for osteoclast maturation and in DAP12 receptor signaling in these cell types involved in bone metabolism. Reviews of these finding can be found in *Expert Opin. Invest. Drugs*, 2004, 13(7), 743 and *Expert Opin. Invest. Drugs*, 2008, 17(5), 641.

Therefore, Syk inhibition offers an opportunity to affect multiple cell types involved in inflammation, and it could be predicted to serve as therapy for autoimmune diseases including rheumatoid arthritis, asthma, systemic lupus erythematosus (SLE), and multiple sclerosis.

The Jak family kinases (Jak1, Jak2, Jak3 and Tyk2) are cytoplasmic tyrosine kinases that associate with membrane bound cytokine receptors. Cytokine binding to their receptor initiates Jak kinase activation via trans and autophosphorylation processes. The activated Jak kinases phosphorylate residues on the cytokine receptors creating phosphotyrosine binding sites for SH2 domain containing proteins such as Signal Transduction Activators of Transcript (STAT) factors and other signal regulators transduction such as SOCS proteins and SHIP phosphatases. Activation of STAT factors via this process leads to their dimerization, nuclear translocation and new mRNA transcription resulting in expression of immunocyte proliferation and survival factors as well as additional cytokines, chemokines and molecules that facilitate cellular trafficking (see *Journal of Immunology*, 2007, 178, p. 2623). Jak kinases transduce signals for many different cytokine families and hence potentially play roles in diseases with widely different pathologies including but not limited to the following examples. Both Jak1 and Jak3 control signaling of the so-called common gamma chain cytokines (IL2, IL4, IL7, IL9, IL15 and IL21), hence simultaneous inhibition of either Jak1 or Jak3 could be predicted to impact Th1 mediated diseases such as rheumatoid arthritis via blockade of IL2, IL7 and IL15 signaling. Th2 mediated diseases such as asthma or atopic dermatitis via IL4 and IL9 signaling blockade. Jak1 and Tyk2 mediate signaling of IL13 (see Int. Immunity, 2000, 12, p. 1499). Hence, blockade of these may also be predicted to have a therapeutic effect in asthma. These two kinases are also thought to mediate Type I interferon signaling; their blockade could therefore be predicted to reduce the severity of systemic lupus erythematosus (SLE). Tyk2 and Jak2 mediate signaling of IL12 and IL23.

Jak2 is also activated in a wide variety of human cancers such as prostate, colon, ovarian and breast cancers, melanoma, leukemia and other haematopoietic malignancies. In addition, somatic point mutation of the Jak2 gene has been identified to be highly associated with classic myeloproliferative disorders (MPD) and infrequently in other myeloid disorders. Constitutive activation of Jak2 activity is also caused by chromosomal translocation in hematopoeitic malignancies. Accordingly, the identification of small-molecule compounds that inhibit, regulate and/or modulate the signal transduction of kinases, particularly Jak2, is desirable as a means to treat or prevent diseases and conditions associated with cancers.

The protein kinase C family is a group of serine/threonine kinases that comprises twelve related isoenzymes. Its members are encoded by different genes and are sub-classified according to their requirements for activation. The classical enzymes (cPKC) require diacylglycerol (DAG), phosphatidylserine (PS) and calcium for activation. The novel PKC's (nPKC) require DAG and PS but are calcium independent. The atypical PKC's (aPKC) do not require calcium or DAG. PKCtheta is a member of the nPKC sub-family (Baier, G., et al., *J. Biol. Chem.*, 1993, 268, 4997). It has a restricted expression pattern, found predominantly in T cells and skeletal muscle (Mischak, H. et al., *FEBS Lett.*, 1993, 326, p. 51), with some expression reported in mast cells (Liu, Y. et al., *J. Leukoc. Biol.*, 2001, 69, p. 831) and endothelial cells (Mattila, P. et al., *Life Sci.*, 1994, 55, p. 1253).

Upon T cell activation, a supramolecular activation complex (SMAC) forms at the site of contact between the T cell and the antigen presenting cell (APC). PKCtheta is the only PKC isoform found to localize at the SMAC (Monks, C. et al., *Nature*, 1997, 385, 83), placing it in proximity with other signaling enzymes that mediate T cell activation processes. In another study (Baier-Bitterlich, G. et al., *Mol. Cell. Biol.*, 1996, 16, 842) the role of PKCtheta in the activation of AP-1, a transcription factor important in the activation of the IL-2 gene, was confirmed. In unstimulated T cells, constitutively active PKCtheta stimulated AP-1 activity while in cells with dominant negative PKCtheta, AP-1 activity was not induced upon activation by PMA.

It has also been shown that PKCtheta-deficient mice show impaired pulmonary inflammation and airway hyperresponsiveness (AHR) in a Th2-dependent murine asthma model, with no defects in viral clearance and Th1-dependent cytotoxic T cell function (Berg-Brown, N. N. et al., *J. Exp. Med.*, 2004, 199, p. 743; Marsland, B. J. et al., *J. Exp. Med.*, 2004, 200, p. 181). Evidence also exists that PKCtheta participates in the IgE receptor (FcεRI)-mediated response of mast cells (Liu, Y. et al., *J. Leukoc. Biol.*, 2001, 69, p. 831).

The studies cited above and others studies confirm the critical role of PKCtheta in T cells activation and in mast cell (MC) signaling. Thus an inhibitor of PKCtheta would be of therapeutic benefit in treating immunological disorders and other diseases mediated by the inappropriate activation of T cells and MC signaling.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

Many autoimmune diseases and disease associated with chronic inflammation, as well as acute responses, have been linked to excessive or unregulated production or activity of one or more cytokines.

The compounds of the invention are also useful in the treatment of cardiovascular disorders, such as acute myocardial infarction, acute coronary syndrome, chronic heart failure, myocardial infarction, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of rheumatoid arthritis, asthma, allergic asthma, osteoarthritis, juvenile arthritis, ankylosing spondylitis, an ocular condition, a cancer, a solid tumor, a sarcoma, fibrosarcoma, osteoma, melanoma, retinoblastoma, a rhabdomyosarcoma, glioblastoma, neuroblastoma, teratocarcinoma, hypersensitivity reactions, hyperkinetic movement disorders, hypersensitivity pneumonitis, hypertension, hypokinetic movement disorders, aordic and peripheral aneuryisms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile spinal muscular atrophy, lymphoma, myeloma, leukaemia, malignant ascites, hematopoietic cancers, a diabetic condition such as insulin-dependent diabetes mellitus glaucoma, diabetic retinopathy or microangiopathy, sickle cell anaemia, chronic inflammation, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, progressive supranucleo palsy, primary pulmonary hypertension, radiation therapy, Raynaud's phenomenon, Raynaud's disease, Refsum's disease, regular narrow QRS tachycardia, renovascular hypertension, restrictive cardiomyopathy, sarcoma, senile chorea, senile dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasulitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, *pneumocystis carinii* pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthritis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of Formula (Ia), Formula (Ib), Formula (Ic), Formula (Id), Formula (Ie), Formula (If), Formula (Ig), Formula (Ih), Formula (Ii) and Formula (Ij) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the compounds of this invention. Non-limiting examples of therapeutic agents for rheumatoid arthritis with which a compound of Formula (Ia), Formula (IB), Formula (Ic), Formula (Id), Formula (Ie), Formula (If), Formula (Ig), Formula (Ih), Formula (Ii), Formula (Ij), Formula (Ik) or Formula (Il) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, MMP-13 and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (U.S. Pat. No. 6,090,382, HUMIRA™), CA2 (REMICADE™), SIMPONI™ (golimumab), CIMZIA™, ACTEMRA™, CDP 571, and soluble p55 or p75 TNF receptors, derivatives, thereof, (p75TNFR1gG (ENBREL™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, JAK1, JAK2, JAK3, p38 or MAP kinase inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™) and p55TNFRIgG (Lenercept), sIL-1RI, sIL-1RII, sIL-6R), antiinflammatory cytokines (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. NIK, IKK, p38 or MAP kinase inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-11, IL-13 and TGFβ). Preferred examples of therapeutic agents for Crohn's disease with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: TNF antagonists, for example, anti-TNF antibodies, D2E7 (U.S. Pat. No. 6,090,382, HUMIRA™), CA2 (REMICADE™), CDP 571, TNFR-Ig constructs, (p75TNFRIgG (ENBREL™) and p55TNFRIgG (LENERCEPT™) inhibitors and PDE4 inhibitors. A compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of Formula (Ia), Formula (Ib), Formula (Ic), Formula (Id), Formula (Ie), Formula (If), Formula (Ig), Formula (Ih), Formula (Ii) or Formula (Ij) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/B erlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of Formula (Ia), Formula (Ib), Formula (Ic), Formula (Id), Formula (Ie), Formula (If), Formula (Ig), Formula (Ih), Formula (Ii) Formula (Ij), Formula (Ik) or Formula (Il) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) may also be combined with agents such as methotrexate, cyclosporine, FK506, rapamycin, mycophenolate mofetil, leflunomide, an S1P1 agonist, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1R1, sIL-1RII, sIL-6R) and antiinflammatory cytokines (e.g. IL-4, IL-10, IL-13 and TGFβ).

Preferred examples of therapeutic agents for multiple sclerosis in which a compound of Formula (Ia), Formula (Ib), Formula (Ic), Formula (Id), Formula (Ie), Formula (If), Formula (Ig), Formula (Ih), Formula (Ii) or Formula (Ij) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of Formula (Ia), Formula (Ib), Formula (Ic), Formula (Id), Formula (Ie), Formula (If), Formula (Ig), Formula (Ih), Formula (Ii) or Formula (Ij) may also be combined with agents, such as alemtuzumab, dronabinol, daclizumab, mitoxantrone, xaliproden hydrochloride, fampridine, glatiramer acetate, natalizumab, sinnabidol, α-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for ankylosing spondylitis with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, and anti-TNF antibodies, D2E7 (U.S. Pat. No. 6,090, 382; HUMIRA™), CA2 (REMICADE™), CDP 571, TNFR-Ig constructs, (p75TNFRIgG (ENBREL™) and p55TNFRIgG (LENERCEPT™)

Non-limiting examples of therapeutic agents for asthma with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/ chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, anti-IL-13 antibody, and metaproterenol sulfate.

Non-limiting examples of therapeutic agents for COPD with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast and roflumilast.

Non-limiting examples of therapeutic agents for HCV with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: Interferon-alpha-2α, Interferon-alpha-2β, Interferon-alpha con1, Interferon-alpha-n1, pegylated interferon-alpha-2α, pegylated interferon-alpha-2β, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of Formula (Ia), Formula (Ib), Formula (Ic), Formula (Id), Formula (Ie), Formula (If), Formula (Ig), Formula (Ih), Formula (Ii) or Formula (Ij) can be combined include the following: prednisone, azathioprine, albuterol, colchicine, albuterol sulfate, digoxin, gamma interferon, methylprednisolone sodium succinate, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril hydrochloride/magnesium carbonate, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (U.S. Pat. No. 6,090,382, HUMIRA™), and efalizumab.

Non-limiting examples of therapeutic agents for restenosis with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: sirolimus, paclitaxel, everolimus, tacrolimus, ABT-578, and acetaminophen.

Non-limiting examples of therapeutic agents for sciatica with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene n-pap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il)) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™).

In this invention, the following definitions are applicable:

A "therapeutically effective amount" is an amount of a compound of Formula (Ia), Formula (Ib), Formula (Ic), Formula (Id), Formula (Ie), Formula (If), Formula (Ig), Formula (Ih), Formula (Ii,r Formula (Ij), Formula (Ik) or Formula (Il) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of Formula (Ia), Formula (Ib), Formula (Ic), Formula (Id), Formula (Ie), Formula (If), Formula (Ig), Formula (Ih), Formula (Ii) or Formula (Ij) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (Ia), Formula (Ib), Formula (Ic), Formula (Id), Formula (Ie), Formula (If), Formula (Ig), Formula (Ih), Formula (Ii) or Formula (Ij) and their salts may exist in more than one crystal form and the present invention includes each crystal form and mixtures thereof.

Certain compounds of Formula (Ia), Formula (Ib), Formula (Ic), Formula (Id), Formula (Ie), Formula (If), Formula (Ig), Formula (Ih), Formula (Ii) or Formula (Ij) and their salts may also exist in the form of solvates, for example hydrates, and the present invention includes each solvate and mixtures thereof.

Certain compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) may contain one or more chiral centers, and exist in different optically active forms. When compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) and mixtures thereof.

Certain compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) may exist in different tautomeric forms or as different geometric isomers, and the present invention includes each tautomer and/or geometric isomer of compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) and mixtures thereof.

Certain compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) and mixtures thereof.

Certain compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) may exist in zwitterionic form and the present invention includes each zwitterionic form of compounds of Formula (Ia), Formula (Ib), Formula (Ic), Formula (Id), Formula (Ie), Formula (If), Formula (Ig), Formula (Ih), Formula (Ii), Formula (Ij), Formula (Ik) or Formula (Il) and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_1-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary pro-drugs release an alcohol of Formula (Ia), Formula (Ib), Formula (Ic), Formula (Id), Formula (Ie), Formula (If), Formula (Ig), Formula (Ih), Formula (Ii), Formula (Ij, Formula (Ik) or Formula (Il)) wherein the free hydrogen of the hydroxyl substituent (e.g., $R^1$ contains hydroxyl) is replaced by $(C_1-C_6)$alkanoyloxymethyl, 1-(($C_1$-$C_6$)alkanoyloxy)ethyl, 1-methyl-1-(($C_1$-$C_6$)alkanoyloxy)ethyl, $(C_1-C_{12})$alkoxycarbonyloxymethyl, N—$(C_1-C_6)$ alkoxycarbonylamino-methyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)$alkyl$)_2$ or glycosyl (the radical resulting from detachment of the hydroxyl of the hemiacetal of a carbohydrate).

As used herein, the term "bridged ($C_5$-$C_{12}$) cycloalkyl group" means a saturated or unsaturated, bicyclic or polycyclic bridged hydrocarbon group having two or three $C_3$-$C_{10}$ cycloalkyl rings. Non bridged cycloalkyls are excluded. Bridged cyclic hydrocarbon may include, such as bicyclo [2.1.1]hexyl, bicyclo[2.2.1]heptyl, bicyclo[2.2.2]octyl, bicyclo[3.2.1]octyl, bicyclo[4.3.1]decyl, bicyclo[3.3.1]nonyl, bornyl, bornenyl, norbornyl, norbornenyl, 6,6-dimethylbicyclo[3.1.1]heptyl, tricyclobutyl, and adamantyl.

As used herein the term "bridged ($C_2$-$C_{10}$) heterocyclyl" means bicyclic or polycyclic aza-bridged hydrocarbon groups and may include azanorbornyl, quinuclidinyl, isoquinuclidinyl, tropanyl, azabicyclo[3.2.1]octanyl, azabicyclo [2.2.1]heptanyl, 2-azabicyclo[3.2.1]octanyl, azabicyclo [3.2.1]octanyl, azabicyclo[3.2.2]nonanyl, azabicyclo[3.3.0] nonanyl, and azabicyclo [3.3.1]nonanyl.

The term "heterocyclic", "heterocyclyl" or "heterocyclylene", as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo [3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d]pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d]pyrrolo[2,3-b]pyridinyl, 1,6-dihydro-1,2,5,6-tetraza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b;2'3'-d]pyridinyl, 6H-3-thia-2,5,6-triaza-as-indacenyl or 1,6-dihydroimidazo[4,5-d]pyrrolo[2,3-b]pyridine.

An "heterocycloalkyl" group, as used herein, is a heterocyclic group that is linked to a compound by an aliphatic group having from one to about eight carbon atoms. For example, a heterocycloalkyl group is a morpholinomethyl group.

As used herein, "alkyl", "alkylene" or notations such as "$(C_1\text{-}C_8)$" include straight chained or branched hydrocarbons which are completely saturated. Examples of alkyls are methyl, ethyl, propyl, isopropyl, butyl, pentyl, hexyl and isomers thereof. As used herein, "alkenyl", "alkenylene", "alkynylene" and "alkynyl" means $C_2\text{-}C_8$ and includes straight chained or branched hydrocarbons which contain one or more units of unsaturation, one or more double bonds for alkenyl and one or more triple bonds for alkynyl.

As used herein, "aromatic" groups (or "aryl" or "arylene" groups) include aromatic carbocyclic ring systems (e.g. phenyl) and fused polycyclic aromatic ring systems (e.g. naphthyl, biphenyl and 1,2,3,4-tetrahydronaphthyl).

As used herein, "cycloalkyl" or "cycloalkylene" means $C_3\text{-}C_{12}$ monocyclic or multicyclic (e.g., bicyclic, tricyclic, spirocyclic, etc.) hydrocarbons that is completely saturated or has one or more unsaturated bonds but does not amount to an aromatic group. Examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: $(C_1\text{-}C_8)$alkyl groups, $(C_2\text{-}C_8)$alkenyl groups, $(C_2\text{-}C_8)$alkynyl groups, $(C_3\text{-}C_{10})$cycloalkyl groups, halogen (F, Cl, Br or I), halogenated $(C_1\text{-}C_8)$alkyl groups (for example but not limited to —$CF_3$), —O—$(C_1\text{-}C_8)$alkyl groups, —OH, —S—$(C_1\text{-}C_8)$alkyl groups, —SH, —NH$(C_1\text{-}C_8)$alkyl groups, —N($(C_1\text{-}C_8)$alkyl)$_2$ groups, —NH$_2$, —C(O)NH$_2$, —C(O)NH$(C_1\text{-}C_8)$alkyl groups, —C(O)N($(C_1\text{-}C_8)$alkyl)$_2$, —NHC(O)H, —NHC(O)$(C_1\text{-}C_8)$alkyl groups, —NHC(O)$(C_3\text{-}C_8)$cycloalkyl groups, —N($(C_1\text{-}C_8)$alkyl)C(O)H, —N($(C_1\text{-}C_8)$alkyl)C(O)$(C_1\text{-}C_8)$alkyl groups, —NHC(O)NH$_2$, —NHC(O)NH$(C_1\text{-}C_8)$alkyl groups, —N($(C_1\text{-}C_8)$alkyl)C(O)NH$_2$ groups, —NHC(O)N($(C_1\text{-}C_8)$alkyl)$_2$ groups, —N($(C_1\text{-}C_8)$alkyl)C(O)N($(C_1\text{-}C_8)$alkyl)$_2$ groups, —N($(C_1\text{-}C_8)$alkyl)C(O)NH($(C_1\text{-}C_8)$alkyl), —C(O)H, —C(O)$(C_1\text{-}C_8)$alkyl groups, —CN, —NO$_2$, —S(O)$(C_1\text{-}C_8)$alkyl groups, —S(O)$_2$$(C_1\text{-}C_8)$alkyl groups, —S(O)$_2$N($(C_1\text{-}C_8)$alkyl)$_2$ groups, —S(O)$_2$NH$(C_1\text{-}C_8)$alkyl groups, —S(O)$_2$NH$(C_3\text{-}C_8)$cycloalkyl groups, —S(O)$_2$NH$_2$ groups, —NHS(O)$_2$$(C_1\text{-}C_8)$ alkyl groups, —N($(C_1\text{-}C_8)$alkyl)S(O)$_2$$(C_1\text{-}C_8)$alkyl groups, —$(C_1\text{-}C_8)$alkyl-O—$(C_1\text{-}C_8)$alkyl groups, —O—$(C_1\text{-}C_8)$alkyl-O—$(C_1\text{-}C_8)$alkyl groups, —C(O)OH, —C(O)O$(C_1\text{-}C_8)$alkyl groups, NHOH, NHO$(C_1\text{-}C_8)$alkyl groups, —O-halogenated $(C_1\text{-}C_8)$alkyl groups (for example but not limited to —OCF$_3$), —S(O)$_2$-halogenated $(C_1\text{-}C_8)$alkyl groups (for example but not limited to —S(O)$_2$CF$_3$), —S-halogenated $(C_1\text{-}C_8)$alkyl groups (for example but not limited to —SCF$_3$), —$(C_1\text{-}C_6)$ heterocycle (for example but not limited to pyrrolidine, tetrahydrofuran, pyran or morpholine), —$(C_1\text{-}C_6)$ heteroaryl (for example but not limited to tetrazole, imidazole, furan, pyrazine or pyrazole), -phenyl, —NHC(O)O—$(C_1\text{-}C_6)$alkyl groups, —N($(C_1\text{-}C_6)$alkyl)C(O)O—$(C_1\text{-}C_6)$alkyl groups, —C(=NH)—$(C_1\text{-}C_6)$alkyl groups, —C(=NOH)—$(C_1\text{-}C_6)$alkyl groups, or —C(=N—O—$(C_1\text{-}C_6)$alkyl)-$(C_1\text{-}C_6)$alkyl groups.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (e.g., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see e.g. Fingl et al., 1975, in "The Pharmacological Basis of Therapeutics", Ch. 1 p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

Parts by Weight

| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (Ia), Formula (Ib), Formula (Ic), Formula (Id), Formula (Ie), Formula (If), Formula (Ig), Formula (Ih), Formula (Ii) or Formula (Ij) as a medicament.

A further aspect of the present invention provides the use of a compound of Formula (Ia), Formula (Ib), Formula (Ic), Formula (Id), Formula (Ie), Formula (If), Formula (Ig), Formula (Ih), Formula (Ii) or Formula (Ij) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (Ia), Formula (Ib), Formula (Ic), Formula (Id), Formula (Ie), Formula (If), Formula (Ig), Formula (Ih), Formula (Ii) or Formula (Ij) to a mammal, particularly a human being, in need thereof.

ABBREVIATIONS aa Amino acids
AcCl Acetyl chloride
AcOH Acetic acid
$Ac_2O$ Acetic anhydride
ATP Adenosine triphosphate
Boc t-Butoxycarbonyl
Boc ON (2-(tert-Butoxycarbonyloxyimino)-2-phenylacetonitrile)
Boc-azide (tert-Butoxycarbonyl azide)
Boc-OSu (tert-Butyl N-succinimidyl carbonate)
$Boc_2O$ di-tert-butyl dicarbonate
BOP—Cl Bis(2-oxo-3-oxazolidinyl)phosphinic chloride
n-BuOH 1-Butanol
t-BuOH tert-Butanol
BSA Bovine serum albumin
n-BuLi n-Butyllithium
sec-BuLi sec-Butyllithium
t-BuLi tert-Butyllithium
Cbz Carboxybenzyl
CDI 1,1'-Carbonyldiimidazole
CT Computed tomography
CyPFt-Bu 1-Dicyclohexylphosphino-2-di-tert-butylphosphinoethylferrocene
d Doublet
dba Dibenzylideneacetone
DBU 1,8-Diazabicyclo[5.4.0]Umdec-7-ene
DCC Dicyclohexylcarbodiimide
DCE 1,2-Dichloroethane
DCI N,N'-Diisopropylcarbodiimide
DCM Dichloromethane (methylene chloride)
dd Doublet of doublets
DDQ 2,3-dichloro-5,6-dicyano-p-benzoquinone
DIAD Diisopropyl azodicarboxylate
DIBAL-H Diisobutylaluminium hydride
DIEA N,N-Diisopropylethylamine
DMA Dimethylacetamide
DMAP 4-(N,N-Dimethylamino)pyridine
DME 1,2-Dimethoxyethane
DMEM Dulbecco's Modified Eagle Medium
DMF N,N-Dimethylformamide
DMSO Dimethyl sulfoxide
DNP-HSA Dinitrophenyl-human serum albumin
D-PBS Dulbecco's phosphate buffered saline
DTT Dithiothreitol
dppf 1,1'-Bis(diphenylphosphino)ferrocene
EDC.HCl N-(3-Dimethylaminopropyl)-N'-ethylcarbodiimide hydrochloride
EDTA Ethylene diamine tetraacetic acid
EGTA Ethylene glycol tetraacetic acid
EPO Erythropoetin
equiv Equivalent(s)
EtI Iodoethane
$Et_2NH$ Diethylamine
EtOAc Ethyl acetate
$Et_2O$ Diethyl ether
EtOH Ethanol
FBS Fetal bovine serum
FLAG DYKDDDDK peptide sequence
Fmoc Fluorenylmethyloxycarbonyl
Fmoc-Cl (9H-fluoren-9-yl)methyl carbonochloridate
FMOC-OSu (9H-fluoren-9-yl)methyl 2,5-dioxopyrrolidin-1-yl carbonate
g Gram(s)
GM-CSF Granulocyte-macrophage colony-stimulating factor
GST Glutathione S-transferase
h Hour(s)
HATU O-(7-Azabenzotriazol-1-yl)-N,N,N',N'-tetramethyluronium hexafluorophosphate
HBSS Hanks buffered salt solution
HEPES N-2-Hydroxyethylpiperazine-N'-2-ethanesulfonic acid
HOBt Hydroxybenzotriazole
HPLC High-pressure liquid chromatography
HPMC Hydroxypropyl methylcellulose
IBCF Isobutylchloroformate
i.d. Intradermal
IFA Incomplete Freunds Adjuvant
IPA Isopropyl alcohol KOAc Potassium acetate
KOt-Bu Potassium tert-butoxide
LC/MS Liquid chromatography/mass spectrometry
LDA Lithium diisopropylamide
LHMDS Lithium bis(trimethylsilyl)amide
m Multiplet
M Molar
MeCN Acetonitrile
Met Iodomethane
MeMgBr Methylmagnesium bromide
MeMgCl Methylmagnesium chloride
MeOH Methyl alcohol
min Minute(s)
mmol Millimole
MOPS 3-(N-Morpholino)-2-hydroxypropanesulfonic acid
MOPSO 3-(N-Morpholino)-propanesulfonic acid
MS Mass spectrometry
MsCl Methanesulfonyl chloride
MUG 4-Methylumbellifery N-acetyl-β-D-glucosaminide
n- Normal (nonbranched)
N Normal
NaBH(OAc)$_3$ Sodium triacetoxyborohydride
Na(CN)BH$_3$ Sodium cyanoborohydride
NaH Sodium hydride
NaOt-Bu Sodium tert-butoxide
NH$_4$OAc Ammonium acetate
NBS N-Bromosuccinimide
NCS N-Chlorosuccinimide
NIS N-Iodosuccinimide
NMM N-Methylmorpholine
NMO N-Methylmorpholine N-oxide
NMP N-methylpyrrolidinone
NMR Nuclear magnetic resonance
OD Optical density
or Optical rotation
OVA Ovalbumin
PBS Phosphate buffered saline
PdCl$_2$(PPh$_3$)$_2$ Bis(triphenylphosphine)palladium(II) dichloride
Pd$_2$dba$_3$ Tris(dibenzylideneacetone)dipalladium(0)
Pd(OAc)$_2$ Palladium(II) acetate
Pd(PPh$_3$)$_4$ Tetrakis(triphenylphosphine)palladium(0)
pH −log [H$^+$]
pNAG Nitrophenyl-N-acetyl-β-D-glucosaminide
PPh$_3$ Triphenylphosphine
ppm Parts per million
i-PrMgBr iso-Propylmagnesium Bromide
PrOH n-Propanol
i-PrOH iso-Propanol
n-PrOH n-Propanol
psi Pounds per square inch
Rac Racemic
rcf Relative centrifugal force
RP-HPLC Reverse-phase high-pressure liquid chromatography
RPM Revolutions per minute
R$_t$ Retention time
rt Room temperature
s Singlet
SEM 2-(Trimethylsilyl)ethoxymethyl
SFC Supercritical fluid chromatography
SLM Standard liters per minute
t Triplet
t- Tertiary
TBAF Tetra-n-butylammonium fluoride
TBDMSOTf tert-Butyldimethylsilyl trifluoromethanesulfonate
TEA Triethylamine
tert- Tertiary
tert-Butyl X-Phos 2-Di-tert-butylphosphino-2',4',6'-triisopropylbiphenyl
TFA Trifluoroacetic acid
TFAA Trifluoracetic anhydride
THF Tetrahydrofuran
TIPS Triisopropylsilyl
TLC Thin layer chromatography
TMS Trimethylsilyl
Ts p-Toluenesulfonyl
TsCl p-Toluenesulfonyl chloride
TsOH p-Toluenesulfonic acid
USP United States Pharmacopeia
UV Ultraviolet
wt % Weight percent
Xantphos 4,5-Bis(diphenylphosphino)-9,9-dimethylxanthene
X-Phos 2-Dicyclohexylphosphino-2',4',6'-triisopropylbiphenyl Assays In Vitro Syk Kinase Activity Measured by Time-Resolved Fluorescence Resonance Energy Transfer (trFRET)

0.14 nM purified Syk catalytic domain (aa 356-635 with a C-terminal His-tag purified in-house by immobilized metal ion affinity chromatography) was mixed with 0.2 μM peptide substrate (biotin-TYR1, Sequence: Biotin-(Ahx)-GAEEE-IYAAFFA-COOH) at varying inhibitor concentrations in reaction buffer: 50 mM MOPSO pH 6.5, 10 mM MgCl$_2$, 2 mM MnCl$_2$, 2.5 mM DTT, 0.01% BSA, 0.1 mM Na$_3$VO$_4$ and 0.001 mM ATP. After about 60 min incubation at rt, the reaction was quenched by addition of EDTA (final concentration: 100 mM) and developed by addition of revelation reagents (final approximate concentrations: 30 mM HEPES pH 7.0, 0.06% BSA, 0.006% Tween-20, 0.24 M KF, 80 ng/mL PT66K (europium labeled anti-phosphotyrosine antibody cat #61T66KLB Cisbio, Bedford, Mass.) and 0.6 μg/mL SAXL (Phycolink streptavidin-allophycocyanin acceptor, cat #PJ255, Prozyme, San Leandro, Calif.). The developed reaction was incubated in the dark either at about 4° C. for about 14 h or for about 60 min at rt, then read via a time-resolved fluorescence detector (Rubystar, BMG) using a 337 nm laser for excitation and monitoring emission wavelengths at 665 nm. Within the linear range of the assay, the observed signal at 665 nm was directly related to phosphorylated product and can be used to calculate the IC$_{50}$ values. For the purpose of the Tables and Examples below, the Syk IC$_{50}$ of each compound, which can be determined using the assay method described herein using the Syk catalytic domain (aa 356-635 with a C-terminal His-tag purified in-house by immobilized metal ion affinity chromatography), is expressed as follows; A=a compound with a Syk IC$_{50}$ less than 0.1 μM, B=a compound with a Syk IC$_{50}$ within the range of 0.1 to 1.0 μM, C=a compound with a Syk IC$_{50}$ within the range of 1.0 to 10.0 μM and D=a compound with a Syk IC$_{50}$ greater than 10 μM.

Purchased Syk full-length enzyme (Millipore cat #14-314; more details in Table 1) was also used to evaluate enzyme potency. Additional kinase assays used to assess selectivity were performed using a similar protocol (see Table 1). Additional purified enzymes Jak1 enzyme (aa 845-1142; expressed as a GST fusion and purified by glutathione affinity chromatography); Jak3 enzyme (aa 811-1103; expressed as a GST fusion and purified by glutathione affinity chromatography); Lck (aa 62-509; purified in-house by DEAE ion-exchange and ATP-sepharose affinity chromatography), and ITK (aa 354-620 with His tag, purified in-house by immobilized metal ion affinity and mono Q ion exchange chromatography) were expressed in SF9 cells. Other enzymes used are available from commercial sources. Enzymes were mixed with biotinylated substrates at varying concentrations of inhibitor in different reaction buffers (see Table 1). After about 60 min incubation at rt, the reaction was quenched by addition of EDTA and developed by addition of revelation reagents (final approximate concentrations: 30 mM HEPES pH 7.0, 0.06% BSA, 0.006% Tween-20, 0.24 M KF, varying amounts of donor europium labeled antibodies and acceptor streptavidin labeled allophycocyanin (SAXL)). The developed reactions were incubated in the dark at about 4° C. for about 14 h or for about 60 min at rt, then read in a time-resolved fluorescence detector (Rubystar, BMG Labtech) as described above.

MOPS buffer contains: 20 mM MOPS pH 7.2, 10 mM $MgCl_2$, 5 mM EGTA, 5 mM Beta-phosphoglycerol, 1 mM $Na_3VO_4$, 0.01% Triton-X-100 and 1 mM DTT Substrates:
Biotin-TYR1-peptide sequence: Biotin-(Ahx)-GAEEE-IYAAFFA-COOH
Biotin-TYR2-peptide sequence: Biotin-(Ahx)-AEEEYF-FLFA-amide
KinEASE S1 peptides were purchased from Cisbio (cat #62STOPEB, Bedford, Mass.)

Detection Reagents:
PT66K was purchased from Cisbio (cat #61T66KLB, Bedford, Mass.)
EuSTK was purchased from Cisbio (cat #62STOPEB, Bedford, Mass.)

TABLE 1

Specific conditions (per 40 μL enzyme reaction) for the various enzymes are detailed below:

| Enzyme | Construct | Substrate | Assay Buffer | Enzyme Conc. (ng/well) | Substrate Conc. | ATP Conc. (mM) | DMSO Conc. (%) | Reaction Time (min) | Detection condition |
|---|---|---|---|---|---|---|---|---|---|
| Jak1 | aa 845-1142 | Biotin-TYR2 | MOPSO | 5 | 2 μM | 0.1 | 5 | 60 | 10 ng/well PT66K, 0.39 μg/well SAXL |
| Jak2 | Millipore cat# 14-640 | Biotin-TYR1 | MOPSO | 5 | 2 μM | 0.1 | 5 | 60 | 8 ng/well PT66K, 0.078 μg/well SAXL |
| Jak3 | aa 811-1103 | Biotin-TYR2 | MOPSO | 0.5 | 2 μM | 0.1 | 5 | 60 | 8 ng/well PT66K, 0.078 μg/well SAXL |
| MARK2/ EMK | Invitrogen cat# 3878 | KinEASE S1 | MOPS | 0.4 | 1 μM | 0.01 | 5 | 60 | 15 ng/well EuSTK, 0.34 μg/well SAXL |
| ITK | aa354-620 | Biotin-TYR1 | MOPSO | 25 | 4 μM | 0.01 | 5 | 60 | 10 ng/well PT66K, 0.078 μg/well SAXL |
| Lck | aa 62-509 | Biotin-TYR1 | MOPSO | 2.1 | 4 μM | 0.01 | 5 | 60 | 10 ng/well PT66K, 0.078 μg/well SAXL |
| Syk (catalytic domain) | aa 356-635 | Biotin-TYR1 | MOPSO | 0.2 | 0.2 μM | 0.001 | 5 | 60 | 10 ng/well PT66K, 0.078 μg/well SAXL |
| Syk (full-length) | Millipore cat #14-314 | Biotin-TYR1 | MOPSO | 3 | 0.1 μM | 0.01 | 5 | 60 | 11.3 ng/well PT66K, 0.075 μg/well SAXL |

Reaction Buffers:
MOPSO buffer contains: 50 mM MOPSO pH 6.5, 10 mM $MgCl_2$, 2 mM $MnCl_2$, 2.5 mM DTT, 0.01% BSA, and 0.1 mM $Na_3VO_4$
HEPES buffer contains: 50 mM HEPES pH 7.1, 2.5 mM DTT, 10 mM $MgCl_2$, 2 mM $MnCl_2$, 0.01% BSA, and 0.1 mM $Na_3VO_4$ SAXL was purchased from Prozyme (cat #PJ25S, San Leandro, Calif.)

Human T-Blasts IL-2 pSTAT5 Cellular Assay

Materials:
Phytohemaglutinin T-blasts were prepared from Leukopacks purchased from Biological Specialty Corporation, Colmar, Pa. 18915, and cryopreserved in 5% DMSO/media prior to assay. For this assay the cells were thawed in assay medium with the following composition: RPMI 1640 medium (Gibco 11875093) with 2 mM L-glutamine (Gibco 25030-081), 10 mM HEPES (Gibco 15630-080), 100 µg/mL Pen/Strep (Gibco 15140-122), and 10% heat inactivated FBS (Gibco 10438026). Other materials used in the assay: DMSO (Sigma D2650), 96-well dilution plates (polypropylene) (Corning 3365), 384-well assay plates (grey, ½ area, 96 well) (PerkinElmer 6005350), D-PBS (Gibco 14040133), IL-2 (R&D 202-IL-10 (10 µg)), Alphascreen pSTAT5 kit (Perkin Elmer TGRS5S10K) and Alphascreen protein A kit (Perkin Elmer 6760617M).

Methods:

T-Blasts were thawed and cultured for about 3 days in media with IL-2 and then for an additional 24 h in media without IL-2 prior to assay. Test compounds or controls were dissolved and serially diluted in 100% DMSO. DMSO stocks were subsequently diluted 1:50 in cell culture media to create the 4× compound stocks (containing 2% DMSO). Cells were plated in 384 well grey plates at $1\times10^5/5$ µL/well in 2.5 µL media followed by addition of 5 µL of 4× test compound in duplicate. Cells were incubated with compound for about 0.5 h at about 37° C. Next, 2.5 µL of IL-2 stock was added at 20 ng/mL final concentration. IL-2 was stored as a 10 µg/mL stock solution, as specified by the manufacturer, at about −20° C. in aliquots and diluted 1:50 with assay media (to 80 ng/mL) just prior to use. The contents of the wells were mixed by carefully tapping sides of plate(s) several times followed by incubation at about 37° C. for about 20 min. The assay was terminated by adding 2.5 ut of 5× AlphaScreen lysis buffer and shaking on an orbital shaker for about 10 min at rt. AlphaScreen acceptor bead mix and donor bead mix were reconstituted following Perkin Elmer's protocol. A mixture of equal volumes of the acceptor beads and donor beads was prepared and 21 µL/well of mixed beads was added to the assay plates. The plates were covered with foil then shaken on orbital shaker for about 16 h on low at about 25° C. Plates were read on an EnVision reader following Perkin Elmer's AlphaScreen protocol instructions with excitation=680 nm, emmission=570 nm. Within the linear range of the assay, the observed signal at 570 nm was directly related to pSTAT5 concentration and can be used to calculate the $IC_{50}$ values.

TF-1 IL-6 pSTAT3 Cellular Assay

Materials:

TF-1 cells (ATCC #CRL-2003). Culture medium: RPMI medium (Gibco 21870) with 2 mM L-glutamine (Gibco 25030-081), 10 mM HEPES (Gibco 15630-080), 100 µg/mL Pen/Strep (Gibco 15140-122), 10% heat inactivated FBS (Gibco 10437-028), and 2 ng/mL GM-CSF (R&D 215-GM-010). Other materials used in this assay: DMSO (Sigma D2650), 96-well dilution plates (polypropylene) (Corning 3365), 384-well assay plates (grey, ½ area, 96 well) (Perkin Elmer 6005350), D-PBS (Gibco 14040133), IL-6 (R&D 206-IL/CF-050 (50 µg)), AlphaScreen pSTAT3 kit (Perkin Elmer TGRS3S10K) and AlphaScreen protein A kit (Perkin Elmer 6760617M).

Methods:

Prior to the assay, cells were cultured for about 18 h in the culture medium without GM-CSF. Test compounds or controls were dissolved and serially diluted in 100% DMSO. DMSO stocks were subsequently diluted 1:50 in cell culture media to create the 4× compound stocks (containing 2% DMSO). Cells were plated in 3384 well grey plates at $1\times10^7/5$ µL/well in 5 µL media followed by addition of 2.5 µL of the 4× test compound stock in duplicate. Cells were incubated with compound for about 0.5 h at about 37° C. followed by addition of 2.5 µL of 400 ng/mL IL-6. IL-6 was stored in 10 ng/mL aliquots using endotoxin free D-PBS (0.1% BSA) at about −20° C. Prior to the assay, IL-6 was diluted to 400 ng/mL in culture media and applied (2.5 µL/well) to all wells, except to negative control wells where 2.5 µL/well of media is added. The contents of the wells were mixed carefully by tapping the side of the plate several times. Plates were incubated at about 37° C. for about 30 min. Cells were lysed by adding 2.5 µL of 5× AlphaScreen cell lysis buffer to all wells, shaken for about 10 min at rt then assayed. Alternatively, assay plates were frozen at about −80° C. and thawed later at P. Using the pSTAT3 SureFire Assay kit (Perkin Elmer #TGRS3S10K), AlphaScreen acceptor bead mix and donor bead mix were reconstituted following Perkin Elmer's protocol. A mixture of equal volumes of the acceptor beads and donor beads was prepared and 21 µL/well of mixed beads was added to the assay plates. The plates were covered with foil then shaken on an orbital shaker for about 16 h on low at about 25° C. Plates were read on an EnVision reader following Perkin Elmer's AlphaScreen protocol instructions with excitation=680 nm, emission=570 nm. Within the linear range of the assay, the observed signal at 570 nm was directly related to pSTAT3 concentration and can be used to calculate the $IC_{50}$ values.

UT7/EPO pSTAT5 Cellular Assay

Materials:

UT7/EPO cells were passaged with erythropoietin (EPO), split twice per week and fresh culture medium was thawed and added at time of split. Culture Medium: DMEM medium (Gibco 11960-044) with 2 mM L-glutamine (Gibco 25030-081), 10 mM HEPES (Gibco 15630-080), 100 U/mL Pen/Strep (Gibco 15140-122), 10% heat inactivated FBS (Gibco 10437-028), EPO (5 µL/mL=7.1 µL of a 7 µg/mL stock per mL of medium). Assay media: DMEM, 2 mM L-glutamine, 5% FBS, 10 mM HEPES. Other materials used in the assay: DMSO (Sigma D2650), 96-well dilution plates (polypropylene) (Corning 3365), 96-well assay plates (white, ½ area, 96 well) (Corning 3642), D-PBS (Gibco 14040133), IL-2 (R&D 202-IL-10 (10 µg)), AlphaScreen pSTAT5 kit (Perkin Elmer TGRS5S10K) and AlphaScreen protein A kit (Perkin Elmer 6760617M)

Methods:

Cells were cultured for about 16 h without EPO prior to running assay. Test compounds or controls were dissolved and serially diluted in 100% DMSO. DMSO stocks were subsequently diluted 1:50 in cell culture media to create the 4× compound stocks (containing 2% DMSO). Using a Corning white 96 well, ½ area plate, cells were plated at $2\times10^5/10$ µL/well in 10 µL media followed by addition of 5 µL of 4× test compound stock in duplicate. Cells were incubated with compound for about 0.5 h at about 37° C. After incubation, 5 µL of EPO was added to afford a final concentration of 1 nM EPO. The contents of the wells were mixed by carefully tapping sides of the plate several times followed by incubation at about 37° C. for about 20 min. 5 ut of 5× AlphaScreen lysis buffer were added followed by shaking on an orbital shaker for about 10 min at rt. 30 µL/well of acceptor beads were added after reconstitution following Perkin Elmer's AlphaScreen protocol, covered with foil and shaken on an orbital shaker for about 2 min on high, then about 2 h on low. Donor beads were reconstituted following Perkin Elmer's AlphaScreen protocol instructions followed by addition of 12 µL/well, covered with foil and shaken on an orbital shaker for about 2 min on high, about 2 h on low. Plates were read on an EnVision reader following Perkin Elmer's AlphaScreen protocol instructions with excitation=680 nm, emmission=570 nm. Within the linear range of the assay, the observed signal at 570 nm was directly related to pSTAT5 concentration and can be used to calculate the $IC_{50}$ values.

Antigen-Induced Degranulation of RBL-2H₃ Cells:

RBL-2H3 cells were maintained in T75 flasks at about 37° C. and 5% $CO_2$, and passaged every 3-4 days. To harvest cells, 20 mL of PBS was used to rinse the flask once, and then 3 mL of Trypsin-EDTA was added and incubated at about 37° C. for about 2 min. Cells were transferred to a tube with 20 mL medium, spun down at 1000 RPM at rt for about 5 min and resuspended at $1 \times 10^6$ cells/mL. Cells were sensitized by adding DNP-specific mouse IgE (Sigma #D8406) to a final concentration of 0.1 µg/mL. 50 ut of cells were added to each well of a 96 well flat bottom plate ($50 \times 10^3$ cells/well) and incubated overnight at about 37° C. in 5% $CO_2$. The next day, compounds were prepared in 100% DMSO at 10 mM. Each compound was then serially diluted 1:4 six times in 100% DMSO. Each compound dilution was then diluted 1:20 and then 1:25, both dilutions in Tyrode's buffer (HBSS with Ca++ and Mg++ (Gibco #14025)+20 mM Hepes (Gibco #15630)+0.2 mg/mL BSA (Sigma #8527,)+5.6 mM glucose (Sigma G8270). Media was aspirated from the cell plates and the cells were rinsed twice with 100 µL of Tyrode's buffer (prewarmed to about 37° C.). 50 ut of compounds diluted in Tyrode's buffer were added to each well and the plates were incubated for about 15 min at about 37° C. in 5% $CO_2$. 50 µL of 0.2 µg/mL DNP-HSA (Bioresearch Technologies, Inc. #D-5059-100) in Tyrode's buffer was then added to each well and the plates were incubated for about 30 min at about 37° C. in 5% $CO_2$. The final concentration of the various components in the incubation mix are 0.002-10 µM compounds, 0.1% DMSO, and 0.1 µg/mL DNP-HSA. As one control, Tyrode's buffer with DNP-HSA was added to a set of wells containing 0.2% DMSO without compounds to determine maximum stimulated release. As a second control, Tyrode's buffer without DNP-HSA was added to a set of wells containing 0.2% DMSO without compounds to determine unstimulated release. At the end of the 30 min incubation, 100 µL of freshly prepared 1 mM 4-methylumbelliferyl N-acetyl-β-D-glucosaminide (MUG; Sigma #M2133) was then added to each well and the plates are incubated for about 45 min at about 37° C. in 5% $CO_2$. The plates were then read on an EnVision plate reader with excitation=355 nm, emission=460 nm. Within the linear range of the assay, the observed signal at 460 nm was directly related to MUG reaction product production and can be used to calculate the $IC_{50}$ values.

Ramos Calcium Flux Cellular Assay

Materials:

Ramos cells (ATCC # CRL-1596) were grown in RPMI medium (Invitrogen #21870-075) supplemented with 10% heat-inactivated FBS (Invitrogen #10438-026) and 1% Pen/Strep (Invitrogen #15140-122). Assay Buffer: HB SS (Invitrogen: #14025-092) with 40 mM Hepes (Invitrogen #15630-080), 0.1% Bovine Serum Albumin (BSA) (30%, Sigma #A8577), 2.5 mM Probenecid (Invitrogen #P36400) and 10 mM Glucose (Sigma #G-7528). Other materials used in this assay: Flou-4-AM dye (Invitrogen #F14201), Pluronic F-127 (Calbiochem #540025), and Donkey anti-human IgM Affinity Purified Fab2 (Jackson ImmunoResearch Laboratories #709-006-073).

Methods:

Cells were seeded at $5 \times 10^5$ cells per mL in culture medium 16-18 hours before assay. Day of assay, cell were centrifuged at 1000 rpm for 5 minutes, resuspended in culture medium and counted. Appropriate volume of cell suspension was centrifuged and set at a concentration of $2 \times 10^6$ cells/mL in assay buffer. Flou-4-AM dye was prepared by adding 25 uL of DMSO and 50 uL of Pluronic F-127 per vial of dye (1 vial of dye per 10 mLs of assay buffer containing cells). Cells were incubated in calcium dye for 1 hour at 37° C. and 5% $CO_2$. After incubation, cells were centrifuged at 1000 rpm for 5 minutes followed by aspiration of the dye buffer. Cell pellet was washed two times in assay buffer (without dye). After washes, pellet was resuspended with assay buffer to about $2 \times 10^6$ cells/mL. 100 uL of cell suspension was seeded into assay plates followed by a 30 minute incubation at room temperature to allow the cells to settle. 50 uL of 4× compound stock was transferred to the cell plate (0.5% final DMSO) and read for calcium flux (Excitation wavelength: 470/495 nm, Emission wave length: 515/575 nm, $1^{st}$ read interval: 1 second, # of reads: 60, # of reads before dispensing: 10, $2^{nd}$ interval read: 6 seconds, # of reads: 30). Cells were incubated with compounds for 30 minutes at room temperature after which 5OuL of 4× anti-IgM stimulus was added to cells (6 ug/mL final) and read for calcium flux (Excitation wavelength: 470/495 nm, Emission wave length: 515/575 nm, $1^{st}$ read interval: 2 second, # of reads: 60, # of reads before dispensing: 10, $2^{nd}$ interval read: 6 seconds, # of reads: 80). IC50s calculated based on inhibition of anti-IgM induced calcium flux Acute in vivo measurement of Fcγ receptor signaling inhibition of the compounds is measured using the:

Reverse Passive Arthus Model

On day 0, OVA was made up at a concentration of 17 mg/mL, in PBS by rocking gently until a solution was formed. 2% Evans Blue solution (Sigma Aldrich, cat #E2129) was then added to double the volume for a final concentration of 8.5 mg/mL of OVA and 1% Evans Blue dye. Anti-OVA antibody (Abazyme), stock concentration 10 mg/mL, was thawed and a 4 mg/mL solution was made with PBS. Compounds were made up in 0.5% HPMC with 0.02% Tween 80, and vortexed for about 15 seconds followed by homogenization for a minimum of about 2 min at 28,000 RPM until there was a fine particulate suspension with no aggregation. Rats were weighed and dosed with compound at a pre-determined time based on compound $T_{max}$ determined in pharmacokinetic studies. Animals were then placed under general anesthesia with a 5% isoflourane and oxygen mixture and shaved. Using a 0.5 cc insulin syringe two sites were injected i.d., 1 site with 100 µL of 4.0 mg/mL of anti-OVA antibody, and 1 site with 100 µL of sterile PBS. Each injection site was circled with a permanent marker to mark the site. Immediately following i.d. injections, animals were injected with 200 µL of the OVA (10 mg/kg)/1% Evans Blue mixture, i.v., using a 0.5 cc insulin syringe. About 4 h post injection animals were euthanized, bled via cardiac puncture and blood was put into plasma separation tubes. Blood samples were stored on ice until centrifugation (within about 2 h of collection). Each injection site was removed with a disposable biopsy punch (Acuderm Acu-Punch Disposable 12 mm), cut into four pieces and placed in a pre-labeled 2 mL eppendorf tube. One mL of DMF (99%) was added to each biopsy tube and they were placed in a heat block at about 50° C. for about 24 h. After incubation, 100 µL of each sample was transferred to a 96 well flat bottom plate and read at 620 nm on a plate reader using the Softmax software. Background was removed by subtracting the OD from the PBS injected site from the OD of the anti-OVA injected site for each individual animal. Plasma samples were spun down in a microcentrifuge (Eppendorf 5415R) for about 5 min at 16.1 rcf. 200 µL of plasma was placed in a 1.7 mL eppendorf tube for drug level measurements and tubes were stored at about −80° C. until evaluation.

Collagen Induced Arthritis (CIA)

Type II Collagen (CII), derived from bovine nasal septum (Elastin Products, cat #CN276) was solubilized in 0.01 M AcOH (150 ut AcOH USP grade, J. T. Baker, order#9522-03, and 250 mL Milli Q Water) to give a concentration of 4 mg/mL. The vial was covered with aluminum foil and placed on a rocker at about 4° C. overnight. The collagen stock solution was diluted 1:1 with incomplete Freunds adjuvant (IFA) (Difco labs, cat #263910) and an emulsion was made in glass Hamilton luer lock syringes (SGE Syringe Perfection VWR cat #007230), to a final concentration of 2 mg/mL. Female Lewis rats, weighing approximately 150 g, (Charles River Laboratories) were anesthetized in an anesthesia chamber using isoflurane (5%) and oxygen. Anesthesia was maintained using a nose cone during the injections. Rats were shaved at the base of the tail and 600 μg of collagen was delivered in three 100 μL i.d. injections on the rump of the rat (n=9 per group). A negative control group was immunized with a 1:1 emulsion of 0.01 M AcOH and IFA (n=6). Animals were boosted on day 6 of the study in the same manner as the immunization. Compound dosing began 10 days after the initial immunization when first signs of disease were observed. Compounds were formulated in an inert vehicle such as 0.5% HPMC (Sigma, cat #H3785)/0.02% Tween 80 (Sigma, cat #4780) in water) and dosed orally once or twice a day for at least 9 days. Baseline paw volume was taken on day 7, prior to disease onset, using a water displacement pleythsmograph (Vgo Basile North America Inc. PA 19473, Model #7140). Rats were lightly anesthetized with an inhalant anesthetic (isoflurane) and both hind paws were dipped into the plethysmograph and the paw volume was recorded. The rats were scored 3 times a week from day 10-18 after immunization. On day 18 after immunization, all rats were exsanguinated by cardiac puncture under isoflurane anesthesia, and the hind paws were collected to assess the impact on bone erosion using micro-CT scans (SCANCO Medical, Southeastern, PA, Model #μCT 40) at a voxel size of 18 μm, a threshold of 400, sigma-gauss 0.8, support-gauss 1.0. Bone volume and density was determined for a 360 μm (200 slice) vertical section encompassing the tarsal section of the paw. The 360 μm section was analyzed from the base of the metatarsals to the top of the tibia, with the lower reference point fixed at the tibiotalar junction. Drug exposure was determined from plasma using LC/MS.

The teachings of all references, including journal articles, patents and published patent applications, are incorporated herein by reference in their entirety.

The following examples are for illustrative purposes and are not to be construed as limiting the scope of the present invention.

General Synthetic Schemes

Compounds of the invention may be prepared using the synthetic transformations illustrated in Schemes I-XVI. Starting materials are commercially available, may be prepared by the procedures described herein, by literature procedures, or by procedures that would be well known to one skilled in the art of organic chemistry.

The General Procedure used is designated its bolded capital letter (e.g. A for General Procedure A).

The numbering of ring fused systems used throughout the General Synthetic Schemes (I-XVI) as assigned according to the CambridgeSoft® ChemDraw Ultra 9.0.7 conventions. See FIG. 1 for some non-limiting examples.

Figure 1

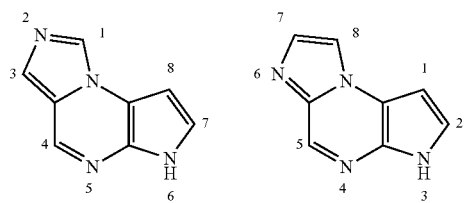

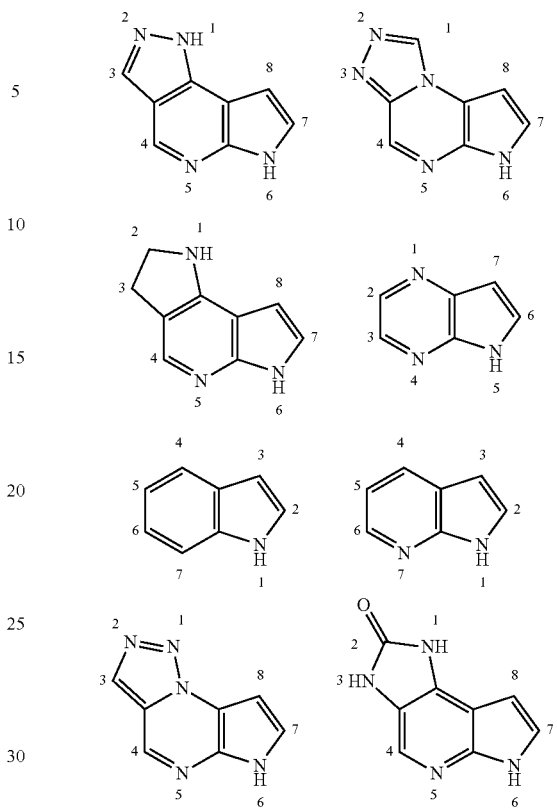

Methods for preparing 2-bromo-5-((2-(trimethylsilyl)ethoxy)methyl)-5H-pyrrolo[2,3-b]pyrazine compounds 5 and 7 of the invention are illustrated in Scheme I. The 2-bromo-5-((2-(trimethylsilyl)ethoxy)methyl)-5H-pyrrolo[2,3-b]pyrazine compounds 5 and 7 are substituted at the 6-position with an $R_1$ substituent and may be optionally substituted at the 7-position with an $R_2$ substituent and/or the 3-position with an $R_5$ substituent. Therefore, $R_2$ and/or $R_5$ can either be hydrogen (for compounds 5) or a substituent (for compounds 7) in Schemes I-III as well as Schemes VI and IX. In Scheme I, 3,5-dibromopyrazin-2-amines 1 may be reacted with terminal alkynes 2 via a Sonogashira coupling (Scheme I, step a) as described by A to give alkyne compounds 3 (for example, Sonogashira, K. et al Tetrahedron Lett., 1975, 4467). The 3,5-dibromopyrazin-2-amines 1 can be obtained from commercial sources or prepared by on skilled in the art (for example, see WO 2008/083070, Example 29, Part B). The terminal alkynes 2 are either commercially available or can be prepared by a method known to one skilled in the art (for example, Heravi, M. et al Tetrahedron 2009, 65, 7761 and Larock, R. C. "Comprehensive Organic Transformations: A Guide to Functional Group Preparations, $2^{nd}$ edition", 1999, Wiley-VCH), or by performing a Sonogashira coupling using an aryl halide with trimethylsilylacetylene as described by A followed by a desilylation as described by Q. The alkynes 3 can then be cyclized to 2-bromo-5H-pyrrolo[2,3-b]pyrazines 4 (Scheme I, step b) using methods known to one skilled in the art, for example with a base as described by B. At this point the 2-bromo-5H-pyrrolo[2,3-b]pyrazines 4 may be protected at the 5-position (Scheme I, step c), by a trimethylsilylethoxymethyl using C for instance or by methods known to one skilled in the art (for example, Larock, R. C. [referenced above] or Greene, T. W. and Wuts, P. G. M. "Protective Groups in Organic Synthesis, 3$^{rd}$ Edition", 1999, Wiley-Interscience) to give 2-bromo-5-((2-(trimethylsilyl)ethoxy) methyl)-5H-pyrrolo[2,3-b]pyrazine compounds 5. Alternatively, the conversion of alkynes 3 to 2-bromo-5-((2-(trimethylsilyl)ethoxy)methyl)-5H-pyrrolo[2,3-b]pyrazine compounds 5 can be carried out in one reaction using methods described in AM (Scheme I, step d). The 2-bromo-5-((2-(trimethylsilyl)ethoxy)methyl)-5H-pyrrolo[2,3-b]pyrazines 5 can be used directly as starting materials for Schemes II, VI and IX or may be further functionalized at the 7-position by treating the 2-bromo-5-((2-(trimethylsilyl)ethoxy)methyl)-5H-pyrrolo[2,3-b]pyrazines 5 with an iodinating agent (Scheme I, step e) to give 2-bromo-7-iodo-5-(((2-(trimethylsilyl)ethoxy)methyl)-5H-pyrrolo[2,3-b]pyrazines 6 by using a method known to one skilled in the art (for example, Ketcha, D. M. et al *J. Org. Chem.* 1989, 54, 4350). Alternatively, one could combine the iodination with incorporation of a protecting group at the 5-position from the 2-bromo-5H-pyrrolo[2,3-b]pyrazines 4 in one pot using the method described in Preparation #5, Step A, to give the 2-bromo-7-iodo-5-((2-(trimethylsilyl)ethoxy)methyl)-5H-pyrrolo[2,3-b]pyrazines 6 directly (Scheme I, step f). The 2-bromo-7-iodo-5-(((2-(trimethylsilyl)ethoxy)methyl)-5H-pyrrolo[2,3-b]pyrazines 6 can then be converted to 7-alkyl-2-bromo-5-((2-(trimethylsilyl)ethoxy)methyl)-5H-pyrrolo[2,3-b]pyrazine compounds 7 by transmetallation of the iodine and reaction of the anion with an alkyl iodide (Scheme I, step g) in a manner described in Preparation #5, Step B. The 7-alkyl-2-bromo-5-((2-(trimethylsilyl)ethoxy)methyl)-5H-pyrrolo[2,3-b]pyrazines 7 can then be used directly as starting materials for Schemes II, VI and IX.

Methods for preparing N-((5-((2-(trimethylsilyl)ethoxy) methyl)-5H-pyrrolo[2,3-b]pyrazin-2-yl)alkyl)amide compounds 14 of the invention are illustrated in Scheme II. The N-((5-((2-(trimethylsilyl)ethoxy)methyl)-5H-pyrrolo[2,3-b] pyrazin-2-yl)alkyl)amides 14 are substituted at the 6-position with an $R_1$ substituent and may be optionally substituted at either the amide position with an $R_3$ substituent and/or the 7-position with an $R_2$ substituent and/or at the methyne position with an $R_6$ substituent and/or at the 4-position with an $R_5$ substituent. Therefore, $R_2$, $R_3$, $R_5$ and/or $R_6$ can either be hydrogen or a substituent in Scheme II and III. In Scheme II, either 2-bromo-5-(((2-(trimethylsilyl)ethoxy)methyl)-5H-pyrrolo[2,3-b]pyrazines 5 or 7-alkyl-2-bromo-5-((2-(trimethylsilyl)ethoxy)methyl)-5H-pyrrolo[2,3-b]pyrazines 7, from commercial sources or Scheme I, can be subjected to a Suzuki coupling with a vinyl boronic acid or vinyl boronate to give an alkene (Scheme II, step a) using methods known to one skilled in the art (for example, Suzuki, A. J. Organometallic Chem. 1999, 576, 147) to give alkenes 8. The vinyl boronic acids and/or vinyl boronic esters used in the Suzuki coupling are either commercially available or can be prepared by methods known to one skilled in the art (Miyaura, N. et al *Chem. Rev.* 1995, 95, 2457). The alkenes 8 can then be cleaved to form either aldehydes or ketones 9 (Scheme II, step b) using the Lemieux-Johnson protocol (for example, Pappo, R. et al *J. Org. Chem.* 1956, 21, 478 or as described in E) or by any other method known to one skilled in the art (Petasis, N. "Oxidative Cleavage of Olefeins Transition Metals for Organic Synthesis, 2$^{nd}$ ed.", pp 427-436, 2004, Wiley-VCH and Larock, R. C. [referenced above]). Alternatively the aldehydes or ketones 9 can be formed directly through transmet- Scheme I:

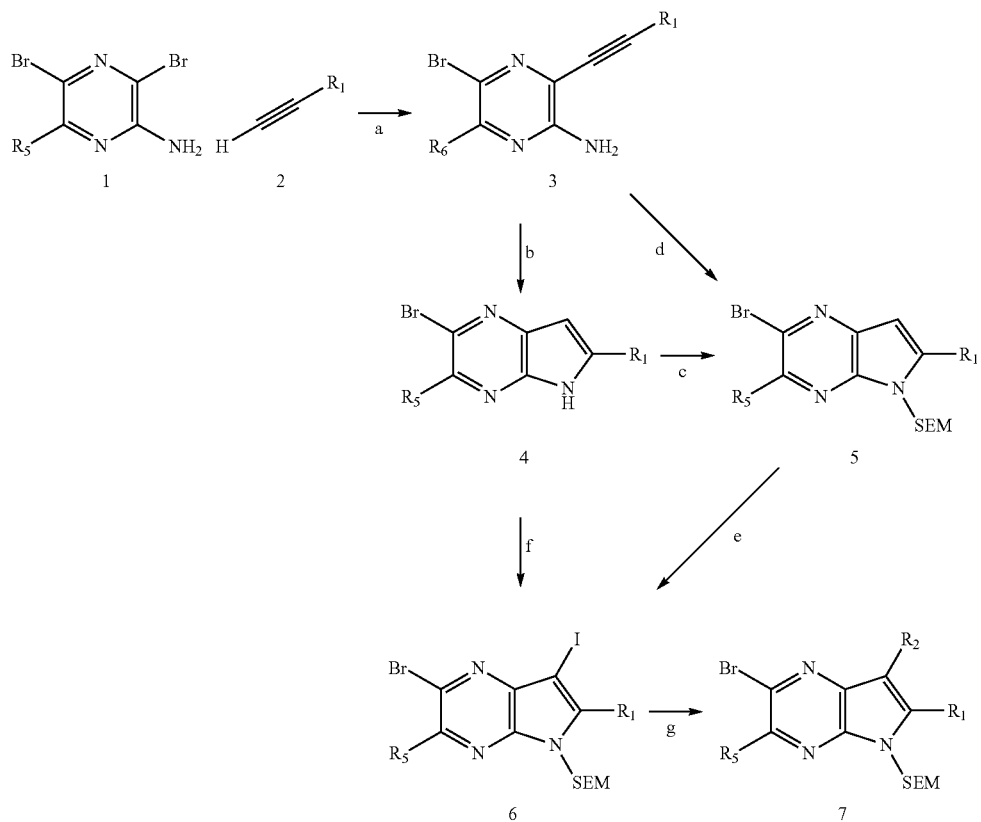

allation of the bromide followed by reaction with an appropriate amide using conditions described in Example #9 (Scheme II, step c). The aldehydes or ketones 9 can then be reduced to alkyl alcohols 10 (Scheme II, step d) using methods known to one skilled in the art (for example, Larock, R. C. [referenced above] or see F). The alkyl alcohols 10 can then be converted to alkyl azides 12 through alkyl chloride intermediates 11 (Scheme II, steps e and f) as described by the sequence of G. The alkyl azides 12 are then reduced by a method known to one skilled in the art (Vaultier, M. *Tetrahedron* 1983, 24, 763 or see I) to give alkyl amines 13 (Scheme II, step g) that are subsequently reacted with carboxylic acids using a peptide coupling agent (for example, Han, S.-Y. *Tetrahedron* 2004, 60, 2447 or see J.1), or using carboxylic acid chlorides or carboxylic acid anhydrides with base (for example, see J.2) to give N-((5-((2-(trimethylsilyl)ethoxy)methyl)-5H-pyrrolo[2,3-b]pyrazin-2-yl)alkyl)amide compounds 14 (Scheme II, step h). Alternatively, where $R_3$ is a hydrogen, the alkyl amines 13 can be reacted with either formates or orthoformates (for example, see J.3) to give the N-((5-((2-(trimethylsilyl)ethoxy)methyl)-5H-pyrrolo[2,3-b]pyrazin-2-yl)alkyl)amides 14 (Scheme II, step h). The N-((5-((2-(trimethylsilyl)ethoxy)methyl)-5H-pyrrolo[2,3-b]pyrazin-2-yl)alkyl)amides 14 prepared in this sequence can be used as a starting material for Scheme III. Additionally, the aldehydes or ketones 9 can be used as a starting material for Scheme XII and the alkyl amines 13 can be used as starting materials in Scheme X, therefore $R_1$ is a substituent and $R_2$, $R_3$, $R_5$ and/or $R_6$ can either be hydrogen or a substituent in Scheme X and Scheme XII.

Scheme II:

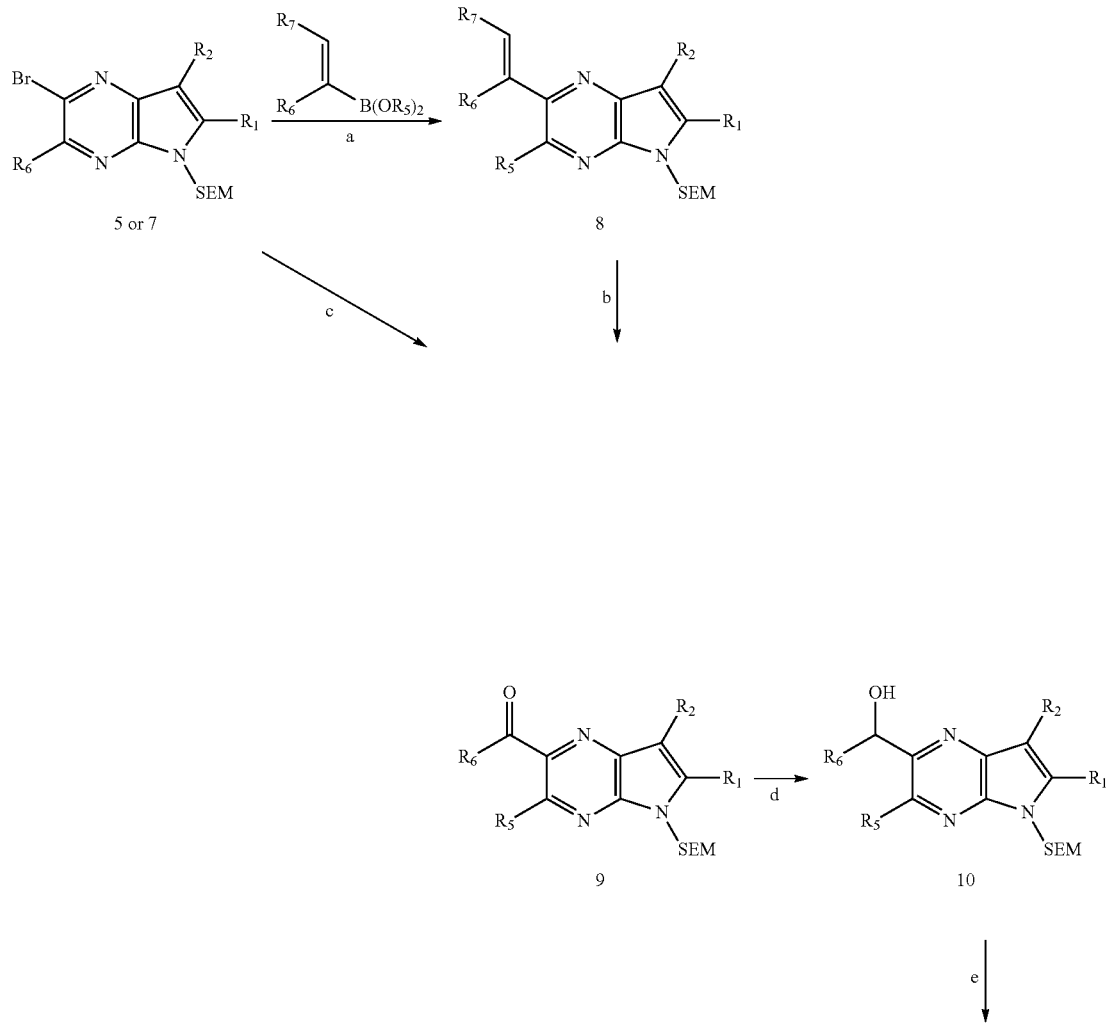

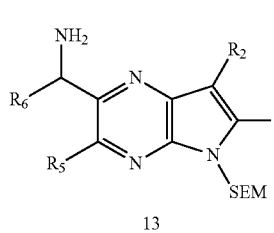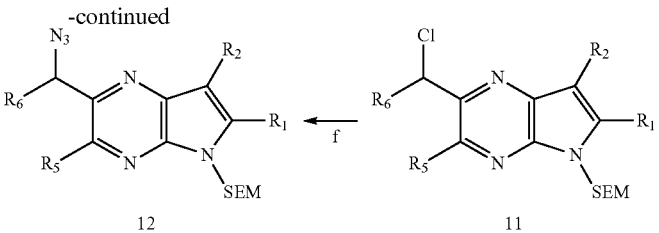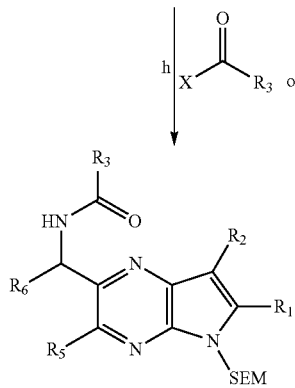

Methods for preparing 6H-imidazo[1,5-a]pyrrolo[2,3-e]pyrazine compounds 19 of the invention are illustrated in Scheme III. 6H-Imidazo[1,5-a]pyrrolo[2,3-e]pyrazines 19 are substituted at the 7-position with an $R_1$ substituent and may be optionally substituted at either the 1-position with an $R_3$ substituent and/or the 8-position with an $R_2$ substituent and/or the 3-position with an $R_6$ substituent and/or the 4-position with an $R_5$ substituent. Therefore, $R_2$, $R_3$, $R_5$ and/or $R_6$ can either be hydrogen or a substituent in Scheme III. In Scheme III, N-((5-((2-(trimethylsilyl)ethoxy)methyl)-5H-pyrrolo[2,3-b]pyrazin-2-yl)alkyl)amides 14 from Scheme II can be converted to 6H-imidazo[1,5-a]pyrrolo[2,3-e]pyrazines 19 through one of several routes. The N-((5-((2-(trimethylsilyl)ethoxy)methyl)-5H-pyrrolo[2,3-b]pyrazin-2-yl)alkyl)amides 14 can be treated with Lawesson's reagent to give N-((5-((2-(trimethylsilyl)ethoxy)methyl)-5H-pyrrolo[2,3-b]pyrazin-2-yl)alkyl)thioamide intermediates 15 (Scheme III, step c) and subsequently cyclized with an activating agent such as a mercury salt, a silver salt or a copper salt (for example, see L.1) to give 6-((2-(trimethylsilyl)ethoxy)methyl)-6H-imidazo[1,5-a]pyrrolo[2,3-e]pyrazines 17 (Scheme III, step d). Alternatively, the conversion of the N-((5-((2-(trimethylsilyl)ethoxy)methyl)-5H-pyrrolo[2,3-b]pyrazin-2-yl)alkyl)amides 14 directly to the 6-((2-(trimethylsilyl)ethoxy)methyl)-6H-imidazo[1,5-a]pyrrolo[2,3-e]pyrazines 17 (Scheme III, step e) can be carried out under anhydrous acidic conditions (for example, see L.2). The SEM protecting group can then be removed by methods known to one skilled in the art (for example, Greene, T. W. and Wuts, P. G. M. [referenced above] or as described in M) to give the 6H-imidazo[1,5-a]pyrrolo[2,3-e]pyrazines 19 (Scheme III, step g). Alternatively, the protecting group can be removed from the N-((5-((2-(trimethylsilyl)ethoxy)methyl)-5H-pyrrolo[2,3-b]pyrazin-2-yl)alkyl)amides 14 first using the methods described above to give N-((5H-pyrrolo[2,3-b]pyrazin-2-yl)methyl)amides 16 (Scheme III, step a) and then cyclized using the same methods described above through N-((5H-pyrrolo[2,3-b]pyrazin-2-yl)alkyl)thioamide intermediates 18 to give the 6H-imidazo[1,5-a]pyrrolo[2,3-e]pyrazines 19 (Scheme III, steps b and f). In either case, further functionalization of any of the intermediates (for instance Compounds 1-7 in Scheme I, Compounds 8-14 in Scheme II and/or Compounds 15-18 in Scheme III) and/or the 6H-imidazo[1,5-a]pyrrolo[2,3-e]pyrazine compounds 19 can be performed with appropriate functionality on $R_1$, $R_2$, $R_3$, $R_5$ and/or $R_6$, if desired, using reactions known to one skilled in the art (see, for example, Larock, R. C. [referenced above] or the General Procedures below). For example, formation of amides or sulfonamides can be achieved by reaction of compounds 19 containing a primary or secondary amine (see, for example, J.1, J.2, J.3 and K). Additionally, amides could be prepared by the saponification of esters to a carboxylic acid (see, for example, V.1 or V.2) and then subsequent reaction with primary or secondary amines (see, for example, J.1, J.2, J.3 and K). Additionally, alcohols may be obtained by the reaction of ketones, aldehydes or esters with Grignard reagents (see, for example, S and AA) or also by reduction of ketones or aldehydes with reducing agents (see, for example, F). Additionally, imines may be formed through the reaction of a Grignard reagent with a nitrile (see, for example AF). Additionally, imines may be hydrolyzed to ketones (see, for example AT). Additionally amines may be formed either through reductive amination of ketones and aldehydes (see, for example AH) or through the reduction of an imine (see, for example AG). Additionally, sulfones may be obtained through oxidation of sulfides (see, for example AR). And alcohols may be converted to ketones through oxidation (see, for example AV or Gabriel T., Marcos F. "Oxidation of Alcohols to Aldehydes and Ketones, 1st Edition", 2006, Springer, N.Y.). Also, deprotection of compounds 19 to yield unprotected compounds can be performed using conditions such as those described in Greene, T. W. and Wuts, P. G. M. [referenced above]. For example, a protecting group such as a t-butoxycarbonyl group can be removed from a protected amine to yield the unprotected amine (see, for example, Example #4, Step C) and the deprotected compounds 19 may then be reacted further as described above. In some cases, the deprotection of multiple protecting groups of a different nature may be removed in one reaction (see, for example, T.1, T.2, T.3 and T.4).

23 can then be treated sequentially with sec-BuLi and DMF to give 4-chloro-1-triisopropylsilyl-1H-pyrrolo[2,3-b]pyridine-5-carbaldehyde compounds 24 and subsequently deprotected (Scheme IV, steps d and e) by a method known to one skilled in the art (for example, Greene, T. W. and Wuts, P. G. M.

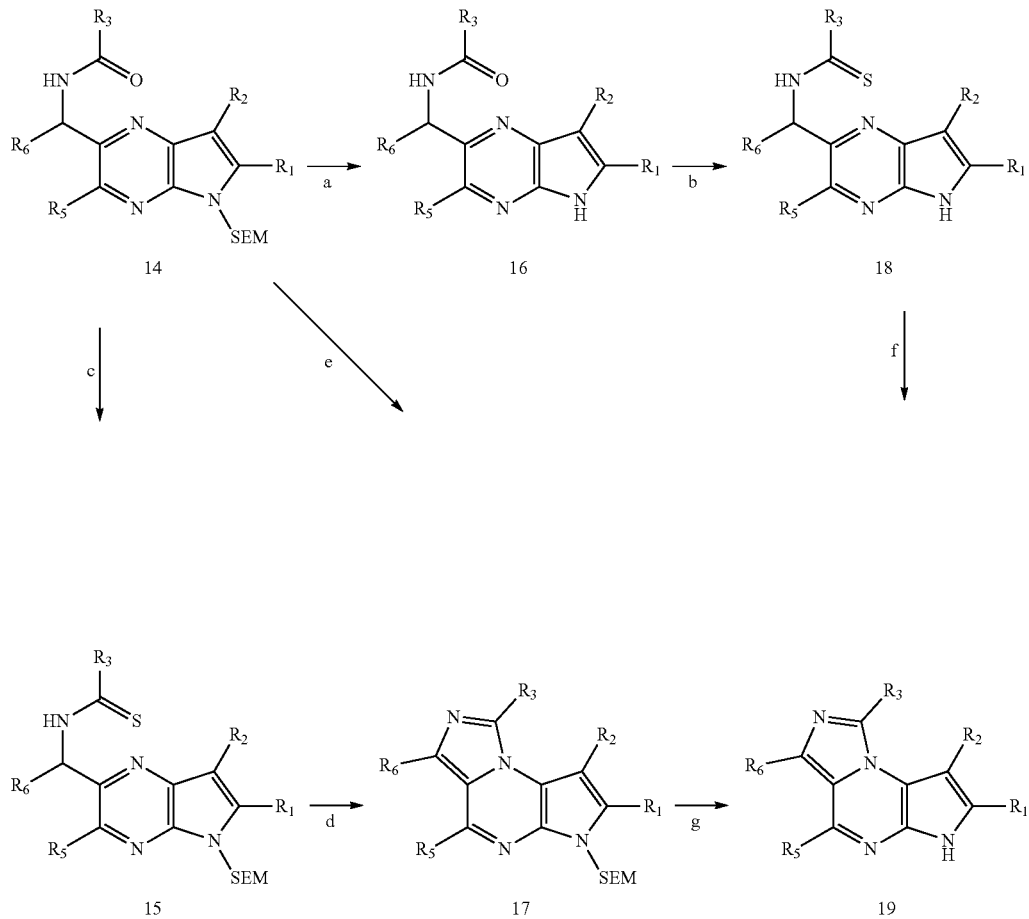

Scheme III

Methods for preparing 1,6-dihydropyrazolo[3,4-d]pyrrolo[2,3-b]pyridine compounds 26 of the invention are illustrated in Scheme IV. The 6-dihydropyrazolo[3,4-d]pyrrolo[2,3-b]pyridines 26 may be optionally substituted at either the 1-position with an $R_3$ substituent and/or at the 8-position with an $R_2$ substituent. Therefore, $R_2$ and/or $R_3$ can either be hydrogen or a substituent in Schemes IV as well as Scheme V. In Scheme IV, the 4-chloro-1-triisopropylsilyl-1H-pyrrolo[2,3-b]pyridines 23 may be prepared either by starting with 4-chloro-1H-pyrrolo[2,3-b]pyridines 20, obtained commercially or prepared using a method known to one skilled in the art, and then protected with a protecting group (see, for example, in Greene, T. W. and Wuts, P. G. M. [referenced above] or see Preparation #1, Step A) (Scheme IV, step a) or starting with commercially available 4-chloro-3-iodo-1H-pyrrolo[2,3-b]pyridine 21 (GLSYNTECH, LLC) which is protected using the method described above (Scheme IV, step b) and can then be converted to 4-chloro-1-triisopropylsilyl-1H-pyrrolo[2,3-b]pyridines 23 by transmetallation of the iodine and reaction of the anion with an alkyl iodide (Scheme IV, step c) in a manner described in Preparation #2, Step B. The 4-chloro-1-triisopropylsilyl-1H-pyrrolo[2,3-b]pyridines

[referenced above]) to give 4-chloro-1H-pyrrolo[2,3-b]pyridine-5-carbaldehyde compounds 25 or preferably, the two previous steps can be conducted in one reaction (Scheme IV, step f) (see, for example, Preparation #1, Step B) to give the 4-chloro-1H-pyrrolo[2,3-b]pyridine-5-carbaldehydes 25. The 4-chloro-1H-pyrrolo[2,3-b]pyridine-5-carbaldehydes 25 can then be converted to 1,6-dihydropyrazolo[3,4-d]pyrrolo[2,3-b]pyridine compounds 26 by treating with hydrazines (Scheme IV, step g) (see, for example, Preparation #1, Step C). Further functionalization of any of the intermediates (for instance compounds 21-25 in Scheme IV) and/or the 1,6-dihydropyrazolo[3,4-d]pyrrolo[2,3-b]pyridine compounds 26 can be performed on $R_2$ and/or $R_3$, if desired, as described for compounds 19 above or in the General Procedures below. The 1,6-dihydropyrazolo[3,4-d]pyrrolo[2,3-b]pyridines 26 prepared in this sequence can be used a starting material for Scheme V. Additionally, 4-chloro-1-triisopropylsilyl-1H-pyrrolo[2,3-b]pyridine compounds 23 can be used as starting materials for Schemes VII and XIV, therefore $R_2$ and/or $R_3$ can either be hydrogen or a substituent in Schemes VII and XIV.

Scheme IV

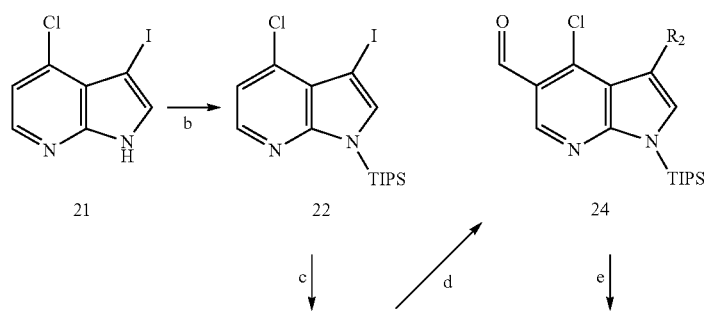

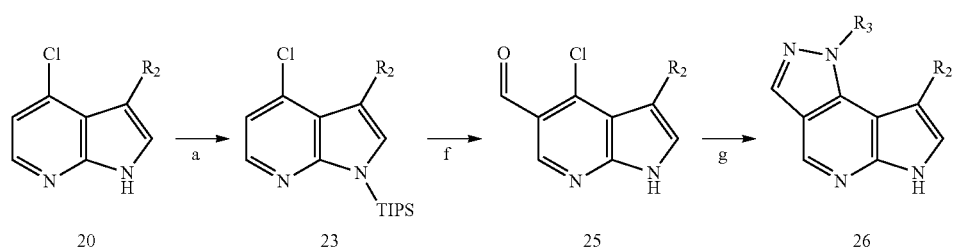

Methods for preparing 7-substituted-1,6-dihydropyrazolo[3,4-d]pyrrolo[2,3-b]pyridine compounds 31 of the invention are illustrated in Scheme V. The 7-substituted-6-dihydropyrazolo[3,4-d]pyrrolo[2,3-b]pyridine compounds 31 are substituted at the 7-position with an $R_1$ substituent and may be optionally substituted at the 1-position and with an $R_3$ substituent and/or at the 8-position with an $R_2$ substituent. Therefore, $R_2$ and/or $R_3$ can either be hydrogen or a substituent in Scheme V. In Scheme V, the 1,6-dihydropyrazolo[3,4-d]pyrrolo[2,3-b]pyridines 26 are protected with a tosyl protecting group (Scheme V, step a) by a method known to one skilled in the art (for example, Greene, T. W. and Wuts, P. G. M. [referenced above] or see Preparation #1, Step D) to give 6-tosyl-1,6-dihydropyrazolo[3,4-d]pyrrolo[2,3-b]pyridines 27. The 6-tosyl-1,6-dihydropyrazolo[3,4-d]pyrrolo[2,3-b]pyridines 27 can then be converted to 7-iodo-6-tosyl-1,6-dihydropyrazolo[3,4-d]pyrrolo[2,3-b]pyridines 28 by treatment with LDA followed by reaction of the anion intermediate with an iodine source (Scheme V, step b) (see, for example Preparation #1, Step E). The resulting 7-iodo-6-tosyl-1,6-dihydropyrazolo[3,4-d]pyrrolo[2,3-b]pyridines 28 can be converted to the 7-substituted-1,6-dihydropyrazolo[3,4-d]pyrrolo[2,3-b]pyridine compounds 31 by either a Suzuki coupling with aryl or heteroaryl boronic acids or esters, a Stille coupling with aryl or vinyl stannanes or a Negishi coupling with an aryl zincate to give 7-substituted-6-tosyl-1,6-dihydropyrazolo[3,4-d]pyrrolo[2,3-b]pyridines 29 (Suzuki, A. [referenced above] or see, for example D, Stille [*Tin Chemistry* 2008, 579-606] or see, for example Preparation #16, Step B, Negishi [Tetrahedron 1999, 55(52), 15067-15070] or see, for example Preparation #13) followed by deprotection (Scheme V, steps c and d) by a method known to one skilled in the art (for example, Greene, T. W. and Wuts, P. G. M. [referenced above] or see N) or the deprotection is done first followed by a Suzuki coupling or Stille coupling (Scheme V, steps e and f) using the same procedures described earlier. Throughout the General Synthetic Schemes, the boronic acids and/or boronic esters used in the Suzuki coupling, the aryl stannanes and/or vinyl stannanes used in the Stille coupling or the zincates used in the Negishi couplings are either commercially available or can be prepared by methods known to one skilled in the art (boronic acids and/or boronic esters Miyaura, N. [referenced above] or see, for example, H; aryl stannanes and/or vinyl stannanes [*J. Med. Chem.*, 1997, 40, 2430-2433] or see, for example Preparation #16, Step A; zincates [referenced above] or see, for example Preparation #13). Further functionalization of any of the intermediates (for instance compounds 26-30 in Scheme V) and/or the 7-substituted-1,6-dihydropyrazolo[3,4-d]pyrrolo[2,3-b]pyridine compounds 31 can be performed on $R_1$, $R_2$ and/or $R_3$, if desired, as described for compounds 19 above or in the General Procedures below. The 6-tosyl-1,6-dihydropyrazolo[3,4-d]pyrrolo[2,3-b]pyridines compounds 27 prepared in this sequence can be used as starting materials for Scheme XI, therefore $R_2$ and/or $R_3$ can either be hydrogen or a substituent in Scheme XI. Additionally, when the $R_2$ substituent is a hydrogen, the 6-tosyl-1,6-dihydropyrazolo[3,4-d]pyrrolo[2,3-b]pyridines compounds 27 prepared in this sequence can be used as starting materials for Scheme XIV, therefore $R_3$ can either be hydrogen or a substituent in Scheme XIV.

Scheme V

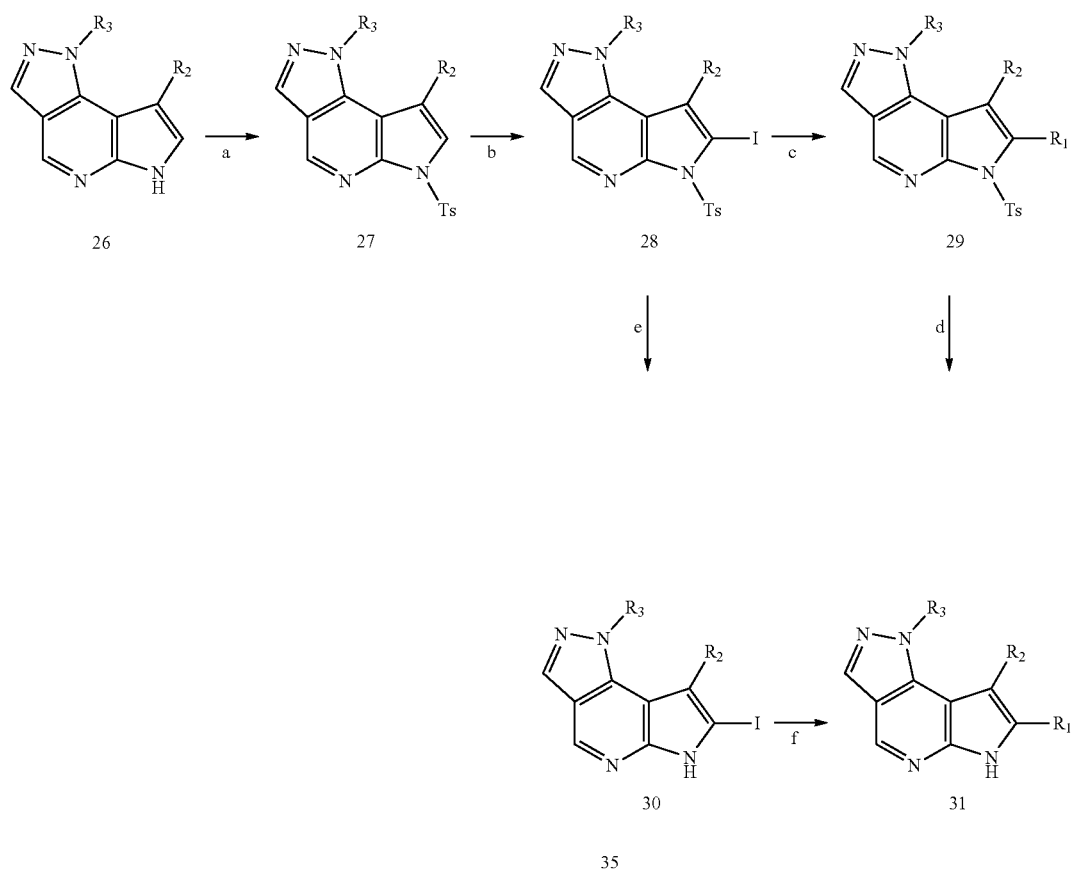

Methods for preparing 6H-pyrrolo[2,3-e][1,2,4]triazolo[4,3-a]pyrazine compounds 37 of the invention are illustrated in Scheme VI. The 6H-pyrrolo[2,3-e][1,2,4]triazolo[4,3-a]pyrazines 37 are substituted at the 7-position with an $R_1$ substituent and may be optionally substituted at the 1-position with an $R_3$ substituent and/or at the 8-position with an $R_2$ substituent and/or at the 4-position with an $R_5$ substituent. Therefore, $R_2$, $R_3$ and/or $R_5$ can either be hydrogen or a substituent in Scheme VI. In Scheme VI, either 2-bromo-5-((2-(trimethylsilyl)ethoxy)methyl)-5H-pyrrolo[2,3-b]pyrazines 5 or 7-alkyl-2-bromo-5-((2-(trimethylsilyl)ethoxy)methyl)-5H-pyrrolo[2,3-b]pyrazines 7 from Scheme I can be subjected to a Buchwald coupling with N-Boc protected hydrazine (Scheme VI, step a) using methods known to one skilled in the art (for example, Hartwig, J. F. Angew. Chem. Int. Ed. 1998, 37, 2046 or see O) to give a mixture tert-butyl 2-(5H-pyrrolo[2,3-b]pyrazin-2-yl)hydrazinecarboxylate regioisomer compounds 32a and 32b. The Boc protecting group can then be removed from the mixture of tert-butyl 2-(5H-pyrrolo[2,3-b]pyrazin-2-yl)hydrazinecarboxylates 32a and 32b (Scheme VI, step b) using methods known to one skilled in the art (for example, Greene, T. W. and Wuts, P. G. M. [referenced above] or see P.2) to give 2-hydrazinyl-5-((2-(trimethylsilyl)ethoxy)methyl)-5H-pyrrolo[2,3-b]pyrazines 33. Alternatively, either 2-bromo-5-((2-(trimethylsilyl)ethoxy)methyl)-5H-pyrrolo[2,3-b]pyrazines 5 or 7-alkyl-2-bromo-5-((2-(trimethylsilyl)ethoxy)methyl)-5H-pyrrolo[2,3-b]pyrazines 7 can be directly converted to 2-hydrazinyl-5-((2-(trimethylsilyl)ethoxy)methyl)-5H-pyrrolo[2,3-b]pyrazines 33 with hydrazine (Scheme IV, step c) using methods known to one skilled in the art (see, for example O).

The 2-hydrazinyl-5-((2-(trimethylsilyl)ethoxy)methyl)-5H-pyrrolo[2,3-b]pyrazines 33 can then be converted to 6-((2-(trimethylsilyl)ethoxy)methyl)-6H-pyrrolo[2,3-e][1,2,4]triazolo[4,3-a]pyrazines 36 by one of several methods. For instance, the 2-hydrazinyl-5-((2-(trimethylsilyl)ethoxy)methyl)-5H-pyrrolo[2,3-b]pyrazines 33 can be reacted with aldehydes to form hydrazones 34 which can be subsequently cyclized (Scheme VI, steps d and e) with an oxidizing agent (see, for example, R.1) or, the 2-hydrazinyl-5-(2-(trimethylsilyl)ethoxy)methyl)-5H-pyrrolo[2,3-b]pyrazines 33 can be reacted with carboxylic acid chlorides or activated carboxylic acids to give hydrazides 35 which can subsequently be cyclized (Scheme VI, steps f and g) using acid or other dehydrating conditions known to one skilled in the art (Huisgen, R. et al Tetrahedron 1962, 17, 3). Alternatively, where $R_1$ is a hydrogen, the 2-hydrazinyl-5-((2-(trimethylsilyl)ethoxy)methyl)-5H-pyrrolo[2,3-b]pyrazines 33 can be reacted with either formates or orthoformates (for example, see R.2) to give the 6-((2-(trimethylsilyl)ethoxy)methyl)-6H-pyrrolo[2,3-e][1,2,4]triazolo[4,3-a]pyrazines 36 (Scheme VI, step h). The resulting 6-((2-(trimethylsilyl)ethoxy)methyl)-6H-pyrrolo[2,3-e][1,2,4]triazolo[4,3-a]pyrazines 36 can be deprotected (Scheme VI, step i) using methods known to one skilled in the art (for example, Greene, T. W. and Wuts, P. G. M. [referenced above] or see M) to give the 6H-pyrrolo[2,3-e][1,2,4]triazolo[4,3-a]pyrazine compounds 37. Further functionalization of any of the intermediates (for instance Compounds 32-36 in Scheme VI) and/or the 6H-pyrrolo[2,3-e][1,2,4]triazolo[4,3-a]pyrazine compounds 37 can be performed on $R_1$, $R_2$, $R_3$ and/or $R_5$, if desired, as described for compounds 19 above or in the General Procedures below.

Scheme VI

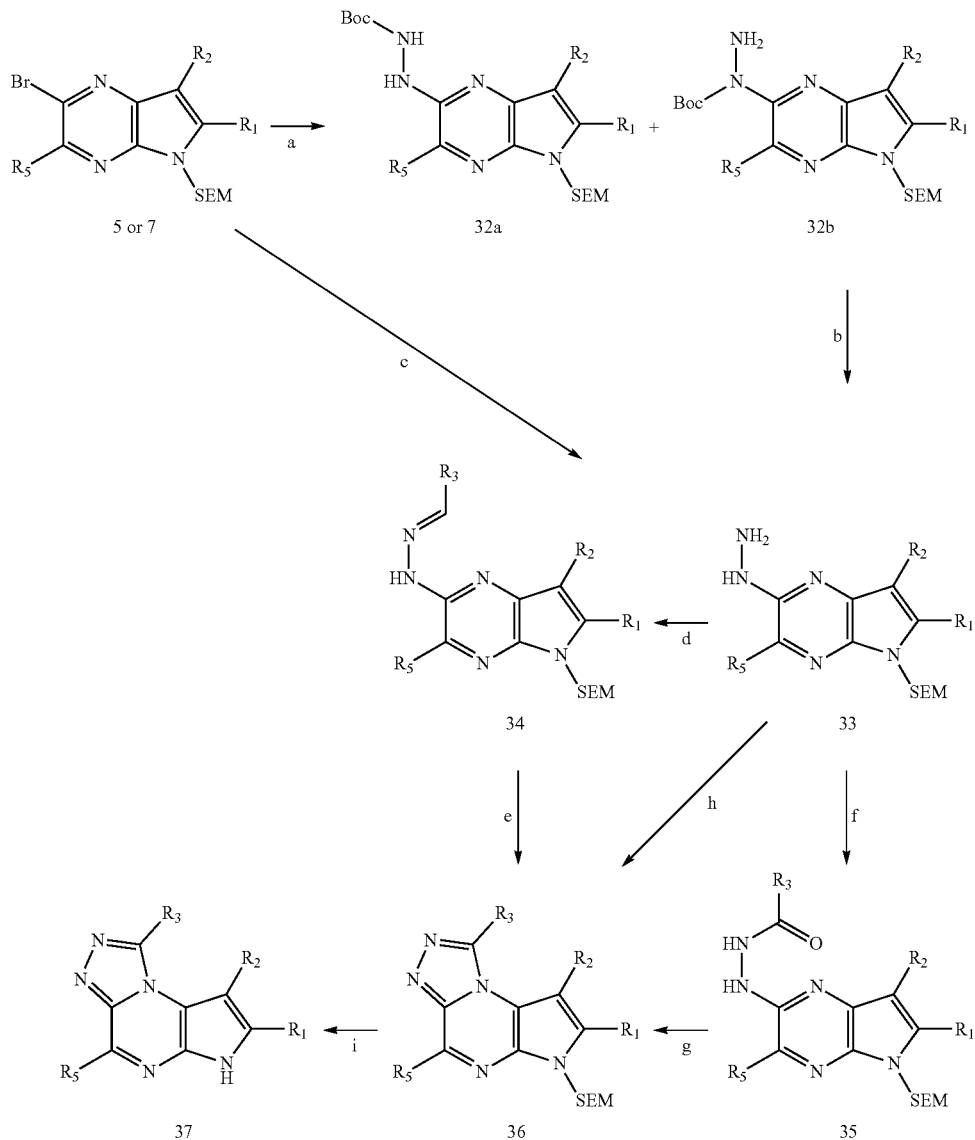

Methods for preparing 1,2,3,6-tetrahydrodipyrrolo[2,3-b:2',3'-d]pyridine compounds 46 of the invention are illustrated in Scheme VII. The 1,2,3,6-tetrahydrodipyrrolo[2,3-b:2',3'-d]pyridines 46 are substituted at the 7-position with an $R_1$ substituent and may be optionally substituted at the 1-position and with an $R_3$ substituent and/or at the 8-position with an $R_2$ substituent. Therefore, $R_2$ and/or $R_3$ can either be hydrogen or a substituent in Scheme VII. In Scheme VII, the 4-chloro-1-triisopropysilylo-1H-pyrrolo[2,3-b]pyridines 23 preapred in Scheme IV can be reacted with sec-BuLi followed by allyl chloride (Scheme VII, step a) to give 5-allyl-1-triisopropylsilyl-1H-pyrrolo[2,3-b]pyridines 38 (see, for example, Preparation #3, Step A). The 5-allyl-1-triisopropyl-silyl-1H-pyrrolo[2,3-b]pyridines 38 can then have the protecting groups exchanged by first removing the TIPS group (Scheme VII, step b) to give 5-allyl-4-chloro-1H-pyrrolo[2,3-b]pyridines 39 and then tosylating (Scheme VII, step c) using methods known to one skilled in the art (for example, Greene, T. W. and Wuts, P. G. M. [referenced above] or see Preparation #3, Steps B and C) to give 5-allyl-4-chloro-1-tosyl-1H-pyrrolo[2,3-b]pyridines 40. The alkene from the 5-allyl-4-chloro-1-tosyl-1H-pyrrolo[2,3-b]pyridines 40 can then be converted to an aldehyde (Scheme VII, step d) by methods known to one skilled in the art (Petasis, N. [referenced above] and Larock, R. C. [referenced above] or see, for example, E or Preparation #3, Step D) to give aldehydes 41. A reductive amination of aldehydes 41 with amines (Scheme VII, step e) can then be performed to give amines 42 (Abdel-Magid, A. F. Org. Proc. Res. & Dev. 2006, 10, 971 and Larock, R. C. [referenced above] or see, for example, AH or Preparation #3, Step E). The amines 42 can then be cyclized (Scheme VII, step f) using methods known to one skilled in the art (Huisgen, R. [referenced above] or see, for example, Preparation #3, Step F) to give the 6-tosyl-1,2,3,6-tetrahydrodipyrrolo[2,3-b:2',3'-d]pyridines 43. The 6-tosyl-1,2,3,6-tetrahydrodipyrrolo[2,3-b:2',3'-d]pyridines 43 can then be iodinated by deprotonation and reacting the resulting anion with an iodide source (see, for example, Preparation #3, Step G) to give 7-iodo-6-tosyl-1,2,3,6-tetrahydrodipyrrolo[2,3-b:2',3'-d]pyridines 44 (Scheme VII, step g). The 7-iodo-6-tosyl-1,2,3,6-tetrahydrodipyrrolo[2,3-b:2',3'-d]pyridines 44 can then be coupled (Scheme VII, step h) with aryl and/or heteroaryl boronic acids and/or boronic esters using Suzuki conditions (Suzuki, A. [referenced above] or see, for example, D) to give 7-substituted 6-tosyl-1,2,3,6-tetrahydrodipyrrolo[2,3-b:2',3'-d]pyridines 45. The 7-substituted 6-tosyl-1,2,3,6-tetrahydrodipyrrolo[2,3-b:2',3'-d]pyridines 45 can then be deprotected (Scheme VII, step i) to give the 1,2,3,6-tetrahydrodipyrrolo[2,3-b:2',3'-d]pyridine compounds 46 using methods known to one skilled in the art (for example, Greene, T. W. and Wuts, P. G. M. [referenced above] or see N). Further functionalization of any of the intermediates (for instance compounds 38-45 in Scheme VII) and/or the 1,2,3,6-tetrahydrodipyrrolo[2,3-b:2',3'-d]pyridine compounds 46 can be performed on $R_1$, $R_2$ and/or $R_3$, if desired, as described for compounds 19 above or in the General Procedures below.

prepared by methods known to one skilled in the art (see, for example, Example #2, Step A), gives the corresponding nitriles 48 (for example see Example #2, Step B, AE or Tetrahedron Letters 1999, 40(47), 8193-8195). Of note is that the bromides 47 are related to the 7-alkyl-2-bromo-5-(((2-(trimethylsilyl)ethoxy)methyl)-5H-pyrrolo[2,3-b]pyrazine compounds 7 from Scheme I where $R_1$ is a hydrogen. Subsequent reduction of nitriles 48 gives (5-tosyl-5H-pyrrolo[2,3-b]pyrazin-2-yl)methanamines 49 (Scheme VIII, step b) using methods known to one skilled in the art (for example, Example #2, Step B or Journal of Medicinal Chemistry 2003, 46(4), 461-473). The coupling of (5-tosyl-5H-pyrrolo[2,3-b]pyrazin-2-yl)methanamines 49 with carboxylic acids or carboxylic acid chlorides provides amides 50 (Scheme VIII, step c) using well known conditions such as those given in J.1 and J.2 (for example, see Example #2, Step C). Alternatively, where $R_1$ is a hydrogen, the (5-tosyl-5H-pyrrolo[2,3-b]pyrazin-2-yl)methanamines 49 can be reacted with either Scheme VII

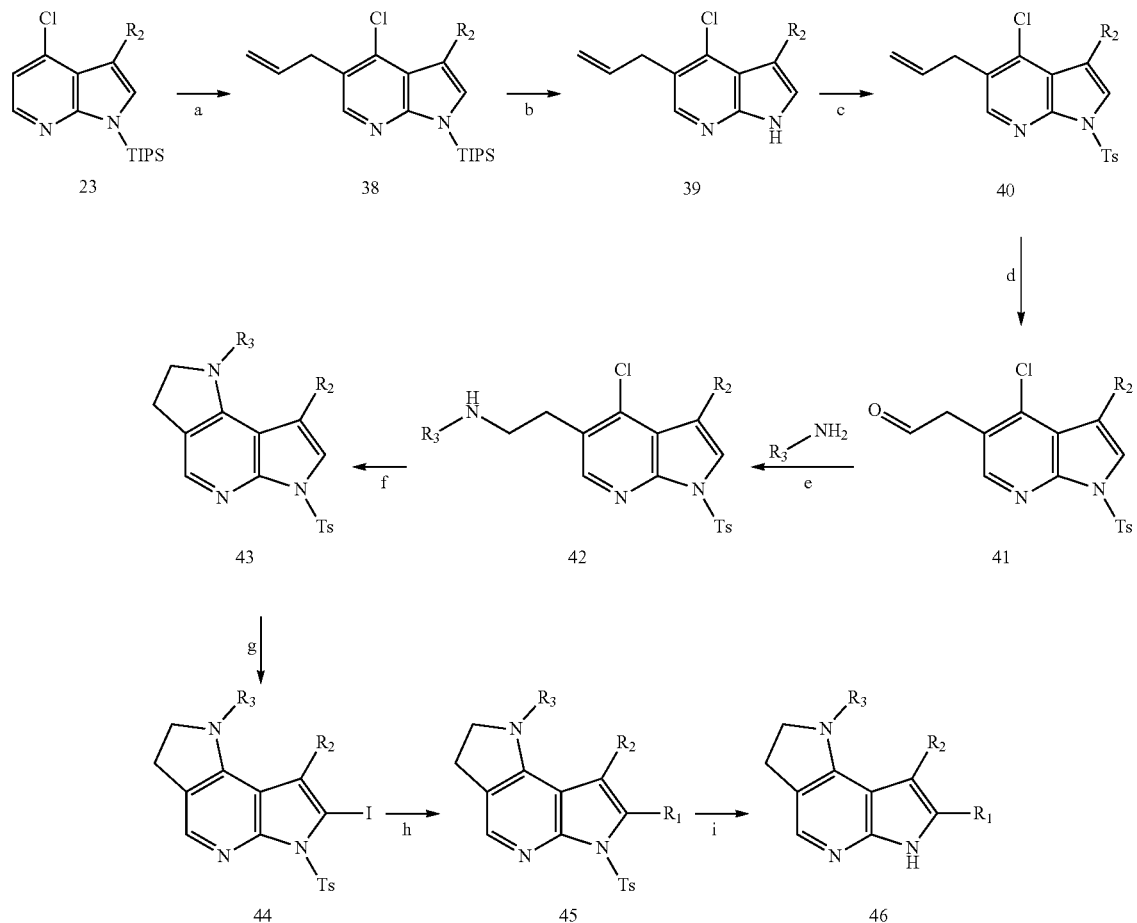

Methods for preparing imidazo[1,5-a]pyrrolo[2,3-e]pyrazine compounds 59 of the invention are illustrated in Scheme VIII. The imidazo[1,5-a]pyrrolo[2,3-e]pyrazine compounds 59 are substituted at the 3-position with an $R_6$ substituent and may be optionally substituted at the 1-position and with an $R_3$ substituent and/or the 8-position with an $R_2$ substituent and/or the 4-position with an $R_5$ substituent. Therefore, $R_2$, $R_3$ and/or $R_5$ can either be hydrogen or a substituent in Scheme VIII. In Scheme VIII, step a, Pd-mediated cyanation of bromides 47, formates or orthoformates (for example, see J.3) to give amides 50 (Scheme VIII, step c). As shown in Scheme VIII, steps d and e, the cyclization of amides 50 can be accomplished by conversion to the thioamides 51 followed by treatment with an activating agent (such as a mercury salt, a silver salt or a copper salt) providing the imidazo[1,5-a]pyrrolo[2,3-e]pyrazines 52 (for example L.1, or see Example #2, Step D). Alternatively, the conversion of the amides 50 directly to the imidazo[1,5-a]pyrrolo[2,3-e]pyrazines 52 (Scheme VIII, step f) can be carried out under anhydrous acidic conditions (for example, see L.2). The imidazo[1,5-a]pyrrolo[2,3-e]pyrazines 52 can then be halogenated in the 3-position (Scheme VIII, step g) using methods known to one skilled in the art (see, for example, Example #2, Step E or see AB) to give 3-haloimidazo[1,5-a]pyrrolo[2,3-e]pyrazines 53. The 3-haloimidazo[1,5-a]pyrrolo[2,3-e]pyrazines 53 can then be coupled (Scheme VIII, step h) with aryl and/or heteroaryl boronic acids and/or boronic esters using Suzuki conditions (Suzuki, A. [referenced above] or see, for example, D, or see, for example, Example #2, Step F) to give 3-substituted-6-tosylimidazo[1,5-a]pyrrolo[2,3-e]pyrazines 54. An alternate sequence to the 3-substituted-6-tosylimidazo[1,5-a]pyrrolo[2,3-e]pyrazines 54 starts with the nitriles 48 being reacted with Grignard reagents (Scheme VIII, step k) followed by reduction of the resulting nitriles 55 (Scheme VIII, step l) to give amines 56 (for example, see AF and AG). The amines 56 can then be reacted with carboxylic acids or carboxylic acid chlorides to provide amides 57 (Scheme VIII, step m) using well known conditions such as those given in J.1 and J.2. Alternatively, where $R_1$ is a hydrogen, the amines 56 can be reacted with either formates or orthoformates (for example, see J.3) to give amides 57 (Scheme VIII, step m). As shown in Scheme VIII, steps o and p, the cyclization of amides 57 can be accomplished by conversion to the thioamides 58 followed by treatment with an activating agent (such as a mercury salt, a silver salt or a copper salt) providing the imidazo[1,5-a]pyrrolo[2,3-e]pyrazines 54 (for example, see L.1). Alternatively, the conversion of the amides 57 directly to the imidazo[1,5-a]pyrrolo[2,3-e]pyrazines 54 (Scheme VIII, step n) can be carried out under anhydrous acidic conditions (for example, see L.2). The 3-substituted-6-tosylimidazo[1,5-a]pyrrolo[2,3-e]pyrazines 54 can then be deprotected (Scheme VIII, step i) to give the 3-substituted-imidazo[1,5-a]pyrrolo[2,3-e]pyrazine compounds 59 using methods known to one skilled in the art (for example, Greene, T. W. and Wuts, P. G. M. [referenced above] or see N). Alternatively, for the 3-haloimidazo[1,5-a]pyrrolo[2,3-e]pyrazines 53, the Suzki reaction and deprotection of the tosyl group can be combined in one reaction to give 3-substituted-imidazo[1,5-a]pyrrolo[2,3-e]pyrazine compounds 59 (for example, see AC). Further functionalization of any of the intermediates (for instance compounds 47-58 in Scheme VIII) and/or the 3-substituted-imidazo[1,5-a]pyrrolo[2,3-e]pyrazine compounds 59 can be performed on $R_2$, $R_3$, $R_5$ and/or $R_6$, if desired, as described for compounds 19 above or in the General Procedures below. The amines 49 and 56 can be used as starting materials for Scheme XVI, therefore $R_2$ and/or $R_5$ can either be hydrogen or a substituent in Scheme XVI. When the $R_2$ substituent is a hydrogen, the 3-substituted-imidazo[1,5-a]pyrrolo[2,3-e]pyrazine compounds 59 can be used as starting materials for Scheme XV, therefore $R_3$ and/or $R_5$ can either be hydrogen or a substituent in Scheme XV.

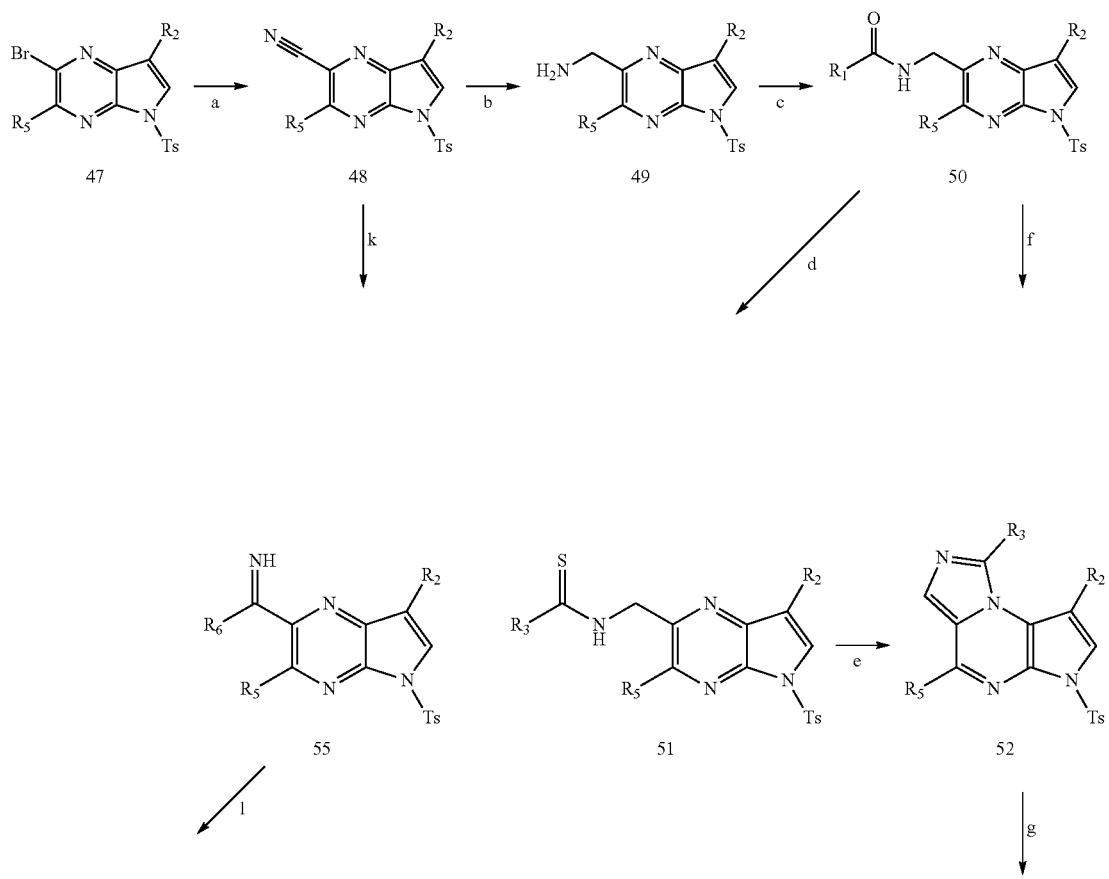

Scheme VIII

-continued

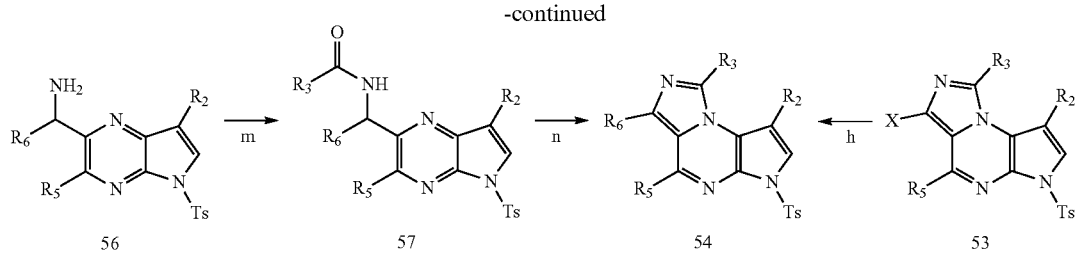

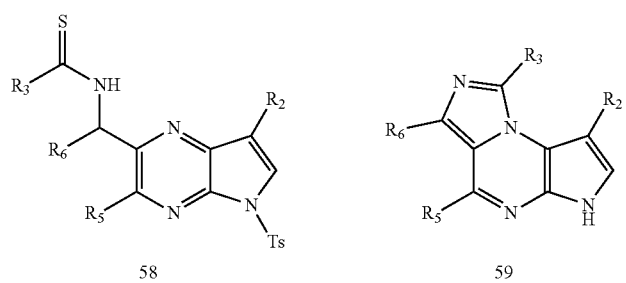

Methods for preparing 3H-imidazo[1,2-a]pyrrolo[2,3-e]pyrazine compounds 64 of the invention are illustrated in Scheme IX. The 3H-imidazo[1,2-a]pyrrolo[2,3-e]pyrazine compounds 64 are substituted at the 2-position with an $R_1$ substituent and may be optionally substituted at the 1-position and with an $R_2$ substituent and/or the 7-position with an $R_4$ substituent and/or the 8-position with and $R_3$ substituent and/or the 4-position with an $R_5$ substituent. Therefore, $R_2$, $R_3$, $R_4$ and/or $R_5$ can either be hydrogen or a substituent in Scheme IX. In Scheme IX, either 2-bromo-5-((2-(trimethylsilyl)ethoxy)methyl)-5H-pyrrolo[2,3-b]pyrazines 5 or 7-alkyl-2-bromo-5-((2-(trimethylsilyl)ethoxy)methyl)-5H-pyrrolo[2,3-b]pyrazines 7 from Scheme I can converted to 5-((2-(trimethylsilyl)ethoxy)methyl)-5H-pyrrolo[2,3-b]pyrazine-2-carboxylic acids 60 by methods known to one skilled in the art (Sheldon, R. A. "Chemicals from Synthesis Gas Catalytic Reactions of CO and H2 Series: Catalysis by Metal Complexes, Vol. 3", 1983, Springer or see, for example, Example #4, Step A). The 5-((2-(trimethylsilyl)ethoxy)methyl)-5H-pyrrolo[2,3-b]pyrazine-2-carboxylic acids 60 are then subjected to a Curtius rearrangement (Lebel, H. and Leogane, O. Org. Lett. 2005, 7, 4107, or see, for example, Example #4, Step B) to give tert-butyl 5-((2-(trimethylsilyl)ethoxy)methyl)-5H-pyrrolo[2,3-b]pyrazin-2-ylcarbamates 61. Alternatively, either the 2-bromo-5-((2-(trimethylsilyl)ethoxy)methyl)-5H-pyrrolo[2,3-b]pyrazines 5 or 7-alkyl-2-bromo-5-((2-(trimethylsilyl)ethoxy)methyl)-5H-pyrrolo[2,3-b]pyrazines 7 can be converted directly to the tert-butyl 5-((2-(trimethylsilyl)ethoxy)methyl)-5H-pyrrolo[2,3-b]pyrazin-2-ylcarbamates 59 by a Buchwald reaction with tert-butyl carbamate using methods known to one skilled in the art (for example, see Preparation #24, Step A or see L. L. Hill, L. R. Moore, R. Huang, R. Craciun, A. J. Vincent, D. A. Dixon, J. Chou, C. J. Woltermann, K. H. Shaughnessy, J. Org. Chem., 2006, 71, 4951-4955). The Boc protecting group can then be removed by methods known to one skilled in the art (for example, Greene, T. W. and Wuts, P. G. M. [referenced above] or see Example #4, Step C) to give 5-((2-(trimethylsilyl)ethoxy)methyl)-5H-pyrrolo[2,3-b]pyrazin-2-amines 62. The 5-((2-(trimethylsilyl)ethoxy)methyl)-5H-pyrrolo[2,3-b]pyrazin-2-amines 62 can then be cyclized to 3-((2-(trimethylsilyl)ethoxy)methyl)-3H-imidazo[1,2-a]pyrrolo[2,3-e]pyrazines 63 using methods described in Example #4, Step D (Scheme IX, step e). The 3-((2-(trimethylsilyl)ethoxy)methyl)-3H-imidazo[1,2-a]pyrrolo[2,3-e]pyrazines 63 can then be deprotected by methods known to one skilled in the art (for example, Greene, T. W. and Wuts, P. G. M. [referenced above] or see Example #4, Step E) to give the 3H-imidazo[1,2-a]pyrrolo[2,3-e]pyrazine compounds 64. Further functionalization of any of the intermediates (for instance compounds 60-63 in Scheme IX) and/or the 3H-imidazo[1,2-a]pyrrolo[2,3-e]pyrazine compounds 64 can be performed on $R_1$, $R_2$, $R_3$, $R_4$ and/or $R_5$, if desired, as described for compounds 19 above or in the General Procedures below.

Scheme IX

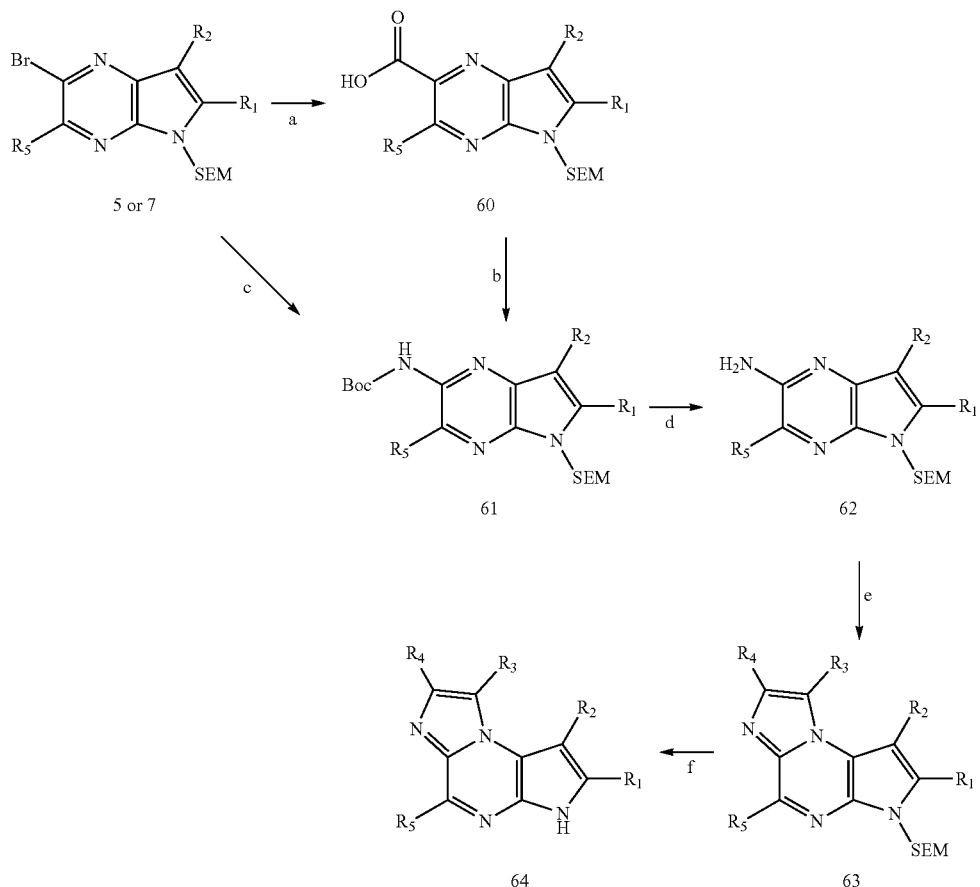

Methods for preparing 6H-imidazo[1,5-a]pyrrolo[2,3-e]pyrazin-1-amine compounds 67 of the invention are illustrated in Scheme X. The 6H-imidazo[1,5-a]pyrrolo[2,3-e]pyrazin-1-amine compounds 67 are substituted at the 7-position with an $R_1$ substituent and may be optionally substituted at the amine position and with an $R_7$ and/or $R_8$ substituent and/or the 8-position with an $R_2$ substituent and/or the 3-position with an $R_6$ substituent and/or the 4-position with an $R_5$ substituent. Therefore, $R_2$, $R_5$, $R_6$, $R_7$ and/or $R_8$ can either be hydrogen or a substituent in Scheme X. In Scheme X, the (5-((2-(trimethylsilyl)ethoxy)methyl)-5H-pyrrolo[2,3-b]pyrazin-2-yl)methanamine 13 from Scheme II can be converted to 3-((5-((2-(trimethylsilyl)ethoxy)methyl)-5H-pyrrolo[2,3-b]pyrazin-2-yl)methyl)ureas 65 (Scheme X, step a) using methods known to one skilled in the art (see, for example, X). The 3-((5-((2-(trimethylsilyl)ethoxy)methyl)-5H-pyrrolo[2,3-b]pyrazin-2-yl)methyl)ureas 65 can then be converted to 6-((2-(trimethylsilyl)ethoxy)methyl)-6H-imidazo[1,5-a]pyrrolo[2,3-e]pyrazin-1-amines 66 (Scheme X, step b) using conditions described in Y. The protecting group can then be removed (Scheme X, step c) to give the 6H-imidazo[1,5-a]pyrrolo[2,3-e]pyrazin-1-amine compounds 67 using standard conditions (for example, Greene, T. W. and Wuts, P. G. M. [referenced above] or see M). Further functionalization of any of the intermediates (for instance compounds 65-66 in Scheme X) and/or the 6H-imidazo[1,5-a]pyrrolo[2,3-e]pyrazin-1-amine compounds 67 can be performed on $R_1$, $R_2$, $R_5$, $R_6$, $R_7$ and/or $R_8$, if desired, as described for compounds 19 above or in the General Procedures below.

Scheme X

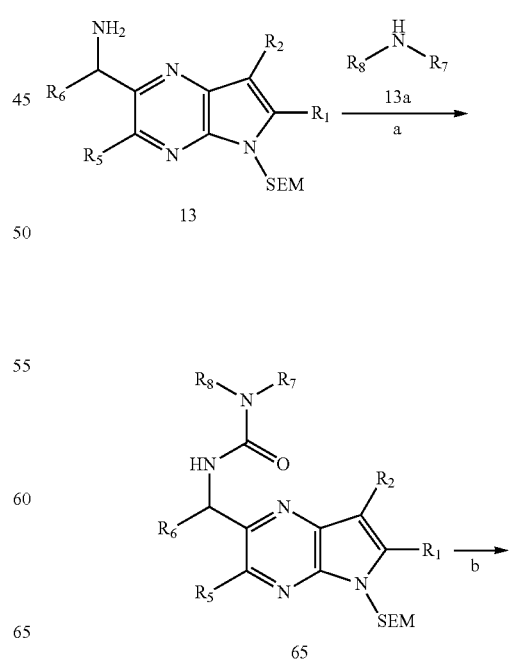

Scheme XI

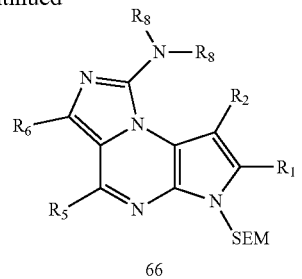

66

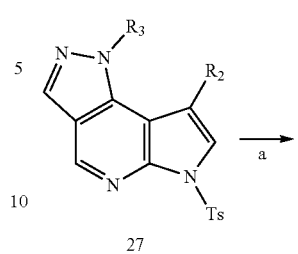

27

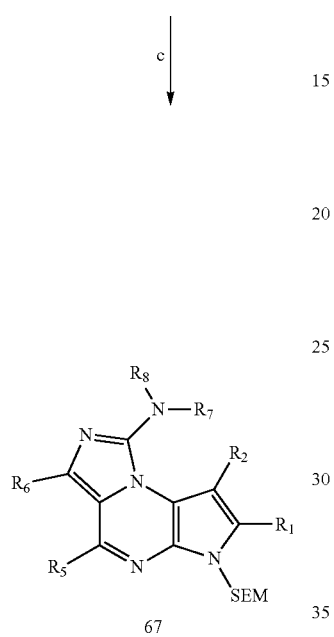

67

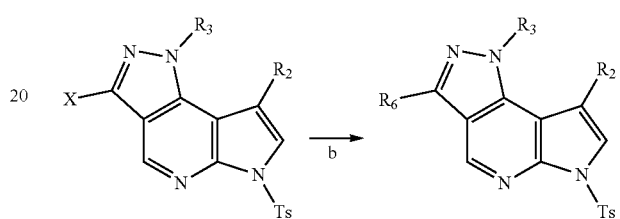

68                69

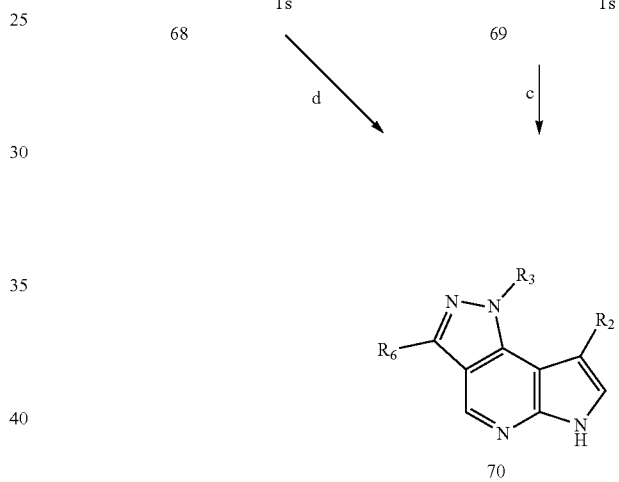

70

Methods for preparing 3-substituted-1,6-dihydropyrazolo[3,4-d]pyrrolo[2,3-b]pyridine compounds 70 of the invention are illustrated in Scheme XI. The 3-substituted-1,6-dihydropyrazolo[3,4-d]pyrrolo[2,3-b]pyridine compounds 70 are substituted at the 3-position with an $R_6$ substituent and may be optionally substituted at the 7-position and with an $R_2$ substituent and/or the 1-position with an $R_3$ substituent. Therefore, $R_2$ and/or $R_3$ can either be hydrogen or a substituent in Scheme XI. In Scheme XI, the 6-tosyl-1,6-dihydropyrazolo[3,4-d]pyrrolo[2,3-b]pyridines compounds 27 from Scheme V can be halogenated in the 3-position by methods known to one skilled in the art (for example, see AJ) to give 3-halo-6-tosyl-1,6-dihydropyrazolo[3,4-d]pyrrolo[2,3-b]pyridines 68 (Scheme XI, step a). The resulting 3-halo-6-tosyl-1,6-dihydropyrazolo[3,4-d]pyrrolo[2,3-b]pyridines 68 can then be can be converted to the 3-substituted-6-tosyl-1,6-dihydropyrazolo[3,4-d]pyrrolo[2,3-b]pyridine compounds 69 by a Suzuki coupling with aryl or heteroaryl boronic acids or esters (Suzuki, A. [referenced above] or see, for example D) followed by deprotection (Scheme XI, steps b and c) by a method known to one skilled in the art (for example, Greene, T. W. and Wuts, P. G. M. [referenced above] or see N). Alternatively, the Suzuki coupling and deprotection can be carried out in one reaction (Scheme XI, step d) using methods described in AC. Further functionalization of any of the intermediates (for instance compounds 68-69 in Scheme XI) and/or the 3-substituted-1,6-dihydropyrazolo[3,4-d]pyrrolo[2,3-b]pyridine compounds 70 can be performed on $R_2$, $R_3$ and/or $R_6$, if desired, as described for compounds 19 above or in the General Procedures below.

Methods for preparing 6H-pyrrolo[2,3-e][1,2,3]triazolo[1,5-a]pyrazine compounds 72 of the invention are illustrated in Scheme XII. The 6H-pyrrolo[2,3-e][1,2,3]triazolo[1,5-a]pyrazine compounds 72 are optionally substituted at the 7-position with an $R_1$ substituent and/or the 8-position with an $R_2$ substituent and/or the 4-position with an $R_5$ substituent and/or the 3-position with an $R_6$ substituent. Therefore, $R_1$, $R_2$, $R_5$ and/or $R_6$ can either be hydrogen or a substituent in Scheme XII. In Scheme XII, the aldhydes or ketones 9 from Scheme II are reacted with sulfonylhydrazides (for example, see AS) to give 6-((5-((2-(trimethylsilyl)ethoxy)methyl)-6H-pyrrolo[2,3-e][1,2,3]triazolo[1,5-a]pyrazines 71 (Scheme XII, step a). The protecting group can then be removed (Scheme XII, step b) to give the 6H-pyrrolo[2,3-e][1,2,3]triazolo[1,5-a]pyrazine compounds 72 using standard conditions (for example, Greene, T. W. and Wuts, P. G. M. [referenced above] or see M). Further functionalization of any of the intermediates (for instance compounds 71 in Scheme XII) and/or the 6H-pyrrolo[2,3-e][1,2,3]triazolo[1,5-a]pyrazine compounds 72 can be performed on $R_1$, $R_2$, $R_5$ and/or $R_6$, if desired, as described for compounds 19 above or in the General Procedures below.

Scheme XII

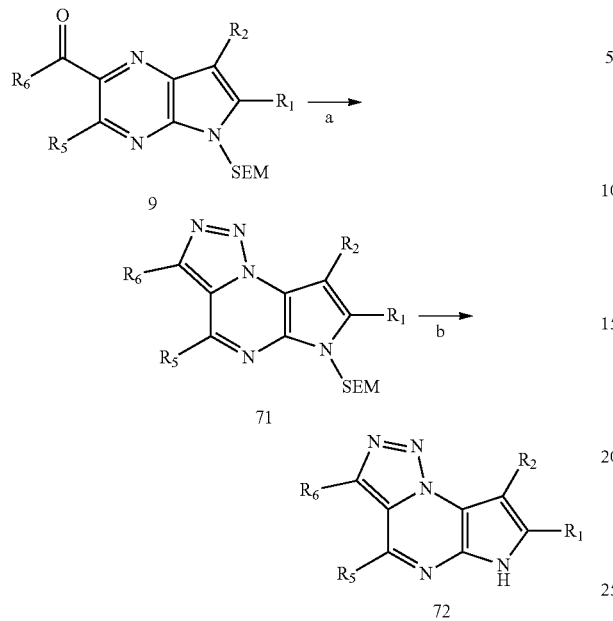

Methods for preparing 1,6-dihydropyrazolo[3,4-d]pyrrolo[2,3-b]pyridine-8-carbonitrile compounds 82 of the invention are illustrated in Scheme XIII. In this scheme, the 1,6-dihydropyrazolo[3,4-d]pyrrolo[2,3-b]pyridine-8-carbonitrile compounds 82 are substituted at the 7-position with an $R_1$ substituent and at the 8-position with a nitrile substituent and optionally substituted at the 1-position with an $R_3$ substituent. Therefore, $R_3$ can either be hydrogen or a substituent in Scheme XIII. In Scheme XIII, the 6-tosyl-1,6-dihydropyrazolo[3,4-d]pyrrolo[2,3-b]pyridines 27a can be halogenated at the 8-position (Scheme XIII, step a) using methods described in AK. The 6-tosyl-1,6-dihydropyrazolo[3,4-d]pyrrolo[2,3-b]pyridines 27a originate from the 6-tosyl-1,6-dihydropyrazolo[3,4-d]pyrrolo[2,3-b]pyridines 27 in Scheme V where the $R_2$ substituent is a hydrogen. The resulting 8-halo-6-tosyl-1,6-dihydropyrazolo[3,4-d]pyrrolo[2,3-b]pyridines 78 can then be converted to 6-tosyl-1,6-dihydropyrazolo[3,4-d]pyrrolo[2,3-b]pyridine-8-carbonitriles 79 (Scheme XIII, step b) using the methods known to one skilled in the art (Littke, A.; Soumeillant, M.; Kaltenbach, R. F., III; Chemey, R. J.; Tarby, C. M.; Kiau, S. *Organic Letters* 2007, 9, 1711-1714 or for example see AE). The 6-tosyl-1,6-dihydropyrazolo[3,4-d]pyrrolo[2,3-b]pyridine-8-carbonitriles 79 can be converted to 7-halo-1,6-dihydropyrazolo[3,4-d]pyrrolo[2,3-b]pyridine-8-carbonitriles 81 by either stepwise by halogenation (Scheme XIII, step c) through 7-chloro-6-tosyl-1,6-dihydropyrazolo[3,4-d]pyrrolo[2,3-b]pyridine-8-carbonitrile intermediates 80 followed by deprotection of the tosyl group (Scheme XIII, step d) or in directly in one reaction (Scheme XIII, step e) using the method described in Preparation #23. Deprotection of the tosyl group by a method known to one skilled in the art (for example, Greene, T. W. and Wuts, P. G. M. [referenced above] or see N) gives the 1,6-dihydropyrazolo[3,4-d]pyrrolo[2,3-b]pyridine-8-carbonitrile compounds 82. Further functionalization of any of the intermediates (for instance compounds 78-81 in Scheme XII) and/or the 6-dihydropyrazolo[3,4-d]pyrrolo[2,3-b]pyridine-8-carbonitrile compounds 82 can be performed on $R_1$ and/or $R_3$, if desired, as described for compounds 19 above or in the General Procedures below.

Scheme XIII

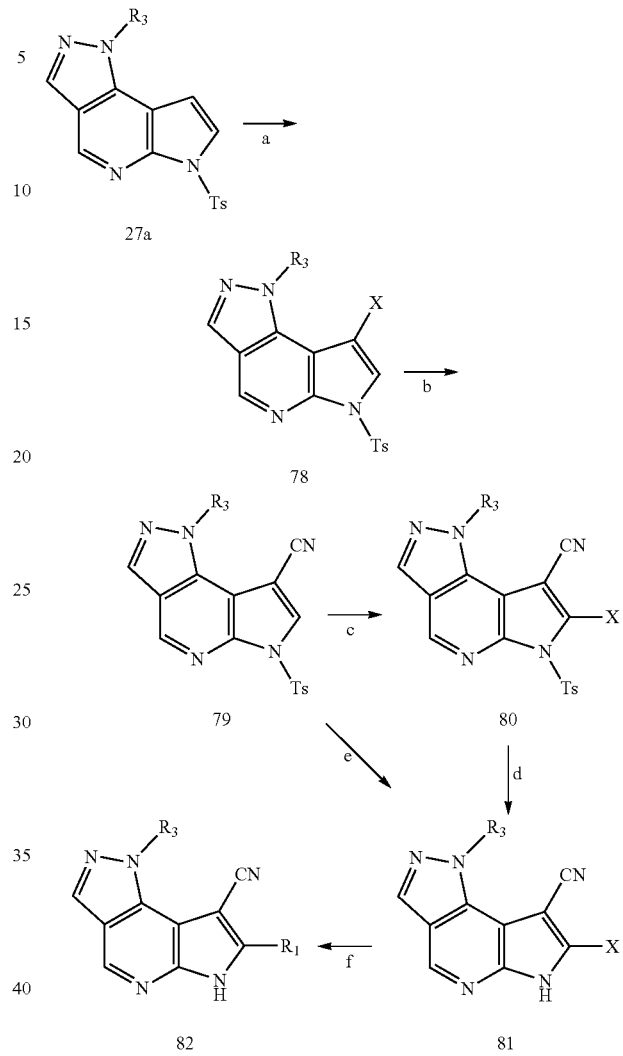

Methods for preparing 3,6-dihydroimidazo[4,5-d]pyrrolo[2,3-b]pyridin-2(1H)-one compounds 89 of the invention are illustrated in Scheme XIV. In this scheme, the 3,6-dihydroimidazo[4,5-d]pyrrolo[2,3-b]pyridin-2(1H)-one compounds 89 are substituted at the 1-position with an $R_3$ substituent and the 3-position with an $R_6$ substituent and optionally substituted at the 8-position with an $R_2$ substituent. Therefore, $R_2$ can either be hydrogen or a substituent in Scheme XIV. In Scheme XIV, the 4-chloro-1-triisopropylsilyl-1H-pyrrolo[2,3-b]pyridines 23 from Scheme IV can be converted to 4-chloro-1-(triisopropylsilyl)-1H-pyrrolo[2,3-b]pyridine-5-carboxylates 83 using the method described in Preparation #12, Step A (Scheme XIV, step a). The chloride is then displaced with an amine while also removing the triisopropyl protecting group to give 4-(amino)-1H-pyrrolo[2,3-b]pyridine-5-carboxylates 84 (Scheme XIV, step b) using the method described in Preparation #12, Step B. At this point, the 7-position can then be protected by a by a trimethylsilylethoxymethyl (Scheme XIV, step c) using C or, for example, Example #8, Step C or by methods known to one skilled in the art (for example, Larock, R. C. [referenced above] or Greene, T. W. and Wuts, P. G. M. [referenced above]) to give 4-(methylamino)-1-((2-(trimethylsilyl)

ethoxy)methyl)-1H-pyrrolo[2,3-b]pyridine-5-carboxylates 85. The ester is then hydrolyzed under basic conditions (for example, see V.1 or Preparation #12, Step D) to give 4-(methylamino)-1-((2-(trimethylsilyl)ethoxy)methyl)-1H-pyrrolo[2,3-b]pyridine-5-carboxylic acids 86 (Scheme XIV, step d). The acid functionality is then subjected to conditions for a Curtius reaction (for example, see Lebel, H. and Leogane, O. Org. Lett. 2005, 7, 4107) and the isocyante intermediate is trapped in situ by the 4-amino group to yield 1-substituted-6-((2-(trimethylsilyl)ethoxy)methyl)-3,6-dihydroimidazo[4,5-d]pyrrolo[2,3-b]pyridin-2(1H)-ones 87 (Scheme XIV, step e) using the procedure described in Preparation #12, Step E. Arylation at the 3-position is accomplished through a copper mediated coupling with an aryl boronic acid (for example see Tet. Lett. 1998, 39(19), 2933-2936) using conditions described in Preparation #13, Step F to give the 3-aryl-1-substituted-6-(2-(trimethylsilyl)ethoxy)methyl)-3,6-dihydroimidazo[4,5-d]pyrrolo[2,3-b]pyridin-2(1H)-ones 88 (Scheme XIV, step f). Finally, removal of the SEM protecting group by a method known to one skilled in the art (for example, Greene, T. W. and Wuts, P. G. M. [referenced above] or see M) gives the 3,6-dihydroimidazo[4,5-d]pyrrolo[2,3-b]pyridin-2(1H)-one compounds 89 (Scheme XIV, step g). Further functionalization of any of the intermediates (for instance compounds 83-87 in Scheme XV) and/or the 3,6-dihydroimidazo[4,5-d]pyrrolo[2,3-b]pyridin-2(1H)-one compounds 89 can be performed on $R_2$, $R_3$ and/or $R_6$, if desired, as described for compounds 19 above or in the General Procedures below.

methods known to one skilled in the art (for example, Greene, T. W. and Wuts, P. G. M. [referenced above]). The 6H-imidazo[1,5-a]pyrrolo[2,3-e]pyrazines 59a originate from the 6H-imidazo[1,5-a]pyrrolo[2,3-e]pyrazines 59a in Scheme V where the $R_2$ substituent is a hydrogen. The protecting groups may be replaced with other protecting groups by removal and then protection at any time of the sequence by methods known to one skilled in the art (for example, Greene, T. W. and Wuts, P. G. M. [referenced above]). Some general procedures for the removal of a protecting group from an N-protected heteroaromatic ring are shown in M, N, P.1 and AY while examples of the introduction of a protecting group to a heteroaromatic NH are shown in C, AM and AX. The 6H-imidazo[1,5-a]pyrrolo[2,3-e]pyrazines 59a can be obtained from Scheme VIII where the $R_2$ substituent is a hydrogen. The resulting 6-protected-6H-imidazo[1,5-a]pyrrolo[2,3-e]pyrazines 90 can then be halogenated in the 8-position with a halogenating agent (for example, see AD) to give 8-halo-6-protected-6H-imidazo[1,5-a]pyrrolo[2,3-e]pyrazines 91 (Scheme XV, step b). The resulting 8-halo-6-protected-6H-imidazo[1,5-a]pyrrolo[2,3-e]pyrazines 91 can then undergo a coupling reaction with a nitrile source to give the 6-protected-6H-imidazo[1,5-a]pyrrolo[2,3-e]pyrazine-8-carbonitrile compounds 92 (Scheme XV, step d) using methods described in AE. Removal of the protecting group (Scheme XV, step d) using methods known to one skilled in the art (for example, see C or AX or Greene, T. W. and Wuts, P. G. M. [referenced above]) gives the 6H-imidazo[1,5-a]pyrrolo[2,3-e]pyrazine-8-carbonitrile compounds 93. Additionally, the 8-halo-6-pro- Scheme XIV

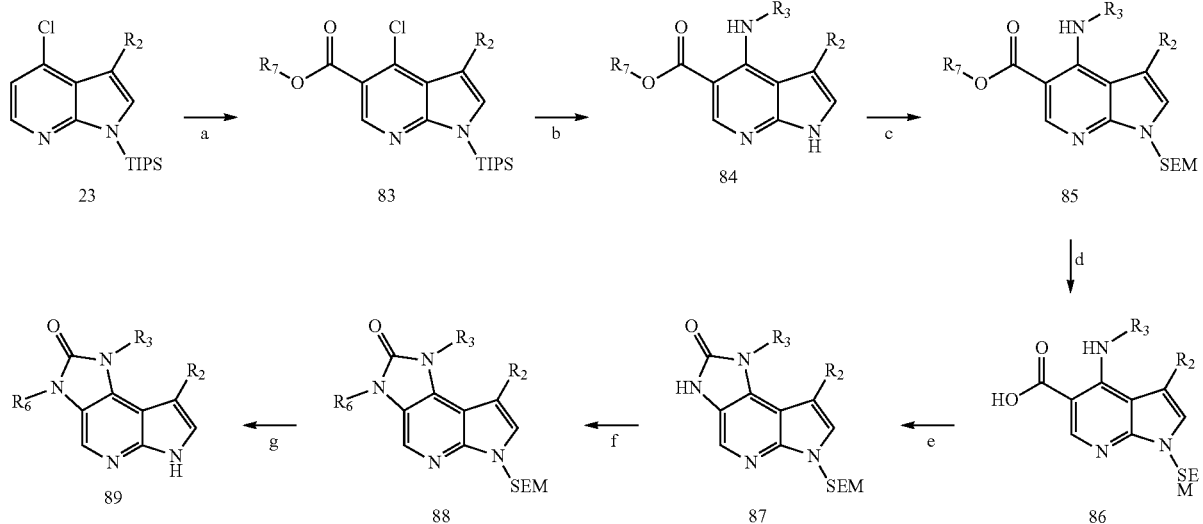

Methods for preparing 6H-imidazo[1,5-a]pyrrolo[2,3-e]pyrazine-8-carbonitrile compounds 91 of the invention are illustrated in Scheme XV. In this scheme, the 6H-imidazo[1,5-a]pyrrolo[2,3-e]pyrazine-8-carbonitrile compounds 91 are substituted at the 3-position with an $R_6$ substituent and at the 8-position with a nitrile substituent and optionally substituted at the 1-position with an $R_3$ substituent and/or 4-position with an $R_5$ substituent. Therefore, $R_3$ and/or $R_5$ can either be hydrogen or a substituent in Scheme XV. In Scheme XV, the 6H-imidazo[1,5-a]pyrrolo[2,3-e]pyrazines 59a can be protected at the 6-position with a suitable protecting group such as a TIPS or a SEM using AX or C (Scheme XV, step a) or by tected-6H-imidazo[1,5-a]pyrrolo[2,3-e]pyrazines 91 could be used as a starting material for an alternate way to prepare 3-substituted-imidazo[1,5-a]pyrrolo[2,3-e]pyrazine compounds 59 (See Scheme VIII) by methods described above (Scheme XV, steps e and f). In either case further functionalization of the intermediates (for instance compounds 90-92 in Scheme XV) and/or the 6H-imidazo[1,5-a]pyrrolo[2,3-e]pyrazine-8-carbonitrile compounds 93 can be performed on $R_3$, $R_5$ and/or $R_6$ or functionalization of the intermediates 54a along with the 3-substituted-imidazo[1,5-a]pyrrolo[2,3-e]pyrazine compounds 59 can be performed on $R_2$, $R_3$, $R_5$ and/or $R_6$, if desired, as described for compounds 19 above or in the General Procedures below.

Scheme XV

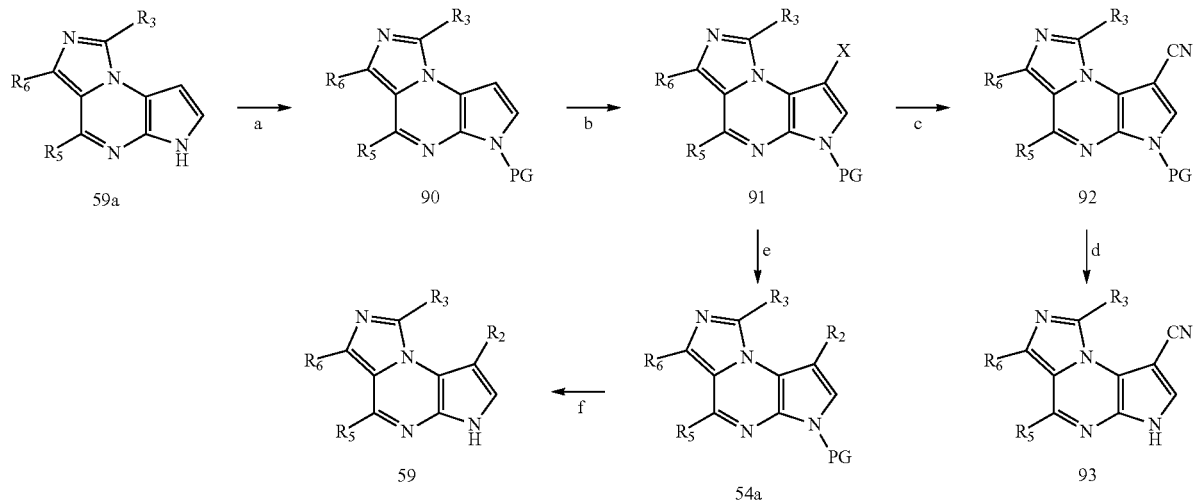

Methods for preparing 6H-imidazo[1,5-a]pyrrolo[2,3-e]pyrazin-1-amine compounds 105 of the invention are illustrated in Scheme XVIII. In this scheme, the 6H-imidazo[1,5-a]pyrrolo[2,3-e]pyrazin-1-amine compounds 105 are substituted at the 3-position with an $R_6$ substituent and may be optionally substituted at the amine position with and $R_7$ and/or $R_8$ substituent and/or at the 8-position with an $R_2$ substituent and/or the 4-position with an $R_5$ substituent. Therefore, $R_2$, $R_5$, $R_7$ and $R_8$ can either be hydrogen or a substituent in Scheme XVI. In Scheme XVI, there are two routes described. The first route involves starting with (5-tosyl-5H-pyrrolo[2,3-b]pyrazin-2-yl)methanamines 49, prepared in Scheme VI, and reacting with amines 49a using methods described in X to give 1-((5-tosyl-5H-pyrrolo[2,3-b]pyrazin-2-yl)methyl)ureas 100 (Scheme XVI, step a). The 1-((5-tosyl-5H-pyrrolo[2,3-b]pyrazin-2-yl)methyl)ureas 100 can then be converted to 6-tosyl-6H-imidazo[1,5-a]pyrrolo[2,3-e]pyrazin-1-amines 101 (Scheme XVI, step b) using conditions described in Y. Halogenation at the 3-position can be done using methods known to one skilled in the art (for example, see AB) to give 3-halo-6-tosyl-6H-imidazo[1,5-a]pyrrolo[2,3-e]pyrazin-1-amines 102 (Scheme XVI, step c). The 6H-imidazo[1,5-a]pyrrolo[2,3-e]pyrazin-1-amine compounds 105 are obtained by a Suzuki coupling (for example, see D or Suzuki A., [referenced above]) followed by deprotection of the tosyl group (Scheme XVI, steps d and g) using methods known to one skilled in the art (for example, see N or Greene, T. W. and Wuts, P. G. M. [referenced above]). Alternatively, the Suzuki reaction and tosyl deprotection could take place in one step (Scheme XVI, step h) in a manner similar to Scheme VI (for example, see AC). A second route starts from amines 56, prepared in Scheme VI, where $R_6$ is a substituent. A similar sequence as described above using X to form the 1-(1-(5-tosyl-5H-pyrrolo[2,3-b]pyrazin-2-yl)alkyl)ureas 103 followed by Y to give 3-substituted-6-tosyl-6H-imidazo[1,5-a]pyrrolo[2,3-e]pyrazin-1-amines 104 (Scheme XVI, steps e and f). Deprotection of the tosyl group as described above then yields 6H-imidazo[1,5-a]pyrrolo[2,3-e]pyrazin-1-amine compounds 105 (Scheme XVI, step g). Compound 105 is related to the 6H-imidazo[1,5-a]pyrrolo[2,3-e]pyrazin-1-amine compounds 67 from Scheme X where the $R_1$ substituent is a hydrogen. Further functionalization of any of the intermediates (for instance compounds 100-104 in Scheme XVI) and/or the 6H-imidazo[1,5-a]pyrrolo[2,3-e]pyrazin-1-amine compounds 105 can be performed on $R_2$, $R_5$, $R_6$, $R_7$ and/or $R_8$, if desired, as described for compounds 19 above or in the General Procedures below.

Scheme XVI

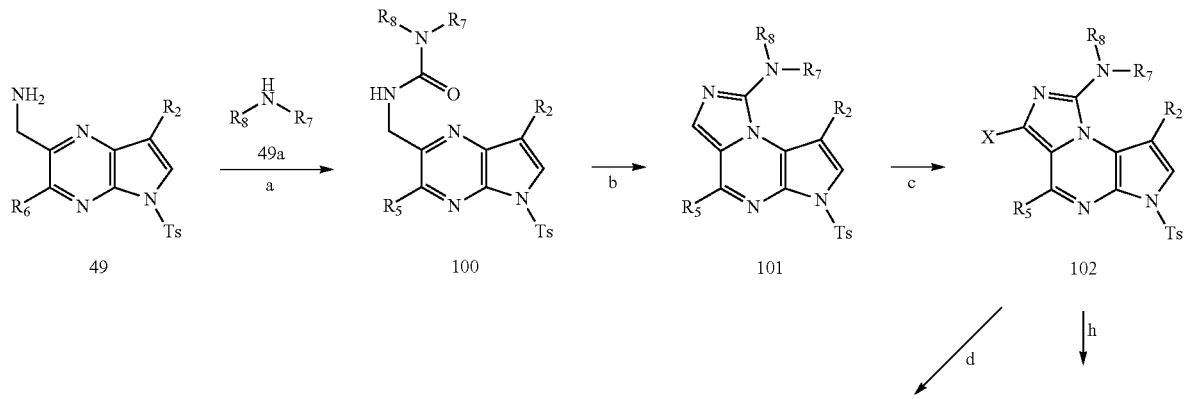

-continued

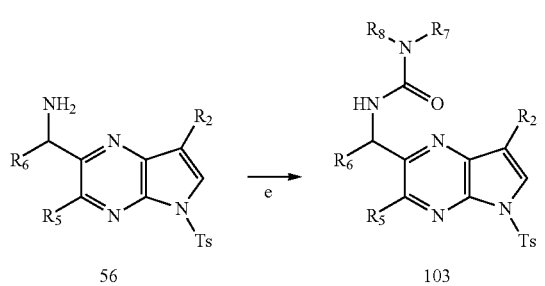

56

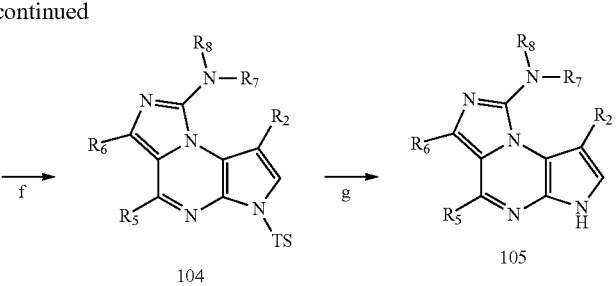

103  104  105

GENERAL PROCEDURES AND EXAMPLES

The general synthetic schemes that were utilized to construct the majority of compounds disclosed in this application are described below in Schemes 1-61. These schemes are provided for illustrative purposes only and are not to be construed as limiting the scope of the invention.

Scheme 1. Sonogashira reaction of a terminal alkyne with an aryl or herteroaryl halide (General Procedure A)

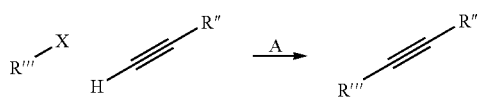

Scheme 2. Formation of 5H-pyrrolo[2,3-b]pyrazine from a 3-alkynylpyrazin-2-amine (General Procedure B)

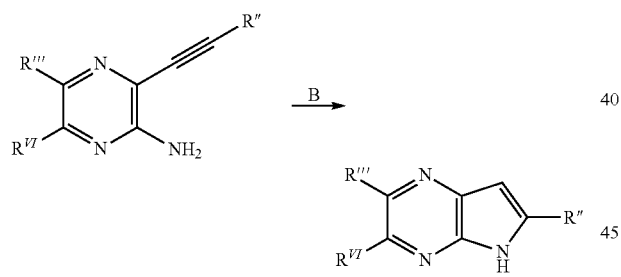

Scheme 3. Formation of an N-SEM protected heteroaromatic ring (General Procedure C)

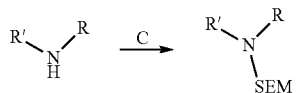

Scheme 4. Suzuki reaction of a boronic acid or boronate with an aryl or heteroaryl halide (General Procedure D)

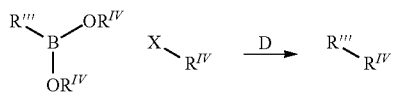

Scheme 5. Lemieuz-Johnson oxidation of an alkene to an aldehyde (General Procedure E)

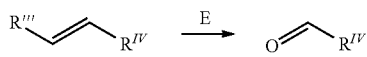

Scheme 6. Reduction of an aldehyde or ketone to an alcohol (General Procedure F)

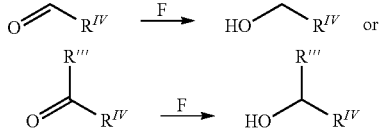

Scheme 7. Conversion of an alkyl alcohol to an alkyl azide (General Procedure G)

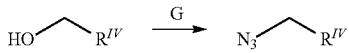

Scheme 8. Conversion of an aryl or heteroaryl halide to an aryl or heteroaryl boronate or aryl or heteroaryl boronic acid (General Procedure H)

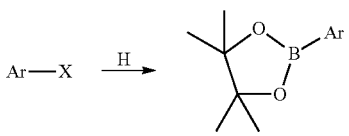

Scheme 9. Reduction of an alkyl azide to an alkyl amine (General Procedure I)

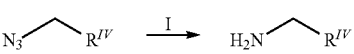

Scheme 10. Formation of an amide from an amine and a carboxylic acid or carboxylate salt (General Procedure J.1)

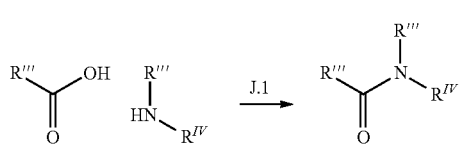

Scheme 11. Formation of an amide from an amine and an carboxylic acid chloride or carboxylic acid anhydride (General Procedure J.2)

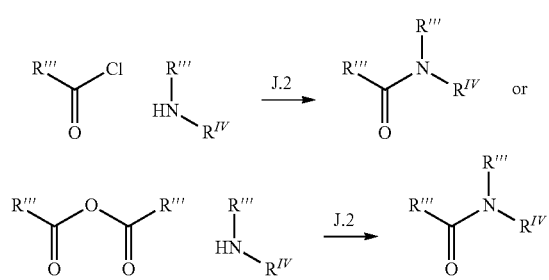

Scheme 12. Formation of a formamide from an amine and a fromate or an orthoformate (General Procedure J.3)

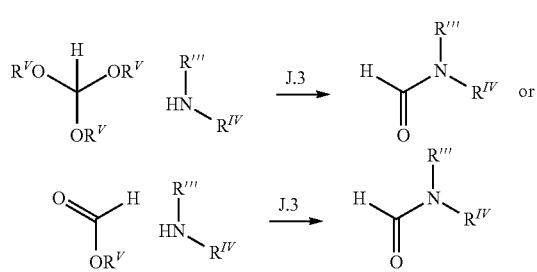

Scheme 13. Formation of a sulfonamide from an amine and a sulfonyl chloride (General Procedure K)

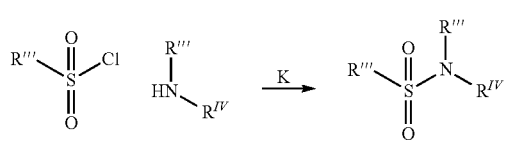

Scheme 14. Cyclization to form a 6H-imidazo[1,5-a]pyrrolo[2,3-e]pyrazine from an N-((5H-pyrrolo[2,3-b]pyrazin-2-yl)methyl)amide with Lawesson's reagent and a mercuric salt (General Procedure L.1)

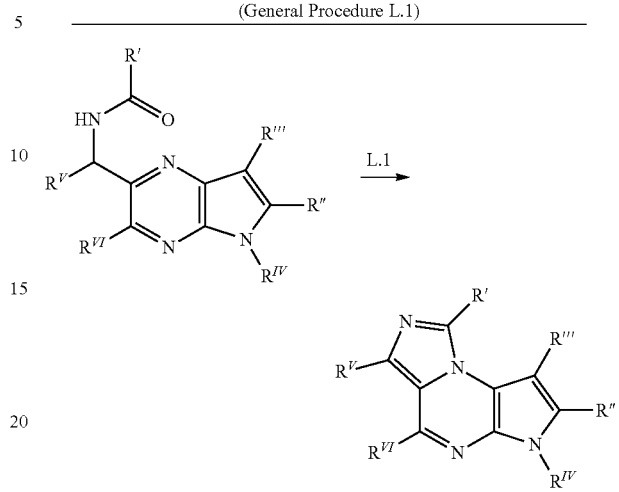

Scheme 15. Cyclization to form a 6H-imidazo[1,5-a]pyrrolo[2,3-e]pyrazine from an N-((5H-pyrrolo[2,3-b]pyrazin-2-yl)methyl)amide with anhydrous acidic conditions (General Procedure L.2)

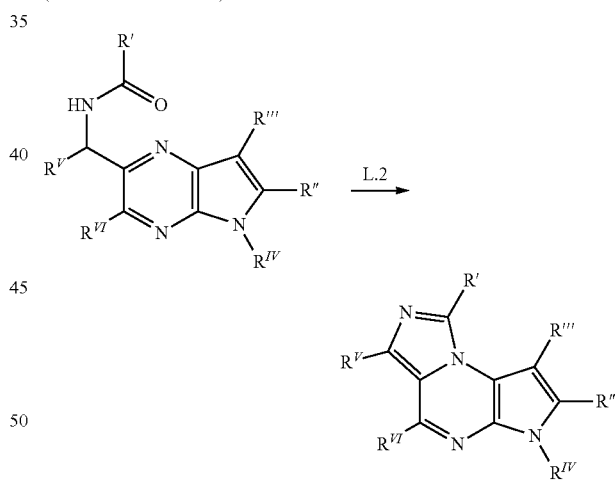

Scheme 16. Removal of a SEM group from an N-SEM protected heteroaromatic ring (General Procedure M)

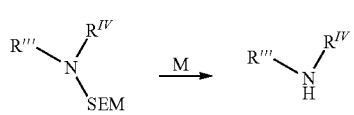

Scheme 17. Removal of a tosyl group from an N-tosyl protected heteroaromatic ring (General Procedure N)

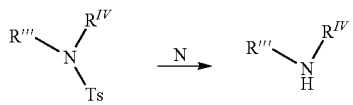

Scheme 22. Removal of a TMS group from a TMS protected alkyne (General Procedure Q)

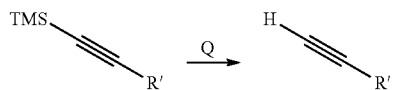

Scheme 18. Reaction of a 2-bromo-5H-pyrrolo[2,3-b]pyrazine with a hydrazine (General Procedure O)

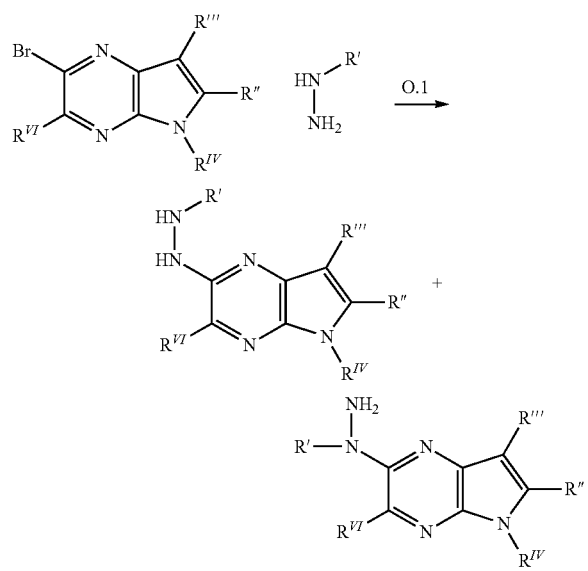

Scheme 23. Formation of a 6H-pyrrolo[2,3-e][1,2,4]triazolo[4,3-a]pyrazine from a 2-hydrazinyl-5H-pyrrolo[2,3-b]pyrazine using an aldehyde (General Procedure R.1)

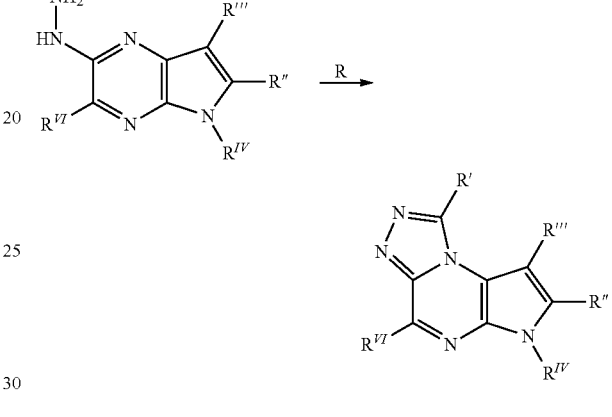

Scheme 19. Removal of a Boc group from an N-Boc protected heteroaromatic ring (General Procedure P.1)

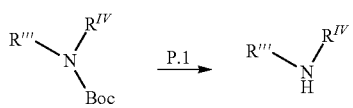

Scheme 24. Formation of a 6H-pyrrolo[2,3-e][1,2,4]triazolo[4,3-a]pyrazine from a 2-hydrazinyl-5H-pyrrolo[2,3-b]pyrazine using an orthoester (General Procedure R.2)

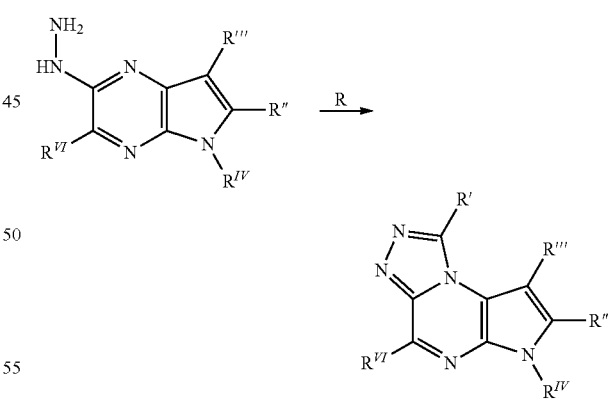

Scheme 20. Removal of a Boc group from an N-Boc protected hydrazine (General Procedure P.2)

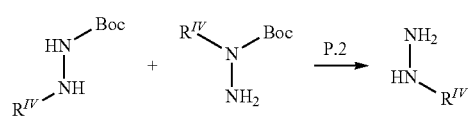

Scheme 21. Removal of a Boc protecting group from an N-Boc protected amine (General Procedure P.3)

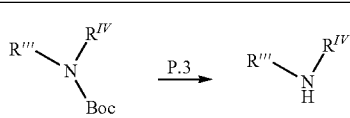

Scheme 25. Reaction of a Grignard reagent with a ketone or aldehyde to give an alcohol (General Procedure S)

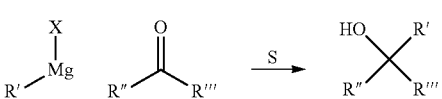

Scheme 26. Removal of a Boc group from an N-Boc proected amine and a SEM group from an N'-SEM protected heteroaromatic ring (General Procedure T.1)

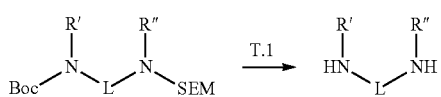

Scheme 27. Removal of a Fmoc group from an N-Fmoc protected amine and a SEM group from an N'-SEM protected heteroaromatic ring (General Procedure T.2)

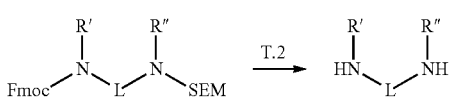

Scheme 28. Removal of a Boc group from an N-Boc protected amine and a tosyl group from an N'-tosyl protected heteroaromatic ring (General Procedure T.3)

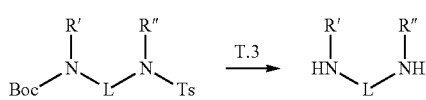

Scheme 29. Removal of an Fmoc group from an N-Fmoc protected amine and tosyl group from an N'-tosyl protected heteroaromatic ring (General Procedure T.4)

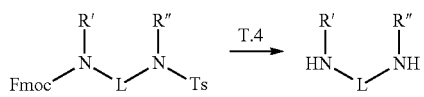

Scheme 30. Alkylation of an indole, 1H-pyrrolo[3,2-b]pyridine or 5H-pyrrolo[2,3-b]pyrazine (General Procedure U)

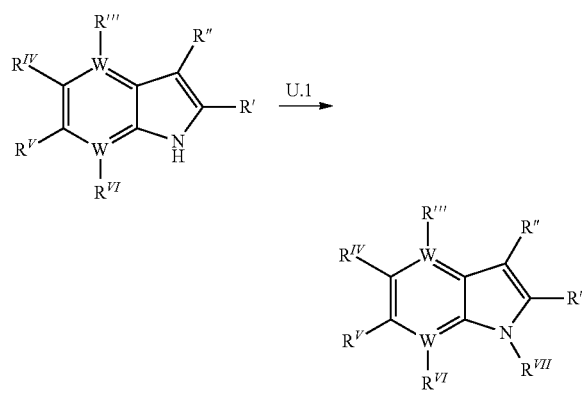

Scheme 31. Conversion of an ester to a carboxylic acid under basic conditions (General Procedure V.1)

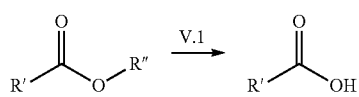

Scheme 32. Conversion of an ester to a carboxylic acid under acidic conditions (General Procedure V.2)

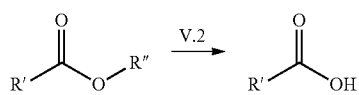

Scheme 33. Preparation fo a ketone from a ketal (General Procedure W)

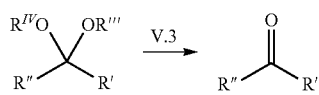

Scheme 34. Formation of a urea from two amines (General Procedure X)

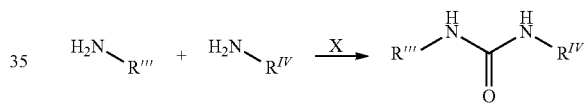

Scheme 35. Formation of 6H-imidazo[1,5-a]pyrrolo[2,3-e]pyrazin-1-amine from a 1-((5H-pyrrolo[2,3-b]pyrazin-2-yl)methyl)urea (General Procedure Y)

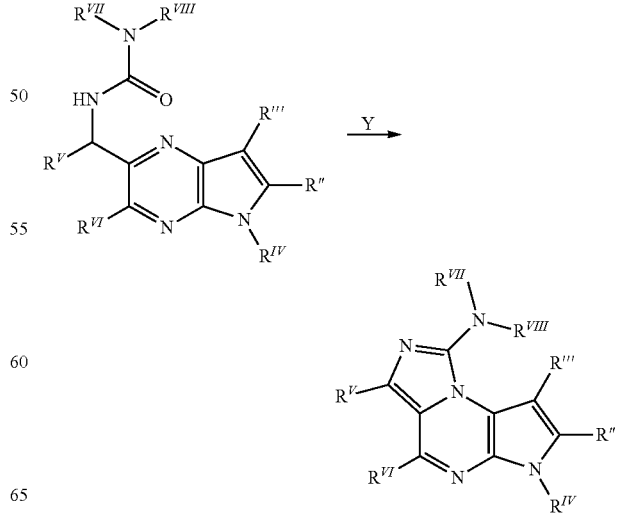

Scheme 36. Removal of a silyl group from an O-silyl protected alcohol (General Procedure Z)

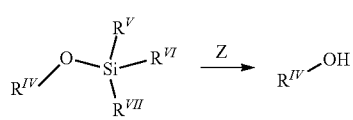

Scheme 37. Grignard addition to an ester to give an alcohol (General Procedure AA)

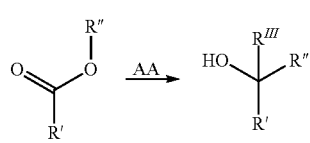

Scheme 38. Conversion of a 6H-imidazo[1,5-a]pyrrolo[2,3-e]pyrazine to a 3-halo-6H-imidazo[1,5-a]pyrrolo[2,3-e]pyrazine (General Procedure AB)

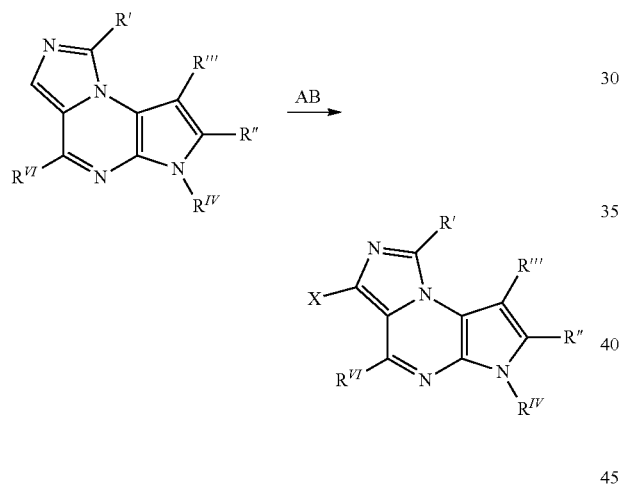

Scheme 39. Suzuki reaction of an aryl or heteroaryl halide with a boronic acid or boronic ester with removal of a tosyl group from an N-tosyl protected heteroaromatic ring (General Procedure AC)

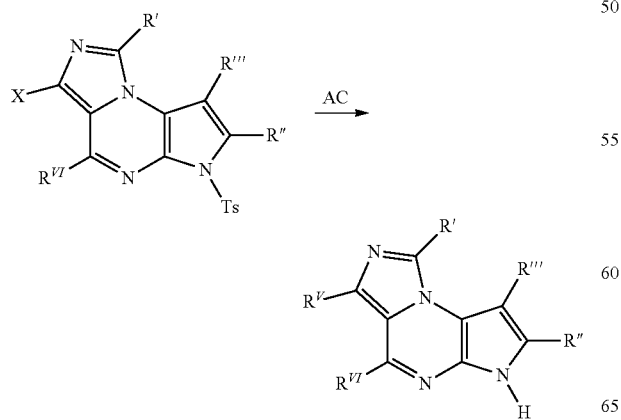

Scheme 40. Conversion of 6H-imidazo[1,5-a]pyrrolo[2,3-e]pyrazine to a 8-halo-6H-imidazo[1,5-a]pyrrolo[2,3-e]pyrazine (General Procedure AD)

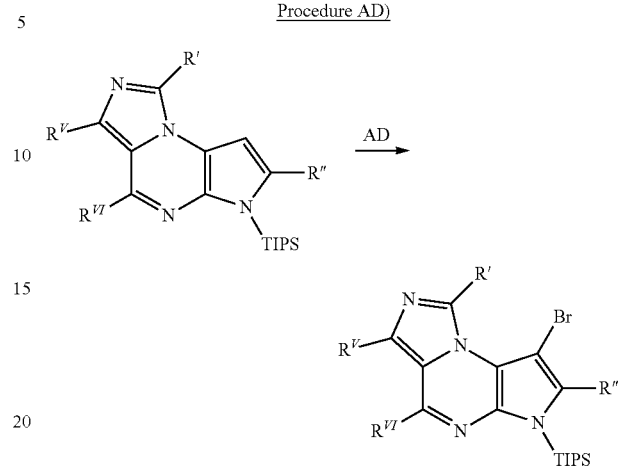

Scheme 41. Cyanation of an aryl halide (General Procedure AE)

Scheme 42. Addition of a Grignard reagent to a nitrile (General Procedure AF)

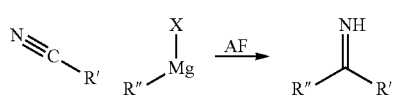

Scheme 43. Reduction of an imine to an amine (General Procedure AG)

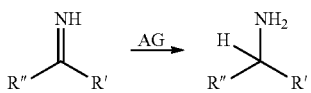

Scheme 44. Reductive amination of an aldehyde or ketone (General Procedure AH)

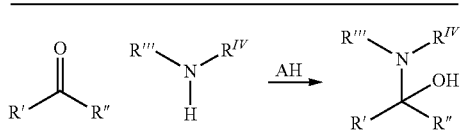

Scheme 45. Halogenation of a 6H-imidazo[1,5-a]pyrrolo[2-3-e]pyrazine to give a 1-halo-6H-imidazo[1,5-a]pyrrolo[2,3-e]pyrazine (General Procedure AI)

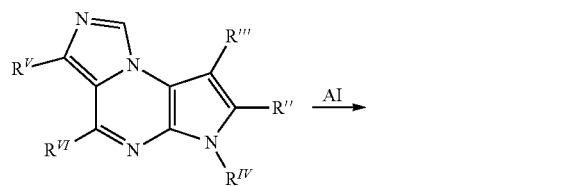

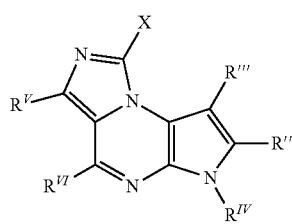

Scheme 46. Halogenation of a 1,6-dihydropyrazolo[3,4-d]pyrrolo[2,3-b]pyridine to give a 3-halo-1,6-dihydropyrazolo[3,4-d]pyrrolo[2,3-b]pyridine (General Procedure AJ)

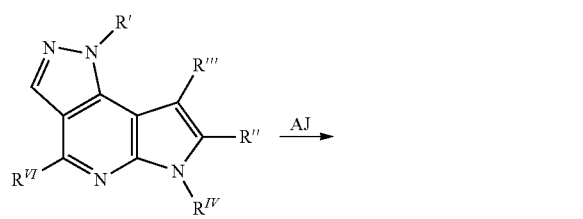

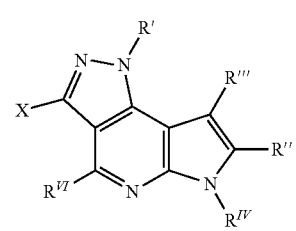

Scheme 47. Halogenation of a 1,6-dihydropyrazolo[3,4-d]pyrrolo[2,3-b]pyridine to give an 8-halo-1,6-dihydropyrazolo[3,4-d]pyrrolo[2,3-b]pyridine (General Procedure AK)

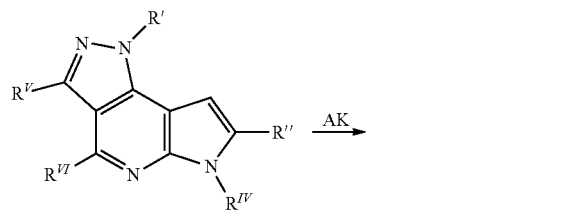

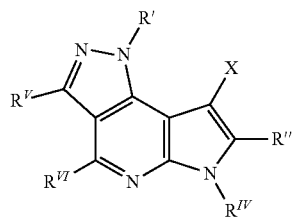

Scheme 48. Formation of a 6-(4-methoxyphenyl)-5-((2-(trimethylsilyl)ethoxy)methyl)-5H-pyrrolo[2,3-b]pyrazine from a 3-((aryl)ethynyl)pyrazin-2-amine from a 3-alkynylpyrazin-2-amine (General Procedure AM)

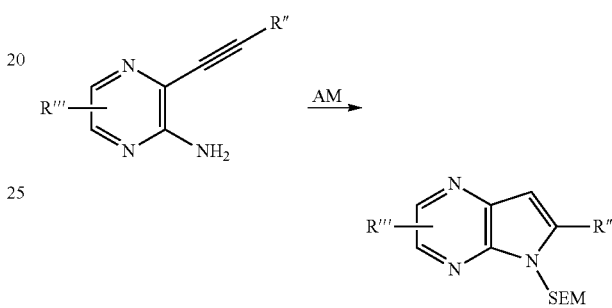

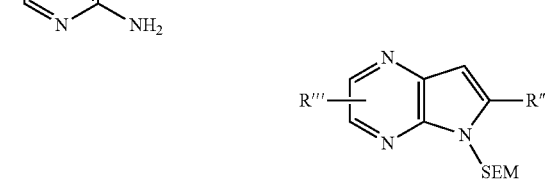

Scheme 49. Hydrolysis of an ester to a carboxylic acid under basic conditions and removal of a tosyl group from an N-tosyl protected heteroaryl ring (General Procedure AN)

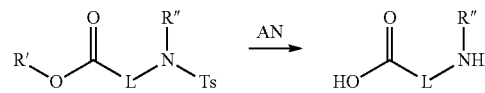

Scheme 50. Formation of an carboxylic acid chloride from a carboxylic acid (General Procedure AO)

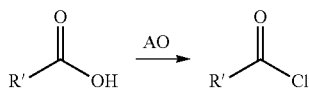

Scheme 51. Formation of an N-Boc protected amine (General Procedure AP.1)

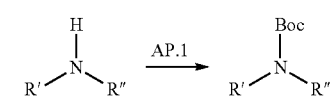

Scheme 52. Formation of an N-Fmoc protected amine (General Procedure AP.2)

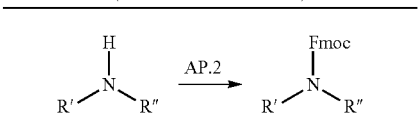

Scheme 53. Formation of a 3-halo-1-alkyl-1H-indole from a 1H-indole or a 3-halo-1-alkyl-1H-pyrrolo[3,2-c]pyridine from a 1H-pyrrolo[3,2-c]pyridine (General Procedure AQ)

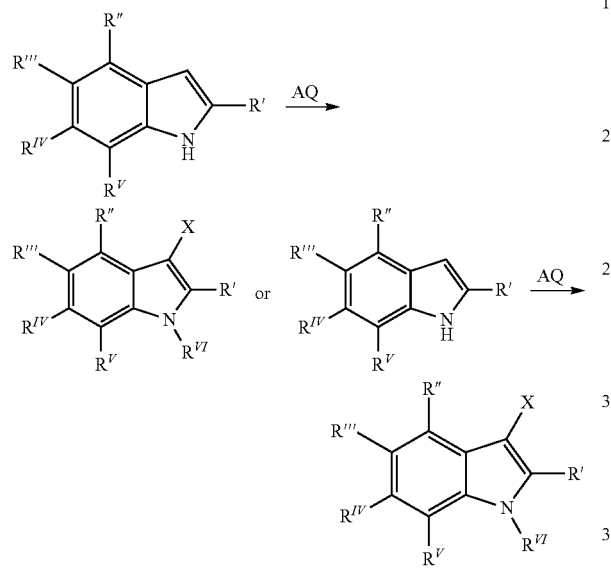

Scheme 54. Oxidation of a sulfide to a sulfone (General Procedure AR)

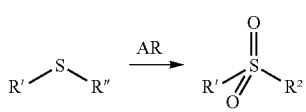

Scheme 55. Preparation of a 6H-pyrrolo[2,3-e][1,2,3]triazole[1,5-a]pyrazine from a 2-carbonyl-5H-pyrrolo[2,3-b]pyrazine (General Procedure AS)

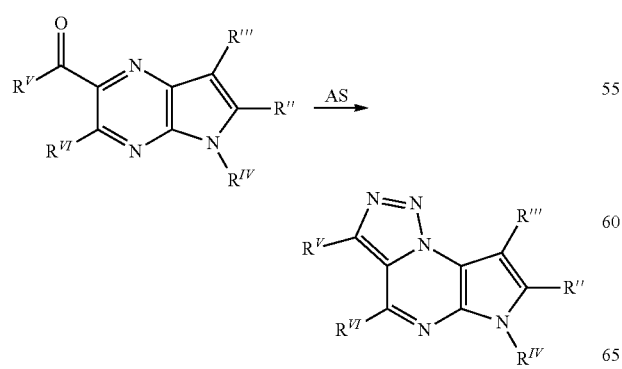

Scheme 56. Hydrolysis of an imine to a ketone (General Procedure AT)

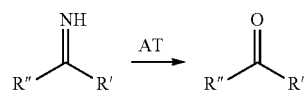

Scheme 57. Preparation of a 1,6-dihydropyrazolo[3,4-d] pyrrolo[2,3-b]pyridine from a 5-carbnyl-4-chloro-1H-pyrrolo[2,3-b]pyridine (General Procedure AU)

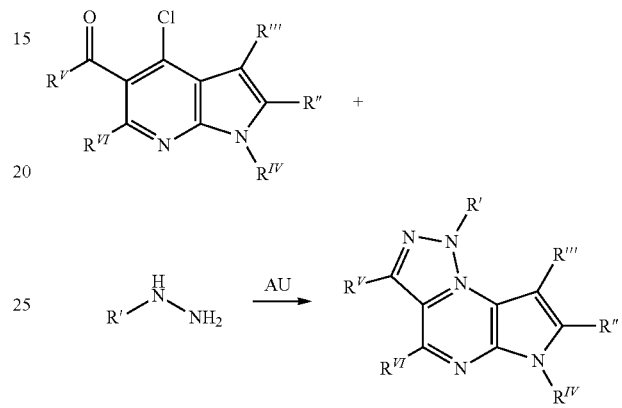

Scheme 58. Oxidation of an alcohol to a ketone (General Procedure AV)

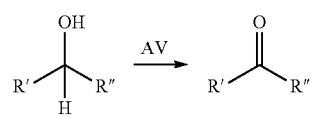

Scheme 59. Removal of a PMB group from an O-PMB protected alcohol (General Procedure AW)

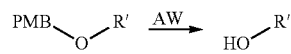

Scheme 60. Formation of an N-TIPS protected heteroaryl ring (General Procedure AX)

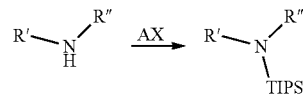

Scheme 61. Removal of a TIPS group from an N-TIPS protected heteroaryl ring (General Procedure AY)

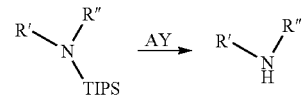

List of General Procedures

| | |
|---|---|
| General Procedure A | Sonogashira reaction of a terminal alkyne with an aryl or heteroaryl halide |
| General Procedure B | Formation of a 5H-pyrrolo[2,3-b]pyrazine from a 3-alkynylpyrazin-2-amine |
| General Procedure C | Formation of an N-SEM protected heteroaromatic ring |
| General Procedure D | Suzuki reaction of a boronic acid or boronate with an aryl or heteroaryl halide |
| General Procedure E | Lemieux-Johnson oxidation of an alkene to an aldehyde |
| General Procedure F | Reduction of an aldehyde or ketone to an alcohol |
| General Procedure G | Conversion of an alkyl alcohol to an alkyl azide |
| General Procedure H | Conversion of an aryl/heteroaryl halide to an aryl/heteroaryl boronate or aryl/heteroaryl boronic acid |
| General Procedure I | Reduction of an alkyl azide to an alkyl amine |
| General Procedure J.1 | Formation of an amide from an amine and a carboxylic acid or carboxylate salt |
| General Procedure J.2 | Formation of an amide from an amine and an carboxylic acid chloride or carboxylic acid anhydride |
| General Procedure J.3 | Formation of a formamide from an amine and a formate or an orthoformate |
| General Procedure K | Formation of a sulfonamide from an amine and a sulfonyl chloride |
| General Procedure L.1 | Cyclization to form a 6H-imidazo[1,5-a]pyrrolo[2,3-e]pyrazine from an N-((5H-pyrrolo[2,3-b]pyrazin-2-yl)methyl)amide with Lawesson's reagent and a mercuric salt |
| General Procedure L.2 | Cyclization to form a 6H-imidazo[1,5-a]pyrrolo[2,3-e]pyrazine from an N-((5H-pyrrolo[2,3-b]pyrazin-2-yl)methyl)amide with anhydrous acidic conditions |
| General Procedure M | Removal of a SEM group from an N-SEM protected heteroaromatic ring |
| General Procedure N | Removal of a tosyl group from an N-tosyl protected heteroaromatic ring |
| General Procedure O | Reaction of a 2-bromo-5H-pyrrolo[2,3-b]pyrazine with a hydrazine |
| General Procedure P.1 | Removal of a Boc group from an N-Boc protected heteroaromatic ring |
| General Procedure P.2 | Removal of a Boc group from an N-Boc protected hydrazine |
| General Procedure P.3 | Removal of a Boc group from an N-Boc protected amine |
| General Procedure Q | Removal of a TMS group from a TMS protected alkyne |
| General Procedure R.1 | Formation of a 6H-pyrrolo[2,3-e][1,2,4]triazolo[4,3-a]pyrazine from a 2-hydrazinyl-5H-pyrrolo[2,3-b]pyrazine using an aldehyde |
| General Procedure R.2 | Formation of a 6H-pyrrolo[2,3-e][1,2,4]triazolo[4,3-a]pyrazine from a 2-hydrazinyl-5H-pyrrolo[2,3-b]pyrazine using an orthoester |
| General Procedure S | Reaction of a Grignard reagent with a ketone or aldehyde to give an alcohol |
| General Procedure T.1 | Removal of a Boc group from an N-Boc proected amine and a SEM group from an N'-SEM protected heteroaromatic ring |
| General Procedure T.2 | Removal of an Fmoc group from an N-Fmoc protected amine and a SEM group from an N'-SEM protected heteroaromatic ring |
| General Procedure T.3 | Removal of a Boc group from an N-Boc protected amine and a tosyl group from an N'-tosyl protected heteroaromatic ring |
| General Procedure T.4 | Removal of an Fmoc group from an N-Fmoc protected amine and a tosyl group from an N'-tosyl protected heteroaromatic ring |
| General Procedure U | Alkylation of an indole, 1H-pyrrolo[3,2-b]pyridine or 5H-pyrrolo[2,3-b]pyrazine |
| General Procedure V.1 | Conversion of an ester to a carboxylic acid under basic conditions |
| General Procedure V.2 | Conversion of an ester to a carboxylic acid under acidic conditions |
| General Procedure W | Preparation of a ketone from a ketal |
| General Procedure X | Formation of a urea from two amines |
| General Procedure Y | Formation of a 6H-imidazo [1,5-a]pyrrolo[2,3-e]pyrazin-1-amine from a 1-((5H-pyrrolo[2,3-b]pyrazin-2-yl)methyl)urea |
| General Procedure Z | Removal of a silyl group from an O-silyl protected alcohol |
| General Procedure AA | Grignard addition to an ester to give an alcohol |
| General Procedure AB | Conversion of a 6H-imidazo[1,5-a]pyrrolo[2,3-e]pyrazine to a 3-halo-6H-imidazo[1,5-a]pyrrolo[2,3-e]pyrazine |
| General Procedure AC | Suzuki reaction of an aryl or heteroaryl halide with a boronic acid or boronic ester with removal of a tosyl group from an N-tosyl protected heteroaromatic ring |
| General Procedure AD | Conversion of a 6H-imidazo[1,5-a]pyrrolo[2,3-e]pyrazine to a 8-halo-6H-imidazo[1,5-a]pyrrolo[2,3-e]pyrazine |
| General Procedure AE | Cyanation of an aryl halide |
| General Procedure AF | Addition of a Grignard reagent to a nitrile |
| General Procedure AG | Reduction of an imine to an amine |
| General Procedure AH | Reductive amination of an aldehyde or ketone |
| General Procedure AI | Halogenation of a 6H-imidazo[1,5-a]pyrrolo[2,3-e]pyrazine to give a 1-halo-6H-imidazo[1,5-a]pyrrolo[2,3-e]pyrazine |

-continued

| General Procedure AJ | Halogenation of a 1,6-dihydropyrazolo[3,4-d]pyrrolo[2,3-b]pyridine to give a 3-halo-1,6-dihydropyrazolo[3,4-d]pyrrolo[2,3-b]pyridine |
|---|---|
| General Procedure AK | Halogenation of a 1,6-dihydropyrazolo[3,4-d]pyrrolo[2,3-b]pyridine to give an 8-halo-1,6-dihydropyrazolo[3,4-d]pyrrolo[2,3-b]pyridine |
| General Procedure AM | Formation of a 6-(4-methoxyphenyl)-5-((2-(trimethylsilyl)ethoxy)methyl)-5H-pyrrolo[2,3-b]pyrazine from a 3-((aryl)ethynyl)pyrazin-2-amine from a 3-alkynylpyrazin-2-amine |
| General Procedure AN | Hydrolysis of an ester to a carboxylic acid under basic conditions and removal of a tosyl group from an N-tosyl protected heteroaryl ring |
| General Procedure AO | Formation of an carboxylic acid chloride from a carboxylic acid |
| General Procedure AP.1 | Formation of an N-Boc protected amine |
| General Procedure AP.2 | Formation of an N-Fmoc protected amine |
| General Procedure AQ | Formation of a 3-halo-1-alkyl-1H-indole from a 1H-indole or a 3-halo-1-alkyl-1H-pyrrolo[3,2-c]pyridine from a 1H-pyrrolo[3,2-c]pyridine |
| General Procedure AR | Oxidation of a sulfide to a sulfone |
| General Procedure AS | Preparation of a 6H-pyrrolo[2,3-e][1,2,3]triazole[1,5-a]pyrazine from a 2-carbonyl-5H-pyrrolo[2,3-b]pyrazine |
| General Procedure AT | Hydrolysis of an imine to a ketone |
| General Procedure AU | Preparation of a 1,6-dihydropyrazolo[3,4-d]pyrrolo[2,3-b]pyridine from a 5-carbonyl-4-chloro-1H-pyrrolo[2,3-b]pyridine |
| General Procedure AV | Oxidation of an alcohol to a ketone |
| General Procedure AW | Removal of a PMB group from an O-PMB protected alcohol |
| General Procedure AX | Formation of an N-TIPS protected heteroaryl ring |
| General Procedure AY | Removal of a TIPS group from an N-TIPS protected heteroaryl ring |

The following examples are ordered according to the final general procedure used in their preparation. The synthetic routes to any novel intermediates are detailed by sequentially listing the general procedure (letter codes) in parentheses after their name with additional reactants or reagents as appropriate. A worked example of this protocol is given below using Example #W.1 as a non-limiting illustration. Example #W.1 is 1-(4-(8-ethyl-1-methyl-6-((2-(trimethylsilyl)ethoxy)methyl)-6H-imidazo[1,5-a]pyrrolo[2,3-e]pyrazin-7-yl)phenyl)ethanone, which was prepared from 8-ethyl-1-methyl-7-(4-(2-methyl-1,3-dioxolan-2-yl)phenyl)-6-((2-(trimethylsilyl)ethoxy)methyl)-6H-imidazo[1,5-a]pyrrolo[2,3-e]pyrazine using W as represented in Scheme A.

Scheme A

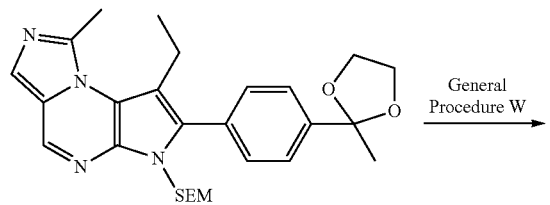

Precursor to Example #W.1

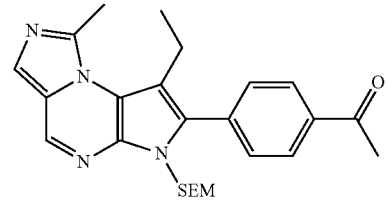

Example #W.1

The precursor to Example #W.1,8-ethyl-1-methyl-7-(4-(2-methyl-1,3-dioxolan-2-yl)phenyl)-6-((2-(trimethylsilyl)ethoxy)methyl)-6H-imidazo[1,5-a]pyrrolo[2,3-e]pyrazine, was prepared as shown in Scheme B. 2-Bromo-7-ethyl-6-(4-(2-methyl-1,3-dioxolan-2-yl)phenyl)-5-((2-(trimethylsilyl)ethoxy)methyl)-5H-pyrrolo[2,3-b]pyrazine (Preparation #5) and (E)-styreneboronic acid are reacted following conditions given in D to give (E)-7-ethyl-6-(4-(2-methyl-1,3-dioxolan-2-yl)phenyl)-2-styryl-5-((2-(trimethylsilyl)ethoxy)methyl)-5H-pyrrolo[2,3-b]pyrazine. This alkene is then cleaved following the conditions given in E to give an aldehyde, reduced using conditions described in F to give an alcohol, converted to an azide following G, and then reduced following conditions given in I to give (7-ethyl-6-(4-(2-methyl-1,3-dioxolan-2-yl)phenyl)-5-((2-(trimethylsilyl)ethoxy)methyl)-5H-pyrrolo[2,3-b]pyrazin-2-yl)methanamine. The amine is then coupled with Ac₂O following conditions described in J.2 and then cyclized using the conditions described in L.1 with mercury(II) trifluoroacetate as the mercury salt to give the precursor to Example #W.1. The reaction sequence detailed above is translated in the preparations and examples section to "prepared using D from Preparation #5 with (E)-styreneboronic acid, E, F, G, I, J.2 with Ac₂O and L.1 with mercury(II) trifluoracetate."

Scheme B

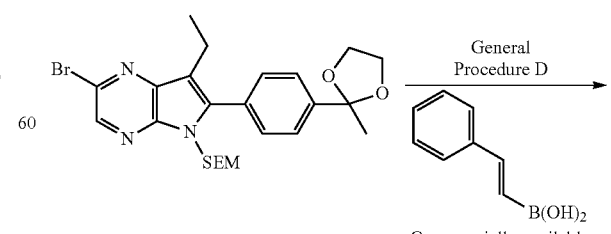

Commercially available from Sigma-Aldrich

-continued

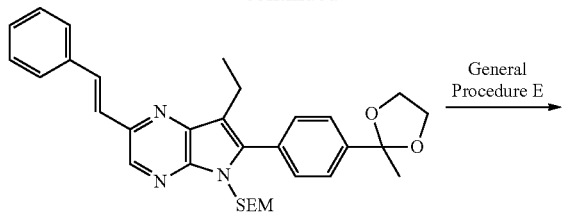

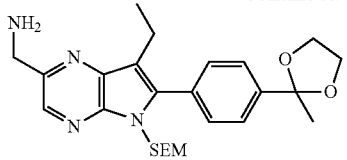

General Procedure E

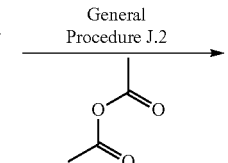

General Procedure J.2

Commercially available from Sigma-Aldrich

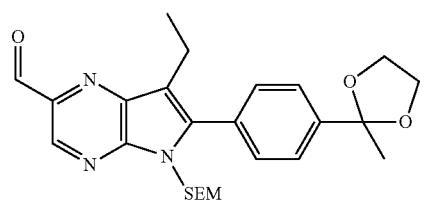

General Procedure F

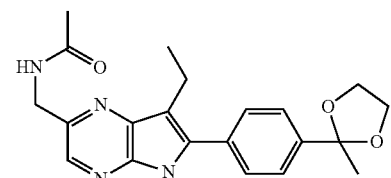

General Procedure L.1

Hg(OC(O)CF$_3$)$_2$

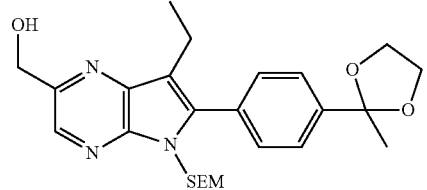

General Procedure G

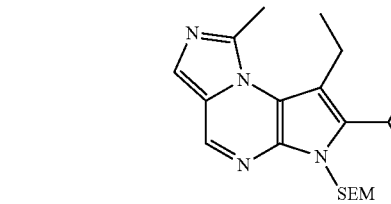

Precursor to Example #W.1

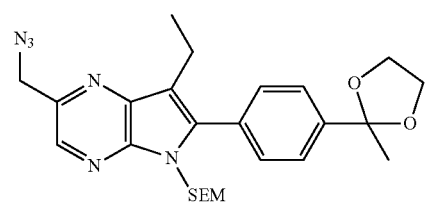

General Procedure I

Analytical Methods

Analytical data is included within the procedures below, in the illustrations of the general procedures, or in the tables of examples. Unless otherwise stated, all $^1$H NMR data were collected on a Varian Mercury Plus 400 MHz or a Varian Inova 600 MHz instrument and chemical shifts are quoted in parts per million (ppm). LC/MS and HPLC data is referenced to the table of LC/MS and HPLC conditions using the lower case method letter provided in Table 2.

TABLE 2

LC/MS and HPLC methods

| Method | Conditions |
|---|---|
| a | LC/MS: The gradient was 5-60% B in 1.5 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography was a 4.6 × 50 mm MAC-MOD Halo C18 column (2.7 µm particles). Detection methods were diode array (DAD) and evaporative light scattering (ELSD) detection as well as positive/negative electrospray ionization. |
| b | LC/MS: The gradient was 5-60% B in 1.5 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography was a 4.6 × 50 mm MAC-MOD Halo C8 column (2.7 µm particles). Detection methods were diode array (DAD) and evaporative light scattering (ELSD) detection as well as positive/negative electrospray ionization. |
| c | LC/MS: The gradient was 5-60% B in 0.75 min then 60-95% B to 1.15 min with a hold at 95% B for 0.75 min (1.3 mL/min flow rate). Mobile phase A was 10 mM NH$_4$OAc, mobile phase B was HPLC grade MeCN. The column used for the chromatography was a 4.6 × 50 mm MAC-MOD Halo C8 column (2.7 µm particles). Detection methods were diode array (DAD) and evaporative light scattering (ELSD) detection as well as positive/negative electrospray ionization. |
| d | The gradient was 0-0.1 min 10% A, 0.1-2.6 min 10-100% A, 2.6-2.9 min 100% A, 2.9-3.0 min 100-10% A then 0.5 min post-run delay. Flow rate was 2 mL/min. Mobile phase A was HPLC grade acetonitrile and mobile phase B was 0.1% trifluoroacetic acid in water. The column used for the chromatography was a Phenomenex Luna Combi-HTS C8(2) 5 µm 100Å (2.1 mm × 50 mm), at a temperature of 55° C. Detection methods were diode array (DAD) and evaporative light scattering (ELSD) detection as well as positive APCI ionization. |
| e | HPLC: The gradient was 5-95% B over 25 min (21 mL/min flow rate). Mobile phase A was 50 mM NH$_4$OAc (pH 4.5) and mobile phase B was HPLC grade |

TABLE 2-continued

LC/MS and HPLC methods

| Method | Conditions |
|---|---|
| | MeCN. The column used for the chromatography was a 21.2 × 250 mm Hypersil C18 HS column (8 μm particles). Detection method was UV, λ = 254 nm. |
| f | LC/MS: The column used for the chromatography is a 4.6 × 100 mm Hypersil Gold PFP column (5 mm particles). The gradient was a hold at 10% B for 0.3 min, then 10-90% B in 3.7 min with a hold at 95% B for 0.3 min (1.3 mL/min flow rate). Mobile phase A was 10 mM NH$_4$OAc, mobile phase B was HPLC grade MeCN. Detection methods were diode array (DAD) and evaporative light scattering (ELSD) detection as well as positive/negative electrospray ionization. |
| g | LC/MS: The gradient was 60-95% B in 1.15 min with a hold at 95% B for 3 min (1.3 mL/min flow rate). The column used for the chromatography was a 4.6 × 50 mm MAC-MOD Halo C8 column (2.7 μm particles). Mobile phase A was 10 mM NH$_4$OAc, mobile phase B was HPLC grade MeCN. Detection methods were diode array (DAD) and evaporative light scattering (ELSD) detection as well as positive/negative electrospray ionization. |
| h | LC/MS: The gradient was 30-60% B in 1.50 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| i | HPLC: Hypersil HS C18 column, 250 mm × 21.2 mm, 8 μm particle size, flow rate 21 mL/min, detection 254 nm, mobile phase A was 0.05N NH$_4$OAc pH 4.5 buffer, mobile phase B was HPLC grade MeCN, 10-100% B over 25 min. |
| j | HPLC: Hypersil HS C18 column, 250 mm × 21.2 mm, 8 μm particle size, flow rate 21 mL/min, detection 254 nm, mobile phase A was 0.05N NH$_4$OAc pH 4.5 buffer, mobile phase B was HPLC grade MeCN, 20-100% B over 25 min. |
| k | HPLC: Hypersil HS C18 column, 250 mm × 21.2 mm, 8 μm particle size, flow rate 21 mL/min, detection 254 nm, mobile phase A was 0.05N ammonium acetate pH 4.5 buffer, mobile phase B was HPLC grade MeCN, 10 to 100% B over 20 min. |
| l | HPLC: Hypersil HS C18 column, 250 mm × 21.2 mm, 8 μm particle size, flow rate 21 mL/min, detection 254 nm, mobile phase A was 0.05N NH$_4$OAc ph 4.5 buffer, mobile phase B was HPLC grade MeCN, 10 to 70% B over 20 min. |
| m | LC/MS: The gradient was 0-0.1 min 10% A, 0.1-1.1 min 10-100% A, 1.1-1 3 min 100% A, then 1.3-1.4 min 100-10% A. Flow rate was 1 mL/min. Mobile phase A was HPLC grade acetonitrile and mobile phase B was 0.1% trifluoroacetic acid in water. The column used was a Waters BEH C8, 1.7 μm (2.1 mm × 30 mm) at a temperature of 55° C. Detection methods were diode array (DAD) and evaporative light scattering (ELSD) detection as well as positive APCI ionization. |
| n | HPLC: Hypersil HS C18 column, 250 mm × 21.2 mm, 8 μm particle size, flow rate 21 mL/min, detection 254 nm, mobile phase A was 0.05N NH$_4$OAc ph 4.5 buffer, mobile phase B was HPLC grade MeCN, 0-50% B over 30 min. |

Purification Methods

Intermediates and final compounds prepared via the General Procedures can be optionally purified using one or more of the Purification Methods described below. The final compounds may be purified by any technique or combination of techniques known to one skilled in the art. Some examples that are not limiting include flash chromatography with a solid phase (e.g. silica gel, alumina, etc.) and a solvent (or combination of solvents) that elutes the desired compounds (e.g. hexanes, heptane, EtOAc, DCM, MeOH, EtOH, MeCN, water, etc.); preparatory TLC with a solid phase (e.g. silica gel, alumina etc.) and a solvent (or combination of solvents) that elutes the desired compounds (e.g. hexanes, heptane, EtOAc, DCM, MeOH, EtOH, MeCN, water, etc.); reverse phase HPLC (see Table 2 for some non-limiting conditions); recrystallization from an appropriate solvent (e.g. MeOH, EtOH, i-PrOH, EtOAc, toluene, etc.) or combination of solvents (e.g. EtOAc/heptane, EtOAc/MeOH, etc.); chiral LC with a solid phase and an appropriate solvent (e.g. EtOH/heptane, MeOH/heptane, i-PrOH/heptane, etc. with or without a modifier such as diethylamine, TFA, etc.) to elute the desired compound; chiral SFC with a solid phase and CO$_2$ with an appropriate modifier (e.g. MeOH, EtOH, i-PrOH with or without additional modifier such as diethylamine, TFA, etc.); precipitation from a combination of solvents (e.g. DMF/water, DMSO/DCM, EtOAc/heptane, etc.); trituration with an appropriate solvent (e.g. EtOAc, DCM, MeCN, MeOH, EtOH, i-PrOH, n-PrOH, etc.); extractions by dissolving a compound in a liquid and washing with an appropriately immiscible liquid (e.g. DCM/water, EtOAc/water, DCM/saturated NaHCO$_3$, EtOAc/saturated NaHCO$_3$, DCM/10% aqueous HCl, EtOAc/10% aqueous HCl, etc.); distillation (e.g. simple, fractional, Kugelrohr, etc.); gas chromatography using an appropriate temperature, carrier gas and flow rate; sublimation at an appropriate temperature and pressure; filtration through a media (e.g. Florosil®, alumina, Celite®, silica gel, etc.) with a solvent (e.g. heptane, hexanes, EtOAc, DCM, MeOH, etc.) or combination of solvents; salt formation with solid support (resin based, e.g. ion exchange) or without. Some descriptions of these techniques can be found in the following references, Gordon, A. J. and Ford, R. A. "The Chemist's Companion", 1972; Palleros, D. R. "Experimental Organic Chemistry", 2000; Still, W. C., Kahn, M. and Mitra, A. J. Org. Chem. 1978, 43, 2923; Yan, B. "Analysis and Purification Methods in Combinatorial Chemistry" 2003; Harwood, L. M., Moody, C. J. and Percy, J. M. "Experimental Organic Chemistry: Standard and Microscale, $2^{nd}$ Edition", 1999; Stichlmair, J. G. and Fair, J. R. "Distillation; Principles and Practices" 1998; Beesley T. E. and Scott, R. P. W. "Chiral Chromatography", 1999; Landgrebe, J. A. "Theory and Practice in the Organic Laboratory, $4^{th}$ Edition", 1993; Skoog, D. A. and Leary, J. J. "Principles of Instrumental Analysis, $4^{th}$ Edition" 1992; Subramanian, G. "Chiral Separation Techniques 3rd Edition" 2007; Kazakevich, Y. and Lobrutto, R. "HPLC for Pharmaceutical Scientists" 2007.

PREPARATIONS AND EXAMPLES

The general synthetic methods used in each General Procedure follow and include an illustration of a compound that was synthesized using the designated General Procedure. None of the specific conditions and reagents noted herein are to be construed as limiting the scope of the invention and are provided for illustrative purposes only. All starting materials are commercially available from Sigma-Aldrich (including Fluka and Discovery CPR) unless otherwise noted after the chemical name. Reagent/reactant names given are as named on the commercial bottle or as generated by IUPAC conventions, CambridgeSoft® ChemDraw Ultra 9.0.7, or AutoNom 2000. Compounds designated as salts (e.g. hydrochloride, acetate) may contain more than one molar equivalent of the salt. For reactions run under microwave heating conditions, the parameters were 300 watts with a maximum pressure of 250 psi.

Preparation #1. 7-Iodo-1-methyl-6-tosyl-1,6-dihydropyrazolo[3,4-d]pyrrolo[2,3-b]pyridine

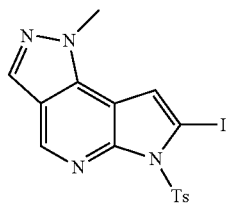 [SMILES: Cc1ccc(S(=O)(=O)n2c(I)cc3c4c(cnc32)cnn4C)cc1]

Step A: 4-Chloro-1-(triisopropylsilyl)-1H-pyrrolo[2,3-b]pyridine

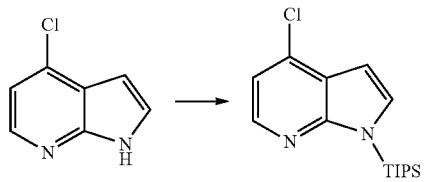

A flask was charged with 4-chloro-1H-pyrrolo[2,3-b]pyridine (6.0 g, 39 mmol, Arkpharm) and THF (100 mL). The mixture was cooled to about 0° C. and 60 wt % NaH (1.89 g, 47.2 mmol) was added portion-wise. The mixture was warmed to rt and after about 45 min. TIPSCl (12.5 mL, 59.0 mmol) was added drop-wise and mixture was allowed to stir overnight at rt. The mixture was quenched with water (100 mL) and extracted with EtOAc (200 mL). The organic layer was dried over anhydrous MgSO$_4$ and concentrated under reduced pressure. The residue was purified by silica gel chromatography with a gradient of 0 to 10% EtOAc/heptane to give 4-chloro-1-(triisopropylsilyl)-1H-pyrrolo[2,3-b]pyridine (11.0 g, 91%): $^1$H NMR (d-DMSO) δ 8.20 (d, J=5.17 Hz, 1H), 7.59 (d, J=3.55 Hz, 1H), 7.23 (d, J=5.16 Hz, 1H), 6.68 (d, J=3.50 Hz, 1H), 1.83 (m, 3H), 1.06 (m, 18H).

Step B:
4-Chloro-1H-pyrrolo[2,3-b]pyridine-5-carbaldehyde

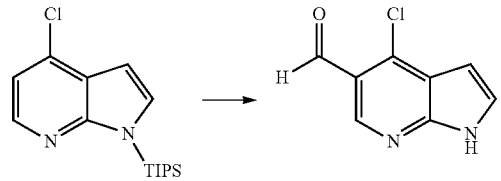

A flask was charged with 4-chloro-1-(triisopropylsilyl)-1H-pyrrolo[2,3-b]pyridine (25.2 g, 82.0 mmol) in THF (400 mL) and cooled to about −78° C. sec-BuLi (1.4 M in cyclohexane, 116 mL, 163 mmol) was added drop-wise over about 15 min. The mixture was stirred at −78° C. for about 1 h. To the mixture was added DMF (18.9 mL, 245 mmol) drop-wise and the temperature was maintained at about −78° C. for about 1 h. The mixture was quenched by the slow addition of a solution of HCl (4.0 M in 1,4-dioxane, 20.4 mL, 82.0 mmol) followed by the addition of saturated aqueous NaHCO$_3$ (100 mL). The mixture was extracted with EtOAc (500 mL). The organic layer was allowed to sit at rt overnight. The precipitate formed was collected by filtration. The filtrate formed more precipitate which was collected by filtration again. The precipitated material from both filtrations was combined to give 4-chloro-1H-pyrrolo[2,3-b]pyridine-5-carbaldehyde (12.9 g, 88%): LC/MS (Table 2, Method a) R$_f$=1.85 min; MS m/z 181 (M+H)$^+$ Step C: 1-Methyl-1,6-dihydropyrazolo[3,4-d]pyrrolo[2,3-b]pyridine

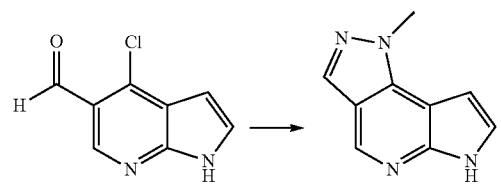

A solution of 4-chloro-1H-pyrrolo[2,3-b]pyridine-5-carbaldehyde (1.37 g, 7.59 mmol) and methylhydrazine (0.59 mL, 11.4 mmol) in n-BuOH (7 mL) was heated to 95° C. After 15 min, aqueous 38% HCl (0.55 mL, 8.83 mmol) was added and the mixture was heated to 120° C. After 4 h, water (10 mL) was added to the mixture and extracted with EtOAc (20 mL). The aqueous layer was separated and basified with saturated aqueous NaHCO$_3$ to pH of 8 and extracted with EtOAc (2×20 mL). The organic layers were combined, dried over anhydrous MgSO$_4$ and concentrated under reduced pressure. The residue was purified via flash chromatography with a gradient of 5 to 60% EtOAc/heptane to give 1-methyl-1,6- dihydropyrazolo[3,4-d]pyrrolo[2,3-b]pyridine (0.960 g, 73%): LC/MS (Table 2, Method b) R$_t$=1.49 min; MS m/z 173 (M+H)$^+$.

Step D: 1-Methyl-6-tosyl-1,6-dihydropyrazolo[3,4-d]pyrrolo[2,3-b]pyridine

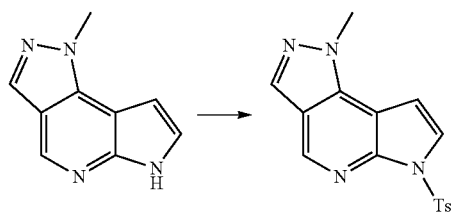 [SMILES: Cn1ncc2cnc3[nH]ccc3c21 ; Cc1ccc(S(=O)(=O)n2ccc3c2ncc2cnn(C)c23)cc1]

A mixture of 60 wt % NaH (1.74 g, 43.6 mmol) in DMF (70 mL) at 0° C. was treated with a mixture of 1-methyl-1,6-dihydropyrazolo[3,4-d]pyrrolo[2,3-b]pyridine (5.00 g, 29.0 mmol) in DMF (20 mL). After 20 min, TsCl (8.30 g, 43.6 mmol) was added. After 2 h, water (90 mL) was added and the precipitate formed was collected by filtration to give 1-methyl-6-tosyl-1,6-dihydropyrazolo[3,4-d]pyrrolo[2,3-b]pyridine (9.0 g, 95%): LC/MS (Table 2, Method c) R$_t$=1.44 min; MS m/z 327 (M+H)$^+$ Step E: 7-Iodo-1-methyl-6-tosyl-1,6-dihydropyrazolo[3,4-d]pyrrolo[2,3-b]pyridine

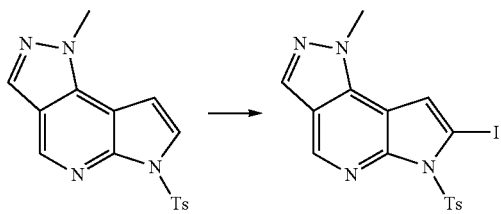 [SMILES: Cc1ccc(S(=O)(=O)n2ccc3c2ncc2cnn(C)c23)cc1 ; Cc1ccc(S(=O)(=O)n2c(I)cc3c4c(cnc32)cnn4C)cc1]

Diisopropylamine (4.32 mL, 30.6 mmol) in THF (20 mL) was cooled to −74° C. n-BuLi (1.6 M in cyclohexane, 21.04 mL, 33.7 mmol) was added drop-wise over 15 min. After about 20 min, the mixture was added to 1-methyl-6-tosyl-1,6-dihydropyrazolo[3,4-d]pyrrolo[2,3-b]pyridine (5.0 g, 15 mmol) in THF (100 mL) at about −74° C. over about 10 min. After about 1 h, a solution of iodine (4.51 g, 17.7 mmol) in THF (30 mL) was added over about 20 min. The mixture was stirred at about −74° C. for about 3 h and then allowed to warm to rt and stirred overnight. To the mixture was added water (80 mL) and the mixture was extracted with EtOAc (3×100 mL). The organic layers were combined, dried over anhydrous MgSO$_4$ and concentrated under reduced pressure. The residue was purified by flash chromatography with a gradient of 0 to 80% EtOAc/heptane to give 7-iodo-1-methyl-6-tosyl-1,6-dihydropyrazolo[3,4-d]pyrrolo[2,3-b]pyridine (2.08 g, 30%): LC/MS (Table 2, Method a) R$_t$=2.44 min; MS m/z 453 (M+H)$^+$.

Preparation #2: 8-Ethyl-1-methyl-6-tosyl-1,6-dihydropyrazolo[3,4-d]pyrrolo[2,3-b]pyridine

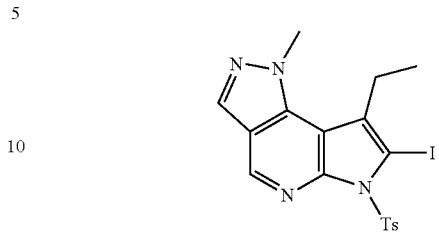

Step A: 4-Chloro-3-iodo-1-(triisopropylsilyl)-1H-pyrrolo[2,3-b]pyridine

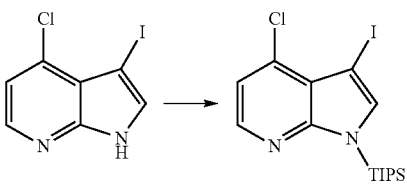

The 4-chloro-3-iodo-1H-pyrrolo[2,3-b]pyridine (5.00 g, 17.9 mmol, US 2006128661 Example 1) in DMF (50 mL) was treated with 60 wt % NaH (0.790 g, 19.7 mmol) then stirred for about 15 min. The TIPSCl (4.18 mL, 19.8 mmol) was then added to the mixture and the mixture was stirred for about 30 min. The solvents were evaporated under reduced pressure then the material was partitioned between saturated aqueous NaHCO$_3$ (50 mL) and EtOAc (50 mL). The layers were separated then the aqueous layer was extracted with EtOAc (25 mL). The combined organics were washed with water (25 mL) then brine (25 mL), dried over anhydrous MgSO$_4$, filtered and concentrated under reduced pressure. The residue was purified by silica gel chromatography using a 120 g silica column and eluting with heptane to give 4-chloro-3-iodo-1-(triisopropylsilyl)-1H-pyrrolo[2,3-b]pyridine (5.34 g, 68%): LC/MS (Table 2, Method g) R$_t$=2.58 min; MS m/z 435 (M+H)$^+$.

Step B: 4-Chloro-3-ethyl-1-(triisopropylsilyl)-1H-pyrrolo[2,3-b]pyridine

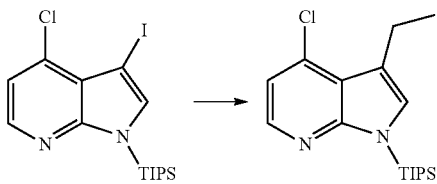

The 4-chloro-3-iodo-1-(triisopropylsilyl)-1H-pyrrolo[2,3-b]pyridine (27.0 g, 62.1 mmol) in THF (300 mL) was cooled to about −75° C. then t-BuLi (1.7 M in pentane, 73.1 mL, 124 mmol) was added over about 30 min keeping the internal temperature below about −70° C. After complete addition, EtI (15.0 mL, 186 mmol) was added. The mixture was warmed slowly to about −40° C. then the mixture was allowed to warm to rt. Saturated aqueous NaHCO$_3$ (50 mL) was added and the mixture was stirred for about 30 min. The mixture was filtered and the solids washed with EtOAc (3×50 mL). The solvents were removed under reduced pressure then the material was partitioned between EtOAc (200 mL) and water (50 mL). The layers were separated then the organic layer was washed with saturated aqueous NaCl (50 mL), dried over anhydrous MgSO$_4$, filtered and concentrated under reduced pressure. The resulting material was treated with MeOH (80 mL) then warmed to about 60° C. The mixture was cooled to rt and the resulting slurry stirred overnight at rt. The solids were collected by filtration then washed with MeOH (10 mL). The filtrate was concentrated under reduced pressure then purified by silica gel chromatography using a 120 g silica gel column and eluting with heptane. The material was stirred with MeOH (15 mL) overnight then the solid was collected by filtration and washed with MeOH (2 mL). The solid material was combined with the first crop of solids and dried under reduced pressure to give 4-chloro-3-ethyl-1-(triisopropylsilyl)-1H-pyrrolo[2,3-b]pyridine (17.4 g, 83%): LC/MS (Table 2, Method g) R$_t$=3.21 min; MS m/z 337 (M+H)$^+$.

Step C: 4-Chloro-3-ethyl-1-(triisopropylsilyl)-1H-pyrrolo[2,3-b]pyridine-5-carbaldehyde

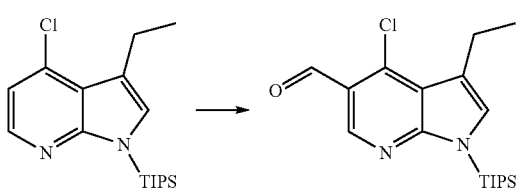

4-Chloro-3-ethyl-1-(triisopropylsilyl)-1H-pyrrolo[2,3-b]pyridine (1.5 g, 4.45 mmol) in THF (25 mL) was cooled to about −70° C. then the sec-BuLi (1.4 M in cyclohexane, 6.36 mL, 8.90 mmol) was added over about 10 min. The mixture was stirred for about 1.25 h at about −70° C. then DMF (1.00 mL, 13.4 mmol) was added over about 5 min. The mixture was stirred for about 30 min then HCl (4.0 M in 1,4-dioxane, 1.11 mL, 4.45 mmol) was added. The mixture was allowed to warm to rt then saturated aqueous NaHCO$_3$ (50 mL) and EtOAc (50 mL) were added. The layers were separated then the aqueous layer was extracted with EtOAc (25 mL) then the combined organics were extracted with saturated aqueous NaCl (25 mL), dried over anhydrous MgSO$_4$, filtered and concentrated under reduced pressure. The material was purified on a 80 g silica gel column with 9:1 heptane/EtOAc as an eluent to give 4-chloro-3-ethyl-1-(triisopropylsilyl)-1H-pyrrolo[2,3-b]pyridine-5-carbaldehyde (1.48 g, 91%): LC/MS (Table 2, Method g) R$_t$=2.44 min; MS m/z 365 (M+H)$^+$.

Step D: 4-Chloro-3-ethyl-1H-pyrrolo[2,3-b]pyridine-5-carbaldehyde

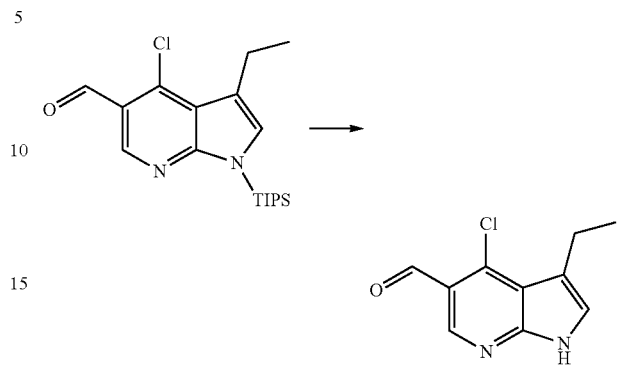

4-Chloro-3-ethyl-1-(triisopropylsilyl)-1H-pyrrolo[2,3-b]pyridine-5-carbaldehyde (1.48 g, 4.05 mmol) in 1,4-dioxane (15 mL) was treated with HCl (4.0 N in 1,4-dioxane, 2.0 mL, 8.1 mmol) then the mixture was stirred for about 16 h at rt. The solvents were evaporated then the material was suspended in Et$_2$O (15 mL) then the solids were collected by filtration and dried under reduced pressure overnight to give 4-chloro-3-ethyl-1H-pyrrolo[2,3-b]pyridine-5-carbaldehyde (0.762 g, 90%): LC/MS (Table 2, Method a) R$_t$=2.21 min; MS m/z 209 (M+H)$^+$.

Step E: 8-Ethyl-1-methyl-1,6-dihydropyrazolo[3,4-d]pyrrolo[2,3-b]pyridine

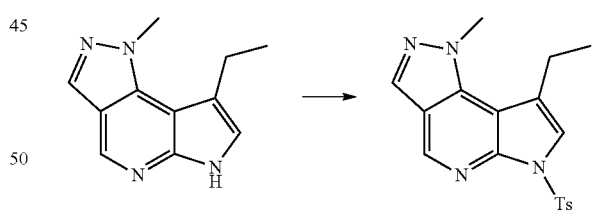

4-Chloro-3-ethyl-1H-pyrrolo[2,3-b]pyridine-5-carbaldehyde (0.76 g, 3.6 mmol) was suspended in n-PrOH (15 mL) then methylhydrazine (0.185 g, 4.01 mmol) was added. The mixture was heated at about 85° C. for about 20 min. The mixture was treated with concentrated aqueous HCl (0.330 mL, 4.01 mmol) then heated at about 110° C. for about 3.5 h. The solvent was evaporated under reduced pressure then the mixture was partitioned between water (20 mL) with aqueous HCl (5.0 N, 2 mL) and EtOAc (20 mL). The layers were separated then the aqueous layer was basified with saturated aqueous NaHCO$_3$ and extracted with EtOAc (3×20 mL). The combined organics were dried over anhydrous MgSO$_4$, filtered and concentrated under reduced pressure to give 8-ethyl-1-methyl-1,6-dihydropyrazolo[3,4-d]pyrrolo[2,3-b]pyridine (0.465 g, 64%): LC/MS (Table 2, Method a) $R_f$=1.83 min; MS m/z 201 (M+H)⁺.

Step F: 8-Ethyl-1-methyl-6-tosyl-1,6-dihydropyrazolo[3,4-d]pyrrolo[2,3-b]pyridine

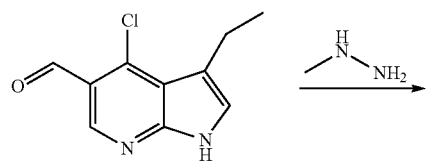

8-Ethyl-1,6-dihydropyrazolo[3,4-d]pyrrolo[2,3-b]pyridine (10.5 g, 56.3 mmol) in DMF (200 mL) was cooled to about 0° C. then treated with 60 wt % NaH (2.36 g, 59.1 mmol). After about 20 min, TsCl (11.3 g, 59.1 mmol) was added in portions. After about 40 min the mixture was poured slowly into ice water (300 mL) and stirred. The solids were collected by filtration then the material was dissolved in DCM (300 mL). The water layer was separated then the organic layer was dried over anhydrous MgSO₄, filtered and concentrated under reduced pressure. The material was triturated with Et₂O then the solids were collected by filtration and dried to constant weight to provide 8-ethyl-1-methyl-6-tosyl-1,6-dihydropyrazolo[3,4-d]pyrrolo[2,3-b]pyridine (14.8 g, 78%): LC/MS (Table 2, Method c) $R_f$=1.55 min; MS m/z 355 (M+H)⁺.

Step G: 8-Ethyl-7-iodo-1-methyl-6-tosyl-1,6-dihydropyrazolo[3,4-d]pyrrolo[2,3-b]pyridine

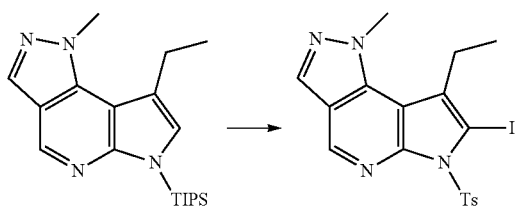

Diisopropylamine (0.260 mL, 1.83 mmol) in THF (5 mL) was cooled to about −70° C. then the n-BuLi (1.6 M in hexanes, 1.04 mL, 1.67 mmol) was added drop-wise. The mixture was stirred at about −70° C. for about 15 min then allowed to warm to about 20° C. The resulting solution was added drop-wise to the 8-ethyl-1-methyl-6-tosyl-1,6-dihydropyrazolo[3,4-d]pyrrolo[2,3-b]pyridine (0.295 g, 0.832 mmol) in THF (5 mL) at about −60 to −70° C. then the mixture was stirred for about 1 h. Iodine (0.239 g, 0.942 mmol) in THF (2 mL) was added drop-wise to the mixture and then it was stirred at about −70° C. for about 1 h. The reaction was treated with AcOH (0.143 mL, 2.50 mmol) then about 1 mL of saturated aqueous NH₄Cl was added then the solution was warmed to rt. The mixture was diluted with EtOAc (50 mL) and water (20 mL) then the layers were separated. The organic layer was washed with saturated aqueous NaCl (20 mL) then dried over anhydrous MgSO₄, filtered and concentrated under reduced pressure. The material was purified on a 10 g silica gel column with 94:6 DCM/EtOAc as an eluent to give 8-Ethyl-7-iodo-1-methyl-6-tosyl-1,6-dihydropyrazolo[3,4-d]pyrrolo[2,3-b]pyridine (0.155 g, 39%): LC/MS (Table 2, Method a) $R_f$=2.78 min; MS m/z 481 (M+H)⁺.

Preparation #3: 7-Iodo-1-methyl-6-tosyl-1,2,3,6-tetrahydrodipyrrolo[2,3-b:2',3'-d]pyridine

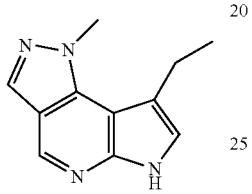

Step A: 5-Allyl-4-chloro-1-(triisopropylsilyl)-1H-pyrrolo[2,3-b]pyridine

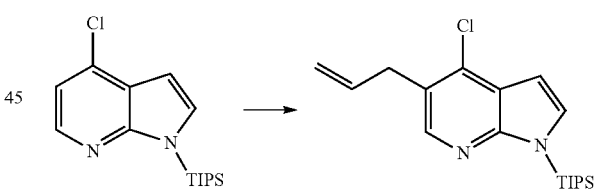

The 4-chloro-1-(triisopropylsilyl)-1H-pyrrolo[2,3-b]pyridine (3.10 g, 10.0 mmol, Preparation #1, Step A) in THF (40 mL) was cooled to about −75° C. then sec-BuLi (1.4 M in hexane, 14.3 mL, 20.0 mmol) was added slowly keeping the temperature below −65° C. The mixture was stirred at about −75° C. for about 45 min then copper(I) cyanide (0.090 g, 1.00 mmol) was added. The mixture was stirred for about 5 min then allyl bromide (2.61 mL, 30.1 mmol) was added drop-wise. After about 10 min saturated aqueous NaHCO₃ (20 mL) and EtOAc (50 mL) were added to the mixture. The mixture was partitioned between water (20 mL) and EtOAc (50 mL). The layers were separated then the aqueous layer was extracted with EtOAc (25 mL). The combined organic layers were washed with saturated aqueous NaHCO₃ (40 mL) then dried over anhydrous MgSO₄, filtered and concentrated in vacuo. The material was purified by flash chromatography on 120 g silica gel with 98:2 heptane/EtOAc as an eluent to give 5-allyl-4-chloro-1-(triisopropylsilyl)-1H-pyrrolo[2,3-b]pyridine (3.2 g, 91%): LC/MS (Table 2, Method g) R$_f$=2.63 min; MS m/z 349 (M+H)$^+$.

Step B: 5-Allyl-4-chloro-1H-pyrrolo[2,3-b]pyridine

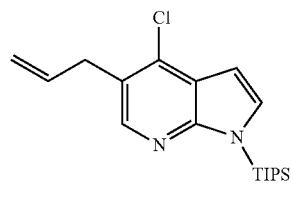
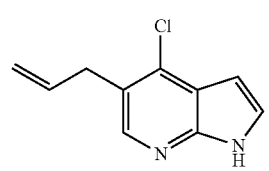

5-Allyl-4-chloro-1-(triisopropylsilyl)-1H-pyrrolo[2,3-b]pyridine (5.38 g, 15.4 mmol) in 1,4-dioxane (75 mL) was treated with HCl (4.0 N in 1,4-dioxane, 5.0 mL, 20 mmol) then stirred at rt.

The mixture was stirred for about 10 h then HCl (4.0 N in 1,4-dioxane, 2.0 mL, 8.0 mmol) was added and the mixture was stirred for about 45 min at rt. The mixture was diluted with Et$_2$O (50 mL), then cooled to about −5° C. and stirred for about 30 min. The solid was collected by filtration, washed with Et$_2$O (3×10 mL) and dried under vacuum at about 65° C. to a constant weight. The material was suspended in water (30 mL) then the mixture was basified with saturated aqueous NaHCO$_3$. The mixture was extracted with EtOAc (40 mL then 20 mL) then the organic layer was dried over anhydrous MgSO$_4$, filtered and concentrated under reduced pressure to give 5-allyl-4-chloro-1H-pyrrolo[2,3-b]pyridine (2.24 g, 75%): LC/MS (Table 2, Method a) R$_f$=2.52 min; MS m/z 193 (M+H)$^+$.

Step C:
5-Allyl-4-chloro-1-tosyl-1H-pyrrolo[2,3-b]pyridine

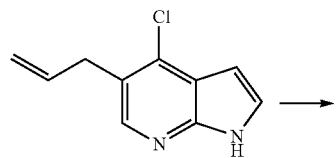
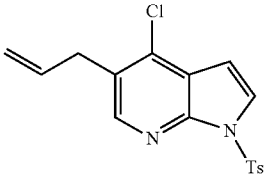

5-Allyl-4-chloro-1H-pyrrolo[2,3-b]pyridine (2.24 g, 11.6 mmol) in DMF (25 mL) was cooled to about 0° C. then treated with 60 wt % NaH (0.558 g, 13.9 mmol). The mixture was stirred for about 30 min then TsCl (2.44 g, 12.8 mmol) was added. The mixture was stirred for about 15 min at about 0° C. then warmed to rt for about 30 min. The solvents were evaporated under reduced pressure then the residue was stirred with DCM (40 mL) and saturated aqueous NaHCO$_3$ (35 mL) for about 15 min. The layers were separated then the aqueous layer was extracted with DCM (20 mL). The combined organic layers were dried over anhydrous MgSO$_4$, filtered and concentrated in vacuo to give 5-allyl-4-chloro-1-tosyl-1H-pyrrolo[2,3-b]pyridine (4.0 g, 111%, crude): LC/MS (Table 2, Method a) R$_f$=3.18 min; MS m/z 347 (M+H)$^+$.

Step D: 2-(4-Chloro-1-tosyl-1H-pyrrolo[2,3-b]pyridin-5-yl)acetaldehyde

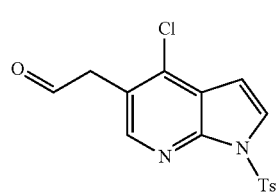

5-Allyl-4-chloro-1-tosyl-1H-pyrrolo[2,3-b]pyridine (3.90 g, 11.2 mmol) in 1,4-dioxane (75 mL) and water (15 mL) was treated with NaIO$_4$ (9.62 g, 45.0 mmol) and OsO$_4$ (2.5% in t-BuOH, 5.65 mL, 0.450 mmol). The mixture was stirred at rt for about 1 h then diluted with EtOAc (100 mL). The solids were collected by filtration and the cake was washed with EtOAc (2×100 mL). The filtrate was washed with water (100 mL) and saturated aqueous NaCl (50 mL) then dried over anhydrous MgSO$_4$, filtered and concentrated under reduced pressure. The material was purified by flash chromatography on silica gel to give 2-(4-chloro-1-tosyl-1H-pyrrolo[2,3-b]pyridin-5-yl)acetaldehyde as a mixture of aldehyde and hydrate (1.45 g, 37%); LC/MS (Table 2, Method b) R$_f$=2.51 min; MS m/z 349 (M+H)$^+$.

Step E: 2-(4-Chloro-1-tosyl-1H-pyrrolo[2,3-b]pyridin-5-yl)-N-methylethanamine

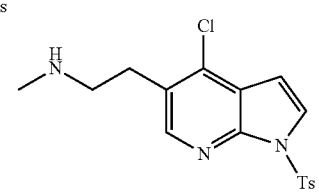

Methylamine gas was bubbled into a solution of 2-(4-chloro-1-tosyl-1H-pyrrolo[2,3-b]pyridin-5-yl)acetaldehyde (1.45 g, 4.16 mmol) in DCE (50 mL) for about 10 min. NaBH(OAc)$_3$ (1.69 g, 7.97 mmol) was added and the mixture was stirred at rt. After about 45 min, the mixture was concentrated under reduced pressure then dissolved in MeOH (25 mL) and treated with NaBH$_4$ (0.236 g, 6.24 mmol). After about 10 min, the mixture was concentrated under reduced pressure then partitioned between DCM (50 mL), saturated aqueous NaHCO$_3$ (20 mL) and water (30 mL). The layers were separated then the aqueous layer was extracted with DCM (20 mL). The organic layers were combined, dried over anhydrous MgSO$_4$, filtered and concentrated in vacuo. The material was purified by preparative reverse phase HPLC (Table 2, Method i). The desired fractions were collected then most of the MeCN was removed under reduced pressure. The solution was basified with saturated aqueous NaHCO$_3$ and the solids were collected by filtration to give 2-(4-chloro-1-tosyl-1H-pyrrolo[2,3-b]pyridin-5-yl)-N-methylethanamine (0.67 g, 44%): LC/MS (Table 2, Method a) R$_t$=1.88 min; MS m/z 364 (M+H)$^+$.

Step F: 1-Methyl-6-tosyl-1,2,3,6-tetrahydrodipyrrolo [2,3-b:2',3'-d]pyridine

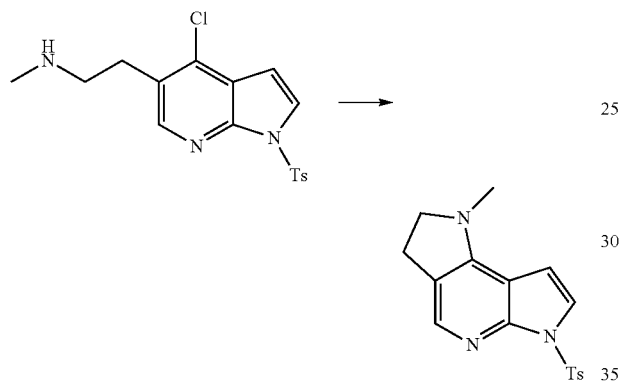

2-(4-Chloro-1-tosyl-1H-pyrrolo[2,3-b]pyridin-5-yl)-N-methylethanamine (0.670 g, 1.84 mmol) in PrOH (20 mL) was heated to about 105° C. for about 44 h. DIEA (0.39 mL, 2.2 mmol) was added and heating was continued at about 105° C. for about 24 h. The mixture was cooled to rt and the solvent was evaporated under reduced pressure. The material was treated with saturated NaHCO$_3$ (15 mL) and water (10 mL) then extracted with DCM (25 mL then 10 mL). The combined organic layers were dried over anhydrous MgSO$_4$, filtered and concentrated in vacuo. The material was purified by flash chromatography on 10 g of silica with EtOAc as an eluent to give 1-methyl-6-tosyl-1,2,3,6-tetrahydrodipyrrolo [2,3-b:2',3'-d]pyridine (0.308 g, 51%): LC/MS (Table 2, Method a) R$_t$=2.53 min; MS m/z 328 (M+H)$^+$.

Step G: 7-Iodo-1-methyl-6-tosyl-1,2,3,6-tetrahydrodipyrrolo[2,3-b:2',3'-d]pyridine

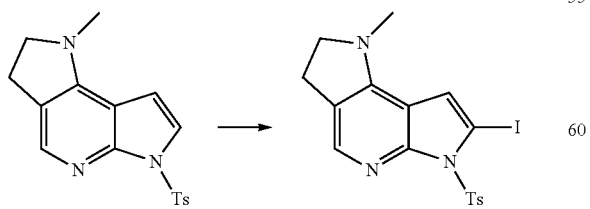

Diisopropylamine (0.29 mL, 2.0 mmol) in THF (5 mL) was cooled to about −70° C. then treated with n-BuLi (1.6 M in hexanes, 1.1 mL, 1.8 mmol) keeping the internal temperature of the reaction at about −60 to −70° C. After about 15 min the mixture was warmed to about 20° C. The mixture was added slowly to the 1-methyl-6-tosyl-1,2,3,6-tetrahydrodipyrrolo [2,3-b:2',3'-d]pyridine (0.300 g, 0.916 mmol) in THF (5.0 mL) at about −60° C. to −70° C. The mixture was stirred at about −70° C. for about 1 h then iodine (0.27 g, 1.1 mmol) in THF (2 mL) was added keeping the temperature of the mixture at about −65 to −70° C. The mixture was stirred for about 1 h at about −70° C. then AcOH (0.16 mL, 2.8 mmol) and about 1 mL saturated aqueous NH$_4$Cl were added. The mixture was warmed to rt then diluted with water (10 mL), saturated aqueous NaHCO$_3$ (5 mL) and DCM (50 mL). The layers were separated then the aqueous layer was extracted with DCM (15 mL). The combined organic layers were dried over anhydrous MgSO$_4$, filtered and concentrated under reduced pressure. The material was triturated in EtOAc (8 mL) then filtered and washed with EtOAc (2 mL) to give the title compound (0.24 g, 58%): LC/MS (Table 2, Method a) R$_t$=2.52 min; MS m/z 454 (M+H)$^+$.

Preparation #4:
2-(4-Iodophenyl)-2-methyl-1,3-dioxolane

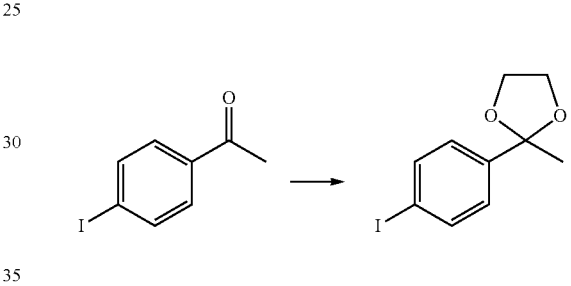

1-(4-Iodophenyl)ethanone (15.0 g, 61 mmol) and ethylene glycol (7.17 g, 122 mmol) in toluene (120 mL) were treated with TsOH—H$_2$O (0.290 g, 1.52 mmol). The flask was equipped with a Dean-Stark apparatus and condenser and heated to reflux for about 4 h. The mixture was cooled and concentrated under reduced pressure to give a material. The material was dissolved in EtOAc (120 mL) then washed with saturated aqueous NaHCO$_3$ (25 mL) then saturated aqueous NaCl (30 mL). The organic layer was dried over anhydrous MgSO$_4$, filtered and concentrated under reduced pressure to give 2-(4-iodophenyl)-2-methyl-1,3-dioxolane (17.54 g, 99%): LC/MS (Table 2, Method a) R$_t$=2.80 min; MS m/z 291 (M+H)$^+$.

Preparation #5: 2-Bromo-7-ethyl-6-(4-(2-methyl-1, 3-dioxolan-2-yl)phenyl)-5-((2-(trimethylsilyl) ethoxy)methyl)-5H-pyrrolo[2,3-b]pyrazine

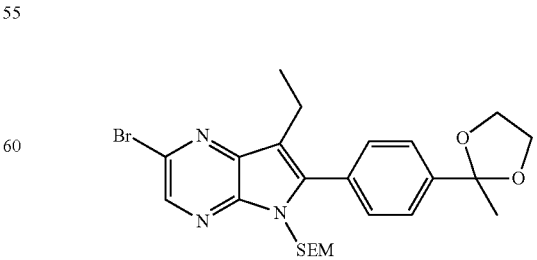

Step A: 2-Bromo-7-iodo-6-(4-(2-methyl-1,3-dioxolan-2-yl)phenyl)-5-((2-(trimethylsilyl)ethoxy)methyl)-5H-pyrrolo[2,3-b]pyrazine

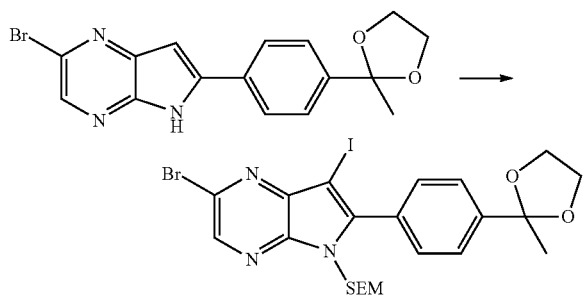

2-Bromo-6-(4-(2-methyl-1,3-dioxolan-2-yl)phenyl)-5H-pyrrolo[2,3-b]pyrazine (15.5 g, 43.0 mmol, prepared using A from Preparation #4 with ethynyltrimethylsilane, Q, A with 3,5-dibromopyrazin-2-amine, and B) in DMF (200 mL) was stirred for about 15 min at rt. The mixture was treated with powdered KOH (2.90 g, 51.6 mmol), then iodine (11.3 g, 44.4 mmol) was added in two roughly equal portions over about 15 min then the mixture was stirred for about 2 h at rt. To the mixture was added 60 wt % NaH (2.07 g, 51.6 mmol) in two roughly equal portions then stirred for about 10 min at rt. The mixture was cooled to about 0° C. then SEMCl (8.01 mL, 45.2 mmol) was added over about 10 min. After stirring for about 10 min at about 0° C. the mixture was allowed to warm to rt. After about 1 h the mixture was concentrated under reduced pressure then partitioned between EtOAc (300 mL) and water (200 mL). The organic layer was washed with saturated aqueous NaCl (100 mL) then the combined aqueous layers were extracted with EtOAc (100 mL). The combined organic layers were dried over anhydrous MgSO₄, filtered and concentrated in vacuo. The material was purified on two successive 120 g silica columns with 8:2 heptane/EtOAc as an eluent to give 2-bromo-7-iodo-6-(4-(2-methyl-1,3-dioxolan-2-yl)phenyl)-5-((2-(trimethylsilyl)ethoxy)methyl)-5H-pyrrolo[2,3-b]pyrazine (20.1 g, 76%): LC/MS (Table 2, Method g) $R_t$=1.76 min; MS m/z 616 (M+H)⁺.

Step B: 2-Bromo-7-ethyl-6-(4-(2-methyl-1,3-dioxotan-2-yl)phenyl)-5-((2-(trimethylsilyl)ethoxy)methyl)-5H-pyrrolo[2,3-b]pyrazine

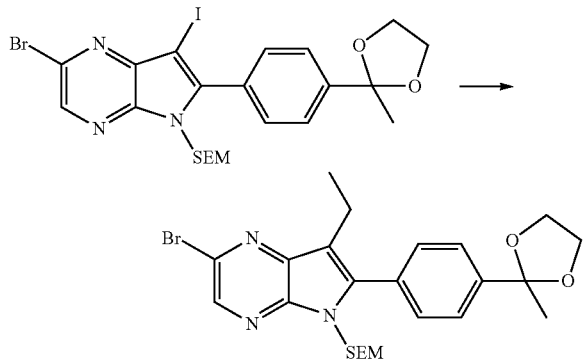

2-Bromo-7-iodo-6-(4-(2-methyl-1,3-dioxolan-2-yl)phenyl)-5-((2-(trimethylsilyl)ethoxy)methyl)-5H-pyrrolo[2,3-b]pyrazine (17.5 g, 28.4 mmol) in THF (200 mL) was cooled to about −75° C. then n-BuLi (1.6 M in hexanes, 19.5 mL, 31.2 mmol) was added keeping the temperature between about −70 and −75° C. The mixture was stirred for about 5 min at about −75° C. The mixture was treated with EtI (6.2 mL, 77 mmol) then the temperature of the mixture was raised to about 15° C. over about 5 to 10 min. The mixture was stirred at about 20° C. for about 30 min then saturated aqueous NH₄Cl (10 mL) was added. The mixture was stirred for about 15 min at about 20° C. then concentrated under reduced pressure. The material was partitioned between Et₂O (200 mL) and water (100 mL) the layers were separated and then the aqueous layer was extracted with Et₂O (100 mL). The combined organic layers were washed with saturated aqueous NaCl (50 mL), dried over anhydrous MgSO₄, filtered and concentrated in vacuo. The material was applied to a 120 g silica column and eluted with 9:1 heptane/EtOAc. The fractions largely free of impurities were collected. The impure fractions were combined and evaporated then a second 80 g silica column was run on this material with 9:1 heptane/EtOAc as an eluent to give a second lot of material largely free of impurities. The material from the two columns were combined then further purified by flash chromatography on a 220 g silica gel cartridge with a gradient of 0 to 10% EtOAc/heptane to give 2-bromo-7-ethyl-6-(4-(2-methyl-1,3-dioxolan-2-yl)phenyl)-5-((2-(trimethylsilyl)ethoxy)methyl)-5H-pyrrolo[2,3-b]pyrazine (7.16 g, 49%): LC/MS (Table 2, Method g) $R_t$=2.0 min; MS m/z 518 (M+H)⁺.

Preparation #6: 3-(5-Methoxy-3-(1-methyl-6-tosyl-1,6-dihydropyrazolo[3,4-d]pyrrolo[2,3-b]pyridin-7-yl)-1H-indol-1-yl)propane-1,2-diol

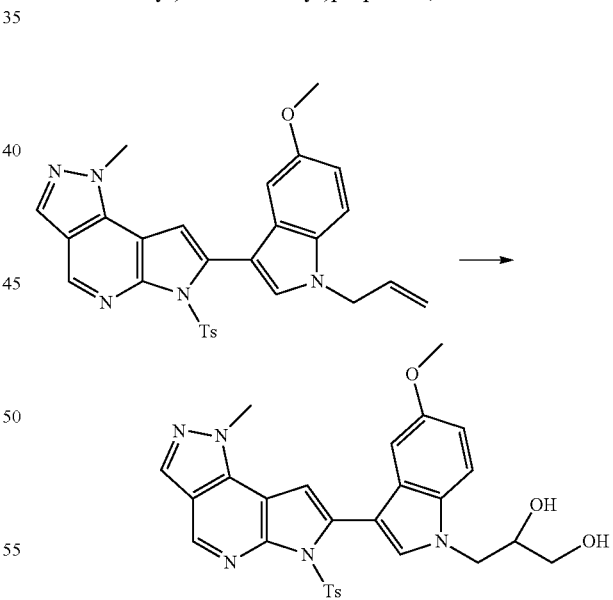

To a flask was added 7-(1-allyl-5-methoxy-1H-indol-3-yl)-1-methyl-6-tosyl-1,6-dihydropyrazolo[3,4-a]pyrrolo[2,3-b]pyridine (0.094 g, 0.184 mmol, prepared using U from Preparation #P.1.1 with allyl chloride), NMO (0.022 g, 0.184 mmol), acetone (3 mL), water (0.3 mL) and OsO₄ (2.5% in t-BuOH, 0.115 mL, 0.009 mmol). The mixture was stirred overnight at rt. The mixture was washed with saturated aqueous Na₂S₂O₃ (10 mL) and extracted with DCM (30 mL). The organic layer was dried over anhydrous MgSO₄ and concentrated in vacuo to provide 3-(5-methoxy-3-(1-methyl-6-tosyl-1,6-dihydropyrazolo[3,4-d]pyrrolo[2,3-b]pyridin-7-yl)-1H-indol-1-yl)propane-1,2-diol (0.091 g, 90%): LC/MS (Table 2, Method c) $R_t$=1.35 min; MS m/z 546 (M+H)$^+$.

Preparation #7: 7-(6,7-Dihydro-5H-pyrrolo[1,2-a]imidazol-3-yl)-1-methyl-6-tosyl-1,6-dihydropyrazolo[3,4-d]pyrrolo[2,3-b]pyridine

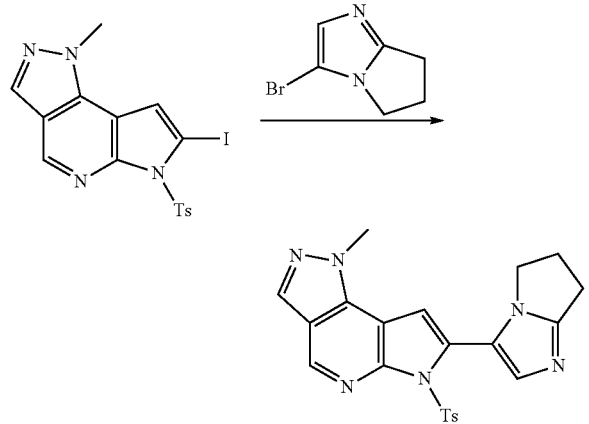

To a flask was added 3-bromo-6,7-dihydro-5H-pyrrolo[1,2-a]imidazole (0.250 g, 1.33 mmol, Apollo) and THF (3 mL). The mixture was cooled to about −30° C. and then i-PrMgBr (2.0 M in THF, 0.735 mL, 1.47 mmol) was added. After about 15 min, in a separate flask, zinc chloride (0.219 g, 1.604 mmol) was dissolved in THF (3 mL) and then the solution was added dropwise to the mixture. After about 30 min at about −20° C., 7-iodo-1-methyl-6-tosyl-1,6-dihydropyrazolo[3,4-d]pyrrolo[2,3-b]pyridine (0.250 g, 0.553 mmol; Preparation #1) and Pd(Ph$_3$P)$_4$ (0.093 g, 0.080 mmol), dissolved in DMF (2 mL) were then added to the mixture and it was then heated to about 80° C. for about 90 min. Water was added (30 mL) and solids were collected by filtration and dried under reduced pressure to provide 7-(6,7-dihydro-5H-pyrrolo[1,2-a]imidazol-3-yl)-1-methyl-6-tosyl-1,6-dihydropyrazolo[3,4-d]pyrrolo[2,3-b]pyridine (0.578 g, 100%): LC/MS (Table 2, Method c) $R_t$=1.27 min; MS m/z 433 (M+H)$^+$.

Preparation #8: 1-(Dimethylamino)-3-(5-methoxy-3-(1-methyl-6-tosyl-1,6-dihydropyrazolo[3,4-d]pyrrolo[2,3-b]pyridin-7-yl)-1H-indol-1-yl)propan-2-ol

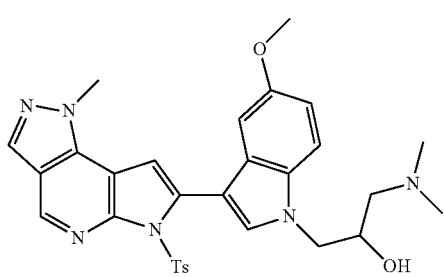 [SMILES: COc1ccc2c(c1)c(-c1cc3c4c(cnc3n1S(=O)(=O)c1ccc(C)cc1)cnn4C)cn2CC(O)CN(C)C]

Step A: 7-(5-Methoxy-1-(oxiran-2-ylmethyl)-1H-indol-3-yl)-1-methyl-6-tosyl-1,6-dihydropyrazolo[3,4-d]pyrrolo[2,3-b]pyridine

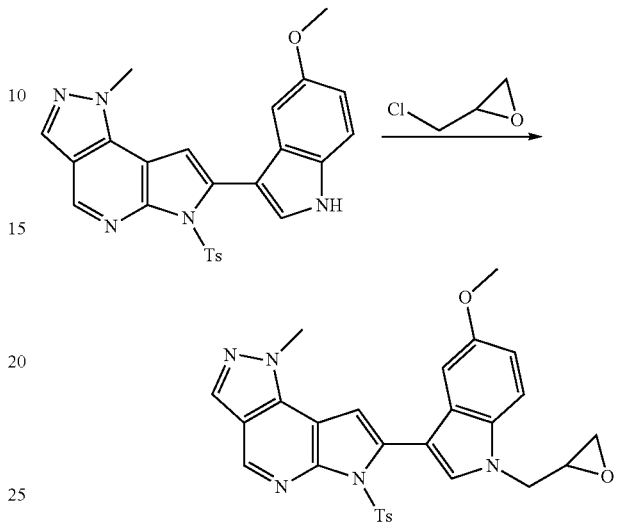

To a reaction flask was added 7-(5-methoxy-1H-indol-3-yl)-1-methyl-6-tosyl-1,6-dihydropyrazolo[3,4-d]pyrrolo[2,3-b]pyridine (0.100 g, 0.212 mmol; Preparation #P.1.1), DMF (3 mL) and 60 wt % NaH (0.010 g, 0.254 mmol) and 2-(chloromethyl)oxirane (0.026 g, 0.276 mmol). The mixture was stirred for about 2 h at rt. The mixture was concentrated in vacuo to provide 7-(5-methoxy-1-(oxiran-2-ylmethyl)-1H-indol-3-yl)-1-methyl-6-tosyl-1,6-dihydropyrazolo[3,4-d]pyrrolo[2,3-b]pyridine (100% yield assumed and carried forward to Step B): LC/MS (Table 2, Method c) $R_t$=1.49 min; MS m/z 528 (M+H)$^+$.

Step B: 1-(Dimethylamino)-3-(5-methoxy-3-(1-methyl-6-tosyl-1,6-dihydropyrazolo[3,4-d]pyrrolo[2,3-b]pyridin-7-yl)-1H-indol-1-yl)propan-2-ol

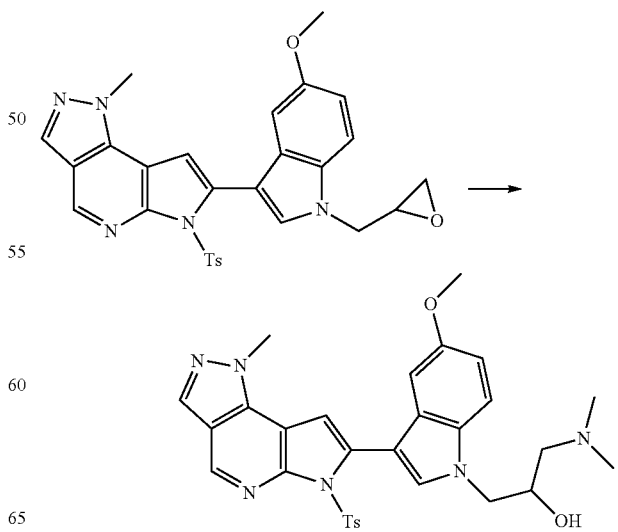

In a flask, a mixture of 7-(5-methoxy-1-(oxiran-2-ylmethyl)-1H-indol-3-yl)-1-methyl-6-tosyl-1,6-dihydropyrazolo[3,4-d]pyrrolo[2,3-b]pyridine (0.212 mmol) in DMF (5 mL) and dimethylamine (0.054 mL, 1.061 mmol) was stirred for about 17 h at rt. Additional dimethylamine (0.054 mL, 1.061 mmol) was added and the mixture was heated to about 50° C. for about 5 h, then at rt for about 17 h. The mixture was concentrated in vacuo to provide 1-(dimethylamino)-3-(5-methoxy-3-(1-methyl-6-tosyl-1,6-dihydropyrazolo[3,4-d]pyrrolo[2,3-b]pyridin-7-yl)-1H-indol-1-yl)propan-2-ol (0.120 g, 99%): LC/MS (Table 2, Method c) $R_t$=1.29 min; MS m/z 573 (M+H)$^+$.

Preparation #9. 3-(7-(5-Methoxy-1-methyl-1H-indol-3-yl)-6-((2-(trimethylsilyl)ethoxy)methyl)-6H-imidazo[1,5-a]pyrrolo[2,3-e]pyrazin-1-yl)propan-1-ol

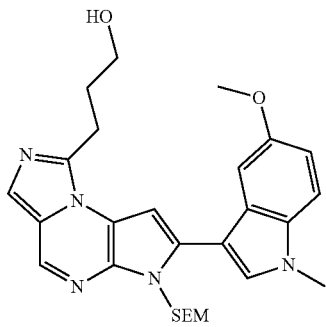 [SMILES: COc1ccc2c(c1)c(-c1cc3c(ncc4cnc(CCCO)n43)n1COCC[Si](C)(C)C)cn2C]

Step A: 4-Hydroxy-N-((6-(5-methoxy-1-methyl-1H-indol-3-yl)-5-((2-(trimethylsilyl)ethoxy)methyl)-5H-pyrrolo[2,3-b]pyrazin-2-yl)methyl)butanamide

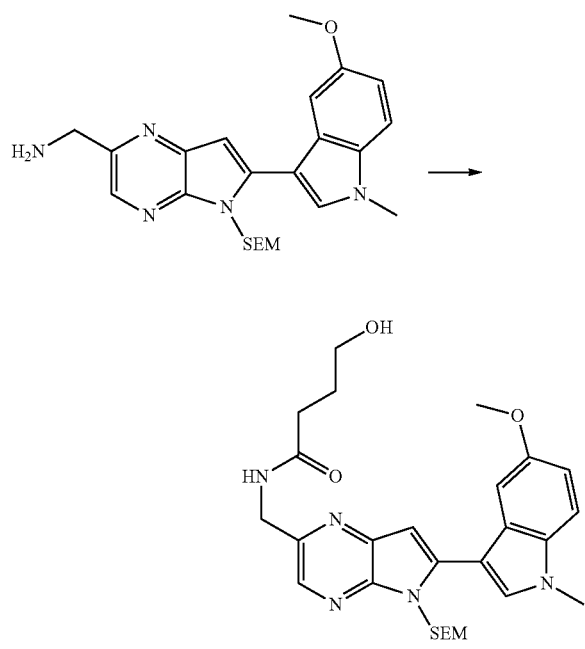

A flask was charged with (6-(5-methoxy-1-methyl-1H-indol-3-yl)-5-((2-(trimethylsilyl)ethoxy)methyl)-5H-pyrrolo[2,3-b]pyrazin-2-yl)methanamine (0.300 g, 0.686 mmol, Preparation #I.1), dihydrofuran-2(3H)-one (0.063 mL, 0.823 mmol), 1,2,4-triazole (0.009 g, 0.13 mmol), DBU (0.021 mL, 0.13 mmol) and DCM (10 mL). The mixture was heated to about 60° C. and stirred overnight. The mixture was concentrated under reduced pressure and the residue was diluted with EtOAc (10 mL) and washed with water (10 mL). The organic layer was dried over anhydrous MgSO$_4$, filtered and concentrated in vacuo. The material was purified by silica gel chromatography with an elution gradient of 0 to 100% EtOAc/heptane to give 4-hydroxy-N-((6-(5-methoxy-1-methyl-1H-indol-3-yl)-5-((2-(trimethylsilyl)ethoxy)methyl)-5H-pyrrolo[2,3-b]pyrazin-2-yl)methyl)butanamide (0.150 g, 42%): LC/MS (Table 2, Method b) $R_t$=2.40 min; MS m/z 524 (M+H)$^+$.

Step B: 4-(tert-Butyldimethylsilyloxy)-N-((6-(5-methoxy-1-methyl-1H-indol-3-yl)-5-((2-(trimethylsilyl)ethoxy)methyl)-5H-pyrrolo[2,3-b]pyrazin-2-yl)methyl)butanamide

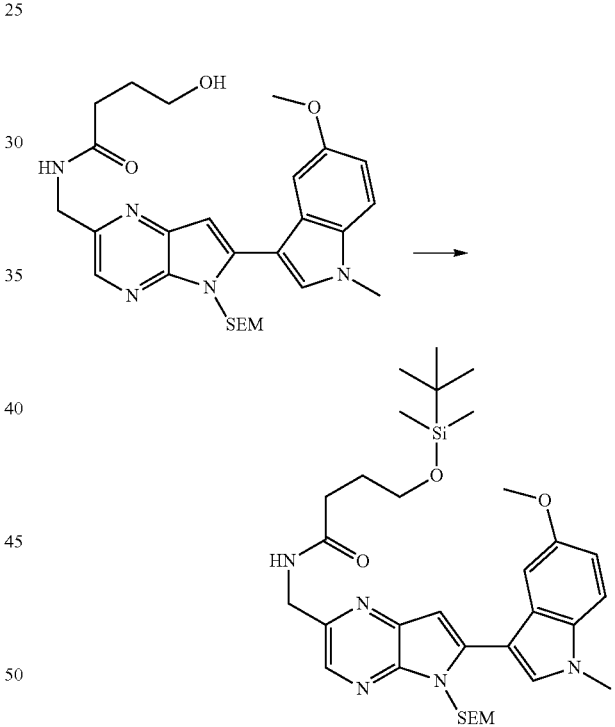

A flask was charged with 4-hydroxy-N-((6-(5-methoxy-1-methyl-1H-indol-3-yl)-5-((2-(trimethylsilyl)ethoxy)methyl)-5H-pyrrolo[2,3-b]pyrazin-2-yl)methyl)butanamide (0.130 g, 0.248 mmol) and DCM (5 mL). The mixture was cooled to about −5° C. To the mixture was added 2,6-lutidine (0.064 mL, 0.54 mmol). After about 2 min, TBDMSOTf (0.063 mL, 0.273 mmol) was added. The mixture was stirred at about −5 to 0° C. for about 2 h. The mixture was concentrated under reduced pressure and the residue was purified using silica gel chromatography with an elution gradient of 0 to 80% EtOAc/heptane to give 4-(tert-butyldimethylsilyloxy)-N-((6-(5-methoxy-1-methyl-1H-indol-3-yl)-5-((2-(trimethylsilyl)ethoxy)methyl)-5H-pyrrolo[2,3-b]pyrazin-2- yl)methyl)butanamide (0.117 g, 74%): LC/MS (Table 2, Method a) $R_f$=3.40 min; MS m/z 638 (M+H)$^+$.

Step C: 4-(tert-Butyldimethylsilyloxy)-N-((6-(5-methoxy-1-methyl-1H-indol-3-yl)-5-((2-(trimethylsilyl)ethoxy)methyl)-5H-pyrrolo[2,3-b]pyrazin-2-yl)methyl)butanethioamide

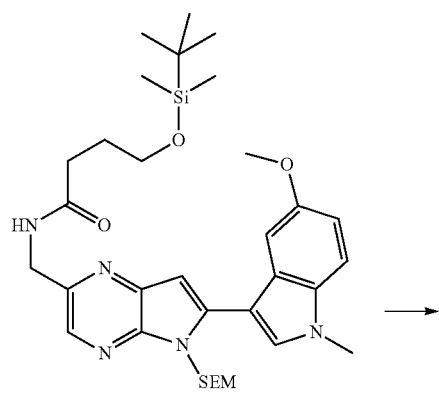

A flask was charged with 4-(tert-butyldimethylsilyloxy)-N-((6-(5-methoxy-1-methyl-1H-indol-3-yl)-5-((2-(trimethylsilyl)ethoxy)methyl)-5H-pyrrolo[2,3-b]pyrazin-2-yl)methyl)butanamide (0.100 g, 0.157 mmol) and 1,4-dioxane (5 mL). Lawesson's Reagent (0.095 g, 0.235 mmol) was added and the mixture was stirred at about 85° C. for about 1 h. The mixture was cooled to rt, concentrated in vacuo and the residue was partitioned with EtOAc (10 mL) and saturated aqueous NaHCO$_3$ (7 mL). The organic layer was separated, dried over anhydrous MgSO$_4$, filtered, and concentrated under reduced pressure to give 4-(tert-butyldimethylsilyloxy)-N-((6-(5-methoxy-1-methyl-1H-indol-3-yl)-5-((2-(trimethylsilyl)ethoxy)methyl)-5H-pyrrolo[2,3-b]pyrazin-2-yl)methyl)butanethioamide (0.103 g, 100%): LC/MS (Table 2, Method b) $R_f$=3.84 min; MS m/z 654 (M+H)$^+$.

Step D: 3-(7-(5-Methoxy-1-methyl-1H-indol-3-yl)-6-((2-(trimethylsilyl)ethoxy)methyl)-6H-imidazo[1,5-a]pyrrolo[2,3-e]pyrazin-1-yl)propan-1-ol

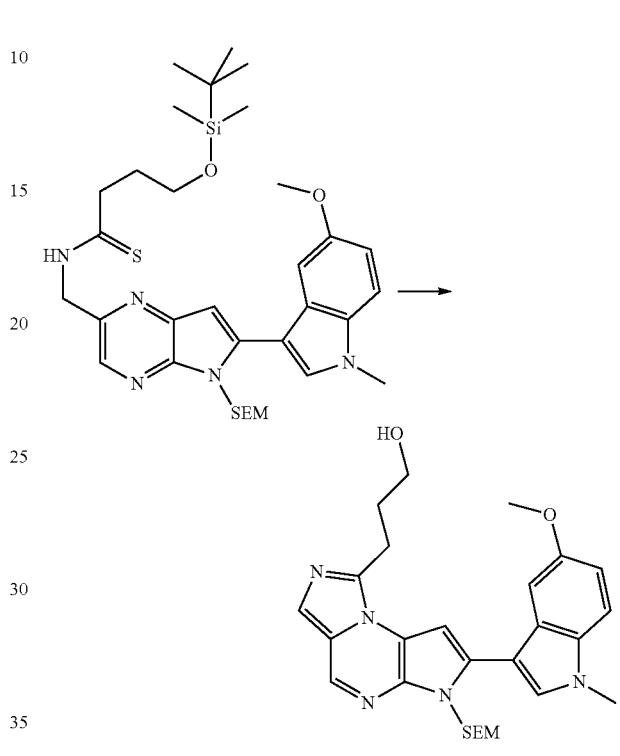

A flask was charged with 4-(tert-butyldimethylsilyloxy)-N-((6-(5-methoxy-1-methyl-1H-indol-3-yl)-5-((2-(trimethylsilyl)ethoxy)methyl)-5H-pyrrolo[2,3-b]pyrazin-2-yl)methyl)butanethioamide (0.158 g, 0.241 mmol) and 1,4-dioxane (3 mL). To the mixture was added bis(2,2,2-trifluoroacetoxy)mercury (0.103 g, 0.241 mmol). The mixture was heated to about 65° C. for 1 h. The mixture was then filtered and concentrated under reduced pressure. The material was purified using silica gel chromatography with an elution gradient of 15 to 100% EtOAc/heptane followed by 0 to 5% MeOH/DCM to give 3-(7-(5-methoxy-1-methyl-1H-indol-3-yl)-6-((2-(trimethylsilyl)ethoxy)methyl)-6H-imidazo[1,5-a]pyrrolo[2,3-e]pyrazin-1-yl)propan-1-ol (0.022 g, 18%): LC/MS (Table 2, Method b) $R_f$=2.59 min; MS m/z 506 (M+H)$^+$.

Preparation #10: N-((7-Ethyl-6-(4-(2-methyl-1,3-dioxolan-2-yl)phenyl)-5-((2-(trimethylsilyl)ethoxy)methyl)-5H-pyrrolo[2,3-b]pyrazin-2-yl)methyl)formamide

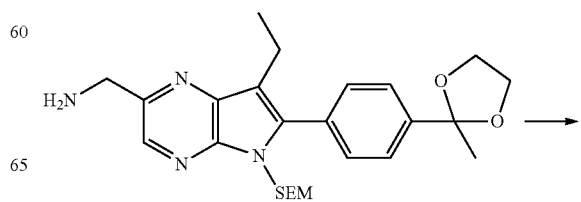

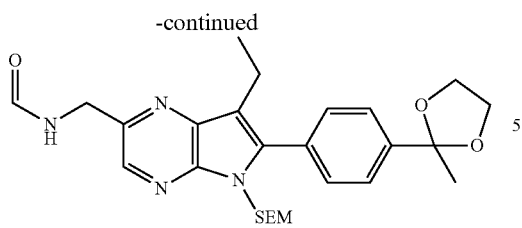

(7-Ethyl-6-(4-(2-methyl-1,3-dioxolan-2-yl)phenyl)-5-((2-(trimethylsilyl)ethoxy)methyl)-5H-pyrrolo[2,3-b]pyrazin-2-yl)methanamine (0.250 g, 0.533 mmol, prepared using D from Preparation #5 with (E)-styrylboronic acid, E, F, G and I) in ethyl formate (3.30 mL, 40.5 mmol) was heated to about 65° C. for about 2 h. The mixture was cooled to rt then the solvent was re removed under reduced pressure to give N-((7-ethyl-6-(4-(2-methyl-1,3-dioxolan-2-yl)phenyl)-5-((2-(trimethylsilyl)ethoxy)methyl)-5H-pyrrolo[2,3-b]pyrazin-2-yl)methyl)formamide (0.265 g, 100%): LC/MS (Table 2, Method b) $R_t$=2.71 min; MS m/z 497 (M+H)$^+$.

Preparation #11. 5-Methoxy-1-methyl-3-(4,4,5,5-tetramethyl-1,3,2-dioxaborolan-2-yl)-1H-indole

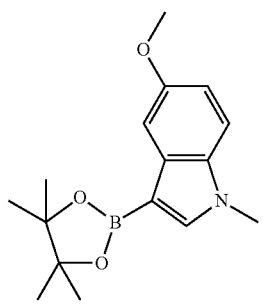

3-Iodo-5-methoxy-1-methyl-1H-indole

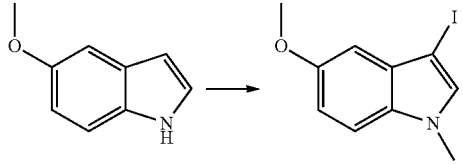

A flask containing 5-methoxy-1H-indole (5.15 g, 35.0 mmol) in DMF (100 mL) at rt was stirred with KOH (2.06 g, 36.7 mmol) for about 15 min and then treated with iodine (9.06 g, 35.7 mmol). After about 30 min, 60 wt % NaH (1.68 g, 42.0 mmol) was added portion-wise. After about 15 min, MeI (2.41 mL, 38.5 mmol) was added and the mixture was stirred for about 15 min. The solvents were evaporated under reduced pressure and the residue was stirred with water (300 mL) for about 15 min at P. The slurry was treated with DCM (100 mL) and the layers were separated. The aqueous layer was extracted with DCM (30 mL) and the combined organics were washed with water (100 mL), dried over anhydrous MgSO$_4$, filtered and concentrated in vacuo to give 3-iodo-5-methoxy-1-methyl-1H-indole (9.90 g, 99%) as a crude intermediate that was carried on to the next step without characterization.

Step B: 5-Methoxy-1-methyl-3-(4,4,5,5-tetramethyl-1,3,2-dioxaborolan-2-yl)-1H-indole

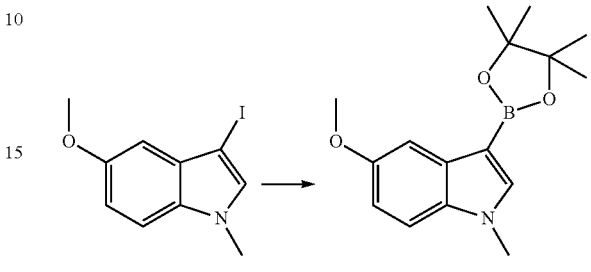

The 3-iodo-5-methoxy-1-methyl-1H-indole (9.90 g, 34.5 mmol) in 1,4-dioxane (200 mL) was treated with PdCl$_2$(dppf)-CH$_2$Cl$_2$ (1.41 g, 1.72 mmol), TEA (33.6 mL, 241 mmol) and 4,4,5,5-tetramethyl-1,3,2-dioxaborolane (28.7 g, 224 mmol). The mixture was heated to about 100° C. for about 40 min. The mixture was cooled to rt and concentrated under reduced pressure. The material was stirred with EtOAc (300 mL) at rt for about 30 min and then filtered. The filtrate was concentrated under reduced pressure and the residue was purified by silica gel chromatography eluting with 100% DCM to give 5-methoxy-1-methyl-3-(4,4,5,5-tetramethyl-1,3,2-dioxaborolan-2-yl)-1H-indole (3.7 g, 37%): LC/MS (Table 2, Method a) $R_t$=2.68 min; MS m/z 288 (M+H)$^+$.

Preparation #12: 1-Cyclohexyl-3-(4-(methylsulfonyl)phenyl)-6-((2-(trimethylsilyl)ethoxy)methyl)-3,6-dihydroimidazo[4,5-d]pyrrolo[2,3-b]pyridin-2(1H)-one

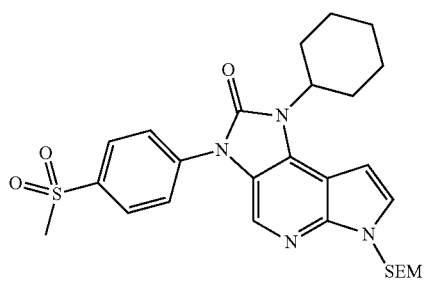 [SMILES: C[Si](C)(C)CCOCn1ccc2c1ncc1c2n(C2CCCCC2)c(=O)n1-c1ccc(S(C)(=O)=O)cc1]

Step A: Ethyl 4-chloro-1-(triisopropylsilyl)-1H-pyrrolo[2,3-b]pyridine-5-carboxylate

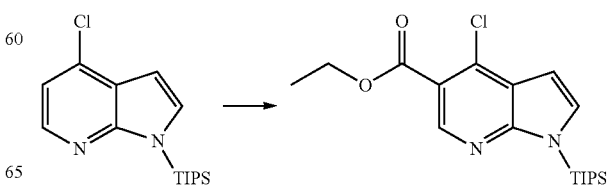

145

To a solution of 4-chloro-1-(triisopropylsilyl)-1H-pyrrolo[2,3-b]pyridine (0.856 g, 2.77 mmol, Preparation #1, Step A) in THF (20 mL) at about −78° C. was added sec-BuLi (4.35 mL1, 6.10 mmol) dropwise. The reaction was stirred at −78° C. for about 80 min. To the mixture was added ethyl chloroformate (0.665 mL, 6.93 mmol. The flask was removed from the cooling bath and stirred for about 70 min at rt. The mixture was quenched by the addition of a saturated aqueous NH₄Cl (5 mL). EtOAc (20 mL) and water (20 mL) were added and the layers were separated. The aqueous layer was extracted with EtOAc (2×15 mL), and the combined organic layers were washed with brine (20 mL). The organic layer was dried over MgSO₄, filtered, and concentrated in vacuo. The material was purified by flash chromatography (40 g Redi-Sep™ silica column) eluting with 0-10% EtOAc in heptane to give ethyl 4-chloro-1-(triisopropylsilyl)-1H-pyrrolo[2,3-b]pyridine-5-carboxylate (1.02 g, 97%): $^1$H NMR (400 MHz, DMSO) δ 8.69 (s, 1H), 7.69 (d, J=3.6, 1H), 6.72 (dd, J=68.4, 3.5, 1H), 4.34 (q, J=7.0, 2H), 1.86 (dt, J=15.0, 7.5, 3H), 1.34 (t, J=7.1, 3H), 1.05 (d, J=7.5, 18H).

Step B: Ethyl 4-(cyclohexylamino)-1H-pyrrolo[2,3-b]pyridine-5-carboxylate

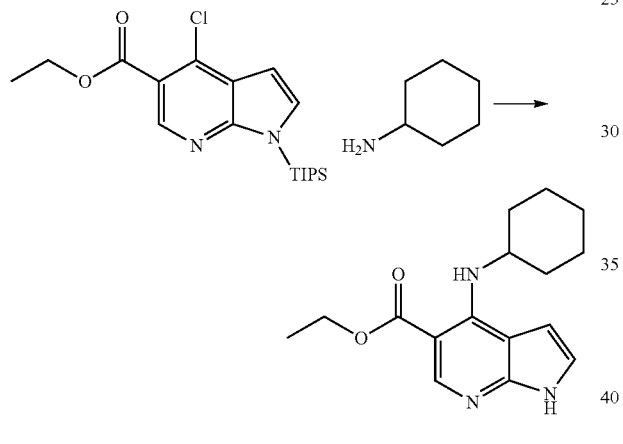

A mixture of ethyl 4-chloro-1-(triisopropylsilyl)-1H-pyrrolo[2,3-b]pyridine-5-carboxylate (1.5 g, 3.9 mmol) and cyclohexylamine (2.34 g, 23.6 mmol) was stirred at about 80° C. for about 24 h. The solvent was removed under reduced pressure. The residue was suspended in Et₂O and the precipitate was collected by filtration and dried under vacuum. The solid was washed with water and dried under vacuum again to give ethyl-4-(cyclohexylamino)-1H-pyrrolo[2,3-b]pyridine-5-carboxylate (0.54 g, 48%): LC/MS (Table 2, Method b) R$_t$=2.56 min.; MS m/z: 288 (M+H)⁺.

Step C: Ethyl 4-(cyclohexylamino)-1-((2-(trimethylsilyl)ethoxy)methyl)-1H-pyrrolo[2,3-b]pyridine-5-carboxylate

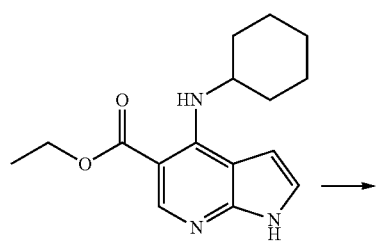

146

-continued

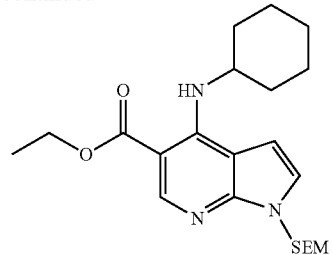

A suspension of NaH (60 wt % in mineral oil, 0.077 g, 1.9 mmol) in DMF (15 mL) was cooled to about 0° C. Ethyl 4-(cyclohexylamino)-1H-pyrrolo[2,3-b]pyridine-5-carboxylate (0.52 g, 1.8 mmol) was added and the resulting mixture was stirred for about 20 min at about 0° C. SEMCl (0.308 g, 1.84 mmol) was added and the resulting mixture was stirred for about 2 h while warming to rt. The solvent was removed under reduced pressure and the residue partitioned between EtOAc (120 mL) and saturated aqueous NH₄Cl (40 mL). The organic phase was isolated, washed with brine (50 mL), dried over anhydrous MgSO₄, filtered and concentrated under reduced pressure to give ethyl 4-(cyclohexylamino)-1-((2-(trimethylsilyl)ethoxy)methyl)-1H-pyrrolo[2,3-b]pyridine-5-carboxylate (0.77 g, 100%): LC/MS (Table 2, Method b) R$_t$=3.29 min.; MS m/z: 418 (M+H)⁺.

Step D: 4-(Cyclohexylamino)-1-((2-(trimethylsilyl)ethoxy)methyl)-1H-pyrrolo[2,3-b]pyridine-5-carboxylic acid

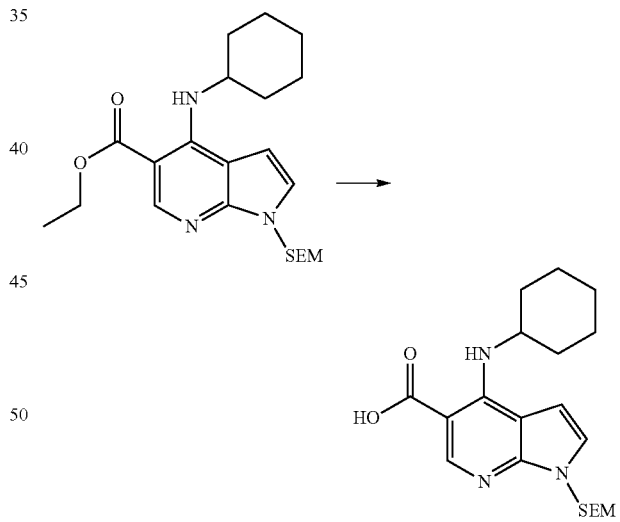

To the suspension of ethyl 4-(cyclohexylamino)-1-((2-(trimethylsilyl)ethoxy)methyl)-1H-pyrrolo[2,3-b]pyridine-5-carboxylate (0.77 g, 1.9 mmol) in 1,4-dioxane (12 mL) was added aquoeous NaOH (1 N, 12 mL, 12 mmol). The mixture was stirred at rt for about 48 h. To the mixture was added EtOH (1 mL) and the mixture was heated at about 50° C. for about 24 h. The mixture was concentrated under reduced pressure and aqueous HCl (0.5 M, 10 mL) was added and the mixture extracted with EtOAc (25 mL). The solid in the organic layer was collected by vacuum filtration. The filtrate and aqueous layer were recombined and separated. The solid was dissolved in EtOAc (~150 mL). The combined organic layers were dried over Na$_2$SO$_4$, filtered and concentrated in vacuo and dried under reduced pressure at about rt to give 4-(cyclohexylamino)-1-((2-(trimethylsilyl)ethoxy)methyl)-1H-pyrrolo[2,3-b]pyridine-5-carboxylic acid (0.713 g, 99%): LC/MS (Table 2, Method b) R$_t$=2.74 min.; MS m/z: 390 (M+H)$^+$.

Step E: 1-Cyclohexyl-6-((2-(trimethylsilyl)ethoxy)methyl)-3,6-dihydroimidazo[4,5-d]pyrrolo[2,3-b]pyridin-2(1H)-one

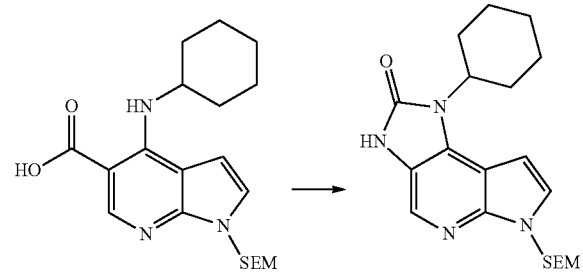 [SMILES: C[Si](C)(C)CCOCn1ccc2c(NC3CCCCC3)c(C(=O)O)cnc21 ; C[Si](C)(C)CCOCn1ccc2c1ncc1[nH]c(=O)n(C3CCCCC3)c12]

4-(Cyclohexylamino)-1-((2-(trimethylsilyl)ethoxy)methyl)-1H-pyrrolo[2,3-b]pyridine-5-carboxylic acid (0.713 g, 1.83 mmol) and TEA (0.638 mL, 4.58 mmol) were combined in 1,4-dioxane (14 mL) to give a suspension. The mixture was stirred until the suspension had dissolved. Diphenylphosphoryl azide (0.790 mL, 3.66 mmol) was added and the reaction heated at about 100° C. for about 5 h. DCM (50 mL) and saturated aqueous NaHCO$_3$ (25 mL) were added and the layers separated. The aqueous layer was extracted with DCM (25 mL). The combined organic layers were washed with brine, dried over MgSO$_4$, filtered, and concentrated in vacuo. The residue was purified by flash column chromatography (40 g Silicycle™ column) eluting with 20-80% EtOAc in DCM. The solvents were removed under reduced pressure. The material was triturated with heptane and the solid was collected by vacuum filtration and washed with heptane. The solid was dried under vacuum at about 50° C. to a constant weight to give 1-cyclohexyl-6-((2-(trimethylsilyl)ethoxy)methyl)-3,6-dihydroimidazo[4,5-d]pyrrolo[2,3-b]pyridin-2(1H)-one (0.501 g, 70%): LC/MS (Table 2, Method b) R$_t$=2.78 min.; MS m/z: 387 (M+H)$^+$.

Step F: 1-Cyclohexyl-3-(4-(methylsulfonyl)phenyl)-6-((2-(trimethylsilyl)ethoxy)methyl)-3,6-dihydroimidazo[4,5-d]pyrrolo[2,3-b]pyridin-2(1H)-one

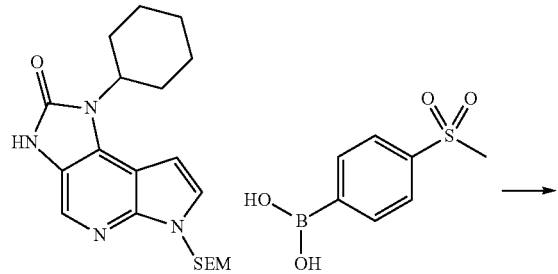

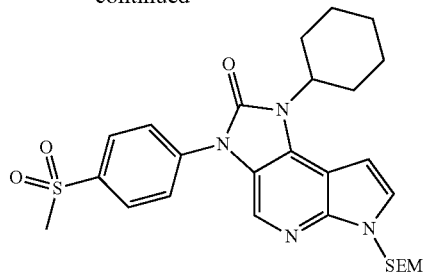

1-Cyclohexyl-6-((2-(trimethylsilyl)ethoxy)methyl)-3,6-dihydroimidazo[4,5-d]pyrrolo[2,3-b]pyridin-2(1H)-one (0.100 g, 0.259 mmol), 4-(methylsulfonyl)phenylboronic acid (0.103 g, 0.517 mmol, Acros), TEA (0.072 mL, 0.52 mmol) and 4 Å molecular sieves (130 mg) were added to DCM (2.6 mL) in a vial. Copper (II) acetate (0.047 g, 0.259 mmol) (Aldrich) was added in one portion and the vial was sealed. The mixture was stirred for about 22 h at rt. DCM (15 mL), water (5 mL), and concentrated NH$_4$OH (5 mL) were added and the layers separated. The aqueous layer was extracted with DCM (5 mL). The combined organic layers were washed with water (10 mL), washed with brine (10 mL), dried over MgSO$_4$, filtered, and concentrated in vacuo. The residue was purified by flash column chromatography (25 g Silicycle™ column) eluting with 10-50% EtOAc in DCM to give 1-cyclohexyl-3-(4-(methylsulfonyl)phenyl)-6-((2-(trimethylsilyl)ethoxy)methyl)-3,6-dihydroimidazo[4,5-d]pyrrolo[2,3-b]pyridin-2(1H)-one (0.068 g, 48%): LCMS (Table 2, Method b) R$_t$=3.16 min.; MS m/z: 541 (M+H)$^+$.

Preparation #13: 1-(6-(4-Methoxyphenyl)-5-((2-(trimethylsilyl)ethoxy)methyl)-5H-pyrrolo[2,3-b]pyrazin-2-yl)ethanone

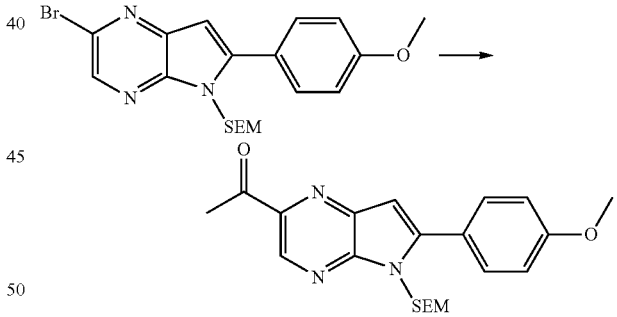

2-Bromo-6-(4-methoxyphenyl)-5-((2-(trimethylsilyl)ethoxy)methyl)-5H-pyrrolo[2,3-b]pyrazine (1.5 g, 3.5 mmol, prepared using A from 3,5-dibromopyrazin-2-amine with 1-ethynyl-4-methoxybenzene, B and C) in THF (20 mL) was cooled to about –75° C. then n-BuLi (1.44 mL, 3.45 mmol) was added dropwise keeping the temperature below –70° C. After about 5 min DMA (1.30 mL, 13.8 mmol) was added keeping the temperature below about –65° C. The mixture was stirred for about 30 min at about –75° C. then allowed to warm slowly to about 0° C. AcOH (~0.5 mL) was added then the mixture was diluted with water (40 mL), saturated aqueous Na$_2$CO$_3$ (20 mL) and EtOAc (40 mL). The layers were separated then the organic layer was washed with brine (20 mL), dried over MgSO$_4$, filtered and concentrated under reduced pressure. The material was purified by flash chromatography on an 80 g silica column with 85:15 DCM/EtOAc as an eluent to give 1-(6-(4-methoxyphenyl)-5-((2-(trimethylsilyl)ethoxy)methyl)-5H-pyrrolo[2,3-b]pyrazin-2-yl)ethanone (1.04 g, 76%): LC/MS (Table 2, Method a) R$_t$=3.42 min; MS m/z 398 (M+H)$^+$.

Preparation #14: 2-Allyl-7-ethyl-6-(4-(2-methyl-1,3-dioxolan-2-yl)phenyl)-5-((2-(trimethylsilyl)ethoxy)methyl)-5H-pyrrolo[2,3-b]pyrazine

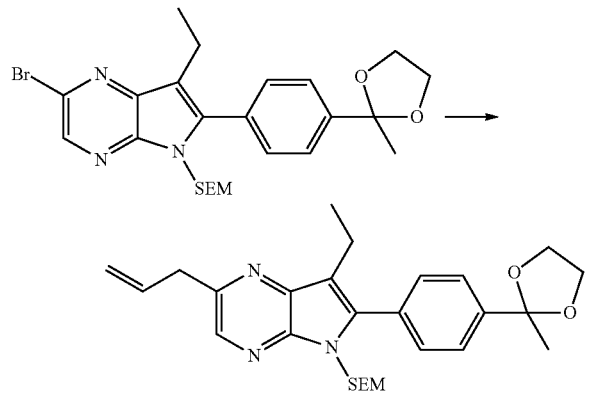

2-Bromo-7-ethyl-6-(4-(2-methyl-1,3-dioxolan-2-yl)phenyl)-5-((2-(trimethylsilyl)ethoxy)methyl)-5H-pyrrolo[2,3-b]pyrazine (0.500 g, 0.964 mmol, Preparation #5) in THF (6 mL) was cooled to about −75° C. then the n-BuLi (2.4 M in hexanes, 0.482 mL, 1.16 mmol) was added dropwise. After about 10 min CuCN (0.009 g, 0.010 mmol) was added followed by allyl bromide (0.250 mL, 2.89 mmol). The mixture was stirred at about −70° C. for about 30 min warmed to about −40° C. the mixture was treated with about 2 mL of saturated aqueous NaHCO$_3$ then warmed to rt. The mixture was diluted with EtOAc (20 mL) and water (10 mL). The layers were separated and the aqueous layer extracted with EtOAc (10 mL). The combined organics were washed with brine (10 mL), dried over MgSO$_4$, filtered and concentrated under reduced pressure. The material was purified on a 10 gram silica column with 9:1 DCM/EtOAc as an eluent to give 2-allyl-7-ethyl-6-(4-(2-methyl-1,3-dioxolan-2-yl)phenyl)-5-((2-(trimethylsilyl)ethoxy)methyl)-5H-pyrrolo[2,3-b]pyrazine (0.323 g, 70%): LC/MS (Table 2, Method b) R$_t$=3.53 min; MS m/z 480 (M+H)$^+$.

Preparation #15: 7-(5-Methoxy-1-methyl-1H-indazol-3-yl)-1-methyl-6-tosyl-1,6-dihydropyrazolo[3,4-d]pyrrolo[2,3-b]pyridine

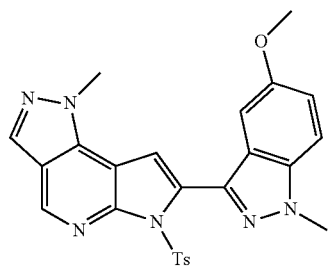 [SMILES: COc1ccc2c(c1)c(-c1cc3c4c(cnc3n1S(=O)(=O)c1ccc(C)cc1)cnn4C)nn2C]

Step A: 5-Methoxy-1-methyl-3-(trimethylstannyl)-1H-indazole

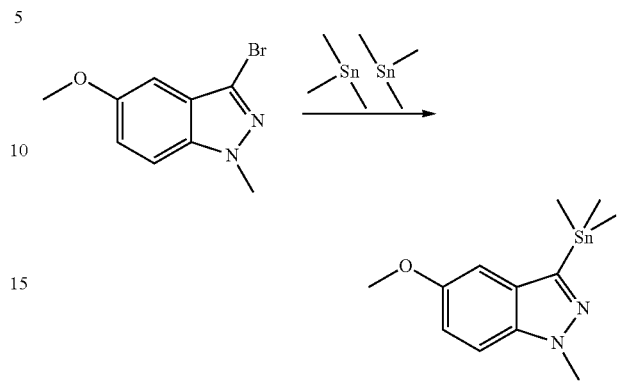

In a flask was added 3-bromo-5-methoxy-1-methyl-1H-indazole (0.18 g, 0.75 mmol, prepared using U from 3-bromo-5-methoxy-1H-indazole [Sinova]) and Pd(Ph$_3$P)$_4$ (0.31 g, 0.27 mmol, Strem) in toluene (6 mL). 1,1,1,2,2,2-Hexamethyldistannane (0.318 g, 0.971 mmol) was added and the resulting solution was heated to about 110° C. for about 1 h. The mixture was cooled to rt, concentrated and then purified on a 12 g silica column eluting with 0 to 30% EtOAc/heptane to provide 5-methoxy-1-methyl-3-(trimethylstannyl)-1H-indazole (0.070 g, 29%): LC/MS (Table 2, Method b) R$_t$=2.59 min; MS m/z 326 (M+H)$^+$.

Step B: 7-(5-Methoxy-1-methyl-1H-indazol-3-yl)-1-methyl-6-tosyl-1,6-dihydropyrazolo[3,4-d]pyrrolo[2,3-b]pyridine

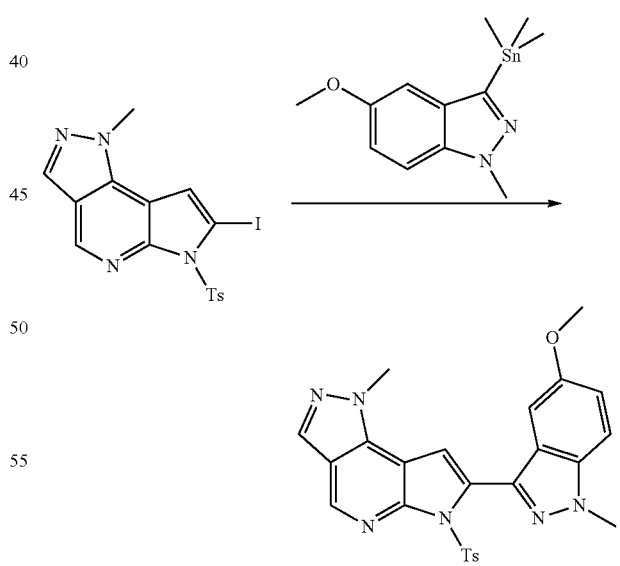

To a flask was added 7-iodo-1-methyl-6-tosyl-1,6-dihydropyrazolo[3,4-d]pyrrolo[2,3-b]pyridine (0.090 g, 0.20 mmol, Preparation #1), Pd(Ph$_3$P)$_4$ (0.018 g, 0.016 mmol) and 5-methoxy-1-methyl-3-(trimethylstannyl)-1H-indazole (0.071 g, 0.22 mmol) in DMF (3 mL) and the mixture was heated to about 80° C. for about 17 h. The mixture was cooled to rt and then loaded directly on 12 g silica column and eluted with 0 to 100% EtOAc/DCM to provide 7-(5-methoxy-1-methyl-1H-indazol-3-yl)-1-methyl-6-tosyl-1,6-dihydropyrazolo[3,4-d]pyrrolo[2,3-b]pyridine (0.045 g, 47%): LC/MS (Table 2, Method c) $R_t$=1.47 min; MS m/z 487 (M+H)$^+$.

Preparation #16: 3-(3-Bromo-6-tosyl-6H-imidazo[1,5-a]pyrrolo[2,3-e]pyrazin-1-yl)picolinaldehyde

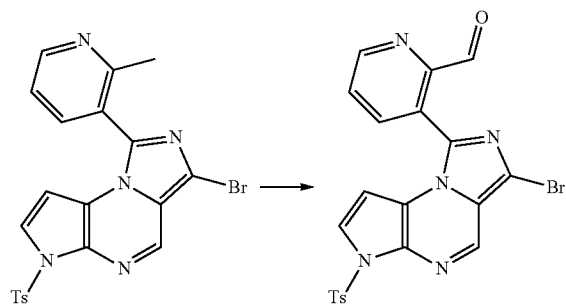 [SMILES: Cc1ccc(S(=O)(=O)n2ccc3c2ncc2c(Br)nc(-c4cccnc4C)n23)cc1 ; Cc1ccc(S(=O)(=O)n2ccc3c2ncc2c(Br)nc(-c4cccnc4C=O)n23)cc1]

The 3-bromo-1-(2-methylpyridin-3-yl)-6-tosyl-6H-imidazo[1,5-a]pyrrolo[2,3-e]pyrazine (0.500 g, 1.03 mmol, prepared using J.1 from Example #2, Step B with 2-methylnicotinic acid, L.2 with POCl$_3$ and AB) in 1,4-dioxane (20 mL) was treated with SeO$_2$ (0.210 g, 1.89 mmol) then the mixture was heated at about 105° C. for about 1 h. The mixture was cooled to rt then water (0.6 mL) was added. The mixture was heated to reflux for about 3 days. The mixture was cooled to rt then concentrated in vacuo. The material was purified using a 10 g silica column eluting with EtOAc. The impure fractions were combined and concentrated then the material was purified using a 10 g silica column eluting with EtOAc. The materials were combined to give 3-(3-bromo-6-tosyl-6H-imidazo[1,5-a]pyrrolo[2,3-e]pyrazin-1-yl)picolinaldehyde (0.355 g, 69%): LC/MS (Table 2, Method b) $R_t$=3.53 min; MS m/z 480 (M+H)$^+$.

Preparation #17: 4-(2-(1-Methyl-3-(1-methyl-6-tosyl-1,6-dihydropyrazolo[3,4-d]pyrrolo[2,3-b]pyridin-7-yl)-1H-indol-5-yloxy)ethyl)morpholine

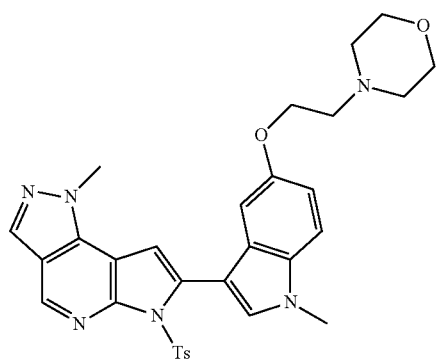 [SMILES: Cc1ccc(S(=O)(=O)n2c(-c3cn(C)c4ccc(OCCN5CCOCC5)cc34)cc3c4c(cnc32)cnn4C)cc1]

Step A: 1-Methyl-3-(1-methyl-6-tosyl-1,6-dihydropyrazolo[3,4-d]pyrrolo[2,3-b]pyridin-7-yl)-1H-indol-5-ol

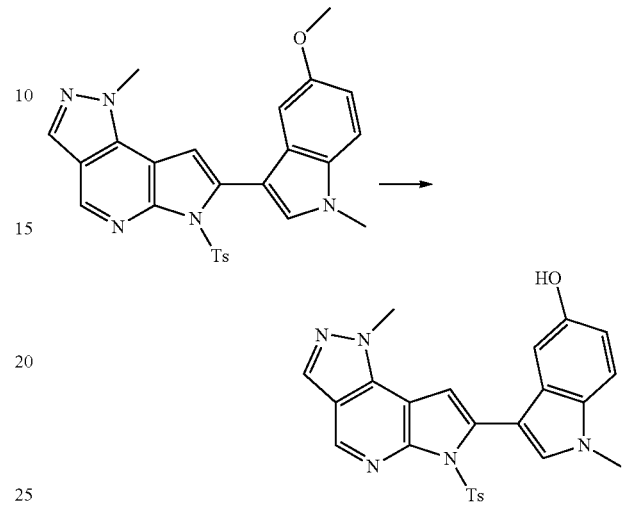

A solution of 7-(5-methoxy-1-methyl-1H-indol-3-yl)-1-methyl-6-tosyl-1,6-dihydropyrazolo[3,4-d]pyrrolo[2,3-b]pyridine (0.22 g, 0.46 mmol, [WO2009/152133, Example #42]) in DCM (10 mL) was cooled to about 0° C. BBr$_3$ (1.0 M in DCM, 1.39 mL, 1.39 mmol) was added dropwise. The mixture was stirred at rt for about 16 h. The mixture was cooled to about 0° C. and MeOH (0.5 mL) was added dropwise followed by a solution of saturated aqueous NaHCO$_3$ (6 mL). The mixture was concentrated in vacuo and the residue was partitioned between EtOAc (2×75 mL) and saturated aqueous NaHCO$_3$ (50 mL). The organic layer was isolated and washed with saturated aqueous NaHCO$_3$ (50 mL), brine (50 mL), dried over Na$_2$SO$_4$, filtered, and concentrated under reduced pressure. The residue was purified by flash chromatography (12 g silica gel column, EtOAc/MeOH/Et$_3$N 100:10:0 to 100:10:1) to give 1-methyl-3-(1-methyl-6-tosyl-1,6-dihydropyrazolo[3,4-d]pyrrolo[2,3-b]pyridin-7-yl)-1H-indol-5-ol (0.21 g, 99%): LC/MS (Table 2, Method a) $R_t$=2.10 min; MS m/z 472 (M+H)$^+$.

Step B: 4-(2-(1-methyl-3-(1-methyl-6-tosyl-1,6-dihydropyrazolo[3,4-d]pyrrolo[2,3-b]pyridin-7-yl)-1H-indol-5-yloxy)ethyl)morpholine

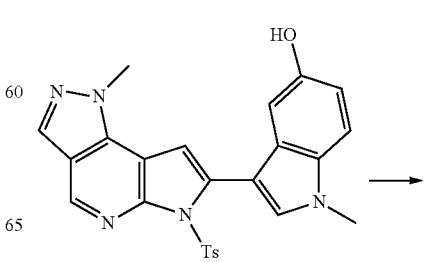

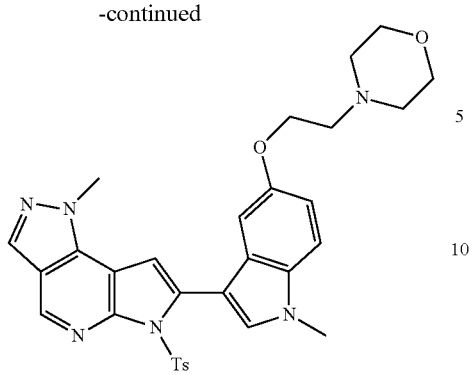

A mixture of 1-methyl-3-(1-methyl-6-tosyl-1,6-dihydropyrazolo[3,4-d]pyrrolo[2,3-b]pyridin-7-yl)-1H-indol-5-ol (0.21 g, 0.42 mmol), 4-(2-chloroethyl)morpholine (0.12 g, 0.78 mmol, Beta Pharm) and $Cs_2CO_3$ (0.42 g, 1.27 mmol) in DMF (4 mL) was heated at about 50° C. for about 20 h. After cooling to rt the mixture was filtered. The filtrate was purified by preparative reverse phase HPLC (Table 2, Method j) to give 4-(2-(1-methyl-3-(1-methyl-6-tosyl-1,6-dihydropyrazolo[3,4-d]pyrrolo[2,3-b]pyridin-7-yl)-1H-indol-5-yloxy)ethyl)morpholine (0.053 g, 21%): LC/MS (Table 2, Method a) $R_t$=2.07 min; MS m/z 585 (M+H)$^+$.

Preparation #18: Methyl 3-iodo-1-methyl-1H-indole-5-carboxylate

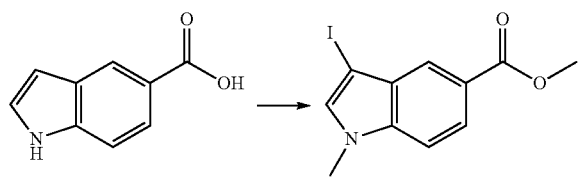

The 1H-indole-5-carboxylic acid (6.5 g, 40.3 mmol) in DMF (50 mL) was treated with powdered KOH (4.75 g, 85 mmol) then stirred for about 15 min. $I_2$ (10.75 g, 42.3 mmol) was added and the mixture was stirred for about 1 h. NaH (60 wt % in mineral oil, 1.94 g, 48.4 mmol) was added, the mixture was stirred for about 15 min then MeI (2.77 mL, 44.4 mmol) was added. After about 1 h an additional portion of NaH (60 wt % in mineral oil, 3.87 g, 97.0 mmol) and MeI (5.6 mL, 89 mmol) were added. The mixture was stirred at rt for about 48 h. The mixture was poured into water (400 mL) then extracted with EtOAc (3×100 mL). The combined organics were washed with water (3×100 mL) then brine (100 mL), dried over $MgSO_4$, filtered and concentrated under reduced pressure to give methyl 3-iodo-1-methyl-1H-indole-5-carboxylate (13.1 g, 103%): LC/MS (Table 2, Method a) $R_t$=2.60 min; MS m/z 316 (M+H)$^+$.

Preparation #19: tert-Butyl (7-bromo-5-tosyl-5H-pyrrolo[2,3-b]pyrazin-2-yl)methylcarbamate

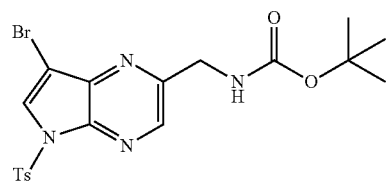 [SMILES: Cc1ccc(S(=O)(=O)n2cc(Br)c3nc(CNC(=O)OC(C)(C)C)cnc32)cc1]

Step A: tert-Butyl (5-tosyl-5H-pyrrolo[2,3-b]pyrazin-2-yl)methylcarbamate

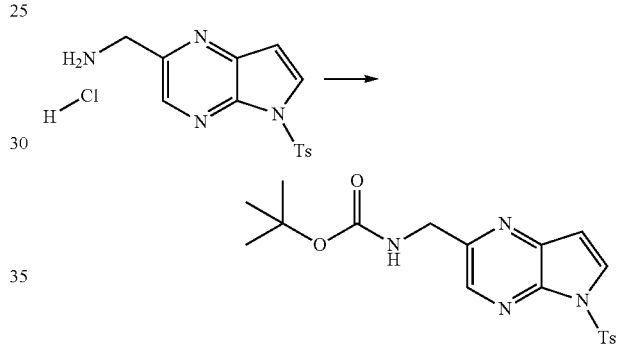

A flask was charged with (5-tosyl-5H-pyrrolo[2,3-b]pyrazin-2-yl)methanamine, hydrochloride (0.400 g, 1.18 mmol, Example #2, Step B), MeCN (5.0 mL), water (1.0 mL), and $Na_2CO_3$ (0.375 g, 3.54 mmol). To the mixture was added $Boc_2O$ (0.271 g, 1.24 mmol). The mixture was stirred at rt for about 30 min. The mixture was filtered and a white solid was collected. The solid and filtrate were combined and partitioned between DCM (30 mL) and water (15 mL). The organic layer was isolated and dried over $MgSO_4$, filtered, and concentrated under reduced pressure to give tert-butyl (5-tosyl-5H-pyrrolo[2,3-b]pyrazin-2-yl)methylcarbamate (0.45 g, 95%): LC/MS (Table 2, Method c) $R_t$=1.51 min; MS m/z 403 (M+H)$^+$.

Step B: tert-Butyl (5H-pyrrolo[2,3-b]pyrazin-2-yl)methylcarbamate

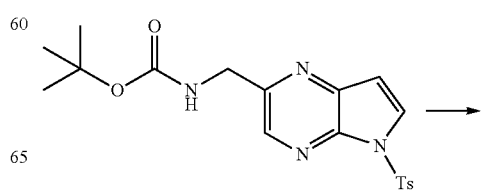

155

-continued

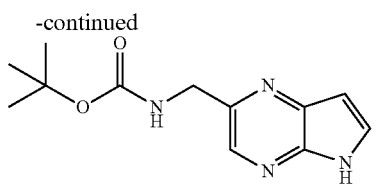

tert-Butyl (5-tosyl-5H-pyrrolo[2,3-b]pyrazin-2-yl)methylcarbamate (5.08 g, 12.6 mmol) in a mixture of 1,4-dioxane (40 mL) and water (10 mL) was treated with NaOH (2.02 g, 50.5 mmol) then heated to about 85° C. for about 75 min. The mixture was cooled to rt then most of the solvent was removed under reduced pressure. The mixture was diluted with water (25 mL) then DCM (25 mL) and EtOAc (50 mL) were added. The layers were separated then the aqueous layer was extracted with EtOAc (2×25 mL). The combined organics were washed with brine (15 mL), dried over MgSO$_4$, filtered and concentrated under reduced pressure to give tert-butyl (5H-pyrrolo[2,3-b]pyrazin-2-yl)methylcarbamate (2.45 g, 78%): LC/MS (Table 2, Method b) R$_t$=1.75 min; MS m/z 249 (M+H)$^+$.

Step C: tert-Butyl (7-bromo-5H-pyrrolo[2,3-b]pyrazin-2-yl)methylcarbamate

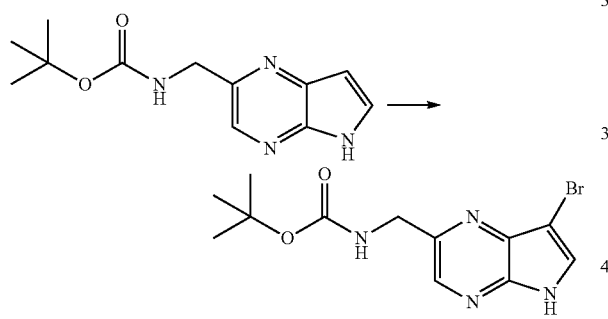

tert-Butyl (5H-pyrrolo[2,3-b]pyrazin-2-yl)methylcarbamate (2.45 g, 9.87 mmol) in DMF (50 mL) was treated with NBS (1.76 g, 9.87 mmol) at P. After about 15 min the solvents were removed under reduced pressure then the material was suspended in water (25 mL). The slurry was stirred for about 30 min then the solids were collected by filtration and dried to a constant weight under vacuum at about 70° C. to give tert-butyl (7-bromo-5H-pyrrolo[2,3-b]pyrazin-2-yl)methylcarbamate (3.15 g, 98%): LC/MS (Table 2, Method b) R$_t$=1.99 min; MS m/z 327 (M+H)$^+$.

Step D: tert-Butyl (7-bromo-5-tosyl-5H-pyrrolo[2,3-b]pyrazin-2-yl)methylcarbamate

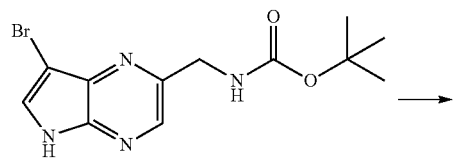

156

-continued

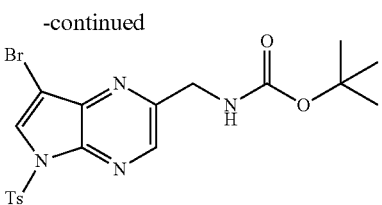

A flask was charged with NaH (60 wt % in mineral oil, 0.025 g, 0.64 mmol) in DMF (2.0 mL). The suspension was cooled to about 0° C., followed by the addition of a solution of tert-butyl (7-bromo-5H-pyrrolo[2,3-b]pyrazin-2-yl)methylcarbamate (0.16 g, 0.49 mmol) in DMF (2.0 mL). The mixture was stirred at about 0° C. for about 10 min and then at rt for about 20 min. The mixture was cooled to about 0° C. followed by the addition of a solution of TsCl (0.112 g, 0.587 mmol) in DMF (1.0 mL). The mixture was stirred at 0° C. for about 20 min and warmed to rt and stirred for about 1 h. To the mixture were added DCM (10 mL) and water (10 mL). The organic layer was isolated and dried over anhydrous MgSO$_4$, filtered and concentrated under reduced pressure. EtOAc (10 mL) and heptane (10 mL) were added and then the mixture was concentrated under reduced pressure to give tert-butyl (7-bromo-5-tosyl-5H-pyrrolo[2,3-b]pyrazin-2-yl)methylcarbamate (0.24 g, 91%): LC/MS (Table 2, Method c) R$_f$=1.59 min; MS m/z 481 (M+H)$^+$.

Preparation #20: 2-Bromo-7-methyl-6-(4-(2-methyl-1,3-dioxolan-2-yl)phenyl)-5-((2-(trimethylsilyl)ethoxy)methyl)-5H-pyrrolo[2,3-b]pyrazine

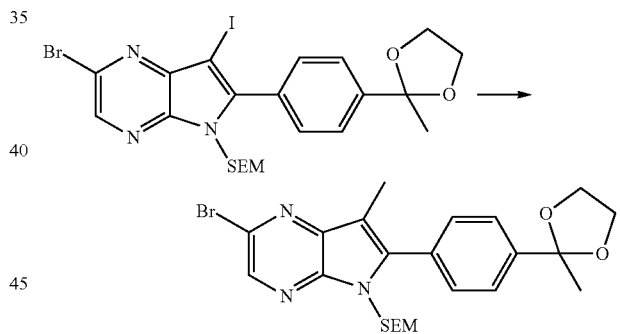

2-Bromo-7-iodo-6-(4-(2-methyl-1,3-dioxolan-2-yl)phenyl)-5-((2-(trimethylsilyl)ethoxy)methyl)-5H-pyrrolo[2,3-b]pyrazine (1.0 g, 1.6 mmol, Preparation #5, Step A) in THF (12 mL) was cooled to about −75° C. then t-BuLi (1.7 M in hexanes, 1.05 mL, 1.79 mmol) was added keeping the temperature about −70 and −75° C. The mixture was stirred for about 5 min at about −75° C. Additional t-BuLi (1.7 M in hexanes, 0.286 mL, 0.487 mmol) was added and the mixture was stirred an additional 15 min. The mixture was treated with MeI (0.461 g, 3.24 mmol) then the temperature of the mixture was raised to about 15° C. over about 10 min. The mixture was stirred at about 20° C. overnight then saturated aqueous NH$_4$Cl (5 mL) was added. The mixture was stirred for about 15 min at about 20° C. then the material was partitioned between EtOAc (50 mL) and water (20 mL). The layers were separated and then the aqueous layer was extracted with EtOAc (10 mL). The combined organic layers were dried over anhydrous MgSO$_4$, filtered and concentrated in vacuo. The material was purified by flash chromatography with a 25 g silica gel column and eluted with 0 to 40% EtOAc/heptane to provide 2-bromo-7-methyl-6-(4-(2-methyl-1,3-dioxolan-2-yl)phenyl)-5-((2-(trimethylsilyl)ethoxy)methyl)-5H-pyrrolo[2,3-b]pyrazine (0.54 g, 66%): LC/MS (Table 2, Method g) R$_f$=2.25 min; MS m/z 504, 506 (M+H)$^+$.

Preparation #21: (trans)-Methyl 2-(azidomethyl)cyclohexanecarboxylate

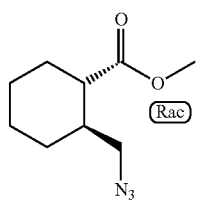

Step A: (trans)-Methyl 2-((methylsulfonyloxy)methyl)cyclohexanecarboxylate

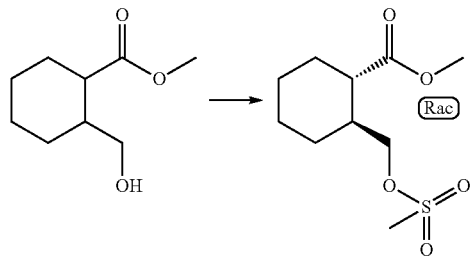 [SMILES: COC(=O)C1CCCCC1CO ; COC(=O)[C@H]1CCCC[C@@H]1COS(C)(=O)=O]

MsCl (0.543 mL, 6.97 mmol) was added to a solution of methyl 2-(hydroxymethyl)cyclohexanecarboxylate (1.0 g, 5.8 mmol, Rieke) in DCM (4 mL) at about 0° C. TEA (0.971 mL, 6.97 mmol) was then added. The mixture was stirred at rt for about 4 h. The mixture was washed with water (10 mL) and extracted with EtOAc (2×10 mL). The combined organic layers were dried over MgSO$_4$, filtered and concentrated under reduced pressure to give (trans)-methyl 2-((methylsulfonyloxy)methyl)cyclohexanecarboxylate (1.4 g, 100%). LC/MS (Table 2, Method c) R$_f$=1.35 min; MS m/z 251 (M+H)$^+$.

Step B: (trans)-Methyl 2-(azidomethyl)cyclohexanecarboxylate

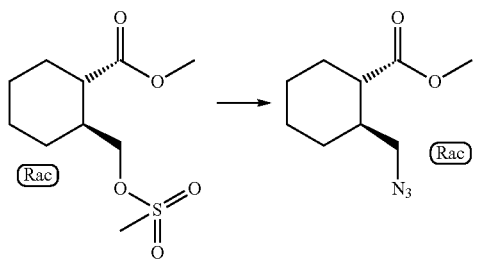

To a solution of (trans)-methyl 2-((methylsulfonyloxy)methyl)cyclohexanecarboxylate (1.4 g, 5.6 mmol) in DMF (6 mL) was added NaN$_3$ (0.730 g, 11.0 mmol). The mixture was heated at about 100° C. for about 3 h. The mixture was diluted with water (30 mL) and extracted with EtOAc (2×45 mL). The combined organic layers were washed with aqueous 1 N NaOH (1×40 mL). The organic layer was dried over MgSO$_4$, filtered and concentrated under reduced pressure to give (trans)-methyl 2-(azidomethyl)cyclohexanecarboxylate (1.1 g, 100%.): $^1$H NMR (400 MHz, CDCL$_3$) δ 3.69 (d, J=6.0, 3H), 3.28-3.15 (m, 2H), 2.24-2.14 (m, 1H), 1.97-1.73 (m, 5H), 1.46 (dd, J=12.2, 3.2, 1H), 1.36-1.05 (m, 3H).

Preparation #22: 2-Bromo-7-ethyl-3-methyl-6-(4-(2-methyl-1,3-dioxolan-2-yl)phenyl)-5-((2-(trimethylsilyl)ethoxy)methyl)-5H-pyrrolo[2,3-b]pyrazine

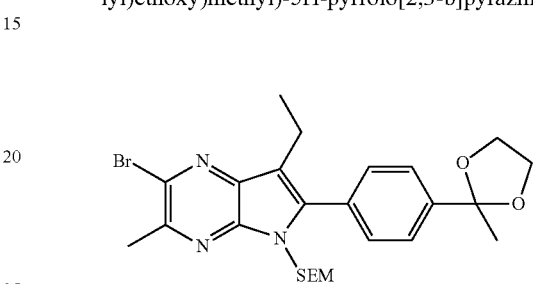

Step A: 2-Bromo-7-iodo-3-methyl-6-(4-(2-methyl-1,3-dioxolan-2-yl)phenyl)-5-((2-(trimethylsilyl)ethoxy)methyl)-5H-pyrrolo[2,3-b]pyrazine

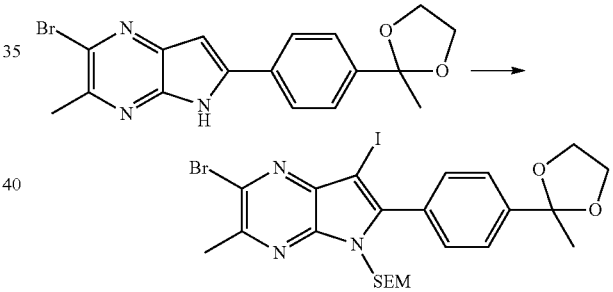

The 2-bromo-3-methyl-6-(4-(2-methyl-1,3-dioxolan-2-yl)phenyl)-5H-pyrrolo[2,3-b]pyrazine (10.4 g, 27.7 mmol, prepared using A from Preparation #4 with ethynyltrimethylsilane, Q, A with 2-amino-3,5-dibromo-6-methylpyrazine [WO2008/083070, Example 29, Part B] and B) in DMF (125 mL) was treated with KOH (1.87 g, 33.3 mmol) at rt. The mixture was stirred for about 10 min and iodine (7.74 g, 30.5 mmol) was added over about 15 min in two equal portions. The mixture was stirred for about 45 min then NaH (60 wt % in mineral oil, 1.33 g, 33.3 mmol) was added in portions over about 5 min. The mixture was stirred for about 10 min then SEMCl (5.17 mL, 29.1 mmol) was added. The mixture was stirred for about 30 min then the solvents were removed under reduced pressure. The material was partitioned between EtOAc (200 mL) and water (200 mL) containing AcOH (3.18 mL, 55.5 mmol). The layers were separated and the aqueous layer was extracted with EtOAc (2×100 mL). The combined organics were washed with water (2×100 mL) then brine (100 mL). The organic layer was dried over anhydrous MgSO$_4$, filtered and concentrated under reduced pressure. The material was dissolved purified with an 80 g silica gel column and eluted with 9:1 Heptane/EtOAc to give 2-bromo-7-iodo-3- methyl-6-(4-(2-methyl-1,3-dioxolan-2-yl)phenyl)-5-((2-(trimethylsilyl)ethoxy)methyl)-5H-pyrrolo[2,3-b]pyrazine (12.7 g, 73%): LC/MS (Table 2, Method g) R$_t$=1.91 min; MS m/z 630 (M+H)$^+$.

Step B: 2-Bromo-7-ethyl-3-methyl-6-(4-(2-methyl-1,3-dioxolan-2-yl)phenyl)-5-((2-(trimethylsilyl)ethoxy)methyl)-5H-pyrrolo[2,3-b]pyrazine

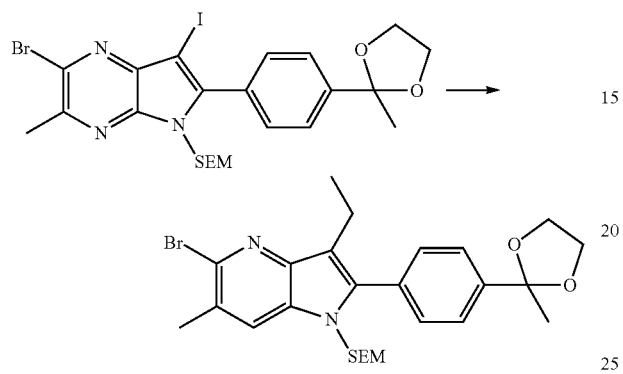

2-Bromo-7-iodo-3-methyl-6-(4-(2-methyl-1,3-dioxolan-2-yl)phenyl)-5-((2-(trimethylsilyl)ethoxy)methyl)-5H-pyrrolo[2,3-b]pyrazine (12.7 g, 20.2 mmol) in THF (200 mL) was cooled to about −75° C. then n-BuLi (1.5 M, 14.8 mL, 22.2 mmol) was added while maintaining the internal temperature of the mixture between −70 and −75° C. The mixture was stirred for about 20 min then the mixture was treated with MeI (6.51 mL, 81 mmol). The cooling bath was removed and replaced with a warm water bath. The temperature of the mixture was raised to about 20° C. over about 10 min. The mixture was stirred at about 20° C. for about 30 min then saturated aqueous NH$_4$Cl (10 mL) was added. The mixture was stirred for about 15 min then concentrated under reduced pressure. The material was partitioned between Et$_2$O (200 mL) and water (100 mL). The organic layer was isolated and the aqueous layer was extracted with Et$_2$O (50 mL). The combined organics were washed with water (50 mL) then brine (50 mL), dried over anhydrous MgSO$_4$, filtered and concentrated under reduced pressure. The material was purified with an 80 g silica column and eluted with 85:15 heptane/Et$_2$O to give 2-bromo-7-ethyl-3-methyl-6-(4-(2-methyl-1,3-dioxolan-2-yl)phenyl)-5-((2-(trimethylsilyl)ethoxy)methyl)-5H-pyrrolo[2,3-b]pyrazine (6.83 g, 64%): LC/MS (Table 2, Method g) R$_t$=2.17 min; MS m/z 532 (M+H)$^+$.

Preparation #23: 7-Bromo-1-methyl-1,6-dihydropyrazolo[3,4-d]pyrrolo[2,3-b]pyridine-8-carbonitrile

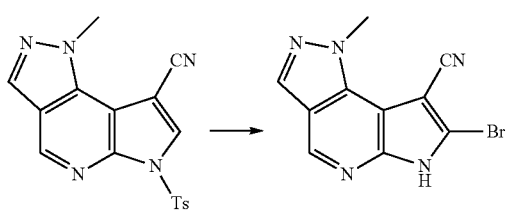 [SMILES: Cc1ccc(S(=O)(=O)n2cc(C#N)c3c2ncc2cnn(C)c23)cc1 ; Cn1ncc2cnc3[nH]c(Br)c(C#N)c3c21]

A 10 mL microwave reaction vial was charged with 1-methyl-6-tosyl-1,6-dihydropyrazolo[3,4-d]pyrrolo[2,3-b]pyridine-8-carbonitrile (0.011 g, 0.30 mmol, prepared using General Procedure AK from Preparation #1, Step D with NBS, General Procedure AE), NBS (0.012 g, 0.66 mmol) and DMF (2 mL). The suspension was heated in a microwave at about 150° C. for about 30 min (250 psi maximum pressure, 2 min ramp, 300 max watts). Additional NBS (134 mg, 0.754 mmol) was added and mixture was stirred at rt for about 2 h. To the reaction mixture was added water (4 mL) and the solid was collected by filtration and washed with water (5 mL). The solid was dried in a vacuum oven at about 70° C. for about 40 min to give 7-bromo-1-methyl-1,6-dihydropyrazolo[3,4-d]pyrrolo[2,3-b]pyridine-8-carbonitrile (0.036 g, 43%): LC/MS (Table 2, Method c) R$_t$=1.25 min; MS m/z: 276 (M+H)$^+$.

Preparation #24: 2-(5-Methoxy-1-methyl-1H-indol-3-yl)-3-((2-(trimethylsilyl)ethoxy)methyl)-3H-imidazo[1,2-a]pyrrolo[2,3-e]pyrazine

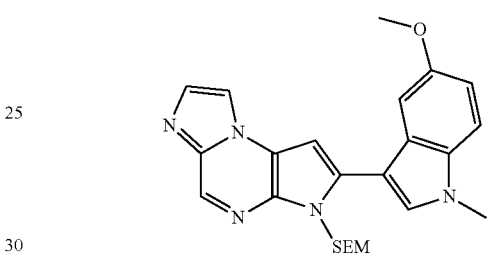

Step A: tert-Butyl 6-(5-methoxy-1-methyl-1H-indol-3-yl)-5-((2-(trimethylsilyl)ethoxy)methyl)-5H-pyrrolo[2,3-b]pyrazin-2-ylcarbamate

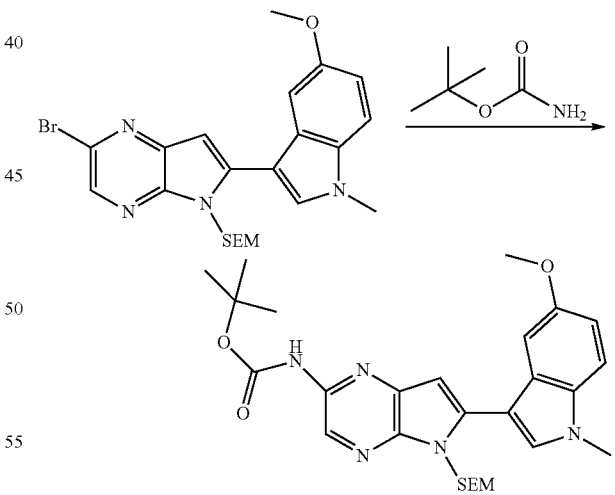

In a flask was added Pd$_2$(dba)$_3$ (0.094 g, 0.10 mmol) and di-tert-butyl(2',4',6'-triisopropylbiphenyl-2-yl)phosphine (0.087 g, 0.21 mmol) in 1,4-dioxane (10 mL). The mixture was heated to about 80° C. for about 10 min. 2-Bromo-6-(5-methoxy-1-methyl-1H-indol-3-yl)-5-((2-(trimethylsilyl)ethoxy)methyl)-5H-pyrrolo[2,3-b]pyrazine (0.500 g, 1.03 mmol, Preparation #C.1), tert-butyl carbamate (0.180 g, 1.54 mmol) and NaOt-Bu (0.148 g, 1.54 mmol) were then added and heating was continued for about 45 min. The mixture was cooled to rt and diluted with EtOAc (20 mL), washed with water (15 mL) and dried over MgSO₄. The mixture was filtered and concentrated in vacuo and purified by a 12 g silica column eluting with 0 to 30% EtOAc/DCM to provide tert-butyl 6-(5-methoxy-1-methyl-1H-indol-3-yl)-5-((2-(trimethylsilyl)ethoxy)methyl)-5H-pyrrolo[2,3-b]pyrazin-2-yl-carbamate (0.224 g, 42%): LC/MS (Table 2, Method g) $R_t$=1.99 min; MS m/z 524 (M+H)⁺.

Step B: 6-(5-Methoxy-1-methyl-1H-indol-3-yl)-5-((2-(trimethylsilyl)ethoxy)methyl)-5H-pyrrolo[2,3-b]pyrazin-2-amine

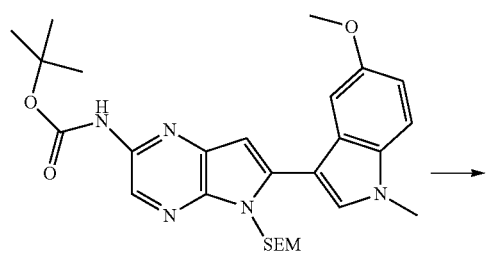

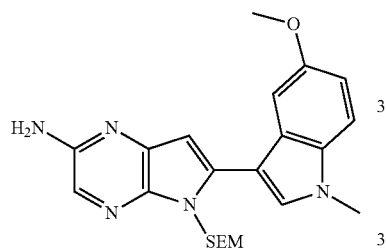

In a flask was added tert-butyl 6-(5-methoxy-1-methyl-1H-indol-3-yl)-5-((2-(trimethylsilyl)ethoxy)methyl)-5H-pyrrolo[2,3-b]pyrazin-2-ylcarbamate (0.200 g, 0.382 mmol) and TFA (0.088 mL, 1.15 mmol) in DCM (1 mL). The mixture was stirred for about 2 h at about 30° C. Additional TFA (0.100 mL, 1.29 mmol) was added and the mixture was stirred at about 40° C. overnight. The mixture was diluted with EtOAc (10 mL) and washed with saturated aqueous Na₂CO₃ (5 mL) and dried over MgSO₄, filtered and concentrated in vacuo. The material was purified by 4 g silica column eluting with 10 to 100% EtOAc/DCM to provide 6-(5-methoxy-1-methyl-1H-indol-3-yl)-5-((2-(trimethylsilyl)ethoxy)methyl)-5H-pyrrolo[2,3-b]pyrazin-2-amine (0.065 g, 40%): LC/MS (Table 2, c) $R_t$=1.62 min; MS m/z 424 (M+H)⁺.

Step C: 2-(5-Methoxy-1-methyl-4H-indol-3-yl)-3-((2-(trimethylsilyl)ethoxy)methyl)-3H-imidazo[1,2-a]pyrrolo[2,3-e]pyrazine

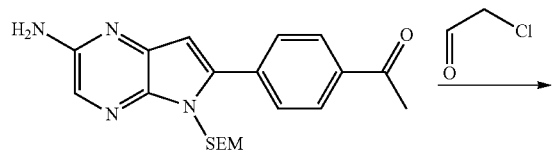

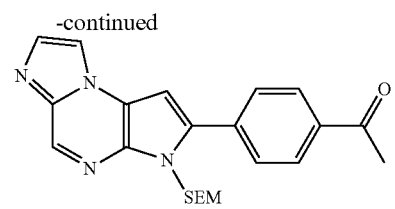

In a round flask was added 6-(5-methoxy-1-methyl-1H-indol-3-yl)-5-((2-(trimethylsilyl)ethoxy)methyl)-5H-pyrrolo[2,3-b]pyrazin-2-amine (0.065 g, 0.15 mmol) and 2-chloroacetaldehyde (~50 wt % solution in water, 0.030 mL, 0.23 mmol) in EtOH (2 mL) and mixture was heated to about 80° C. for about 45 min. The mixture was concentrated under reduced pressure to give 2-(5-methoxy-1-methyl-1H-indol-3-yl)-3-((2-(trimethylsilyl)ethoxy)methyl)-3H-imidazo[1,2-a]pyrrolo[2,3-e]pyrazine (0.065 g, 95%): LC/MS (Table 2, b) $R_t$=1.79 min; MS m/z 448 (M+H)⁺.

Preparation #25: 1-(4-(1-Ethyl-3H-dipyrrolo[1,2-a: 2',3'-e]pyrazin-2-yl)phenyl)ethanone

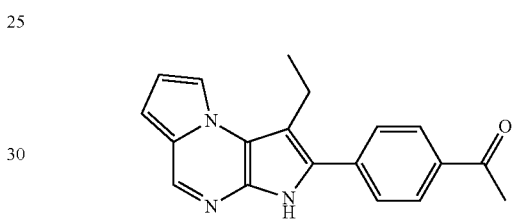

Step A: 3-(7-Ethyl-6-(4-(2-methyl-1,3-dioxolan-2-yl)phenyl)-5-((2-(trimethylsilyl)ethoxy)methyl)-5H-pyrrolo[2,3-b]pyrazin-2-yl)propane-1,2-diol

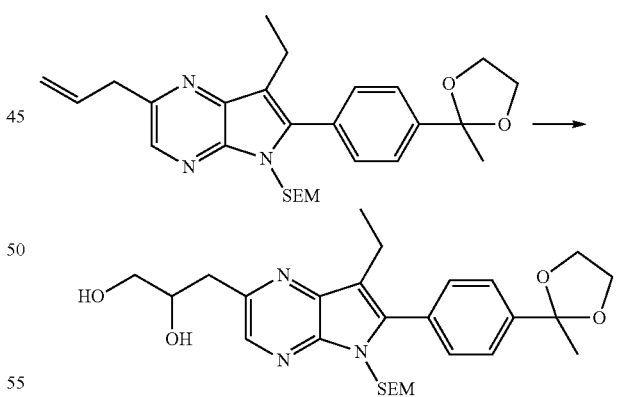

2-Allyl-7-ethyl-6-(4-(2-methyl-1,3-dioxolan-2-yl)phenyl)-5-((2-(trimethylsilyl)ethoxy)methyl)-5H-pyrrolo[2,3-b]pyrazine (0.323 g, 0.673 mmol, Preparation #14) in acetone (9 mL) and water (1 mL) was treated with NMO (0.083 g, 0.707 mmol) and 2.5 wt % OsO₄ in t-BuOH (0.42 mL, 0.034 mmol). The mixture was stirred at rt for about 1.5 h. The mixture was concentrated under reduced pressure and then the material was purified using a 10 g silica column with 95:5 DCM/MeOH as an eluent to give 3-(7-ethyl-6-(4-(2-methyl-1,3-dioxolan-2-yl)phenyl)-5-((2-(trimethylsilyl)ethoxy)methyl)-5H-pyrrolo[2,3-b]pyrazin-2-yl)propane-1,2-diol (0.21 g, 61%): LC/MS (Table 2, Method b) R$_t$=2.55 min; MS m/z 514 (M+H)$^+$.

Step B: 1-Ethyl-2-(4-(2-methyl-1,3-dioxolan-2-yl)phenyl)-3-((2-(trimethylsilyl)ethoxy)methyl)-3H-dipyrrolo[1,2-a:2',3'-e]pyrazine

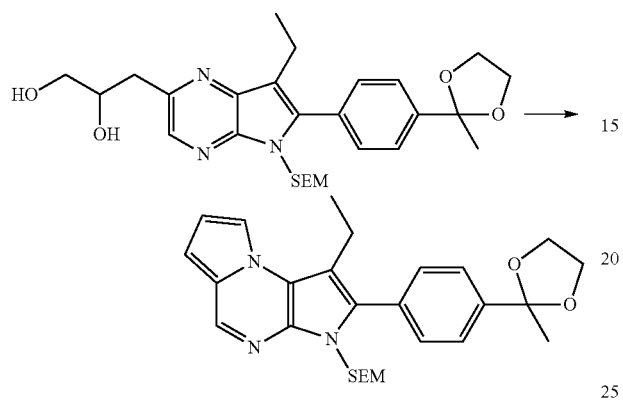

3-(7-Ethyl-6-(4-(2-methyl-1,3-dioxolan-2-yl)phenyl)-5(trimethylsilyl)ethoxy)methyl)-5H-pyrrolo[2,3-b]pyrazin-2-yl)propane-1,2-diol (0.21 g, 0.41 mmol) and PPh$_3$ (0.225 g, 0.858 mmol) in DCM (10 mL) was treated with CBr$_4$ (0.285 g, 0.858 mmol) then stirred at rt for about 7 h. TEA (0.344 mL, 2.47 mmol) was added and the mixture was stirred for about 20 min. The mixture was concentrated under reduced pressure and then purified using a 10 g silica column eluting with EtOAc to give 1-ethyl-2-(4-(2-methyl-1,3-dioxolan-2-yl)phenyl)-3-((2-(trimethylsilyl)ethoxy)methyl)-3H-dipyrrolo[1,2-a:2',3'-e]pyrazine (0.194 g, 99%): LC/MS (Table 2, Method b) R$_t$=3.21 min; MS m/z 478 (M+H)$^+$.

Step C: 1-(4-(1-Ethyl-3H-dipyrrolo[1,2-a:2',3'-e]pyrazin-2-yl)phenyl)ethanone

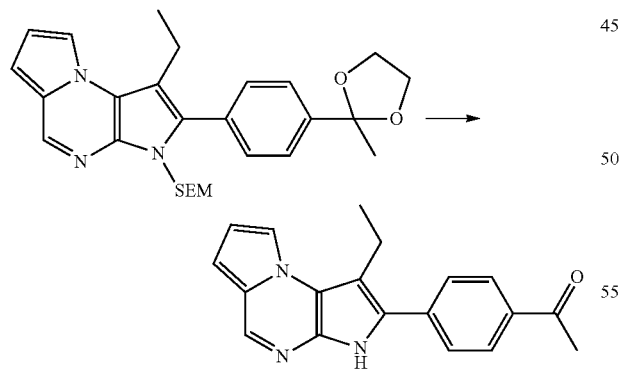

1-Ethyl-2-(4-(2-methyl-1,3-dioxolan-2-yl)phenyl)-3-((2-(trimethylsilyl)ethoxy)methyl)-3H-dipyrrolo[1,2-a:2',3'-e]pyrazine (0.194 g, 0.406 mmol) was dissolved in acetone (6 mL) then treated with concentrated aqueous HCl (36 wt %, 0.170 mL, 2.08 mmol). The mixture was stirred at rt for 30 min. The solvents were evaporated under reduced pressure and then the material was treated with DCM (3 mL) and TFA (1.5 mL, 19 mmol). The mixture was stirred at rt for about 15 min then the solvents were evaporated under reduced pressure. The residue was dissolved in 1,4-dioxane (4 mL) then treated with concentrated aqueous NH$_4$OH (26 wt %, 2 mL, 13.87 mmol). The mixture was stirred at rt for 30 min then warmed to about 50° C. for about 15 min. The mixture was cooled to rt and the solvents removed under reduced pressure. The material was treated with water (15 mL) then stirred for about 5 min at rt. The solids were collected by filtration then dried under vacuum at about 60° C. to a constant weight to give 1-(4-(1-ethyl-3H-dipyrrolo[1,2-a:2',3'-e]pyrazin-2-yl)phenyl)ethanone (0.074 g, 60%): LC/MS (Table 2, Method b) R$_t$=2.37 min; MS m/z 304 (M+H)$^+$.

Preparation #26: 4-(4-Iodo-2-methylphenyl)morpholine

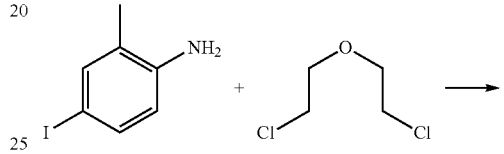

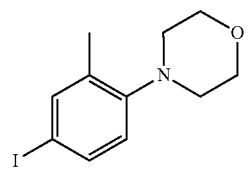

A flask was charged with 4-iodo-2-methylaniline (2.0 g, 8.6 mmol), 2,2'-dichloroethyl ether (2.45 g, 17.2 mmol), NH$_4$Br (8.28 g, 25 mmol), and an aqueous NaOH solution (42 wt %, 4.10 g, 42.9 mmol). The mixture was refluxed overnight. The reaction mixture was cooled to rt and diluted with EtOAc (20 mL). The organic layer was separated, and the aqueous layer extracted with EtOAc (20 mL). The combined organic layers were washed with water (20 mL), dried over MgSO$_4$ and concentrated under reduced pressure. The material was purified on silica gel eluting with 10:1 hexane/EtOAc to give 4-(4-iodo-2-methylphenyl)morpholine (1.3 g, 50%): $^1$H NMR (CDCl$_3$, 400 MHz): 7.48 (d, J=8.4 Hz, 2H), 6.76 (s, 2H), 3.84-3.82 (m, 4H), 2.88-2.85 (m, 4H), 2.26 (s, 3H).

Preparation #27: 1-(4-(8-methyl-3H-imidazo[1,2-a]pyrrolo[2,3-e]pyrazin-2-yl)phenyl)ethanone

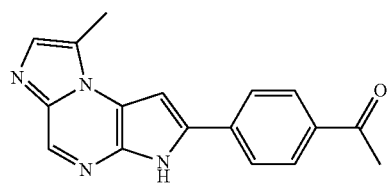 [SMILES: CC(=O)c1ccc(-c2cc3c(ncc4ncc(C)n43)[nH]2)cc1]

Step A: tert-Butyl 6-(4-(2-methyl-1,3-dioxolan-2-yl)phenyl)-5-((2-(trimethylsilyl)ethoxy)methyl)-5H-pyrrolo[2,3-b]pyrazin-2-ylcarbamate

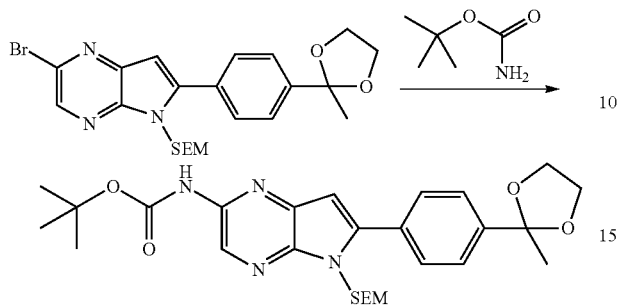

Palladium (II) acetate (0.027 g, 0.12 mmol), phenyl boronic acid (0.030 g, 0.25 mmol), and X-Phos (0.122 g, 0.257 mmol) were combined in a vial and purged with N$_2$. Degassed 1,4-dioxane (2.9 mL) was transferred in via a canula. The mixture was allowed to stir for about 1 h at rt. This mixture was then transferred via canula into degassed tert-amyl alcohol (11.5 mL). The mixture was then transferred to a degassed mixture of the solids tert-butylcarbamate (0.955 g, 8.16 mmol), K$_2$CO$_3$ (1.69 g, 12.2 mmol), and 2-bromo-6-(4-(2-methyl-1,3-dioxolan-2-yl)phenyl)-5-((2-(trimethylsilyl)ethoxy)methyl)-5H-pyrrolo[2,3-b]pyrazine (2.0 g, 4.1 mmol, prepared using A from Preparation #4 with ethynyltrimethylsilane, Q, A with 3,5-dibromopyrazin-2-amine and B).

The mixture was then heated at about 95° C. for about 18 h. The mixture was cooled to rt and EtOAc (~25 mL) added. The mixture was filtered to remove the solids and the filter pad was washed with EtOAc (25 mL). The solvents were removed under reduced pressure. The residue was purified by flash column chromatography (120 g Silicycle™ column) eluting with 10-40% EtOAc/heptane to give tert-butyl 6-(4-(2-methyl-1,3-dioxolan-2-yl)phenyl)-5-((2-(trimethylsilyl)ethoxy)methyl)-5H-pyrrolo[2,3-b]pyrazin-2-ylcarbamate (1.44 g, 67%): LC/MS (Table 2, Method h) R$_t$=2.03 min.; MS m/z: 527 (M+H)$^+$.

Step B: tert-Butyl 6-(4-(2-methyl-1,3-dioxolan-2-yl)phenyl)-5-((2-(trimethylsilyl)ethoxy)methyl)-5H-pyrrolo[2,3-b]pyrazin-2-yl(2-methylallyl)carbamate

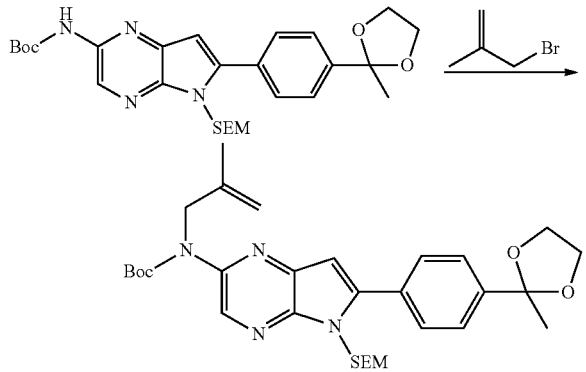

tert-Butyl 6-(4-(2-methyl-1,3-dioxolan-2-yl)phenyl)-5-((2-(trimethylsilyl)ethoxy)methyl)-5H-pyrrolo[2,3-b]pyrazin-2-ylcarbamate (0.50 g, 0.95 mmol) and Cs$_2$CO$_3$ (1.55 g, 4.75 mmol) were combined in DMF (19 mL). 3-Bromo-2-methylpropene (0.191 mL, 1.90 mmol) was added and the mixture was heated at about 65° C. for about 3 h. EtOAc (50 mL) and water (50 mL) were added and the layers separated. The organic layer was washed with 5% aqueous LiCl (3×15 mL) and brine (15 mL), dried over Na$_2$SO$_4$, filtered, and concentrated in vacuo to give tert-butyl 6-(4-(2-methyl-1,3-dioxolan-2-yl)phenyl)-5-((2-(trimethylsilyl)ethoxy)methyl)-5H-pyrrolo[2,3-b]pyrazin-2-yl(2-methylallyl)carbamate (0.584 g, 106%): LC/MS (Table 2, Method h) R$_t$=2.43 min.; MS m/z: 581 (M+H)$^+$.

Step C: tert-Butyl 6-(4-(2-methyl-1,3-dioxotan-2-yl)phenyl)-5-((2-(trimethylsilyl)ethoxy)methyl)-5H-pyrrolo[2,3-b]pyrazin-2-yl(2-oxopropyl)carbamate

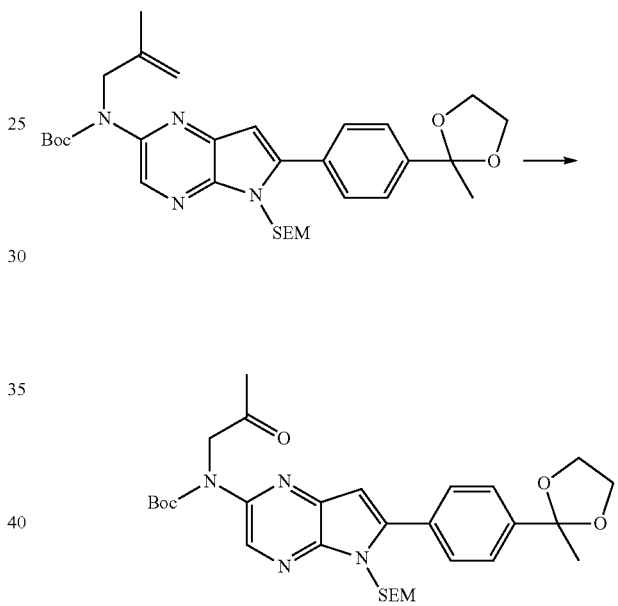

tert-Butyl 6-(4-(2-methyl-1,3-dioxolan-2-yl)phenyl)-5-((2-(trimethylsilyl)ethoxy)methyl)-5H-pyrrolo[2,3-b]pyrazin-2-yl(2-methylallyl)carbamate (0.55 g, 0.95 mmol) and NaIO$_4$ (0.194 mL, 3.79 mmol) were combined in a mixture of 1,4-dioxane (14.0 mL) and water (4.9 mL). To the mixture was added OsO$_4$ (2.5 wt % in t-BuOH, 0.475 mL, 0.038 mmol) and the mixture stirred for about 6 h at rt. EtOAc (50 mL) and water (30 mL) were added and the layers separated. The aqueous layer was extracted with EtOAc (20 mL). The combined organic layers were washed with brine (10 mL), dried over Na$_2$SO$_4$, filtered, and concentrated in vacuo. The residue was purified by flash column chromatography (40 g Redi-Sep™ silica gel) eluting with 50-100% EtOAc/heptane. The mixture was added to NaIO$_4$ (0.194 mL, 3.79 mmol), acetone (14.0 mL) and water (4.9 mL). To the mixture was added OsO$_4$ (2.5 wt % in t-BuOH, 0.475 mL, 0.038 mmol) and the mixture stirred for about 3 h at rt. EtOAc (50 mL) and water (30 mL) were added and the layers separated. The organic layer was washed with brine (10 mL), dried over MgSO$_4$, filtered, and concentrated in vacuo to give tert-butyl 6-(4-(2-methyl-1,3-dioxolan-2-yl)phenyl)-5-((2-(trimethylsilyl)ethoxy)methyl)-5H-pyrrolo[2,3-b]pyrazin-2-yl(2-oxopropyl)carbamate (0.473 g, 86%): LC/MS (Table 2, Method h) R$_f$=2.05 min.; MS m/z: 583 (M+H)$^+$.

Step D: 1-(4-(8-Methyl-3H-imidazo[1,2-a]pyrrolo[2,3-e]pyrazin-2-yl)phenyl)ethanone

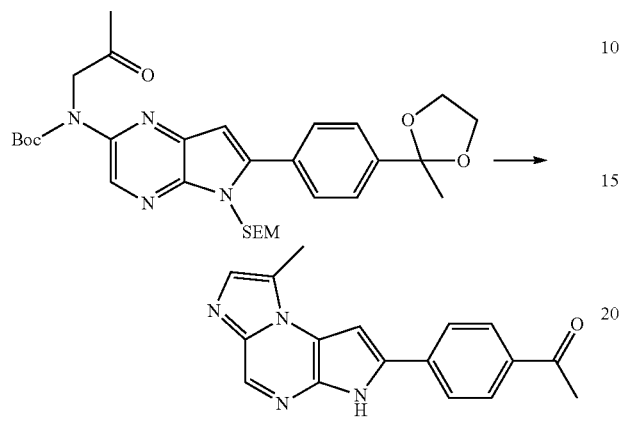

tert-Butyl 6-(4-(2-methyl-1,3-dioxolan-2-yl)phenyl)-5-((2-(trimethylsilyl)ethoxy)methyl)-5H-pyrrolo[2,3-b]pyrazin-2-yl(2-oxopropyl)carbamate (0.425 g, 0.729 mmol) was stirred in TFA (4.0 mL, 52 mmol). To the mixture was added TFAA (4 mL, 28.3 mmol) and the reaction stirred for about 20 h at rt. The solvents were removed under vacuum and 1,4-dioxane (12 mL) was added along with concentrated NH$_4$OH (8 mL). The mixture was stirred for about 3 h. The resulting solid was collected by vacuum filtration washed with water and dried under vacuum at about 50° C. in the presence of P$_2$O$_5$ to a constant weight give 1-(4-(8-methyl-3H-imidazo[1,2-a]pyrrolo[2,3-e]pyrazin-2-yl)phenyl)ethanone (0.121 g, 57%): LC/MS (Table 2, Method h) R$_f$=1.06 min.; MS m/z: 291 (M+H)$^+$.

Preparation #28: tert-Butyl 3-(4-(6-tosyl-6H-imidazo[1,5-a]pyrrolo[2,3-e]pyrazin-3-yl)phenoxy)pyrrolidine-1-carboxylate

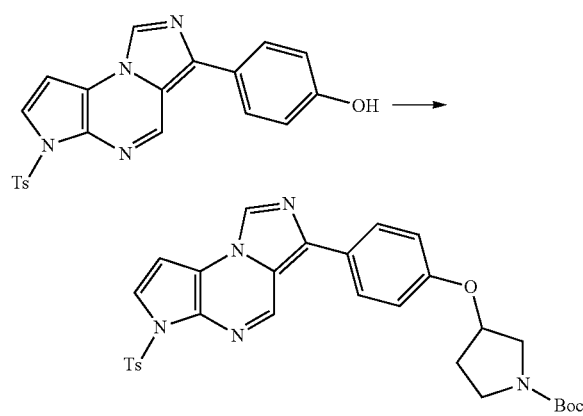

To a mixture of 4-(6-tosyl-6H-imidazo[1,5-a]pyrrolo[2,3-e]pyrazin-3-yl)phenol (0.1 g, 0.247 mmol, Prepared using AF from Preparation #AE.1 with (4-tert-butoxyphenyl)magnesium bromide [Novel], AG, J.3 with ethyl formate and L.2 with POCl$_3$) and PPh$_3$ (0.10 g, 0.40 mmol) in THF (1 mL) was added DIAD (0.077 mL, 0.40 mmol). The mixture was stirred at rt for about 20 min and tert-butyl 3-hydroxypyrrolidine-1-carboxylate (0.058 g, 0.31 mmol) was added. The mixture was stirred at rt for about 20 h and the mixture was purified directly by silica gel (25 g) chromatography eluting with a gradient of 40 to 90% EtOAc/DCM to afford tert-butyl 3-(4-(6-tosyl-6H-imidazo[1,5-a]pyrrolo[2,3-e]pyrazin-3-yl)phenoxy)pyrrolidine-1-carboxylate (0.14 g, 100%): LC/MS (Table 2, Method c) R$_f$=1.51 min; MS m/z 574 (M+H)$^+$.

Preparation #29: 1-Methyl-4-(2-methyl-4-(4,4,5,5-tetramethyl-1,3,2-dioxaborolan-2-yl)phenyl)piperazine Step A: 1-Methyl-4-o-tolylpiperazine

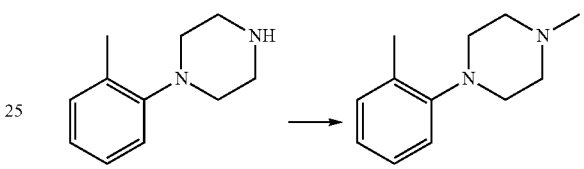

To a solution of 1-o-tolylpiperadine (3.0 g, 17 mmol) in MeOH (100 mL) was added paraformaldehyde (3.3 g, 19 mmol), AcOH (0.3 mL) and MgSO$_4$ (4.08 g, 34 mmol). The mixture was stirred for about 1 h at rt and then NaBH$_4$ (1.3 g, 34 mmol) was added. The mixture was heated to about 100° C. for about 16 h. After cooling to rt the reaction mixture was filtered through Celite® and the filter was washed with MeOH (5×20 mL). Then the filtrate was concentrated in vacuo to give 1-methyl-4-(2-methyl-4-(4,4,5,5-tetramethyl-1,3,2-dioxaborolan-2-yl)phenyl)piperazine, (3.0 g, 93%). $^1$H NMR (CDCl$_3$, 400 MHz): 7.17 (d, J=7.2 Hz, 2H), 7.03 (d, J=8.0 Hz, 1H), 6.97 (s, 1H), 2.95-2.93 (m, 4H), 2.58 (s, 4H), 2.36 (s, 3H), 2.30 (s, 3H).

Step B: 1-(4-Iodo-2-methylphenyl)-4-methylpiperazine

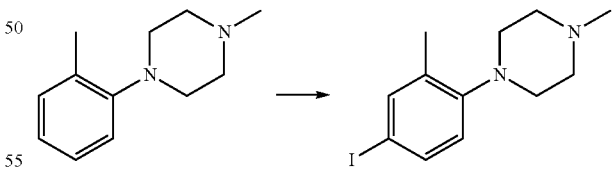

To a mixture of bis(pyridine)iodonium tetrafluoroborate (2.15 g, 5.78 mmol) and DCM (50 mL) at rt was added 1-methyl-4-o-tolylpiperazine (1.00 g, 5.26 mmol). A solution of trifluoromethanesulfonic acid (1 mL, 11 mmol) in DCM (25 mL) was added over about 3 min at rt. The mixture was then treated with saturated aqueous Na$_2$S$_2$O$_3$ (30 mL), extracted with DCM (2×50 mL), washed with brine, dried over Na$_2$SO$_4$, filtered and concentrated in vacuo. The residue was purified by silica gel column chromatography (EtOAc/ petroleum ether: 20%-100%) to give 1-(4-iodo-2-methylphenyl)-4-methylpiperazine, (0.40 g, 24%).

Step C: 1-Methyl-4-(2-methyl-4-(4,4,5,5-tetramethyl-1,3,2-dioxaborolan-2-yl)phenyl)piperazine

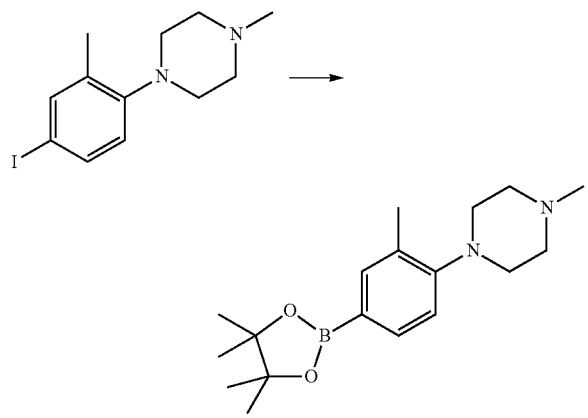

A solution of 1-(4-iodo-2-methylphenyl)-4-methylpiperazine (2.0 g, 6.3 mmol), KOAc (1.86 g, 18.4 mmol), bis(pinacolato)diboron (1.9 g, 7.6 mmol), and 1,1'-bis(diphenylphosphino)ferrocene-palladium(II) dichloride DCM complex (0.20 g, 0.25 mmol) in toluene (40 mL) was purged with N₂, then heated to about 80° C. for about 16 h. Then the mixture was filtered, washed with EtOAc (40 mL) and the filtrate was concentrated in vacuo. The residue was purified by silica gel chromatography (EtOAc/petroleum ether; 20%-100%) to give 1-methyl-4-(2-methyl-4-(4,4,5,5-tetramethyl-1,3,2-dioxaborolan-2-yl)phenyl)piperazine (1.07 g, 54%). $^1$H NMR (CDCl₃, 400 MHz): 7.62 (d, J=6.8 Hz, 2H), 7.00 (s, 1H), 2.99-2.97 (m, 4H), 2.59 (s, 4H), 2.37 (s, 3H), 2.29 (s, 3H), 1.26 (s, 12H).

Preparation #30. Preparation of 3-(4-(4,4,5,5-tetramethyl-1,3,2-dioxaborolan-2-yl)phenyl)oxetan-3-ol

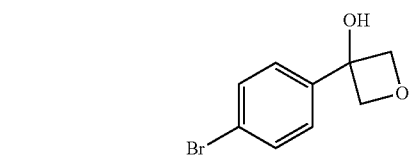

Step A: 3-(4-(4,4,5,5-tetramethyl-1,3,2-dioxaborolan-2-yl)phenyl)oxetan-3-ol

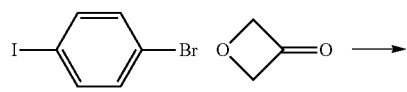

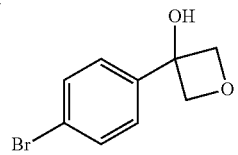

Reference for formation of 4-lithiobromobenzene: Organometallics, 2009, 28, 4406-4415.

1-Bromo-4-iodobenzene (0.65 g, 2.3 mmol, Lancaster) was stirred in pentane (7 mL) and then n-BuLi (1.6 M in hexane, 1.4 mL, 2.3 mmol) was added dropwise at rt. The mixture was and the stirred for 1 h. A white precipitate formed and the precipitate was allowed to settled. The pentane was removed by pipette. The mixture was diluted with pentane (7 mL) back up to the original volume. The mixture was then added to a solution of 3-oxetanone (0.315 g, 4.37 mmol) in THF (7 mL) that was cooled in an ice bath. The mixture was then allowed to come to rt and stirred for about 2 h. The mixture was quenched by the addition of saturated NH₄Cl (10 mL) and allowed to stir overnight. EtOAc (15 mL) was added and the layers separated. The aqueous layer was then extracted with EtOAc (5 mL). The combined organic layers were washed with brine (5 mL), dried over MgSO₄, filtered, and concentrated in vacuo. The solid was purified by flash column chromatography (40 g Silicycle™ column) eluting with 20-50% EtOAc/heptane. The solid was recrystallized by dissolving in a mixture of heptane and DCM and concentrating under reduced pressure until a precipitate had formed. The solid was collected by filtration and washed with heptane (10 mL) to provide 3-(4-bromophenyl)oxetan-3-ol (0.333 g, 63%): $^1$H NMR (400 MHz, DMSO) δ 7.65-7.43 (m, 4H), 6.42 (s, 1H), 4.68 (dd, J=50.6, 6.8, 4H).

Step B. 3-(4-(4,4,5,5-tetramethyl-1,3,2-dioxaborolan-2-yl)phenyl)oxetan-3-ol

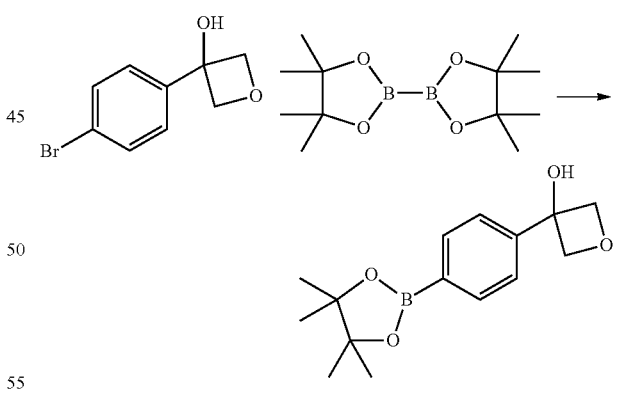

3-(4-bromophenyl)oxetan-3-ol (0.333 g, 1.45 mmol), bis(pinacolato)diboron (0.406 g, 1.60 mmol), and KOAc (0.428 g, 4.36 mmol) were combined in DMF (3.6 mL). The mixture was degassed by bubbling nitrogen directly into the mixture for about 10 min. 1,1'-bis(diphenylphosphino)ferrocene-palladium(II)dichloride dichloromethane complex (0.059 g, 0.073 mmol) was added, degassing was continued for about 10 min. The mixture was heated at 80° C. for 4 h. The mixture was allowed to cool rt and EtOAc (25 mL) and water (15 mL) were added. The mixture was filtered through a syringe filter and the layers were separated. The aqueous layer was extracted with EtOAc (10 mL). The combined organic layers were washed with 5% aqueous LiCl (3×15 mL) and brine (10 mL), dried over MgSO$_4$, filtered, and concentrated in vacuo. The residue was purified by flash column chromatography (25 g Silicycle™ column) eluting with 50-100% EtOAc/heptane to give 3-(4-(4,4,5,5-tetramethyl-1,3,2-dioxaborolan-2-yl)phenyl)oxetan-3-ol (0.265 g, 66%): $^1$H NMR (400 MHz, DMSO) δ 7.69 (d, J=8.3, 2H), 7.61 (d, J=8.3, 2H), 6.38 (s, 1H), 4.76 (d, J=6.8, 2H), 4.62 (d, J=6.8, 2H), 1.28 (s, 12H).

General Procedure A: Sonogashira Reaction of a Terminal Alkyne with an Aryl or Heteroaryl Halide A mixture of an aryl halide (preferably 1.0 equiv) an organic solvent or mixture of solvents (such as THF, MeCN, DMF, Et$_2$O or 1,4-dioxane, preferably THF), a terminal alkyne (0.67 to 1.5 equiv, preferably 0.9 to 1.2 equiv), a palladium catalyst (such as Pd(PPh$_3$)$_4$, Pd(PPh$_3$)$_2$Cl$_2$, preferably Pd(PPh$_3$)$_2$Cl$_2$; 0.01 to 1.0 equiv, preferably 0.025 to 0.10 equiv), copper(I) iodide (0.01 to 1.0 equiv, preferably 0.045 to 0.10 equiv) and a base (such as TEA, DIEA, K$_2$CO$_3$, Cs$_2$CO$_3$ or diethylamine, preferably TEA, 1.0 to 5.0 equiv, preferably 1.5 to 4.5 equiv) is stirred at about −10 to 90° C. (preferably about 15 to 80° C.) for about 5 min to 24 h (preferably about 30 min to 2 h). The mixture is cooled to rt. The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure A

Preparation #A.1: 5-Bromo-3-((1-methyl-1H-pyrazol-4-yl)ethynyl)pyrazin-2-amine

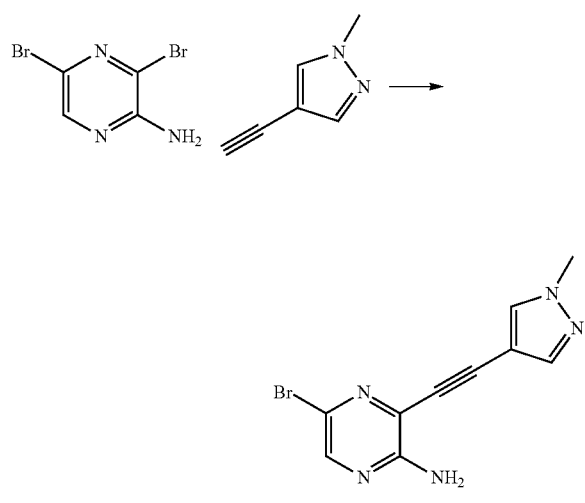

To a round bottom flask was added 4-ethynyl-1-methyl-1H-pyrazole (8.5 g, 80 mmol, Preparation #Q.1), 3,5-dibromopyrazin-2-amine (16.8 g, 66.4 mmol), THF (166 mL), PdCl$_2$(PPh$_3$)$_2$ (2.33 g, 3.32 mmol), copper(I) iodide (0.633 g, 3.32 mmol) and TEA (27.8 mL, 199 mmol). The mixture was heated to about 70° C. for about 1 h. The mixture was cooled to rt. The solids were filtered away and rinsed with THF (50 mL). The filtrate was partitioned with water (300 mL) and the mixture was extracted with EtOAc (400 mL). The organic layer was dried with anhydrous MgSO$_4$, filtered and concentrated in vacuo. The residue was triturated with EtOH (100 mL) and the solid material was collected by filtration. The mother liquor was purified by flash chromatography (300 g silica gel column, heptane/EtOAc 10:1 to 0:1) to give 5-bromo-3-((1-methyl-1H-pyrazol-4-yl)ethynyl)pyrazin-2-amine (15.2 g, 82%): LC/MS (Table 2, Method c) R$_t$=1.40 min; MS m/z 278 (M+H)$^+$.

General Procedure B: Formation of a 5H-pyrrolo[2,3-b]pyrazine from a 3-alkynylpyrazin-2-amine To a flask containing an alkyne in a solvent (such as NMP, DMF, DMA, preferably DMF or NMP) is added a base (such as NaH, KOt-Bu, NaOH, KOH, NaOt-Bu, preferably NaH or KOt-Bu; 0.9 to 5.0 equiv, preferably 0.9 to 2.0 equiv) either in portions or all at once. The mixture is stirred for about 30 min to 24 h (preferably about 45 min to 3 h) at about −10° C. to 45° C. (preferably about 0 to 30° C.). Optionally, more base (0.1 to 1.0 equiv, preferably 0.1 to 0.3 equiv) is added and the mixture is stirred for about 30 min to 12 h (preferably about 1 to 3 h) at about −10° C. to 45° C. (preferably about 0 to 30° C.). The mixture may be optionally quenched with aqueous acid (such as aqueous AcOH or aqueous HCl, preferably aqueous AcOH) and stirred for about 5 to 30 min (preferably about 10 to 15 min). The mixture is then diluted with water and the solid is collected by vacuum filtration to give the target compound. Alternatively, the mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure B

Preparation #B.1: 2-Bromo-6-(5-methoxy-1-methyl-1H-indol-3-yl)-5H-pyrrolo[2,3-b]pyrazine

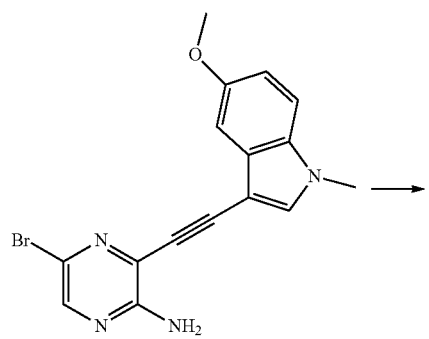

To a round bottom flask was added 5-bromo-3-((5-methoxy-1-methyl-1H-indol-3-yl)ethynyl)pyrazin-2-amine (11.1 g, 30.9 mmol, prepared using General Procedure A from ethynyltrimethylsilane with 3,5-dibromopyrazine-2-amine, Q, A with 3-iodo-5-methoxy-1-methyl-1H-indole (Preparation #11, Step A), NMP (100 mL) and KOt-Bu (6.94 g, 61.9 mmol). The mixture was stirred at rt for about 45 min and then warmed to about 45° C. for about 1.25 h. The mixture was cooled to about 0° C. and then diluted with water (550 mL). The solid was collected by filtration and washed with water (100 mL). The material was dried under vacuum at about 65° C. overnight to give 2-bromo-6-(5-methoxy-1-methyl-1H-indol-3-yl)-5H-pyrrolo[2,3-b]pyrazine (6.61 g; 60%): LC/MS (Table 2, Method a) $R_t$=2.47 min; MS m/z 357 (M+H)$^+$.

General Procedure C: Formation of an N-SEM Protected Heteroaromatic Ring

To a solution of a heteroaromatic ring (1 equiv) at about −10 to 25° C. (preferably about 0° C.) in an organic solvent (such as THF, 1,4-dioxane or DMF, preferably DMF) is added a base (such as NaH, Cs$_2$CO$_3$ or KOH, preferably NaH; 1 to 3 equiv, preferably 1.2 equiv). The mixture is stirred for about 1 to 60 min (preferably about 15 min to 1 h) at about −10 to 25° C. (preferably about 0° C.). SEMCl (1 to 3 equiv, preferably 1.5 equiv) is then added to the mixture. The mixture is stirred at about 0 to 25° C. (preferably about 20° C.) for about 5 min to 24 h (preferably about 15 min to 1 h). The mixture is then optionally poured slowly into ice water and stirred to provide a suspension. The solids are optionally collected by filtration and dried to provide the target compound. Alternatively, the mixture is optionally concentrated in vacuo to give final compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure C

Preparation #C.1: 2-Bromo-6-(5-methoxy-1-methyl-1H-indol-3-yl)-5-((2-(trimethylsilyl)ethoxy)methyl)-5H-pyrrolo[2,3-b]pyrazine

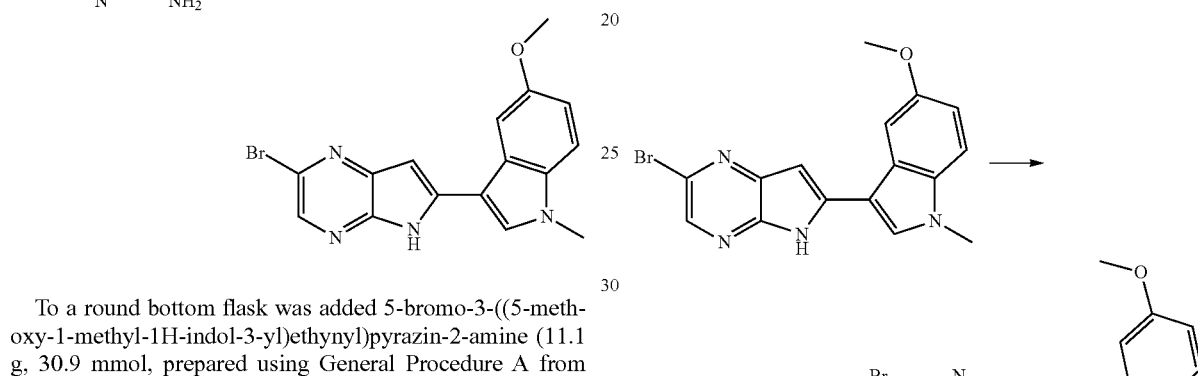

2-Bromo-6-(5-methoxy-1-methyl-1H-indol-3-yl)-5H-pyrrolo[2,3-b]pyrazine (0.500 g, 1.40 mmol; Preparation #B.1) in DMF (15 mL) was cooled to about 0° C. and then treated with 60 wt % NaH (0.112 g, 2.80 mmol). The mixture was stirred for about 15 min at about 0° C. followed by the addition of SEMCl (0.372 mL, 2.10 mmol). The mixture was warmed to rt for about 15 min then was concentrated under reduced pressure and purified on a 40 g silica gel column eluting with DCM to provide 2-bromo-6-(5-methoxy-1-methyl-1H-indol-3-yl)-5-((2-(trimethylsilyl)ethoxy)methyl)-5H-pyrrolo[2,3-b]pyrazine (0.61 g, 89%): LC/MS (Table 2, Method b) $R_t$=3.88 min; MS m/z 487 (M+H)$^+$.

General Procedure D: Suzuki Reaction of a Boronic Acid or Boronate with an Aryl or Heteroaryl Halide To a mixture of an aryl halide (1 equiv) in a solvent mixture (such as 1,4-dioxane/water, EtOH/water, MeCN/water, or EtOH/1,4-dioxane/water, preferably 1,4-dioxane/water or EtOH/1,4-dioxane/water) or a single solvent system (such as DMF) is added a boronic acid or ester (1 to 2 equiv, preferably 1.1 to 1.5 equiv), a palladium catalyst (such as Pd(PPh$_3$)$_4$, PdCl$_2$(PPh$_3$)$_2$, Pd$_2$dba$_3$, Pd(OAc)$_2$, PdCl$_2$(dppf)-CH$_2$Cl$_2$ or SiliaCat DPP-Pd®, preferably Pd(PPh$_3$)$_4$ or PdCl$_2$(PPh$_3$)$_2$, SiliaCat DPP-Pd®; 0.02 to 1.0 equiv, preferably 0.04 to 0.07) and a base (such as Na$_2$CO$_3$, Cs$_2$CO$_3$, CsF K$_3$PO$_4$, NaOt-Bu, KOt-Bu, KOAc, preferably Na$_2$CO$_3$ or Cs$_2$CO$_3$; 1 to 5 equiv, preferably 2 to 3 equiv). Optionally, copper (I) iodide (0.05 to 0.15 equiv, preferably 0.09 to 0.11 equiv) may be added to the reaction mixture. The reaction mixture is heated to about 60 to 120° C. (preferably about 80 to 100° C.) for about 1 to 24 h (preferably about 2 to 5 h) in an oil bath, or optionally heated in a microwave at about 100 to 200° C. for about 5 min to 2 h. The catalyst is optionally removed by filtration. The mixture is optionally concentrated in vacuo to give the final compound. Alternatively, the reaction mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure D

Preparation #D.1: tert-Butyl 5-methoxy-3-(1-methyl-6-tosyl-1,6-dihydropyrazolo[3,4-d]pyrrolo[2,3-b]pyridin-7-yl)-1H-indole-1-carboxylate A flask was charged with 7-iodo-1-methyl-6-tosyl-1,6-dihydropyrazolo[3,4-d]pyrrolo[2,3-b]pyridine (0.80 g, 1.76 mmol, Preparation #1), tert-butyl 5-methoxy-3-(4,4,5,5-tetramethyl-1,3,2-dioxaborolan-2-yl)-1H-indole-1-carboxylate (0.792 g, 2.12 mmol, prepared using H from tert-butyl 3-bromo-5-methoxy-1H-indole-1-carboxylate (SynChem) with 4,4,5,5-tetramethyl-1,3,2-dioxaborolane), Cs$_2$CO$_3$ (1.44 g, 4.42 mmol), PdCl$_2$(PPh$_3$)$_2$ (0.074 g, 0.106 mmol), water (2.6 mL) and 1,4-dioxane (8.0 mL). The mixture was heated to about 85° C. for about 2 h and then cooled to rt. The mixture was diluted with DCM (60 mL) and washed with water (30 mL). The organic layer was dried over anhydrous MgSO$_4$, filtered and concentrated in vacuo. The crude material was purified by silica gel chromatography eluting with a gradient of 0 to 20% EtOAc/DCM to afford tert-butyl 5-methoxy-3-(1-methyl-6-tosyl-1,6-dihydropyrazolo[3,4-d]pyrrolo[2,3-b]pyridin-7-yl)-1H-indole-1-carboxylate (1.01 g, 100%): LC/MS (Table 2, Method c) R$_t$=1.71 min; MS m/z 572 (M+H)$^+$.

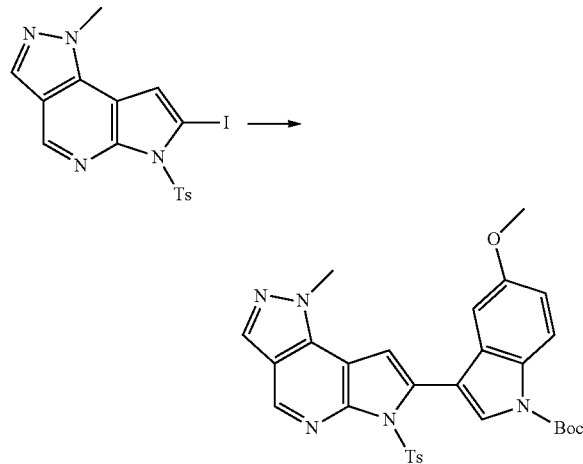

TABLE D.1

Examples prepared from 7-iodo-1-methyl-1,6-dihydropyrazolo[3,4-d]pyrrolo [2,3-b]pyridine (Prepared using General Procedure N from 7-iodo-1-methyl-6-tosyl-1,6-dihydropyrazolo[3,4-d]pyrrolo[2,3-b]pyridine [Preparation #1] with NaOH) with a boronic acid or boronate using General Procedure D

| Boronic acid or boronate | Product | Example # | R$_t$ min (Table 2, Method) | m/z ESI+ (M+H)$^+$ | Syk IC$_{50}$ |
|---|---|---|---|---|---|
| 3-Cyanophenylboronic acid | | D.1.1 | 1.24 (c) | 274 | ND |

TABLE D.2

Examples prepared from 2-(4-(4,4,5,5-tetramethyl-1,3,2-dioxaborolan-2-yl)phenyl)propan-2-ol (Preparation #H.1) with an aryl halide using General Procedure D

| Aryl halide | Product | Example # | R$_t$ min (Table 2, Method) | m/z ESI+ (M+H)$^+$ | Syk IC$_{50}$ |
|---|---|---|---|---|---|
| (R)-3-Bromo-1-(piperidin-3-yl)-6-H-imidazo[1,5-a]pyrrolo[2,3-e]pyrazine(prepared using J.1 from Example #2, Step B with (S)-1-(tert-butoxycarbonyl)piperidine-3-carboxylic acid, L.1, AB, N and P.3) | | D.2.1 | 1.09 (c) | 376 | A |

TABLE D.2-continued

Examples prepared from 2-(4-(4,4,5,5-tetramethyl-1,3,2-dioxaborolan-2-yl)phenyl)propan-2-ol (Preparation #H.1) with an aryl halide using General Procedure D

| Aryl halide | Product | Example # | $R_t$ min (Table 2, Method) | m/z ESI+ (M+H)+ | Syk IC$_{50}$ |
|---|---|---|---|---|---|
| (S)-1-(3-3-Bromo-6H-imidazo[1,5-a]pyrrolo[2,3-e]pyrazin-1-yl)piperidine-1-carbonyl)cyclopropanecarbonitrile (prepared using J.1 from Example #2, Step B with (S)-1-(tert-butoxycarbonyl)piperidine-3-carboxylic acid, L.1, AB, N, P.3 and J.1 with 1-cyanocyclopropanecarboxylic acid) | | D.2.2 | 1.91 (A) | 469 | B |
| 7-Bromo-1-methyl-1,6-dihydropyrazolo[3,4-d]pyrrolo[2,3-b]pyridine-8-carbonitrile (Preparation #23) | | D.2.3 | 1.86 (a) | 332 | A |
| (3-(3-Bromo-6H-imdiazo[1,5-a]pyrrolo[2,3-e]pyrazin-1-yl)pyridin-2-yl)pyridin-2-yl)methanol(prepared using F from Preparation #16 and N) | | D.2.4 | 1.64 (a) | 400 | B |

TABLE D.3

Examples prepared from 2-(4-(1-bromo-6H-imidazo[1,5-a]pyrrolo[2,3-e]pyrazin-3-yl)phenyl)propan-2-ol (prepared using General Procedure N from 2-(4-(1-bromo-6-tosyl-6H-imidazo[1,5-a]pyrrolo[2,3-e]pyrazin-3-yl)phenyl)propan-2-ol [Preparation #AI.1 with NaOH]) using General Procedure D

| Boronate/Boronic acid | Product | Example # | $R_t$ min (Table 2, Method) | m/z ESI+ (M+H)+ | Syk IC$_{50}$ |
|---|---|---|---|---|---|
| 3-(5,5-Dimethyl-1,3,2-dioxaborinan-2-yl)picolinonitrile {Frontier} | | D.3.1 | 1.79 (a) | 395 | A |

General Procedure E: Lemieux-Johnson Oxidation of an Alkene to an Aldehyde

To a solution of an alkene (1 equiv) in an organic solvent (such as THF or 1,4-dioxane, preferably 1,4-dioxane) is added OsO$_4$ (0.02 to 0.1 equiv, preferably 0.04 equiv) and NaIO$_4$ (2 to 10 equiv, preferably 4 equiv). Water (10 to 30 equiv, preferably 16 equiv) is added and the mixture is stirred at rt for about 1 to 20 h (preferably about 1 to 5 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water Illustration of General Procedure E Preparation #E.1: 3-(2-Formyl-5-((2-(trimethylsilyl)
ethoxy)methyl)-5H-pyrrolo[2,3-b]pyrazin-6-yl)ben-
zoic acid Illustration of General Procedure F Preparation #F.1: (6-(5-Methoxy-1-methyl-1H-indol-
3-yl)-5-((2-(trimethylsilyl)ethoxy)methyl)-5H-pyr-
rolo[2,3-b]pyrazin-2-yl)methanol

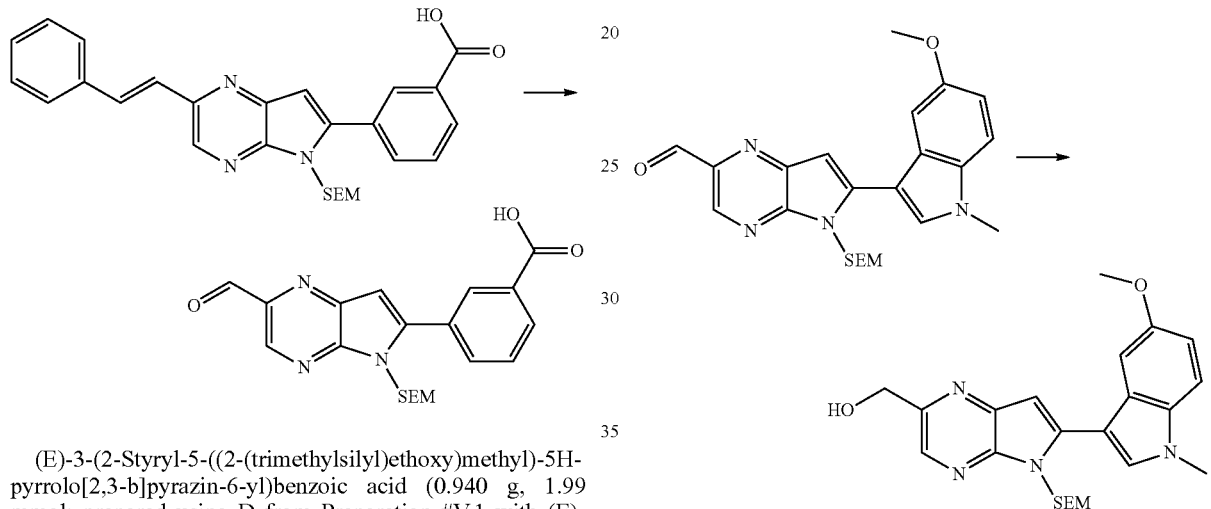

(E)-3-(2-Styryl-5-((2-(trimethylsilyl)ethoxy)methyl)-5H-pyrrolo[2,3-b]pyrazin-6-yl)benzoic acid (0.940 g, 1.99 mmol; prepared using D from Preparation #V.1 with (E)-styrylboronic acid), $OsO_4$ (2.5 wt % in t-BuOH, 1.00 mL, 0.080 mmol) and $NaIO_4$ (1.71 g, 7.97 mmol) were added to a stirred mixture of 1,4-dioxane (10 mL) and water (2 mL) at rt. After about 4.5 h the mixture was diluted with water (30 mL) and extracted with EtOAc (40 mL). The organic layer was dried over anhydrous $MgSO_4$ and concentrated under reduced pressure to provide 3-(2-formyl-5-((2-(trimethylsilyl)ethoxy)methyl)-5H-pyrrolo[2,3-b]pyrazin-6-yl)benzoic acid (0.792 g, 100%): LC/MS (Table 2, Method c) $R_t$=1.45 min; MS m/z 398 (M+H)$^+$.

General Procedure F: Reduction of an Aldehyde or Ketone to an Alcohol

A reducing agent (or such as NaBH(OAc)$_3$, $NaBH_4$, $NaBH_3CN$ preferably such as $NaBH_4$; 1.0 to 2.0 equiv, preferably 1.0 equiv) is added to a solution of an aldehyde or ketone (1 equiv) in an organic solvent or mixture of organic solvents (such as THF, 1,4-dioxane or EtOH, preferably a mixture of 1,4-dioxane and EtOH) at about 0 to 30° C. (preferably about 25° C.). The reaction is stirred for about 5 min to 48 h (preferably about 1 to 16 h) at about 0 to 30° C. (preferably about 25° C.). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, acetic acid or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

6-(5-Methoxy-1-methyl-1H-indol-3-yl)-5-((2-(trimethylsilyl)ethoxy)methyl)-5H-pyrrolo[2,3-b]pyrazine-2-carbaldehyde (5.03 g, 11.5 mmol, prepared using D from Preparation #C.1. with (E)-styrylboronic acid and E) in 1,4-dioxane (65 mL) and EtOH (13 mL) was treated with NaBH$_4$ (0.436 g, 11.5 mmol) then stirred overnight at rt. The reaction mixture was concentrated under reduced pressure then the residue was partitioned between EtOAc (125 mL) and saturated aqueous NaHCO$_3$ (100 mL). The layers were separated then the aqueous layer was extracted with EtOAc (75 mL). The combined organic layers were extracted with brine (50 mL) then dried over anhydrous MgSO$_4$, filtered and concentrated under reduced pressure. The material was purified by flash chromatography on neutral alumina with 8:2 DCM/EtOAc then 7:3 DCM/EtOAc then finally EtOAc to give (6-(5-methoxy-1-methyl-1H-indol-3-yl)-5-((2-(trimethylsilyl)ethoxy)methyl)-5H-pyrrolo[2,3-b]pyrazin-2-yl)methanol (3.19 g, 63%): LC/MS (Table 2, Method a) $R_t$=2.76 min; MS m/z 439 (M+H)$^+$.

General Procedure G: Conversion of an Alkyl Alcohol to an Alkyl Azide

To a solution of an alkyl alcohol (1 equiv) in an organic solvent (such as DCM, THF, Et$_2$O or 1,4-dioxane, preferably DCM) is added a chlorinating agent (such as thionyl chloride or oxalyl chloride, preferably thionyl chloride; 1 to 2 equiv, preferably 1.1 to 1.5 equiv). The mixture is stirred at rt for about 5 min to 4 h (preferably about 5 min to 2 h). The mixture is concentrated under reduced pressure. The residue is dissolved in DMF and treated with an azide (such as NaN$_3$, LiN$_3$ or nicotinoyl azide, preferably NaN$_3$; 1 to 4 equiv, preferably 2 to 3 equiv) for about 1 to 48 h (preferably about 2 to 24 h). The mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.
Illustration of General Procedure G Preparation #G.1: 2-(Azidomethyl)-6-(5-methoxy-1-methyl-1H-indol-3-yl)-5-((2-(trimethylsilyl)ethoxy)methyl)-5H-pyrrolo[2,3-b]pyrazine

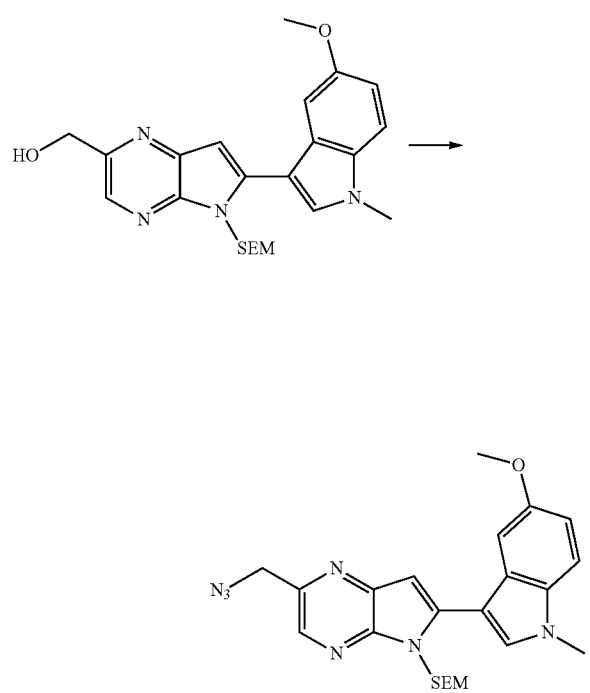

A flask was charged with (6-(5-methoxy-1-methyl-1H-indol-3-yl)-5-((2-(trimethylsilyl)ethoxy)methyl)-5H-pyrrolo[2,3-b]pyrazin-2-yl)methanol (4.00 g, 9.12 mmol, Preparation #F.1), DCM (90 mL) and thionyl chloride (0.732 mL, 10.0 mmol). The mixture was stirred at rt for about 40 min and concentrated under reduced pressure. The residue was dissolved in DMF (90 mL) and treated with NaN$_3$ (1.48 g, 22.8 mmol). The mixture was stirred overnight at rt. The solution was diluted with water (150 mL). The suspension was extracted with EtOAc (3×125 mL). The combined organic layers were dried over anhydrous MgSO$_4$, filtered and concentrated under reduced pressure to give 2-(azidomethyl)-6-(5-methoxy-1-methyl-1H-indol-3-yl)-5-((2-(trimethylsilyl)ethoxy)methyl)-5H-pyrrolo[2,3-b]pyrazine (4.23 g, 100%): LC/MS (Table 2, Method b) R$_t$=3.16 min; MS m/z 464 (M+H)$^+$.

General Procedure H: Conversion of an Aryl or Heteroaryl Halide to an Aryl or Heteroaryl Boronate or Aryl or Heteroaryl Boronic Acid A boronic acid or boronate could be prepared by any of the two methods below.
Method 1:
A flask is charged with an aryl or heteroaryl halide (1 equiv), and a borane or diborane (such as 4,4,5,5-tetramethyl-1,3,2-dioxaborolane or bis(pincaolato)diboron; 1 to 4 equiv, preferably 1 to 2 equiv), a base (such as KOAc, Na$_2$CO$_3$ or CsCO$_3$, preferably KOAc, 1 to 6 equiv, preferably 1 to 3 equiv), a palladium catalyst (such as PdCl$_2$(dppf), 0.02-1 equiv, preferably 0.03 to 0.08 equiv) and an organic solvent (such as THF, 1,4-dioxane, DMSO or DCM, preferably 1,4-dioxane or DMSO). The mixture is heated at about 60 to 110° C. (preferably about 80 to 105° C.) for about 1 to 48 h (preferably about 2 to 10 h). The mixture is optionally concentrated in vacuo to give the targeted compound. The reaction mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.
Method 2:
The aryl or heteroaryl halide (1 equiv) in an organic solvent (such as THF, 1,4-dioxane or Et$_2$O, preferably THF) is cooled to about −65° C. to −75° C. To the mixture is slowly added n-BuLi (1 to 5 equiv, preferably 1 to 3 equiv). After about 30 to 45 min, a borate (such as trimethylborate, triethyl borate, tributyl borate and triisopropyl borate, preferably triethyl borate; 1 to 4 equiv, preferably 2 to 3 equiv) is added. The mixture is then allowed to stir for about 1 to 5 h and optionally allowed to come to rt. The mixture is optionally concentrated in vacuo. The mixture is optionally treated with an aqueous solution of HCl (1 to 6 N) and extracted with a suitable organic solvent (such as DCM, EtOAc or Et$_2$O, preferably EtOAc). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure H

Preparation #H.1: 2-(4-(4,4,5,5-Tetramethyl-1,3,2-dioxaborolan-2-yl)phenyl)propan-2-ol

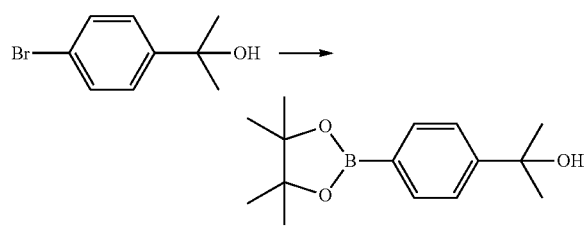

A flask was charged with 2-(4-bromophenyl)propan-2-ol (5.00 g, 23.3 mmol, prepared according to *Bioorg. Med. Chem. Lett.* 2007, 17, 662), bis(pinacolato)diboron (6.49 g, 25.6 mmol), KOAc (6.84 g, 69.7 mmol), PdCl$_2$(dppf)-CH$_2$Cl$_2$ (0.949 g, 1.16 mmol) and DMSO (155 mL). The mixture was heated to about 80° C. for about 4 h. After cooling to rt, the mixture was partitioned between brine (400 mL) and EtOAc (100 mL). The organic layer was isolated and the aqueous phase was extracted with two further portions of EtOAc (2×50 mL). The organic layers were combined, washed with brine (5×100 mL), dried over anhydrous MgSO$_4$ and concentrated in vacuo. The crude material was purified by silica gel flash chromatography with a gradient of 0 to 100% EtOAc/hexanes to give 2-(4-(4,4,5,5-Tetramethyl-1,3,2-dioxaborolan-2-yl)phenyl)propan-2-ol (2.76 g, 45%): $^1$H NMR (d-DMSO) δ 7.80 (s, J=8, 2H), 7.50 (s, J=8, 2H), 1.58 (s, 6H), 1.34 (s, 12H).

General Procedure I: Reduction of an Alkyl Azide to an Alkyl Amine

Method 1:

A phosphine (such as triphenylphospine, tributylphosphine or tri-tert-butylphosphine, preferably triphenylphosphine; 1.0 to 1.05 equiv, preferably 1.0 equiv) and water (3 to 13 equiv, preferably 8 equiv) are added to a solution of an alkyl azide (1 equiv) in an organic solvent (such as THF) at about 25° C. The mixture is heated at about 60 to 75° C. (preferably about 65° C.) for about 45 min to 16 h (preferably about 4 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Method 2:

To an azide (preferably 1 equiv) in an organic solvent such as EtOH, MeOH, EtOAc or THF (preferably MeOH) is added a catalyst such as 20 wt % palladium hydroxide on carbon or 10% wt palladium on carbon (preferably 10% wt palladium on carbon, 0.05 to 0.5 eq., preferably 0.1 to 0.3 equiv). The mixture is then stirred at rt under hydrogen (1 atmosphere pressure) of for about 1 to 48 h, preferably about 4 to 16 h. The catalyst is removed by filtration through a pad of Celite® and the filtrate is concentrated under reduced pressure to yield the targeted compound.

Illustration of General Procedure I

Preparation #I.1: (6-(5-Methoxy-1-methyl-1H-indol-3-yl)-5-((2-(trimethylsilyl)ethoxy)methyl)-5H-pyrrolo[2,3-b]pyrazin-2-yl)methanamine

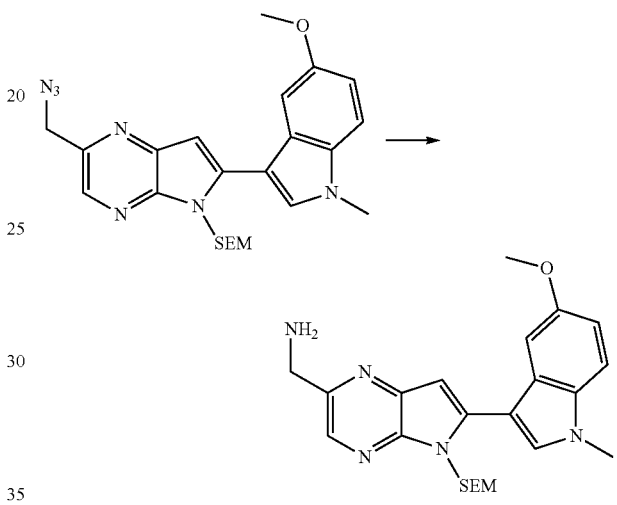

2-(Azidomethyl)-6-(5-methoxy-1-methyl-1H-indol-3-yl)-5-((2-(trimethylsilyl)ethoxy)methyl)-5H-pyrrolo[2,3-b]pyrazine (4.23 g, 9.12 mmol, Preparation #G.1) in THF (100 mL) was treated with triphenylphosphine (2.39 g, 9.12 mmol) and water (1.4 mL, 78 mmol). The mixture was heated at about 65° C. for about 4 h. The mixture was cooled to rt and concentrated under reduced pressure. The material was purified by flash chromatography on silica gel with 98:2 then 9:1 DCM/MeOH containing 2.5 vol % of a solution of 37% aqueous NH$_4$OH to give (6-(5-methoxy-1-methyl-1H-indol-3-yl)-5-((2-(trimethylsilyl)ethoxy)methyl)-5H-pyrrolo[2,3-b]pyrazin-2-yl)methanamine (2.32 g, 58%): LC/MS (Table 2, Method a) R$_t$=2.30 min; MS m/z 438 (M+H)$^+$.

General Procedure J.1: Formation of an Amide from an Amine and a Carboxylic Acid or Carboxylate Salt To a flask is added in no particular order, a carboxylic acid or carboxylate salt (1 to 5 equiv, preferably 1.1 to 1.5 equiv) an amine (1 to 5 equiv, preferably 1 to 1.5 equiv), an organic solvent (such as DCM, DCE, THF, or 1,4-dioxane, preferably DCM), a peptide coupling reagent (such as BOP—Cl, IBCF, HATU, DCI or EDC.HCl, preferably HATU; 1 to 10 equiv, preferably 1 to 2 equiv), a base (such as TEA, DIEA, pyridine or DIEA, preferably DIEA; 1 to 20 equiv, preferably 1 to 5 equiv) and optionally HOBt (0 to 5 equiv, preferably 0 to 1 equiv). The mixture is then stirred at about 10 to 60° C. (preferably about 25 to 50° C.) for about 15 min to 48 h (preferably about 15 min to 12 h). The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure J.1

Preparation #J.1.1: 3-(1-Methyl-6-tosyl-1,6-dihydro-pyrazolo[3,4-d]pyrrolo[2,3-b]pyridin-7-yl)-N-(2-morpholinoethyl)benzamide

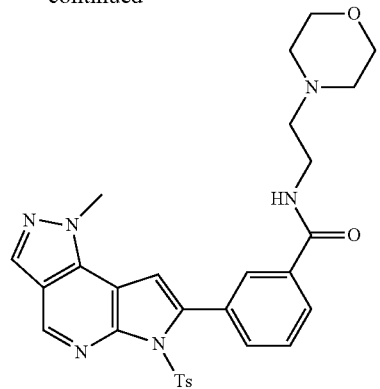

A flask was charged with 3-(1-methyl-6-tosyl-1,6-dihydropyrazolo[3,4-d]pyrrolo[2,3-b]pyridin-7-yl)benzoic acid (0.10 g, 0.22 mmol, prepared using D from Preparation #1 with 3-boronobenzoic acid), DIEA (0.039 mL, 0.224 mmol), HATU (0.085 g, 0.224 mmol) and DMF (3 mL). The mixture was stirred at about 40° C. for about 30 min. To the mixture was added 2-morpholinoethanamine (0.038 mL, 0.291 mmol). The mixture was allowed to stir at about 40° C. for about 2 h. The mixture was stirred overnight at rt and then diluted with EtOAc (10 mL) and washed with water (10 mL). The aqueous layer was further extracted with EtOAc (2×10 mL). The combined organic layers were dried over anhydrous MgSO$_4$, filtered and concentrated under reduced pressure. The residue was purified by silica gel chromatography with an elution gradient of 0 to 7.5% MeOH/DCM to give 3-(1-methyl-6-tosyl-1,6-dihydropyrazolo[3,4-d]pyrrolo[2,3-b]pyridin-7-yl)-N-(2-morpholinoethyl)benzamide (0.123 g, 98%): LC/MS (Table 2, Method c) R$_t$=1.20 min; MS m/z 559 (M+H)$^+$.

TABLE J.1.1

Examples prepared from (3-(1-methyl-1,6-dihydropyrazolo[3,4-d]pyrrolo[2,3-b]pyridin-7-yl)phenyl)methanamine [Example #T.3.1.1] with a carboxylic acid using General Procedure J.1

| Carboxylic Acid | Product | Example # | R$_t$ min (Table 2, Method) | m/z ESI+ (M+H)$^+$ | Syk IC$_{50}$ |
|---|---|---|---|---|---|
| 2-(Dimethylamino)acetic acid | | J.1.1.1 | 1.53 (a) | 363 | B |
| 3-Methoxypropanoic acid | | J.1.1.2 | 1.69 (a) | 364 | B |

TABLE J.1.1-continued

Examples prepared from (3-(1-methyl-1,6-dihydropyrazolo[3,4-d]pyrrolo[2,3-b]pyridin-7-yl)phenyl)methanamine [Example #T.3.1.1] with a carboxylic acid using General Procedure J.1

| Carboxylic Acid | Product | Example # | $R_t$ min (Table 2, Method) | m/z ESI+ (M+H)+ | Syk IC$_{50}$ |
|---|---|---|---|---|---|
| 3-Morpholinopropanic acid | | J.1.1.3 | 1.49 (a) | 419 | B |
| Pentanoic acid | | J.1.1.4 | 2.07 (a) | 362 | B |

TABLE J.1.2

Examples prepared from 3-(4-methoxyphenyl)-6H-imidazo[1,5-a]pyrrolo[2,3-e]pyrazine-1-carboxylic acid [Example #AN.1.2] with an amine using General Procedure J.1

| Amine | Product | Example # | $R_t$ min (Table 2, Method) | m/z ESI+ (M + H)+ | Syk IC$_{50}$ |
|---|---|---|---|---|---|
| 2-Aminoethanol | | J.1.2.1 | 1.62 (a) | 352 | A |

TABLE J.1.3

Examples prepared from 4-(4-(1-methyl-6H-imidazo[1,5-a]pyrrolo[2,3-e]pyrazin-3-yl)phenyl)piperidin-4-ol [Example #P.3.2.3] with a carboxylic acid using General Procedure J.1

| Carboxylic Acid | Product | Example # | $R_t$ min (Table 2, Method) | m/z ESI+ (M + H)+ | Syk IC$_{50}$ |
|---|---|---|---|---|---|
| 2-Cyanoacetic acid | | J.1.3.1 | 1.42 (a) | 415 | A |

TABLE J.1.4
Examples prepared from 1-methyl-3-(1-methyl-1,6-dihydropyrazolo[3,4-d]pyrrolo[2,3-b]pyridin-7-yl)-1H-indole-6-carboxylic acid (Example #AN.1.4) with an amine using General Procedure J.1
| Amine | Product | Example # | R$_t$ min (Table 2, Method) | m/z ESI+ (M + H)$^+$ | Syk IC$_{50}$ |
|---|---|---|---|---|---|
| Dimethylamine | 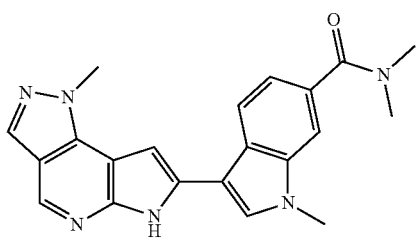 [SMILES: CN(C)C(=O)c1ccc2c(-c3cc4c(ncc5cnn(C)c54)[nH]3)cn(C)c2c1] | J.1.4.1 | 1.70 (a) | 373 | A |
| 3-Amino-2,2-dimethylpropan-1-ol | 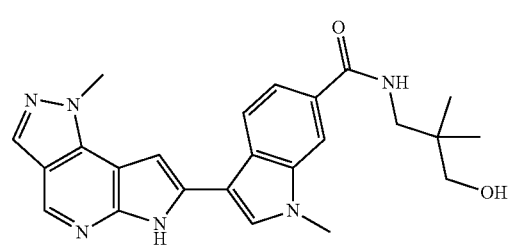 [SMILES: Cn1cc(-c2cc3c(ncc4cnn(C)c43)[nH]2)c2ccc(C(=O)NCC(C)(C)CO)cc21] | J.1.4.2 | 1.81 (a) | 431 | A |
| 2-Amino-2-methylpropan-1-ol | 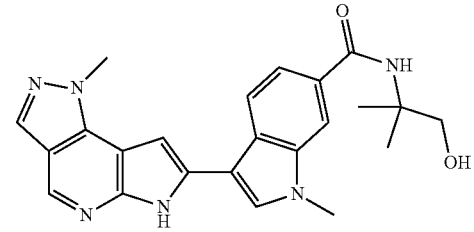 [SMILES: Cn1cc(-c2cc3c(ncc4cnn(C)c43)[nH]2)c2ccc(C(=O)NC(C)(C)CO)cc21] | J.1.4.3 | 1.78 (a) | 417 | A |
| 2-Morpholinoethanamine | 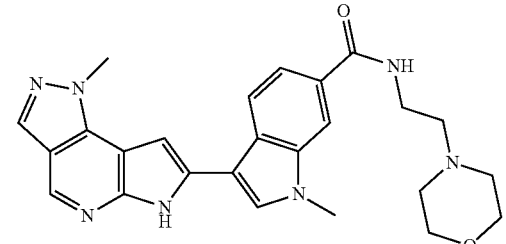 | J.1.4.4 | 1.80 (a) | 431 | A |

TABLE J.1.5

Examples prepared from 7-(4-acetylphenyl)-6H-imidazo[1,5-a]pyrrolo[2,3-e]pyrazine-1-carboxylic acid (prepared using A from 2-(4-iodophenyl)-2-methyl-1,3-dioxolane [Preparation #4] with ethynyltrimethylsilane, Q, A with 3,5-dibromopyrazin-2-amine, B, C, D with (E)-styrylboronic acid, E, F, G, I, J.2 with methyl 2-chloro-2-oxoacetate, L.1 with mercury(II) acetate, W, M and V.1) with an amine using J.1

| Amine | Product | Example # | R$_t$ min (Table 2, Method) | m/z ESI+ (M + H)$^+$ | Syk IC$_{50}$ |
|---|---|---|---|---|---|
| Pyrrolidine | 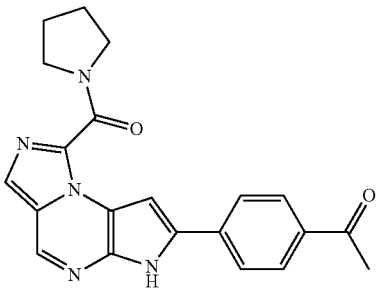 [SMILES: CC(=O)c1ccc(-c2cc3c(ncc4cnc(C(=O)N5CCCC5)n43)[nH]2)cc1] | J.1.5.1 | 1.88 (a) | 374 | A |
| N1,N1-Dimethylethane-1,2-diamine | 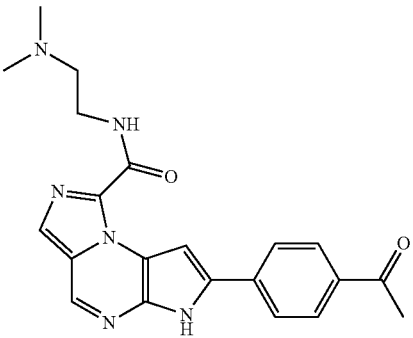 [SMILES: CC(=O)c1ccc(-c2cc3c(ncc4cnc(C(=O)NCCN(C)C)n43)[nH]2)cc1] | J.1.5.2 | 1.52 (a) | 391 | B |

TABLE J.1.6

Examples prepared from 2-chloro-4-(1-methyl-6H-imidazo[1,5-a]pyrrolo[2,3-e]pyrazin-3-yl)benzoic acid (prepared using D from 3-bromo-1-methyl-6-tosyl-6H-imidazo[1,5-a]pyrrolo[2,3-e]pyrazine [Preparation #AB.1] with 3-chloro-4-(methoxycarbonyl)phenylboronic acid [Combiblocks] and AN) with an amine using J.1

| Amine | Product | Example # | R$_t$ min (Table 2, Method) | m/z ESI+ (M + H)$^+$ | Syk IC$_{50}$ |
|---|---|---|---|---|---|
| Propan-1-amine | 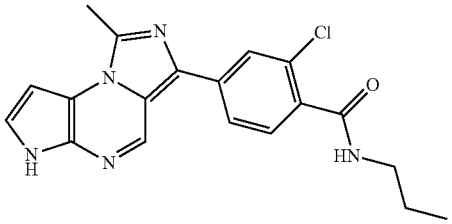 [SMILES: CCCNC(=O)c1ccc(-c2nc(C)n3c2cnc2[nH]ccc23)cc1Cl] | J.1.6.1 | 1.85 (a) | 368 | B |

TABLE J.1.7

Examples prepared from 2-methoxy-5-(1-methyl-6H-imidazo[1,5-a]pyrrolo[2,3-e]pyrazin-3-yl)benzoic acid (prepared using AC from 3-carboxy-4-methoxyphenylboronic acid [Frontier] and 2-methoxy-5-(1-methyl-6H-imidazo[1,5-a]pyrrolo[2,3-e]pyrazin-3-yl)benzoic acid [Preparation #AB.1]) with an amine using General Procedure J.1

| Amine | Product | Example # | $R_t$ min (Table 2, Method) | m/z ESI+ (M + H)+ | Syk IC$_{50}$ |
|---|---|---|---|---|---|
| Propylamine | | J.1.7.1 | 1.79 (b) | 364 | B |
| N1,N1-Dimethylethane-1,2-diamine | | J.1.7.2 | 1.46 (b) | 393 | B |
| Ethanolamine | | J.1.7.3 | 1.54 (b) | 366 | B |
| Ammonia | | J.1.7.4 | 1.59 (b) | 322 | B |

TABLE J.1.8

Examples prepared from 1-methyl-3-(1-methyl-1,6-dihydropyrazolo[3,4-d]pyrrolo[2,3-b]pyridin-7-yl)-1H-indole-5-carboxylic acid (Example #AN.1.1) with an amine using General Procedure J.1

| Amine | Product | Example # | $R_t$ min (Table 2, Method) | m/z ESI+ (M + H)+ | Syk IC$_{50}$ |
|---|---|---|---|---|---|
| 2-Morpholinoethanamine | 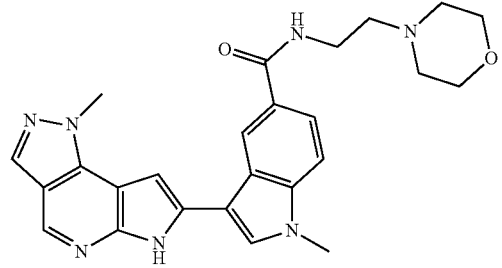 [SMILES: Cn1cc(-c2cc3c(ncc4cnn(C)c43)[nH]2)c2cc(C(=O)NCCN3CCOCC3)ccc21] | J.1.8.1 | 1.52 (a) | 458 | A |
| N1,N1-Dimethylethane-1,2-diamine | 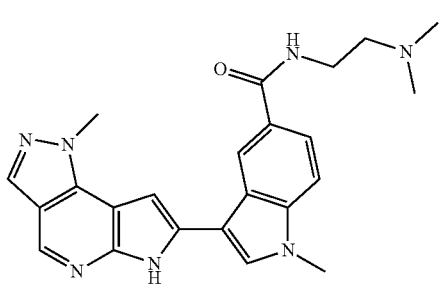 [SMILES: CN(C)CCNC(=O)c1ccc2c(c1)c(-c1cc3c(ncc4cnn(C)c43)[nH]1)cn2C] | J.1.8.2 | 1.52 (a) | 416 | B |
| Piperidin-4-ylmethanol | 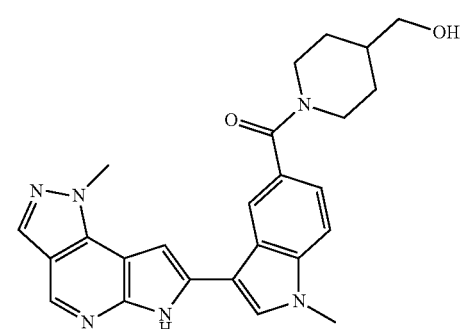 | J.1.8.3 | 1.56 (a) | 443 | A |
| Dimethylamine | 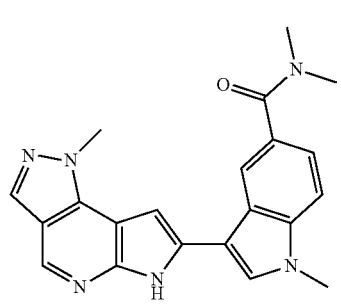 [SMILES: CN(C)C(=O)c1ccc2c(c1)c(-c1cc3c(ncc4cnn(C)c43)[nH]1)cn2C] | J.1.8.4 | 1.68 (a) | 373 | A |
| 2,2-Dimethyl-3-(methylamino)propan-1-ol (ChemBridge) | 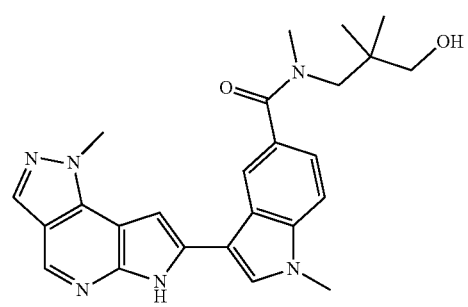 [SMILES: CN(CC(C)(C)CO)C(=O)c1ccc2c(c1)c(-c1cc3c(ncc4cnn(C)c43)[nH]1)cn2C] | J.1.8.5 | 1.85 (a) | 445 | A |

TABLE J.1.8-continued

Examples prepared from 1-methyl-3-(1-methyl-1,6-dihydropyrazolo[3,4-d]pyrrolo[2,3-b]pyridin-7-yl)-1H-indole-5-carboxylic acid (Example #AN.1.1) with an amine using General Procedure J.1

| Amine | Product | Example # | R$_t$ min (Table 2, Method) | m/z ESI+ (M + H)$^+$ | Syk IC$_{50}$ |
|---|---|---|---|---|---|
| 2-Amino-1-(4-methylpiperazin-1-yl)ethanone dihydrochloride (Oakwood) | | J.1.8.6 | 1.43 (a) | 485 | A |
| Ethanolamine | | J.1.8.7 | 1.49 (a) | 389 | A |

General Procedure J.2: Formation of an Amide from an Amine and an Acid Chloride or Acid Anhydride To a solution of an amine (1 equiv) in an organic solvent (such as DCM, THF, Et$_2$O or 1,4-dioxane, preferably THF) is added a base (such as TEA, DIEA or pyridine; 1 to 2 equiv, preferably 1 to 1.5 equiv) and an acid chloride or an acid anhydride (1 to 2 equiv, preferably 1.1 to 1.5 equiv). The mixture is allowed to stir at about 10 to 60° C. (preferably about 25 to 50° C.) for about 5 min to 12 h (preferably about 5 min to 3 h). The mixture is optionally neutralized with AcOH. The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure J.2

Preparation #J.2.1: N-((6-(5-Methoxy-1-methyl-1H-indol-3-yl)-5-((2-(trimethylsilyl)ethoxy)methyl)-5H-pyrrolo[2,3-b]pyrazin-2-yl)methyl)acetamide

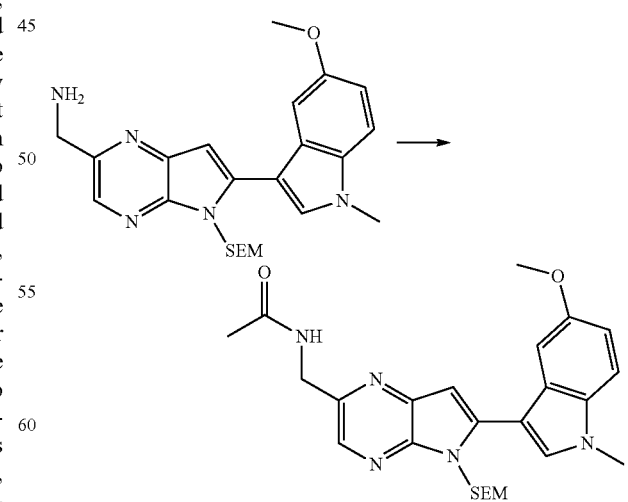

(6-(5-Methoxy-1-methyl-1H-indol-3-yl)-5-((2-(trimethylsilyl)ethoxy)methyl)-5H-pyrrolo[2,3-b]pyrazin-2-yl)methanamine (0.185 g, 0.423 mmol, Preparation #I.1) in THF (5 mL) was treated with pyridine (0.044 mL, 0.55 mmol) and Ac$_2$O (0.044 mL, 0.46 mmol). After about 5 min the mixture was treated with AcOH (0.024 mL, 0.42 mmol), diluted with EtOAc (20 mL) and then washed with water (15 mL) and brine (10 mL). The organic layer was dried over anhydrous MgSO$_4$, filtered and evaporated under reduced pressure to give N-((6-(5-Methoxy-1-methyl-1H-indol-3-yl)-5-((2-(trimethylsilyl)ethoxy)methyl)-5H-pyrrolo[2,3-b]pyrazin-2-yl)methyl)acetamide (0.207 g, 102%, crude): LC/MS (Table 2, Method a) R$_t$=2.63 min; MS m/z 480 (M+H)$^+$.

TABLE J.2.1

Examples prepared from Ac$_2$O or AcCl and an amine using General Procedure J.2

| Amine | Product | Example # | R$_t$ min (Table 2, Method) | m/z ESI+ (M + H)$^+$ | Syk IC$_{50}$ |
|---|---|---|---|---|---|
| (R)-7-(5-Methoxy-1-methyl-1H-indol-3-yl)-1-(pyrrolidin-3-yl)-6H-imidazo[1,5-a]pyrrolo[2,3-e]pyrazine diacetate (Example #T.1.1.2) | | J.2.1.1 | 1.75 (a) | 429 | B |
| (cis)-3-(7-(3-(Methylsulfonyl)phenyl)-6H-imidazo[1,5-a]pyrrolo[2,3-e]pyrazin-1-yl)cyclopentanamine (Example #T.1.1.5) | | J.2.1.2 | 1.56 (a) | 438 | B |
| 3-(7-(1-Methyl-1H-pyrazol-4-yl)-6H-imidazo[1,5-a]pyrrolo[2,3-e]pyrazin-1-yl)propan-1-amine (prepared using A from Preparation #Q.1 with 3,5-dibromopyrazin-2-amine, B, C, D with (E)-styrylboronic acid, E, F, G, I, J.1 with 4-(tert-butoxycarbonylamino)butyric acid, L.1 with mercury(II) trifluoroacetate and T.1) | | J.2.1.3 | 1.19 (a) | 338 | B |
| 2-(4-(1-Cyclohexyl-6H-imidazo[1,5-a]pyrrolo[2,3-e]pyrazin-3-yl)phenyl)propan-2-amine (Example #P.3.1.1) | | J.2.1.4 | 2.21 (a) | 414 | A |

TABLE J.2.1-continued

Examples prepared from Ac₂O or AcCl and an amine using General Procedure J.2

| Amine | Product | Example # | $R_t$ min (Table 2, Method) | m/z ESI+ $(M + H)^+$ | Syk IC$_{50}$ |
|---|---|---|---|---|---|
| 3-(1,2,3,6-Tetrahydropyridin-4-yl)-6H-imidazo[1,5-a]pyrrolo[2,3-e]pyrazine (Example #P.3.1.4) | | J.2.1.5 | 1.24 (a) | 282 | C |
| 4-(4-(1-Methyl-6H-imidazo[1,5-a]pyrrolo[2,3-e]pyrazin-3-yl)phenyl)piperidin-4-ol hydrochloride (Example #P.3.1.5) | | J.2.1.6 | 1.35 | 390 | A |
| cis-3-(3-(4-Methoxyphenyl)-6H-imidazo[1,5-a]pyrrolo[2,3-e]pyrazin-1-yl)cyclohexanamine (Example #T.3.1.4) | | J.2.1.7 | 1.84 (a) | 404 | B |
| 2-(4-(1-(Aminomethyl)-6H-imidazo[1,5-a]pyrrolo[2,3-e]pyrazin-3-yl)phenyl)propan-2-ol (Example #AC.5.6) | | J.2.1.8 | 1.35 (a) | 364 | B |
| (1S,3R)-3-(7-(5-methoxy-1-methyl-1H-indol-3-yl)-6H-imidazo[1,5-a]pyrrolo[2,3-e]pyrazin-1-yl)cyclopentanamine (Example #T.1.1.1) | | J.2.1.9 | 1.83 (a) | 443 | A |

TABLE J.2.2

Examples prepared from 1-methyl-3-(1-methyl-1,6-dihydropyrazolo[3,4-d]pyrrolo[2,3-b]pyridin-7-yl)-1H-indole-5-carbonyl chloride (prepared using General Procedure AO from 1-methyl-3-(1-methyl-1,6-dihydropyrazolo[3,4-d]pyrrolo[2,3-b]pyridin-7-yl)-1H-indole-5-carboxylic acid [Example #AN.1]) with an amine using General Procedure J.2

| Amine | Product | Example # | $R_t$ min (Table 2, Method) | m/z ESI+ (M + H)+ | Syk IC$_{50}$ |
|---|---|---|---|---|---|
| 2-Amino-2-methylpropan-1-ol | | J.2.2.1 | 1.73 (a) | 415 | A |
| 3-Amino-2,2-dimethylpropan-1-ol | | J.2.2.2 | 1.80 (a) | 431 | A |

TABLE J.2.3

Examples prepared from 2-(2-(1-methyl-1,6-dihydropyrazolo[3,4-d]pyrrolo[2,3-b]pyridin-7-yl)-1H-pyrrol-1-yl)acetyl chloride (Preparation #AO.1) with an amine using General Procedure J.2

| Amine | Product | Example # | $R_t$ min (Table 2, Method) | m/z ESI+ (M + H)+ | Syk IC$_{50}$ |
|---|---|---|---|---|---|
| 3-Ethoxypropan-1-amine | | J.2.3.1 | 1.72 (a) | 381 | C |
| Morpholine | | J.2.3.2 | 1.64 (a) | 365 | C |

TABLE J.2.3-continued

Examples prepared from 2-(2-(1-methyl-1,6-dihydropyrazolo[3,4-d]pyrrolo[2,3-b]pyridin-7-yl)-1H-pyrrol-1-yl)acetyl chloride (Preparation #AO.1) with an amine using General Procedure J.2

| Amine | Product | Example # | $R_t$ min (Table 2, Method) | m/z ESI+ $(M+H)^+$ | Syk $IC_{50}$ |
|---|---|---|---|---|---|
| 1-Methylpiperazine | (structure) | J.2.3.3 | 1.30 (a) | 378 | D |

General Procedure J.3: Formation of a Formamide from an Amine and a Formate or Orthoformate An amine (1 equiv) is dissolved in a formate or an orthoformate (1 to 300 equiv, preferably about 50 equiv) and a base (such as TEA, DIPEA, pyridine, 2,6-lutidine, preferably DIPEA; 0.5 to 3 equiv, preferably about 1.3 equiv) is optionally added. The mixture is heated to about 20 to 90° C. (preferably about 60° C.) for about 0.5 to 17 h (preferably about 3 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, acetic acid or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure J.3

Preparation #J.3.1: (4-Methoxyphenyl)(5-tosyl-5H-pyrrolo[2,3-b]pyrazin-2-yl)methanamine

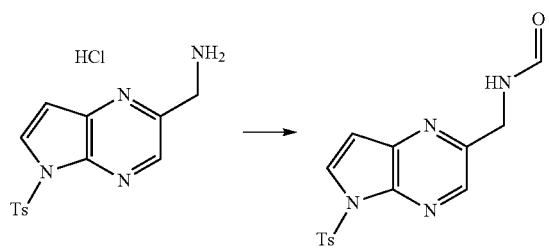 [SMILES: Cc1ccc(S(=O)(=O)n2ccc3nc(CN)cnc32)cc1 ; Cl ; Cc1ccc(S(=O)(=O)n2ccc3nc(CNC=O)cnc32)cc1]

(5-Tosyl-5H-pyrrolo[2,3-b]pyrazin-2-yl)methanamine hydrochloride (4.00 g, 11.8 mmol, Example #2, Step B) was suspended in ethyl formate (50 mL, 610 mmol) and then DIPEA (3.09 mL, 17.7 mmol) was added. The mixture was heated to about 60° C. After about 3 h the mixture was cooled to rt and concentrated to under reduced pressure. The material was triturated with water (75 mL) and the solids collected by filtration and washed with additional water (50 mL). The material was dried under vacuum at about 60° C. to provide (4-methoxyphenyl)(5-tosyl-5H-pyrrolo[2,3-b]pyrazin-2-yl)methanamine (3.66 g, 94%): LC/MS (Table 2, Method a) $R_t$=1.80 min; MS m/z 331 (M+H)$^+$.

General Procedure K: Formation of a Sulfonamide from an Amine and a Sulfonyl Chloride To a flask is added an amine (1.0 equiv), an organic solvent (such as DCM or DMF, preferably DMF), a base (such as TEA, DIEA, NaHCO$_3$, NaH, KOt-Bu or NaOt-Bu, preferably TEA or DIEA; 1.0 to 5.0 equiv, preferably 1.0 to 3.0 equiv) and a sulfonyl chloride (0.9 to 2.0 equiv, preferably 1.0 to 1.25 equiv). The mixture is stirred at about 0 to 80° C. (preferably about 15 to 25° C.) for about 5 min to 12 h (preferably about 5 min to 1 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure K

Example #K.1: N-(3-(1-Methyl-1,6-dihydropyrazolo[3,4-d]pyrrolo[2,3-b]pyridin-7-yl)benzyl)methanesulfonamide

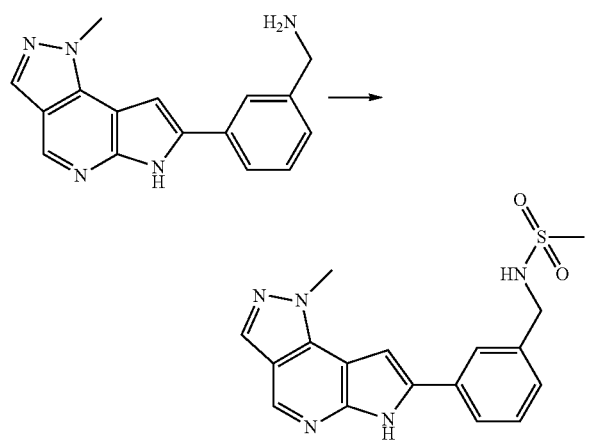

To a flask was added (3-(1-methyl-1,6-dihydropyrazolo[3,4-d]pyrrolo[2,3-b]pyridin-7-yl)phenyl)methanamine (0.075 g, 0.27 mmol, Example #T.3.1), DMF (2.7 mL), DIEA (0.118 mL, 0.676 mmol) and MsCl (0.025 mL, 0.325 mmol). The mixture was stirred at rt for about 10 min. The mixture was purified directly by flash chromatography (25 g silica gel column, DCM/MeOH 1:0 to 10:1 with 2% 2.0 M $NH_3$ in EtOH). The solid was dried under reduced pressure at about 60° C. for about 1 h to give N-(3-(1-methyl-1,6-dihydropyrazolo[3,4-d]pyrrolo[2,3-b]pyridin-7-yl)benzyl)methanesulfonamide (0.057 g, 58%): LC/MS (Table 2, Method a) $R_t$=1.84 min; MS m/z 356 (M+H)$^+$. Syk $IC_{50}$=B.

THF, preferably 1,4-dioxane) and Lawesson's reagent (0.4 to 2 equiv, preferably 0.5 to 1.0 equiv). The mixture is heated at about 15 to 90° C. (preferably about 50 to 85° C.) for about 15 min to 24 h (preferably about 30 min to 3 h). Optionally, additional Lawesson's reagent (0.2 to 1.0 equiv, preferably 0.4 to 0.8 equiv) may be added and the mixture stirred about 15 min to 6 h (preferably about 30 min to 2 h) at about 15 to 90° C. (preferably about 50 to 90° C. The mixture is optionally filtered at rt through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give an intermediate. Either the intermediate or the solution may be optionally partitioned between water and an organic solvent (such as EtOAc, $Et_2O$ or DCM). The organic layer is isolated and may optionally be washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give an intermediate. The resulting intermediate is added to a flask along with an organic solvent (such as 1,4-dioxane or THF, preferably 1,4-dioxane). To the mixture is added a mercury salt (such as mercury(II) acetate or mercury(II) trifluoroacetate, preferably mercury(II) trifluoroacetate or both; 0.8 to 1.2 equiv, preferably 1.0 to 1.1 equiv). The mixture is stirred at about 15 to 90° C. (preferably about 50 to 85° C.) for about 5 min to 24 h (preferably about 15 min to 12 h). Optionally, additional mercury salt may be added (0.1 to 1.0 equiv, preferably 1.0 equiv) and the mixture is stirred about 15 min to 6 h (preferably about 15 min to 2 h). The mixture is optionally filtered through a media (such as silica gel or Celite®) which is rinsed with an appropriate solvent (such as EtOAc, 1,4-dioxane, THF, MeCN, DCM, $Et_2O$, MeOH, EtOH) and then

TABLE K.1

Examples prepared from cyclopropylsulfonyl chloride [Matrix] with an amine using General Procedure K

| Amine | Product | Example # | $R_t$ min (Table 2, Method) | m/z ESI+ (M + H)$^+$ | Syk $IC_{50}$ |
|---|---|---|---|---|---|
| (1S,3R)-3-(7-(5-Methoxy-1-methyl-1H-indol-3-yl)-6H-imidazo[1,5-a]pyrrolo[2,3-e]pyrazin-1-yl)cyclopentanamine (Example #T.1.1) | | K.1.1 | 2.09 (a) | 505 | A |

General Procedure L.1: Cyclization to Form a 6H-imidazo[1,5-a]pyrrolo[2,3-e]pyrazine from an N-((5H-pyrrolo[2,3-b]pyrazin-2-yl)methyl)amide with Lawesson's Reagent and a Mercuric Salt To a flask is added an N-((5H-pyrrolo[2,3-b]pyrazin-2-yl)methyl)amide (1.0 equiv), a solvent (such as 1,4-dioxane or optionally concentrated in vacuo to give the targeted compound as a residue. Either the residue or the solution may be optionally partitioned between water and an organic solvent (such as EtOAc, $Et_2O$ or DCM). The organic layer is isolated and may optionally be washed in no particular order with water and/or aqueous solutions containing an acid (such as HCl, AcOH or $NH_4Cl$) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure L.1

Example #L.1.1: 7-(5-Methoxy-1-methyl-1H-indol-3-yl)-1-(trifluoromethyl)-6H-imidazo[1,5-a]pyrrolo[2,3-e]pyrazine

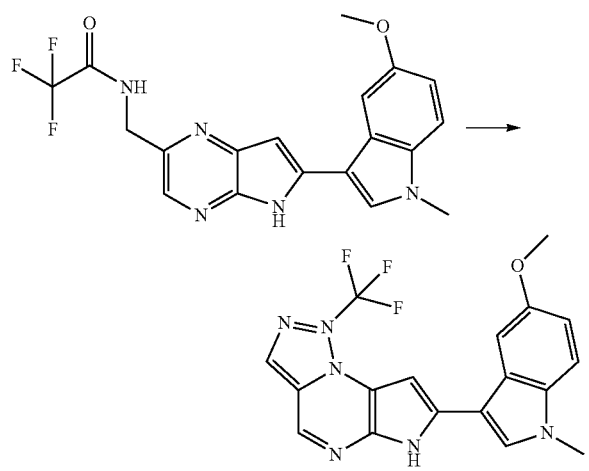

To a round bottom flask was added 2,2,2-trifluoro-N-((6-(5-methoxy-1-methyl-1H-indol-3-yl)-5H-pyrrolo[2,3-b]pyrazin-2-yl)methyl)acetamide (0.086 g, 0.213 mmol, prepared using J.1 from Preparation #I.1 with trifluoroacetic anhydride and M with TBAF), 1,4-dioxane (5 mL) and Lawesson's reagent (0.052 g, 0.128 mmol). The mixture was heated at about 85° C. for about 90 min. More Lawesson's reagent (0.052 g, 0.128 mmol) was added and the mixture was stirred at about 85° C. for about 3 h. The mixture was cooled to rt and stirred overnight. To the mixture was added mercury (II) acetate (0.075 g, 0.235 mmol) and the mixture was stirred at rt for about 16 h. The mixture was diluted with EtOAc (50 mL) and filtered through Celite®. The organic layer was washed with water (50 mL), dried with anhydrous MgSO$_4$, filtered and concentrated in vacuo to give a residue. The residue was added to a round bottom flask and 1,4-dioxane (5 mL) and mercury(II) trifluoroacetate (0.122 g, 0.286 mmol) were added. The mixture was stirred at rt for about 30 min. The mixture was diluted with EtOAc (50 mL), filtered through Celite® and concentrated in vacuo. The crude material was purified by flash chromatograph (40 g silica gel column, DCM/MeOH 1:0 to 10:1) to give a solid. The material was purified again by flash chromatography (120 g silica gel column, heptane/EtOAc 1:0 to 0:1) to give a solid. The solid was purified by reverse phase preparatory HPLC (Table 2, method e) to give fractions with product. The fractions were combined and extracted with EtOAc (50 mL). The organic was washed with water (50 mL), dried with anhydrous MgSO$_4$, filtered and concentrated in vacuo. The solid was dried in under reduced pressure at about 60° C. for about 16 h to give the title compound (0.007 g, 7%): LC/MS (Table 2, Method a) R$_t$=2.41 min; MS m/z 386 (M+H)$^+$. Syk IC$_{50}$=B.

TABLE L.1.1

Examples prepared from a 5H-pyrrolo[2,3-b]pyrazin-2-yl)methyl)amide using General Procedure L

| 5H-Pyrrolo[2,3-b]pyrazin-2-yl)methyl)amide | Product | Example # | R$_t$ min (Table 2, Method) | m/z ESI+ (M + H)$^+$ | Syk IC$_{50}$ |
|---|---|---|---|---|---|
| 2-Cyclopropyl-N-((6-(5-methoxy-1-methyl-1H-indol-3-yl)-5H-pyrrolo[2,3-b]pyrazin-2-yl)methyl)acetamide (prepared using J.1 from Preparation #I.1 with cyclopropylacetic acid [Lancaster] and M with TBAF) | | L.1.1.1 | 2.13 (a) | 372 | ND |
| N-((6-(5-Methoxy-1-methyl-1H-indol-3-yl)-5H-pyrrolo[2,3-b]pyrazin-2-yl)methyl) cyclopropanecarboxamide (prepared using J.2 from Preparation #I.1 with cyclopropanecarbonyl chloride and M with TBAF) | | L.1.1.2 | 2.10 (a) | 358 | ND |

General Procedure L.2: Cyclization to Form a 6H-imidazo[1,5-a]pyrrolo[2,3-e]pyrazine from an N-((5H-pyrrolo[2,3-b]pyrazin-2-yl)methyl)amide with Anhydrous Acidic Conditions To a solution of an amide (1 to 3 equiv, preferably 1 equiv) in an organic solvent (such as 1,4-dioxane, DCE, THF or DCM, preferably DCE) is added an acid (such as $POCl_3$, TFAA, TFA, $SOCl_2$, or $PCl_5$, preferably $POCl_3$; 1 to 30 equiv, preferably 3 to 15 equiv). The mixture is heated at about 25 to 120° C. (preferably about 60 to 100° C.) for about 0.5 to 16 h (preferably about 1 to 8 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, EtOH) and then optionally concentrated in vacuo to give a residue as the target compound. Either the residue or the solution may be optionally partitioned between water and an organic solvent (such as EtOAc, $Et_2O$ or DCM). The organic layer is isolated and may optionally be washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl $Na_2SO_3$ or $Na_2S_2O_3$). The organic solution may then be optionally dried with a drying agent (such as anhydrous $MgSO_4$ or $Na_2SO_4$), filtered and concentrated in vacuo to give the target compound.

Illustration of General Procedure L.2

Preparation #L.2.1:
6-Tosyl-6H-imidazo[1,5-a]pyrrolo[2,3-e]pyrazine

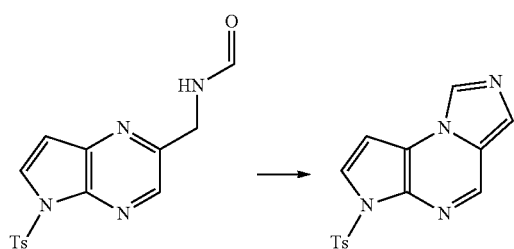 [SMILES: Cc1ccc(S(=O)(=O)n2ccc3nc(CNC=O)cnc32)cc1 ; Cc1ccc(S(=O)(=O)n2ccc3c2ncc2cncn23)cc1]

N-((5-tosyl-5H-pyrrolo[2,3-b]pyrazin-2-yl)methyl)formamide (3.66 g, 11.1 mmol, prepared using J.3 from Example #2, Step C with ethyl formate) was suspended in DCE (80 mL) then $POCl_3$ (1.08 mL, 11.6 mmol) was added. The mixture was heated to about 80° C. for about 90 min and then cooled to rt. The mixture was treated with about 50 mL saturated aqueous $NaHCO_3$ and then stirred for about 15 min. The layers were separated and aqueous layer was extracted with DCM (40 mL). The combined organics were dried over $MgSO_4$, filtered and evaporated under reduced pressure to give 6-tosyl-6H-imidazo[1,5-a]pyrrolo[2,3-e]pyrazine (3.46 g, 100%): LC/MS (Table 2, Method a) $R_t$=1.97 min; MS m/z 313 $(M+H)^+$.

General Procedure M: Removal of a SEM Group from an N-SEM Protected Heteroaromatic Ring Either of the following two procedures may be used:
1. To a solution of an N-SEM-protected heteroaromatic ring (1 equiv) in an organic solvent (such as DMF, 1,4-dioxane, or DCM, preferably DCM) is added TFA (5 to 50 equiv, preferably 30 equiv) and the reaction is stirred at about 0 to 50° C. (preferably about 15 to 25° C.) for about 1 to 48 h (preferably about 4 to 16 h). Alternatively, additional TFA (5 to 20 equiv, preferably 10 equiv) may be added. The mixture is concentrated under reduced pressure then the material is dissolved in an organic solvent (such as MeOH, EtOH, THF or 1,4-dioxane, preferably MeOH or 1,4-dioxane), an aqueous base (such as ethylenediamine or $NH_4OH$, preferably $NH_4OH$) is added and the mixture is heated to about 30 to 100° C. (preferably about 50 to 80° C.) for about 0.5 to 10 h (preferably about 1 to 5 h).

2. To a solution of an N-SEM-protected heteroaromatic ring (1 equiv) in an organic solvent (such as DMF, 1,4-dioxane, or DCM, preferably DMF) is added TBAF (1 to 10 equiv, preferably 4 equiv) followed by ethylene diamine (5 to 40 equiv, preferably about 30 equiv) and the mixture is stirred at about 30 to 110° C. (preferably about 90° C.) for about 1 to 20 h (preferably about 2 h). Optionally, additional TBAF (1 to 10 equiv, preferably 2 equiv) may be added and the mixture is stirred at about 30 to 110° C. (preferably about 90° C.) for about 1 to 20 h (preferably about 2 h).

For either method, the targeted compound may optionally be isolated by cooling the mixture and filtering the precipitate. Alternatively, the mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

Illustration of General Procedure M

Example #M.1

7-(5-Methoxy-1-methyl-1H-indol-3-yl)-1-(tetrahydro-2H-pyran-3-yl)-6H-imidazo[1,5-a]pyrrolo[2,3-e]pyrazine

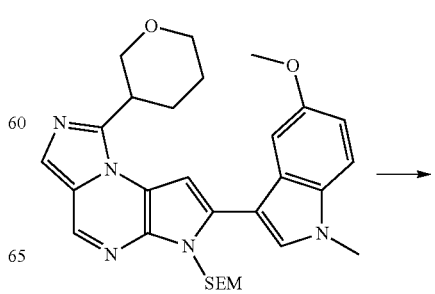

-continued

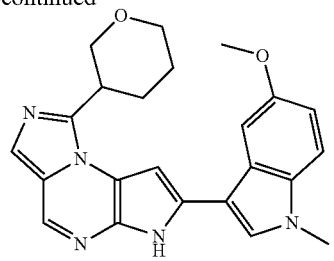

To a mixture of 7-(5-methoxy-1-methyl-1H-indol-3-yl)-1-(tetrahydro-2H-pyran-3-yl)-6-((2-(trimethylsilyl)ethoxy)methyl)-6H-imidazo[1,5-a]pyrrolo[2,3-e]pyrazine (0.245 g, 0.461 mmol; prepared using J.1 from Preparation #I.1 with tetrahydro-2H-pyran-2-carboxylic acid [Acella], and L.1 with mercury(II) trifluoroacetate) in DCM (5 mL) was added TFA (0.887 mL, 11.5 mmol). After stirring at rt for about 15 h, the mixture was concentrated in vacuo. The material was dissolved in MeOH (5 mL) and then treated with a 30% aqueous NH$_4$OH solution (1.79 mL, 13.8 mmol). The mixture was heated to about 60° C. for about 1 h then cooled to rt. Water was added (10 mL) and the solids were collected by filtration then washed with water (10 mL). The material was dried in a vacuum oven at about 60° C. for about 16 h to provide 7-(5-methoxy-1-methyl-1H-indol-3-yl)-1-(tetrahydro-2H-pyran-3-yl)-6H-imidazo[1,5-a]pyrrolo[2,3-e]pyrazine (0.072 g, 39%): LC/MS (Table 2, Method a) R$_t$=2.16 min; MS m/z 402 (M+H)$^+$. Syk IC$_{50}$=A.

TABLE M.1

| | | | | | |
|---|---|---|---|---|---|
| Examples prepared from an N-SEM protected heteroaromatic ring with TFA followed by NH$_4$OH using General Procedure M | | | | | |
| N-SEM protected heteroaromatic ring | Product | Example # | R$_t$ min (Table 2, Method) | m/z ESI+ (M + H)$^+$ | Syk IC$_{50}$ |
| 7-(5-Methoxy-1-methyl-1H-indol-3-yl)-1-(2,2,2-trifluoroethyl)-6-((2-(trimethylsilyl)ethoxy)methyl)-6H-imidazo[1,5-a]pyrrolo[2,3-e]pyrazine (prepared using J.1 from Preparation #I.1 with 3,3,3-trifluoropropanoic acid and L.1 with mercury(II) trifluoroacetate) | | M.1.1 | 2.23 (a) | 400 | A |
| 7-(3-(Methylsulfonyl)phenyl)-1-(trifluoromethyl)-6-((2-(trimethylsilyl)ethoxy)methyl)-6H-imidazo[1,5-a]pyrrolo[2,3-e]pyrazine (prepared using A from ethynyltrimethylsilane with 1-bromo-3-(methylsulfonyl)benzene [Oakwood], Q, A with 3,5-dibromopyrazin-2-amine, B, C, D with (E)-styrylboronic acid, E, F, G, I, J.2 with trifluoroacetic anhydride and L.1 with mercury(II) trifluoroacetate) | | M.1.2 | 1.25 (c) | 381 | B |
| 1-Methyl-7-(3-(methylsulfonyl)phenyl)-6-((2-(trimethylsilyl)ethoxy)methyl)-6H-imidazo[1,5-a]pyrrolo[2,3-e]pyrazine (prepared using A from ethynyltrimethylsilane with 1-bromo-3-(methylsulfonyl)benzene [Oakwood], Q, A with 3,5-dibromopyrazin-2-amine B, C, D with (E)-styrylboronic acid E, F, G, I, J.2, with Ac$_2$O and L.1 with mercury(II) trifluoroacetate) | | M.1.3 | 1.52 (a) | 327 | A |

TABLE M.1-continued

Examples prepared from an N-SEM protected heteroaromatic ring with TFA followed by NH₄OH using General Procedure M

| N-SEM protected heteroaromatic ring | Product | Example # | $R_t$ min (Table 2, Method) | m/z ESI+ (M + H)⁺ | Syk IC$_{50}$ |
|---|---|---|---|---|---|
| 2,2,2-Trifluoro-N-(3-(7-(3-(methylsulfonyl)phenyl)-6-((2-(trimethylsilyl)ethoxy)methyl)-6H-imidazo[1,5-a]pyrrolo[2,3-e]pyrazin-1-yl)propyl)acetamide (prepared using A from ethynyltrimethylsilane with 1-bromo-3-(methylsulfonyl)benzene [Oakwood], Q, A with 3,5-dibromopyrazin-2-amine B, C, D with (E)-styrylbononic acid E, F, G, I, J.1 with 4-(tert-butoxycarbonylamino)butyric acid and L.1 with mercury(II) trifluoroacetate) | | M.1.4 | 1.20 (c) | 466 | B |
| 7-(3-(Methylsulfonyl)phenyl)-1-(tetrahydro-2H-pyran-3-yl)-6-((2-(trimethylsilyl)ethoxy)methyl)-6H-imidazo[1,5-a]pyrrolo[2,3-e]pyrazine (prepared using A from ethynyltrimethylsilane with 1-bromo-3-(methylsulfonyl)benzene [Oakwood], Q, A with 3,5-dibromopyrazin-2-amine B, C, D with (E)-styrylboronic acid E, F, G, I, J.1 with tetrahydro-2H-pyran-3-carboxylic acid [JW Pharm] and L.1 with mercury(II) trifluoroacetate) | | M.1.5 | 1.85 (a) | 397 | B |
| 3-(7-(3-(Methylsulfonyl)phenyl)-6-((2-(trimethylsilyl)ethoxy)methyl)-6H-imidazo[1,5-a]pyrrolo[2,3-e]pyrazin-1-yl)cyclopentanol (prepared using A from ethynyltrimethylsilane with 1-bromo-3-(methylsulfonyl)benzene [Oakwood], Q, A with 3,5-dibromopyrazin-2-amine B, C, D with (E)-styrylboronic acid E, F, G, I, J.1 with 3-oxocyclopentanecarboxylic acid, L.1 with mercury(II) trifluoroacetate and F) | | M.1.6 | 1.55 (a) | 397 | B |
| 3-(7-(5-Methoxy-1-methyl-1H-indol-3-yl)-6-((2-(trimethylsilyl)ethoxy)methyl)-6H-imidazo[1,5-a]pyrrolo[2,3-e]pyrazin-1-yl)propan-1-ol (Preparation #9) | | M.1.7 | 1.88 (a) | 376 | A |

TABLE M.1-continued

Examples prepared from an N-SEM protected heteroaromatic ring with TFA followed by NH$_4$OH using General Procedure M

| N-SEM protected heteroaromatic ring | Product | Example # | R$_t$ min (Table 2, Method) | m/z ESI+ (M + H)$^+$ | Syk IC$_{50}$ |
|---|---|---|---|---|---|
| 7-(5-Methoxy-1-methyl-1H-indol-3-yl)-N,N-dimethyl-6-((2-(trimethylsilyl)ethoxy)methyl)-6H-imidazo[1,5-a]pyrrolo[2,3-e]pyrazin-1-amine (Preparation #Y.1) | | M.1.8 | 2.04 (a) | 361 | A |
| 2-(4-(8-Ethyl-1-methyl-6-((2-(trimethylsilyl)ethoxy)methyl)-6H-imidazo[1,5-a]pyrrolo[2,3-e]pyrazin-7-yl)phenyl)propan-2-ol (Preparation #S.1) | | M.1.9 | 1.88 (a) | 335 | B |
| 7-(5-Methoxy-1-methyl-1H-indol-3-yl)-1-(tetrahydro-2H-pyran-4-yl)-6-((2-(trimethylsilyl)ethoxy)methyl)-6H-imidazo[1,5-a]pyrrolo[2,3-e]pyrazine (prepared using J.1 from Preparation #I.1 with tetrahydro-2H-pyran-4-carboxylic acid [Matrix] and L.1 with mercury(II) trifluoroacetate) | | M.1.10 | 2.16 (a) | 402 | A |
| 3-(1-Methyl-6-((2-(trimethylsilyl)ethoxy)methyl)-6H-imidazo[1,5-a]pyrrolo[2,3-e]pyrazin-7-yl)-N-(2-morpholinoethyl)benzamide (prepared using F from Preparation #E.1, G, I, J.2 with acetic anhydride, L.1 with mercury(II) trifluoroacetate and J.1 with 2-morpholinoethanamine) | | M.1.11 | 1.52 (a) | 405 | B |
| 1-Methyl-7-(1-methyl-1H-pyrazol-4-yl)-6-((2-(trimethylsilyl)ethoxy)methyl)-6H-pyrrolo[2,3-e][1,2,4]triazolo[4,3-a]pyrazine (Preparation #R.1.1) | | M.1.12 | 1.38 (a) | 254 | C |

TABLE M.1-continued

Examples prepared from an N-SEM protected heteroaromatic ring with TFA followed by NH₄OH using General Procedure M

| N-SEM protected heteroaromatic ring | Product | Example # | $R_t$ min (Table 2, Method) | m/z ESI+ (M + H)⁺ | Syk IC$_{50}$ |
|---|---|---|---|---|---|
| 3-(7-(5-Methoxy-1-methyl-1H-indol-3-yl)-6H-imidazo[1,5-a]pyrrolo[2,3-e]pyrazin-1-yl)propanenitrile (prepared using J.1 from Preparation #I.1 with 3-cyanopropanoic acid [Tyger Scientific] and L.1 with mercury(II) trifluoroacetate) | | M.1.13 | 1.29 (d) | 371 | A |
| 7-(5-Methoxy-1-methyl-1H-indol-3-yl)-1-(3-methoxypropyl)-6H-imidazo[1,5-a]pyrrolo[2,3-e]pyrazine (prepared using J.1 from Preparation #I.1 with 4-methoxybutanoic acid [Enamine] and L.1 with mercury(II) trifluoroacetate) | | M.1.14 | 1.37 (d) | 390 | A |
| N-methyl-7-p-tolyl-6-((2-(trimethylsilyl)ethoxy)methyl)-6H-imidazo[1,5-a]pyrrolo[2,3-e]pyrazin-1-amine (prepared using A from 1-ethynyl-4-methylbenzene with 3,5-dibromopyrazin-2-amine, B, C, D with (E)-styrylboronic acid, E, F, G, I, X with methanamine hydrochloride and Y) | | M.1.15 | 1.95 (a) | 278 | B |
| N,N-dimethyl-7-p-tolyl-6-((2-(trimethylsilyl)ethoxy)methyl)-6H-imidazo[1,5-a]pyrrolo[2,3-e]pyrazin-1-amine (prepared using A from 1-ethynyl-4-methylbenzene with 3,5-dibromopyrazin-2-amine, B, C, D with (E)-styrylboronic acid, E, F, G, I, X with dimethylamine and Y) | | M.1.16 | 2.17 (a) | 292 | B |
| 7-(5-Methoxy-1-methyl-1H-indol-3-yl)-1-(pyrrolidin-1-yl)-6-((2-(trimethylsilyl)ethoxy)methyl)-6H-imidazo[1,5-a]pyrrolo[2,3-e]pyrazine (prepared using X from Preparation #I.1 with pyrrolidine and Y) | | M.1.17 | 2.23 (a) | 387 | A |

TABLE M.1-continued

Examples prepared from an N-SEM protected heteroaromatic ring with TFA followed by NH₄OH using General Procedure M

| N-SEM protected heteroaromatic ring | Product | Example # | R, min (Table 2, Method) | m/z ESI+ (M + H)⁺ | Syk IC₅₀ |
|---|---|---|---|---|---|
| 1-(Pyrrolidin-1-yl)-7-p-tolyl-6-((2-(trimethylsilyl)ethoxy)methyl)-6H-imidazo[1,5-a]pyrrolo[2,3-e]pyrazine amine (prepared using A from 1-ethynyl-4-methylbenzene with 3,5-dibromopyrazin-2-amine, B, C, D with (E)-styrylboronic acid, E, F, G, I, X with pyrrolidine and Y) | | M.1.18 | 2.36 (a) | 318 | B |
| 7-(4-Methoxyphenyl)-1-methyl-6-((2-(trimethylsilyl)ethoxy)methyl)-6H-pyrrolo[2,3-e][1,2,4]triazolo[4,3-a]pyrazine (prepared using O from Preparation #AM.1 with tert-butyl hydrazinecarboxylate, P.2 and R.1 with acetaldehyde) | | M.1.19 | 1.70 (a) | 280 | C |
| 2-(5-Methoxy-1-methyl-1H-indol-3-yl)-3-((2-(trimethylsilyl)ethoxy)methyl)-3H-imidazo[1,2-a]pyrrolo[2,3-e]pyrazine (Preparation #24) | | M.1.20 | 1.93 (a) | 318 | B |
| 7-(5-Methoxy-1-methyl-1H-indol-3-yl)-N-(2-methoxyethyl)-N-methyl-6-((2-(trimethylsilyl)ethoxy)methyl)-6H-imidazo[1,5-a]pyrrolo[2,3-e]pyrazin-1-amine (prepared using X from Preparation #I.1 with 2-methoxy-N-methylethanamine [TCI] and Y) | | M.1.21 | 2.07 (a) | 405 | A |
| 7-(4-Methoxyphenyl)-1,3-dimethyl-6-((2-(trimethylsilyl)ethoxy)methyl)-6H-imidazo[1,5-a]pyrrolo[2,3-e]pyrazine (prepared using F from Preparation #13, G, I, J.2 with Ac₂O and L.1 with mercury(II) trifluoroacetate) | | M.1.22 | 1.86 (a) | 293 | B |
| 7-(4-Methoxyphenyl)-3-methyl-6-((2-(trimethylsilyl)ethoxy)methyl)-6H-imidazo[1,5-a]pyrrolo[2,3-e]pyrazine (prepared using F from Preparation #13, G, I, J.3 with ethyl formate and L.1 with mercury(II) trifluoroacetate) | | M.1.23 | 1.86 (a) | 279 | C |

TABLE M.1-continued

Examples prepared from an N-SEM protected heteroaromatic ring with TFA followed by NH₄OH using General Procedure M

| N-SEM protected heteroaromatic ring | Product | Example # | R$_t$ min (Table 2, Method) | m/z ESI+ (M + H)⁺ | Syk IC$_{50}$ |
|---|---|---|---|---|---|
| 1-Cyclohexyl-3-(4-(methylsulfonyl)phenyl)-6-((2-(trimethylsilyl)ethoxy)methyl)-3,6-dihydroimidazo[4,5-d]pyrrolo[2,3-b]pyridin-2(1H)-one (Preparation #12) | | M.1.24 | 2.12 (b) | 411 | D |
| 7-(4-Methoxyphenyl)-1-methyl-6-((2-(trimethylsilyl)ethoxy)methyl)-6H-imidazo[1,5-a]pyrrolo[2,3-e]pyrazine (prepared using D from Preparation #AM.1 with E-phenylethenylboronic acid, E, F, G, I, J.2 with Ac₂O, L.1 with mercury(II) trifluoroacetate) | | M.1.25 | 1.83 (a) | 279 | A |

TABLE M.2

Examples prepared from an N-SEM protected heteroaromatic ring with TBAF using General Procedure M

| N-SEM protected heteroaromatic ring | Product | Example # | R$_t$ min (Table 2, Method) | m/z ESI+ (M + H)⁺ | Syk IC$_{50}$ |
|---|---|---|---|---|---|
| 1-Methyl-7-(1-methyl-1H-pyrazole-4-yl)-6-((2-(trimethylsilyl)ethoxy)methyl)-6H-imidazo[1,5-a]pyrrolo[2,3-e]pyrazine (prepared using B from Preparation #A.1, C, D with(E)-styrylboronic acid, E, F, G, I, J.2 with Ac₂O and L.1 with mercury(II) acetate) | | M.2.1 | 1.29 (a) | 253 | B |
| 7-(1-Methyl-1H-pyrazol-4-yl)-1-phenyl-6-((2-(trimethylsilyl)ethoxy)methyl)-6H-imidazo[1,5-a]pyrrolo[2,3-e]pyrazine (prepared using B from Preparation #A.1, C, D with (E)-styrylboronic acid, E, F, G, I, J.2 with benzoyl chloride and L.1 with mercury(II) acetate) | | M.2.2 | 1.73 (a) | 315 | ND |
| 3-(4-Methoxyphenyl)-1-methyl-6-(2-((trimethylsilyl)methoxy)ethyl)-1,6-dihydropyrazolo[3,4-d]pyrrolo[2,3-b]pyridine-8-carbonitrile (prepared using C from Example #AK.1 and AE) | | M.2.3 | 1.99 (a) | 302 (M − H)⁻ | A |

TABLE M.2-continued

Examples prepared from an N-SEM protected heteroaromatic ring with TBAF using General Procedure M

| N-SEM protected heteroaromatic ring | Product | Example # | $R_f$ min (Table 2, Method) | m/z ESI+ (M + H)+ | Syk IC$_{50}$ |
|---|---|---|---|---|---|
| 3-(4-(2-Hydroxypropan-2-yl)phenyl)-1-methyl-6-((2-(trimethylsilyl)ethoxy)methyl)-6H-imidazo[1,5-a]pyrrolo[2,3-e]pyrazine-8-carbonitrile (prepared using C from Example #AY.1 and AE) | | M.2.4 | 1.71 (a) | 332 | A |

General Procedure N: Removal of a Tosyl Protecting Group from an N-Tosyl Protected Heteroaromatic Ring To a solution of an N-tosyl heteroaromatic ring (1 equiv) in an organic solvent (such as 1,4-dioxane or MeOH, preferably MeOH) is added an aqueous solution of a base (such as 1 to 6 N; NaOH or KOH; 4 to 20 equiv, preferably 2 to 15 equiv). The mixture is then either heated at about 60 to 110° C. (preferably about 70 to 95° C.) in an oil bath for about 1 to 48 h (preferably about 2 to 16 h) or heated in a microwave at about 120° C. for about 20 min (250 psi maximum pressure, 2 min ramp time, 300 max watts). The mixture is optionally concentrated in vacuo to give the targeted compound. The mixture is optionally filtered directly or through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure N

Example #N.1

1-(3-(1-Methyl-1,6-dihydropyrazolo[3,4-d]pyrrolo[2,3-b]pyridin-7-yl)phenyl)-N-(2-(4-methylpiperazin-1-yl)ethyl)acetamide

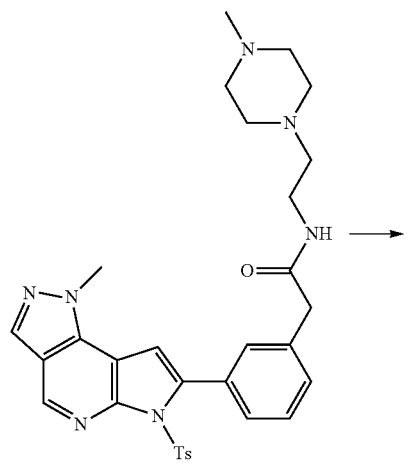 → 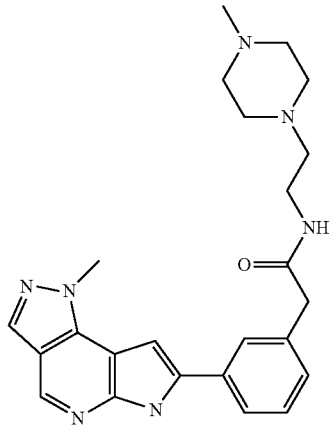

A microwave reaction tube was charged with 2-(3-(1-methyl-6-tosyl-1,6-dihydropyrazolo[3,4-d]pyrrolo[2,3-b]pyridin-7-yl)phenyl)-N-(2-(4-methylpiperazin-1-yl)ethyl)acetamide (0.05 g, 0.085 mmol, prepared using D from Preparation #1 with 2-(3-(4,4,5,5-tetramethyl-1,3,2-dioxaborolan-2-yl)phenyl)acetic acid [Frontier] and J.1 with 2-(4-methylpiperazin-1-yl)ethanamine hydrochloride [Anichem]) and MeOH (3 mL). To the mixture was added an aqueous solution of NaOH (5 N, 0.17 mL, 0.854 mmol). The reaction tube was sealed and heated in a microwave at about 120° C. for about 20 min (250 psi maximum pressure, 2 min ramp time, 300 max watts). The mixture was filtered, concentrated under reduced pressure and purified by silica gel chromatography with an elution gradient of 0 to 10% MeOH/DCM to give the title compound (0.007 g, 19%): LC/MS (Table 2, Method a) R$_f$=1.58 min.; MS m/z 432 (M+H)+. Syk IC$_{50}$=C.

TABLE N.1

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk IC$_{50}$ |
|---|---|---|---|---|---|
| 2-(4-(1-Methyl-6-tosyl-1,6-dihydropyrazolo[3,4-d]pyrrolo[2,3-b]pyridin-7-yl)phenyl)propan-2-ol (prepared using D from Preparation #1 with Preparation #H.1) | | N.1.1 | 1.77 (a) | 307 | A |
| 4-(3-(1-Methyl-6-tosyl-1,6-dihydropyrazolo[3,4-d]pyrrolo[2,3-b]pyridin-7-yl)benzyl)morpholine (prepared using D from Preparation #1 with 4-(3-(4,4,5,5-tetramethyl-1,3,2-dioxaborolan-2-yl)benzyl)morpholine) | | N.1.2 | 1.50 (a) | 348 | ND |
| N-(3-(1-Methyl-6-tosyl-1,6-dihydropyrazolo[3,4-d]pyrrolo[2,3-b]pyridin-7-yl)benzyl)acetamide (prepared using D from Preparation #1 with 3-(acetamidomethyl)phenylboronic acid [Combi-Blocks]) | | N.1.3 | 1.74 (a) | 320 | A |
| N-Methyl-3-(1-methyl-6-tosyl-1,6-dihydropyrazolo[3,4-d]pyrrolo[2,3-b]pyridin-7-yl)benzamide (prepared using D from Preparation #1 with 3-boronobenzoic acid and J.1 with methylamine) | | N.1.4 | 1.28 (c) | 306 | A |
| 7-(3-Fluorophenyl)-1-methyl-6-tosyl-1,6-dihydropyrazolo[3,4-d]pyrrolo[2,3-b]pyridine (prepared using D from Preparation #1 with 3-fluorophenylboronic acid) | | N.1.5 | 1.41 (c) | 267 | ND |
| 3-(1-Methyl-6-tosyl-1,6-dihydropyrazolo[3,4-d]pyrrolo[2,3-b]pyridin-7-yl)-N-(2-morpholinoethyl)benzamide (Preparation #J.1.1) | | N.1.6 | 1.04 (c) | 405 | A |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk $IC_{50}$ |
|---|---|---|---|---|---|
| N-(3-Methoxypropyl)-3-(1-methyl-6-tosyl-1,6-dihydropyrazolo[3,4-d]pyrrolo[2,3-b]pyridin-7-yl)benzamide (prepared using D from Preparation #1 with 3-boronobenzoic acid and J.1 with 3-methoxypropan-1-amine) | | N.1.7 | 1.16 (c) | 364 | B |
| (3-(1-Methyl-6-tosyl-1,6-dihydropyrazolo[3,4-d]pyrrolo[2,3-b]pyridin-7-yl)phenyl)(pyrrolidin-1-yl)methanone (prepared using D from Preparation #1 with 3-boronobenzoic acid and J.1 with pyrrolidine) | | N.1.8 | 1.19 (c) | 346 | B |
| N-Methyl-2-(3-(1-methyl-6-tosyl-1,6-dihydropyrazolo[3,4-d]pyrrolo[2,3-b]pyridin-7-yl)phenyl)acetamide (prepared using D from Preparation #1 with 2-(3-(4,4,5,5-tetramethyl-1,3,2-dioxaborolan-2-yl)phenyl)acetic acid [Frontier] and J.1 with methanamine hydrochloride) | | N.1.9 | 1.10 (c) | 320 | B |
| N-(3-Hydroxy-2,2-dimethylpropyl)-2-(3-(1-methyl-6-tosyl-1,6-dihydropyrazolo[3,4-d]pyrrolo[2,3-b]pyridin-7-yl)phenyl)acetamide (prepared using D from Preparation #1 with 2-(3-(4,4,5,5-tetramethyl-1,3,2-dioxaborolan-2-yl)phenyl)acetic acid [Frontier] and J.1 with 3-amino-2,2-dimethylpropan-1-ol [Alpha Aesar]) | | N.1.10 | 1.80 (a) | 392 | ND |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ $(M+H)^+$ | Syk $IC_{50}$ |
|---|---|---|---|---|---|
| N-(3-Methoxypropyl)-2-(3-(1-methyl-6-tosyl-1,6-dihydropyrazolo[3,4-d]pyrrolo[2,3-b]pyridin-7-yl)phenyl)acetamide (prepared using D from Preparation #1 with 2-(3-(4,4,5,5-tetramethyl-1,3,2-dioxaborolan-2-yl)phenyl)acetic acid [Frontier] and J.1 with 3-methoxypropan-1-amine) | 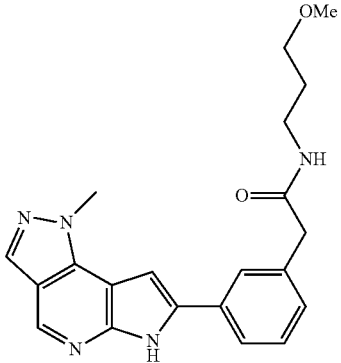 [SMILES: COCCCNC(=O)Cc1cccc(-c2cc3c(ncc4cnn(C)c43)[nH]2)c1] | N.1.11 | 1.14 (c) | 378 | B |
| 2-(3-(1-Methyl-6-tosyl-1,6-dihydropyrazolo[3,4-d]pyrrolo[2,3-b]pyridin-7-yl)phenyl)-N-(2-morpholinoethyl)acetamide (prepared using D from Preparation #1 with 2-(3-(4,4,5,5-tetramethyl-1,3,2-dioxaborolan-2-yl)phenyl)acetic acid [Frontier] and J.1 with 2-morpholinoethanamine) | 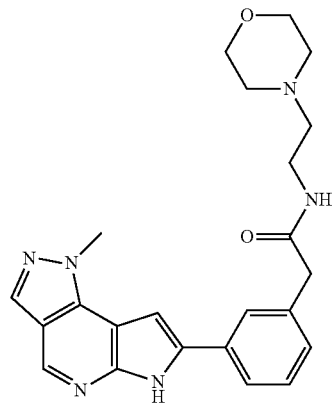 [SMILES: Cn1ncc2cnc3[nH]c(-c4cccc(CC(=O)NCCN5CCOCC5)c4)cc3c21] | N.1.12 | 1.47 (a) | 419 | B |
| 3-(1-Methyl-6-tosyl-1,6-dihydropyrazolo[3,4-d]pyrrolo[2,3-b]pyridin-7-yl)benzenesulfonamide (prepared using D from Preparation #1 with 3-sulfamoylphenylboronic acid [Combi-Blocks]) | 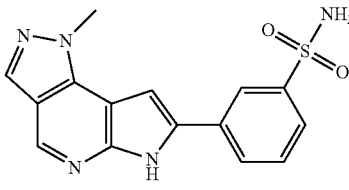 | N.1.13 | 1.51 (a) | 328 | A |
| 7-(4-Methoxyphenyl)-1-methyl-6-tosyl-1,6-dihydropyrazolo[3,4-d]pyrrolo[2,3-b]pyridine (prepared using D from Preparation #1 with 4-methoxyphenylboronic acid) | 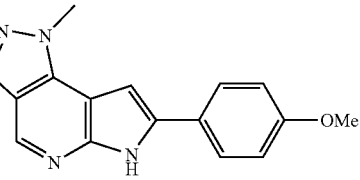 | N.1.14 | 2.83 (f) | 279 | A |
| 8-Ethyl-1-methyl-7-(1-methyl-1H-indol-5-yl)-6-tosyl-1,6-dihydropyrazolo[3,4-d]pyrrolo[2,3-b]pyridine (prepared using D from Preparation #2 with 1-methyl-1H-indol-5-ylboronic acid [Frontier]) | 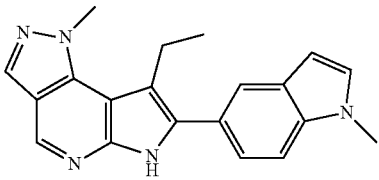 [SMILES: CCc1c(-c2ccc3c(ccn3C)c2)[nH]c2ncc3cnn(C)c3c12] | N.1.15 | 2.29 (a) | 330 | C |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)$^+$ | Syk IC$_{50}$ |
|---|---|---|---|---|---|
| 8-Ethyl-1-methyl-7-(1-methyl-1H-indol-4-yl)-6-tosyl-1,6-dihydropyrazolo[3,4-d]pyrrolo[2,3-b]pyridine (prepared using D from Preparation #2 with 1-methyl-1H-indol-4-ylboronic acid [Maybridge]) | | N.1.16 | 2.30 (a) | 330 | D |
| 7-(5-Fluoro-1-methyl-1H-indol-3-yl)-1-methyl-6-tosyl-1,6-dihydropyrazolo[3,4-d]pyrrolo[2,3-b]pyridine (prepared using U from 5-fluoro-1H-indole [Matrix] with MeI, H with 4,4,5,5-tetramethyl-1,3,2-dioxaborolane) and D with Preparation #1) | | N.1.17 | 2.12 (a) | 320 | A |
| 7-(Benzofuran-3-yl)-1-methyl-6-tosyl-1,6-dihydropyrazolo[3,4-d]pyrrolo[2,3-b]pyridine (prepared using D from Preparation #1 with 2-(benzofuran-3-yl)-4,4,5,5-tetramethyl-1,3,2-dioxaborolane [Maybridge]) | | N.1.18 | 2.15 (a) | 289 | ND |
| 7-(5-Methoxy-1H-indol-3-yl)-1-methyl-6-tosyl-1,6-dihydropyrazolo[3,4-d]pyrrolo[2,3-b]pyridine (Preparation #P.1.1) | | N.1.19 | 1.92 (a) | 318 | A |
| 2-(4-(8-Ethyl-1-methyl-6-tosyl-1,6-dihyropyrazolo[3,4-d]pyrrolo[2,3-b]pyridin-7-yl)phenyl)propan-2-ol (prepared using D from Preparation #2 with Preparation #H.1) | | N.1.20 | 2.02 (a) | 335 | A |
| 8-Ethyl-1-methyl-7-(3-(methylsulfonyl)phenyl)-6-tosyl-1,6-dihyropyrazolo[3,4-d]pyrrolo[2,3-b]pyridine (prepared using D from Preparation #2 with 3-(methylsulfonyl)phenylboronic acid [Combiblocks]) | | N.1.21 | 1.96 (a) | 355 | B |
| 7-(5-Methoxy-1-methyl-1H-indol-3-yl)-1-methyl-6-tosyl-1,2,3,6-tetrahydrodipyrrolo[2,3-b:2',3'-d]pyridine (prepared using D from Preparation #3 with Preparation #11) | | N.1.22 | 1.91 (a) | 333 | C |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ $(M + H)^+$ | Syk $IC_{50}$ |
|---|---|---|---|---|---|
| 2-(4-(1-Methyl-6-tosyl-1,2,3,6-tetrahydrodipyrrolo[2,3-b:2',3'-d]pyridin-7-yl)phenyl)propan-2-ol (prepared using D from Preparation #3 with Preparation #H.1) | | N.1.23 | 1.75 (a) | 308 | C |
| 1-Methyl-7-(1-methyl-1H-indol-3-yl)-1,6-dihydropyrazolo[3,4-d]pyrrolo[2,3-b]pyridine (prepared using U from 3-iodo-1H-indole [3B Scientific] with MeI, H with 4,4,5,5-tetramethyl-1,3,2-dioxaborolane and D with Preparation #1) | | N.1.24 | 2.14 (a) | 302 | A |
| 2-(5-Methoxy-3-(1-methyl-6-tosyl-1,6-dihydropyrazolo[3,4-d]pyrrolo[2,3-b]pyridin-7-yl)-1H-indol-1-yl)-N,N-dimethylacetamide (Preparation #U.1) | | N.1.25 | 1.94 (a) | 403 | A |
| 3-(5-Methoxy-3-(1-methyl-6-tosyl-1,6-dihydropyrazolo[3,4-d]pyrrolo[2,3-b]pyridin-7-yl)-1H-indol-1-yl)propane-1,2-diol (Preparation #6) | | N.1.26 | 1.75 (a) | 392 | A |
| 7-(6,7-Dihydro-5H-pyrrolo[1,2-a]imidazol-3-yl)-1-methyl-6-tosyl-1,6-dihydropyrazolo[3,4-d]pyrrolo[2,3-b]pyridine (Preparation #7) | | N.1.27 | 1.41 (a) | 279 | C |
| 2-(5-Methoxy-3-(1-methyl-6-tosyl-1,6-dihydropyrazolo[3,4-d]pyrrolo[2,3-b]pyridin-7-yl)-1H-indol-1-yl)-N-(2-methoxyethyl)acetamide (prepared using J.1 from Preparation #V.2.1 with 2-methoxyethaneamine) | | N.1.28 | 1.92 (a) | 433 | A |

TABLE N.1-continued

Examples prepared from an N-tosyl protected heteroaryl ring with NaOH using General Procedure N

| N-Tosyl protected heteroaryl ring | Product | Example # | R$_t$ min (Table 2, Method) | m/z ESI+ (M + H)$^+$ | Syk IC$_{50}$ |
|---|---|---|---|---|---|
| 1-(Dimethylamino)-3-(5-methoxy-3-(1-methyl-6-tosyl-1,6-dihyropyrazolo[3,4-d]pyrrolo[2,3-b]pyridin-7-yl)-1H-indol-1-yl)propan-2-ol (Preparation #8) | | N.1.29 | 1.70 (a) | 419 | B |
| 3-(8-Ethyl-1-methyl-6-tosyl-1,6-dihydropyrazolo[3,4-d]pyrrolo[2,3-b]pyridin-7-yl)-N-(2-morpholinoethyl)benzamide (prepared using J.1 from 3-(4,4,5,5-tetramethyl-1,3,2-dioxaborolan-2-yl)benzoic acid with 2-morpholinoethanamine and D with Preparation #2) | | N.1.30 | 1.65 (a) | 433 | C |
| 4-(4-(8-Ethyl-1-methyl-6-tosyl-1,6-dihydropyrazolo[3,4-d]pyrrolo[2,3-b]pyridin-7-yl)phenyl)morpholine (prepared using D from Preparation #2 with 4-morpholinophenylboronic acid [AsymChem]) | | N.1.31 | 2.09 (a) | 362 | B |
| N,N-Dimethyl-3-(1-methyl-6-tosyl-1,6-dihydropyrazolo[3,4-d]pyrrolo[2,3-b]pyridin-7-yl)benzenesulfonamide (prepared using D from Preparation #1 with 3-(N,N-dimethylsulfamoyl)phenylboronic acid [Combi-blocks]) | | N.1.32 | 2.02 (a) | 356 | A |
| N-Methyl-3-(1-methyl-6-tosyl-1,6-dihydropyrazolo[3,4-d]pyrrolo[2,3-b]pyridin-7-yl)benzenesulfonamide (prepared using D from Preparation #1 with 3-(N-methylsulfamoyl)phenylboronic acid [Combi-blocks]) | | N.1.33 | 1.81 (a) | 342 | A |
| N-(2-Hydroxyethyl)-3-(1-methyl-6-tosyl-1,6-dihydropyrazolo[3,4-d]pyrrolo[2,3-b]pyridin-7-yl)benzenesulfonamide (prepared using D from Preparation #1 with 3-(N-(2-hydroxyethyl)sulfamoyl)phenylboronic acid [Combi-blocks]) | | N.1.34 | 1.09 (c) | 372 | A |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ $(M + H)^+$ | Syk $IC_{50}$ |
|---|---|---|---|---|---|
| 8-Ethyl-7-(5-methoxy-1-methyl-1H-indol-3-yl)-1-methyl-6-tosyl-1,6-dihydropyrazolo[3,4-d]pyrrolo[2,3-b]pyridine (prepared using D from Preparation #2 with Preparation #11) | | N.1.35 | 2.28 (a) | 360 | C |
| 4-(8-Ethyl-1-methyl-6-tosyl-1,6-dihydropyrazolo[3,4-d]pyrrolo[2,3-b]pyridin-7-yl)-N-(2-morpholinoethyl)benzamide (prepared using J.1 from 4-(4,4,5,5-tetramethyl-1,3,2-dioxaborolan-2-yl)benzoic acid with 2-morpholinoethanamine, D with Preparation #2) | | N.1.36 | 1.58 (a) | 433 | B |
| 7-(1,3-Dimethyl-1H-pyrazol-4-yl)-8-ethyl-1-methyl-1,6-dihydropyrazolo[3,4-d]pyrrolo[2,3-b]pyridine (prepared using D from Preparation #2 with 1,3-dimethyl-4-(4,4,5,5-tetramethyl-1,3,2-dioxaborolan-2-yl)-1H-pyrazole [Maybridge]) | | N.1.37 | 1.08 (d) | 295 | C |
| 7-(1,5-Dimethyl-1H-pyrazol-4-yl)-8-ethyl-1-methyl-1,6-dihydropyrazolo[3,4-d]pyrrolo[2,3-b]pyridine (preparation using D from Preparation #2 with 1,5-dimethyl-4-(4,4,5,5-tetramethyl-1,3,2-dioxaborolan-2-yl)-1H-pyrazole [Maybridge]) | | N.1.38 | 1.08 (d) | 295 | C |
| 3-(8-Ethyl-1-methyl-1,6-dihydropyrazolo[3,4-d]pyrrolo[2,3-b]pyridin-7-yl)-N-propylbenzamide (prepared using J.1 from 3-(4,4,5,5-tetramethyl-1,3,2-dioxaborolan-2-yl)benzoic acid with propan-1-amine and D with Preparation #2) | | N.1.39 | 1.34 (d) | 362 | C |
| N,N-diethyl-3-(8-ethyl-1-methyl-6-tosyl-1,6-dihydropyrazolo[3,4-d]pyrrolo[2,3-b]pyridin-7-yl)benzenesulfonamide (prepared using D from Preparation #2 with 3-(N,N-diethylsulfamoyl)phenylboronic acid [Combi-blocks]) | | N.1.40 | 2.31 (a) | 412 | C |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ $(M + H)^+$ | Syk $IC_{50}$ |
|---|---|---|---|---|---|
| 3-(1-Methyl-6-tosyl-1,6-dihydropyrazolo[3,4-d]pyrrolo[2,3-b]pyridin-7-yl)-N-(2-morpholinoethyl)benzenesulfonamide (prepared using K from 3-bromobenzene-1-sulfonyl chloride with 2-morpholinoethanamine, H with bis(pinacolato)diboron and D with Preparation #1) | | N.1.41 | 1.57 (a) | 441 | B |
| N-(2-Methoxyethyl)-3-(1-methyl-6-tosyl-1,6-dihydropyrazolo[3,4-d]pyrrolo[2,3-b]pyridin-7-yl)benzenesulfonamide (prepared using K from 3-bromobenzene-1-sulfonyl chloride with 2-methoxyethanamine, H with bis(pinacolato)diboron and D with Preparation #1) | | N.1.42 | 1.83 (a) | 386 | B |
| 8-Ethyl-7-(4-methoxyphenyl)-1-methyl-6-tosyl-1,6-dihydropyrazolo[3,4-d]pyrrolo[2,3-b]pyridine (prepared using D from Preparation #2 with 4-methoxyphenylboronic acid) | | N.1.43 | 2.20 (a) | 307 | B |
| 8-Ethyl-1-methyl-7-(1-methyl-1H-pyrazol-4-yl)-6-tosyl-1,6-dihydropyrazolo[3,4-d]pyrrolo[2,3-b]pyridine (prepared using D from Preparation #2 with 1-methyl-1H-pyrazol-4-ylboronic acid) | | N.1.44 | 1.79 (a) | 281 | B |
| 4-(2-(4-(8-Ethyl-1-methyl-6-tosyl-1,6-dihydropyrazolo[3,4-d]pyrrolo[2,3-b]pyridin-7-yl)phenoxy)ethyl)morpholine (prepared using D from Preparation #2 with 4-(2-morpholinoethoxy)phenylboronic acid [Combiblocks]) | | N.1.45 | 1.61 (a) | 406 | B |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk IC$_{50}$ |
|---|---|---|---|---|---|
| 1-Methyl-7-(1-methyl-1H-indol-5-yl)-6-tosyl-1,6-dihydropyrazolo[3,4-d]pyrrolo[2,3-b]pyridine (prepared using D from Preparation #1 with 1-methyl-1H-indol-5-ylboronic acid) | | N.1.46 | 2.09 (a) | 302 | B |
| 7-(2,4-Dimethylphenyl)-1-methyl-6-tosyl-1,6-dihydropyrazolo[3,4-d]pyrrolo[2,3-b]pyridine (prepared using D from Preparation #1 with 2,4-dimethylphenylboronic acid [Alfa Aesar]) | | N.1.47 | 2.25 (a) | 277 | C |
| 1-Cyclohexyl-3-(5-methoxy-1-methyl-1H-indol-3-yl)-6-tosyl-6H-imidazo[1,5-a]pyrrolo[2,3-e]pyrazine (prepared using D from Example #2, Step E with Preparation #11) | | N.1.48 | 2.73 (a) | 400.2 | C |
| 2-(4-(1-Cyclohexyl-6-tosyl-6H-imidazo[1,5-a]pyrrolo[2,3-e]pyrazin-3-yl)phenyl)propan-2-ol (prepared using D from Example #2, Step E with Preparation #H.1) | | N.1.49 | 2.35 (a) | 375.2 | A |
| 2-(4-(1-Methyl-6-tosyl-6H-imidazo[1,5-a]pyrrolo[2,3-e]pyrazin-3-yl)phenyl)propan-2-ol (prepared using D from Preparation #AB.1 with Preparation #H.1) | | N.1.50 | 1.70 (a) | 307.5 | A |
| N-((1S,3R)-3-(3-(4-(2-Hydroxypropan-2-yl)phenyl)-6-tosyl-6H-imidazo[1,5-a]pyrrolo[2,3-e]pyrazin-1-yl)cyclopentyl)cyclopropanesulfonamide (prepared using K from Preparation #P.3.1 with cyclopropanesulfonyl chloride [Matrix]) | | N.1.51 | 1.95 (a) | 480.1 | A |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk $IC_{50}$ |
|---|---|---|---|---|---|
| N-((1S,3R)-3-(3-(4-(Prop-1-en-2-yl)phenyl)-6-tosyl-6H-imidazo[1,5-a]pyrrolo[2,3-e]pyrazin-1-yl)cyclopentyl)cyclopropanesulfonamide (prepared using K from Preparation #P.3.1 with cyclopropanesulfonyl chloride [Matrix]) | | N.1.52 | 1.50 (c) | 462.15 | B |
| 2-(4-(6-Tosyl-6H-imidazo[1,5-a]pyrrolo[2,3-e]pyrazin-3-yl)phenyl)propan-2-ol (prepared using AB from Preparation #L.2.1 and D with Preparation #H.1) | | N.1.53 | 1.62 (a) | 293.4 | A |
| 3-(4-Methoxyphenyl)-1-methyl-6-tosyl-6H-imidazo[1,5-a]pyrrolo[2,3-e]pyrazine (prepared using D from 4-methoxyphenylboronic acid with Example #AB.1) | | N.1.54 | 1.78 (a) | 279 | A |
| 3-(5-Methoxy-1-methyl-1H-indol-3-yl)-1-methyl-6-tosyl-6H-imidazo[1,5-a]pyrrolo[2,3-e]pyrazine (prepared using D from Preparation #I1 with Preparation #AB.1) | | N.1.55 | 1.90 (a) | 332 | B |
| 1-Methyl-3-(quinolin-5-yl)-6-tosyl-6H-imidazo[1,5-a]pyrrolo[2,3-e]pyrazine (prepared using D from quinolin-5-ylboronic acid [Frontier] with Preparation #AB.1) | | N.1.56 | 1.55 (a) | 300 | ND |
| 1-Methyl-3-(7-methyl-1H-indol-4-yl)-6-tosyl-6H-imidazo[1,5-a]pyrrolo[2,3-e]pyrazine (prepared using D from 7-methyl-4-(4,4,5,5-tetramethyl-1,3,2-dioxaborolan-2-yl)-1H-indole [Syntask Labs Inc] with Preparation #AB.1) | | N.1.57 | 1.75 (a) | 302 | C |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk $IC_{50}$ |
|---|---|---|---|---|---|
| 2-(4-(6-Tosyl-1-(trifluoromethyl)-6H-imidazo[1,5-a]pyrrolo[2,3-e]pyrazin-3-yl)phenyl)propan-2-ol (prepared using J.2 from Example #2, Step B with TFAA, L.2 with POCl$_3$, AB and D with Preparation #H.1) | | N.1.58 | 2.16 (a) | 361 | B |
| 2-(4-(1-(Dimethylamino)-6-tosyl-6H-imidazo[1,5-a]pyrrolo[2,3-e]pyrazin-3-yl)phenyl)propan-2-ol (prepared using X from Example #2, Step B with dimethylamine, Y, AB and D with Preparation #H.1) | | N.1.59 | 1.85 (a) | 336 | A |
| 2-(4-(8-Ethyl-1-methyl-6-tosyl-1,6-dihydropyrazolo[3,4-d]pyrrolo[2,3-b]pyridin-3-yl)phenyl)propan-2-ol (prepared using D from Preparation #AJ.1 with Preparation #H.1) | | N.1.60 | 1.94 (a) | 335 | C |
| (S)-3-(4-(Methylsulfonyl)phenyl)-1-(piperidin-3-yl)-6-tosyl-6H-imidazo[1,5-a]pyrrolo[2,3-e]pyrazine (prepared using AF from Example #2, Step B cyano intermediate with (4-(methylthio)phenyl)magnesium bromide, AG, AR, J.1 with (S)-1-(tert-butoxycarbonyl)piperidine-3-carboxylic acid [CNH tech] and L.2 with POCl$_3$) | | N.1.61 | 1.19 (a) | 396 | B |
| 3-Hydroxy-1-(3-(3-(4-(methylsulfonyl)phenyl)-6-tosyl-6H-imidazo[1,5-a]pyrrolo[2,3-e]pyrazin-1-yl)piperidin-1-yl)propan-1-one (prepared using AF from Example #2, Step B cyano intermediate with (4-(methylthio)phenyl)magnesium bromide, AG, AR, J.1 with (S)-1-(tert-butoxycarbonyl)piperidine-3-carboxylic acid [CNH tech], L.2 with POCl$_3$ and J.1 with 3-hydroxypropanoic acid [TCI]) | | N.1.62 | 1.46 (a) | 468 | C |

TABLE N.1-continued

Examples prepared from an N-tosyl protected heteroaryl ring with NaOH using General Procedure N

| N-Tosyl protected heteroaryl ring | Product | Example # | R, min (Table 2, Method) | m/z ESI+ (M + H)+ | Syk IC50 |
|---|---|---|---|---|---|
| 3-Hydroxy-1-(3-(3-(4-(methylsulfonyl)phenyl)-6-tosyl-6H-imidazo[1,5-a]pyrrolo[2,3-e]pyrazin-1-yl)piperidin-1-yl)propan-1-one (prepared using AF from Example #2, Step B cyano intermediate with (4-(methylthio)phenyl)magnesium bromide, AG, AR, J.1 with (S)-1-(tert-butoxycarbonyl)piperidine-3-carboxylic acid [CNH tech], L.2 with POCl₃ and J.1 with 3-hydroxypropanoic acid [TCI]) | | N.1.63 | 1.62 (a) | 482 | C |
| N,N-Dimethyl-1-(1-(3-(4-(methylsulfonyl)phenyl)-6-tosyl-6H-imidazo[1,5-a]pyrrolo[2,3-e]pyrazin-1-yl)pyrrolidin-3-yl)methanamine (prepared using AF from Example #2, Step B cyano intermediate with (4-(methylthio)phenyl)magnesium bromide, AG, AR, X with N,N-dimethyl-1-(pyrrolidin-3-yl)methanamine [Oakwood] and L.2 with POCl₃) | | N.1.64 | 1.43 (a) | 439 | C |
| N-((trans)-1-(Cyclopropylsulfonyl)-5-(3-(4-(2-hydroxypropan-2-yl)phenyl)-6-tosyl-6H-imidazo[1,5-a]pyrrolo[2,3-e]pyrazin-1-yl)pyrrolidin-3-yl)acetamide (prepared using K from 4-N-Boc-4(R)-amino-pyrrolidine-2(R)-carboxylic acid methyl ester hydrochloride [APAC] with cyclopropanesulfonyl chloride [Oakwood], V.1, J.1 with Example #2, Step B, P.3, J.2 with acetic anhydride, L.2 with TFAA, AB and D with Preparation #H.1) | | N.1.65 | 1.49 (a) | 523 | C |
| 2-(4-(1-(3-(Aminomethyl)pyrrolidin-1-yl)-6-tosyl-6H-imidazo[1,5-a]pyrrolo[2,3-e]pyrazin-3-yl)phenyl)propan-2-ol (prepared using X from Example #2, Step B with tert-butyl pyrrolidin-3-ylmethylcarbamate [TygerSci], Y, AB and D with Preparation #H.1) | | N.1.66 | 1.25 (a) | 391 | A |

TABLE N.1-continued

Examples prepared from an N-tosyl protected heteroaryl ring with NaOH using General Procedure N

| N-Tosyl protected heteroaryl ring | Product | Example # | R, min (Table 2, Method) | m/z ESI+ (M + H)+ | Syk IC$_{50}$ |
|---|---|---|---|---|---|
| 8-Ethyl-3-(3-fluoro-4-methoxyphenyl)-1-methyl-6-tosyl-1,6-dihydropyrazolo[3,4-d]pyrrolo[2,3-b]pyridine (prepared using D from Preparation #AJ.1 with 3-fluoro-4-methoxyphenylboronic acid) | | N.1.67 | 0.77 (m) | 325 | B |
| 8-Ethyl-1-methyl-3-(quinoxalin-6-yl)-6-tosyl-1,6-dihydropyrazolo[3,4-d]pyrrolo[2,3-b]pyridine (prepared using D from Preparation #AJ.1 with quinoxalin-6-yl]boronic acid) | | N.1.68 | 0.72 (m) | 329 | C |
| 8-Ethyl-3-(4-isopropoxyphenyl)-1-methyl-6-tosyl-1,6-dihydropyrazolo[3,4-d]pyrrolo[2,3-b]pyridine (prepared using D from Preparation #AJ.1 with 4-isopropoxyphenylboronic acid) | | N.1.69 | 0.85 (m) | 335 | B |
| N-Cyclopropyl-4-(8-ethyl-1-methyl-6-tosyl-1,6-dihydropyrazolo[3,4-d]pyrrolo[2,3-b]pyridin-3-yl)benzamide (prepared using D from Preparation #AJ.1 with 4-(cyclopropylcarbamoyl)phenyl boronic acid)) | | N.1.70 | 0.70 (m) | 360 | B |
| 4-(8-Ethyl-1-methyl-6-tosyl-1,6-dihydropyrazolo[3,4-d]pyrrolo[2,3-b]pyridin-3-yl)phenyl)methanol (prepared using D from Preparation #AJ.1 with 4-(hydroxymethyl)phenylboronic acid) | | N.1.71 | 0.66 (m) | 307 | B |
| 4-(8-Ethyl-1-methyl-6-tosyl-1,6-dihydropyrazolo[3,4-d]pyrrolo[2,3-b]pyridin-3-yl)benzenesulfonamide (prepared using D from Preparation #AJ.1 with 4-(4,4,5,5-tetramethyl-1,3,2-dioxaborolan-2-yl)benzenesulfonamide) | | N.1.72 | 0.60 (m) | 356 | B |
| 8-Ethyl-1-methyl-3-(thiophen-3-yl)-6-tosyl-1,6-dihydropyrazolo[3,4-d]pyrrolo[2,3-b]pyridine (prepared using D from Preparation #AJ.1 with thiophen-3-ylboronic acid) | | N.1.73 | 0.73 (m) | 283 | B |

TABLE N.1-continued

Examples prepared from an N-tosyl protected heteroaryl ring with NaOH using General Procedure N

| N-Tosyl protected heteroaryl ring | Product | Example # | R, min (Table 2, Method) | m/z ESI+ (M + H)+ | Syk IC50 |
|---|---|---|---|---|---|
| 8-Ethyl-3-(4-methoxyphenyl)-1-methyl-6-tosyl-1,6-dihydropyrazolo[3,4-d]pyrrolo[2,3-b]pyridine (prepared using D from Preparation #AJ.1 with 4-methoxyphenylboronic acid) | | N.1.74 | 0.76 (m) | 307 | C |
| 8-Ethyl-1-methyl-3-(pyridin-3-yl)-6-tosyl-1,6-dihydropyrazolo[3,4-d]pyrrolo[2,3-b]pyridine (prepared using D from Preparation #AJ.1 with pyridin-3-ylboronic acid) | | N.1.75 | 0.51 (m) | 278 | C |
| 8-Ethyl-1-methyl-3-(1-methyl-1H-pyrazol-4-yl)-6-tosyl-1,6-dihydropyrazolo[3,4-d]pyrrolo[2,3-b]pyridine (prepared using D from Preparation #AJ.1 with 1-methyl-1H-pyrazol-4-ylboronic acid) | | N.1.76 | 0.61 (m) | 281 | B |
| 8-Ethyl-1-methyl-6-tosyl-3-(3,4,5-trimethoxyphenyl)-1,6-dihydropyrazolo[3,4-d]pyrrolo[2,3-b]pyridine (prepared using D from Preparation #AJ.1 with 3,4,5-trimethoxyphenylboronic acid) | | N.1.77 | 0.75 (m) | 367 | C |
| 2-(4-(1-((trans)-2-(Aminomethyl)cyclohexyl)-6-tosyl-6H-imidazo[1,5-a]pyrrolo[2,3-e]pyrazin-3-yl)phenyl)propan-2-ol (prepared using I from Preparation #21, AP.1, V.1, J.1 with Example #2, Step B, L.1, AB, P.3 and D with Example #H.1) | | N.1.78 | 1.46 (a) | 404 | B |
| 8-Ethyl-7-(4-(2-methoxyethoxy)phenyl)-1-methyl-6-tosyl-1,6-dihydropyrazolo[3,4-d]pyrrolo[2,3-b]pyridine (prepared using D from Preparation #2 with 4-(2-methoxyethoxy)phenylboronic acid [ChemBridge]) | | N.1.79 | 2.14 (a) | 351 | B |
| 2-(4-(8-Ethyl-1-methyl-6-tosyl-1,6-dihydropyrazolo[3,4-d]pyrrolo[2,3-b]pyridin-7-yl)phenoxy)-N,N-dimethylethanamine (prepared using D from Preparation #2 with N,N-dimethyl-2-(4-(4,4,5,5-tetramethyl-1,3,2-dioxaborolan-2-yl)phenoxy)ethanamine [CombiBlocks]) | | N.1.80 | 1.52 (a) | 364 | C |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk IC$_{50}$ |
|---|---|---|---|---|---|
| 7-(1-Isopropyl-5-methoxy-1H-indol-3-yl)-1-methyl-6-tosyl-1,6-dihydropyrazolo[3,4-d]pyrrolo[2,3-b]pyridine (prepared using H from Preparation #AQ.1 with 4,4,5,5-tetramethyl-1,3,2-dioxaborolane and D with Preparation #1) | | N.1.81 | 2.35 (a) | 360 | B |
| 7-(1-Isopropyl-1H-indol-3-yl)-1-methyl-6-tosyl-1,6-dihydropyrazolo[3,4-d]pyrrolo[2,3-b]pyridine (prepared using AQ from 1H-indole and 2-iodopropane, H with 4,4,5,5-tetramethyl-1,3,2-dioxaborolane and D with Preparation #1) | | N.1.82 | 2.35 (a) | 330 | B |
| 7-(5-Methoxy-1-methyl-1H-indazol-3-yl)-1-methyl-6-tosyl-1,6-dihydropyrazolo[3,4-d]pyrrolo[2,3-b]pyridine (Preparation #15) | | N.1.83 | 1.99 (a) | 333 | B |
| 2-(4-(1-(Tetrahydro-2H-pyran-4-yl)-6-tosyl-6H-imidazo[1,5-a]pyrrolo[2,3-e]pyrazin-3-yl)phenyl)propan-2-ol (prepared using J.1 from Example #2, Step B with tetrahydro-2H-pyran-4-carboxylic acid [Matrix] L.1 with mercury(II) trifluoroacetate, AB and D with Preparation #H.1) | | N.1.84 | 1.80 (a) | 377 | B |
| 3-(4-Methoxyphenyl)-1-(4-methylpiperazin-1-yl)-6-tosyl-6H-imidazo[1,5-a]pyrrolo[2,3-e]pyrazine (prepared using X from Preparation #AG.1 with 4-methyl-piperazine-1-carbonyl chloride and Y) | | N.1.85 | 1.57 (a) | 363 | C |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk IC$_{50}$ |
|---|---|---|---|---|---|
| 3-(4-Methoxyphenyl)-1-(1-methylpiperidin-4-yl)-6-tosyl-6H-imidazo[1,5-a]pyrrolo[2,3-e]pyrazine (prepared using J.1 from Preparation #AG.1 with 1-methylpiperidine-4-carboxylic acid and L.1 with mercury(II) trifluoroacetate) | | N.1.86 | 1.49 (a) | 362 | C |
| 1-Cyclopropyl-3-(4-methoxyphenyl)-6-tosyl-6H-imidazo[1,5-a]pyrrolo[2,3-e]pyrazine (prepared using J.1 from Preparation #AG.1 with cyclopropanecarboxylic acid and L.1 with mercury(II) trifluoroacetate) | | N.1.87 | 207 (a) | 305 | A |
| 1-(2-Methoxyethyl)-3-(4-methoxyphenyl)-6-tosyl-6H-imidazo[1,5-a]pyrrolo[2,3-e]pyrazine (prepared using J.1 from Preparation #AG.1 with 3-methoxypropanoic acid and L.1 with mercury(II) trifluoroacetate) | | N.1.88 | 1.90 (a) | 323 | B |
| 1-(3-(4-Methoxyphenyl)-6-tosyl-6H-imidazo[1,5-a]pyrrolo[2,3-e]pyrazin-1-yl)-N,N-dimethylmethanamine (prepared using J.1 from Preparation #AG.1 with dimethylaminoacetic acid and L.1 with mercury(II) trifluoroacetate) | | N.1.89 | 1.58 (a) | 322 | C |
| 3-(4-(Methylsulfonyl)phenyl)-6-tosyl-6H-imidazo[1,5-a]pyrrolo[2,3-e]pyrazine (prepared using J.3 from Preparation #AR.1 with ethyl formate | | N.1.90 | 1.61 (a) | 313 | A |
| 1-Isopropyl-3-(4-methoxyphenyl)-6-tosyl-6H-imidazo[1,5-a]pyrrolo[2,3-e]pyrazine (prepared using J.2 from Preparation #AG.1 with isobutyryl chloride and L.1 with mercury(II) trifluoroacetate) | | N.1.91 | 2.27 (a) | 307 | B |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ $(M + H)^+$ | Syk $IC_{50}$ |
|---|---|---|---|---|---|
| 3-(4-Methoxyphenyl)-1-propyl-6-tosyl-6H-imidazo[1,5-a]pyrrolo[2,3-e]pyrazine (prepared using J.2 from Preparation #AG.1 with butyryl chloride and L.1 with mercury(II) trifluoroacetate) | | N.1.92 | 2.17 (a) | 307 | A |
| 2-((3-(4-Methoxyphenyl)-6-tosyl-6H-imidazo[1,5-a]pyrrolo[2,3-e]pyrazin-1-yl)methylamino)cyclohexanol (prepared using J.2 from Preparation #AG.1 with cinnamoyl chloride, L.1 with POCl$_3$, E and AH with 2-aminocyclohexanol [TCI]) | | N.1.93 | 1.66 (a) | 392 | C |
| 2-((3-(4-(Methylsulfonyl)phenyl)-6-tosyl-6H-imidazo[1,5-a]pyrrolo[2,3-e]pyrazin-1-yl)methyl)morpholine (prepared using J.1 from Preparation #AR.1 with 4-(tert-butoxycarbonyl)morpholine-2-carboxylic acid, L.1 with mercury(II) trifluoroacetate and P.3) | | N.1.94 | 1.35 (a) | 412 | B |
| (R)-3-Hydroxy-1-(3-(3-(4-(2-hydroxypropan-2-yl)phenyl)-6-tosyl-6H-imidazo[1,5-a]pyrrolo[2,3-e]pyrazin-1-yl)-4-methylpiperazin-1-yl)propan-1-one (prepared using J.1 from Example #2, Step B with lithium (R)-4-(tert-butoxycarbonyl)-1-methylpiperazine-2-carboxylate, L.1 with mercury(II) trifluoroacetate, AB, P.3, J.1 with 3-hydroxypropanoic acid [TCI] and D with Preparation #H.1) | | N.1.95 | 1.44 (a) | 462 | B |
| 2-(4-(1-((4-Methylpiperazin-1-yl)methyl)-6-tosyl-6H-imidazo[1,5-a]pyrrolo[2,3-e]pyrazin-3-yl)phenyl)propan-2-ol (prepared using J.2 from Example #2, Step B with cinnamoyl chloride, L.2 with POCl$_3$, E, AB, D with Preparation #H.1 and AH with 1-methylpiperazine) | | N.1.96 | 1.20 (a) | 405 | C |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk IC$_{50}$ |
|---|---|---|---|---|---|
| 2-(4-(1-((1,4-Diazepan-1-yl)methyl)-6-tosyl-6H-imidazo[1,5-a]pyrrolo[2,3-e]pyrazin-3-yl)phenyl)propan-2-ol (prepared using J.2 from Example #2, Step B with cinnamoyl chloride, L.2 with POCl$_3$, E, AB, D with Preparation #H.1, AH with tert-butyl 1,4-diazepane-1-carboxylate and P.3) | | N.1.97 | 1.25 (a) | 405 | B |
| 3-(4-Methoxyphenyl)-6-tosyl-6H-imidazo[1,5-a]pyrrolo[2,3-e]pyrazine (prepared using J.3 from Preparation #AG.1 with ethyl formate and L.2 with POCl$_3$) | | N.1.98 | 1.84 (a) | 265 | A |
| tert-Butyl 4-hydroxy-4-(4-(1-methyl-6-tosyl-6H-imidazo[1,5-a]pyrrolo[2,3-e]pyrazin-3-yl)phenyl)piperdine-1-carboxylate (prepared using AP.1 from 4-(4-bromophenyl)piperidin-4-ol, H with 4,4,4',4',5,5,5',5'-octamethyl-2,2'-bi(1,3,2-dioxaborolane and D with Preparation #AB.1) | | N.1.99 | 1.94 (a) | 448 | A |
| 1-Methyl-7-(1-methyl-1H-pyrrolo[3,2-c]pyridin-3-yl)-6-tosyl-1,6-dihydropyrazolo[3,4-d]pyrrolo[2,3-b]pyridine (prepared using AQ from 1H-pyrrolo[3,2-c]pyridine [Apin] with MeI, H with 2-isopropoxy-4,4,5,5-tetramethyl-1,3,2-dioxaborolane and D with Preparation #1) | | N.1.100 | 1.29 (a) | 303 | B |
| 2-(1-Methyl-3-(1-methyl-6-tosyl-1,6-dihyropyrazolo[3,4-d]pyrrolo[2,3-b]pyridin-7-yl)-1H-indol-5-yl)propan-2-ol (prepared using H from Preparation #18 with 4,4,5,5-tetramethyl-1,3,2-dioxaborolane), AA and D with Preparation #1) | | N.1.101 | 1.86 (a) | 360 | A |
| 2-(3-Fluoro-4-(1-methyl-6-tosyl-6H-imidazo[1,5-a]pyrrolo[2,3-e]pyrazin-3-yl)phenyl)propan-2-ol (prepared using D from Preparation #AB.1 with 2-fluoro-4-(methoxycarbonyl)phenylboronic acid [Combiblocks] and AA with MeMgBr) | | N.1.102 | 1.75 (a) | 325 | B |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ $(M + H)^+$ | Syk $IC_{50}$ |
|---|---|---|---|---|---|
| 2-(3-Chloro-4-(1-methyl-6-tosyl-6H-imidazo[1,5-a]pyrrolo[2,3-e]pyrazin-3-yl)phenyl)propan-2-ol (prepared using D from Preparation #AB.1 with 2-methyl 3-chloro-4-(4,4,5,5-tetramethyl-1,3,2-dioxaborolan-2-yl)benzoate [Combiblocks] and AA with MeMgBr) | | N.1.103 | 1.72 (a) | 341 | C |
| 2-(3-Chloro-4-(1-methyl-6-tosyl-6H-imidazo[1,5-a]pyrrolo[2,3-e]pyrazin-3-yl)phenyl)propan-2-ol (prepared using D from preparation #AB.1 with methyl 3-methyl-4-(4,4,5,5-tetramethyl-1,3,2-dioxaborolan-2-yl)benzoate [Frontier] and AA with MeMgBr) | | N.1.104 | 1.74 (a) | 321 | C |
| 2-(3-(4-Methoxyphenyl)-6-tosyl-6H-imidazo[1,5-a]pyrrolo[2,3-e]pyrazin-1-yl)-N,N-dimethylethanamine (prepared using J.1 from Preparation #AG.1 with 3-(dimethylamino)propanoic acid, and L1 with mercury(II) trifluoroacetate) | | N.1.105 | 1.47 (a) | 336 | C |
| 3-(4-(Methylsulfonyl)phenyl)-6-tosyl-6H-pyrrolo[2,3-e][1,2,3]triazolo[1,5-a]pyrazine (prepared using AR from Preparation #AT.1 and AS) | | N.1.106 | 1.68 (a) | 298 | C |
| 3-(4-Methoxyphenyl)-6-tosyl-6H-pyrrolo[2,3-e][1,2,3]triazolo[1,5-a]pyrazine (Preparation #AS.1) | | N.1.107 | 1.93 (a) | 266 | B |
| 2-(2-Chloro-4-(1-methyl-6-tosyl-6H-imidazo[1,5-a]pyrrolo[2,3-e]pyrazin-3-yl)phenyl)propan-2-ol (prepared using D from preparation #AB.1 with 3-chloro-4-(methoxycarbonyl)phenylboronic acid [Combiblocks] and AA with MeMgCl) | | N.1.108 | 1.89 (a) | 341 | A |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ (M + H)+ | Syk IC$_{50}$ |
|---|---|---|---|---|---|
| 2-(4-(1-(2-(Hydroxymethyl)phenyl)-6-tosyl-6H-imidazo[1,5-a]pyrrolo[2,3-e]pyrazin-3-yl)phenyl)propan-2-ol (prepared using D from Preparation #AI.1 with 2-(4,4,5,5-tetramethyl-1,3,2-dioxaborolan-2-yl)benzaldehyde and F) | | N.1.109 | 1.87 (a) | 399 | A |
| 2-(4-(8-(Hydroxymethyl)-6-tosyl-6H-imidazo[1,5-a]pyrrolo[2,3-e]pyrazin-3-yl)phenyl)propan-2-ol (prepared using P.3 from Preparation #19, J.3 with ethyl formate, L.2 with POCl$_3$, D with (E)-styrylboronic acid, AB, D with Preparation #H.1, E and F) | | N.1.110 | 1.46 (a) | 323 | B |
| 7-(1,5-Dimethyl-1H-indol-3-yl)-1-methyl-1,6-dihydropyrazolo[3,4-d]pyrrolo[2,3-b]pyridine (prepared using AQ from 5-methyl-1H-indole and MeI, H with-2-isopropoxy-4,4,5,5-tetramethyl-1,3,2-dioxaborolane) and D with Preparation #1) | | N.1.111 | 2.22 (a) | 316 | A |
| 4-(2-(1-Methyl-3-(1-methyl-1,6-dihydropyrazolo[3,4-d]pyrrolo[2,3-b]pyridin-7-yl)-1H-indol-5-yloxy)ethyl)morpholine (Preparation #17) | | N.1.112 | 1.64 (a) | 431 | A |
| (3-(4-Methoxyphenyl)-6-tosyl-6H-imidazo[1,5-a]pyrrolo[2,3-e]pyrazin-1-yl)methanol (Prepared using J.2 from Preparation #AG.1 with cinnamoyl chloride, L.2 with POCl$_3$, E and F) | | N.1.113 | 1.51 (a) | 295 | B |

TABLE N.1-continued

Examples prepared from an N-tosyl protected heteroaryl ring with NaOH using General Procedure N

| N-Tosyl protected heteroaryl ring | Product | Example # | $R_t$ min (Table 2, Method) | m/z ESI+ $(M + H)^+$ | Syk $IC_{50}$ |
|---|---|---|---|---|---|
| N-((3-(4-Methoxyphenyl)-6-tosyl-6H-imidazo[1,5-a]pyrrolo[2,3-e]pyrazin-1-yl)methyl)cyclopropanamine (Preparation #AH.1) | | N.1.114 | 1.56 (a) | 334 | C |
| 1-Methyl-7-(3-methyl-4-(4-methylpiperazin-1-yl)phenyl)-6-tosyl-1,6-dihydropyrazolo[3,4-d]pyrrolo[2,3-b]pyridine (prepared using D from Preparation #1 with Preparation #29) | | N.1.115 | 1.54 (a) | 361 | A |
| 7-(5-Methoxy-1-methyl-1H-pyrrolo[3,2-b]pyridin-3-yl)-1-methyl-6-tosyl-1,6-dihydropyrazolo[3,4-d]pyrrolo[2,3-b]pyridine (prepared using U from 3-bromo-5-methoxy-1H-pyrrolo[3,2-b]pyridine with MeI, H with 2-isopropoxy-4,4,5,5-tetramethyl-1,3,2-dioxaborolane and D with Preparation #1) | | N.1.116 | 2.10 (a) | 333 | B |
| 1-Methyl-7-(5-methyl-5H-pyrrolo[2,3-b]pyrazin-7-yl)-6-tosyl-1,6-dihydropyrazolo[3,4-d]pyrrolo[2,3-b]pyridine (prepared using U from 7-bromo-5H-pyrrolo[2,3-b]pyrazine with MeI, H with 2-isopropoxy-4,4,5,5-tetramethyl-1,3,2-dioxaborolane and D with Preparation #1) | | N.1.117 | 1.70 (a) | 304 | B |
| 1-(3-((3-(4-(2-hydroxypropan-2-yl)phenyl)-6-tosyl-6H-imidazo[1,5-a]pyrrolo[2,3-e]pyrazin-1-yl)methyl)piperidin-1-yl)ethanone (prepared using J.1 from Example #2, Step B with 2-(1-(tert-butoxycarbonyl)piperidin-3-yl)acetic acid [Matrix], P.3, J.2 with Ac₂O and pyridine, L.2 with TFAA/TFA, AB, AC with Preparation #H.1) | | N.1.118 | 1.72 (a) | 432 | ND |

TABLE N.1-continued

Examples prepared from an N-tosyl protected heteroaryl ring with NaOH using General Procedure N

| N-Tosyl protected heteroaryl ring | Product | Example # | R$_t$ min (Table 2, Method) | m/z ESI+ (M + H)$^+$ | Syk IC$_{50}$ |
|---|---|---|---|---|---|

TABLE N.2

Examples prepared from an N-tosyl protected heteroaryl ring with KOH using General Procedure N

| N-Tosyl protected heteroaryl ring | Product | Example # | R$_t$ min (Table 2, Method) | m/z ESI + (M + H)$^+$ | Syk IC$_{50}$ |
|---|---|---|---|---|---|
| 1-Methyl-7-(pyridin-4-yl)-6-tosyl-1,6-dihydropyrazolo[3,4-d]pyrrolo[2,3-b]pyridine (prepared using D from Preparation #1 with pyridin-4-ylboronic acid [Boron Molecular]) | | N.2.1 | 1.55 (a) | 250 | B |
| 1-Methyl-7-(pyridin-3-yl)-6-tosyl-1,6-dihydropyrazolo[3,4-d]pyrrolo[2,3-b]pyridine (prepared using D from Preparation #1 with pyridin-3-ylboronic acid) | | N.2.2 | 1.67 (a) | 250 | B |
| N,N-Dimethyl-2-(4-(1-methyl-6-tosyl-1,6-dihydropyrazolo[3,4-d]pyrrolo[2,3-b]pyridin-7-yl)phenoxy)ethanamine (prepared using D from Preparation #1 with 4-(2-(dimethylamino)ethoxy)phenyl boronic acid [Combi-Blocks]) | | N.2.3 | 1.68 (a) | 336 | B |
| 4-(2-(4-(1-Methyl-6-tosyl-1,6-dihydropyrazolo[3,4-d]pyrrolo[2,3-b]pyridin-7-yl)phenoxy)ethyl)morpholine (prepared using D from Preparation #1 with 4-(2-morpholinoethoxy)phenylboronic acid [CombiBlocks]) | | N.2.4 | 1.64 (a) | 378 | A |
| 4-(3-(4-(1-Methyl-6-tosyl-1,6-dihydropyrazolo[3,4-d]pyrrolo[2,3-b]pyridin-7-yl)phenoxy)propyl)morpholine (prepared using D from Preparation #1 with 4-(3-morpholinopropoxy)phenylboronic acid [CombiBlocks]) | | N.2.5 | 1.69 (a) | 392 | A |
| 1-Methyl-7-(quinolin-5-yl)-6-tosyl-1,6-dihydropyrazolo[3,4-d]pyrrolo[2,3-b]pyridine (prepared using D from Preparation #1 with quinolin-5-ylboronic acid [Frontier]) | | N.2.6 | 1.90 (a) | 300 | C |

TABLE N.2-continued

Examples prepared from an N-tosyl protected heteroaryl ring with KOH using General Procedure N

| N-Tosyl protected heteroaryl ring | Product | Example # | $R_t$ min (Table 2, Method) | m/z ESI+ $(M + H)^+$ | Syk $IC_{50}$ |
|---|---|---|---|---|---|
| 1-Methyl-7-(quinolin-6-yl)-6-tosyl-1,6-dihydropyrazolo[3,4-d]pyrrolo[2,3-b]pyridine (prepared using D from Preparation #1 with 6-(4,4,5,5-tetramethyl-1,3,2-dioxaborolan-2-yl)quinoline) | | N.2.7 | 1.83 (a) | 300 | B |
| 1-Methyl-7-(quinoxalin-6-yl)-6-tosyl-1,6-dihydropyrazolo[3,4-d]pyrrolo[2,3-b]pyridine (prepared using D from Preparation #1 with quinoxalin-6-ylboronic acid [Asymchem]) | | N.2.8 | 1.86 (a) | 301 | B |
| 2-(5-Methoxy-3-(1-methyl-6-tosyl-1,6-dihydropyrazolo[3,4-d]pyrrolo[2,3-b]pyridin-7-yl)-1H-indol-1-yl)-1-morpholinoethanone (prepared using U from Preparation #P.1.1 with 2-chloro-1-morpholin-4-yl-ethanone [Maybridge]) | | N.2.9 | 1.87 (a) | 445 | A |
| 2-(5-Methoxy-3-(1-methyl-6-tosyl-1,6-dihydropyrazolo[3,4-d]pyrrolo[2,3-b]pyridin-7-yl)-1H-indol-1-yl)-1-morpholinoethanone (prepared using U from Preparation #P.1.1 with 2-chloro-1-morpholin-4-yl-ethanone [Maybridge]) | | N.2.10 | 1.60 (a) | 376 | ND |
| 4-(2-(5-Methoxy-3-(1-methyl-6-tosyl-1,6-dihydropyrazolo[3,4-d]pyrrolo[2,3-b]pyridin-7-yl)-1H-indol-1-yl)ethyl)morpholine (prepared using U from Preparation #P.1.1 with 4-(2-chloroethyl)morpholine hydrochloride) | | N.2.11 | 1.88 (a) | 431 | A |
| 2-(5-Methoxy-3-(1-methyl-6-tosyl-1,6-dihydropyrazolo[3,4-d]pyrrolo[2,3-b]pyridin-7-yl)-1H-indol-1-yl)ethanol (Preparation #Z.1) | | N.2.12 | 2.09 (a) | 362 | A |

TABLE N.2-continued

Examples prepared from an N-tosyl protected heteroaryl ring with KOH using General Procedure N

| N-Tosyl protected heteroaryl ring | Product | Example # | $R_t$ min (Table 2, Method) | m/z ESI+ $(M+H)^+$ | Syk $IC_{50}$ |
|---|---|---|---|---|---|
| 2-(5-Methoxy-3-(1-methyl-6-tosyl-1,6-dihydropyrazolo[3,4-d]pyrrolo[2,3-b]pyridin-7-yl)-1H-indol-1-yl)-N,N-dimethylethanamine (prepared using U from Preparation #P.1.1 with 2-2-chloro-N,N-dimethylethanamine hydrochloride) | | N.2.13 | 1.62 (a) | 389 | B |
| 2-(5-Methoxy-3-(1-methyl-6-tosyl-1,6-dihydropyrazolo[3,4-d]pyrrolo[2,3-b]pyridin-7-yl)-1H-indol-1-yl)-1-(4-methylpiperazin-1-yl)ethanone (prepared using J.1 from Preparation #V.2.1 with 1-methylpiperazine) | | N.2.14 | 1.64 (a) | 458 | A |

General Procedure O: Reaction of a 2-bromo-5H-pyrrolo[2,3-b]pyrazine with a Hydrazine To a flask is added in no particular order a 2-bromo-5H-pyrrolo[2,3-b]pyrazine (1.0 equiv) an organic solvent (such as 1,4-dioxane), and a hydrazine (0.9 to 10.0 equiv, preferably 1.5 equiv). Optionally, a palladium catalyst (such as Pd (PPh$_3$)$_4$, Pd(PPh$_3$)$_2$Cl$_2$ or alternatively Pd$_2$ dba$_3$ and a ligand (such as tert-butyl X-phos (1:2 ratio), X-Phos (1:2 ratio) or xantphos (1:2 ratio)), preferably Pd$_2$ dba$_3$ plus a ligand (such as tert-butyl X-Phos (1:2 ratio); 0.01 to 1.0 equiv, preferably 0.10 equiv) and a base (such as KOt-Bu, NaOt-Bu, Cs$_2$CO$_3$, preferably NaOt-Bu or KOt-Bu; 1.0 to 2.0 equiv, preferably 1.5 equiv) may be added. The mixture is heated to about 40 to 150° C. (preferably about 80° C.) either thermally or in a microwave reactor for about 5 min to 24 h (preferably about 1 to 4 h). The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give the target compounds as a residue. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure O

Preparation #O.1: tert-Butyl 2-(6-(1-methyl-1H-pyrazol-4-yl)-5-((2-(trimethylsilyl)ethoxy)methyl)-5H-pyrrolo[2,3-b]pyrazin-2-yl)hydrazinecarboxylate

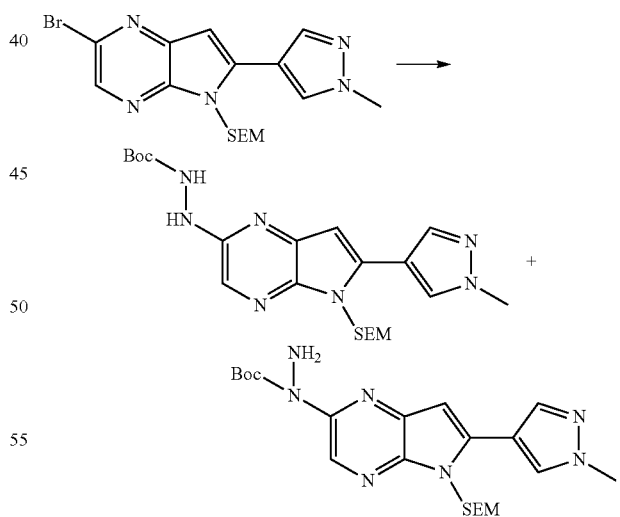

To a flask was added Pd$_2$ dba$_3$ (0.309 g, 0.338 mmol), tert-Butyl X-Phos (0.287 g, 0.676 mmol) and 1,4-dioxane (25 mL). The mixture was heated to about 80° C. for about 10 min and then 2-bromo-6-(1-methyl-1H-pyrazol-4-yl)-5-((2-(trimethylsilyl)ethoxy)methyl)-5H-pyrrolo[2,3-b]pyrazine (1.38 g, 3.38 mmol, prepared using B from Preparation #A.1 and C), tert-butyl hydrazinecarboxylate (0.670 g, 5.07 mmol) and NaOt-Bu (0.487 g, 5.07 mmol) were then added and mixture was heated at about 80° C. for about 1 h. The mixture was cooled, filtered through Celite® and the filter pad was rinsed with EtOAc. The filtrate was concentrated in vacuo then purified by flash chromatography (40 g silica column eluting with 0 to 100% EtOAc/DCM to provide tert-butyl 2-(6-(1-methyl-1H-pyrazol-4-yl)-5-((2-(trimethylsilyl)ethoxy)methyl)-5H-pyrrolo[2,3-b]pyrazin-2-yl)hydrazinecarboxylate (0.510 g, 33%): LC/MS (Table 2, Method c) $R_f$=1.59 min; MS m/z 460 (M+H)$^+$.

General Procedure P.1 Removal of a Boc Group from an N-Boc Protected Heteroaromatic Ring To a solution of an N-Boc protected heteroaromatic ring (1 equiv) in an organic solvent (such as DCM, 1,4-dioxane, or MeOH, preferably 1,4-dioxane) is added an acid (such as TFA or HCl, preferably TFA; 2 to 35 equiv, preferably 20 to 30 equiv). The reaction is stirred at about 0 to 100° C. (preferably about 20 to 60° C.) for about 1 to 24 h (preferably about 1 to 6 h). Optionally, additional acid (2 to 35 equiv, preferably 20 to 25 equiv) may be added and the mixture stirred at about 0 to 100° C. (preferably about 20 to 60° C.) for about 1 to 24 h (preferably about 1 to 6 h). If a solid is present in the mixture, the mixture may be optionally filtered and the solid washed with an organic solvent such as 1,4-dioxane or Et$_2$O. The resulting solid is then optionally dried under reduced pressure to give the targeted compound. Alternatively, the mixture may be optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure P.1

Preparation #P.1.1: 7-(5-Methoxy-1H-indol-3-yl)-1-methyl-6-tosyl-1,6-dihydropyrazolo[3,4-d]pyrrolo[2,3-b]pyridine

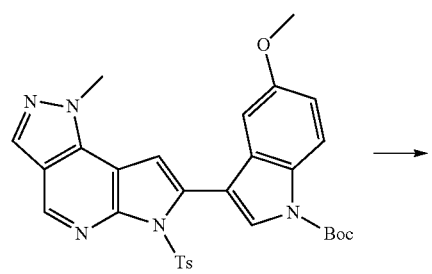

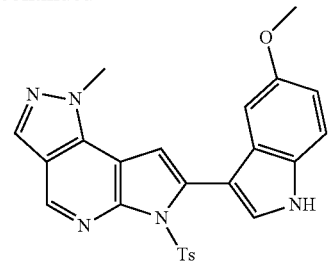

tert-Butyl 5-methoxy-3-(1-methyl-6-tosyl-1,6-dihydropyrazolo[3,4-d]pyrrolo[2,3-b]pyridin-7-yl)-1H-indole-1-carboxylate (1.75 g, 3.06 mmol; Preparation #D.1) in DCM (30 mL) was treated with TFA (5.9 mL, 77 mmol) and then stirred at rt. After about 3 h the mixture was concentrated and diluted with water (50 mL). The mixture was extracted with DCM (3×25 mL) then the combined organics were dried over anhydrous MgSO$_4$, filtered then concentrated under reduced pressure. The material was purified by flash chromatography on 80 g of silica gel using 8:2 DCM/EtOAc as an eluent to give 7-(5-methoxy-1H-indol-3-yl)-1-methyl-6-tosyl-1,6-dihydropyrazolo[3,4-d]pyrrolo[2,3-b]pyridine (1.11 g, 77%): LC/MS (Table 2, Method a) $R_t$=2.34 min; MS m/z 472 (M+H)$^+$.

General Procedure P.2: Removal of a Boc Group from an N-Boc Protected Hydrazine

To a flask is added a Boc protected hydrazine (1.0 equiv), an organic solvent (such as DCM, DCE, THF, 1,4-dioxane, or MeOH; preferably DCM or 1,4-dioxane) and an acid (such as HCl, TFA, H$_2$SO$_4$, HBr or TsOH, preferably HCl; 1.0 to 50 equiv, preferably 1.0 to 5.0 equiv). The mixture is stirred at about 0 to 80° C. (preferably about 50 to 70° C.) for about 5 min to 24 h (preferably about 15 min to 1 h). The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may optionally be washed with water, and/or aqueous solutions containing an acid (such as HCl, AcOH or NH$_4$Cl), and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure

Preparation #P.2.1: 2-Hydrazinyl-6-(1-methyl-1H-pyrazol-4-yl)-5-((2-(trimethylsilyl)ethoxy)methyl)-5H-pyrrolo[2,3-b]pyrazine

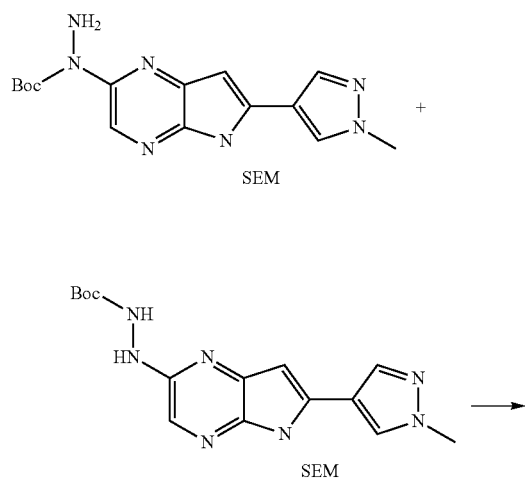

To a flask was added tert-butyl 2-(6-(1-methyl-1H-pyrazol-4-yl)-5-((2-(trimethylsilyl)ethoxy)methyl)-5H-pyrrolo[2,3-b]pyrazin-2-yl)hydrazinecarboxylate (0.152 g, 0.331 mmol, Preparation #O.1), HCl (4.0 M in 1,4-dioxane, 0.827 mL, 3.31 mmol) and 1,4-dioxane (5 mL). The mixture was heated to about 60° C. for about 1 h then stirred at rt overnight. The mixture was diluted with EtOAc (10 mL), washed with aqueous saturated NaHCO$_3$, dried over anhydrous MgSO$_4$ and concentrated in vacuo to give 2-hydrazinyl-6-(1-methyl-1H-pyrazol-4-yl)-5-((2-(trimethylsilyl)ethoxy)methyl)-5H-pyrrolo[2,3-b]pyrazine (0.100 g, 84%): LC/MS (Table 2, Method c) R$_t$=1.43 min; MS m/z 360 (M+H)$^+$.

General Procedure P.3. Removal of a Boc Group from an N-Boc Protected Amine

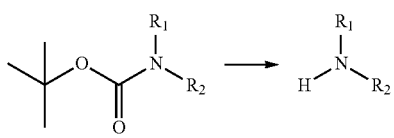

To flask is added an N-Boc protected amine (1.0 equiv), an organic solvent (such as DCM, DCE, THF, 1,4-dioxane, or MeOH; preferably DCM or 1,4-dioxane) and an acid (such as HCl, TFA, H$_2$SO$_4$, HBr, or TsOH; preferably TFA or HCl, 1.0 to 50 equiv; preferably 1.0 to 5.0 equiv). The mixture is stirred at about 0 to 80° C. (preferably 50 to 70° C.) for about 5 min to 24 h (preferably about 15 min to 1 h). The mixture is optionally filtered to collect the solid intermediate. Alternatively, the reaction mixture is filtered through a media (such as silica gel or Celite®) which is rinsed with an appropriate solvent (such as EtOAc, 1,4-dioxane, THF, ACN, DCM, Et$_2$O, MeOH, or EtOH) and then optionally concentrated in vacuo to give the intermediate. Either the intermediate or the solution may be optionally partitioned between water and an organic solvent (such as EtOAc, Et$_2$O or DCM). The organic layer is isolated and may be optionally be washed with water, and/or aqueous solutions containing an acid (such as HCl, AcOH or NH$_4$Cl), and/or aqueous solutions containing a base (such as NaHCO$_3$, Na$_2$CO$_3$, NaOH, KOH or NH$_4$OH) and/or aqueous solutions containing an inorganic salt (such as NaCl or Na$_2$SO$_3$). The organic solution may then be optionally dried with a drying agent (such as MgSO$_4$ or Na$_2$SO$_4$), filtered and concentrated in vacuo to give the target compound.

Illustration of General Procedure P.3

Preparation #P.3.1: 2-(4-(1-((1R,3S)-3-aminocyclopentyl)-6-tosyl-6H-imidazo[1,5-a]pyrrolo[2,3-e]pyrazin-3-yl)phenyl)propan-2-ol, hydrochloric acid

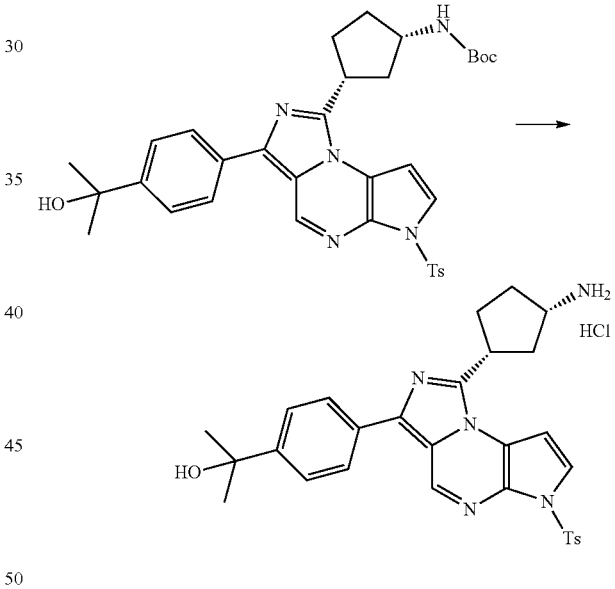

To a flask was added tert-butyl (1S,3R)-3-(3-(4-(2-hydroxypropan-2-yl)phenyl)-6-tosyl-6H-imidazo[1,5-a]pyrrolo[2,3-e]pyrazin-1-yl)cyclopentylcarbamate (0.48 g, 0.76 mmol; prepared using J.1 from Example #2, Step B with (1R,3S)-3-(tert-butoxycarbonylamino)cyclopentanecarboxylic acid [PepTech], L.1 with mercury(II) trifluoroacetate, AB and D with Preparation #H.1), 1,4-dioxane (7.6 mL) and HCl (4.0 M in 1,4-dioxane, 1.9 mL, 7.6 mmol). The reaction mixture was heated to about 60° C. for about 30 min. The mixture was cooled to rt and diluted with Et$_2$O (20 mL). The solid was collected by filtration, washed with Et$_2$O (10 mL) and dried under reduced pressure at about 60° C. overnight to give 2-(4-(1-((1R,3S)-3-aminocyclopentyl)-6-tosyl-6H-imidazo[1,5-a]pyrrolo[2,3-e]pyrazin-3-yl)phenyl)propan-2-ol, hydrochloric acid (0.39 g, 91% yield): LC/MS (Table 2, Method a) R$_t$=3.06 min; MS m/z 574 (M+H)$^+$.

TABLE P.3.1

Examples Prepared from an N-Boc Protected Amine using General Procedure P.3

| Boc Protected Amine | Product | Example # | $R_t$ min (Table 2, Method) | m/z ESI+ $(M+H)^+$ | Syk $IC_{50}$ |
|---|---|---|---|---|---|
| tert-Butyl 2-(4-(1-cyclohexyl-6H-imidazo[1,5-a]pyrrolo[2,3-e]pyrazin-3-yl)phenyl)propan-2-ylcarbamate (prepared using AP.1 from 2-(4-bromophenyl)propan-2-amine, hydrochloric acid [Akos], H with 4,4,4',4',5,5,5'-heptamethyl-2,2'-bi(1,3,2-dioxaborolane) and D with Example #2, Step E and N) | | P.3.1.1 | 1.79 (a) | 374 | B |
| tert-Butyl (1S,3R)-3-(3-(4-methoxyphenyl)-6H-imidazo[1,5-a]pyrrolo[2,3-e]pyrazin-1-yl)cyclopentylcarbamate (prepared using J.1 from Example #2, Step B with (1R,3S)-3-(tert-butoxycarbonylamino)cyclopentanecarboxylic acid, L.1 with mercury(II) trifluoroacetate, AB and AC with 4-methoxyphenylboronic acid) | | P.3.1.2 | 1.61 (a) | 348 | B |
| tert-Butyl 2-(4-(8-ethyl-1-methyl-1,6-dihydropyrazolo[3,4-d]pyrrolo[2,3-b]pyridin-7-yl)phenyl)propan-2-ylcarbamate (prepared using H from Preparation #AP.1.1 with bis(pinacolato)diboron, D with Preparation #2 and N) | | P.3.1.3 | 1.56 (a) | 334 | B |
| tert-Butyl 4-(6H-imidazo[1,5-a]pyrrolo[2,3-e]pyrazin-3-yl)-5,6-dihydropyridine-1(2H)-carboxylate (prepared using J.3 from Example #2 Step B, with ethyl formate, L.2 with POCl$_3$, AB and AC with 4-(4,4,5,5-tetramethyl-[1,3,2]dioxaborolan-2-yl)-3,6-dihydro-2H-pyridine-1-carboxylic acid tert-butyl ester [Carbocore] | | P.3.1.4 | 0.86 (a) | 240 | D |
| tert-Butyl 4-hydroxy-4-(4-(1-methyl-6H-imidazo[1,5-a]pyrrolo[2,3-e]pyrazin-3-yl)phenyl)piperidine-1-carboxylate carboxylate (prepared using AP.1 from 4-(4-bromophenyl)piperidin-4-ol, H with 4,4,4',4',5,5,5',5'-octamethyl-2,2'-bi(1,3,2-dioxaborolane and AC from Preparation #AB.1 | | P.3.1.5 | 1.25 (a) | 348 | A |

TABLE P.3.1-continued

Examples Prepared from an N-Boc Protected Amine using General Procedure P.3

| Boc Protected Amine | Product | Example # | $R_t$ min (Table 2, Method) | m/z ESI+ (M + H)$^+$ | Syk IC$_{50}$ |
|---|---|---|---|---|---|
| tert-Butyl 4-(4-(6H-imidazo[1,5-a]pyrrolo[2,3-e]pyrazin-3-yl)phenyl)-4-hydroxypiperidine-1-carboxylate (prepared using J.3 from Example #2 Step B, with ethyl formate, L.2 with POCl$_3$, AB and AC with tert-butyl 4-hydroxy-4-(4-(4,4,5,5-tetramethyl-1,3,2-dioxaborolan-2-yl)phenyl)piperidine-1-carboxylate (prepared using AP.1 from 4-(4-bromophenyl)piperidin-4-ol and H with 4,4,4',4',5,5,5',5'-octamethyl-2,2'-bi(1,3,2-dioxaborolane)) | | P.3.1.6 | 1.06 (a) | 334 | A |
| tert-Butyl 4-((3-(4-(2-hydroxypropan-2-yl)phenyl)-6H-imidazo[1,5-a]pyrrolo[2,3-e]pyrazin-1-yl)methyl)piperazine-1-carboxylate (prepared using J.2 from Example #2, Step B with cinnamoyl chloride, L.2 with POCl$_3$, E, AB, D with Preparation #H.1 and AH with tert-butyl piperazine-1-carboxylate and N) | | P.3.1.7 | 1.16 (a) | 391 | B |
| tert-Butyl 4-((3-(4-(2-hydroxypropan-2-yl)phenyl)-6H-imidazo[1,5-a]pyrrolo[2,3-e]pyrazin-1-yl)methyl)piperazine-1-carboxylate (prepared using J.2 from Example #2, Step B with cinnamoyl chloride, L.2 with POCl$_3$, E, AB, D with Preparation #H.1 and AH with tert-butyl piperidin-4-ylcarbamate and N) | | P.3.1.8 | 1.13 (a) | 405 | B |
| trans-tert-Butyl-3-(3-(4-(2-hydroxypropan-2-yl)phenyl)-6H-imidazo[1,5-a]pyrrolo[2,3-e]pyrazin-1-yl)cyclohexylcarbamate (Prepared using J.1 from Example #2, Step B with trans-3-(tert-butoxycarbonylamino)cyclohexanecarboxylic acid [AMRI], L.1 with mercury(II) acetate, AB and AC with Preparation #H.1) | | P.3.1.9 | 1.42 (a) | 390 | A |

TABLE P.3.1-continued

Examples Prepared from an N-Boc Protected Amine using General Procedure P.3

| Boc Protected Amine | Product | Example # | R, min (Table 2, Method) | m/z ESI+ (M + H)+ | Syk IC₅₀ |
|---|---|---|---|---|---|
| (R)-tert-Butyl 3-(3-(4-(2-hydroxypropan-2-yl)phenyl)-6H-imidazo[1,5-a]pyrrolo[2,3-e]pyrazin-1-yl)pyrrolidine-1-carboxylate (Prepared using J.1 from Example #2, Step B with(R)-1-(tert-butoxycarbonyl)pyrrolidine-3-carboxylic acid [Astatech], L.1 with mercury(II) trifluoroacetate, AB and AC with Preparation #H.1) | | P.3.1.10 | 1.19 (a) | 362 | B |
| tert-Butyl (1R,4R)-4-(3-(4-(methylsulfonyl)phenyl)-6H-imidazo[1,5-a]pyrrolo[2,3-e]pyrazin-1-yl)cyclohexylcarbamate (prepared using J.1 from Example #2, Step B, L.1 with mercury(II) trifluoroacetate, AB, AC with 4-(methylsulfonyl)phenyl boronic acid [Acros]) | | P.3.1.11 | 1.40 (b) | 410 | B |
| tert-Butyl 4-(4-methoxyphenyl)-6H-imidazo[1,5-a]pyrrolo[2,3-e]pyrazin-8-yl)-5,6-dihydropyridine-1(2H)-carboxylate (prepared using P.3 with Preparation # 19, J.3 with ethyl formate, L.2 with POCl₃, D with tert-butyl 4-(4,4,5,5-tetramethyl-1,3,2-dioxaborolan-2-yl)-5,6-dihydropyridine-1(2H)-carboxylate [Carbocore], AB with NIS and AC with 4-methoxyphenylboronic acid) | | P.3.1.12 | 1.46 (a) | 346 | C |
| tert-Butyl 4-((3-(4-(2-hydroxypropan-2-yl)phenyl)-6H-imidazo[1,5-a]pyrrolo[2,3-e]pyrazin-1-yl)methyl)-2-methylpiperazine-1-carboxylate (prepared using J.2 from Example #2, Step B with cinnamoyl chloride, L.2 with POCl₃, E, AB, D with Preparation #H.1, AH and N) | | P.3.1.13 | 1.47 (a) | 405 | B |

General Procedure Q: Removal of a TMS Group from a TMS Protected Alkyne

To a flask containing a TMS protected alkyne (1 equiv) in an organic solvent (such as 1,4-dioxane, MeOH or EtOH, preferably MeOH) is added a base (such as $K_2CO_3$, DBU or $NaCO_3$, preferably DBU or $K_2CO_3$; 1 to 10 equiv, preferably 1 to 2 equiv). The mixture is stirred at about 0 to 100° C. (preferably about 10 to 30° C.) for about 1 to 48 h (preferably about 1 to 8 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et₂O, MeOH, or EtOH) and then optionally concentrated in vacuo to give a residue. Either the residue or the solution may be optionally partitioned between water and an organic solvent (such as EtOAc, Et₂O or DCM). The organic layer is isolated and may be optionally washed in no particular order with water and/or aqueous solutions containing an acid (such as HCl, AcOH or NH₄Cl) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

Illustration of General Procedure Q

Preparation #Q.1: 4-Ethynyl-1-methyl-1H-pyrazole

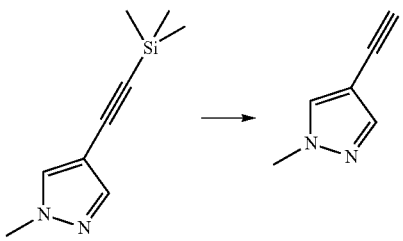

In a flask was added 1-methyl-4-((trimethylsilyl)ethynyl)-1H-pyrazole (4.20 g, 23.5 mmol, prepared using A from ethynyltrimethylsilane with 4-iodo-1-methyl-1H-pyrazole), $K_2CO_3$ (6.51 g, 47.1 mmol) and MeOH (50 mL). The mixture was stirred for about 1 h. The mixture was concentrated under reduced pressure to provide 4-ethynyl-1-methyl-1H-pyrazole (2.01 g, 80%): $^1$H NMR (DMSO) δ ppm 7.70-7.48 (m, 2H), 3.84 (s, 1H), 3.81 (s, 3H).

General Procedure R.1 Formation of a 6H-pyrrolo[2,3-e][1,2,4]triazolo[4,3-a]pyrazine from a 2-hydrazinyl-5H-pyrrolo[2,3-b]pyrazine Using an Aldehyde To a flask is added a 2-hydrazinyl-5H-pyrrolo[2,3-b]pyrazine (1.0 equiv), an organic solvent (such as DCM, DCE, THF, 1,4-dioxane or MeOH; preferably DCM) and an aldehyde (1.0 to 20 equiv, preferably 5 equiv). The mixture is stirred at about 0 to 80° C. (preferably about 10 to 30° C.) for about 5 min to 12 h (preferably about 1 to 2 h). The mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give an intermediate as a residue. Either the residue or the solution may be optionally partitioned between water and an organic solvent (such as EtOAc, $Et_2O$ or DCM). The organic layer is isolated and may optionally be washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give an intermediate. The intermediate is then added to a flask followed by the addition of an organic solvent (such as DCM, MeOH or DMF; preferably DMF) and an oxidizing agent (such as iodobenzene diacetate or copper(II) chloride, preferably copper(II) chloride; 1.0 to 5.0 equiv, preferably 1.0 to 2.0 equiv). The mixture is stirred at about 0 to 100° C. (preferably about 80 to 90° C.) for about 15 min to 24 h (preferably about 1 to 5 h). The mixture is optionally diluted with water and the solid is collected by vacuum filtration to give the target compound. Alternatively, the mixture may optionally be partitioned between water and an organic solvent (such as EtOAc, $Et_2O$ or DCM). The organic layer is isolated and may optionally be washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). Once washed the organic solution may be optionally dried with a drying agent (such as anhydrous $MgSO_4$ or $Na_2SO_4$), filtered and concentrated in vacuo to give the target compound.

Illustration of General Procedure R

Preparation #R.1.1: 1-Methyl-7-(1-methyl-1H-pyrazol-4-yl)-6-((2-(trimethylsilyl)ethoxy)methyl)-6H-pyrrolo[2,3-e][1,2,4]triazolo[4,3-a]pyrazine

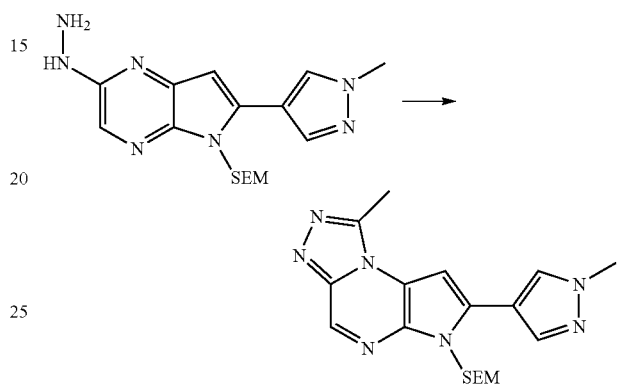

To a flask was added 2-hydrazinyl-6-(1-methyl-1H-pyrazol-4-yl)-5-((2-(trimethylsilyl)ethoxy)methyl)-5H-pyrrolo[2,3-b]pyrazine (0.100 g, 0.278 mmol, Preparation #P.2.1) and acetaldehyde (0.079 mL, 1.3 mmol) in DCM (3 mL). The mixture was stirred at rt for about 90 min. The mixture was concentrated in vacuo to give a residue. The residue was transferred to a flask and copper(II) chloride (0.075 g, 0.56 mmol) in DMF (3 mL) was added. The mixture was heated to about 90° C. for about 2 h. The mixture was cooled to rt, diluted with ice water (50 mL) and the solid was collected by filtration. The solid was taken up in DCM/MeOH and the insoluble solids were collected by filtration while the mother liquor was purified by flash chromatography (25 g silica gel column, DCM/EtOAc/MeOH 1:0:0 to 0:1:0 to 9:0:1) to give a solid. The solids were combined to give 1-methyl-7-(1-methyl-1H-pyrazol-4-yl)-6-((2-(trimethylsilyl)ethoxy)methyl)-6H-pyrrolo[2,3-e][1,2,4]triazolo[4,3-a]pyrazine (0.04 g, 37%): LC/MS (Table 2, Method c) $R_t$=1.48 min; MS m/z 384 (M+H)$^+$.

General Procedure R.2: Formation of a 6H-pyrrolo[2,3-e][1,2,4]triazolo[4,3-a]pyrazine from a 2-hydrazinyl-5H-pyrrolo[2,3-b]pyrazine using an Orthoester To a flask is added a 2-hydrazinyl-5H-pyrrolo[2,3-b]pyrazine (1.0 equiv), an orthoester (such as triethyl orthoformate or trimethyl orthoformate, preferably triethyl orthoformate, 1 to 50 equiv, preferably 10 equiv) and optionally an organic solvent (such as DCM, DCE, THF, 1,4-dioxane or MeOH; preferably DCM). The mixture is stirred at about 0 to 110° C. (preferably about 90 to 100° C.) for about 5 min to 48 h (preferably about 1 to 24 h). The mixture may be concentrated to dryness to provide the targeted compound. The mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give an intermediate or the targeted compound. The residue or the solution may be optionally partitioned between water and an organic solvent (such as EtOAc, Et₂O or DCM). The organic layer is isolated and may optionally be washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the target compound.

Illustration of General Procedure R.2

Preparation #R.2.1: 8-Methyl-7-(4-(2-methyl-1,3-dioxolan-2-yl)phenyl)-6-((2-(trimethylsilyl)ethoxy)methyl)-6H-pyrrolo[2,3-e][1,2,4]triazolo[4,3-a]pyrazine

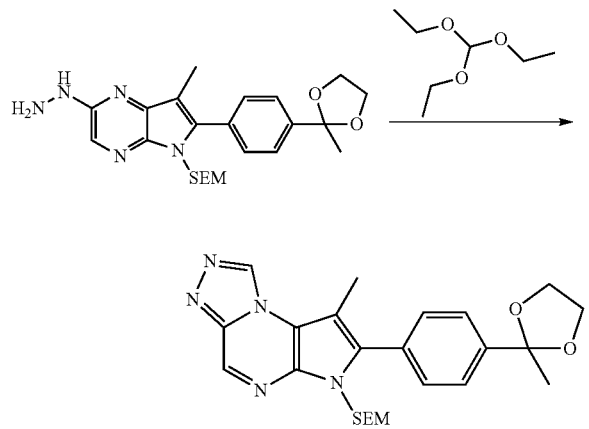

To a flask was added 2-hydrazinyl-7-methyl-6-(4-(2-methyl-1,3-dioxolan-2-yl)phenyl)-5-((2-(trimethylsilyl)ethoxy)methyl)-5H-pyrrolo[2,3-b]pyrazine (0.357 g, 0.784 mmol, prepared using O from Preparation #20 with hydrazine hydrate) in triethyl orthoformate (3.91 mL, 23.5 mmol). The mixture was heated to about 100° C. for about 20 h. The mixture was concentrated in vacuo to give a residue. The residue was loaded directly on a silica gel column and eluted with 0 to 8% MeOH/DCM to provide 8-methyl-7-(4-(2-methyl-1,3-dioxolan-2-yl)phenyl)-6-((2-(trimethylsilyl)ethoxy)methyl)-6H-pyrrolo[2,3-e][1,2,4]triazolo[4,3-a]pyrazine (0.220 g, 60%): LC/MS (Table 2, Method g) $R_t$=1.66 min; MS m/z 466 (M+H)⁺.

General Procedure S: Reaction of a Grignard Halide Reagent with a Ketone or Aldehyde to Give an Alcohol To a solution of an alkylmagnesium halide (2 to 12 equiv, preferably 5 to 10 equiv) in an organic solvent (such as THF or Et₂O, preferably THF) at about −40 to 25° C. (preferably about −20 to 0° C.) is added slowly a solution of the ketone or aldehyde (1 equiv) in THF. Alternatively, the alkylmagnesium halide (2 to 12 equiv, preferably 5 to 10 equiv) is added to a solution of the ketone or aldehyde (1 equiv) in an organic solvent (such as THF or Et₂O, preferably THF) at about −40 to 25° C. (preferably about −20 to 0° C.). The mixture is stirred at about −40 to 25° C. (preferably about −20 to 0° C.) for about 1 to 3 h (preferably about 2 h). The addition of the reagents may be optionally done portion-wise. To the mixture is added a saturated aqueous solution of NaHCO₃ or NH₄Cl. The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et₂O, MeOH, or EtOH) and then optionally concentrated in vacuo to give a residue. Either the residue or the solution may be optionally partitioned between water and an organic solvent (such as EtOAc, Et₂O or DCM). The organic layer is isolated and may be optionally washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the targeted compound.

Illustration of General Procedure S

Preparation #S.1: 2-(4-(8-Ethyl-1-methyl-6-((2-(trimethylsilyl)ethoxy)methyl)-6H-imidazo[1,5-a]pyrrolo[2,3-e]pyrazin-7-yl)phenyl)propan-2-ol

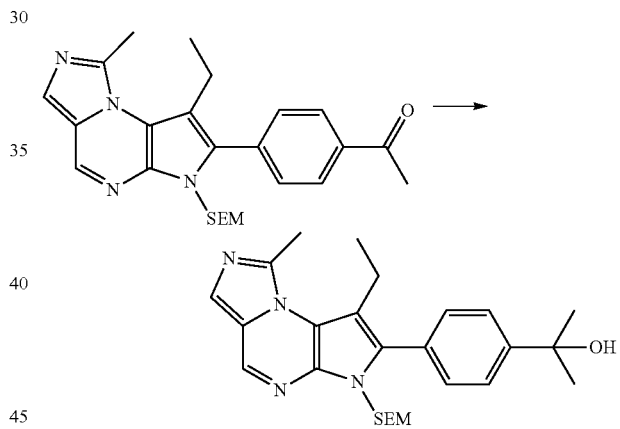

1-(4-(8-Ethyl-1-methyl-6-((2-(trimethylsilyl)ethoxy)methyl)-6H-imidazo[1,5-a]pyrrolo[2,3-e]pyrazin-7-yl)phenyl)ethanone (0.092 g, 0.205 mmol, Preparation #W.1) in THF (5 mL) was cooled to about −20° C. and MeMgCl (3.0 M in THF, 0.1 mL, 0.3 mmol) was added. After about 5 min MeMgCl (3.0 M in THF, 0.1 mL, 0.3 mmol) was added then the mixture was warmed to about 0° C. MeMgCl (3.0 M in THF, 0.2 mL, 0.6 mmol) was added and the mixture was allowed to warm to about 15° C. over about 2 h. MeMgCl (3.0 M in THF, 0.2 mL, 0.600 mmol) was added to THF (3 mL) and the solution was added to the mixture portion-wise. An aqueous solution of NH₄Cl (4 mL) was added slowly. The mixture was diluted with water (20 mL) and EtOAc (25 mL). The layers were separated and the aqueous layer was extracted with EtOAc (15 mL). The combined organics were dried over anhydrous MgSO₄, filtered and concentrated in vacuo to give 2-(4-(8-ethyl-1-methyl-6-((2-(trimethylsilyl)ethoxy)methyl)-6H-imidazo[1,5-a]pyrrolo[2,3-e]pyrazin-7-yl)phenyl)propan-2-ol (0.108 g, 113%): LC/MS (Table 2, Method a) $R_t$=2.96 min.; MS m/z 465 (M+H)⁺.

TABLE S.1

Examples prepared from methyl Grignard and a ketone or aldehyde using General Procedure S

| Ketone or Aldehyde | Product | Example # | R$_t$ min (Table 2, Method) | m/z ESI+ (M + H)$^+$ | Syk IC$_{50}$ |
|---|---|---|---|---|---|
| 1-(4-(8-Ethyl-6H-imidazo[1,5-a]pyrrolo[2,3-e]pyrazin-7-yl)phenyl)ethanone (prepared using L.1 from Preparation #10 with mercuric(II) trifluoroacetate, W and M with TFA) | | S.1.1 | 1.83 (a) | 320 | A |
| 1-(4-(1-(Dimethylamino)-8-ethyl-6H-imidazo[1,5-a]pyrrolo[2,3-e]pyrazin-7-yl)phenyl)ethanone (prepared using D from Preparation #5 with (E)-styrylboronic acid, E, F, G, I, X with dimethylamine, Y and M with TFA and NH$_4$OH) | | S.1.2 | 2.00 (a) | 364 | B |
| 1-(4-(1-Methyl-1,6-dihydropyrazolo[3,4-d]pyrrolo[2,3-b]pyridin-3-yl)phenyl)ethanone (Example #W.1.1) | | S.1.3 | 1.71 (a) | 307 | A |
| 1-(4-(8-Methyl-6H-pyrrolo[2,3-e][1,2,4]triazolo[4,3-a]pyrazin-7-yl)phenyl)ethanone (prepared using W from Preparation #R.2.1 and M) | | S.1.4 | 1.56 (a) | 308 | B |
| 1-(4-(1,8-Dimethyl-6H-pyrrolo[2,3-e][1,2,4]triazolo[4,3-a]pyrazin-7-yl)phenyl)ethanone (prepared using O from Preparation #20 with hydrazine hydrate, R.1 with acetaldehyde, W and M) | | S.1.5 | 1.60 (a) | 322 | C |
| 1-(4-(1-Ethyl-3H-dipyrrolo[1,2-a:2',3'-e]pyrazin-2-yl)phenyl)ethanone (Preparation #25) | | S.1.6 | 2.36 (a) | 320 | A |
| 1-(4-(8-Ethyl-4-methyl-6H-imidazo[1,5-a]pyrrolo[2,3-e]pyrazin-7-yl)phenyl)ethanone (prepared using D from Preparation #22 with (E)-styrylboronic acid, E, F, G, I, J.3 with ethyl formate, L.1 with mercury(II) trifluoroacetate, W and M) | | S.1.7 | 1.84 (a) | 335 | B |

TABLE S.1-continued

Examples prepared from methyl Grignard and a ketone or aldehyde using General Procedure S

| Ketone or Aldehyde | Product | Example # | $R_t$ min (Table 2, Method) | m/z ESI+ $(M+H)^+$ | Syk $IC_{50}$ |
|---|---|---|---|---|---|
| 1-(4-(8-Ethyl-6H-pyrrolo[2,3-e][1,2,3]triazolo[1,5-a]pyrazin-7-yl)phenyl)ethanone (prepared using D from Preparation #5 with (E)-styrylboronic acid, E, AS, W and M) | | S.1.8 | 1.93 (a) | 322 | A |
| 1-(4-(8-Ethyl-6H-pyrrolo[2,3-e][1,2,4]triazolo[4,3-a]pyrazin-7-yl)phenyl)ethanone (prepared using O from Preparation #5 with hydrazine hydrate, R.2 with triethylorthoformate, W, and M) | | S.1.9 | 1.71 (a) | 322 | B |
| 1-(4-(8-Methyl-3H-imidazo[1,2-a]pyrrolo[2,3-e]pyrazin-2-yl)phenyl)ethanone (Preparation #27) | | S.1.10 | 1.57 (b) | 307 | B |
| 1-(5-(1-Methyl-6H-imidazo[1,5-a]pyrrolo[2,3-e]pyrazin-3-yl)thiophen-2-yl)ethanone (prepared using D from Preparation #AB.1 with 5-acetylthiophen-2-ylboronic acid and N) | | S.1.11 | 1.57 (a) | 313.1 | A |

General Procedure T.1: Removal of a Boc Group from an N-Boc Protected Amine and a SEM Group from an N'-SEM Protected Heteroaromatic Ring An acid (such as TFA or HCl, preferably TFA; 5 to 60 equiv, preferably 20 to 50 equiv) is added to a solution of the N-SEM and N'-Boc protected substrate (1 equiv) in an organic solvent (such as DCM) at about 25° C. The mixture is stirred for about 1 to 16 h (preferably about 1.5 h) before evaporation of the solvents under reduced pressure. The material is dissolved in an organic solvent (such as MeOH, EtOH, THF or 1,4-dioxane, preferably MeOH or 1,4-dioxane) then the mixture is treated with concentrated aqueous NH$_4$OH (30 to 50 equiv, preferably 45 equiv). The mixture is heated at about 50 to 65° C. (preferably about 60° C.) for about 15 min to 2 h (preferably about 30 min). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure T.1

Example #T.1.1 cis-3-(7-(5-Methoxy-1-methyl-1H-indol-3-yl)-6H-imidazo[1,5-a]pyrrolo[2,3-e]pyrazin-1-yl)cyclopentanamine diacetate

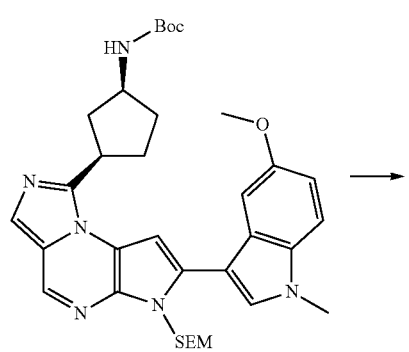

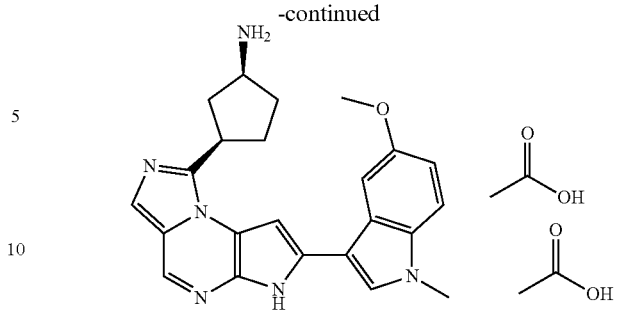

tert-Butyl cis-3-(7-(5-methoxy-1-methyl-1H-indol-3-yl)-6-((2-(trimethylsilyl)ethoxy)methyl)-6H-imidazo[1,5-a]pyrrolo[2,3-e]pyrazin-1-yl)cyclopentylcarbamate (0.331 g, 0.524 mmol, prepared using J.1 from Preparation #I.1 with cis-3-(tert-butoxycarbonylamino)cyclopentanecarboxylic acid [Peptech], and L.1 with mercury(II) trifluoroacetate) in DCM (8 mL) was treated with TFA (2.0 mL, 26 mmol) then stirred for about 1.5 h at rt. The solvents were removed under reduced pressure then the material was dissolved in 1,4-dioxane (4 mL) and treated with concentrated aqueous NH$_4$OH (2.5 mL, 24 mmol). The mixture was heated at about 60° C. for about 30 min. The mixture was concentrated under reduced pressure then dissolved in AcOH (1 mL) and DMF (3.5 mL) then the material was purified by preparative reverse phase HPLC (Table 2, Method i) to give cis-3-(7-(5-methoxy-1-methyl-1H-indol-3-yl)-6H-imidazo[1,5-a]pyrrolo[2,3-e]pyrazin-1-yl)cyclopentanamine diacetate (0.145 g, 53%): LC/MS (Table 2, Method a) R$_f$=1.73 min; MS m/z 401.2 (M+H)$^+$. Syk IC$_{50}$=A.

TABLE T.1.1

Examples Prepared from an N-SEM and N'-Boc Protected Substrate with TFA using General Procedure T.1

| N-SEM and N'-Boc Protected Substrate | Product | Example # | R$_t$ min (Table 2, Method) | m/z ESI+ (M + H)$^+$ | Syk IC$_{50}$ |
|---|---|---|---|---|---|
| tert-Butyl 2-(7-(5-methoxy-1-methyl-1H-indol-3-yl)-6-((2-(trimethylsilyl)ethoxy)methyl)-6H-imidazo[1,5-a]pyrrolo[2,3-e]pyrazin-1-yl)pyrrolidine-1-carboxylate (prepared using J.1 from Preparation #I.1 with 1-(tert-butoxycarbonyl)pyrrolidine-2-carboxylic acid and L.1 with mercury(II) acetate) | 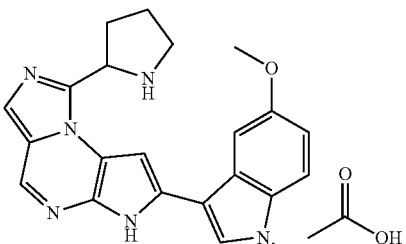 | T.1.1.1 | 1.63 (a) | 387 | ND |
| (3R)-tert-Butyl 3-(7-(5-methoxy-1-methyl-1H-indol-3-yl)-6-((2-(trimethylsilyl)ethoxy)methyl)-6H-imidazo[1,5-a]pyrrolo[2,3-e]pyrazin-1-yl)pyrrolidine-1-carboxylate (prepared using J.1 from Preparation #I.1 with (R)-1-(tert-butoxycarbonyl)pyrrolidine-3-carboxylic acid, [Astatech] and L.1 with mercury(II) trifluoroacetate) | 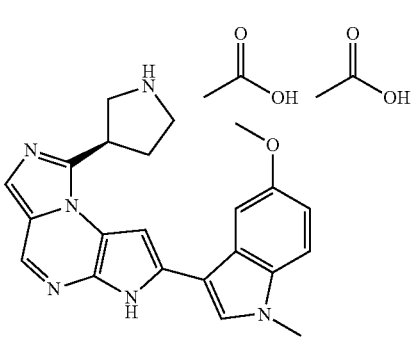 | T.1.1.2 | 1.64 (a) | 387 | A |

TABLE T.1.1-continued

Examples Prepared from an N-SEM and N'-Boc Protected Substrate with TFA using General Procedure T.1

| N-SEM and N'-Boc Protected Substrate | Product | Example # | $R_t$ min (Table 2, Method) | m/z ESI+ $(M + H)^+$ | Syk $IC_{50}$ |
|---|---|---|---|---|---|
| tert-Butyl 3-(7-(5-methoxy-1-methyl-1H-indol-3-yl)-6-((2-(trimethylsilyl)ethoxy)methyl)-6H-imidazo[1,5-a]pyrrolo[2,3-e]pyrazin-1-yl)propylcarbamate (prepared using J.1 from Preparation #I.1 with 4-(tert-butoxycarbonylamino)butyric acid and L.1 with mercury(II) trifluoroacetate) | | T.1.1.3 | 2.00 (a) | 375 | A |
| tert-Butyl 2-(7-(5-methoxy-1-methyl-1H-indol-3-yl)-6-((2-(trimethylsilyl)ethoxy)methyl)-6H-imidazo[1,5-a]pyrrolo[2,3-e]pyrazin-1-yl)ethylcarbamate (prepared using J.1 from Preparation #I.1 with 3-(tert-butoxycarbonylamino)propanoic acid and L.1 with mercury(II) trifluoroacetate) | | T.1.1.4 | 1.75 (a) | 361 | A |
| (cis)-tert-Butyl 3-(7-(3-(methylsulfonyl)phenyl)-6-((2-(trimethylsilyl)ethoxy)methyl)-6H-imidazo[1,5-a]pyrrolo[2,3-e]pyrazin-1-yl)cyclopentylcarbamate (prepared using A from ethynyltrimethylsilane with 1-bromo-3-(methylsulfonyl)benzene [Oakwood], Q, A with 3,5-dibromopyrazin-2-amine B, C, D with (E)-styrylboronic acid E, F, G, I, J.1 with 3-(tert-butoxycarbonylamino) cyclopentanecarboxylic acid [Peptech] and L.1 with mercury(II) trifluoroacetate) | | T.1.1.5 | 1.39 (a) | 396 | B |
| tert-Butyl 3-(7-(3-(methylsulfonyl)phenyl)-6-((2-(trimethylsilyl)ethoxy)methyl)-6H-imidazo[1,5-a]pyrrolo[2,3-e]pyrazin-1-yl)propylcarbamate (prepared using A from ethynyltrimethylsilane with 1-bromo-3-(methylsulfonyl)benzene [Oakwood], Q, A with 3,5-dibromopyrazin-2-amine B, C, D with (E)-styrylboronic acid E, F, G, I, J.1 with 4-(tert-butoxycarbonylamino)butyric acid and L.1 with mercury(II) trifluoroacetate) | | T.1.1.6 | 1.24 (a) | 370 | B |

General Procedure T.2: Removal of an Fmoc Group from an N-Fmoc Protected Amine and a SEM Group from an N'-SEM Protected Heteroaromatic Ring To a flask was added a compound with an N-Fmoc-N'-SEM protecting group (1.0 equiv), an organic solvent (such as DMF or THF, preferably DMF), TBAF (3 to 20 equiv, preferably 4-10 equiv) and ethylenediamine (10 to 50 equiv, preferably 20 to 30 equiv). The mixture is stirred at about 15 to 100° C. (preferably about 80 to 90° C.) for about 1 to 24 h (preferably about 6 h). The mixture is cooled to rt. The mixture is optionally concentrated in vacuo to give the final compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound. Intermediates and final compounds prepared via this General Procedure can be optionally purified using one or more of the Purification Methods described above.

Illustration of General Procedure T.2

Example #T.2.1

(7-(5-Methoxy-1-methyl-1H-indol-3-yl)-6H-imidazo [1,5-a]pyrrolo[2,3-e]pyrazin-1-yl)methanamine

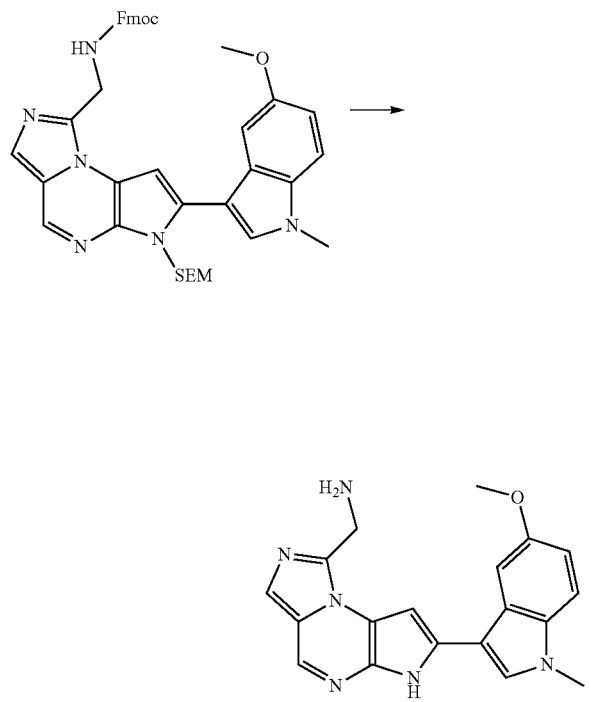

To a round bottom flask was added (9H-fluoren-9-yl)methyl (7-(5-methoxy-1-methyl-1H-indol-3-yl)-6-((2-(trimethylsilyl)ethoxy)methyl)-6H-imidazo[1,5-a]pyrrolo[2,3-e] pyrazin-1-yl)methylcarbamate (0.300 g, 0.429 mmol, prepared using J.1 from Preparation #I.1 with 2-(((9H-fluoren-9-yl)methoxy)carbonylamino)acetic acid and L.1 with mercury(II) trifluoroacetate), DMF (10 mL), TBAF (1.0 M in THF, 1.72 mL, 1.72 mmol) and ethylenediamine (0.870 mL, 12.9 mmol). The mixture was heated to about 85° C. for about 6 h. The mixture was cooled to rt and concentrated in vacuo. The crude material was purified by flash chromatography (120 g silica gel column, DCM/MeOH 1:0 to 10:1). The solid was purified by reverse phase preparatory HPLC (Table 2, Method e) to give fractions with the title compound. The fractions were combined and concentrated in vacuo until a precipitate formed. The solid was collected by vacuum filtration and then dried under reduced pressure at about 60° C. for about 16 h to give (7-(5-methoxy-1-methyl-1H-indol-3-yl)-6H-imidazo[1,5-a]pyrrolo[2,3-e]pyrazin-1-yl)methanamine (0.021 g, 14%): LC/MS (Table 2, Method a) R$_f$=1.53 min; MS m/z 347 (M+H)$^+$. Syk IC$_{50}$=B.

General Procedure T.3. Removal of a Boc Group from an N-Boc Protected Amine and a Tosyl Group from an N'-Tosyl Protected Heteroaromatic Ring To a flask is added an N-Boc-N'-tosyl protected compound (1.0 equiv), an organic solvent (such as DCM, DCE, THF, 1,4-dioxane or MeOH, preferably DCM or 1,4-dioxane) and an acid (such as HCl, TFA, H$_2$SO$_4$, HBr or TsOH, preferably TFA or HCl; 1.0 to 50 equiv, preferably 1.0 to 5.0 equiv). The mixture is stirred at about 0 to 80° C. (preferably about 60 to 80° C.) for about 5 min to 24 h (preferably about 15 min to 4 h). The mixture is cooled to rt and optionally filtered to collect the solid intermediate. If no solid is present, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give the intermediate. Either the intermediate or the solution may be optionally partitioned between water and an organic solvent (such as EtOAc, Et$_2$O or DCM). The organic layer is isolated and may optionally be washed with water, and/or aqueous solutions containing an acid (such as HCl, AcOH or NH$_4$Cl), and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$, or Na$_2$S$_2$O$_3$). The organic solution may then be optionally dried with a drying agent (such as anhydrous MgSO$_4$ or Na$_2$SO$_4$), filtered and concentrated in vacuo to give the intermediate. The intermediate is then added to a flask along with an organic solvent (such as 1,4-dioxane or MeOH, preferably MeOH) is added an aqueous solution of a base (1 to 6 M, such as NaOH or KOH; 4 to 20 equiv, preferably 2 to 15 equiv). The mixture is then either heated at about 60 to 110° C. (preferably about 70 to 95° C.) for about 1 to 12 h (preferably about 2 to 8 h) or heated in a microwave at about 100 to 170° C. (preferably about 120 to 150° C.) for about 5 to 30 min (preferably 15 to 20 min) (250 psi maximum pressure, 2 min ramp time, 300 max watts). The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure T.3

Example #T.3.1

(3-(1-Methyl-1,6-dihydropyrazolo[3,4-d]pyrrolo[2,3-b]pyridin-7-yl)phenyl)methanamine

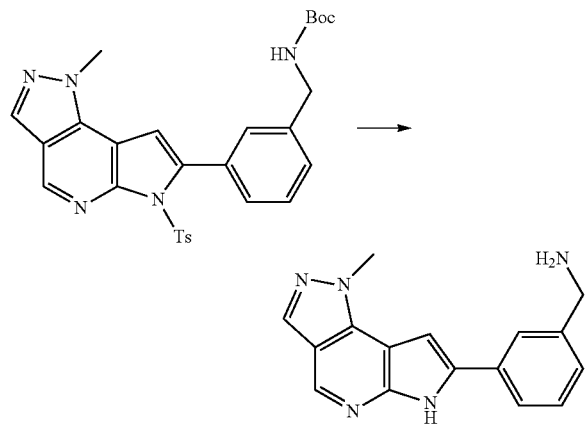

To a round bottom flask was added tert-butyl 3-(1-methyl-6-tosyl-1,6-dihydropyrazolo[3,4-a]pyrrolo[2,3-b]pyridin-7-yl)benzylcarbamate (1.22 g, 2.30 mmol, prepared using D from Preparation #1 with 3-((tert-butoxycarbonylamino)methyl)phenylboronic acid [Frontier]), 1,4-dioxane (23 mL) and HCl (4.0 M in 1,4-dioxane, 5.74 mL, 23.0 mmol). The mixture was cooled to The mixture was heated to about 60° C. for about 1 h and then heated to about 80° C. for about 2 h. rt. The solid was collected by filtration and dried in a vacuum oven at about 60° C. for about 1 h to give a material. The material was added to a round bottom flask along with KOH (0.676 g, 12.1 mmol) and MeOH (12 mL). The mixture was heated to about 60° C. for about 30 min. The mixture was cooled to rt, diluted with water (50 mL) and the pH was adjusted to about 5 with AcOH. The aqueous layer was washed with DCM (2×50 mL). The pH of aqueous layer was adjusted to about 9 with solid $NaHCO_3$ and the aqueous was extracted with DCM (2×50 mL). The organic layer was dried with anhydrous $MgSO_4$, filtered and concentrated in vacuo to give the title compound (0.334 g, 100%): LC/MS (Table 2, Method a) $R_t$=1.50 min; MS m/z 278 $(M+H)^+$. Syk $IC_{50}$=C.

TABLE T.3.1

Examples Prepared from an N-Boc and N'-Tosyl Protected Substrate with NaOH using General Procedure T.3

| N-Boc and N'-Tosyl Protected Substrate | Product | Example # | $R_t$ min (Table 2, Method) | m/z ESI+ $(M+H)^+$ | Syk $IC_{50}$ |
|---|---|---|---|---|---|
| tert-Butyl 3-(1-cyclohexyl-6-tosyl-6H-imidazo[1,5-a]pyrrolo[2,3-e]pyrazin-3-yl)-5-methoxy-1H-indole-1-carboxylate (prepared using H from tert-butyl 3-bromo-5-methoxy-1H-indole-1-carboxylate [Synchem] with 4,4,5,5-tetramethyl-1,3,2-dioxaborolane and D with Example #2, Step E) | | T.3.1.1 | 2.44 (a) | 386.2 | C |
| tert-Butyl 2-(1-methyl-6-tosyl-1,6-dihydropyrazolo[3,4-d]pyrrolo[2,3-b]pyridin-7-yl)-1H-pyrrole-1-carboxylate (prepared using D from Preparation #1 with 1-(tert-butoxycarbonyl)-1H-pyrrol-2-ylboronic acid) | | T.3.1.2 | 1.64 (a) | 238 | B |
| tert-Butyl-cis-3-(3-(4-methoxyphenyl)-6-tosyl-6H-imidazo[1,5-a]pyrrolo[2,3-e]pyrazin-1-yl)cyclohexylcarbamate (prepared using J.1 from Preparation #AG.1 with cis-3-(tert-butoxycarbonylamino)cyclohexanecarboxylic acid) [Chem-Impex] and L.1 with mercury(II) trifluoroacetate) | | T.3.1.3 | 1.60 (a) | 362 | B |

TABLE T.3.1-continued

Examples Prepared from an N-Boc and N'-Tosyl Protected Substrate with NaOH using General Procedure T.3

| N-Boc and N'-Tosyl Protected Substrate | Product | Example # | $R_t$ min (Table 2, Method) | m/z ESI + (M + H)+ | Syk IC$_{50}$ |
|---|---|---|---|---|---|
| tert-Butyl 4-((3-(4-methoxyphenyl)-6-tosyl-6H-imidazo[1,5-a]pyrrolo[2,3-e]pyrazin-1-yl)methyl)piperazine-1-carboxylate (prepared using J.2 from Preparation #AG.1 with cinnamoyl chloride, L.2 with POCl$_3$, E and AH with tert-butyl piperazine-1-carboxylate) | | T.3.1.4 | 1.41 (a) | 363 | B |
| tert-Butyl 3-(4-(6-tosyl-6H-imidazo[1,5-a]pyrrolo[2,3-e]pyrazin-3-yl)phenoxy)pyrrolidine-1-carboxylate (Preparation #28) | | T.3.1.5 | 1.14 (a) | 320 | B |
| tert-Butyl 2-(hydroxymethyl)-4-((3-(4-methoxyphenyl)-6-tosyl-6H-imidazo[1,5-a]pyrrolo[2,3-e]pyrazin-1-yl)methyl)piperazine-1-carboxylate (prepared using J.2 from Preparation #AG.1 with cinnamoyl chloride, L.2 with POCl$_3$ and E and AH) | | T.3.1.6 | 1.44 (a) | 393 | B |

General Procedure T.4: Removal of an Fmoc Group from an N-Fmoc Protected Amine and a Tosyl Group from an N-Tosyl Protected Heteroaromatic Ring To a solution of a substrate containing an N-tosyl heteroaromatic ring and an N'-Fmoc protected amine (1 equiv) in an organic solvent (such as 1,4-dioxane or MeOH, preferably 1,4-dioxane) is added a base (such as 1 to 6 N; LiOH, NaOH, KOH or NaOMe preferably NaOH or KOH; 4 to 20 equiv, preferably 2 to 15 equiv). The mixture is then either heated at about 60 to 110° C. (preferably about 70 to 95° C.) in an oil bath for about 1 to 12 h (preferably about 1 to 8 h) or heated in a microwave at about 120° C. for about 20 min (250 psi maximum pressure, 2 min ramp time, 300 max watts). The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure T.4

Example #T.4.1

2-(4-(1-((2-aminoethoxymethyl)-6H-imidazo[1,5-a]pyrrolo[2,3-e]pyrazin-3-yl)phenyl)propan-2-ol

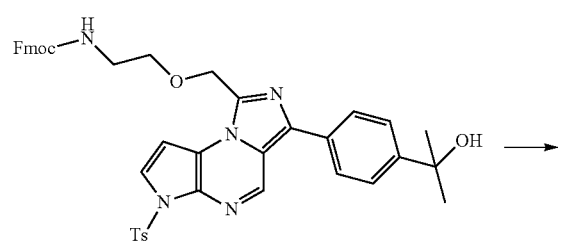

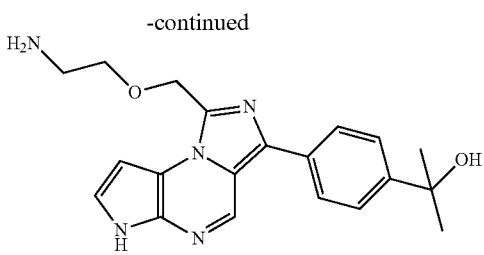

To a solution of (9H-fluoren-9-yl)methyl 2-((3-(4-(2-hydroxypropan-2-yl)phenyl)-6-tosyl-6H-imidazo[1,5-a]pyrrolo[2,3-e]pyrazin-1-yl)methoxy)ethylcarbamate (0.030 g, 0.040 mmol, Preparation #AW.1) in 1,4-dioxane (1 mL) was added NaOH (5.0 N aqueous, 0.040 mL, 0.20 mmol). The mixture was heated at about 70° C. for about 4 h. The mixture was then concentrated under reduced pressure, dissolved in MeOH/DMSO (1:1) (2 mL) and purified via reverse phase preparatory HPLC (Table 2, Method n). The desired fractions were collected and concentrated under reduced pressure. The residue was dissolved in water (4 mL) and lyophilized for 16 h to give 2-(4-(1-((2-aminoethoxy)methyl)-6H-imidazo[1,5-a]pyrrolo[2,3-e]pyrazin-3-yl)phenyl)propan-2-ol (6.5 mg, 44%): LC/MS (Table 2, Method a) $R_f$=1.30 min.; MS m/z: 364 (M–H)⁻.

TABLE T.4.1

Examples prepared from a substrate containing an N'-Fmoc protected amine and an N-tosyl protected heteroaromatic ring with NaOH using General Procedure T.4

| Substrate containing an N'-Fmoc protected amine and an N-tosyl protected heteroaromatic ring | Product | Example # | $R_t$, min (Table 2, Method) | m/z ESI + (M + H)⁺ | Syk IC$_{50}$ |
|---|---|---|---|---|---|
| (9H-Fluoren-9-yl)methyl 2-((3-(4-(methylsulfonyl)phenyl)-6-tosyl-6H-imidazo[1,5-a]pyrrolo[2,3-e]pyrazin-1-yl)methoxy)ethylcarbamate (prepared using AF from Example #2, Step B cyano intermediate with (4-(methylthio)phenyl)magnesium bromide, AG, AR, J.1 with 2-(2-(((9H-fluoren-9-yl)methoxy)carbonylamino)ethoxy)acetic acid [Chem Impex] and L.1 with mercury(II) trifluoroacetate) | | T.4.1.1 | 1.11 (a) | 386 | B |
| (9H-Fluoren-9-yl)methyl 4-((3-(4-(2-hydroxypropan-2-yl)phenyl)-6-tosyl-6H-imidazo[1,5-a]pyrrolo[2,3-e]pyrazin-1-yl)methyl)piperidine-1-carboxylate (prepared using AF from Example #2, Step B cyano intermediate with (4-(2-(4-methoxybenzyloxy)propan-2-yl)phenyl)magnesium bromide [NOVEL], AG, J.1 with 2-(1-(((9H-fluoren-9-yl)methoxy)carbonyl)piperidin-4-yl)acetic acid, L.1 with mercury(II) trifluoroacetate and AW) | | T.4.1.2 | 1.24 (a) | 390 | A |
| (9H-Fluoren-9-yl)methyl 4-(3-(4-(2-hydroxypropan-2-yl)phenyl)-6-tosyl-6H-imidazo[1,5-a]pyrrolo[2,3-e]pyrazin-1-yl)-2-methylbutan-2-ylcarbamate (prepared using AF from Example #2, Step B with (4-(2-(4-methoxybenzyloxy)propan-2-yl)phenyl)magnesium bromide [NOVEL], AG, J.1 with Example #AP.2.1, L.1 with mercury(II) trifluoroacetate and AW) | | T.4.1.3 | 1.26 (a) | 378 | B |

General Procedure U: Alkylation of an Indole, 1H-pyrrolo[3,2-b]pyridine or 5H-pyrrolo[2,3-b]pyrazine To a solution of an indole or 1H-pyrrolo[3,2-b]pyridine or 5H-pyrrolo[2,3-b]pyrazine (1 equiv) in an organic solvent (such as DMF or THF, preferably DMF) is added a base (such as NaH, KOH, or $Cs_2CO_3$, preferably NaH; 1 to 3 equiv, preferably 1.5 equiv). Optionally, NaI (1 to 5 equiv, preferably 1 to 2 equiv) may be added to mixture. After about 5 to 30 min (preferably about 10 to 15 min) an alkyl halide (1 to 6 equiv, preferably 2 equiv) is added and the mixture is stirred at about 20 to 120° C. (preferably about 40 to 80° C.) for about 0.5 to 48 h (preferably about 1 to 24 h). The mixture is cooled to rt and optionally, more base (1 to 3 equiv, preferably 1 to 2 equiv) is added to the mixture and the mixture is stirred at about 20 to 120° C. (preferably about 40 to 80° C.) for about 0.5 to 48 h (preferably about 1 to 24 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

Illustration of General Procedure U

Preparation #U.1: 2-(5-Methoxy-3-(1-methyl-6-tosyl-1,6-dihydropyrazolo[3,4-d]pyrrolo[2,3-b]pyridin-7-yl)-1H-indol-1-yl)-N,N-dimethylacetamide

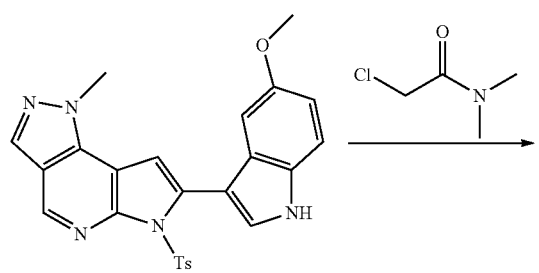

7-(5-Methoxy-1H-indol-3-yl)-1-methyl-6-tosyl-1,6-dihydropyrazolo[3,4-d]pyrrolo[2,3-b]pyridine (0.100 g, 0.212 mmol; Preparation #P.1.1) and 60 wt % NaH (0.009 g, 0.212 mmol) were suspended in DMF (3 mL). After about 10 min, 2-chloro-N,N-dimethylacetamide (0.052 g, 0.424 mmol, Pfaltz-Bauer) was added and mixture was stirred at rt. After about 1 h additional 60 wt % NaH (0.005 g, 0.212 mmol) was added and the mixture was heated to about 40° C. for about 16 h. The mixture was concentrated in vacuo and purified on a 4 g silica column eluting with EtOAc to provide 2-(5-methoxy-3-(1-methyl-6-tosyl-1,6-dihydropyrazolo[3,4-d]pyrrolo[2,3-b]pyridin-7-yl)-1H-indol-1-yl)-N,N-dimethylacetamide (0.097 g, 82%): LC/MS (Table 2, Method c) $R_f$=1.46 min; MS m/z 557 $(M+H)^+$.

General Procedure V.1: Conversion of an Ester to a Carboxylic Acid Under Basic Conditions To a flask containing an ester (1 equiv) either neat or in an organic solvent (such as 1,4-dioxane, MeOH, or THF/MeOH, preferably 1,4-dioxane) is added an aqueous base (such as aqueous $Na_2CO_3$, KOH, $Cs_2CO_3$, $K_2CO_3$, NaOH or LiOH, preferably KOH, $K_2CO_3$ and/or NaOH, 1 to 10 equiv, preferably 2 to 6 equiv). The mixture is stirred at about 0 to 100° C. (preferably about 10 to 25° C.) for about 1 to 48 h (preferably about 4 to 24 h). Optionally, more base is added (such as aqueous $Na_2CO_3$, KOH, $Cs_2CO_3$, $K_2CO_3$, NaOH or LiOH, preferably KOH, $K_2CO_3$ or NaOH, 1 to 10 equiv, preferably 2 to 6 equiv) and the mixture is stirred at about 0 to 100° C. (preferably about 10 to 25° C.) for about 1 to 48 h (preferably about 4 to 24 h). The mixture is then acidified with the addition of a suitable aqueous acid (such as aqueous HCl or AcOH). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

Illustration of General Procedure V.1

Preparation #V.1.1: 3-(2-Bromo-5-((2-(trimethylsilyl)ethoxy)methyl)-5H-pyrrolo[2,3-b]pyrazin-6-yl)benzoic acid

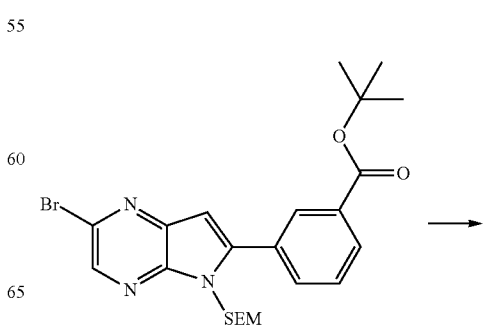

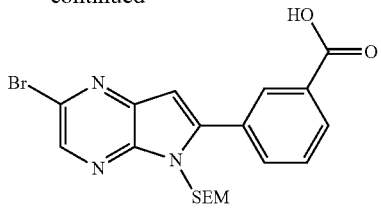

tert-Butyl 3-(2-bromo-5-((2-(trimethylsilyl)ethoxy)methyl)-5H-pyrrolo[2,3-b]pyrazin-6-yl)benzoate (2.5 g, 4.96 mmol, prepared using A from tert-butyl 3-bromobenzoate [Frontier Scientific] with trimethylsilylacetylene, Q with $K_2CO_3$, A with 3,5-dibromopyrazin-2-amine, B and C) and $K_2CO_3$ (0.685 g, 4.96 mmol) in MeOH (20 mL) were added to a flask. The mixture was heated to about 60° C. for about 17 h. An aqueous 40% NaOH solution (2 mL) was added and the mixture was heated to about 60° C. for about 17 h. The mixture was cooled to rt and acidified with about 3 mL of 5 N aqueous HCl and then extracted with EtOAc (100 mL). The solids were removed by filtration then the filtrate was dried over anhydrous $MgSO_4$ and concentrated under reduced pressure to provide 3-(2-bromo-5-((2-(trimethylsilyl)ethoxy)methyl)-5H-pyrrolo[2,3-b]pyrazin-6-yl)benzoic acid (2.01 g, 90%): LC/MS (Table 2, Method b) $R_t$=2.80 min; MS m/z 448 $(M+H)^+$.

General Procedure V.2: Conversion of an Ester to an Acid Under Acidic Conditions To a solution of an ester (1 equiv) in an organic solvent (such as DCM, 1,4-dioxane, EtOH, water or MeOH, preferably DCM) or a mixture of solvents (such as DCM and MeOH or 1,4-dioxane and EtOH) is added an acid (such as TFA or HCl, preferably TFA; 2 to 100 equiv, preferably about 60 equiv). The mixture is stirred at about 0 to 100° C. (preferably about 50° C.) for about 1 to 24 h (preferably about 16 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.
Illustration of General Procedure V.2

Preparation #V.2.1: 2-(5-Methoxy-3-(1-methyl-6-tosyl-1,6-dihydropyrazolo[3,4-d]pyrrolo[2,3-b]pyridin-7-yl)-1H-indol-1-yl)acetic acid

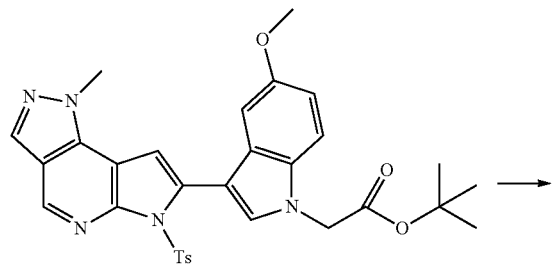

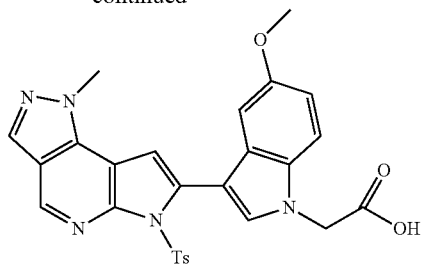

tert-Butyl 2-(5-methoxy-3-(1-methyl-6-tosyl-1,6-dihydropyrazolo[3,4-a]pyrrolo[2,3-b]pyridin-7-yl)-1H-indol-1-yl)acetate (0.350 g, 0.598 mmol, prepared using U from Preparation #P.1.1 with tert-butyl 2-chloroacetate), TFA (1.15 mL, 14.9 mmol) and DCM (5 mL) were heated to about 50° C. for about 16 h. The solvents were removed under reduced pressure then the residue was partitioned between EtOAc (15 mL) and a saturated aqueous $NaHCO_3$ (15 mL). The aqueous layer was acidified with 5 N aqueous HCl then extracted with EtOAc (20 mL). The organic solution was dried over anhydrous $MgSO_4$ then filtered. The filtrate was concentrated to give 2-(5-methoxy-3-(1-methyl-6-tosyl-1,6-dihydropyrazolo[3,4-d]pyrrolo[2,3-b]pyridin-7-yl)-1H-indol-1-yl)acetic acid (0.316 g, 100%): LC/MS (Table 2, Method c) $R_t$=1.35 min; MS m/z 530 $(M+H)^+$.

General Procedure W: Preparation of a Ketone from a Ketal

An acid (such as TFA, TsOH, or aqueous HCl, preferably aqueous HCl; 25 to 75 equiv, preferably 50 equiv) is added to a solution of a ketal (1 equiv) in an organic solvent (such as DCM, DCE, EtOAc, THF, 1,4-dioxane, $Et_2O$, MeOH, EtOH, i-PrOH, or acetone, preferably acetone). The mixture is stirred at about 0 to 50° C. (preferably about 10 to 25° C.) for about 5 min to 16 h (preferably about 1 to 4 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

Illustration of General Procedure W

Preparation #W.1: 1-(4-(8-Ethyl-1-methyl-6-((2-(trimethylsilyl)ethoxy)methyl)-6H-imidazo[1,5-a]pyrrolo[2,3-e]pyrazin-7-yl)phenyl)ethanone

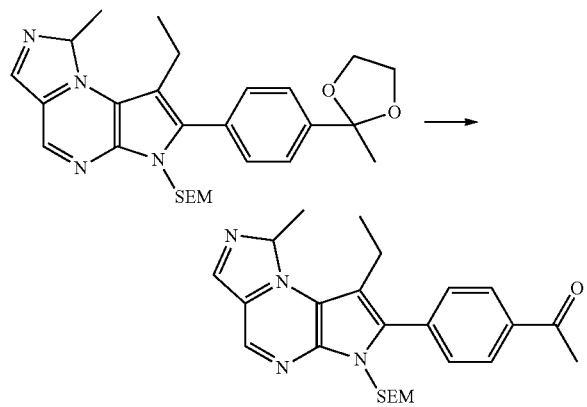

8-Ethyl-1-methyl-7-(4-(2-methyl-1,3-dioxolan-2-yl)phenyl)-6-((2-(trimethylsilyl)ethoxy)methyl)-6H-imidazo[1,5-a]pyrrolo[2,3-e]pyrazine (0.147 g, 0.298 mmol, prepared using D from Preparation #5 with (E)-styreneboronic acid, E, F, G, I, J.2 with Ac$_2$O and L.1 with mercury(II) trifluoracetate) was dissolved in acetone (10 mL) then HCl (5.0 N aqueous, 3.0 mL, 15 mmol) was added. The mixture was stirred at rt for about 1 h. The mixture was concentrated under reduced pressure then treated with saturated aqueous NaHCO$_3$ (5 mL) and water (10 mL). The layers were separated then the aqueous mixture was extracted with DCM (25 mL then 2×10 mL). The combined organic layers were dried over anhydrous MgSO$_4$, filtered and concentrated under reduced pressure to give 1-(4-(8-ethyl-1-methyl-6-((2-(trimethylsilyl)ethoxy)methyl)-6H-imidazo[1,5-a]pyrrolo[2,3-e]pyrazin-7-yl)phenyl)ethanone (0.092 g, 69%): LC/MS (Table 2, Method a) R$_t$=3.30 min; MS m/z 449 (M+H)$^+$.

amine is then added either all at once or in portions (1 to 2 equiv) and the mixture is allowed to stir at about 0 to 80° C. (preferably about 20 to 50° C.) for about 1 to 72 h (preferably about 3 to 24 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure X

Preparation #X.1: 3-((6-(5-Methoxy-1-methyl-1H-indol-3-yl)-5-((2-(trimethylsilyl)ethoxy)methyl)-5H-pyrrolo[2,3-b]pyrazin-2-yl)methyl)-1,1-dimethylurea

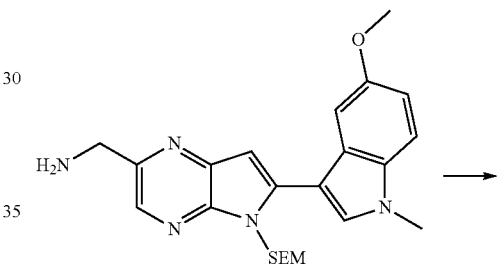

TABLE W.1

Examples prepared from a Ketal with HCl using General Procedure W

| Ketal | Product | Example # | R$_t$ min (Table 2, Method) | m/z ESI + (M + H)$^+$ | Syk IC$_{50}$ |
|---|---|---|---|---|---|
| 1-Methyl-3-(4-(2-methyl-1,3-dioxolan-2-yl)phenyl)-1,6-dihydropyrazolo[3,4-d]pyrrolo[2,3-b]pyridine (prepared using S from Preparation #1 Step B with (4-(2-methyl-1,3-dioxolan-2-yl)phenyl)magnesium bromide [NOVEL], AV, AH with methylhydrazine) | | W.1.1 | 1.95 (a) | 291 | B |

General Procedure X: Formation of a urea from two amines

A flask is charged with an amine (1 equiv), CDI (1 to 2 equiv) and an organic solvent (such as THF, 1,4-dixoane, Et$_2$O, or DCM, preferably THF). To the mixture is added a base (such as DIEA, TEA or pyridine, preferable DIEA; 2 to 5 equiv, preferably 2 to 3 equiv). The mixture is allowed to stir at about 0 to 80° C. (preferably about 20 to 50° C.) for about 1 to 8 h (preferably about 1 to 6 h). A second amine is then added (1 to 2 equiv) and the mixture is allowed to stir at about 0 to 80° C. (preferably about 20 to 50° C.) for about 1 to 72 h (preferably about 3 to 24 h). Optionally, more of the second -continued

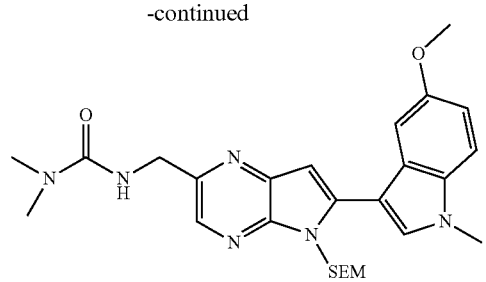

A flask was charged with (6-(5-methoxy-1-methyl-1H-indol-3-yl)-5-((2-(trimethylsilyl)ethoxy)methyl)-5H-pyrrolo[2,3-b]pyrazin-2-yl)methanamine (0.413 g, 0.944 mmol, Preparation #I.1), CDI (0.184 g, 1.13 mmol), DIEA (0.412 mL, 2.36 mmol) and THF (10 mL). The mixture was allowed to stir at rt for about 1 h. Dimethylamine (2.0 M in THF, 0.472 mL, 0.944 mmol) was added to the mixture. After about 4 h, additional dimethylamine (2.0 M in THF, 0.236 mL, 0.472 mmol) was added. After about 12 h, dimethylamine (2.0 M in THF, 0.236 mL, 0.472 mmol) was added. After about 8 h, the mixture was concentrated under reduced pressure and the residue was dissolved in DCM (10 mL). The organic solution was then washed with water (2×4 mL). The organic layer was dried over anhydrous MgSO$_4$ and concentrated in vacuo. The residue was purified by silica gel chromatography eluting with 0 to 10% MeOH/DCM to give 3-((6-(5-Methoxy-1-methyl-1H-indol-3-yl)-5-((2-(trimethylsilyl)ethoxy)methyl)-5H-pyrrolo[2,3-b]pyrazin-2-yl)methyl)-1,1-dimethylurea (0.114 g, 24%): LC/MS (Table 2, Method b) R$_t$=2.62 min; MS m/z 509 (M+H)$^+$.

General Procedure Y: Formation of a 6H-imidazo[1,5-a]pyrrolo[2,3-e]pyrazin-1-amine from a 1-((5H-pyrrolo[2,3-b]pyrazin-2-yl)methyl)urea A flask is charged with a 1-((5H-pyrrolo[2,3-b]pyrazin-2-yl)methyl)urea (1 equiv), an organic solvent such as DCM or DCE (preferably DCE) and POCl$_3$ (1 to 5 equiv, preferably 1 to 3 equiv). The mixture is then heated to about 60 to 100° C. (preferably about 65 to 85° C.) for about 1 to 12 h (preferably about 1 to 4 h). The mixture is optionally concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$, or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.
Illustration of General Procedure Y Preparation #Y.1: 7-(5-Methoxy-1-methyl-1H-indol-3-yl)-N,N-dimethyl-6-((2-(trimethylsilyl)ethoxy)methyl)-6H-imidazo[1,5-a]pyrrolo[2,3-e]pyrazin-1-amine

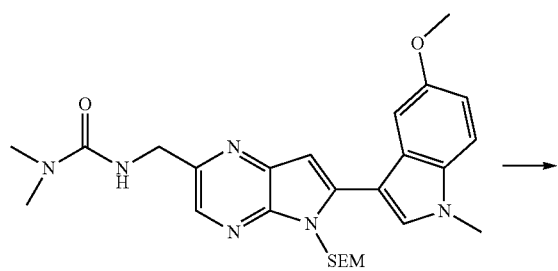

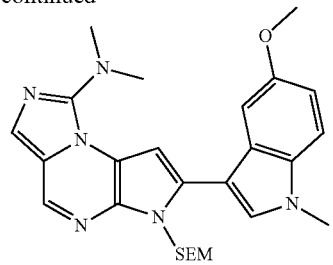

A flask was charged with 3-((6-(5-methoxy-1-methyl-1H-indol-3-yl)-5-((2-(trimethylsilyl)ethoxy)methyl)-5H-pyrrolo[2,3-b]pyrazin-2-yl)methyl)-1,1-dimethylurea (0.114 g, 0.224 mmol, Preparation #X.1) and DCE (5 mL). A solution of POCl$_3$ (0.063 mL, 0.672 mmol) in DCE (2 mL) was added and mixture was heated to about 85° C. for about 3 h. The mixture was concentrated under reduced pressure and then diluted with EtOAc (15 mL) and washed with saturated aqueous NaCl (10 mL). The organic layer was dried with anhydrous MgSO$_4$, filtered and concentrated in vacuo. The material was purified using silica gel chromatography with an elution gradient of 0 to 100% EtOAc/heptane to give 7-(5-methoxy-1-methyl-1H-indol-3-yl)-N,N-dimethyl-6-((2-(trimethylsilyl)ethoxy)methyl)-6H-imidazo[1,5-a]pyrrolo[2,3-e]pyrazin-1-amine (0.47 g, 43%): LC/MS (Table 2, Method b) R$_t$=3.14 min; MS m/z: 491 (M+H)$^+$.

General Procedure Z: Removal of a Silyl Group from an O-Silyl Protected Alcohol

An acid (such as TFA, TsOH, aqueous HCl, preferably aqueous HCl) (1 to 10 equiv, preferably 6 equiv) is added to a solution of the silyl protected alcohol (1 equiv) in an organic solvent (such as DCM, DCE, EtOAc, THF, 1,4-dioxane, Et$_2$O, MeOH, EtOH, i-PrOH, preferably MeOH). The mixture is stirred for about 5 min to 1 h (preferably about 15 min) at about 0 to 50° C. (preferably about 15 to 30° C.). The mixture is optionally concentrated in vacuo to give final compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure Z

Preparation #Z.1: 2-(5-Methoxy-3-(1-methyl-6-tosyl-1,6-dihydropyrazolo[3,4-d]pyrrolo[2,3-b]pyridin-7-yl)-1H-indol-1-yl)ethanol

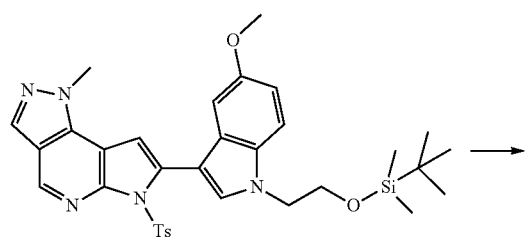

7-(1-(2-(tert-Butyldimethylsilyloxy)ethyl)-5-methoxy-1H-indol-3-yl)-1-methyl-6-tosyl-1,6-dihydropyrazolo[3,4-d]pyrrolo[2,3-b]pyridine (0.130 g, 0.212 mmol, prepared using U from Preparation #P.1.1 with (2-bromoethoxy)(tert-butyl)dimethylsilane) was dissolved in MeOH (5 mL) then HCl (37% aqueous, 0.15 g, 1.3 mmol) was added. The mixture was stirred at rt for about 15 min. The mixture was concentrated under reduced pressure to give 2-(5-methoxy-3-(1-methyl-6-tosyl-1,6-dihydropyrazolo[3,4-d]pyrrolo[2,3-b]pyridin-7-yl)-1H-indol-1-yl)ethanol (0.10 g, 91%): LC/MS (Table 2, Method b) $R_t$=2.19 min; MS m/z: 516 (M+H)⁺.

General Procedure AA: Grignard Addition to an Ester to Give an Alcohol

To a solution of an alkylmagnesium halide (2 to 12 equiv, preferably 5 to 10 equiv) in an organic solvent (such as THF or Et₂O, preferably THF) at about −60 to 25° C. (preferably about −45 to 0° C.) is added slowly a solution of the ester (1 equiv) in THF. Alternatively, the alkylmagnesium halide (2 to 12 equiv, preferably 5 to 10 equiv) is added to a solution of the ester (1 equiv) in an organic solvent (such as THF or Et₂O, preferably THF) at about −60 to 25° C. (preferably about −45 to 0° C.). The mixture is stirred at about −40 to 25° C. (preferably about 0° C. to 25° C.) for about 30 min to 3 h (preferably about 1 h). The addition of the reagents may be optionally done portion-wise. To the mixture is added an organic acid such as AcOH or a saturated aqueous solution of NaHCO₃ or NH₄Cl. The mixture is optionally concentrated in vacuo to give the targeted compound. The mixture is optionally filtered through a media (such as silica gel or Celite®) which is rinsed with an appropriate solvent (such as EtOAc, 1,4-dioxane, THF, MeCN, DCM, Et₂O, MeOH, or EtOH) and then optionally concentrated in vacuo to give a residue. Either the residue or the solution may be optionally partitioned between water and an organic solvent (such as EtOAc, Et₂O or DCM). The organic layer is isolated and may be optionally washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the targeted compound.

Illustration of General Procedure AA

Preparation #AA.1: 2-(1-Methyl-3-(1-methyl-6-tosyl-1,6-dihydropyrazolo[3,4-d]pyrrolo[2,3-b]pyridin-7-yl)-1H-indol-5-yl)propan-2-ol

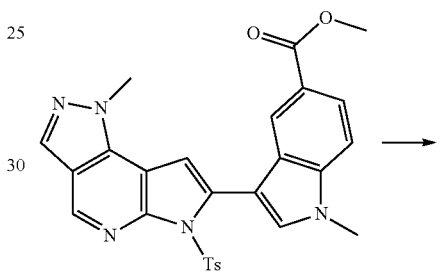

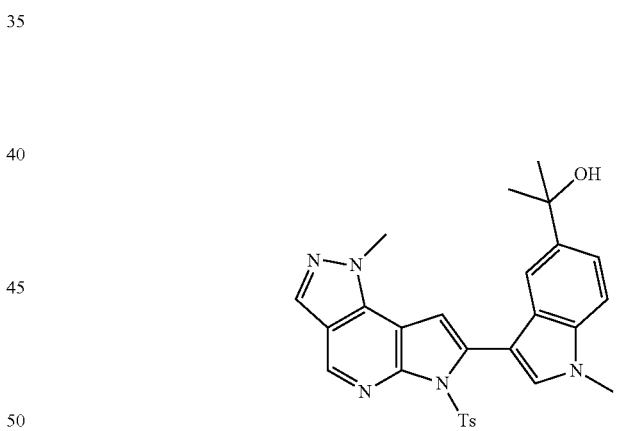

A solution of MeMgCl (3 M in THF, 0.65 mL, 1.95 mmol) in THF (4 mL) was cooled to about −40° C. then methyl 1-methyl-3-(1-methyl-6-tosyl-1,6-dihydropyrazolo[3,4-d]pyrrolo[2,3-b]pyridin-7-yl)-1H-indole-5-carboxylate (0.125 g, 0.243 mmol, prepared using D from Preparation #1 and Preparation #18 in THF (3 mL) was added. The mixture was warmed to rt and stirred for about 1 h. The mixture was treated with AcOH (~0.75 mL) then the mixture was diluted with water (30 mL). The mixture was extracted with EtOAc (2×25 mL). The combined organics were washed with brine, dried over anhydrous MgSO₄, filtered and concentrated in vacuo to give 2-(1-methyl-3-(1-methyl-6-tosyl-1,6-dihydropyrazolo[3,4-d]pyrrolo[2,3-b]pyridin-7-yl)-1H-indol-5-yl)propan-2-ol (0.115 g, 92%): LC/MS (Table 2, Method a) $R_t$=2.26 min; MS m/z 514 (M+H)⁺.

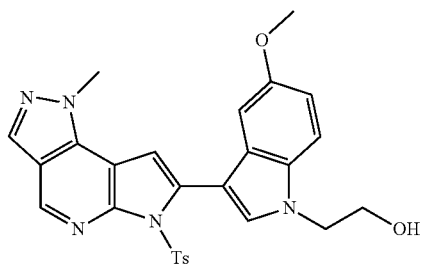

TABLE AA.1

Examples prepared from methyl Grignard with an ester using General Procedure AA

| Ester | Product | Example # | R, min (Table 2, Method) | m/z ESI + (M + H)+ | Syk IC50 |
|---|---|---|---|---|---|
| Methyl 7-(5-methoxy-1-methyl-1H-indol-3-yl)-6H-imidazo[1,5-a]pyrrolo[2,3-e]pyrazine-1-carboxylate (prepared using J.2 from Preparation #I.1 with mono-methyl oxalyl chloride, L.1 with mercury(II) trifluoroacetate and M) | 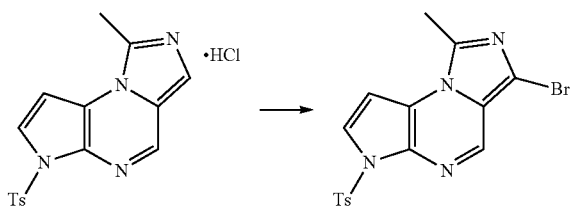 [SMILES: Cc1ccc(S(=O)(=O)n2ccc3c2ncc2cnc(C)n23)cc1 ; Cl ; Cc1ccc(S(=O)(=O)n2ccc3c2ncc2c(Br)nc(C)n23)cc1] | AA.1.1 | 1.90 | 376 | A |

General Procedure AB: Conversion of a 6H-imidazo[1,5-a]pyrrolo[2,3-e]pyrazine to a 3-halo-6H-imidazo[1,5-a]pyrrolo[2,3-e]pyrazine The 6H-imidazo[1,5-a]pyrrolo[2,3-e]pyrazine (1 equiv) is dissolved or suspended in a suitable solvent such as DMF, DCE, DCM, 1,4-dioxane, Et$_2$O or THF (preferably DCM or DMF). The mixture is stirred at about −40° C. to rt (preferably rt) and treated with halogenating agent (such as NBS, NIS, NCS, Br$_2$, or pyridinium tribromide, preferably NBS or NIS, 0.8 to 1.2 equiv, preferably 0.8 to 1.0 equiv) and the reaction stirred for about 5 min to 24 h (preferably 5 min to 2 h) at about −30° C. to 50° C. (preferably rt). The mixture is optionally poured into water and the product isolated by vacuum filtration. The reaction is optionally concentrated in vacuo. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure AB

Preparation #AB.1: 3-Bromo-1-methyl-6-tosyl-6H-imidazo[1,5-a]pyrrolo[2,3-e]pyrazine To a mixture of 1-methyl-6-tosyl-6H-imidazo[1,5-a]pyrrolo[2,3-e]pyrazine hydrochloride (2.11 g, 5.81 mmol) in DMF (58 ml) was added NBS (1.03 g, 5.81 mmol). The mixture was stirred for about 2 h at rt. The mixture was poured into rapidly stirred water (~300 mL). Saturated aqueous NaHCO$_3$ (~15 mL) was added and the mixture stirred for about 1 h. The solid was collected by filtration and washed with water (~50 mL). The solid was dissolved in DCM (100 mL) and washed with saturated aqueous Na$_2$CO$_3$ (20 mL). The layers were separated and the aqueous layer was extracted with DCM (2×15 mL). The combined organic layers were washed with brine (10 mL), dried over MgSO$_4$, filtered, and concentrated in vacuo. The residue was purified by flash column chromatography (80 g Silicycle™ column) eluting with 10% EtOAc in DCM to give 3-bromo-1-methyl-6-tosyl-6H-imidazo[1,5-a]pyrrolo[2,3-e]pyrazine (1.62 g, 69%): LCMS (Table 2, Method b) R$_t$=2.52 min.; MS m/z: 404.96, 406 (M+H)$^+$.

General Procedure AC: Suzuki Reaction of an Aryl or Heteroaryl Halide with a Boronic Acid or Boronic Ester with Removal of a Tosyl Group from an N-Tosyl Protected Heteroaromatic Ring To a mixture of an aryl halide (1 equiv) in a solvent mixture (such as 1,4-dioxane/water, EtOH/water, MeCN/water, EtOH/1,4-dioxane/water, preferably 1,4-dioxane/water or EtOH/1,4-dioxane/water) or a single solvent system such as DMF is added a boronic acid or ester (1 to 2 equiv, preferably 1.1 to 1.5 equiv), a palladium catalyst (such as Pd(PPh$_3$)$_4$, PdCl$_2$(PPh$_3$)$_2$, Pd$_2$dba$_3$, Pd(OAc)$_2$, PdCl$_2$(dPPf)-CH$_2$Cl$_2$ or SiliaCat DPP-Pd®, preferably Pd(PPh$_3$)$_4$, PdCl$_2$(PPh$_3$)$_2$, or SiliaCat DPP-Pd®; 0.02 to 1.0 equiv, preferably 0.04 to 0.07) and a base (such as Na$_2$CO$_3$, Cs$_2$CO$_3$, CsF K$_3$PO$_4$, NaOt-Bu, KOt-Bu, KOAc, preferably Na$_2$CO$_3$ or Cs$_2$CO$_3$; 1 to 5 equiv, preferably 2 to 3 equiv). Optionally, copper (I) iodide (0.05 to 0.15 equiv, preferably 0.09 to 0.11 equiv) may be added to the reaction mixture. The reaction mixture is heated to about 60 to 120° C. (preferably about 80 to 100° C.) for about 1 to 24 h (preferably about 2 to 5 h), or optionally heated in a microwave at about 100 to 200° C. for about 5 min to 2 h. Optionally, additional boronic acid or ester (0.1 to 1 equiv) and/or Pd catalyst (0.01 to 0.1 equiv) may be added and further heating (at the previously specified temperature, for about 1 to 6 h) may be applied. Optionally a metal hydroxide base (NaOH, KOH, LiOH, or some combination thereof, preferably NaOH) may be added, along with further heating at about 60 to 120° C. (preferably about 80 to 100° C.) for about 30 min to 2 h (preferably 1 h). The mixture is optionally concentrated in vacuo to give the targeted compound. Alternatively, the mixture is optionally filtered (possibly through a media such as silica gel or Celite®) which is rinsed with an appropriate solvent (such as EtOAc, 1,4-dioxane, THF, MeCN, DCM, Et$_2$O, MeOH, EtOH or some combination thereof) and then optionally concentrated in vacuo to give a residue. Either the residue or the solution may be optionally partitioned between water and an organic solvent (such as EtOAc, Et₂O or DCM). The organic layer is isolated and may be optionally washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the targeted compound. Intermediates and final compounds prepared via this General Procedure can be optionally purified using one or more of the Purification Methods described above.

Illustration of General Procedure AC

Preparation #AC.1: 4-(1-Methyl-6H-imidazo[1,5-a]pyrrolo[2,3-e]pyrazin-3-yl)benzaldehyde

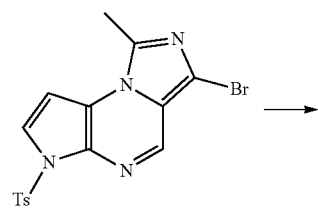

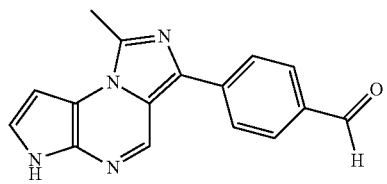

To a microwave reaction vial containing 3-bromo-1-methyl-6-tosyl-6H-imidazo[1,5-a]pyrrolo[2,3-e]pyrazine (0.100 g, 0.247 mmol, Preparation #AB.1), 4-formylphenylboronic acid (0.074 g, 0.493 mmol, Lancaster) and SiliaCat® DPP-Pd (0.031 g, 0.025 mmol, Silicycle) in 1,4-dioxane (1.0 mL) and EtOH (1.0 mL) was added a solution of Cs₂CO₃ (0.177 g, 0.543 mmol) in water (0.3 mL). The mixture was heated in a microwave at 150° C. for 30 min. The mixture was filtered through a filtration tube with a polyethylene frit, and the resulting solid was rinsed with EtOAc (5 mL). The solid was dissolved in a 9:1 DCM/MeOH solution and filtered. The filtrate was concentrated under reduced pressure followed by drying overnight in a vacuum oven at about 65° C. to give the title compound (0.052 g, 76%): LC/MS (Table 2, Method c) $R_f$=1.67 min.; MS m/z: 277 (M+H)⁺.

TABLE AC.1

Examples prepared from 3-bromo-1-methyl-6-tosyl-6H-imidazo[1,5-a]pyrrolo[2,3-e]pyrazine (Preparation #AB.1) with a boronic acid or boronic ester using General Procedure AC

| Boronic Acid or Boronate | Product | Example # | $R_f$ min (Table 2, Method) | m/z ESI + (M + H)⁺ | Syk IC₅₀ |
|---|---|---|---|---|---|
| 2,4-Dimethoxyphenylboronic acid [Lancaster] | | AC.1.1 | 1.74 (a) | 309 | C |
| 2-(Hydroxymethyl)-4-methoxyphenylboronic acid [Frontier] | | AC.1.2 | 1.79 (a) | 309 | C |
| (5-(4,4,5,5-tetramethyl-1,3,2-dioxaborolan-2-yl)pyridin-2-yl)methanol | | AC.1.3 | 1.46 (a) | 280 | B |

TABLE AC.1-continued

Examples prepared from 3-bromo-1-methyl-6-tosyl-6H-imidazo[1,5-a]pyrrolo[2,3-e]pyrazine (Preparation #AB.1) with a boronic acid or boronic ester using General Procedure AC

| Boronic Acid or Boronate | Product | Example # | $R_t$ min (Table 2, Method) | m/z ESI+ $(M + H)^+$ | Syk $IC_{50}$ |
|---|---|---|---|---|---|
| 3-(Propylcarbamoyl)phenylboronic acid [Combiblocks] | | AC.1.4 | 1.68 (a) | 334 | B |
| Quinoxalin-5-ylboronic acid (prepared using H from 5-bromoquinoxaline (Spectra) with bis(pinacolato)diboron) | | AC.1.5 | 1.99 (a) | 301 | D |
| 4-(Methylsulfonyl)phenylboronic acid [Acros] | | AC.1.6 | 1.71 (a) | 327 | B |
| 4-(1-Hydroxy-2-methylpropan-2-yl)phenylboronic acid (prepared using H from 2-(4-chlorophenyl)-2-methylpropan-1-ol [Betapharma]) | | AC.1.7 | 1.78 (a) | 321 | A |
| 8-Methoxyquinolin-5-ylboronic acid) | | AC.1.8 | 1.62 (a) | 330 | ND |
| 4-(N-Methylsulfamoyl)phenylboronic acid [Frontier] | | AC.1.9 | 1.68 (a) | 342 | A |

TABLE AC.1-continued

Examples prepared from 3-bromo-1-methyl-6-tosyl-6H-imidazo[1,5-a]pyrrolo[2,3-e]pyrazine
(Preparation #AB.1) with a boronic acid or boronic ester using General Procedure AC

| Boronic Acid or Boronate | Product | Example # | $R_t$ min (Table 2, Method) | m/z ESI + (M + H)$^+$ | Syk IC$_{50}$ |
|---|---|---|---|---|---|
| 4-(N,N-Dimethylsulfamoyl)phenylboronic acid [Combi Blocks] | 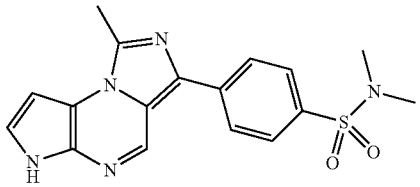 [SMILES: Cc1nc(-c2ccc(S(=O)(=O)N(C)C)cc2)c2cnc3[nH]ccc3n12] | AC.1.10 | 1.89 (a) | 356 | B |
| 4-(Isopropylsulfonyl)phenylboronic acid [CombiBlocks] | 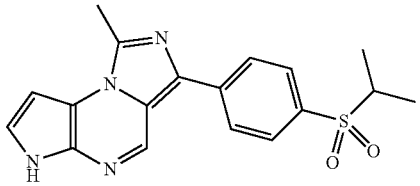 [SMILES: Cc1nc(-c2ccc(S(=O)(=O)C(C)C)cc2)c2cnc3[nH]ccc3n12] | AC.1.11 | 1.77 (a) | 355 | B |
| 1-Methyl-4-(4-(4,4,5,5-tetramethyl-1,3,2-dioxaborolan-2-yl)phenylsulfonyl)piperazine (prepared using K from 4-bromobenzene-1-sulfonyl chloride with 1-methylpiperazine and H with 4,4,4',4',5,5,5',5'-octamethyl-2,2'-bi(1,3,2-dioxaborolane)) | 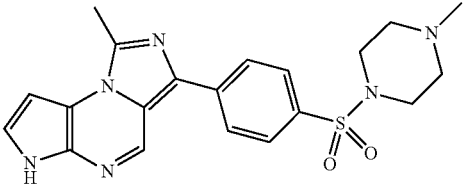 [SMILES: Cc1nc(-c2ccc(S(=O)(=O)N3CCN(C)CC3)cc2)c2cnc3[nH]ccc3n12] | AC.1.12 | 1.57 (a) | 411 | C |
| 4-(4,4,5,5-Tetramethyl-[1,3,2]dioxaborolan-2-yl)-3,6-dihydro-2H-pyridine-1-carboxylic acid tert-butyl ester [Carbocore] | 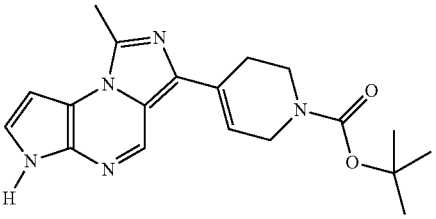 [SMILES: Cc1nc(C2=CCN(C(=O)OC(C)(C)C)CC2)c2cnc3[nH]ccc3n12] | AC.1.13 | 1.96 (a) | 354 | C |
| 4-(2-(4-(4,4,5,5-Tetramethyl-1,3,2-dioxaborolan-2-yl)phenoxy)ethyl)morpholine [Combiblocks] | 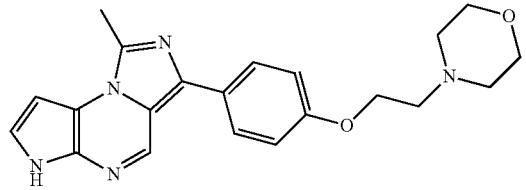 [SMILES: Cc1nc(-c2ccc(OCCN3CCOCC3)cc2)c2cnc3[nH]ccc3n12] | AC.1.14 | 1.47 (a) | 378 | A |
| 4-(2-Methoxyethoxy)phenylboronic acid [Chembridge] | 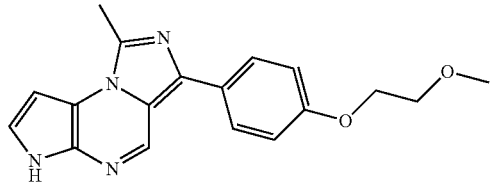 [SMILES: COCCOc1ccc(-c2nc(C)n3c2cnc2[nH]ccc23)cc1] | AC.1.15 | 1.84 (a) | 323 | B |
| 2-(4-(4,4,5,5-Tetramethyl-1,3,2-dioxaborolan-2-yl)phenoxy)acetonitrile [Boronmolecular] | 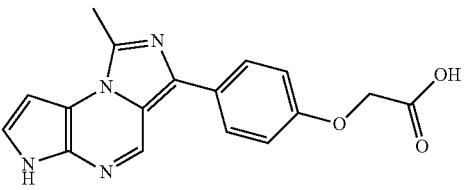 [SMILES: Cc1nc(-c2ccc(OCC(=O)O)cc2)c2cnc3[nH]ccc3n12] | AC.1.16 | 1.42 (a) | 323 | B |

TABLE AC.1-continued

Examples prepared from 3-bromo-1-methyl-6-tosyl-6H-imidazo[1,5-a]pyrrolo[2,3-e]pyrazine (Preparation #AB.1) with a boronic acid or boronic ester using General Procedure AC

| Boronic Acid or Boronate | Product | Example # | R$_t$ min (Table 2, Method) | m/z ESI + (M + H)$^+$ | Syk IC$_{50}$ |
|---|---|---|---|---|---|
| 4-Methoxy-2-methylphenylboronic acid | | AC.1.17 | 1.90(a) | 293 | D |
| 2-Fluoro-4-methoxyphenylboronic acid [Combiblocks] | | AC.1.18 | 1.88 (a) | 297 | C |
| 2-Chloro-4-methoxyphenylboronic acid [Combiblocks] | | AC.1.19 | 1.92 (a) | 313 | C |
| 3-Fluoro-4-(2-hydroxypropan-2-yl)phenylboronic acid [Chemmaker] | | AC.1.20 | 1.83 (a) | 325 | A |
| 6-Methoxypyridin-3-ylboronic acid | | AC.1.21 | 1.73 (a) | 280 | B |
| Pyridin-3-ylboronic acid [Digital Specialties] | | AC.1.22 | 1.41 (a) | 250 | C |
| 2-Methoxypyrimidin-5-ylboronic acid [Combiblocks] | | AC.1.23 | 1.65 (a) | 281 | C |

TABLE AC.1-continued

Examples prepared from 3-bromo-1-methyl-6-tosyl-6H-imidazo[1,5-a]pyrrolo[2,3-e]pyrazine
(Preparation #AB.1) with a boronic acid or boronic ester using General Procedure AC

| Boronic Acid or Boronate | Product | Example # | R$_t$ min (Table 2, Method) | m/z ESI + (M + H)$^+$ | Syk IC$_{50}$ |
|---|---|---|---|---|---|
| Potassium trifluoro(6-(2 hydroxypropan-2-yl)pyridin-3-yl)borate [Chemmaker] | | AC.1.24 | 1.57 (a) | 308 | B |
| 4-Methoxy-3,5-dimethylphenylboronic acid | | AC.1.25 | 2.04 (b) | 307 | A |
| 2,3-Dihydrobenzofuran-5-boronic acid (Frontier) | | AC.1.26 | 1.99 (b) | 291 | B |
| 4-(2-Methyl-4-(4,4,5,5-tetramethyl-1,3,2-dioxaborolan-2-yl)phenyl)morpholine (prepared from 4-(4-iodo-2-methylphenyl)morpholine (prepared using H from Preparation #26 with bis(pinacolato)diboron) | | AC.1.27 | 1.97 (b) | 348 | A |
| 2-Methyl-1-(4-(4,4,5,5-tetramethyl-1,3,2-dioxaborolan-2-yl)-1H-pyrazol-1-yl)propan-2-ol (WO2008/44022 A1, Intermediate 33) | | AC.1.28 | 1.28 (b) | 311 | B |
| 4-(Propylcarbamoyl) phenylboronic acid | | AC.1.29 | 1.65 (a) | 334 | A |
| 1-Methyl-4-(2-methyl-4-(4,4,5,5-tetramethyl-1,3,2-dioxaborolan-2-yl)phenyl)piperazine | | AC.1.30 | 1.49 (a) | 361 | A |

TABLE AC.1-continued

Examples prepared from 3-bromo-1-methyl-6-tosyl-6H-imidazo[1,5-a]pyrrolo[2,3-e]pyrazine
(Preparation #AB.1) with a boronic acid or boronic ester using General Procedure AC

| Boronic Acid or Boronate | Product | Example # | $R_t$ min (Table 2, Method) | m/z ESI + $(M + H)^+$ | Syk $IC_{50}$ |
|---|---|---|---|---|---|
| 5-Methoxythiophen-2-ylboronic acid | | AC.1.31 | 1.82 (a) | 285 | A |
| 5-Acetylthiophen-2-ylboronic acid | | AC.1.32 | 1.65 (a) | 297 | B |
| 3-(4-(4,4,5,5-Tetramethyl-1,3,2-dioxaborolan-2-yl)phenyl)oxetan-3-ol (Preparation #30) | | AC.1.33 | 1.37 (a) | 321 | B |
| 4-(Hydroxymethyl)phenylboronic acid | | AC.1.34 | 1.44 (a) | 279 | B |
| 2-Methyl-1-(4-(4,4,5,5-tetramethyl-1,3,2-dioxaborolan-2-yl)phenyl)propan-2-ol (prepared using S from ethyl 4-bromophenylacetate and H with bis(pinacolato)diboron) | | AC.1.35 | 1.69 (a) | 321 | B |
| 4-(1-(Hydroxymethyl)cyclopropyl)-phenylboronic acid (Combi-Blocks) | | AC.1.36 | 1.66 (a) | 319 | B |
| 4-Methoxy-3-methylphenylboronic acid | | AC.1.37 | 1.93 (a) | 293 | B |

TABLE AC.1-continued

Examples prepared from 3-bromo-1-methyl-6-tosyl-6H-imidazo[1,5-a]pyrrolo[2,3-e]pyrazine
(Preparation #AB.1) with a boronic acid or boronic ester using General Procedure AC

| Boronic Acid or Boronate | Product | Example # | $R_t$ min (Table 2, Method) | m/z ESI + $(M + H)^+$ | Syk $IC_{50}$ |
|---|---|---|---|---|---|
| 4-(Cyclopropanesulfonamidomethyl) phenylboronic acid (prepared using K from 4-aminomethylphenylboronic acid hydrochloride (Combi-Blocks) with cyclopropanesulfonyl chloride (Matrix)) | | AC.1.38 | 1.63 (a) | 382 | B |
| 3-(Methylsulfonyl) phenylboronic acid (Matrix) | | AC.1.39 | 1.58 (a) | 327 | B |
| 4-(N-Cyclopropylsulfonamide) phenylboronic acid pinacol ester (Frontier) | | AC.1.40 | 1.75 (a) | 368 | B |
| 3,4-Dimethoxyphenylboronic acid (Lancaster) | | AC.1.41 | 1.67 (a) | 309 | A |
| 3-Chloro-4-methoxyphenylboronic acid | | AC.1.42 | 2.00 (a) | 313 | B |

TABLE AC.2

Examples prepared from Preparation #1 with a boronic acid or boronate using
General Procedure AC

| Boronic acid or boronate | Product | Example # | $R_t$ min (Table 2, Method) | m/z ESI+ $(M + H)^+$ | Syk $IC_{50}$ |
|---|---|---|---|---|---|
| 5-Methoxy-1-methyl-3-(4,4,5,5-tetramethyl-1,3,2-dioxaborolan-2-yl)-1H-pyrrolo[2,3-c]pyridine [Biopharm] | | AC.2.1 | 1.74 (a) | 333 | A |

TABLE AC.2-continued

Examples prepared from Preparation #1 with a boronic acid or boronate using General Procedure AC

| Boronic acid or boronate | Product | Example # | $R_t$ min (Table 2, Method) | m/z ESI+ (M + H)+ | Syk IC$_{50}$ |
|---|---|---|---|---|---|
| 5-Methoxy-1-methyl-3-(4,4,5,5-tetramethyl-1,3,2-dioxaborolan-2-yl)-1H-pyrrolo[2,3-b]pyridine [Boropharm] | | AC.2.2 | 1.87 (a) | 333 | A |

TABLE AC.3

Examples prepared from 3-bromo-1-cyclohexyl-6-tosyl-6H-imidazo[1,5-a]pyrrolo[2,3-e]pyrazine (Example #2, Step E) with a boronic acid or boronate using General Procedure AC

| Boronic acid or boronate | Product | Example # | $R_t$ min (Table 2, Method) | m/z ESI+ (M + H)+ | Syk IC$_{50}$ |
|---|---|---|---|---|---|
| Methoxyphenylboronic acid | | AC.3.1 | 0.83 (m) | 347 | C |
| Fluorophenylboronic acid | | AC.3.2 | 0.85 (m) | 335.0 | C |
| Acetamidophenylboronic acid | | AC.3.3 | 0.76 (m) | 374.0 | B |

TABLE AC.3-continued

Examples prepared from 3-bromo-1-cyclohexyl-6-tosyl-6H-imidazo[1,5-a]pyrrolo[2,3-e]pyrazine (Example #2, Step E) with a boronic acid or boronate using General Procedure AC

| Boronic acid or boronate | Product | Example # | R$_t$ min (Table 2, Method) | m/z ESI+ (M + H)$^+$ | Syk IC$_{50}$ |
|---|---|---|---|---|---|
| 3-Acetylphenylboronic acid | 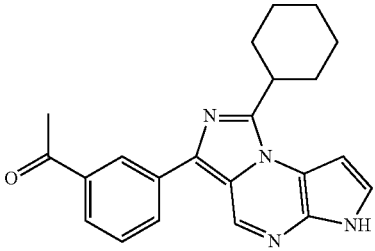 [SMILES: CC(=O)c1cccc(-c2nc(C3CCCCC3)n3c2cnc2[nH]ccc23)c1] | AC.3.4 | 0.88 (m) | 359.0 | B |
| Benzo[b]thiophen-2-ylboronic acid as boronic | 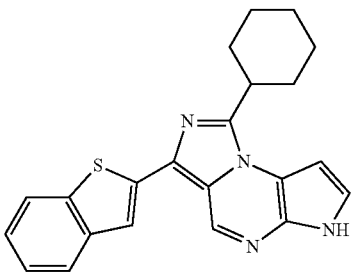 [SMILES: c1ccc2sc(-c3nc(C4CCCCC4)n4c3cnc3[nH]ccc34)cc2c1] | AC.3.5 | 1.01 (m) | 373.0 | ND |
| Isoquinolin-4-ylboronic acidlel | 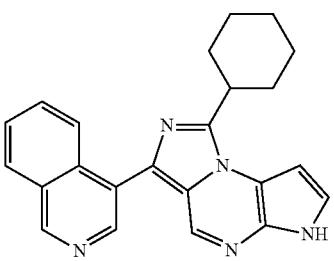 [SMILES: c1ccc2c(-c3nc(C4CCCCC4)n4c3cnc3[nH]ccc34)cncc2c1] | AC.3.6 | 0.80 (m) | 368.0 | ND |
| 4-Acetamidophenylboronic acid | 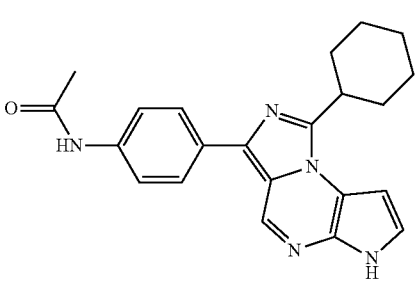 [SMILES: CC(=O)Nc1ccc(-c2nc(C3CCCCC3)n3c2cnc2[nH]ccc23)cc1] | AC.3.7 | 0.73 (m) | 374.0 | B |
| 1-Methyl-1H-indol-5-ylboronic acid | 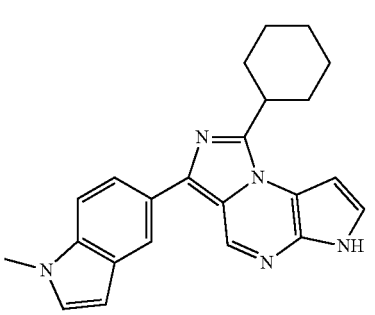 [SMILES: Cn1ccc2cc(-c3nc(C4CCCCC4)n4c3cnc3[nH]ccc34)ccc21] | AC.3.8 | 0.78 (m) | 370.0 | B |

TABLE AC.3-continued

Examples prepared from 3-bromo-1-cyclohexyl-6-tosyl-6H-imidazo[1,5-a]pyrrolo[2,3-e]pyrazine (Example #2, Step E) with a boronic acid or boronate using General Procedure AC

| Boronic acid or boronate | Product | Example # | $R_t$ min (Table 2, Method) | m/z ESI+ (M + H)+ | Syk IC$_{50}$ |
|---|---|---|---|---|---|
| 1-Methyl-1H-pyrazol-4-ylboronic acid | | AC.3.9 | 0.90 (m) | 320.8 | ND |
| Quinolin-3-ylboronic acid | | AC.3.10 | 0.85 (m) | 368.0 | ND |
| 4-tert-Butylphenylboronic acid | | AC.3.11 | 0.94 (m) | 373.1 | ND |
| 4-(2-Cyanopropan-2-yl)phenylboronic acid | | AC.3.12 | 0.87 (m) | 384.0 | ND |
| 4-(Methylcarbamoyl)phenyl-boronic acid | | AC.3.13 | 0.77 (m) | 374.0 | ND |

TABLE AC.3-continued

Examples prepared from 3-bromo-1-cyclohexyl-6-tosyl-6H-imidazo[1,5-a]pyrrolo[2,3-e]pyrazine (Example #2, Step E) with a boronic acid or boronate using General Procedure AC

| Boronic acid or boronate | Product | Example # | R$_t$ min (Table 2, Method) | m/z ESI+ (M + H)$^+$ | Syk IC$_{50}$ |
|---|---|---|---|---|---|
| 4-((4-Methylpiperazin-1-yl)methyl)phenylboronic acid | | AC.3.14 | 0.68 (m) | 429.4 | B |
| 4-Sulfamoylphenylboronic acid | | AC.3.15 | 0.77 (m) | 395.9 | B |
| Pyrazin-2-ylboronic acid | | AC.3.16 | 0.89 (m) | 319.2 | C |
| 4-(2-Methoxyethylcarbamoyl)phenyl-boronic acid | | AC.3.17 | 0.80 (m) | 418.1 | B |
| 4-(Methylsulfonamidomethyl)phenylboronic acid | | AC.3.18 | 0.73 (m) | 424.0 | B |

TABLE AC.3-continued

Examples prepared from 3-bromo-1-cyclohexyl-6-tosyl-6H-imidazo[1,5-a]pyrrolo[2,3-e]pyrazine (Example #2, Step E) with a boronic acid or boronate using General Procedure AC

| Boronic acid or boronate | Product | Example # | $R_t$ min (Table 2, Method) | m/z ESI+ $(M + H)^+$ | Syk $IC_{50}$ |
|---|---|---|---|---|---|
| 4-(2-Acetamidoethyl)phenylboronic acid | | AC.3.19 | 0.74 (m) | 402.0 | B |
| 4-(1-(Hydroxymethyl)cyclopropyl)phenylboronic acid | | AC.3.20 | 0.79 (m) | 387.1 | ND |
| 3-(N-(2-Hydroxyethyl)sulfamoyl)phenylboronic acid | | AC.3.21 | 0.81 (m) | 440 | B |
| 4-(Dimethylcarbamoyl)phenylboronic acid | | AC.3.22 | 0.81 (m) | 388 | B |
| Pyridin-4-ylboronic acid | | AC.3.23 | 0.75 (m) | 318 | B |

TABLE AC.3-continued

Examples prepared from 3-bromo-1-cyclohexyl-6-tosyl-6H-imidazo[1,5-a]pyrrolo[2,3-e]pyrazine (Example #2, Step E) with a boronic acid or boronate using General Procedure AC

| Boronic acid or boronate | Product | Example # | R$_t$ min (Table 2, Method) | m/z ESI+ (M + H)$^+$ | Syk IC$_{50}$ |
|---|---|---|---|---|---|
| Furan-3-ylboronic acid | | AC.3.24 | 0.75 (m) | 307 | ND |
| Pyrimidin-5-ylboronic acid | | AC.3.25 | 0.87 (m) | 319 | ND |
| N-(2-(Dimethylamino)ethyl)-4-(4,4,5,5-tetramethyl-1,3,2-dioxaborolan-2-yl)benzamide | | AC.3.26 | 0.73 (m) | 431 | B |
| m-Tolylboronic acid | | AC.3.27 | 0.85 (m) | 331 | ND |
| Morpholino(4-(4,4,5,5-tetramethyl-1,3,2-dioxaborolan-2-yl)phenyl)methanone | | AC.3.28 | 0.81 (m) | 430 | B |

TABLE AC.3-continued

Examples prepared from 3-bromo-1-cyclohexyl-6-tosyl-6H-imidazo[1,5-a]pyrrolo[2,3-e]pyrazine (Example #2, Step E) with a boronic acid or boronate using General Procedure AC

| Boronic acid or boronate | Product | Example # | R$_t$ min (Table 2, Method) | m/z ESI+ (M + H)$^+$ | Syk IC$_{50}$ |
|---|---|---|---|---|---|
| 4-(N,N-Dimethylsulfamoyl)phenyl-boronic acid [CombiBlocks] | 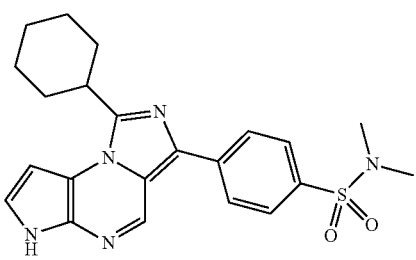 | AC.3.29 | 2.69 (a) | 424 | B |
| 4-(Isopropylsulfonyl)phenyl-boronic acid [CombiBlocks] | 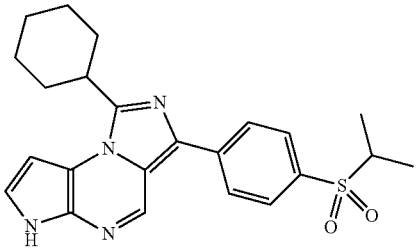 [SMILES: CC(C)S(=O)(=O)c1ccc(-c2nc(C3CCCCC3)n3c2cnc2[nH]ccc23)cc1] | AC.3.30 | 2.69 (a) | 426 | B |
| 4-(Methylsulfonyl)phenylboronic acid [Acros] | 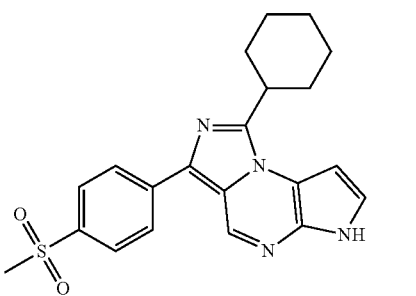 [SMILES: CS(=O)(=O)c1ccc(-c2nc(C3CCCCC3)n3c2cnc2[nH]ccc23)cc1] | AC.3.31 | 2.39 (a) | 395 | A |
| N-(4-(4,4,5,5-Tetramethyl-1,3,2-dioxaborolan-2-yl)phenyl)methanesulfonamide | 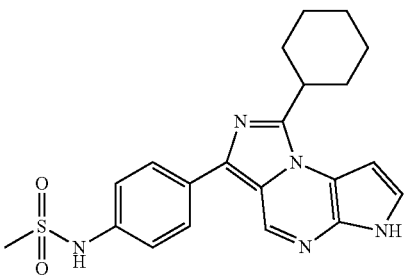 [SMILES: CS(=O)(=O)Nc1ccc(-c2nc(C3CCCCC3)n3c2cnc2[nH]ccc23)cc1] | AC.3.31 | 2.25 (a) | 410 | A |
| p-Tolylboronic Acid | 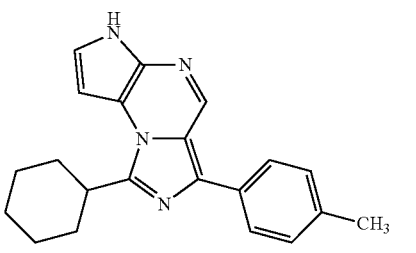 [SMILES: Cc1ccc(-c2nc(C3CCCCC3)n3c2cnc2[nH]ccc23)cc1] | AC.3.32 | 0.83 (m) | 331 | B |

TABLE AC.4

Examples prepared from 3-iodo-6-tosyl-6H-imidazo[1,5-a]pyrrolo[2,3-e]pyrazine (prepared using J.3 from Example #2, Step B with ethyl formate, L.2 with POCl₃, and AB) with a boronate or boronic acid using General Procedure AC

| Boronate/Boronic acid | Product | Example # | R, min (Table 2, Method) | m/z ESI+ (M + H)⁺ | Syk IC₅₀ |
|---|---|---|---|---|---|
| 4-(1-Hydroxy-2-methylpropan-2-yl)phenylboronic acid (prepared using H from 2-(4-chlorophenyl)-2-methylpropan-1-ol [Betapharma] with 4,4,4',4',5,5,5',5'-octamethyl-2,2'-bi(1,3,2-dioxaborolane) | 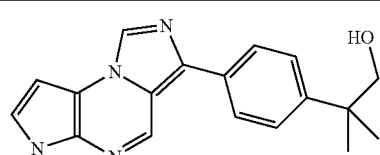 | AC.4.1 | 1.79 (a) | 307 | A |
| (4-(4,4,5,5-Tetramethyl-1,3,2-dioxaborolan-2-yl)phenyl)methanol | 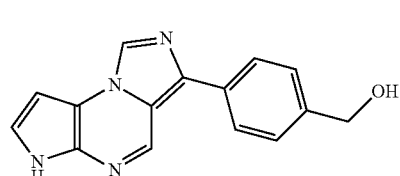 | AC.4.2 | 1.56 (a) | 265 | B |
| 2-Methoxypyridin-4-ylboronic acid | 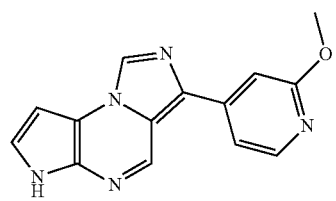 [SMILES: COc1cc(-c2ncn3c2cnc2[nH]ccc23)ccn1] | AC.4.3 | 1.73 (a) | 266 | B |
| 1-(4-(4,4,5,5-Tetramethyl-1,3,2-dioxaborolan-2-yl)pyridin-2-yl)ethanone [Small Molecules Inc.] | 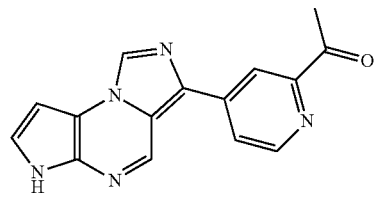 [SMILES: CC(=O)c1cc(-c2ncn3c2cnc2[nH]ccc23)ccn1] | AC.4.4 | 1.70 (a) | 278 | B |
| 2-methyl-4-(4,4,5,5-tetramethyl-1,3,2-dioxaborolan-2-yl)pyridine [Combi Phos] | 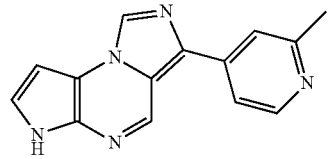 [SMILES: Cc1cc(-c2ncn3c2cnc2[nH]ccc23)ccn1] | AC.4.5 | 1.23 (a) | 250 | B |
| 3-Fluoro-4-(2-hydroxypropan-2-yl)phenylboronic acid [Chemmaker] | 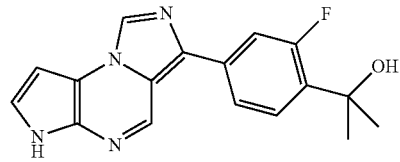 [SMILES: CC(C)(O)c1ccc(-c2ncn3c2cnc2[nH]ccc23)cc1F] | AC.4.6 | 1.81 (a) | 311 | A |
| 4-(Propylcarbamoyl)phenyl-boronic acid (prepared using J.1 from 4-boronobenzoic acid with propan-1-amine) | 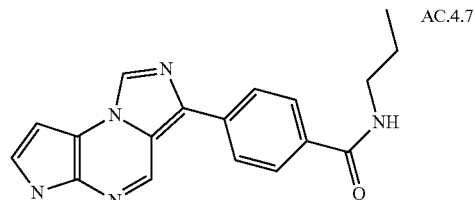 | AC.4.7 | 1.81 (a) | 320 | B |

TABLE AC.4-continued

Examples prepared from 3-iodo-6-tosyl-6H-imidazo[1,5-a]pyrrolo[2,3-e]pyrazine (prepared using J.3 from Example #2, Step B with ethyl formate, L.2 with POCl₃, and AB) with a boronate or boronic acid using General Procedure AC

| Boronate/Boronic acid | Product | Example # | $R_t$ min (Table 2, Method) | m/z ESI+ $(M + H)^+$ | Syk $IC_{50}$ |
|---|---|---|---|---|---|
| 3,4-Dimethoxyphenylboronic acid (Lancaster) | | AC.4.8 | 1.58 (a) | 295 | A |
| 3-Chloro-4-methoxyphenylboronic acid | | AC.4.9 | 1.91 (a) | 299 | A |
| 4-Methoxy-3-methylphenylboronic acid | | AC.4.10 | 1.89 (a) | 279 | A |

TABLE AC.5

Examples prepared from 2-(4-(4,4,5,5-tetramethyl-1,3,2-dioxaborolan-2-yl)phenyl)propan-2-ol (Preparation #H.1) with a heteroaryl halide using general procedure AC

| Heteroaryl Halide | Product | Example # | $R_t$ min (Table 2, Method) | m/z ESI+ $(M + H)^+$ | Syk $IC_{50}$ |
|---|---|---|---|---|---|
| (R)-1-(2-(3-Bromo-6-tosyl-6H-imidazo[1,5-a]pyrrolo[2,3-e]pyrazin-1-yl)pyrrolidin-1-yl)ethanone (prepared using J.1 from Example #2, Step B with N-acetyl-D-proline, L.2 with TFA and TFAA and AB) | | AC.5.1 | 1.69 (b) | 404 | B |
| N-((3R,5R)-5-(3-Bromo-6-tosyl-6H-imidazo[1,5-a]pyrrolo[2,3-e]pyrazin-1-yl)-1-(cyclopropylsulfonyl)pyrrolidin-3-yl)acetamide (prepared 4-N-Boc-4(R)-amino-pyrrolidine-2(R)-carboxylic acid methyl ester hydrochloride (APAC), with cyclopropyl sulfinyl chloride, V.1, J.1 with Example #2, Step B) | | AC.5.2 | 1.56 (b) | 523 | B |

TABLE AC.5-continued

Examples prepared from 2-(4-(4,4,5,5-tetramethyl-1,3,2-dioxaborolan-2-yl)phenyl)propan-2-ol (Preparation #H.1) with a heteroaryl halide using general procedure AC

| Heteroaryl Halide | Product | Example # | R, min (Table 2, Method) | m/z ESI+ (M + H)+ | Syk IC$_{50}$ |
|---|---|---|---|---|---|
| 3-Bromo-1-(2-methylpyridin-3-yl)-6-tosyl-6H-imidazo[1,5-a]pyrrolo[2,3-e]pyrazine (prepared using J.1 from Example #2, Step B with 2-methylnicotinic acid, L.2 with POCl$_3$ and AJ) | | AC.5.3 | 1.72 (a) | 384 | B |
| 3-Iodo-8-(1,2,3,6-tetrahydropyridin-4-yl)-6-tosyl-6H-imidazo[1,5-a]pyrrolo[2,3-e]pyrazine (prepared using P.3 from Preparation #19, J.3 with ethyl formate, L.2 with POCl$_3$, D with tert-butyl 4-(4,4,5,5-tetramethyl-1,3,2-dioxaborolan-2-yl)-5,6-dihydropyridine-1(2H)-carboxylate [Carbocore], AB and P.3) | | AC.5.4 | 1.48 (a) | 374 | C |
| 3-(3-Bromo-6-tosyl-6H-imidazo[1,5-a]pyrrolo[2,3-e]pyrazin-1-yl)propan-1-amine (prepared using J.1 from Example #2, Step B with 4-(tert-butoxycarbonylamino)butanoic acid, L.1 with mercury(II) trifluoroacetate, AB and P.3) | | AC.5.5 | 1.16 (a) | 350 | B |
| (3-Bromo-6-tosyl-6H-imidazo[1,5-a]pyrrolo[2,3-e]pyrazin-1-yl)methanamine (prepared using J.1 from Example #2, Step B with 2-(tert-butoxycarbonylamino)acetic acid, L.1 with mercury(II) trifluoroacetate, AB and P.3) | | AC.5.6 | 1.08 (a) | 322 | C |
| N-((3-Bromo-6-tosyl-6H-imidazo[1,5-a]pyrrolo[2,3-e]pyrazin-1-yl)methyl)-2-hydroxyacetamide (prepared using J.1 from Example #2, Step B with 2-(tert-butoxy carbonylamino)acetic acid, L.1 with mercury(II) trifluoroacetate, AB, P.3 and J.1 with 2-hydroxyacetic acid | | AC.5.7 | 1.29 (a) | 380 | B |

TABLE AC.5-continued

Examples prepared from 2-(4-(4,4,5,5-tetramethyl-1,3,2-dioxaborolan-2-yl)phenyl)propan-2-ol (Preparation #H.1) with a heteroaryl halide using general procedure AC

| Heteroaryl Halide | Product | Example # | R<sub>t</sub> min (Table 2, Method) | m/z ESI+ (M + H)<sup>+</sup> | Syk IC<sub>50</sub> |
|---|---|---|---|---|---|
| 3-Bromo-1-cyclopropyl-6H-imidazo[1,5-a]pyrrolo[2,3-e]pyrazine (Prepared using J.2 from Example #2, Step B with cyclopropanecarbonyl chloride, L.2 with POCl<sub>3</sub> and AB) | | AC.5.8 | 1.85 (a) | 333 | A |
| (R)-1-(2-(3-Bromo-6-tosyl-6H-imidazo[1,5-a]pyrrolo[2,3-e]pyrazin-1-yl)pyrrolidin-1-yl)ethanone (prepared using J.1 from Example #2, Step B with N-acetyl-L-proline (Sigma), L.2 with TFA and TFAA and AB) | | AC.5.9 | 1.69 (b) | 404 | C |

TABLE AC.6

Examples prepared from 2-(4-(1-bromo-6-tosyl-6H-imidazo[1,5-a]pyrrolo[2,3-e]pyrazin-3-yl)phenyl)propan-2-ol (Preparation #AI.1) using General Procedure AC

| Boronate/Boronic acid | Product | Example # | R<sub>t</sub> min (Table 2, Method) | m/z ESI+ (M + H)<sup>+</sup> | Syk IC<sub>50</sub> |
|---|---|---|---|---|---|
| Pyridin-3-ylboronic acid [Digital Specialties] | | AC.6.1 | 1.73 (a) | 370 | A |

General Procedure AD: Conversion of a 6H-imidazo[1,5-a]pyrrolo[2,3-e]pyrazine to a 8-halo-6H-imidazo[1,5-a]pyrrolo[2,3-e]pyrazine To a mixture of 6H-imidazo[1,5-a]pyrrolo[2,3-e]pyrazine (1 equiv) in a solvent such as DMF, DCE, DCM, 1,4-dioxane, Et<sub>2</sub>O or THF (preferably DCM or THF) at about −40° C. to 25° C. (preferably about −20° C. to −10° C.) is added a halogenating agent (such as NBS, NIS, NCS, Br<sub>2</sub>, or pyridinium tribromide, preferably NBS or NIS; 0.8 to 1.2 equiv, preferably 0.8 to 1.0 equiv). The mixture is stirred at about −40° C. to 25° C. (preferably about −20° C. to −10° C.) for about 5 min to 2 h (preferably about 15 to 45 min). The mixture is optionally concentrated in vacuo to give the targeted compound or optionally diluted with an appropriate solvent (such as water, EtOAc, 1,4-dioxane, THF, MeCN, DCM, Et<sub>2</sub>O, MeOH, or EtOH) and then the targeted compound is collected by filtration. The mixture is optionally filtered through a media (such as silica gel or Celite®) which is rinsed with an appropriate solvent (such as water, EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure AD

Preparation #AD.1.1: 2-(4-(8-Bromo-1-methyl-6-(triisopropylsilyl)-6H-imidazo[1,5-a]pyrrolo[2,3-e]pyrazin-3-yl)phenyl)propan-2-ol

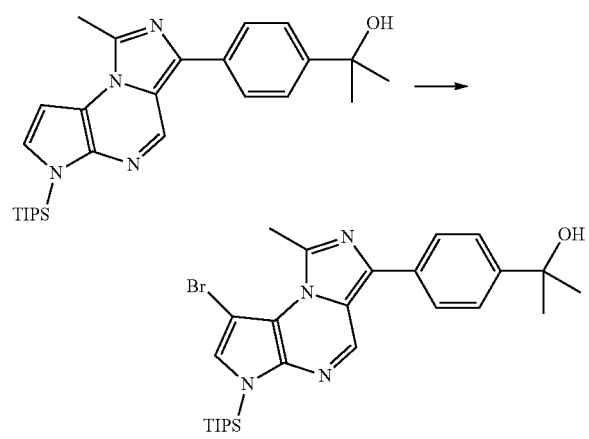

To a solution of 2-(4-(1-methyl-6-(triisopropylsilyl)-6H-imidazo[1,5-a]pyrrolo[2,3-e]pyrazin-3-yl)phenyl)propan-2-ol (1.5 g, 3.2 mmol, Preparation #AX.1) in DCM (32.4 ml) at about −20° C. was added NBS (0.46 g, 2.6 mmol). The mixture was stirred at about −20° C. for about 40 min. The mixture was diluted with DCM (100 mL) and washed with saturated aqueous NaHCO$_3$ (75 mL). The organic phase was dried over Na$_2$SO$_4$, filtered and concentrated in vacuo. The residue was purified by flash chromatography (120 g silica gel column; 0 to 50% EtOAc/heptane) to give 2-(4-(8-bromo-1-methyl-6-(triisopropylsilyl)-6H-imidazo[1,5-a]pyrrolo[2,3-e]pyrazin-3-yl)phenyl)propan-2-ol (0.52 g, 29%). LC/MS (Table 2, Method h) R$_t$=2.51 min; MS m/z 543 (M+H)$^+$.

General Procedure AE: Cyanation of an Aryl Halide

To a solution of a heteroaryl halide (preferably 1 equiv) in an organic solvent (such as 1,4-dioxane, NMP, DMA or DMF, preferably DMA) is added a cyanide salt (such as KCN or Zn(CN)$_2$, preferably Zn(CN)$_2$; 0.5 to 4 equiv, preferably 0.5 to 2 equiv), a palladium catalyst (such as Pd(Ph$_3$P)$_4$, PdCl$_2$(dppf) or Pd(OCOCF$_3$)$_2$, preferably Pd(OCOCF$_3$)$_2$; 0.01 to 1 equiv, preferably 0.02 to 1 equiv). Additives such as Rac-2-(di-butylphosphino)-1-1'-binapthyl (0.02 to 2 equiv, preferably 0.3 to 0.8 equiv), zinc (0.1 to 1 equiv, preferably 0.1 to 0.5 equiv), copper(I) iodide (1 to 4 equiv, preferably 1 to 2 equiv) and/or 18-crown-6 (0.01 to 1.0 equiv, preferably 0.06 to 0.07 equiv) may optionally be added. The mixture is heated either thermally at about 50 to 110° C. (preferably about 50 to 95° C.) for about 1 to 24 h (preferably about 5 to 20 h) or in a microwave at about 90 to 200° C. (preferably about 100 to 150° C.) for about 0.5 to 2 h (preferably about 0.5 to 1 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AE

Preparation #AE.1:
5-Tosyl-5H-pyrrolo[2,3-b]pyrazine-2-carbonitrile

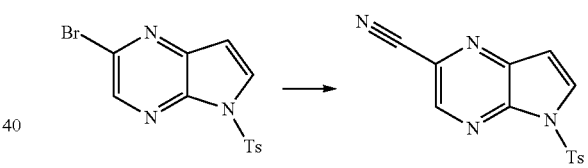

A 3 L round bottom flask was put through 5 evacuation/purge cycles with argon. The flask was charged with 2-bromo-5-tosyl-5H-pyrrolo[2,3-b]pyrazine (75 g, 213 mmol, Syngene), zinc (2.65 g, 40.5 mmol), racemic-2-(di-t-butylphosphino)-1,1'-binaphthyl (7.47 g, 18.7 mmol) and palladium(II) trifluoroacetate (3.04 g, 9.16 mmol) and the flask was purged with argon for about 30 min., followed by addition of DMA (1.5 L) which had been purged for about 30 min. with argon. The mixture was stirred at about 50° C. for about 30 min. while bubbling argon through the mixture. Zn(CN)$_2$ (14.0 g, 119 mmol) was added portion-wise to the solution over about 15 min. The temperature was increased to about 95° C. and stirred for about 18 h under an argon atmosphere. The mixture was cooled to ambient temperature and then added to water at about 10° C. (10.5 L). The slurry was stirred for about 30 min. at about 10° C. and the precipitate was isolated by filtration, washed with water (1 L) and dried in vacuo overnight. The crude material was triturated for about 3 h with 4:1 MeOH/DCM (600 mL). The solid was filtered, washed with MeOH (250 mL) and the solid was dried in vacuo to constant mass to give 5-tosyl-5H-pyrrolo[2,3-b]pyrazine-2-carbonitrile (45.6 g, 70%): LC/MS (Table 2, Method a) R$_t$=2.44 min.; MS m/z: 299.16 (M+H)$^+$

TABLE AE.1

Examples prepared from an aryl bromide using General Procedure AE

| Aryl bromide | Product | Example # | R$_t$ min (Table 2, Method) | m/z ESI+ (M + H)$^+$ | Syk IC$_{50}$ |
|---|---|---|---|---|---|
| 2-(4-(8-Bromo-1-(tetrahydro-2H-pyran-4-yl)-6H-imidazo[1,5-a]pyrrolo[2,3-e]pyrazin-3-yl)phenyl)propan-2-ol (prepared using AD from Preparation #N.1.84) | (structure) | AE.1.1 | 1.90 (a) | 402 | C |

General Procedure AF: Addition of a Grignard Reagent to a Nitrile

To a stirred solution or suspension of the aryl nitrile (preferably 1.0 equiv) in an organic solvent (such as THF, 1,4-dioxane, toluene or Et$_2$O, preferably THF) is optionally added molecular sieves (4A, beads, 8-12 mesh). The mixture is stirred at rt for about 15 min to 24 h (preferably 1 h). A solution of a Grignard reagent (1.0 equiv to 2.0 equiv, preferably 1.2 equiv) in an organic solvent (such as THF or Et$_2$O, preferably THF) is added dropwise at about 0° C. to 40° C. (preferably 10° C. to 25° C.). The mixture is stirred at rt for about 30 min to 16 h (preferably about 1 to 2 h). The mixture is concentrated in vacuo to give the targeted compound, which is used immediately in the next step.

Illustration of General Procedure AF

Preparation #AF.1: (4-Methoxyphenyl)(5-tosyl-5H-pyrrolo[2,3-b]pyrazin-2-yl)methanimine

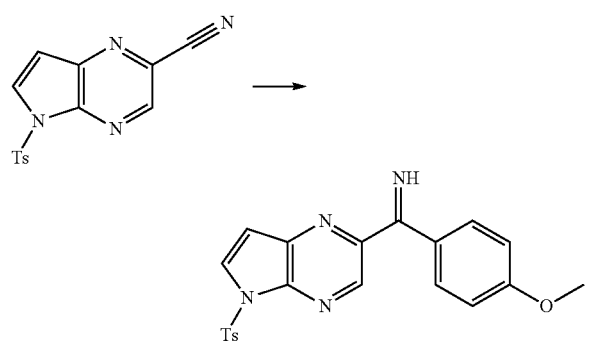

To a suspension of 5-tosyl-5H-pyrrolo[2,3-b]pyrazine-2-carbonitrile (0.500 g, 1.68 mmol) in anhydrous THF (3.35 mL) was added molecular sieves (4A, beads, 8-12 mesh, 0.643 g). The mixture was stirred at rt for about 40 min. A solution of (4-methoxyphenyl)magnesium bromide (0.5 M in THF, 4.12 mL, 2.01 mmol,) was added dropwise over about 3 min. The mixture was stirred at rt for about 2 h. The mixture was concentrated in vacuo to give (4-methoxyphenyl)(5-tosyl-5H-pyrrolo[2,3-b]pyrazin-2-yl)methanimine which was assumed to be quantitative and used immediately in the next step: LC/MS (Table 2, Method b) R$_f$=2.25 min; MS m/z: 407 (M+H)$^+$.

General Procedure AG: Reduction of an Imine to an Amine

To a flask containing an imine (1 equiv) in an organic solvent (such as THF, MeOH, 1,4-dioxane, EtOH, or n-PrOH, preferably MeOH) is added a reducing agent (such as NaBH(OAc)$_3$, NaBH$_4$, or NaB(CN)H$_3$, preferably NaBH$_4$; 0.5 to 2.0 equiv, preferably 1.0 equiv). The mixture is stirred for about 5 min to 48 h (preferably about 0.5 to 1 h) at about 0 to 30° C. (preferably about 25° C.). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure AG

Preparation #AG.1: (4-Methoxyphenyl)(5-tosyl-5H-pyrrolo[2,3-b]pyrazin-2-yl)methanamine

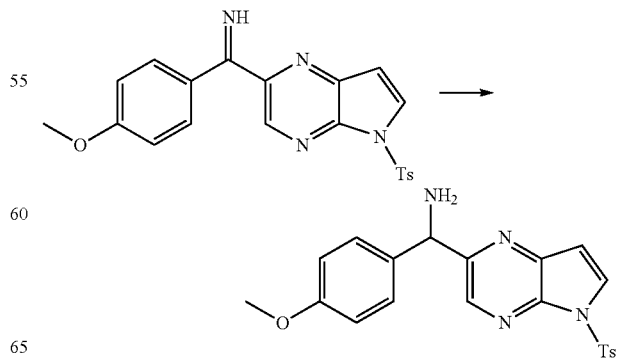

To a flask was added (4-methoxyphenyl)(5-tosyl-5H-pyrrolo[2,3-b]pyrazin-2-yl)methanimine (1.36 g, 3.35 mmol, Preparation #AF.1) and NaBH$_4$ (0.127 g, 3.35 mmol) in MeOH (20 mL). The mixture was stirred for about 30 min at rt. The mixture was concentrated in vacuo, DCM (10 mL) was added to the residue and the insoluble material was removed via filtration. The filtrate was loaded on a 40 g silica column and product was eluted with 50 to 100% EtOAc/DCM to provide (4-methoxyphenyl)(5-tosyl-5H-pyrrolo[2,3-b]pyrazin-2-yl)methanamine (0.595 g, 44%): $^1$H NMR (d-DMSO) δ 8.56 (s, 1H), 8.29-8.24 (m, 1H), 8.02-7.96 (m, 2H), 7.43 (dd, J=8.3, 0.9 Hz, 2H), 7.36-7.31 (m, 2H), 6.96 (d, J=4.1 Hz, 1H), 6.84 (m, 2H), 5.22 (s, 1H), 3.68 (s, 3H), 2.33 (s, 3H).

General Procedure AH: Reductive Amination of an Aldehyde or Ketone

An aldehyde or ketone (preferably 1.0 equiv) and an amine (1.0 to 2.2 equiv) are added in an organic solvent or mixture of organic solvents (such as DCM, DCE or MeOH, or a mixture of DCE and MeOH, preferably DCE) at P. AcOH (0.1 equiv to 5.0 equiv) is optionally added. The mixture is stirred at rt for about 15 min to 96 h. A reducing agent (such as NaBH(OAc)$_3$, Na(CN)BH$_3$, Na(CN)BH$_4$, MP-Cyanoborohydride from Biotage™, 0.5 to 5.0 equiv, preferably 3.0 equiv), is added as solid or as a solution in an organic solvent (as DCM, DCE or MeOH, or a mixture of DCE and MeOH). The mixture is stirred at rt for about 30 min to 72 h. The crude mixture may be optionally partitioned between water and an organic solvent (such as EtOAc, Et$_2$O or DCM). The organic layer is isolated and may be optionally washed with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl or Na$_2$SO$_3$). The organic solution may then be optionally dried with a drying agent (such as MgSO$_4$ or Na$_2$SO$_4$), filtered and concentrated in vacuo to give the targeted compound.

Illustration of General Procedure AH

Preparation #AH.1: N-((3-(4-Methoxyphenyl)-6-tosyl-6H-imidazo[1,5-a]pyrrolo[2,3-e]pyrazin-1-yl)methyl)cyclopropanamine

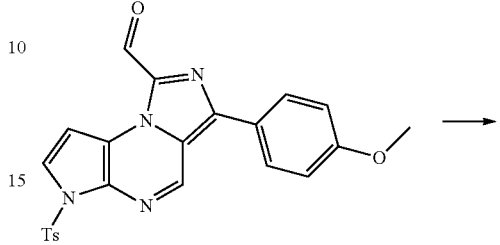

3-(4-Methoxyphenyl)-6-tosyl-6H-imidazo[1,5-a]pyrrolo[2,3-e]pyrazine-1-carbaldehyde (0.075 g, 0.17 mmol), AcOH (0.048 mL, 0.84 mmol), and cyclopropanamine (0.026 mL, 0.37 mmol) were added in DCE (1.68 mL). The mixture was stirred at rt for 30 min. MP-Cyanoborohydride (0.23 g, 0.50 mmol, 2.15 mmol/g, Biotage™) was added in one portion. The mixture was stirred at 25° C. for 72 h. The mixture was purified directly by flash chromatography (40 g silica gel column, MeOH/DCM 0% to 10%) to give N-((3-(4-methoxyphenyl)-6-tosyl-6H-imidazo[1,5-a]pyrrolo[2,3-e]pyrazin-1-yl)methyl)cyclopropanamine (0.050 g, 61%): LC/MS (Table 2, Method c) R$_f$=1.49 min; MS m/z: 488 (M+H)$^+$.

TABLE AH.1

Examples prepared from 4-(1-methyl-6H-imidazo[1,5-a]pyrrolo[2,3-e]pyrazin-3-yl)benzaldehyde (Preparation #AC.1) with an amine using General Procedure AH

| Amine | Product | Example # | R$_f$ min (Table 2, Method) | m/z ESI+ (M + H)$^+$ | Syk IC$_{50}$ |
|---|---|---|---|---|---|
| Morpholine | | AH.1.1 | 1.70 (a) | 348 | B |

General Procedure AI: Halogenation of a 6H-imidazo[1,5-a]pyrrolo[2,3-e]pyrazine to Give a 1-halo-6H-imidazo[1,5-a]pyrrolo[2,3-e]pyrazine The 6H-imidazo[1,5-a]pyrrolo[2,3-e]pyrazine (1 equiv) is dissolved or suspended in an suitable solvent such as DMF, DCE, DCM, 1,4-dioxane, Et$_2$O or THF (preferably DMF). The mixture is treated with brominating agent (such as NBS, bromine or pyridinium tribromide, preferably NBS; 0.9 to 1.1 equiv, preferably 0.95 to 1.05 equiv). The mixture is stirred at about 20 to 35° C. (preferably about 25° C. to 30° C.) for about 30 min to 3 h (preferably about 1 h). The mixture is optionally concentrated in vacuo to give the targeted compound or optionally diluted with an appropriate solvent (such as water, EtOAc, 1,4-dioxane, THF, MeCN, DCM, Et$_2$O, MeOH, or EtOH) and the targeted compound collected by filtration. The mixture is optionally filtered through a media (such as silica gel or Celite®) which is rinsed with an appropriate solvent (such as water, EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure AI

Preparation #AI.1: 2-(4-(1-Bromo-6-tosyl-6H-imidazo[1,5-a]pyrrolo[2,3-e]pyrazin-3-yl)phenyl)propan-2-ol

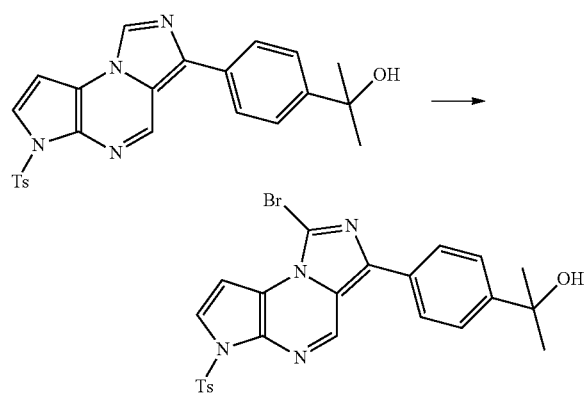

2-(4-(6-Tosyl-6H-imidazo[1,5-a]pyrrolo[2,3-e]pyrazin-3-yl)phenyl)propan-2-ol (0.285 g, 0.638 mmol, prepared using J.3 from Example #2, Step B with ethyl formate, L.2 with POCl$_3$, AB and D with Preparation #H.1) was dissolved in DMF (3 mL) then treated with NBS (0.114 g, 0.638 mmol). The mixture was stirred for about 15 min then diluted with water (20 mL). The solid was collected by filtration then washed with water (5 mL). The material was dried under vacuum at about 70° C. to a constant weight to give 2-(4-(1-bromo-6-tosyl-6H-imidazo[1,5-a]pyrrolo[2,3-e]pyrazin-3-yl)phenyl)propan-2-ol (0.285 g, 85%): LC/MS (Table 2, Method b) R$_t$=2.58 min; MS m/z 527 (M+H)$^+$.

General Procedure AJ: Halogenation of a 1,6-dihydropyrazolo[3,4-d]pyrrolo[2,3-b]pyridine to give a 3-halo-1,6-dihydropyrazolo[3,4-d]pyrrolo[2,3-b]pyridine To a solution of a 1,6-dihydropyrazolo[3,4-d]pyrrolo[2,3-b]pyridine (preferably 1 equiv) in an organic solvent (such as DCM, DMF, MeOH or THF, preferably THF) is added a halogenating reagent (such as bromine, pyridinium hydrobromide perbromide, NBS, iodine, NIS, NCS preferably NBS; 0.8 to 3 equiv, preferably 1 to 2 equiv). The reaction is stirred at about −20 to 150° C. (preferably about −20 to 60° C.) for about 10 min to 48 h (preferably about 10 min to 24 h). If the reaction has not proceeded to completion as monitored by LC/MS, HPL or TLC, additional NBS (0.1 0 2.0 equiv) may be added until the reaction does not proceed any further. The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AJ

Preparation #AJ.1: 3-Bromo-8-ethyl-1-methyl-6-tosyl-1,6-dihydropyrazolo[3,4-d]pyrrolo[2,3-b]pyridine

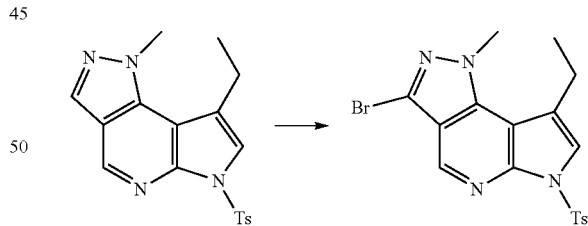

NBS (0.708 g, 3.98 mmol) was added to a solution of 8-ethyl-1-methyl-6-tosyl-1,6-dihydropyrazolo[3,4-d]pyrrolo[2,3-b]pyridine (1.41 g, 3.98 mmol, Preparation #2, Step F) in THF (60 mL). The mixture was allowed to stir at rt. After 16 h additional NBS (0.106 g, 0.597 mmol) was added and reaction was stirred for about 3 h, then another portion of NBS (0.142 g, 0.796 mmol) was added. After another 1 h three equal portions of NBS (0.213 g, 1.19 mmol) were added over about 6 h. The mixture was then diluted with saturated aqueous Na$_2$S$_2$O$_3$ (50 mL) and extracted with EtOAc (2×20 mL). The combined organic layers were dried over MgSO$_4$, filtered and concentrated under reduced pressure. The residue was suspended in Et$_2$O (10 mL) and sonicated for about 3 min.

The precipitate was collected by filtration, washed with Et₂O (10 mL) and dried in a vacuum oven at about 60° C. for about 3 h to give 3-bromo-8-ethyl-1-methyl-6-tosyl-1,6-dihydropyrazolo[3,4-d]pyrrolo[2,3-b]pyridine (1.3 g, 75%): LC/MS (Table 2, Method c) R$_t$=1.58 min.; MS m/z: 433 (M+H)⁺.

General Procedure AK: Halogenation of a 1,6-dihydropyrazolo[3,4-d]pyrrolo[2,3-b]pyridine to give an 8-halo-1,6-dihydropyrazolo[3,4-d]pyrrolo[2,3-b]pyridine To a mixture of 1,6-dihydropyrazolo[3,4-d]pyrrolo[2,3-b]pyridine (1 equiv) a solvent such as DMF, DCM, or THF (preferably DMF) at about 0° C. to 60° C. (preferably about 15 to 50° C.) is added a halogenating agent (such as NBS, NIS, NCS, Br₂, or pyridinium tribromide preferably NBS or NIS; 0.8 to 1.2 equiv, preferably 0.8 to 1.0 equiv). The mixture is stirred at about 0° C. to 60° C. (preferably about 15 to 50° C.) for about 1 to 24 h (preferably about 8 to 16 h). Optionally, additional halogenating agent (such as NBS, NIS, NCS, Br₂, or pyridinium tribromide preferably NBS or NIS; 0.2 to 2 equiv, preferably 0.5 equiv) may be added and the mixture stirred at about 0° C. to 60° C. (preferably about 15 to 50° C.) for about 1 to 6 h (preferably about 3 h). The mixture is optionally diluted with an appropriate solvent such as water and the targeted compound collected by filtration. The mixture is optionally concentrated in vacuo to give the targeted compound or optionally diluted with an appropriate solvent (such as water, EtOAc, 1,4-dioxane, THF, MeCN, DCM, Et₂O, MeOH, or EtOH) and the targeted compound collected by filtration. The mixture is optionally filtered through a media (such as silica gel or Celite®) which is rinsed with an appropriate solvent (such as water, EtOAc, 1,4-dioxane, THF, MeCN, DCM, Et₂O, MeOH, or EtOH) and then optionally concentrated in vacuo to give a residue. Either the residue or the solution may be optionally partitioned between water and an organic solvent (such as EtOAc, Et₂O or DCM). The organic layer is isolated and may be optionally washed in no particular order with water, and/or aqueous solutions containing an acid (such as HCl, AcOH or NH₄Cl), and/or aqueous solutions containing a base (such as NaHCO₃, Na₂CO₃, NaOH, KOH or NH₄OH), and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the targeted compound.

Illustration of General Procedure AK

Example #AK.1

8-Bromo-3-(4-methoxyphenyl)-1-methyl-1,6-dihydropyrazolo[3,4-d]pyrrolo[2,3-b]pyridine

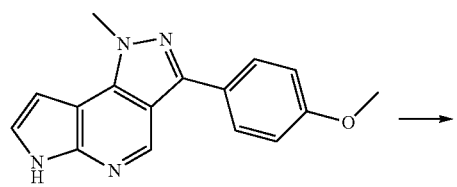

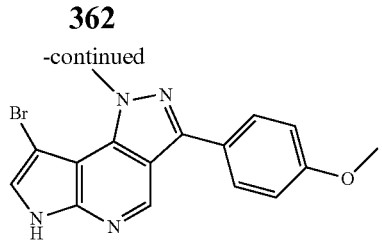

To a solution of 3-(4-methoxyphenyl)-1-methyl-1,6-dihydropyrazolo[3,4-d]pyrrolo[2,3-b]pyridine (0.264 g, 0.949 mmol; Example #AU.1.1) in DMF (3 mL) was added NBS (0.169 g, 0.949 mmol). The mixture was allowed to stir at about rt for about 16 h. Additional NBS (0.085 mg, 0.478 mmol) was added and the mixture was heated to about 50° C. for about 3 h. The mixture was purified by flash chromatography (40 g silica gel column, 10 to 100% EtOAc/heptane) to give 8-bromo-3-(4-methoxyphenyl)-1-methyl-1,6-dihydropyrazolo[3,4-d]pyrrolo[2,3-b]pyridine (0.150 g, 44%). LC/MS (Table 2, Method a) R$_t$=2.35 min.; MS m/z: 357 (M+H)⁺. Syk IC₅₀=A.

General Procedure AM: Formation of a 5-((2-(trimethylsilyl)ethoxy)methyl)-5H-pyrrolo[2,3-b]pyrazine from a 3-((aryl)ethynyl)pyrazin-2-amine To a flask containing an alkyne in a solvent (such as NMP, DMF, DMA, preferably DMF or NMP) was added a base (such as NaH, KOt-Bu, NaOH, KOH, NaOt-Bu, preferably NaH or KOt-Bu; 0.9 to 2.0 equiv, preferably 0.9 to 1.2 equiv) either in portions or all at once. The reaction mixture is stirred for about 30 min to 24 h (preferably about 1 to 3 h) at about −10° C. to 40° C. (preferably 0 to 20° C.). Optionally, more base (0.1 to 1.0 equiv, preferably 0.1 to 0.3 equiv) is added and the reaction mixture is stirred for about 30 min to 12 h (preferably about 1 to 3 h) at about −10° C. to 45° C. (preferably 0 to 20° C.). SEMCl (1 to 3 equiv, preferably 1.5 equiv) is then added to the mixture. The mixture is stirred at about 0 to 25° C. (preferably about 20° C.) for about 5 min to 24 h (preferably about 15 min to 4 h). The mixture is then optionally poured slowly into ice water and stirred to provide a suspension. The solids are optionally collected by filtration and dried to provide the target compound. Alternatively, the mixture is optionally filtered through a media (such as silica gel or Celite®) which is rinsed with an appropriate solvent (such as EtOAc, 1,4-dioxane, THF, MeCN, DCM, Et₂O, MeOH, or EtOH) and then optionally concentrated in vacuo to give a residue. Alternatively, optionally the mixture is optionally concentrated in vacuo to give a residue. Either the residue or the reaction mixture may be optionally partitioned between water and an organic solvent (such as EtOAc, Et₂O or DCM). The organic layer is isolated and may be optionally washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the target compound.

Illustration of General Procedure AM

Preparation #AM.1: 2-Bromo-6-(4-methoxyphenyl)-5-((2-(trimethylsilyl)ethoxy)methyl)-5H-pyrrolo[2,3-b]pyrazine

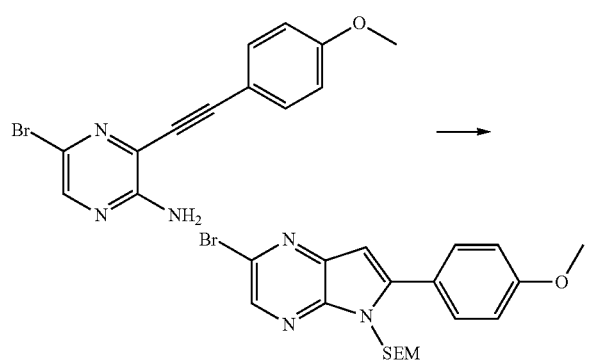

To a round bottom flask was added 5-bromo-3-((4-methoxyphenyl)ethynyl)pyrazin-2-amine (11.9 g, 39.1 mmol, prepared using A from 1-ethynyl-4-methoxybenzene with 3,5-dibromopyrazin-2-amine), DMF (98 mL) and NaH (60% in mineral oil) (2.03 g, 50.8 mmol). The reaction mixture was stirred at room temperature for about 2 h and then 2-(trimethylsilyl)ethoxymethyl chloride (7.63 mL, 43.0 mmol) was added. The reaction mixture was stirred at rt for about 2 h. To the reaction mixture was added NaH (60% in mineral oil) (0.469 g, 19.55 mmol). The reaction mixture was stirred for about 24 h at rt. The reaction mixture was quenched with water (400 mL) and extracted with EtOAc (3×250 mL). The organic layer was washed with brine (250 mL), dried with MgSO$_4$, filtered and concentrated in vacuo. The crude material was purified by flash chromatography (300 g Silicycle® column, DCM/MeOH 1:0 to 10:1) to give the title compound (14.3 g; 84%): LC/MS (Table 2, Method b) R$_t$=3.11 min; MS m/z 436.2 (M+H)$^+$.

General Procedure AN: Hydrolysis of an Ester to a Carboxylic Acid Under Basic Conditions and Removal of a Tosyl Group from an N-Tosyl Protected Heteroaryl Ring To a flask containing a compound with and ester functionality and a tosyl-protected heteroaromatic ring (1 equiv) either neat or in an organic solvent (such as 1,4-dioxane, MeOH, or THF/MeOH, preferably 1,4-dioxane) is added a base or combination of bases (such as aqueous or solid Na$_2$CO$_3$, KOH, Cs$_2$CO$_3$, K$_2$CO$_3$, NaOH or LiOH, preferably LiOH, or NaOH; 1 to 10 equiv, preferably 5 to 10 equiv). The mixture is stirred at about 0 to 100° C. (preferably about 40 to 85° C.) for about 1 to 48 h (preferably about 1 to 24 h). Optionally, more base is added (such as aqueous or solid Na$_2$CO$_3$, KOH, Cs$_2$CO$_3$, K$_2$CO$_3$, NaOH or LiOH, preferably LiOH or NaOH, 1 to 10 equiv, preferably 2 to 6 equiv) and the mixture is stirred at about 0 to 100° C. (preferably about 10 to 100° C.) for about 1 to 48 h (preferably about 4 to 24 h). The mixture is then acidified with the addition of a suitable aqueous acid (such as aqueous HCl or AcOH). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure AN

Example #AN.1

1-Methyl-3-(1-methyl-1,6-dihydropyrazolo[3,4-d]pyrrolo[2,3-b]pyridin-7-yl)-1H-indole-5-carboxylic acid

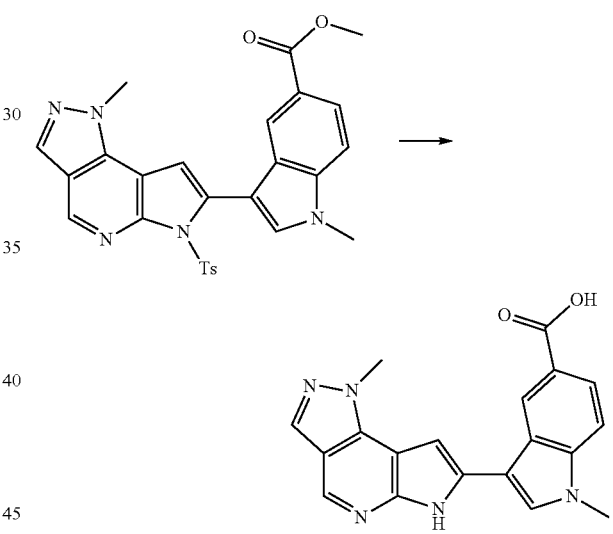

To a flask was added methyl 1-methyl-3-(1-methyl-6-tosyl-1,6-dihydropyrazolo[3,4-d]pyrrolo[2,3-b]pyridin-7-yl)-1H-indole-5-carboxylate (0.42 g, 0.82 mmol, prepared using D from Preparation #1 with methyl 1-methyl-3-(4,4,5,5-tetramethyl-1,3,2-dioxaborolan-2-yl)-1H-indole-5-carboxylate [Preparation #19]) and NaOH (0.30 g, 7.5 mmol) in 1,4-dioxane (10 mL) and water (2 mL). The mixture was heated to about 85° C. After about 1 h, LiOH (0.196 g, 8.18 mmol) was added and heating was continued at about 100° C. for about 5 h. The mixture was cooled and concentrated under reduced pressure to remove most of the organics. The mixture was diluted with water (30 mL) then adjusted to about pH 4 with AcOH. The mixture was filtered and the solids washed with water (5 mL). The solids were dried to a constant weight under vacuum at about 60° C. to give 1-methyl-3-(1-methyl-1,6-dihydropyrazolo[3,4-d]pyrrolo[2,3-b]pyridin-7-yl)-1H-indole-5-carboxylic acid the title compound (0.17 g, 60%): LC/MS (Table 2, Method a) R$_t$=1.73 min; MS m/z 346 (M+H)$^+$. Syk IC$_{50}$=A.

TABLE AN.1

Examples prepared from an ester containing an N-tosyl protected heteroaromatic ring with NaOH using General Procedure AN

| Ester | Product | Example # | R, min (Table 2, Method) | m/z ESI+ (M + H)+ | Syk IC$_{50}$ |
|---|---|---|---|---|---|
| Methyl 3-(4-methoxyphenyl)-6-tosyl-6H-imidazo[1,5-a]pyrrolo[2,3-e]pyrazine-1-carboxylate (prepared using J.2 from Preparation #AF.1 with mono-methyl oxalyl chloride and L.1 with mercury(II)trifluoroacetate) | | AN.1.1 | 1.53 (a) | 309 | B |
| Methyl 2-(2-(1-methyl-6-tosyl-1,6-dihydropyrazolo[3,4-d]pyrrolo[2,3-b]pyridin-7-yl)-1H-pyrrol-1-yl)acetate (prepared using D from Preparation #1 with 1-(tert-butoxycarbonyl)-1H-pyrrol-2-ylboronic acid, P.1, U with methyl 2-bromoacetate) | | AN.1.2 | 1.45 (a) | 296 | D |
| Methyl 1-methyl-3-(1-methyl-6-tosyl-1,6-dihydropyrazolo[3,4-d]pyrrolo[2,3-b]pyridin-7-yl)-1H-indole-6-carboxylate (prepared using AQ from methyl 1H-indole-6-carboxylate] and MeI, H with 4,4,5,5-tetramethyl-1,3,2-dioxaborolane) and D with Preparation #1) | | AN.1.3 | 1.73 (a) | 346 | A |

General Procedure AO: Formation of an Acid Chloride from a Carboxylic Acid

To a flask containing a carboxylic acid (1 equiv) either neat or in an organic solvent (such as 1,4-dioxane, DCE, or DCM, preferably DCM) is added chlorinating agent (such as thionyl chloride, oxalyl chloride or 1-chloro-N,N-2-trimethyl-1-propenylamine, preferably oxalyl chloride, 1 to 10 equiv, preferably 1 to 3 equiv). A catalytic amount of DMF may be added to initiate the reaction. The mixture is stirred at about 0 to 100° C. (preferably about 10 to 25° C.) for about 0.5 to 48 h (preferably about 0.5 to 1 h). Optionally, more chlorinating agent is added (such as thionyl chloride, oxalyl chloride or 1-chloro-N,N-2-trimethyl-1-propenylamine, preferably oxalyl chloride, 1 to 10 equiv, preferably 1 to 3 equiv) and the mixture is stirred at about 0 to 100° C. (preferably about 10 to 25° C.) for about 1 to 48 h (preferably about 1 h). The mixture is then concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give the targeted compound.

Illustration of General Procedure AO

Preparation #AO.1: 2-(2-(1-Methyl-1,6-dihydropyrazolo[3,4-d]pyrrolo[2,3-b]pyridin-7-yl)-1H-pyrrol-1-yl)acetyl chloride

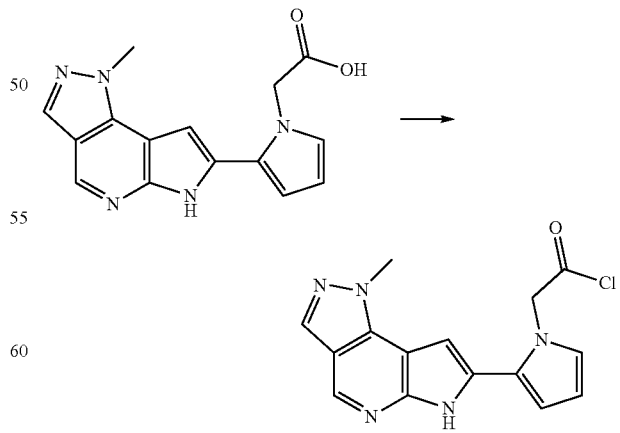

To a flask was added 2-(2-(1-methyl-1,6-dihydropyrazolo[3,4-d]pyrrolo[2,3-b]pyridin-7-yl)-1H-pyrrol-1-yl)acetic acid (0.125 g, 0.423 mmol, Example #AN.1.2) and oxalyl chloride (0.275 mL, 0.550 mmol) in DCM (4 mL) followed by a drop of DMF. The mixture was stirred for about 40 min at rt and then concentrated to dryness to afford 2-(2-(1-methyl-1,6-dihydropyrazolo[3,4-d]pyrrolo[2,3-b]pyridin-7-yl)-1H-pyrrol-1-yl)acetyl chloride. The mixture was used immediately in the next step. Analytics were performed by quenching a sample with MeOH and methyl ester is the observed (M+H)$^+$: LC/MS (Table 2, Method c) R$_t$=1.30 min; MS m/z 310 (M+H)$^+$.

General Procedure AP.1: Formation of an N-Boc Protected Amine

To a solution of an amine or amine salt (preferably 1 equiv) in an organic solvent (such as MeCN, 1,4-dioxane, DCM, DMF or THF, preferably DCM) is added an aqueous base such as Na$_2$CO$_3$, NaOH, K$_2$CO$_3$ or NaHCO$_3$, preferably Na$_2$CO$_3$ (2 to 20 equiv, preferably 2 to 10 equiv) or an organic base such as TEA or DIEA, preferably TEA (1 to 5 equiv, preferably 1 to 2 equiv) followed by addition of a Boc transfer reagent such as BoC$_2$O, Boc ON, Boc-azide or Boc-OSu preferably Boc$_2$O (1 to 4 equiv, preferably 1 to 2 equiv). The addition of base is optional if an amine salt is not used. The mixture is stirred at about 0 to 40° C. (preferably about 0 to 25° C.) for about 2 to 24 h (preferably about 2 to 16 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AP.1

Preparation #AP.1.1: tert-Butyl 2-(4-bromophenyl)propan-2-ylcarbamate

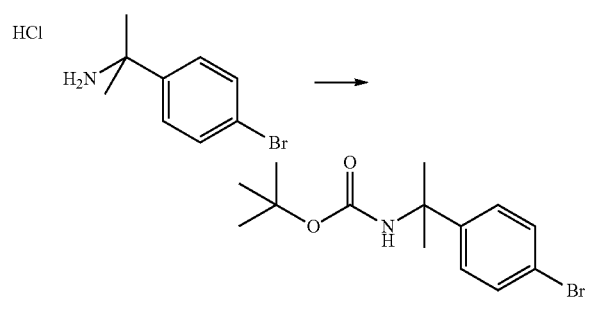

To a solution of 2-(4-bromophenyl)propan-2-amine, hydrochloric acid (1.0 g, 4.0 mmol, AKOS) in DCM (30 mL) at about 0° C. was added TEA (1.11 mL, 7.98 mmol). A solution of BOC$_2$O (1.623 ml, 7.01 mmol) in DCM (10 mL) was added dropwise over about 10 min. After about 30 min, the ice bath was removed and the mixture was stirred overnight at rt. The mixture was diluted with water (30 mL) and extracted with DCM (2×30 mL). The organic layers were combined, dried over MgSO4, filtered, and concentrated in vacuo. The crude material was purified by flash chromatograph (40 g silica gel column, 0-40% EtOAc/Heptane) to give tert-butyl 2-(4-bromophenyl)propan-2-ylcarbamate the title compound (1.13 g, 90%): LC/MS (Table 2, Method b) R$_t$=2.66 min.; MS m/z: 315 (M+H)$^+$.

General Procedure AP.2: Formation of an N-Fmoc Protected Amine

To a solution of an amine or amine salt (preferably 1 equiv) in an organic solvent (such as MeCN, 1,4-dioxane, DCM or THF, preferably 1,4-dioxane) is added an aqueous base such as Na$_2$CO$_3$, NaOH, K$_2$CO$_3$ or NaHCO$_3$, preferably Na$_2$CO$_3$ (2 to 20 equiv, preferably 2 to 10 equiv) or an organic base such as TEA or DIEA, preferably TEA (1 to 5 equiv, preferably 1 to 2 equiv) followed by addition of an Fmoc reagent such as Fmoc-Cl or FMOC-OSu, preferably Fmoc-Cl (1 to 4 equiv, preferably 1 to 2 equiv). The mixture is stirred at about 0° C. to 40° C. (preferably ambient temperature) for about 2 to 24 h (preferably about 2 to 16 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AP.2

Preparation #AP.2.1: 4-(((9H-Fluoren-9-yl)methoxy)carbonylamino)-4-methylpentanoic acid

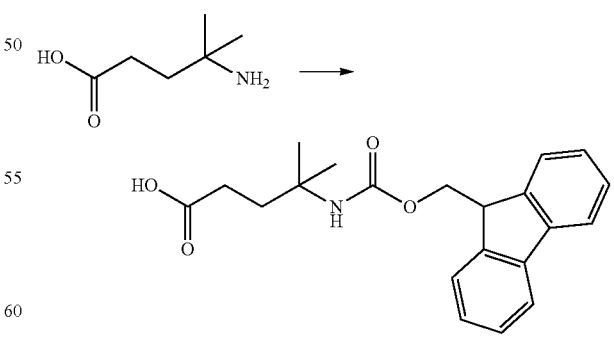

A stirred solution containing 4-amino-4-methylpentanoic acid (0.90 g, 6.86 mmol, Chembridge), Na$_2$CO$_3$ (2.9 g, 27. mmol), and 1,4-dioxane (10 mL) was cooled in an ice bath and Fmoc-Cl (2.1 mg, 8.2 mmol) dissolved in 1,4-dioxane (10 mL) was added in over about 2 min. The mixture was stirred at about 0° C. for about 1 h and then allowed to warm to rt. The mixture was neutralized with aqueous 6 N HCl and extracted with EtOAc (3×25 mL). The combined organic layers were dried over MgSO4, filtered and concentrated under reduced pressure. The crude material was purified by flash chromatograph (40 g silica gel column, 10-60% EtOAc/Heptane) to give 4-(((9H-fluoren-9-yl)methoxy)carbonylamino)-4-methylpentanoic acid the title compound (1.2 g, 49%): LC/MS (Table 2, Method b) $R_f$=2.31 min.; MS m/z: 352 (M−H)+.

General Procedure AQ: Formation of a 3-halo-1-alkyl-1H-indole from a 1H-indole or a 3-halo-1-alkyl-1H-pyrrolo[3,2-c]pyridine from a 1H-pyrrolo[3,2-c]pyridine To a solution of an indole or 1H-pyrrolo[3,2-c]pyridine (1 equiv) in an organic solvent (such as DMF or THF, preferably DMF) is added a base (such as NaH, KOH, NaOH or $Cs_2CO_3$, preferably NaOH; 1 to 3 equiv, preferably 1.0 to 1.05 equiv). A halogenating agent (such as bromine or iodine, preferably iodine; 0.95 to 1.1 equiv, preferably 1.0 to 1.05 equiv) is added in one portion or optionally portion wise. The mixture is stirred at about 0 to 45° C. (preferably about 20 to 30° C.) for about 0.5 to 3 h (preferably about 1 to 2 h). The mixture at is stirred at about −5 to 35° C. (preferably about 0 to 25° C.) then NaH (1 to 4 equiv, preferably 2 to 2.5 equiv) is added in one portion or optionally portion wise. After about 5 to 30 min (preferably about 10 to 15 min) an alkyl halide (1 to 6 equiv, preferably 1.2 to 2 equiv) is added and the mixture is stirred at about 15 to 45° C. (preferably about 20 to 30° C.) for about 0.5 to 48 h (preferably about 1 to 2 h). Additional alkyl halide (0.2 to 1 equiv, preferably 0.5-0.7 equiv) is optionally added during this reaction time if the reaction is not progressing as monitored by TLC, HPLC or LC/MS. The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.
Illustration of General Procedure AQ Preparation #AQ.1:
3-Iodo-1-isopropyl-5-methoxy-1H-indole

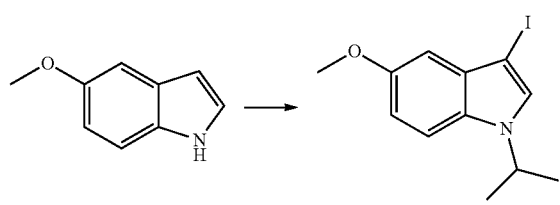

5-Methoxy-1H-indole (4.50 g, 30.6 mmol) in DMF (50 mL) was treated with KOH (1.80 g, 32.1 mmol) then stirred for about 10 min at rt. Iodine (7.84 g, 30.9 mmol) was added and the mixture was stirred for about 1 h. The NaH (60 wt % in mineral oil, 3.06 g, 76 mmol) was added and the mixture was stirred for about 15 min. The 2-iodopropane (3.67 mL, 36.7 mmol) was added and the mixture stirred for about 1 h. A second portion of 2-iodopropane (1.83 mL, 18.4 mmol) was added then the mixture was stirred for about 15 min. The mixture was treated with water (10 mL) then poured into water (250 mL). The mixture was extracted with $Et_2O$ (2×75 mL). The combined organics were washed with water (2×100 mL) then brine (50 mL). The organic layer was dried over $MgSO_4$, filtered and concentrated in vacuo to give 3-iodo-1-isopropyl-5-methoxy-1H-indole (10.5 g, 110%): LC/MS (Table 2, Method a) $R_f$=2.95 min; MS m/z 316 (M+H)+.

General Procedure AR: Oxidation of a Sulfide to a Sulfone

To a solution of a sulfide (preferably 1 equiv) in an organic solvent (such as DCM, THF, preferably THF) at about 0 to 30° C., preferably about 0° C., is added an oxidizing agent (such as m-CPBA, Oxone®, preferably Oxone®) (1 to 4 equiv, preferably 2 equiv). The reaction is stirred at about 0 to 30° C., preferably about 0° C. for about 0.25 to 24 h (preferably about 1 h). The mixture is then concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, or EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl, $Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

Preparation #AR.1: (4-(Methylsulfonyl)phenyl)(5-tosyl-5H-pyrrolo[2,3-b]pyrazin-2-yl)methanamine

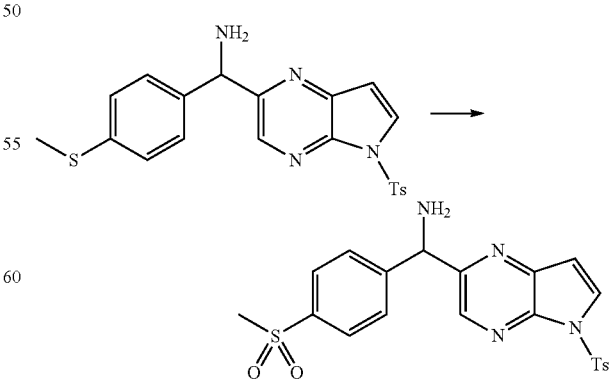

In a round flask was added (4-(methylthio)phenyl)(5-tosyl-5H-pyrrolo[2,3-b]pyrazin-2-yl)methanamine (0.453 g, 1.067 mmol, prepared using AF from Preparation #AE.1 with 4-(methylthio)phenyl)magnesium bromide and AG) and THF (5 mL) and mixture was cooled to about 0° C. Oxone® (1.312 g, 2.134 mmol) in water (2 mL) was added and the mixture was stirred for about 1 h. The mixture was diluted with water (5 mL) and extracted with DCM (10 mL), dried over MgSO$_4$ and concentrated to provide (4-(methylsulfonyl)phenyl)(5-tosyl-5H-pyrrolo[2,3-b]pyrazin-2-yl)methanamine (0.487 g, 100%): LC/MS (Table 2, Method c) R$_t$=1.25 min; MS m/z 457 (M+H)$^+$.

TABLE AR.1

Examples prepared from a sulfide using General Procedure AR

| Sulfide | Product | Example # | R$_t$ min (Table 2, Method) | m/z ESI+ (M + H)$^+$ | Syk IC$_{50}$ |
|---|---|---|---|---|---|
| 1-Methyl-3-(4-(methylthio)phenyl)-1,6-dihydropyrazolo[3,4-d]pyrrolo[2,3-b]pyridine (Example #AU.1) | | AR.1.1 | 1.81 (a) | 327 | B |

General Procedure AS: Preparation of a 6H-pyrrolo[2,3-e][1,2,3]triazole[1,5-a]pyrazine from a 2-carbonyl-5H-pyrrolo[2,3-b]pyrazine To a 2-carbonyl-5H-pyrrolo[2,3-b]pyrazine (1 equiv) in an organic solvent or solvent system (such as MeOH, EtOH, PrOH, i-PrOH, 1,4-dioxane or PrOH/1,4-dioxane, preferably PrOH/1,4-dioxane) is added 4-methylbenzenesulfonohydrazide (0.9 to 1.5 equiv, preferably 1.0 to 1.1 equiv). Optionally a catalytic amount (0.01 to 0.05 equiv, preferably 0.02 equiv) of an inorganic acid such as HCl is added to the reaction mixture. The mixture is stirred at about 20 to 110° C. (preferably about 95 to 100° C.) for about 0.5 to 15 h (preferably about 2 to 4 h). The solvents are removed under reduced pressure then the material is treated with morpholine (20 to 120 equiv, preferably 20 to 40 equiv). The mixture is stirred at about 90 to 130° C. (preferably about 95 to 105° C.) for about 5 min to 1 h (preferably about 10 to 15 min) then cooled to rt. The mixture is optionally concentrated in vacuo to give the targeted compound or optionally diluted with an appropriate solvent or combination of solvents (such as water, EtOAc, 1,4-dioxane, THF, MeCN, DCM, Et$_2$O, MeOH, or EtOH) and the target compound collected by filtration. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, or EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure AS

Preparation #AS.1: 3-(4-Methoxyphenyl)-6-tosyl-6H-pyrrolo[2,3-e][1,2,3]triazolo[1,5-a]pyrazine

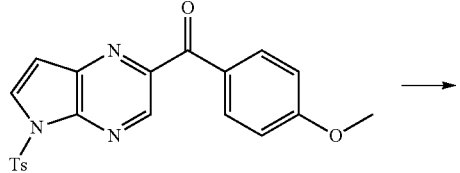

-continued

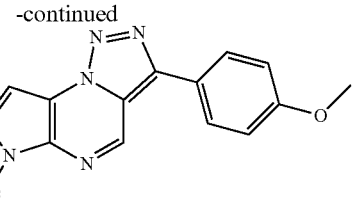

The (4-methoxyphenyl)(5-tosyl-5H-pyrrolo[2,3-b]pyrazin-2-yl)methanone (2.25 g, 5.52 mmol, prepared using AT from Preparation #AF.1) was dissolved in 1,4-dioxane (25 mL) and PrOH (5 mL) then treated with 4-methylbenzenesulfonohydrazide (1.08 g, 5.80 mmol). The mixture was heated to about 100° C. for about 2 h then it was treated with 1 drop concentrated HCl. The mixture was stirred about 1 h at about 100° C. and then the mixture was concentrated under reduced pressure. The material was dissolved in morpholine (15.0 mL, 172 mmol) then the mixture was heated to about 100° C. for about 15 min. The mixture was cooled to rt and concentrated on the under reduced pressure. The material was treated with water (100 mL) and EtOAc (~40 mL). The mixture was stirred for about 10 min then filtered. The solids were washed with EtOAc (~7 mL) then dried to a constant weight under vacuum at about 70° C. to give 3-(4-methoxyphenyl)-6-tosyl-6H-pyrrolo[2,3-e][1,2,3]triazolo[1,5-a]pyrazine (0.760 g, 33%): LC/MS (Table 2, Method a) R$_t$=2.74 min; MS m/z 420 (M+H)$^+$.

General Procedure AT: Hydrolysis of an Imine to a Ketone

To an imine (1 equiv) in an organic solvent (such as MeOH, EtOH, PrOH, i-PrOH, THF or 1,4-dioxane, preferably THF) is added an aqueous inorganic acid (such as 1 to 6 N HCl, 6 N or concentrated (36 wt %) hydrochloric acid; 2 to 10 equiv, preferably 3 to 6 equiv). The mixture is stirred at about 15 to 40° C. (preferably about 20 to 25° C.) for about 30 min to 24 h (preferably about 1 to 4 h). The mixture is optionally concentrated in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, Et₂O, MeOH, or EtOH) and then optionally concentrated in vacuo to give a residue. Either the residue or the solution may be optionally partitioned between water and an organic solvent (such as EtOAc, Et₂O or DCM). The organic layer is isolated and may be optionally washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaCl, Na₂SO₃ or Na₂S₂O₃). The organic solution may then be optionally dried with a drying agent (such as anhydrous MgSO₄ or Na₂SO₄), filtered and concentrated in vacuo to give the targeted compound.

Illustration of General Procedure AT

Preparation #AT.1: (4-(Methylthio)phenyl)(5-tosyl-5H-pyrrolo[2,3-b]pyrazin-2-yl)methanone

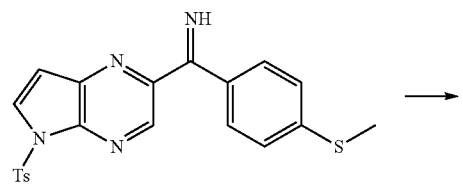

(4-(Methylthio)phenyl)(5-tosyl-5H-pyrrolo[2,3-b]pyrazin-2-yl)methanimine (1.00 g, 2.37 mmol, prepared using AF from Preparation #AE.1 with (4-(methylthio)phenyl)magnesium bromide) was dissolved in THF (25 mL) then 6 N HCl (1.18 mL, 7.10 mmol) was added. The mixture was stirred rt for about 1 h then concentrated under reduced pressure. Saturated aqueous NaHCO₃ (40 mL) and water (10 mL) were added then the mixture was extracted with DCM (50 mL and 15 mL). The combined organics were dried over anhydrous MgSO₄, filtered and concentrated under reduced pressure to give (4-(methylthio)phenyl)(5-tosyl-5H-pyrrolo[2,3-b]pyrazin-2-yl)methanone (0.754 g, 75%): LC/MS (Table 2, Method b) $R_f$=2.77 min; MS m/z 424 (M+H)⁺.

General Procedure AU: Preparation of a 1,6-dihydropyrazolo[3,4-d]pyrrolo[2,3-b]pyridine from a 5-carbonyl-4-chloro-1H-pyrrolo[2,3-b]pyridine To a solution of a 5-carbonyl-4-chloro-1H-pyrrolo[2,3-b]pyridine in an organic solvent (such as MeCN, 1,4-dioxane, DCM, THF or n-BuOH, preferably n-BuOH) is added a hydrazine. An acid (such as HCl or AcOH, preferably HCl; 0.5 to 3 equiv preferably 0.5 to 1 equiv) may be optionally added. The reaction is stirred at about 50 to 110° C. (preferably about 80 to 100° C.) for about 0.5 to 24 h (preferably about 1 to 10 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et₂O, MeOH, EtOH) and then optionally concentrated in vacuo to give a residue as the target compound. Either the residue or the solution may be optionally partitioned between water and an organic solvent (such as EtOAc, Et₂O or DCM). The organic layer is isolated and may optionally be washed in no particular order with water and/or aqueous solutions containing an acid (such as HCl, AcOH or NH₄Cl) and/or aqueous solutions containing a base (such as NaHCO₃, Na₂CO₃, NaOH, KOH or NH₄OH) and/or aqueous solutions containing an inorganic salt (such as NaClNa₂SO₃ or Na₂S₂O₃). The organic solution may then be optionally dried with a drying agent (such as anhydrous MgSO₄ or Na₂SO₄), filtered and concentrated in vacuo to give the target compound.

Illustration of General Procedure AU

Example #AU.1

1-Methyl-3-(4-(methylthio)phenyl)-1,6-dihydropyrazolo[3,4-d]pyrrolo[2,3-b]pyridine

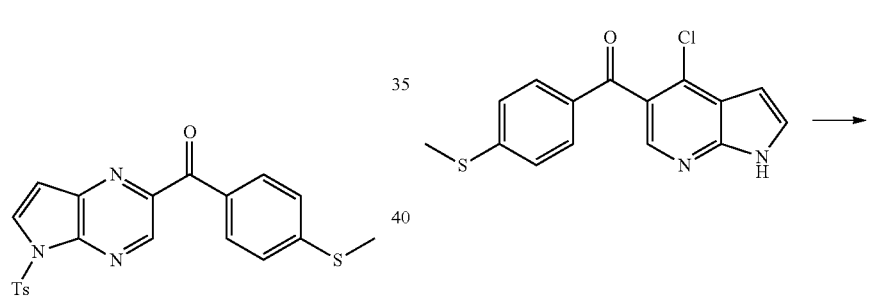

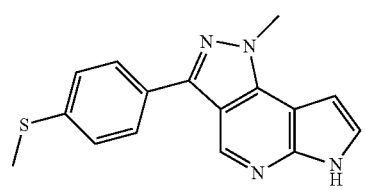

To (4-chloro-1H-pyrrolo[2,3-b]pyridin-5-yl)(4-(methylthio)phenyl)methanone (0.20 g, 0.66 mmol, prepared using S from 4-chloro-1H-pyrrolo[2,3-b]pyridine-5-carbaldehyde [Preparation #1, Step B] and AV) in BuOH (4 mL) was added methylhydrazine (0.052 mL, 0.991 mmol). The mixture was stirred for about 1.5 h at about 95° C. and then cooled to rt. The resulting precipitate was collected by filtration, washed with EtOAc (2 mL) and dried in a vacuum oven at about 70° C. for about 2 h to give 1-methyl-3-(4-(methylthio)phenyl)-1,6-dihydropyrazolo[3,4-d]pyrrolo[2,3-b]pyridine (0.15 g, 77%): LC/MS (Table 2, Method a) $R_f$=2.23 min.; MS m/z: 295 (M+H)⁺. Syk IC₅₀=A.

TABLE AU.1

Examples prepared from (4-chloro-1H-pyrrolo[2,3-b]pyridin-5-yl)(4-methoxyphenyl)methanone (Preparation #AV.1) with a hydrazine using General Procedure AU

| Hydrazine | Product | Example # | $R_t$ min (Table 2, Method) | m/z ESI+ (M + H)+ | Syk $IC_{50}$ |
|---|---|---|---|---|---|
| Methylhydrazine | (structure) | AU.1.1 | 1.96 (a) | 279 | A |
| Hydrazine | (structure) | AU.1.2 | 1.68 (a) | 265 | A |
| 2-Hydrazinylethanol | (structure) | AU.1.3 | 1.76 (a) | 309 | B |

General Procedure AV: Oxidation of an Alcohol to a Ketone

To a solution of an alcohol (preferably 1 equiv) in DCM is added an oxidizing reagent, such as Dess-Martin periodinane, pyridinium dichromate or pyridinium chlorochromate, preferably Dess-Martin periodinane (1.0 to 1.5 equiv, preferably 1.2 equiv). The reaction is stirred at rt for about 0.5 to 24 h (preferably about 1 to 16 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AV

Preparation #AV.1: (4-chloro-1H-pyrrolo[2,3-b]pyridin-5-yl)(4-methoxyphenyl)methanone

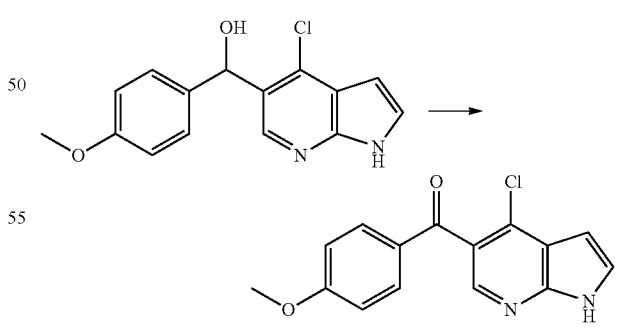

To a solution of (4-chloro-1H-pyrrolo[2,3-b]pyridin-5-yl)(4-methoxyphenyl)methanol (2.34 g, 8.10 mmol, prepared using S from Preparation #1, Step B with (4-(2-methyl-1,3-dioxolan-2-yl)phenyl)magnesium bromide [NOVEL]) and DCM (30 mL) was added Dess-Martin periodinane (3.44 g, 8.10 mmol). The mixture was stirred at rt for about 3 h. Water was added (15 mL) and the resulting precipitate was collected by filtration and dried under reduced pressure at about 60° C. for about 2 h to give (4-chloro-1H-pyrrolo[2,3-b]pyridin-5-yl)(4-methoxyphenyl)methanone (2.14 g, 92%): LC/MS (Table 2, Method b) R$_f$=2.17 min.; MS m/z: 287 (M+H)$^+$.

General Procedure AW: Removal of a PMB Group from an O-PMB Protected Alcohol

To a PMB protected alcohol (preferably 1 equiv) in a mixture of solvents, such as DCM and water (1:1 to 7:1, preferably 5:1) is added an oxidizing agent (such as DDQ or CAN, preferably DDQ; 1 to 3 equiv, preferably 1 to 2 equiv). The reaction mixture is stirred at rt for about 30 min to 24 h (preferably about 30 min to 8 h). The mixture may optionally be concentrated in vacuo to give the target compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue as the target compound. Either the residue or the solution may be optionally partitioned between water and an organic solvent (such as EtOAc, Et$_2$O or DCM). The organic layer is isolated and may optionally be washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaClNa$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the target compound.

Illustration of General Procedure AW

Preparation #AW.1: (9H-Fluoren-9-yl)methyl 2-((3-(4-(2-hydroxypropan-2-yl)phenyl)-6-tosyl-6H-imidazo[1,5-a]pyrrolo[2,3-e]pyrazin-1-yl)methoxy)ethylcarbamate

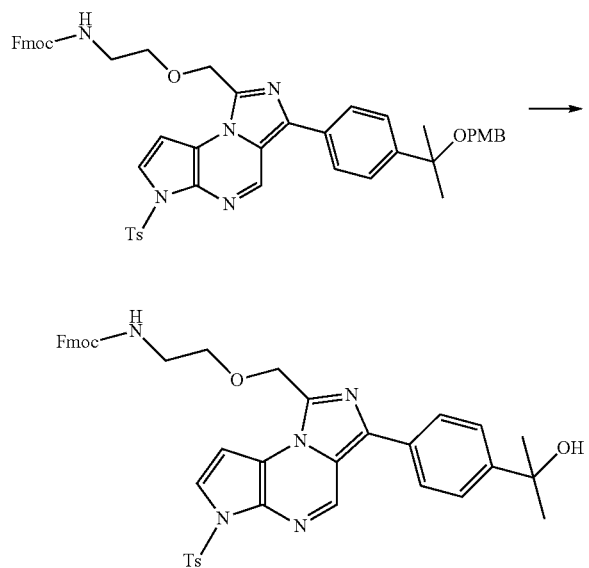

To a solution of (9H-fluoren-9-yl)methyl 2-((3-(4-(2-(4-methoxybenzyloxy)propan-2-yl)phenyl)-6-tosyl-6H-imidazo[1,5-a]pyrrolo[2,3-e]pyrazin-1-yl)methoxy)ethylcarbamate (0.077 g, 0.089 mmol, prepared using AF from Example #2, Step B cyano intermediate with ((4-(2-(4-methoxybenzyloxy)propan-2-yl)phenyl)magnesium bromide [NOVEL], AG, J.1 with 2-(2-(((9H-fluoren-9-yl)methoxy)carbonylamino)ethoxy)acetic acid [Chem Impex] and L.1 with mercury(II) trifluoroacetate) in DCM (0.94 mL) and Water (0.05 mL) was added DDQ (0.030 gg, 0.134 mmol). The mixture was stirred at rt for about 45 min. The mixture was directly purified by flash chromatography (12 g silica gel column, 35 to 100% EtOAc/heptane) to give (9H-fluoren-9-yl)methyl 2-((3-(4-(2-hydroxypropan-2-yl)phenyl)-6-tosyl-6H-imidazo[1,5-a]pyrrolo[2,3-e]pyrazin-1-yl)methoxy)ethylcarbamate (0.03 g, 45%): LC/MS (Table 2, Method b) R$_f$=2.90 min.; MS m/z: 742 (M+H)$^+$.

General Procedure AX: Formation of an N-TIPS Protected Heteroaryl Ring

To a mixture of a heteroaryl ring containing an NH functionality (1 equiv) at about −40 to 25° C. (preferably about −20° C.) in an organic solvent (such as THF, 1,4-dioxane or DMF, preferably THF) is added a base (such as NaH, Cs$_2$CO$_3$ or KOH, preferably NaH; 1 to 3 equiv, preferably 1.05-1.1 equiv). The mixture is stirred for about 1 to 60 min (preferably about 15 min to 1 h) at about −40 to 25° C. (preferably about −20° C.). TIPSCl (1 to 3 equiv, preferably 1.05-1.1 equiv) is added to the mixture, which is then stirred at about −40 to 25° C. (preferably about −20° C.) for about 5 min to 24 h (preferably about 15 min to 1 h). The mixture is then optionally diluted slowly with ice water or a saturated solution of NaCl in ice water and stirred. The solids are optionally collected by filtration and dried to provide the target compound. Alternatively, the mixture is optionally concentrated in vacuo to give final compound. Alternatively, the mixture is optionally filtered through a media (such as silica gel or Celite®) which is rinsed with an appropriate solvent (such as EtOAc, 1,4-dioxane, THF, MeCN, DCM, Et$_2$O, MeOH, EtOH) and then optionally concentrated in vacuo to give a residue. Either the residue or the solution may be optionally partitioned between water and an organic solvent (such as EtOAc, Et$_2$O or DCM). The organic layer is isolated and may be optionally washed in no particular order with water and/or aqueous solutions containing an acid (such as HCl, AcOH or NH$_4$Cl) and/or aqueous solutions containing a base (such as NaHCO$_3$, Na$_2$CO$_3$, NaOH, KOH or NH$_4$OH) and/or aqueous solutions containing an inorganic salt (such as NaCl, Na$_2$SO$_3$ or Na$_2$S$_2$O$_3$). The organic solution may then be optionally dried with a drying agent (such as anhydrous MgSO$_4$ or Na$_2$SO$_4$), filtered and concentrated in vacuo to give the targeted compound.

Illustration of General Procedure AX

Preparation #AX.1: 2-(4-(1-Methyl-6-(triisopropylsilyl)-6H-imidazo[1,5-a]pyrrolo[2,3-e]pyrazin-3-yl)phenyl)propan-2-ol

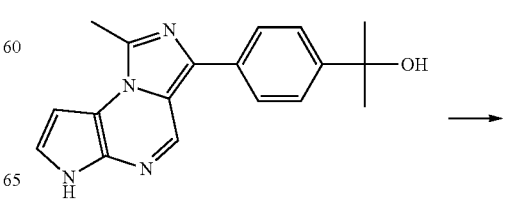

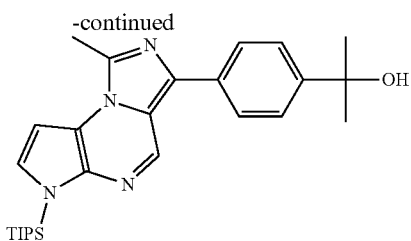

To a solution of 2-(4-(1-methyl-6H-imidazo[1,5-a]pyrrolo[2,3-e]pyrazin-3-yl)phenyl)propan-2-ol (1.03 g, 3.36 mmol; Example #N.1.50) in THF (32 ml) at about −20° C. was added NaH (0.148 g, 3.70 mmol). The mixture was allowed to stir at about −20° C. for about 20 min. TIPSCl (0.790 ml, 3.70 mmol) was added and the resulting solution was allowed to stir at about −20° C. for about 1 h. The mixture was treated with 15 mL of an ice cold saturated aqueous NaCl solution and the resulting mixture was partitioned between EtOAc (100 mL) and water (50 mL). The layers were separated and the aqueous phase was extracted with EtOAc (3×25 mL). The combined organic phases were washed with saturated aqueous NaCl solution (100 mL), dried over $Na_2SO_4$, filtered, and concentrated in vacuo to give 2-(4-(1-methyl-6-(triisopropylsilyl)-6H-imidazo[1,5-a]pyrrolo[2,3-e]pyrazin-3-yl)phenyl)propan-2-ol (1.5 g, 96%). LC/MS (Table 2, Method h) $R_t$=2.28 min; MS m/z 463 (M+H)$^+$.

General Procedure AY: Removal of a TIPS Group from an N-TIPS Protected Heteroaryl Ring To a solution of a N-TIPS-protected heteroaryl ring compound (1 equiv) in an organic solvent (such as THF, DMF, 1,4-dioxane, or DCM, preferably THF) is added TBAF (1 to 10 equiv, preferably 10 equiv) and the mixture is stirred at about 0 to 60° C. (preferably about 10 to 30° C.) for about 15 min to 4 h (preferably about 1 h). Optionally, additional TBAF (1 to 10 equiv, preferably 2 equiv) may be added to the mixture and stirred at about 0 to 60° C. (preferably about 10 to 30° C.) for about 15 min to 2 h (preferably about 1 h). The mixture may be optionally isolated by concentration in vacuo to give the targeted compound. Alternatively, the mixture is optionally filtered through a media (such as silica gel or Celite®) which is rinsed with an appropriate solvent (such as EtOAc, 1,4-dioxane, THF, MeCN, DCM, $Et_2O$, MeOH, EtOH) and then optionally concentrated in vacuo to give a residue. Either the residue or the solution may be optionally partitioned between water and an organic solvent (such as EtOAc, $Et_2O$ or DCM). The organic layer is isolated and may be optionally washed in no particular order with water and/or aqueous solutions containing an acid (such as HCl, AcOH or $NH_4Cl$) and/or aqueous solutions containing a base (such as $NaHCO_3$, $Na_2CO_3$, NaOH, KOH or $NH_4OH$) and/or aqueous solutions containing an inorganic salt (such as NaCl$Na_2SO_3$ or $Na_2S_2O_3$). The organic solution may then be optionally dried with a drying agent (such as anhydrous $MgSO_4$ or $Na_2SO_4$), filtered and concentrated in vacuo to give the targeted compound.

Illustration of General Procedure AY

Example #AY.1: 2-(4-(8-Bromo-1-methyl-6H-imidazo[1,5-a]pyrrolo[2,3-e]pyrazin-3-yl)phenyl)propan-2-ol

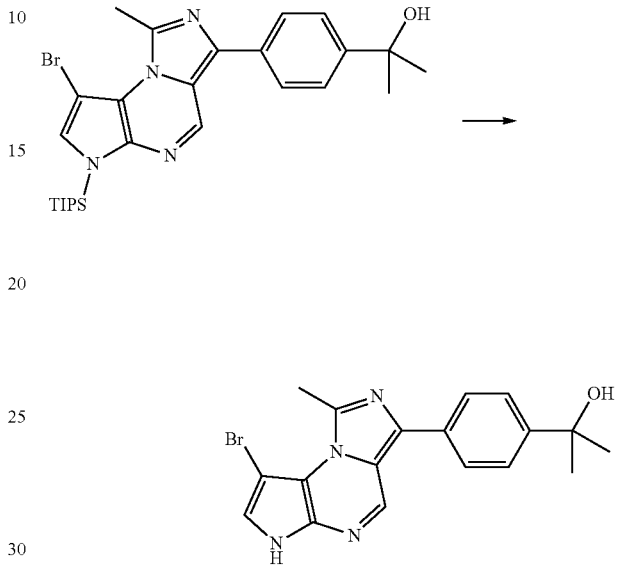

To a mixture of 2-(4-(8-bromo-1-methyl-6-(triisopropylsilyl)-6H-imidazo[1,5-a]pyrrolo[2,3-e]pyrazin-3-yl)phenyl)propan-2-ol (0.300 g, 0.554 mmol; Preparation #AD.1) in THF (5 mL) was added TBAF (0.504 mL, 0.554 mmol). The mixture was stirred at about rt for about 1 h and then was partitioned between DCM (50 mL) and water (25 mL). The layers were separated and the aqueous phase was extracted with DCM (3×20 mL). The combined organic phases were washed with brine (100 mL) and then the solid was collected by filtration to give 2-(4-(8-bromo-1-methyl-6H-imidazo[1,5-a]pyrrolo[2,3-e]pyrazin-3-yl)phenyl)propan-2-ol (0.082 g, 39%). LC/MS (Table 2, Method a) $R_t$=1.87 min.; MS m/z: 387 (M+H)$^+$. Syk IC$_{50}$=A.

Example #1

Preparation of N-(2-(dimethylamino)ethyl)-2-(3-(1-methyl-1,6-dihydropyrazolo[3,4-d]pyrrolo[2,3-b]pyridin-7-yl)phenyl)acetamide

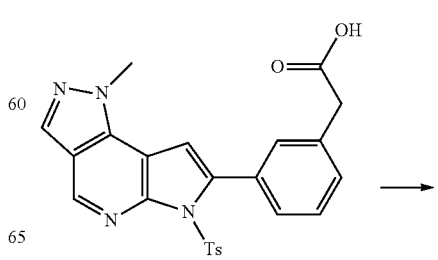

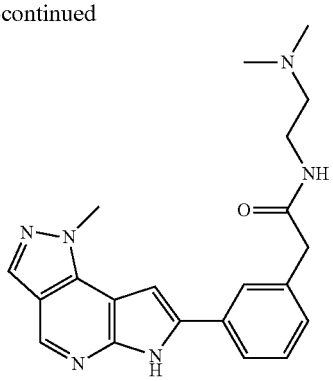

A flask was charged with 2-(3-(1-methyl-6-tosyl-1,6-dihydropyrazolo[3,4-d]pyrrolo[2,3-b]pyridin-7-yl)phenyl)acetic acid (0.09 g, 0.195 mmol, prepared using D from Preparation #1 with 2-(3-(4,4,5,5-tetramethyl-1,3,2-dioxaborolan-2-yl)phenyl)acetic acid [Frontier]), HOBt (0.026 g, 0.195 mmol), DCI (0.03 mL, 0.195 mmol) and DCM (7 mL). The mixture was stirred at rt for about 30 min and N1,N1-dimethylethylene diamine (0.021 mL, 0.195 mmol) was added. The mixture was allowed to stir at rt for about 3 h. The mixture was concentrated under reduced pressure to half the original volume and purified by silica gel chromatography with an elution gradient of 0 to 40% MeOH/DCM with 2% of a solution of $NH_3$ (2.0 M in EtOH). The solid was washed with water (2 mL) and dried in a vacuum oven at about 60° C. for about 16 h to N-(2-(dimethylamino)ethyl)-2-(3-(1-methyl-1,6-dihydropyrazolo[3,4-d]pyrrolo[2,3-b]pyridin-7-yl)phenyl)acetamide (0.025 g, 34%): LC/MS (Table 2, Method a) $R_f$=1.46 min; MS m/z: 377 (M+H)$^+$. Syk $IC_{50}$=B.

Example #2

1-Cyclohexyl-3-phenyl-6H-imidazo[1,5-a]pyrrolo[2,3-e]pyrazine

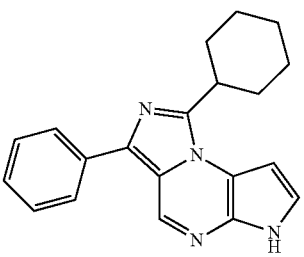 [SMILES: c1ccc(-c2nc(C3CCCCC3)n3c2cnc2[nH]ccc23)cc1]

Step A: 2-Bromo-5-tosyl-5H-pyrrolo[2,3-b]pyrazine

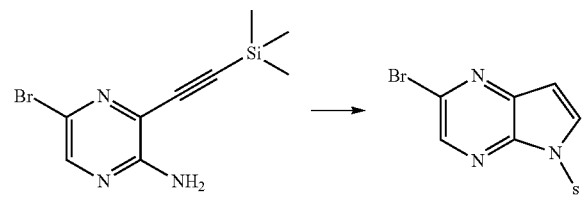

To a solution of 5-bromo-3-((trimethylsilyl)ethynyl)pyrazin-2-amine (3.00 g, 11.1 mmol, prepared using A from 3,5-dibromopyrazin-2-amine with ethynyltrimethylsilane) in DMF (60 mL) at about 0° C. was added 60 wt % NaH (0.577 g, 14.4 mmol) in three portions. After about 15 min, TsCl (2.75 g, 14.4 mmol) was added and the mixture was allowed to warm slowly to rt. After about 16 h, the mixture was poured into ice-cold water (120 mL) and the precipitate was collected by vacuum filtration. The crude solid was dissolved in DCM (15 mL) and purified by silica gel chromatography eluting with DCM to give 2-bromo-5-tosyl-5H-pyrrolo[2,3-b]pyrazine (2.16 g, 52%): LC/MS (Table 2, Method c) $R_f$=1.58 min; MS m/z: 352 (M+H)$^+$.

Step B:
(5-Tosyl-5H-pyrrolo[2,3-b]pyrazin-2-yl)methanamine hydrochloride

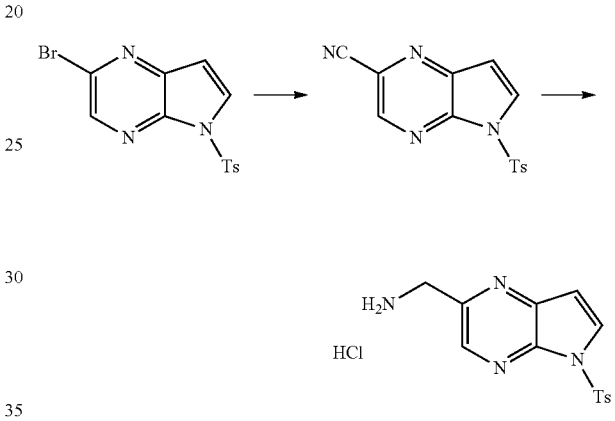

A reactor was charged with 2-bromo-5-tosyl-5H-pyrrolo[2,3-b]pyrazine (98.8 g, 281 mmol), zinc dust (3.50 g, 53.3 mmol), palladium(II) trifluoroacetate (4.0 g, 12 mmol), and racemic-2-(di-t-butylphosphino)-1,1'-binapthyl (9.8 g, 24.7 mmol). The flask was equipped with a powder addition device into which zinc cyanide (10.0 g, 157 mmol) was placed to be added at a later step. The vessel was purged with argon for no longer than about 30 min and then argon sparged DMA (2 L) was added to the reactor. The mixture was stirred and heated to about 50° C. while maintaining an argon sparge. The resulting solution was further heated to about 95° C. while adding the zinc cyanide, from the powder addition device, portion-wise over about 15 min. Upon reaching about 95° C., the mixture was stirred for about an additional 16 h. The reaction mixture was cooled to rt, resulting in the precipitation of salts. The mixture was filtered through a Buchner funnel containing filter-aid and the filter cake was washed with DMA (20 mL). A solution of the crude product in DMA was added to cold (<10° C.) water (16 L) and stirred for about 30 min. The resulting suspension was filtered and the filter cake was rinsed again with water (1 L). The resulting wet cake was dried in a vacuum oven at about 50° C. The crude solid was dissolved in DCM (1.5 L) and further dried over anhydrous $MgSO_4$. After filtration, the solution was passed through a pad of silica (140 g), washing with additional solvent until only predominantly impurities were detected eluting off the pad. The solvent was removed under reduced pressure and the crude solid was triturated with MeOH/DCM (4:1, 10 volumes of solvent per gram of crude solid) at rt for about 5 h. The solid was filtered and washed with MeOH (300 mL). The product was dried in a vacuum oven to provide 5-tosyl-5H-pyrrolo[2,3-b]pyrazine-2-carbonitrile (58.8 g, 70%) as a solid: ¹H NMR (CDCl₃) δ 8.67 (s, 1H), 8.21 (d, J=4.2 Hz, 1H), 8.07 (d, J=8.4 Hz, 2H), 7.34 (d, J=8.1 Hz, 2H), 6.89 (d, J=4.2 Hz, 1H), 2.42 (s, 3H). A 2-L 316-stainless steel pressure reactor was charged with 5% Pd/C (15.4 g of 63.6 wt % water wet material, 5.6 g dry basis, Johnson Matthey A503032-5), 5-tosyl-5H-pyrrolo[2,3-b]pyrazine-2-carbonitrile (55 g, 184 mmol), THF (1.1 L), deionized water (165 mL), HCl (37 wt % aqueous, 30 mL, 369 mmol) and quinoline (1.1 mL, 9.0 mmol). The vessel was purged, pressurized, and maintained at 40 psi with hydrogen supplied from a high pressure reservoir. The mixture was vigorously agitated at about 25° C. After about 5 h the reactor was vented and purged with nitrogen to remove most of the dissolved hydrogen, and the reaction mixture was filtered to remove the catalyst. The reactor and catalyst cake were rinsed with THF:H₂O (1:1THF: H₂O (2×40 mL)). The combined filtrate and rinses were concentrated and EtOH (500 mL) was added. After two additional solvent switches with EtOH (2×500 mL), the crude residue was concentrated under reduced pressure to give a residue (76 g) that was suspended in EtOH (550 mL) and stirred at rt for about 4 h. The solid was collected by filtration and washed with cold EtOH (50 mL). The wet cake was dried in a vacuum oven to provide (5-tosyl-5H-pyrrolo[2,3-b]pyrazin-2-yl)methanamine hydrochloride (51.2 g, 82%): LC/MS (Table 2, Method a) R$_f$=1.44 min; MS m/z: 303 (M+H)⁺.

Step C: N-((5-Tosyl-5H-pyrrolo[2,3-b]pyrazin-2-yl)methyl)cyclohexanecarboxamide

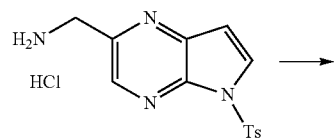

To a suspension of crude (5-tosyl-5H-pyrrolo[2,3-b]pyrazin-2-yl)methanamine hydrochloride (assumed 0.498 mmol) in DCM (10 mL) was added TEA (0.208 mL, 1.49 mmol) followed by cyclohexanecarbonyl chloride (0.101 mL, 0.747 mmol). The mixture was stirred for 30 min at rt and then was diluted with DCM and washed with saturated aqueous NaHCO₃ (25 mL) and brine (25 mL). The organic layer was dried over anhydrous Na₂SO₄, filtered, and concentrated under reduced pressure. The material was purified by silica gel chromatography eluting with a gradient of 40 to 80% EtOAc in DCM to provide N-((5-Tosyl-5H-pyrrolo[2,3-b]pyrazin-2-yl)methyl)cyclohexanecarboxamide as a tan solid (0.081 g, 39%). LC/MS (Table 2, Method a) R$_f$=2.40 min; MS m/z: 413 (M+H)⁺.

Step D: 1-Cyclohexyl-6-tosyl-6H-imidazo[1,5-a]pyrrolo[2,3-e]pyrazine

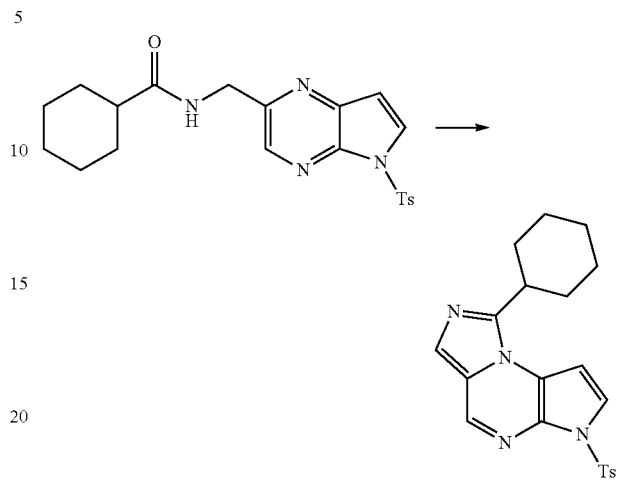

To a solution of N-((5-tosyl-5H-pyrrolo[2,3-b]pyrazin-2-yl)methyl)cyclohexanecarboxamide (0.081 g, 0.196 mmol) in THF (1 mL) at rt was added 2,4-bis(4-phenoxyphenyl)-1,3-dithia-2,4-diphosphetane-2,4-disulfide (0.104 g, 0.196 mmol, TCI). After about 15 h at rt, the mixture was concentrated under reduced pressure. The residue was suspended in EtOAc/DCM (1:1) and filtered through a plug of silica gel (5 g) eluting with EtOAc/DCM (1:1, approximately 100 mL). The filtrate was concentrated under reduced pressure to provide a residue. The residue was dissolved in THF (1 mL) and mercury(II) acetate (0.0626 g, 0.196 mmol) was added. After about 30 min at rt, additional mercury(II) acetate (0.0626 g, 0.196 mmol) was added. After about 4 h at rt, the mixture was diluted with EtOAc, filtered, concentrated under reduced pressure. The residue was purified by silica gel chromatography eluting with a gradient of 50 to 95% EtOAc in heptane to provide 1-cyclohexyl-6-tosyl-6H-imidazo[1,5-a]pyrrolo[2,3-e]pyrazine (0.020 g, 25%): LC/MS (Table 2, Method a) R$_f$=2.77 min; MS m/z: 395 (M+H)⁺.

Step E: 3-Bromo-1-cyclohexyl-6-tosyl-6H-imidazo[1,5-a]pyrrolo[2,3-e]pyrazine

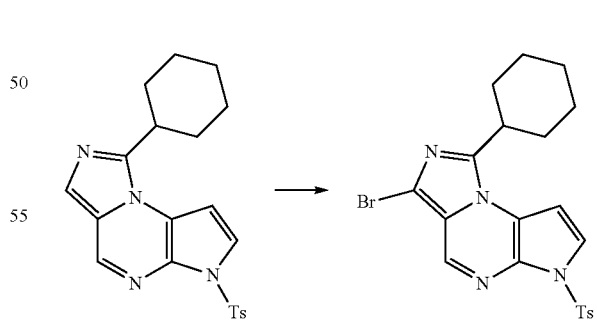

To a solution of 1-cyclohexyl-6-tosyl-6H-imidazo[1,5-a]pyrrolo[2,3-e]pyrazine (0.27 g, 0.672 mmol) in THF (10 mL) at about 0° C. was added a solution of NBS (0.12 g, 0.672 mmol) in THF (2 mL). After about 30 min, the mixture was diluted with EtOAc (20 mL) and saturated aqueous NaHCO₃ (20 mL). The organic layer was separated, concentrated in vacuo, and purified by chromatography on silica gel (40 g)

eluting with EtOAc:DCM:heptane (1:1:2) to provide 3-Bromo-1-cyclohexyl-6-tosyl-6H-imidazo[1,5-a]pyrrolo[2,3-e]pyrazine (0.27 g, 83%). LC/MS (Table 2, Method a) $R_t$=3.12 min; MS m/z 473 (M+H)$^+$.

Step F: 1-Cyclohexyl-3-phenyl-6H-imidazo[1,5-a]pyrrolo[2,3-e]pyrazine

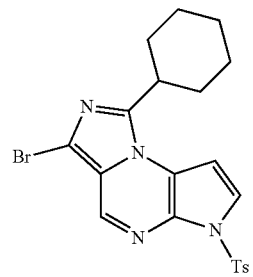

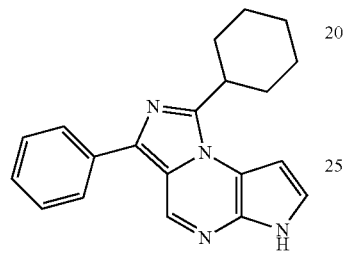

To a solution of 3-bromo-1-cyclohexyl-6-tosyl-6H-imidazo[1,5-a]pyrrolo[2,3-e]pyrazine (0.27 g, 0.056 mmol) and PdCl$_2$(dppf).DCM (0.0046 g, 0.0056 mmol) in THF (1 mL) was added a solution of phenylboronic acid (0.12 g, 0.098 mmol) and Na$_2$CO$_3$ (0.009 g, 0.084 mmol) in water (0.25 mL). The mixture was heated to about 60° C. After about 6 h, the mixture was cooled to rt and was diluted with EtOAc (5 mL) and brine (5 mL). The organic layer was separated and concentrated in vacuo. The residue was dissolved in 1,4-dioxane (5 mL) and aqueous NaOH (2 N, 1 mL) was added. The mixture was heated to about 65° C. After about 15 h, the mixture was cooled to rt and aqueous HCl (1 N, 3 mL) and EtOAc (5 mL) were added. The organic layer was separated, concentrated in vacuo, and the residue was purified by chromatography on silica gel (12 g) eluting with 20 to 80% EtOAc in DCM to provide 1-cyclohexyl-3-phenyl-6H-imidazo[1,5-a]pyrrolo[2,3-e]pyrazine (0.005 g, 28%): LC/MS (Table 2, Method a) $R_f$=2.75 min; MS m/z: 317 (M+H)$^+$. Syk IC$_{50}$=C.

Example #3

(E)-3-(1-Cyclohexyl-6H-imidazo[1,5-a]pyrrolo[2,3-e]pyrazin-3-yl)acrylic acid

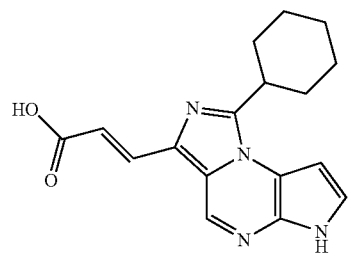 [SMILES: O=C(O)/C=C/c1nc(C2CCCCC2)n2c1cnc1[nH]ccc12]

Step A: (E)-Ethyl 3-(1-cyclohexyl-6-tosyl-6H-imidazo[1,5-a]pyrrolo[2,3-e]pyrazin-3-yl)acrylate

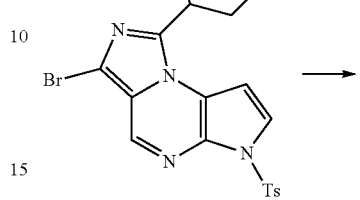

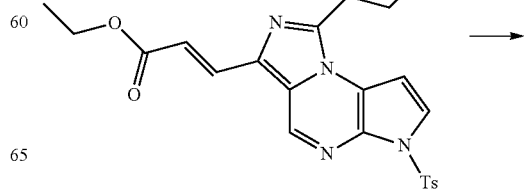

To a solution of 3-bromo-1-cyclohexyl-6-tosyl-6H-imidazo[1,5-a]pyrrolo[2,3-e]pyrazine (0.026 g, 0.056 mmol, Example #2, Step E) and PdCl$_2$(dppf).DCM (0.005 g, 0.006 mmol) in THF (1 mL) was added (E)-ethyl 3-(4,4,5,5-tetramethyl-1,3,2-dioxaborolan-2-yl)acrylate (0.052 g, 0.23 mmol) and Na$_2$CO$_3$ (0.021 g, 0.20 mmol) followed by water (0.25 mL). The mixture was heated to about 65° C. After about 15 h, the mixture was cooled to rt and directly purified by chromatography on silica gel (12 g) eluting with 20 to 80% EtOAc:DCM (1:1) in heptane to provide (E)-ethyl 3-(1-cyclohexyl-6-tosyl-6H-imidazo[1,5-a]pyrrolo[2,3-e]pyrazin-3-yl)acrylate (0.045 g, 70%): LC/MS (Table 2, Method a) $R_t$=3.15 min; MS m/z: 493 (M+H)$^+$.

Step B: (E)-3-(1-cyclohexyl-6H-imidazo[1,5-a]pyrrolo[2,3-e]pyrazin-3-yl)acrylic acid -continued

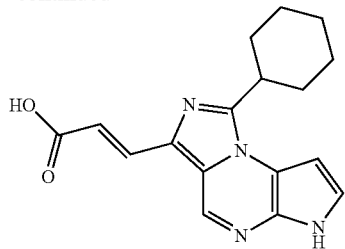

To a solution of (E)-ethyl 3-(1-cyclohexyl-6-tosyl-6H-imidazo[1,5-a]pyrrolo[2,3-e]pyrazin-3-yl)acrylate (0.064 g, 0.13 mmol) in 1,4-dioxane (5 mL) was added aqueous NaOH (2 N, 1.30 mL, 2.60 mmol). The mixture was heated to about 65° C. After about 15 h, the mixture was cooled to rt and the pH of the reaction mixture was adjusted to about pH=1 with concentrated HCl. The mixture was partially concentrated in vacuo and the precipitate was collected by filtration and dried in vacuo to provide (E)-3-(1-cyclohexyl-6H-imidazo[1,5-a]pyrrolo[2,3-e]pyrazin-3-yl)acrylic acid (0.015 g, 37%): LC/MS (Table 2, Method a) $R_t$=1.85 min; MS m/z: 311 (M+H)$^+$. Syk IC$_{50}$=B.

Example #4

2-(4-(1-Ethyl-3H-imidazo[1,2-a]pyrrolo[2,3-e]pyrazin-2-yl)phenyl)propan-2-ol

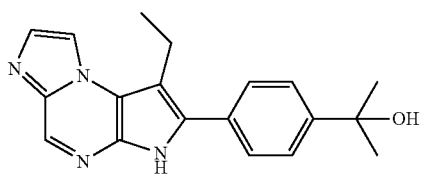 [SMILES: CCc1c(-c2ccc(C(C)(C)O)cc2)[nH]c2ncc3nccn3c12]

Step A: 7-Ethyl-6-(4-(2-methyl-1,3-dioxolan-2-yl)phenyl)-5-((2-(trimethylsilyl)ethoxy)methyl)-5H-pyrrolo[2,3-b]pyrazine-2-carboxylic acid

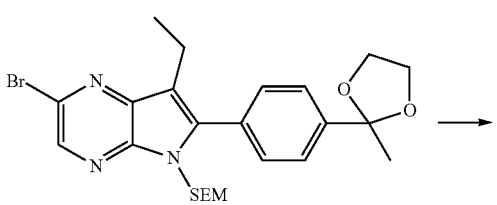

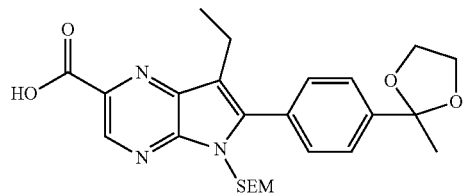

A mixture of 2-bromo-7-ethyl-6-(4-(2-methyl-1,3-dioxolan-2-yl)phenyl)-5-((2-(trimethylsilyl)ethoxy)methyl)-5H-pyrrolo[2,3-b]pyrazine (2.00 g, 3.86 mmol, Preparation #5) and PdCl$_2$(PPh$_3$)$_2$ (0.406 g, 0.579 mmol) in DMF (25 mL) was degassed under reduced pressure and the solution was placed under an atmosphere of CO. MeOH (4.70 mL, 116 mmol) and TEA (2.15 mL, 15.4 mmol) were added and then the mixture was degassed under reduced pressure and the solution placed under an atmosphere of CO. The mixture was then heated to 95° C. under an atmosphere of CO maintained via a balloon for 6.5 h. The solvents were evaporated under reduced pressure then the material was dissolved in 1,4-dioxane (50 mL). Water (10 mL) and LiOH (0.65 g, 27 mmol) were added then the mixture was heated to 75° C. for 90 min. The mixture was cooled to rt and then most of the 1,4-dioxane was removed under reduced pressure. The mixture was treated with water (50 mL) and Et$_2$O (50 mL). The layers were separated then the organic layer was extracted with water (4×50 mL). The combined aqueous extracts were acidified with aqueous HCl (5.0 N, 6.2 mL, 31 mmol) and then extracted with DCM (50 mL, 2×30 mL). The organics were combined and dried over anhydrous MgSO$_4$ then filtered and concentrated under reduced pressure to give 7-ethyl-6-(4-(2-methyl-1,3-dioxolan-2-yl)phenyl)-5-((2-(trimethylsilyl)ethoxy)methyl)-5H-pyrrolo[2,3-b]pyrazine-2-carboxylic acid (0.92 g, 49%): LC/MS (Table 2, Method a) $R_t$=2.63 min; MS m/z 484 (M+H)$^+$.

Step B: tert-Butyl 7-ethyl-6-(4-(2-methyl-1,3-dioxolan-2-yl)phenyl)-5-((2-(trimethylsilyl)ethoxy)methyl)-5H-pyrrolo[2,3-b]pyrazin-2-ylcarbamate

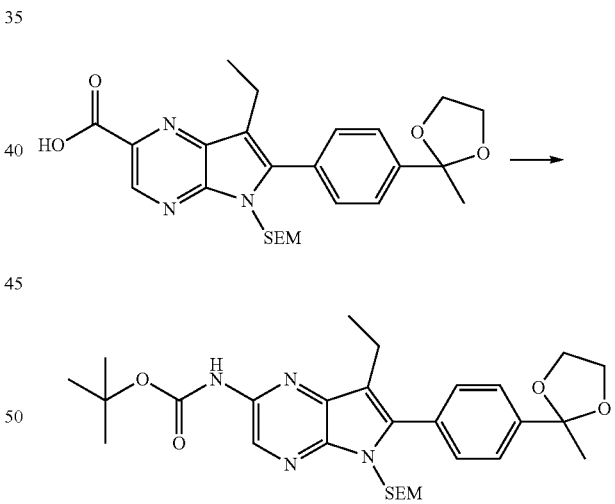

A mixture of 7-ethyl-6-(4-(2-methyl-1,3-dioxolan-2-yl)phenyl)-5-((2-(trimethylsilyl)ethoxy)methyl)-5H-pyrrolo[2,3-b]pyrazine-2-carboxylic acid (0.92 g, 1.9 mmol) in t-BuOH (10 mL), was treated with diphenylphosphoryl azide (0.538 g, 1.96 mmol). The mixture was stirred for about 10 min at rt and then warmed to about 75° C. for about 15 min. TEA (0.583 mL, 4.18 mmol) was added and the mixture was heated at about 75° C. for about 16 h. The mixture was cooled to rt then the solvents were evaporated under reduced pressure. The material was purified on a 40 g silica gel column with 75:25 heptane/EtOAc as an eluent to give tert-butyl 7-ethyl-6-(4-(2-methyl-1,3-dioxolan-2-yl)phenyl)-5-((2-(trimethylsilyl)

ethoxy)methyl)-5H-pyrrolo[2,3-b]pyrazin-2-ylcarbamate (0.71 g, 67%): LC/MS (Table 2, Method b) R$_t$=3.61 min; MS m/z 555 (M+H)$^+$.

Step C: 1-(4-(2-Amino-7-ethyl-5-((2-(trimethylsilyl)ethoxy)methyl)-5H-pyrrolo[2,3-b]pyrazin-6-yl)phenyl)ethanone

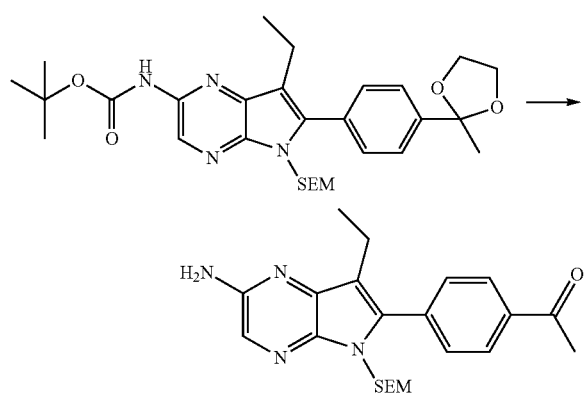

tert-Butyl 7-ethyl-6-(4-(2-methyl-1,3-dioxolan-2-yl)phenyl)-5-((2-(trimethylsilyl)ethoxy)methyl)-5H-pyrrolo[2,3-b]pyrazin-2-ylcarbamate (0.35 g, 0.631 mmol) in 1,4-dioxane (5 mL) was treated with TFA (0.073 mL, 0.946 mmol) then the solution was stirred for about 15 min at rt. The mixture was heated to about 60° C. for about 15 min and then TFA (0.145 mL, 1.88 mmol) was added and heating continued at about 75° C. for about 1 h. The solution was cooled to rt then concentrated (37%) aqueous HCl (0.083 mL, 1.015 mmol) was added. The mixture was stirred for about 15 min at rt then warmed to about 75° C. for about 4 h. The mixture was cooled then treated with saturated aqueous NaHCO$_3$ (10 mL), EtOAc (25 mL) and water (10 mL). The layers were separated then the aqueous layer extracted with EtOAc (15 mL). The organics were combined then dried over anhydrous MgSO$_4$, filtered and concentrated under reduced pressure. The material was purified on a 10 g silica gel column with EtOAc as an eluent to give 1-(4-(2-amino-7-ethyl-5-((2-(trimethylsilyl)ethoxy)methyl)-5H-pyrrolo[2,3-b]pyrazin-6-yl)phenyl)ethanone (0.217 g, 84%): LC/MS (Table 2, Method a) R$_t$=2.72 min; MS m/z 411 (M+H)$^+$.

Step D: 1-(4-(1-Ethyl-3-((2-(trimethylsilyl)ethoxy)methyl)-3H-imidazo[1,2-a]pyrrolo[2,3-e]pyrazin-2-yl)phenyl)ethanone

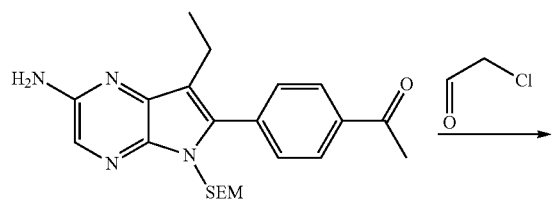

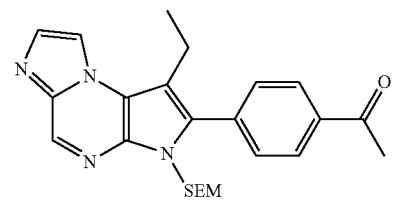

1-(4-(2-Amino-7-ethyl-5-((2-(trimethylsilyl)ethoxy)methyl)-5H-pyrrolo[2,3-b]pyrazin-6-yl)phenyl)ethanone (0.217 g, 0.529 mmol) in EtOH (5 mL) was treated with 2-chloroacetaldehyde (~50 wt % solution in water, 0.100 g, 0.634 mmol). The mixture was heated to about 80° C. for about 2 h then cooled to rt and concentrated under reduced pressure. The material was purified by on a 10 gram silica column with EtOAc then 9:1 DCM/MeOH as eluents to give 1-(4-(1-ethyl-3-((2-(trimethylsilyl)ethoxy)methyl)-3H-imidazo[1,2-a]pyrrolo[2,3-e]pyrazin-2-yl)phenyl)ethanone (0.12 g, 52%): LC/MS (Table 2, Method a) R$_t$=3.06 min; MS m/z 435 (M+H)$^+$.

Step E: 1-(4-(1-Ethyl-3H-imidazo[1,2-a]pyrrolo[2,3-e]pyrazin-2-yl)phenyl)ethanone

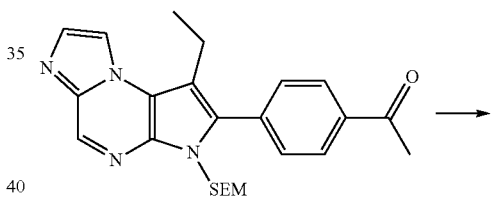

1-(4-(1-Ethyl-3-((2-(trimethylsilyl)ethoxy)methyl)-3H-imidazo[1,2-a]pyrrolo[2,3-e]pyrazin-2-yl)phenyl)ethanone (0.12 g, 0.28 mmol) in DCM (2 mL) was treated with TFA (1.50 mL, 19.5 mmol) then stirred at rt for about 45 min. The solvents were evaporated under reduced pressure then the material was dissolved in 1,4-dioxane (2 mL) and treated with ~28 wt % aqueous NH$_4$OH (1.2 mL, 31 mmol). The mixture was stirred for about 15 min then diluted with water (10 mL). The volatiles were removed by evaporation under reduced pressure (bath temp 40° C., 85 mm Hg) then the mixture was further diluted with water (20 mL). The solids were collected by filtration then the material was dried to constant weight under vacuum at about 60° C. to give 1-(4-(1-ethyl-3H-imidazo[1,2-a]pyrrolo[2,3-e]pyrazin-2-yl)phenyl)ethanone (0.062 g, 74%): LC/MS (Table 2, Method a) R$_t$=1.92 min; MS m/z 305 (M+H)$^+$.

Step F: 2-(4-(1-Ethyl-3H-imidazo[1,2-a]pyrrolo[2,3-e]pyrazin-2-yl)phenyl)propan-2-ol

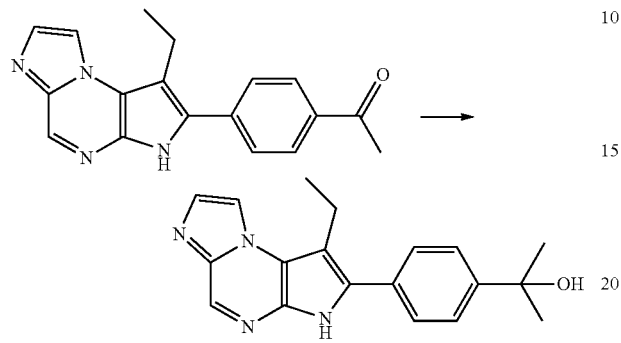

MeMgCl (3 M in THF, 0.54 mL, 1.6 mmol) was added to THF (3 mL) then cooled to about −20° C. 1-(4-(1-Ethyl-3H-imidazo[1,2-a]pyrrolo[2,3-e]pyrazin-2-yl)phenyl)ethanone (0.062 g, 0.204 mmol) was suspended in THF (3 mL) then added to the MeMgCl solution with stirring while maintaining the temperature of the mixture at about −15 to −20° C. The flask with the 1-(4-(1-ethyl-3H-imidazo[1,2-a]pyrrolo[2,3-e]pyrazin-2-yl)phenyl)ethanone was rinsed with THF (2 mL) then this solution was also added to the MeMgCl mixture. The mixture was stirred for about 10 min then AcOH (1 mL) was added. The material was purified in two equal portions by preparative reverse phase HPLC (Table 2, method j). The fractions from the preparative HPLC containing the title compound were concentrated under reduced pressure to remove most or all of the 1,4-dioxane. The mixture was basified with saturated aqueous NaHCO$_3$ and the solids collected by filtration. The material was dried overnight under vacuum at about 60° C. to give 2-(4-(1-ethyl-3H-imidazo[1,2-a]pyrrolo[2,3-e]pyrazin-2-yl)phenyl)propan-2-ol (0.033 g, 51%): LC/MS (Table 2, Method a) R$_t$=1.85 min; MS m/z 321 (M+H)$^+$. Syk IC$_{50}$=B Example #5: N-(3-(7-(5-Methoxy-1-methyl-1H-indol-3-yl)-6H-imidazo[1,5-a]pyrrolo[2,3-e]pyrazin-1-yl)propyl)acetamide

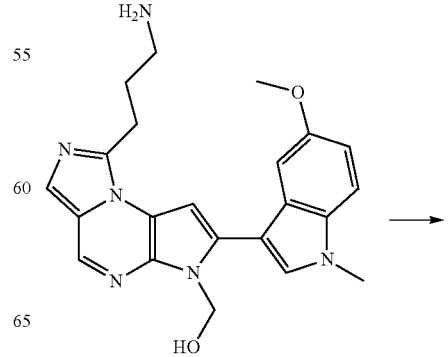

Step A: (1-(3-Aminopropyl)-7-(5-methoxy-1-methyl-1H-indol-3-yl)-6H-imidazo[1,5-a]pyrrolo[2,3-e]pyrazin-6-yl)methanol

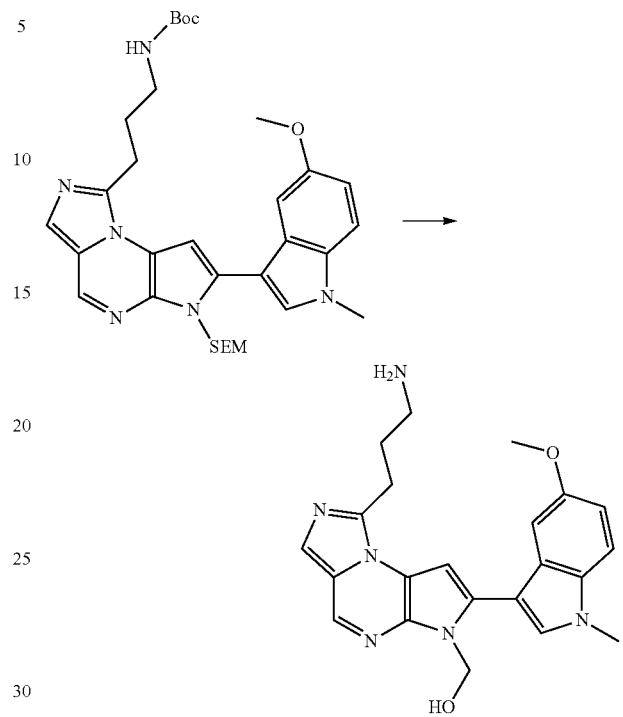

To a solution of tert-butyl 3-(7-(5-methoxy-1-methyl-1H-indol-3-yl)-6-((2-(trimethylsilyl)ethoxy)methyl)-6H-imidazo[1,5-a]pyrrolo[2,3-e]pyrazin-1-yl)propylcarbamate (0.347 g, 0.574 mmol, prepared using J.1 from Preparation #I.1 with 4-(tert-butoxycarbonylamino)butyric acid and L.1 with mercury(II) trifluoroacetate) in DCM (5 mL) at rt was added TFA (1.10 mL, 14.3 mmol). After about 16 h, the mixture was concentrated in vacuo to provide (1-(3-aminopropyl)-7-(5-methoxy-1-methyl-1H-indol-3-yl)-6H-imidazo[1,5-a]pyrrolo[2,3-e]pyrazin-6-yl)-methanol (0.232 g, 100%): LC/MS (Table 2, Method c) R$_t$=1.26 min; MS m/z 405 (M+H)$^+$.

Step B: N-(3-(6-(Hydroxymethyl)-7-(5-methoxy-1-methyl-1H-indol-3-yl)-6H-imidazo[1,5-a]pyrrolo[2,3-e]pyrazin-1-yl)propyl)acetamide 393
-continued

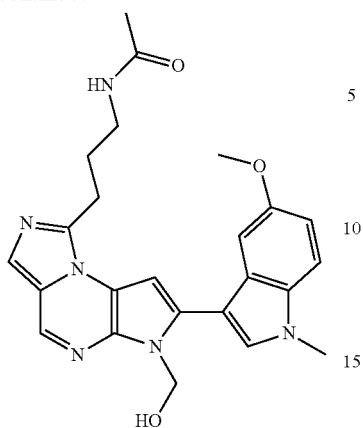

To a solution of (1-(3-aminopropyl)-7-(5-methoxy-1-methyl-1H-indol-3-yl)-6H-imidazo[1,5-a]pyrrolo[2,3-e]pyrazin-6-yl)methanol (0.116 g, 0.287 mmol) in THF (3 mL) at rt was added Ac$_2$O (0.032 mL, 0.344 mmol) and pyridine (1.0 mL, 12.36 mmol). After about 10 min, additional Ac$_2$O (0.027 mL, 0.287 mmol) was added. After about 15 min the mixture was diluted with aqueous NaHCO$_3$ (10 mL) and extracted with EtOAc (20 mL). The organic layer was dried over anhydrous MgSO$_4$, filtered and concentrated in vacuo to give N-(3-(6-(hydroxymethyl)-7-(5-methoxy-1-methyl-1H-indol-3-yl)-6H-imidazo[1,5-a]pyrrolo[2,3-e]pyrazin-1-yl)propyl)acetamide (0.128 g, 100%): LC/MS (Table 2, Method c) R$_t$=1.26 min; MS m/z 447 (M+H)$^+$.

Step C: N-(3-(7-(5-Methoxy-1-methyl-1H-indol-3-yl)-6H-imidazo[1,5-a]pyrrolo[2,3-e]pyrazin-1-yl)propyl)acetamide

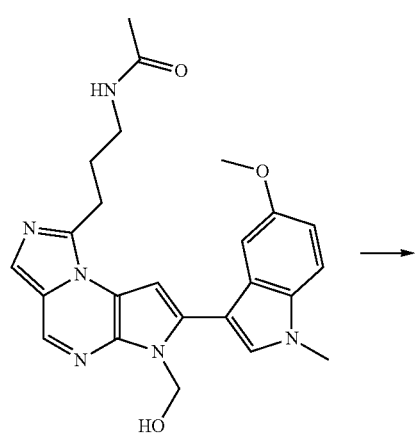

394
-continued

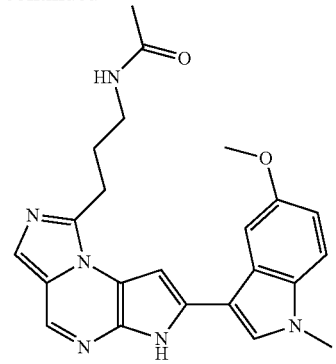

To a solution of N-(3-(6-(hydroxymethyl)-7-(5-methoxy-1-methyl-1H-indol-3-yl)-6H-imidazo[1,5-a]pyrrolo[2,3-e]pyrazin-1-yl)propyl)acetamide (0.128 g, 0.287 mmol) in MeOH (3 mL) at rt was added 30 wt % aqueous NH$_4$OH (0.37 mL, 2.87 mmol) and the mixture was heated to about 60° C. for about 30 min. The mixture was cooled to about 0° C. and was sonicated to provide a solid which was collected by filtration. The solid material was taken up in EtOAc (15 mL) and washed with water (10 mL). The organics were dried over anhydrous MgSO$_4$, filtered and concentrated in vacuo. The resulting residue was purified by a 12 g silica column eluting with 0 to 10% MeOH in DCM to provide N-(3-(7-(5-methoxy-1-methyl-1H-indol-3-yl)-6H-imidazo[1,5-a]pyrrolo[2,3-e]pyrazin-1-yl)propyl)acetamide (0.025 g, 21%): LC/MS (Table 2, Method c) R$_t$=1.25 min; MS m/z 417 (M+H)$^+$. Syk IC$_{50}$=A Example #6

3-(3-(4-(2-Hydroxypropan-2-yl)phenyl)-6H-imidazo[1,5-a]pyrrolo[2,3-e]pyrazin-1-yl)picolinonitrile

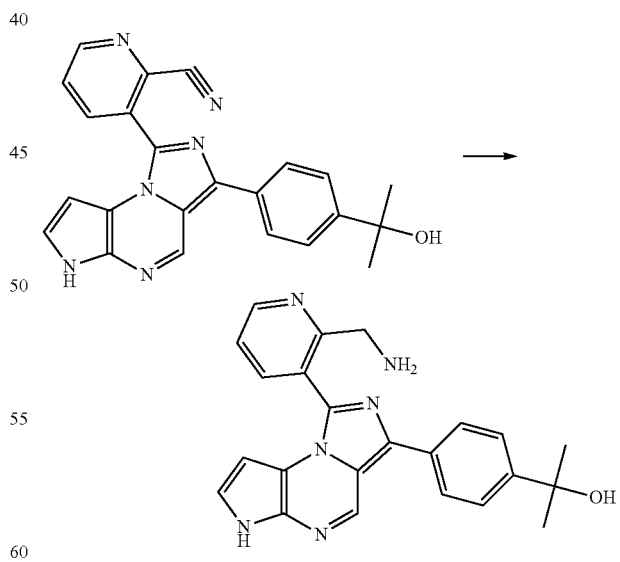

The 3-(3-(4-(2-hydroxypropan-2-yl)phenyl)-6H-imidazo[1,5-a]pyrrolo[2,3-e]pyrazin-1-yl)picolinonitrile (0.030 g, 0.076 mmol, prepared using AC from Preparation #AI.1 with 3-(5,5-dimethyl-1,3,2-dioxaborinan-2-yl)picolinonitrile [Frontier]) in AcOH (2 mL) was treated with 10% Pd/C (0.025 g, 0.023 mmol) then stirred under an atmosphere of hydrogen at ambient pressure and temperature. After about 100 min the mixture was diluted with DMF (3 mL) then filtered. The material was purified by preparative reverse phase HPLC (Table 2, Method i). The fractions were concentrated then lyophilized. The material was purified using a 5 g Si-Carbonate (Silicycle™) eluting with MeOH. The material was triturated with 1:3 EtOAc/heptane (5 mL) and the solid was collected by filtration and dried to a constant weight at about 70° C. under vacuum to give 3-(3-(4-(2-hydroxypropan-2-yl)phenyl)-6H-imidazo[1,5-a]pyrrolo[2,3-e]pyrazin-1-yl)picolinonitrile (0.0098 g, 32%): LC/MS (Table 2, Method a) $R_f$=1.79 min; MS m/z 395 (M+H)$^+$. Syk IC$_{50}$=C.

Example #7

2-(4-(1-(2-(Aminomethyl)phenyl)-6H-imidazo[1,5-a]pyrrolo[2,3-e]pyrazin-3-yl)phenyl)propan-2-ol

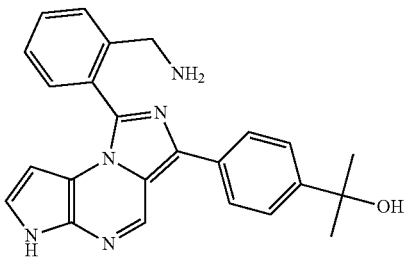 [SMILES: CC(C)(O)c1ccc(-c2nc(-c3ccccc3CN)n3c2cnc2[nH]ccc23)cc1]

Step A: 2-(2-(3-(4-(2-Hydroxypropan-2-yl)phenyl)-6-tosyl-6H-imidazo[1,5-a]pyrrolo[2,3-e]pyrazin-1-yl)benzyl)isoindoline-1,3-dione

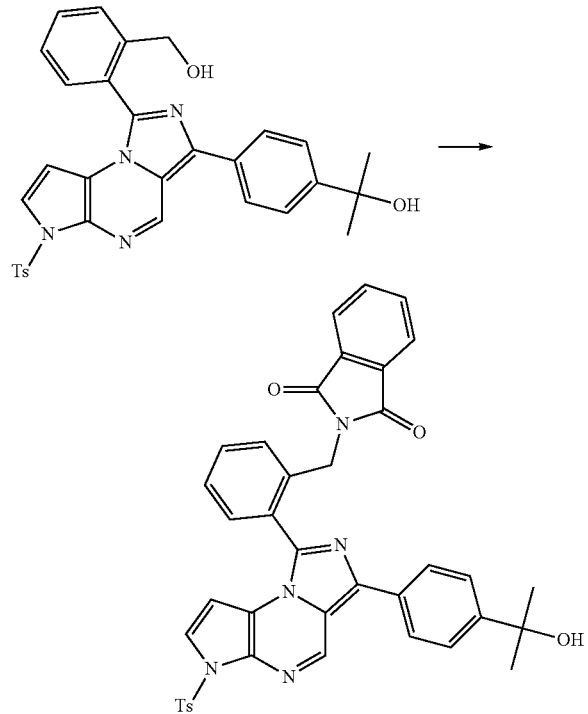

The 2-(4-(1-(2-(hydroxymethyl)phenyl)-6-tosyl-6H-imidazo[1,5-a]pyrrolo[2,3-e]pyrazin-3-yl)phenyl)propan-2-ol (0.125 g, 0.226 mmol, prepared using D from Preparation #AI.1 with 2-(4,4,5,5-tetramethyl-1,3,2-dioxaborolan-2-yl)benzaldehyde and F), PPh$_3$ (0.065 g, 0.25 mmol) and phthalimde (0.037 g, 0.249 mmol) were added to THF (4 mL). DIAD (0.048 mL, 0.249 mmol) was added and the mixture was stirred at rt for about 30 min. An additional portion of the PPh$_3$ (0.065 g, 0.249 mmol), phthalimde (0.037 g, 0.249 mmol) and DIAD (0.048 mL, 0.249 mmol) were added then the mixture was stirred for about 15 min at rt. The mixture was concentrated under reduced pressure and then purified using a 10 g silica column eluting with EtOAc to give 2-(2-(3-(4-(2-Hydroxypropan-2-yl)phenyl)-6-tosyl-6H-imidazo[1,5-a]pyrrolo[2,3-e]pyrazin-1-yl)benzyl)isoindoline-1,3-dione (0.23 g, 149%): LC/MS (Table 2, Method b) $R_f$=2.58 min; MS m/z 682 (M+H)$^+$.

Step B: 2-(4-(1-(2-(Aminomethyl)phenyl)-6H-imidazo[1,5-a]pyrrolo[2,3-e]pyrazin-3-yl)phenyl)propan-2-ol

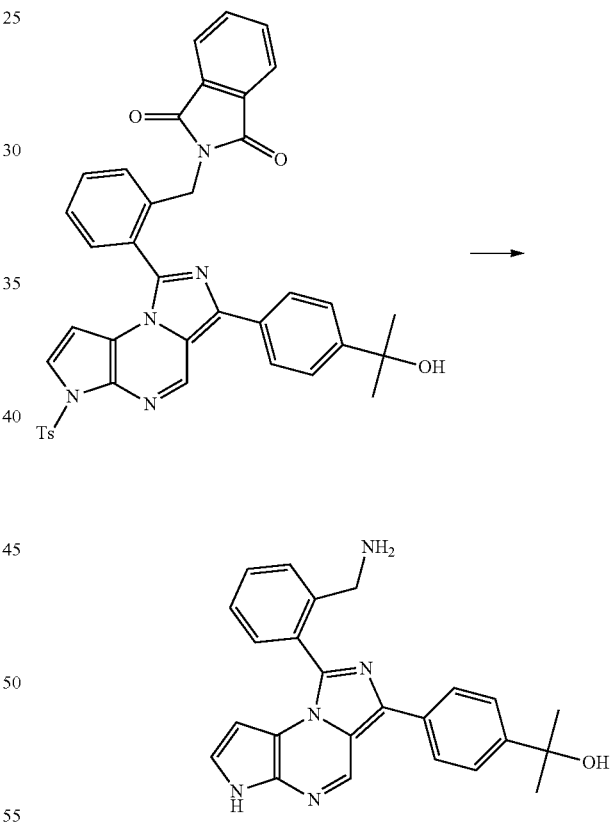

The 2-(2-(3-(4-(2-hydroxypropan-2-yl)phenyl)-6-tosyl-6H-imidazo[1,5-a]pyrrolo[2,3-e]pyrazin-1-yl)benzyl)isoindoline-1,3-dione (0.154 g, 0.226 mmol) in EtOH (4 mL) was treated with hydrazine (0.147 mL, 4.68 mmol) then heated to about 85° C. for about 15 min. The mixture was diluted with EtOAc (20 mL). The insoluble material was removed by filtration and washed with EtOAc (5 mL). The filtrate was concentrated under reduced pressure then the material was dissolved in 1,4-dioxane (4 mL) and treated with aqueous NaOH (50 wt %, 0.260 g, 3.25 mmol). The mixture was heated in a microwave at about 120° C. for about 20 min. The mixture was concentrated under reduced pressure then dissolved in AcOH (1 mL) and DMF (3 mL). The material was purified by preparative reverse phase HPLC (Table 2, Method i). The fractions with desired material were collected and lyophilized. The material was purified using a 5 g Si-Carbonate column (Silicycle™) and eluting wiht MeOH. The material was treated with EtOAc (~10 mL) then concentrated under reduced pressure. This was repeated several times until a yellow solid was obtained. The material was triturated with EtOAc (3 mL) and heptane (15 mL) and the solid was collected by filtration and dried to constant weight under vacuum at about 70° C. to give 2-(4-(1-(2-(aminomethyl)phenyl)-6H-imidazo[1,5-a]pyrrolo[2,3-e]pyrazin-3-yl)phenyl)propan-2-ol (0.022 g, 25%): LC/MS (Table 2, Method a) $R_t$=1.62 min; MS m/z 398 (M+H)$^+$. Syk IC$_{50}$=B.

Example #8

1-Methyl-3-(1-methyl-1,6-dihydropyrazolo[3,4-d]pyrrolo[2,3-b]pyridin-7-yl)-N-(methylsulfonyl)-1H-indole-5-carboxamide

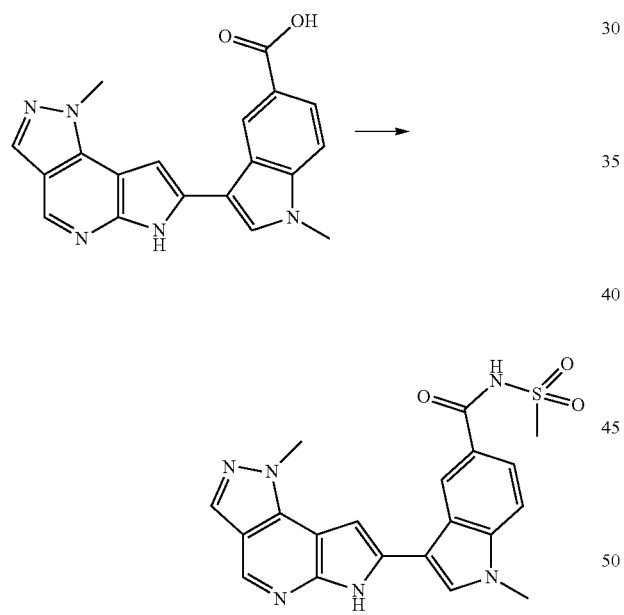

1-Methyl-3-(1-methyl-1,6-dihydropyrazolo[3,4-d]pyrrolo[2,3-b]pyridin-7-yl)-1H-indole-5-carboxylic acid (0.047 g, 0.14 mmol, Example #AN.1), methanesulfonamide (0.039 g, 0.41 mmol) and EDC (0.065 g, 0.34 mmol) were combined in a mixture of DCE (1.31 mL) and t-BuOH (1.31 mL). DMAP (0.050 g, 0.41 mmol) was added and the mixture was stirred at rt for about 16 h. The mixture was purified by flash chromatography (12 g silica gel column, (6:3:1 CHCl$_3$/MeOH/saturated NH$_4$OH)/EtOAc 50-85%) to give 1-methyl-3-(1-methyl-1,6-dihydropyrazolo[3,4-d]pyrrolo[2,3-b]pyridin-7-yl)-N-(methylsulfonyl)-1H-indole-5-carboxamide (0.024 g, 42%): LC/MS (Table 2, Method a) $R_t$=1.55 min; MS m/z 423 (M+H)$^+$. Syk IC$_{50}$=A.

Example #9

(7-(5-Methoxy-1-methyl-1H-indol-3-yl)-1-methylpyrazolo[3,4-d]pyrrolo[2,3-b]pyridin-6(1H)-yl) methyl dihydrogen phosphate

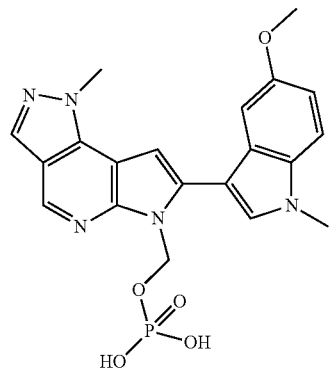 [SMILES: COc1ccc2c(c1)c(-c1cc3c4c(cnc3n1COP(=O)(O)O)cnn4C)cn2C]

Step A: Di-tert-butyl (7-(5-methoxy-1-methyl-1H-indol-3-yl)-1-methylpyrazolo[3,4-d]pyrrolo[2,3-b]pyridin-6(1H)-yl)methyl phosphate

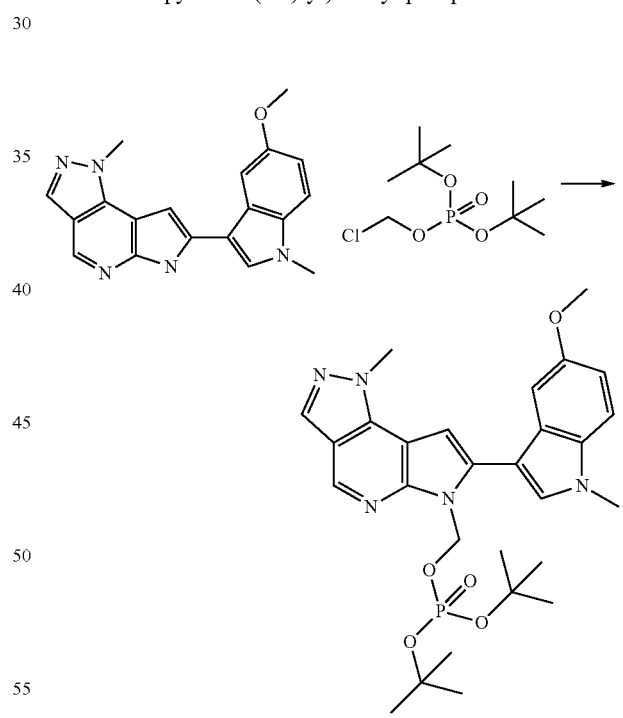

7-(5-Methoxy-1-methyl-1H-indol-3-yl)-1-methyl-1,6-dihydropyrazolo[3,4-d]pyrrolo[2,3-b]pyridine (1.00 g, 3.02 mmol [WO2009/152133, Example #42]) and NaH (60 wt % in mineral oil, 0.200 g, 5.00 mmol) were added to DMF (40 mL) then the mixture was stirred at rt for about 10 min. Then NaI (0.068 g, 0.453 mmol) and di-tert-butyl chloromethyl phosphate (1.60 g, 6.19 mmol, [Journal of Medicinal Chemistry (2008), 51(5), 1111-1114]) were added then the mixture was warmed to about 60° C. for about 45 min. The mixture was cooled to rt then concentrated under reduced pressure. The material was partitioned between water (50 mL) and EtOAc (50 mL). The organic layer was isolated and the aqueous layer was extracted with EtOAc (2×50 mL) then DCM (2×30 mL). The combined organics were dried over anhydrous MgSO₄, filtered and concentrated under reduced pressure. The material was purified using an 80 g silica column and eluting with EtOAc to give di-tert-butyl (7-(5-methoxy-1-methyl-1H-indol-3-yl)-1-methylpyrazolo[3,4-d]pyrrolo[2,3-b]pyridin-6(1H)-yl)methyl phosphate (0.486 g, 29%): LC/MS (Table 2, Method a) $R_f$=2.68 min; MS m/z 554 (M+H)⁺.

Step B: (7-(5-Methoxy-1-methyl-1H-indol-3-yl)-1-methylpyrazolo[3,4-d]pyrrolo[2,3-b]pyridin-6(1H)-yl)methyl dihydrogen phosphate

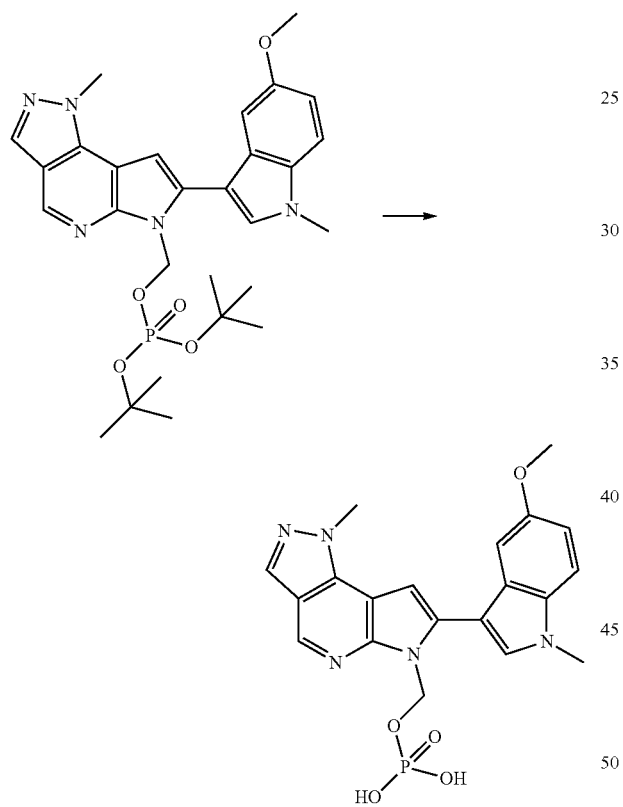

Di-tert-butyl (7-(5-methoxy-1-methyl-1H-indol-3-yl)-1-methylpyrazolo[3,4-d]pyrrolo[2,3-b]pyridin-6(1H)-yl)methyl phosphate (0.486 g, 0.878 mmol) was dissolved in DCM (10 mL) then TFA (1.00 mL, 13.0 mmol) was added. The mixture was stirred 10 min then concentrated under reduced pressure. The material was dissolved in DMF (12 mL) and the material was purified by preparative reverse phase HPLC (Table 2, Method i). The fractions containing the title compound were collected then concentrated under reduced pressure to remove most of the MeCN. The solid was collected by filtration and washed with water (0.5 mL). The solid was dried to constant weight at about 60° C. under vacuum to give (7-(5-methoxy-1-methyl-1H-indol-3-yl)-1-methylpyrazolo[3,4-d]pyrrolo[2,3-b]pyridin-6(1H)-yl)methyl dihydrogen phosphate (0.165 g, 43%): LC/MS (Table 2, Method a) $R_f$=1.58 min; MS m/z 442 (M+H)⁺. Syk IC₅₀=C.

Example #10

(7-(5-Methoxy-1-methyl-1H-indol-3-yl)-1-methyl-6H-imidazo[1,5-a]pyrrolo[2,3-e]pyrazin-6-yl)methyl disodium phosphate

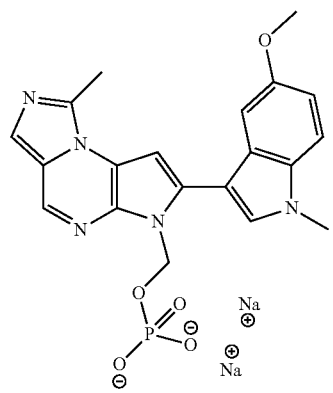 [SMILES: COc1ccc2c(c1)c(-c1cc3c(ncc4cnc(C)n43)n1COP(=O)([O-])[O-])cn2C ; [Na+] ; [Na+]]

Step A: Di-tert-butyl (7-(5-methoxy-1-methyl-1H-indol-3-yl)-1-methyl-6H-imidazo[1,5-a]pyrrolo[2,3-e]pyrazin-6-yl)methyl phosphate

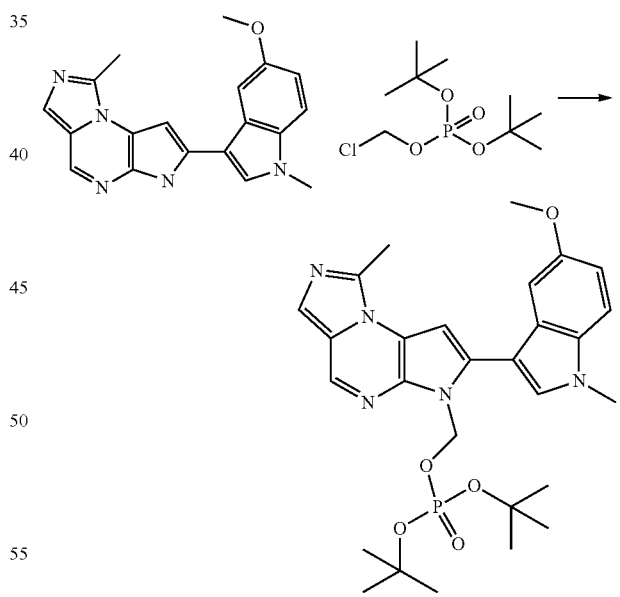

7-(5-Methoxy-1-methyl-1H-indol-3-yl)-1-methyl-6H-imidazo[1,5-a]pyrrolo[2,3-e]pyrazine (1.00 g, 3.02 mmol, [WO2009/152133, Example #20]) was dissolved in DMF (40 mL) then treated with NaH (60 wt % in mineral oil, 0.205 g, 5.13 mmol). The mixture was stirred at rt for about 10 min then NaI (0.068 g, 0.453 mmol) and di-tert-butyl chloromethyl phosphate (1.561 g, 6.04 mmol, [Journal of Medicinal Chemistry (2008), 51(5), 1111-1114]) was added. The mixture was then heated to about 60° C. for about 1 h. The mixture was cooled to rt and concentrated under reduced pressure. The material was stirred with EtOAc (125 mL) and the insoluble material was removed by filtration. The filtrate was concentrated under reduced pressure then the material was purified using a 40 g silica column and eluting with EtOAc to give di-tert-butyl (7-(5-methoxy-1-methyl-1H-indol-3-yl)-1-methyl-6H-imidazo[1,5-a]pyrrolo[2,3-e]pyrazin-6-yl)methyl phosphate (0.800 g, 48%): LC/MS (Table 2, Method a) $R_f$=2.51 min; MS m/z 554 (M+H)$^+$.

Step B: (7-(5-Methoxy-1-methyl-1H-indol-3-yl)-1-methyl-6H-imidazo[1,5-a]pyrrolo[2,3-e]pyrazin-6-yl)methyl dihydrogen phosphate

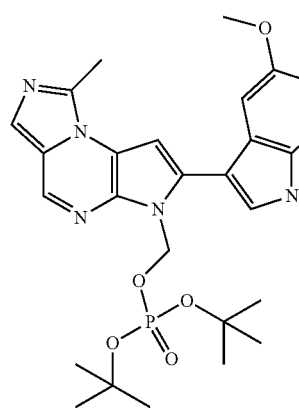

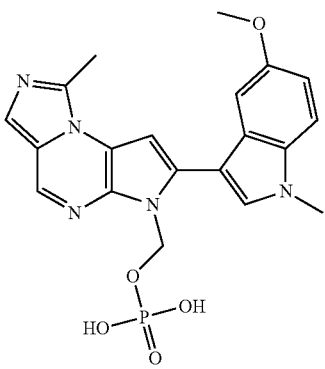

Di-tert-butyl (7-(5-methoxy-1-methyl-1H-indol-3-yl)-1-methyl-6H-imidazo[1,5-a]pyrrolo[2,3-e]pyrazin-6-yl)methyl phosphate (0.2 g, 0.361 mmol) was dissolved in DCM (5 mL) then TFA (0.2 mL, 2.60 mmol) was added. After about 20 min at rt the reaction mixture was concentrated under reduced pressure. The material was dissolved in DMF (7.5 mL) then the material was purified by preparative reverse phase HPLC (Table 2, Method i). The fractions were collected and concentrated under reduced pressure to remove most or all of the MeCN. The solid was collected by filtration and dried under vacuum to a constant weight at about 60° C. to provide (7-(5-methoxy-1-methyl-1H-indol-3-yl)-1-methyl-6H-imidazo[1,5-a]pyrrolo[2,3-e]pyrazin-6-yl)methyl dihydrogen phosphate (0.065 g, 41%): LC/MS (Table 2, Method a) $R_f$=1.42 min; MS m/z 442 (M+H)$^+$.

Step C: (7-(5-Methoxy-1-methyl-1H-indol-3-yl)-1-methyl-6H-imidazo[1,5-a]pyrrolo[2,3-e]pyrazin-6-yl)methyl disodium phosphate

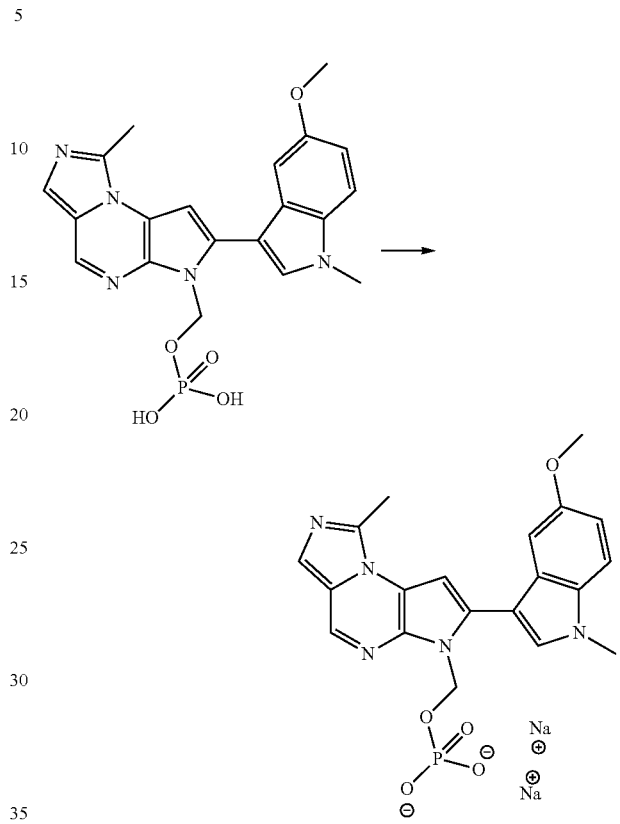

(7-(5-Methoxy-1-methyl-1H-indol-3-yl)-1-methyl-6H-imidazo[1,5-a]pyrrolo[2,3-e]pyrazin-6-yl)methyl dihydrogen phosphate (0.065 g, 0.15 mmol) was suspended in water (5 mL). The mixture was treated with NaOMe (25 wt % in MeOH, 63.6 mg, 0.295 mmol). The resulting solution was lyophilized to give (7-(5-methoxy-1-methyl-1H-indol-3-yl)-1-methyl-6H-imidazo[1,5-a]pyrrolo[2,3-e]pyrazin-6-yl)methyl disodium phosphate (0.073 g, 102%): LC/MS (Table 2, Method a) $R_f$=1.42 min; MS m/z 442 (M+H)$^+$. Syk IC$_{50}$=C.

Example #11

2-(4-(7-Bromo-1-methyl-6H-imidazo[1,5-a]pyrrolo[2,3-e]pyrazin-3-yl)phenyl)propan-2-ol

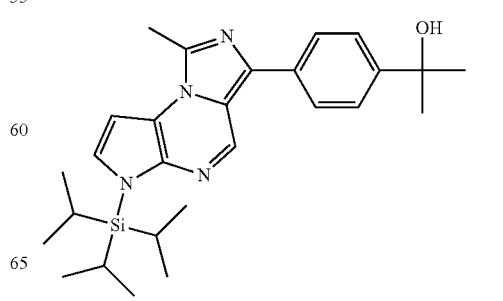

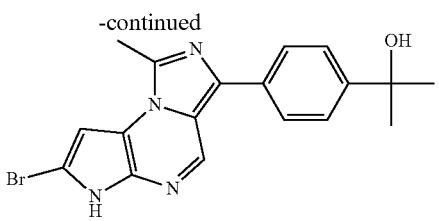

To a solution of 2-(4-(1-methyl-6-(triisopropylsilyl)-6H-imidazo[1,5-a]pyrrolo[2,3-e]pyrazin-3-yl)phenyl)propan-2-ol (0.755 g, 1.63 mmol, Preparation #AX.1) in DCM (16.3 ml) at about −20° C. was added NBS (0.462 g, 2.59 mmol). The resulting suspension was allowed to stir at about −20° C. for about 15 min. The mixture was concentrated under reduced pressure and the residue was purified by flash chromatography (40 g silica gel column; gradient elution with 0 to 50% EtOAc/heptane) to give 2-(4-(7-bromo-1-methyl-6H-imidazo[1,5-a]pyrrolo[2,3-e]pyrazin-3-yl)phenyl)propan-2-ol (0.11 g, 18%). LC/MS (Table 2, Method a) $R_t$=2.41 min; MS m/z 385 (M+H)$^+$. Syk IC$_{50}$=B.

Example #12

Methyl 2-(4-(1-methyl-6H-imidazo[1,5-a]pyrrolo[2,3-e]pyrazin-3-yl)-1H-pyrazol-1-yl)acetate

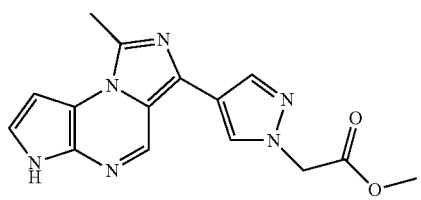 [SMILES: COC(=O)Cn1cc(-c2nc(C)n3c2cnc2[nH]ccc23)cn1]

Step A: 2-(4-(1-methyl-6H-imidazo[1,5-a]pyrrolo[2,3-e]pyrazin-3-yl)-1H-pyrazol-1-yl)acetic acid

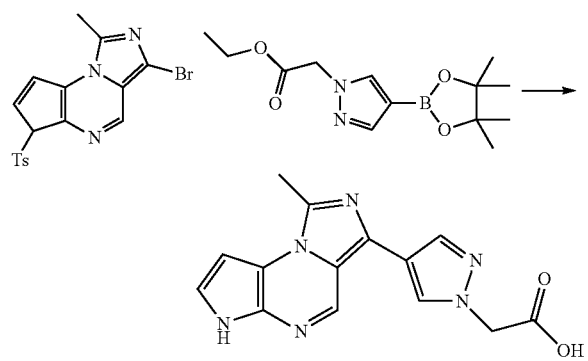

3-Bromo-1-methyl-6-tosyl-6H-imidazo[1,5-a]pyrrolo[2,3-e]pyrazine (0.356 g, 0.878 mmol) (Preparation #AB.1), 1-(ethoxycarbonylmethyl)-1H-pyrazole-4-boronic acid, pinacol ester (0.295 g, 1.05 mmol), and Cs$_2$CO$_3$ (0.1716 g, 2.20 mmol) were combined in 1,4-dioxane (7.0 mL) and water (1.8 mL). The mixture was degassed by bubbling N$_2$ directly into the mixture. After about 10 min, PdCl$_2$(PPh$_3$)$_2$ (0.043 g, 0.061 mmol) was added and degassing continued for about 5 more min. The mixture was heated at about 85° C. for about 16 h. Aqueous NaOH (1 N, 3 mL) was added and heating continued for about 2 h. The mixture was allowed to cool to rt and aqueous HCl (1 N, 10 mL) was added. The mixture was concentrated in vacuo to give 2-(4-(1-methyl-6H-imidazo[1,5-a]pyrrolo[2,3-e]pyrazin-3-yl)-1H-pyrazol-1-yl)acetic acid: LCMS (Table 2, Method b) $R_t$=1.37 min.; MS m/z: 297 (M+H)$^+$ Step B: Methyl 2-(4-(1-methyl-6H-imidazo[1,5-a]pyrrolo[2,3-e]pyrazin-3-yl)-1H-pyrazol-1-yl)acetate

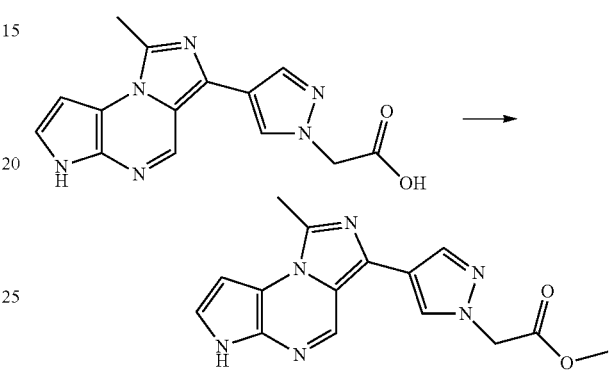

AcCl (20 mL) was added slowly with stirring to MeOH (100 mL) that was cooled in an ice bath. After about 1 h the solution was transferred to the 2-(4-(1-methyl-6H-imidazo[1,5-a]pyrrolo[2,3-e]pyrazin-3-yl)-1H-pyrazol-1-yl)acetic acid. The solvents were removed under reduced pressure and saturated Na$_2$CO$_3$ (25 mL) was added. The product was extracted with DCM (5×20 mL). The combined organic layers were dried over MgSO$_4$, filtered, and concentrated in vacuo. The residue was purified by flash chromatography (40 g silica gel) and eluted with a gradient of 2-9% MeOH in DCM to give methyl 2-(4-(1-methyl-6H-imidazo[1,5-a]pyrrolo[2,3-e]pyrazin-3-yl)-1H-pyrazol-1-yl)acetate (0.109 g, 40%): LCMS (Table 2, Method b) $R_t$=1.46 min.; MS m/z: 311 (M+H)$^+$. Syk IC$_{50}$=B.

What is claimed:
1. A compound of formula (Ie)

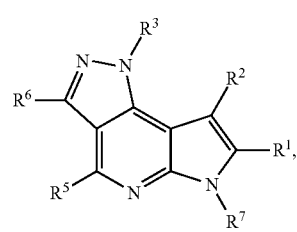

Formula (Ie)

or pharmaceutically acceptable salts, or stereoisomers thereof wherein $R^1$ is H, deuterium, halogen, CF$_3$, CN, OR$^a$, N(R$^a$)(R$^b$), OCF$_3$, —C(O)—N(R$^a$)(R$^b$), —C(O)—OR$^a$, —C(O)-optionally substituted (C$_1$-C$_6$)alkyl, —C(O)-optionally substituted (C$_3$-C$_6$)cycloalkyl, —C(O)-optionally substituted (C$_6$-C$_{10}$)aryl, —C(O)-optionally substituted (C$_1$-C$_{10}$)heteroaryl, —C(O)-optionally substituted (C$_1$-C$_{10}$)heterocyclyl, —S-optionally substituted (C$_1$-C$_6$)

alkyl, —S(O)-optionally substituted ($C_1$-$C_6$)alkyl, —S(O)$_2$-optionally substituted ($C_1$-$C_6$)alkyl, —S(O)$_2$N($R^a$)($R^b$), optionally substituted ($C_1$-$C_6$)alkyl, optionally substituted ($C_1$-$C_6$)alkoxy, optionally substituted ($C_2$-$C_6$)alkenyl, optionally substituted ($C_2$-$C_6$)alkynyl, optionally substituted ($C_3$-$C_{10}$)cycloalkyl, optionally substituted azaindolyl, optionally substituted azepinyl, optionally substituted azetidinyl, optionally substituted benzo(b)thienyl, optionally substituted benzofuranyl, optionally substituted benzimidazolyl, optionally substituted benzoxazolyl, optionally substituted benzothiazolyl, optionally substituted benzothiadiazolyl, optionally substituted benzoxadiazolyl, optionally substituted 6,7-dihydro-5H-cyclopentapyrimidinyl, optionally substituted furanyl, optionally substituted imidazolyl, optionally substituted imidazopyridinyl, optionally substituted 5,6,7,8-tetrahydro-imidazo[1,2-a]pyrazinyl, optionally substituted 5,6,7,8-tetrahydro-imidazo[1,5-a]pyrazinyl, optionally substituted 5,6,7,8-tetrahydro[1,2,4]-triazolo[4,3-a]pyrazinyl, optionally substituted indazolyl, optionally substituted indolinyl, optionally substituted indolyl, optionally substituted isoindolinyl, optionally substituted isoxazolyl, optionally substituted isothiazolyl, optionally substituted morpholinyl, optionally substituted oxadiazolyl, optionally substituted oxazolyl, optionally substituted phenyl, optionally substituted piperazinyl, optionally substituted piperidinyl, optionally substituted purinyl, optionally substituted pyranyl, optionally substituted pyrazolo[3,4-d]pyrimidinyl, optionally substituted pyridinyl, optionally substituted pyrimidinyl, optionally substituted pyrrolidinyl, optionally substituted 6,7-dihydro-5H-pyrrolo[1,2-a]imidazolyl, optionally substituted pyrrolyl, optionally substituted pyrrolo[3,2-c]pyrimidinyl, optionally substituted pyrrolo[2,3-d]pyrimidinyl, optionally substituted pyrrolo[2,3-b]pyridinyl, optionally substituted octahydropyrrolo[3,4-c]pyrrolyl, optionally substituted quinazolinyl, optionally substituted quinolinyl, optionally substituted quinuclidinyl, optionally substituted quinoxalinyl, optionally substituted thiomorpholinyl, optionally substituted tetrahydropyranyl, optionally substituted tetrahydrofuranyl, optionally substituted tetrahydroindolyl, optionally substituted thiazolyl, optionally substituted thienyl, optionally substituted tetrazolyl, optionally substituted thiadiazolyl, optionally substituted [1,3,5]triazinyl, optionally substituted triazolyl, or optionally substituted tropanyl; or $R^1$ is —$Z^{101}$-$L^1$-$Z^{102}$ wherein $Z^{101}$ is optionally substituted ($C_1$-$C_6$)alkylene, optionally substituted ($C_1$-$C_{10}$)heterocyclylene, or optionally substituted ($C_6$-$C_{10}$)arylene;

$L^1$ is —CH$_2$C(O), —C(O)—, —C(O)CH$_2$—, —N($R^a$)—, -optionally substituted ($C_1$-$C_4$)alkylene-N($R^a$)C(O)—, -optionally substituted ($C_1$-$C_4$)alkylene-C(O)N($R^a$)—, —C(O)N($R^a$)—, —N($R^a$)C(O)—, —C(O)N($R^a$)-optionally substituted ($C_1$-$C_4$)alkylene-, —N($R^a$)C(O)-optionally substituted ($C_1$-$C_4$)alkylene-, —C(O)N($R^a$)-optionally substituted ($C_1$-$C_4$)alkylene-C(O), —N($R^a$)C(O)-optionally substituted ($C_1$-$C_4$)alkylene-C(O)—, —C(O)-optionally substituted ($C_1$-$C_4$)alkylene-N($R^a$)C(O)—, —C(O)-optionally substituted ($C_1$-$C_4$)alkylene-C(O)N($R^a$)—, -optionally substituted ($C_1$-$C_4$)alkylene-N($R^a$)C(O)—, —N($R^a$)C(O)-optionally substituted ($C_1$-$C_4$)alkylene, -optionally substituted ($C_1$-$C_4$)alkylene-N($R^a$)C(O)-optionally substituted ($C_1$-$C_4$)alkylene-, -optionally substituted ($C_1$-$C_4$)alkylene-C(O)N($R^a$)-optionally substituted ($C_1$-$C_4$)alkylene-, -optionally substituted ($C_1$-$C_4$)alkylene-N($R^a$)S(O)$_2$—, -optionally substituted ($C_1$-$C_4$)alkylene-S(O)$_2$ N($R^a$)—, —N($R^a$)S(O)$_2$CH$_2$—, —S(O)$_2$N($R^a$)-optionally substituted ($C_1$-$C_4$)alkylene-, —C(O)N($R^a$)S(O)$_2$—, —S(O)$_2$N($R^a$)C(O)—, —S(O)$_2$N($R^a$)—, —N($R^a$)S(O)$_2$—, —O—($C_1$-$C_4$)alkylene-, ($C_1$-$C_6$)alkylene-O—, —C(O)N($R^a$)—($C_1$-$C_6$)alkylene-C(O)—, or —C(O)—($C_1$-$C_6$)alkylene-N($R^a$)C(O)—;

$Z^{102}$ is H, —CN, —N($R^a$)($R^b$), —OR$^a$, optionally substituted ($C_1$-$C_6$)alkyl, optionally substituted ($C_1$-$C_4$) alkoxy, optionally substituted ($C_3$-$C_{10}$)cycloalkyl, optionally substituted ($C_6$-$C_{10}$)aryl, optionally substituted ($C_1$-$C_{10}$)heteroaryl, optionally substituted ($C_1$-$C_{10}$)heterocyclyl, optionally substituted bridged ($C_5$-$C_{12}$)cycloalkyl, or optionally substituted bridged ($C_2$-$C_{10}$)heterocyclyl;

$R^2$ is H, deuterium, halogen, CF$_3$, CN, OR$^a$, N($R^a$)($R^b$), OCF$_3$, —C(O)-optionally substituted ($C_1$-$C_6$)alkyl, —C(O)-optionally substituted ($C_3$-$C_6$)cycloalkyl, —S-optionally substituted ($C_1$-$C_6$)alkyl, —S(O)$_2$-optionally substituted ($C_1$-$C_6$)alkyl, —S(O)$_2$N($R^a$)($R^b$), optionally substituted ($C_1$-$C_6$)alkoxy, —C(O)N($R^a$)($R^b$), —S(O)$_2$-optionally substituted ($C_1$-$C_6$)alkyl, optionally substituted ($C_1$-$C_6$)alkyl, optionally substituted ($C_2$-$C_6$)alkenyl, optionally substituted ($C_2$-$C_6$)alkynyl, optionally substituted ($C_3$-$C_{10}$)cycloalkyl, optionally substituted ($C_6$-$C_{10}$)aryl, optionally substituted ($C_1$-$C_{10}$)heteroaryl, or optionally substituted ($C_1$-$C_{10}$)heterocyclyl;

$R^3$ is H or methyl;

$R^5$ is H, deuterium, N($R^a$)($R^b$), halogen, CN, CF$_3$, OR$^a$, optionally substituted ($C_1$-$C_6$)alkyl, OCF$_3$, —C(O)-optionally substituted ($C_1$-$C_6$)alkyl, —C(O)-optionally substituted ($C_3$-$C_6$)cycloalkyl, —S-optionally substituted ($C_1$-$C_6$)alkyl, —S(O)-optionally substituted ($C_1$-$C_6$)alkyl, —S(O)$_2$-optionally substituted ($C_1$-$C_6$)alkyl, —S(O)$_2$N($R^a$)($R^b$), optionally substituted ($C_1$-$C_6$)alkyl, or optionally substituted ($C_1$-$C_6$)alkoxy;

$R^6$ is H, deuterium, halogen, CF$_3$, CN, —C(O)—N($R^a$)($R^b$), —C(O)—OR$^a$, —C(O)-optionally substituted ($C_1$-$C_6$)alkyl, —C(O)-optionally substituted ($C_3$-$C_6$)cycloalkyl, —C(O)-optionally substituted ($C_6$-$C_{10}$)aryl, —C(O)-optionally substituted ($C_1$-$C_{10}$)heteroaryl, —C(O)-optionally substituted ($C_1$-$C_{10}$)heterocyclyl, —S-optionally substituted ($C_1$-$C_6$)alkyl, —S(O)-optionally substituted ($C_1$-$C_6$)alkyl, —S(O)$_2$-optionally substituted ($C_1$-$C_6$)alkyl, —S(O)$_2$N($R^a$)($R^b$), optionally substituted ($C_1$-$C_6$)alkyl, optionally substituted ($C_2$-$C_6$) alkenyl, optionally substituted ($C_2$-$C_6$)alkynyl, optionally substituted ($C_3$-$C_{10}$)cycloalkyl, optionally substituted ($C_1$-$C_{10}$)heteroaryl, optionally substituted ($C_1$-$C_{10}$) heterocyclyl, or optionally substituted ($C_6$-$C_{10}$) aryl;

or $R^6$ is —$Z^{201}$-$L^2$-$Z^{202}$ wherein $Z^{201}$ is optionally substituted ($C_1$-$C_6$)alkylene, optionally substituted ($C_1$-$C_{10}$)heteroarylene, optionally substituted ($C_1$-$C_{10}$)heterocyclylene, or optionally substituted ($C_6$-$C_{10}$)arylene;

$L^2$ is a bond, optionally substituted ($C_1$-$C_4$)alkylene, —CH$_2$C(O), —C(O)—, —C(O)CH$_2$—, —N($R^a$)—, —O—, -optionally substituted ($C_1$-$C_4$)alkylene-N($R^a$)C(O)—, -optionally substituted ($C_1$-$C_4$)alkylene-C(O)N($R^a$)—, —C(O)N($R^a$)—, —N($R^a$)C(O)—, —C(O)N($R^a$)S(O)$_2$—, —S(O)$_2$N($R^a$)C(O)—, —C(O)N($R^a$)-optionally substituted ($C_1$-$C_4$) alkylene-, —N($R^a$)C(O)-optionally substituted ($C_1$-

$C_4$)alkylene-, -optionally substituted ($C_1$-$C_4$) alkylene-N($R^a$)C(O)-optionally substituted ($C_1$-$C_4$)alkylene-, -optionally substituted ($C_1$-$C_4$)alkylene-C(O)N($R^a$)-optionally substituted ($C_1$-$C_4$)alkylene-, -optionally substituted ($C_1$-$C_4$)alkylene-N($R^a$)S(O)$_2$—, -optionally substituted ($C_1$-$C_4$)alkylene-S(O)$_2$N($R^a$)—, —N($R^a$)S(O)$_2$CH$_2$—, —S(O)$_2$N($R^a$)-optionally substituted ($C_1$-$C_4$)alkylene-, —S(O)$_2$—, —S(O)$_2$N($R^a$)—, —N($R^a$)S(O)$_2$—, —($C_1$-$C_4$)alkylene-O—, or —O—($C_1$-$C_4$)alkylene-;

$Z^{202}$ is H, —CN, —N($R^a$)($R^b$), —OR$^a$, optionally substituted ($C_1$-$C_6$)alkyl, optionally substituted ($C_1$-$C_4$) alkoxy, optionally substituted ($C_3$-$C_{10}$)cycloalkyl, optionally substituted ($C_6$-$C_{10}$)aryl, optionally substituted ($C_1$-$C_{10}$)heteroaryl, optionally substituted ($C_1$-$C_{10}$)heterocyclyl, optionally substituted bridged ($C_5$-$C_{12}$)cycloalkyl, or optionally substituted bridged ($C_2$-$C_{10}$)heterocyclyl;

$R^7$ is H, deuterium, optionally substituted-(CH$_2$)$_n$—P(=O)(OR$^a$)(OR$^a$), optionally substituted —(CH$_2$)$_n$—O—P(=O)(OR$^a$)(OR$^a$), optionally substituted-(CH$_2$)$_n$—P(=O)(OR$^a$)(R$^a$), or —CH=CH—P(=O)(OR$^a$)(OR$^a$);

$R^a$ and $R^b$ are each independently H, deuterium, an optionally substituted ($C_1$-$C_{10}$)alkyl, optionally substituted ($C_2$-$C_{10}$)alkenyl, optionally substituted ($C_2$-$C_{10}$)alkynyl, an optionally substituted ($C_1$-$C_{10}$)alkyl-O—($C_1$-$C_{10}$)alkyl, optionally substituted ($C_3$-$C_{10}$)cycloalkyl, an optionally substituted ($C_6$-$C_{10}$)aryl, optionally substituted ($C_1$-$C_{10}$)heteroaryl, optionally substituted ($C_1$-$C_{10}$)heterocyclyl, optionally substituted —($C_1$-$C_6$)alkylene-($C_3$-$C_{10}$)cycloalkyl, an optionally substituted —($C_1$-$C_6$)alkylene-($C_6$-$C_{10}$)aryl, optionally substituted —($C_1$-$C_6$)alkylene-($C_1$-$C_{10}$)heteroaryl, or optionally substituted —($C_1$-$C_6$)alkylene-($C_1$-$C_{10}$)heterocyclyl;

$R^e$ for each occurrence is independently a bond, an optionally substituted ($C_1$-$C_{10}$)alkylene, an optionally substituted ($C_2$-$C_{10}$)alkenylene, an optionally substituted ($C_2$-$C_{10}$)alkynylene, an optionally substituted —($C_1$-$C_{10}$)alkylene-O—($C_1$-$C_{10}$)alkylene group, an optionally substituted ($C_3$-$C_{10}$)cycloalkylene, an optionally substituted ($C_6$-$C_{10}$)arylene, an optionally substituted ($C_1$-$C_{10}$)heteroarylene, or an optionally substituted ($C_1$-$C_{10}$) heterocyclylene; and n is 1, 2 or 3;

wherein the optional substituent is selected from the group consisting of: ($C_1$-$C_8$)alkyl groups, ($C_2$-$C_8$)alkenyl groups, ($C_2$-$C_8$)alkynyl groups, ($C_3$-$C_{10}$)cycloalkyl groups, halogen, halogenated ($C_1$-$C_8$)alkyl groups, —OH, —S—($C_1$-$C_8$)alkyl groups, —SH, —NH($C_1$-$C_8$) alkyl groups, —N(($C_1$-$C_8$)alkyl)$_2$ groups, —NH$_2$, —C(O)NH$_2$, —C(O)NH($C_1$-$C_8$)alkyl groups, —C(O)N(($C_1$-$C_8$)alkyl)$_2$, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)NH$_2$, —NHC(O)NH($C_1$-$C_8$)alkyl groups, —N(($C_1$-$C_8$)alkyl)C(O)NH$_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —C(O)H, —C(O)($C_1$-$C_8$)alkyl groups, —CN, —NO$_2$, —S(O)($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$NH$_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$) alkyl groups, NHOH, NHO($C_1$-$C_8$)alkyl groups, —O-halogenated ($C_1$-$C_8$)alkyl groups, —S(O)$_2$-halogenated ($C_1$-$C_8$)alkyl groups, —S-halogenated ($C_1$-$C_8$) alkyl groups, —($C_1$-$C_6$) heterocyclyl, —($C_1$-$C_6$) heteroaryl, -phenyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$)alkyl groups, and —C(=N—O—($C_1$-$C_6$) alkyl)-($C_1$-$C_6$)alkyl groups;

provided that $R^1$ and $R^6$ are not both H.

2. The compound of claim 1 wherein $R^1$ is H, halogen, CF$_3$, CN, OH, N($R^a$)($R^b$), OCF$_3$, —C(O)-optionally substituted ($C_1$-$C_6$)alkyl, —C(O)-optionally substituted ($C_3$-$C_6$)cycloalkyl, —S-optionally substituted ($C_1$-$C_6$)alkyl, —S(O)$_2$-optionally substituted ($C_1$-$C_6$)alkyl, —S(O)$_2$N($R^a$)($R^b$), optionally substituted ($C_1$-$C_6$)alkoxy, optionally substituted azaindolyl, optionally substituted azepinyl, optionally substituted azetidinyl, optionally substituted benzo(b)thienyl, optionally substituted benzofuranyl, optionally substituted benzimidazolyl, optionally substituted benzoxazolyl, optionally substituted benzothiazolyl, optionally substituted benzothiadiazolyl, optionally substituted benzoxadiazolyl, optionally substituted 6,7-dihydro-5H-cyclopentapyrimidinyl, optionally substituted furanyl, optionally substituted imidazolyl, imidazopyridinyl, 5,6,7,8-tetrahydro-imidazo[1,2-a]pyrazinyl, 5,6,7,8-tetrahydro-imidazo[1,5-a]pyrazinyl, 5,6,7,8-tetrahydro[1,2,4]-triazolo[4,3-a]pyrazinyl, optionally substituted indazolyl, optionally substituted indolinyl, optionally substituted indolyl, optionally substituted isoindolinyl, optionally substituted isoxazolyl, optionally substituted isothiazolyl, optionally substituted morpholinyl, optionally substituted oxadiazolyl, optionally substituted oxazolyl, optionally substituted phenyl, optionally substituted piperazinyl, optionally substituted piperidinyl, optionally substituted purinyl, optionally substituted pyranyl, optionally substituted pyrazolo[3,4-d]pyrimidinyl, optionally substituted pyridinyl, optionally substituted pyrimidinyl, optionally substituted pyrrolidinyl, 6,7-dihydro-5H-pyrrolo[1,2-a]imidazolyl, optionally substituted pyrrolyl, optionally substituted pyrrolo[3,2-c]pyrimidinyl, optionally substituted pyrrolo[2,3-d]pyrimidinyl, optionally substituted pyrrolo[2,3-b]pyridinyl, optionally substituted octahydropyrrolo[3,4-c]pyrrolyl, optionally substituted quinazolinyl, optionally substituted quinolinyl, optionally substituted quinuclidinyl, optionally substituted quinoxalinyl, optionally substituted thiomorpholinyl, optionally substituted tetrahydropyranyl, optionally substituted tetrahydrofuranyl, optionally substituted tetrahydroindolyl, optionally substituted thiazolyl, optionally substituted thienyl, optionally substituted tetrazolyl, optionally substituted thiadiazolyl, optionally substituted [1,3,5]triazinyl, optionally substituted triazolyl, or optionally substituted tropanyl; or $R^1$ is —$Z^{101}$-$L^1$-$Z^{102}$ wherein $Z^{101}$ is optionally substituted ($C_1$-$C_6$)alkylene, optionally substituted ($C_1$-$C_{10}$)heterocyclylene, or optionally substituted ($C_6$-$C_{10}$)arylene;

$L^1$ is —CH$_2$C(O), —C(O)—, —C(O)CH$_2$—, N($R^a$)—, -optionally substituted ($C_1$-$C_4$)alkylene-N($R^a$)C(O)—, -optionally substituted ($C_1$-$C_4$)alkylene-C(O)N($R^a$)—, —C(O)N($R^a$)—, —N($R^a$)C(O)—, —C(O)N($R^a$)-optionally substituted ($C_1$-$C_4$)alkylene-, —N($R^a$)C(O)-optionally substituted ($C_1$-$C_4$)alkylene-, -optionally substituted ($C_1$-$C_4$)alkylene-N($R^a$)

C(O)—, -optionally substituted (C$_1$-C$_4$)alkylene-N(R$^a$)C(O)-optionally substituted (C$_1$-C$_4$)alkylene-, -optionally substituted (C$_1$-C$_4$)alkylene-C(O)N(R$^a$)-optionally substituted (C$_1$-C$_4$)alkylene-, -optionally substituted (C$_1$-C$_4$)alkylene-N(R$^a$)S(O)$_2$—, -optionally substituted (C$_1$-C$_4$)alkylene-S(O)$_2$N(R$^a$)—, —N(R$^a$)S(O)$_2$CH$_2$—, —S(O)$_2$N(R$^a$)-optionally substituted (C$_1$-C$_4$)alkylene-, —S(O)$_2$N(R$^a$)—, —N(R$^a$)S(O)$_2$— or —O—(C$_1$-C$_4$)alkylene-; and Z$^{102}$ is —N(R$^a$)(R$^b$), -optionally substituted (C$_1$-C$_4$)alkyl, optionally substituted (C$_1$-C$_4$)alkoxy, optionally substituted (C$_1$-C$_{10}$)heteroaryl, or optionally substituted (C$_1$-C$_{10}$)heterocyclyl.

3. The compound of claim 2 wherein R$^1$ is H, halogen, CF$_3$, CN, OH, N(R$^a$)(R$^b$), OCF$_3$, —C(O)-optionally substituted (C$_1$-C$_6$)alkyl, —C(O)-optionally substituted (C$_3$-C$_6$)cycloalkyl, —S-optionally substituted (C$_1$-C$_6$)alkyl, —S(O)$_2$-optionally substituted (C$_1$-C$_6$)alkyl, —S(O)$_2$N(R$^a$)(R$^b$), optionally substituted (C$_1$-C$_6$)alkoxy, optionally substituted benzofuranyl, optionally substituted benzo[b]thienyl, optionally substituted furanyl, optionally substituted imidazolyl, imidazopyridinyl, 5,6,7,8-tetrahydro-imidazo[1,2-a]pyrazinyl, 5,6,7,8-tetrahydro-imidazo[1,5-a]pyrazinyl, 5,6,7,8-tetrahydro[1,2,4]-triazolo[4,3-a]pyrazinyl, optionally substituted indazolyl, optionally substituted indolinyl, optionally substituted indolyl, optionally substituted isoxazolyl, optionally substituted oxadiazolyl, optionally substituted oxazolyl, optionally substituted phenyl, optionally substituted pyrazolo[3,4-d]pyrimidinyl, optionally substituted pyridinyl, optionally substituted pyrimidinyl, optionally substituted pyrrolyl, optionally substituted octahydropyrrolo[3,4-c]pyrrolyl, optionally substituted pyrrolo[2,3-c]pyridinyl, optionally substituted quinolinyl, optionally substituted thiazolyl, optionally substituted thienyl, or optionally substituted tetrazolyl; or R$^1$ is —Z$^{101}$-L$^1$-Z$^{102}$ wherein Z$^{101}$ is optionally substituted (C$_1$-C$_6$)alkylene, optionally substituted (C$_1$-C$_{10}$)heterocyclylene, or optionally substituted (C$_6$-C$_{10}$) arylene;

L$^1$ is —CH$_2$C(O), —C(O)—, —C(O)CH$_2$—, N(R$^a$)—, -optionally substituted (C$_1$-C$_4$)alkylene-N(R$^a$)C(O)—, -optionally substituted (C$_1$-C$_4$)alkylene-C(O)N(R$^a$)—, —C(O)N(R$^a$)—, —N(R$^a$)C(O)—, —C(O)N(R$^a$)-optionally substituted (C$_1$-C$_4$)alkylene-, —N(R$^a$)C(O)-optionally substituted (C$_1$-C$_4$)alkylene-, —C(O)N(R$^a$)-optionally substituted (C$_1$-C$_4$)alkylene-C(O), —N(R$^a$)C(O)-optionally substituted (C$_1$-C$_4$)alkylene-C(O)—, —C(O)-optionally substituted (C$_1$-C$_4$)alkylene-N(R$^a$)C(O)—, —C(O)-optionally substituted (C$_1$-C$_4$)alkylene-C(O)N(R$^a$)—, -optionally substituted (C$_1$-C$_4$)alkylene-N(R$^a$)C(O)-optionally substituted (C$_1$-C$_4$)alkylene-, -optionally substituted (C$_1$-C$_4$)alkylene-C(O)N(R$^a$)-optionally substituted (C$_1$-C$_4$)alkylene-, -optionally substituted (C$_1$-C$_4$)alkylene-N(R$^a$)S(O)$_2$—, -optionally substituted (C$_1$-C$_4$)alkylene-S(O)$_2$N(R$^a$)—, —N(R$^a$)S(O)$_2$CH$_2$—, —S(O)$_2$N(R$^a$)-optionally substituted (C$_1$-C$_4$)alkylene-, —C(O)N(R$^a$)S(O)$_2$—, —S(O)$_2$N(R$^a$)C(O—), —S(O)$_2$N(R$^a$)—, —N(R$^a$)S(O)$_2$— or —O—(C$_1$-C$_4$)alkylene-; and Z$^{102}$ is, —N(R$^a$)(R$^b$), -optionally substituted (C$_1$-C$_4$)alkyl, optionally substituted (C$_1$-C$_4$)alkoxy, optionally substituted (C$_1$-C$_{10}$)heteroaryl, or optionally substituted (C$_1$-C$_{10}$)heterocyclyl.

4. The compound of claim 3 wherein Z$^{101}$ is optionally substituted phenyl.

5. The compound of claim 4 wherein Z$^{102}$ is —N(R$^a$)(R$^b$), -optionally substituted (C$_1$-C$_4$)alkyl, optionally substituted morpholinyl, optionally substituted piperazinyl, optionally substituted piperidinyl, or optionally substituted pyrrolidinyl.

6. The compound of claim 1 wherein R$^2$ is H, halogen, CF$_3$, CN, OR$^a$, N(R$^a$)(R$^b$), OCF$_3$, —C(O)-optionally substituted (C$_1$-C$_6$)alkyl, —C(O)-optionally substituted (C$_3$-C$_6$)cycloalkyl, —S-optionally substituted (C$_1$-C$_6$)alkyl, —S(O)$_2$-optionally substituted (C$_1$-C$_6$)alkyl, —S(O)$_2$N(R$^a$)(R$^b$), optionally substituted (C$_1$-C$_6$)alkyl, optionally substituted (C$_1$-C$_6$)alkoxy, —C(O)N(R$^a$)(R$^b$), optionally substituted (C$_1$-C$_6$)alkyl, optionally substituted (C$_2$-C$_6$)alkenyl, optionally substituted (C$_2$-C$_6$)alkynyl, optionally substituted (C$_3$-C$_{10}$)cycloalkyl, optionally substituted azetidinyl, optionally substituted morpholinyl, optionally substituted piperazinyl, optionally substituted piperidinyl, optionally substituted pyranyl, optionally substituted pyrrolidinyl, optionally substituted thiomorpholinyl, optionally substituted tetrahydropyranyl, optionally substituted tetrahydrofuranyl, optionally substituted tetrahydroindolyl, optionally substituted tetrahydropyridinyl or optionally substituted tropanyl.

7. The compound of claim 1 wherein R$^6$ is optionally substituted (C$_1$-C$_6$)alkyl, optionally substituted (C$_2$-C$_6$)alkenyl, optionally substituted (C$_3$-C$_6$)cycloalkyl, optionally substituted dihydrobenzofuranyl, optionally substituted benzo[b]thienyl, optionally substituted furanyl, optionally substituted indolyl, optionally substituted isoquinolinyl, optionally substituted phenyl, optionally substituted piperidinyl, optionally substituted pyridinyl, optionally substituted pyrido[3,2-b]oxazin-3-(4H)-one, optionally substituted pyrimidinyl, optionally substituted pyrazolyl, optionally substituted quinolinyl, optionally substituted quinoxalinyl, optionally substituted tetrahydropyridinyl, or optionally substituted thienyl;

or

R$^6$ is —Z$^{201}$-L$^2$-Z$^{202}$ wherein

Z$^{201}$ is optionally substituted (C$_1$-C$_6$)alkylene, optionally substituted phenyl, optionally substituted piperidinyl, optionally substituted pyrazolyl, optionally substituted thienyl, or optionally substituted tetrhydropyridinyl;

L$^2$ is a bond, —CH$_2$C(O)—, —C(O)CH$_2$, —C(O)—, —C(O)N(R$^a$)—, —N(R$^a$)C(O), —S(O)$_2$, optionally substituted (C$_1$-C$_6$)alkylene, -optionally substituted (C$_1$-C$_4$)alkylene-S(O)$_2$N(R$^a$)—, -optionally substituted (C$_1$-C$_4$)alkylene-N(R$^a$)S(O)$_2$—, —S(O)$_2$N(R$^a$)-optionally substituted (C$_1$-C$_4$)alkylene-, or —O—(C$_1$-C$_4$)alkylene-; and Z$^{202}$ is —CN, —N(R$^a$)(R$^b$), —OR$^a$, optionally substituted (C$_1$-C$_6$)alkyl, optionally substituted (C$_3$-C$_6$)cycloalkyl, optionally substituted morpholinyl, optionally substituted oxetanyl, optionally substituted piperazinyl or optionally substituted piperidinyl.

8. A compound of formula (Ie)

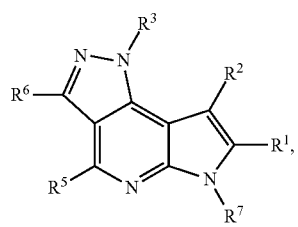

Formula (Ie)

or pharmaceutically acceptable salts, or stereoisomers thereof wherein $R^1$ is H, deuterium, halogen, $CF_3$, CN, $OR^a$, $N(R^a)(R^b)$, $OCF_3$, —C(O)—$N(R^a)(R^b)$, —C(O)—$OR^a$, —C(O)-optionally substituted $(C_1-C_6)$alkyl, —C(O)-optionally substituted $(C_3-C_6)$cycloalkyl, —C(O)-optionally substituted $(C_6-C_{10})$aryl, —C(O)-optionally substituted $(C_1-C_{10})$heteroaryl, —C(O)-optionally substituted $(C_1-C_{10})$heterocyclyl, —S-optionally substituted $(C_1-C_6)$alkyl, —S(O)-optionally substituted $(C_1-C_6)$alkyl, —$S(O)_2$-optionally substituted $(C_1-C_6)$alkyl, —$S(O)_2N(R^a)(R^b)$, optionally substituted $(C_1-C_6)$alkyl, optionally substituted $(C_1-C_6)$alkoxy, optionally substituted $(C_2-C_6)$alkenyl, optionally substituted $(C_2-C_6)$alkynyl, optionally substituted $(C_3-C_{10})$cycloalkyl, optionally substituted $(C_1-C_{10})$heteroaryl, optionally substituted $(C_1-C_{10})$ heterocyclyl, or optionally substituted $(C_6-C_{10})$aryl; or $R^1$ is —$Z^{101}$-$L^1$-$Z^{102}$ wherein
$Z^{101}$ is optionally substituted $(C_1-C_6)$alkylene, optionally substituted $(C_1-C_{10})$heteroarylene, optionally substituted $(C_1-C_{10})$heterocyclylene, or optionally substituted $(C_6-C_{10})$arylene;
$L^1$ is a bond, optionally substituted $(C_1-C_4)$alkylene, —$CH_2C(O)$, —C(O)—, —$C(O)CH_2$—, —$N(R^a)$—, —O—, -optionally substituted $(C_1-C_4)$alkylene-N$(R^a)C(O)$—, -optionally substituted $(C_1-C_4)$alkylene-$C(O)N(R^a)$—, —$C(O)N(R^a)$—, —$N(R^a)C(O)$—, —$C(O)N(R^a)$-optionally substituted $(C_1-C_4)$alkylene-, —$N(R^a)C(O)$-optionally substituted $(C_1-C_4)$alkylene-, —$C(O)N(R^a)$-optionally substituted $(C_1-C_4)$alkylene-C(O), —$N(R^a)C(O)$-optionally substituted $(C_1-C_4)$alkylene-C(O)—, —C(O)-optionally substituted $(C_1-C_4)$alkylene-$N(R^a)C(O)$—, —C(O)-optionally substituted $(C_1-C_4)$alkylene-C(O)N$(R^a)$—, -optionally substituted $(C_1-C_4)$alkylene-N$(R^a)C(O)$—, —$N(R^a)C(O)$-optionally substituted $(C_1-C_4)$alkylene, -optionally substituted $(C_1-C_4)$alkylene-N$(R^a)C(O)$-optionally substituted $(C_1-C_4)$alkylene-, -optionally substituted $(C_1-C_4)$alkylene-C$(O)N(R^a)$-optionally substituted $(C_1-C_4)$alkylene-, -optionally substituted $(C_1-C_4)$alkylene-$N(R^a)S(O)_2$—, -optionally substituted $(C_1-C_4)$alkylene-$S(O)_2 N(R^a)$—, —$N(R^a)S(O)_2CH_2$—, —$S(O)_2N(R^a)$-optionally substituted $(C_1-C_4)$alkylene-, —$C(O)N(R^a)S(O)_2$—, —$S(O)_2N(R^a)C(O)$—, —$S(O)_2$—, —$S(O)_2N(R^a)$—, —$N(R^a)S(O)_2$—, —O—$(C_1-C_4)$alkylene-, $(C_1-C_6)$alkylene-O—, —$C(O)N(R^a)$—$(C_1-C_6)$alkylene-C(O)—, or —C(O)—$(C_1-C_6)$alkylene-$N(R^a)C(O)$—;
$Z^{102}$ is H, —CN, —$N(R^a)(R^b)$, —$OR^a$, optionally substituted $(C_1-C_6)$alkyl, optionally substituted $(C_1-C_4)$alkoxy, optionally substituted $(C_3-C_{10})$cycloalkyl, optionally substituted $(C_6-C_{10})$aryl, optionally substituted $(C_1-C_{10})$heteroaryl, optionally substituted $(C_1-C_{10})$heterocyclyl, optionally substituted bridged $(C_1-C_{12})$cycloalkyl, or optionally substituted bridged $(C_2-C_{10})$heterocyclyl;

$R^2$ is H, deuterium, halogen, $CF_3$, CN, $OR^a$, $N(R^a)(R^b)$, $OCF_3$, —C(O)-optionally substituted $(C_1-C_6)$alkyl, —C(O)-optionally substituted $(C_3-C_6)$cycloalkyl, —S-optionally substituted $(C_1-C_6)$alkyl, —$S(O)_2$-optionally substituted $(C_1-C_6)$alkyl, —$S(O)_2N(R^a)(R^b)$, optionally substituted $(C_1-C_6)$alkoxy, —$C(O)N(R^a)(R^b)$, —$S(O)_2$-optionally substituted $(C_1-C_6)$alkyl, optionally substituted $(C_1-C_6)$alkyl, optionally substituted $(C_2-C_6)$alkenyl, optionally substituted $(C_2-C_6)$alkynyl, optionally substituted $(C_3-C_{10})$cycloalkyl, optionally substituted $(C_6-C_{10})$aryl, optionally substituted $(C_1-C_{10})$heteroaryl, or optionally substituted $(C_1-C_{10})$heterocyclyl;

$R^3$ is -A-D-E-G, wherein:
A is a bond;
D is an optionally substituted nitrogen-containing $(C_2-C_{10})$heterocyclylene;
E is —$R^e$—C(O)—$R^e$-, where in all cases, E is linked to a nitrogen atom in D;
G is H;
$R^e$ for each occurrence is independently a bond, an optionally substituted $(C_1-C_{10})$alkylene, an optionally substituted $(C_2-C_{10})$alkenylene, an optionally substituted $(C_2-C_{10})$alkynylene, an optionally substituted —$(C_1-C_{10})$alkylene-O—$(C_1-C_{10})$alkylene group, an optionally substituted $(C_3-C_{10})$cycloalkylene, an optionally substituted $(C_6-C_{10})$arylene, an optionally substituted $(C_1-C_{10})$heteroarylene, or an optionally substituted $(C_1-C_{10})$heterocyclylene;

$R^5$ is H, deuterium, $N(R^a)(R^b)$, halogen, CN, $CF_3$, $OR^a$, optionally substituted $(C_1-C_6)$alkyl, $OCF_3$, —C(O)-optionally substituted $(C_1-C_6)$alkyl, —C(O)-optionally substituted $(C_3-C_6)$cycloalkyl, —S-optionally substituted $(C_1-C_6)$alkyl, —S(O)-optionally substituted $(C_1-C_6)$alkyl, —$S(O)_2$-optionally substituted $(C_1-C_6)$alkyl, —$S(O)_2N(R^a)(R^b)$, optionally substituted $(C_1-C_6)$alkyl, or optionally substituted $(C_1-C_6)$alkoxy;

$R^6$ is H, deuterium, halogen, $CF_3$, CN, —C(O)—$N(R^a)(R^b)$, —C(O)—$OR^a$, —C(O)-optionally substituted $(C_1-C_6)$alkyl, —C(O)-optionally substituted $(C_3-C_6)$cycloalkyl, —C(O)-optionally substituted $(C_6-C_{10})$aryl, —C(O)-optionally substituted $(C_1-C_{10})$heteroaryl, —C(O)-optionally substituted $(C_1-C_{10})$heterocyclyl, —S-optionally substituted $(C_1-C_6)$alkyl, —S(O)-optionally substituted $(C_1-C_6)$alkyl, —$S(O)_2$-optionally substituted $(C_1-C_6)$alkyl, —$S(O)_2N(R^a)(R^b)$, optionally substituted $(C_1-C_6)$alkyl, optionally substituted $(C_2-C_6)$alkenyl, optionally substituted $(C_2-C_6)$alkynyl, optionally substituted $(C_3-C_{10})$cycloalkyl, optionally substituted $(C_1-C_{10})$heteroaryl, optionally substituted $(C_1-C_{10})$heterocyclyl, or optionally substituted $(C_6-C_{10})$aryl;
or
$R^6$ is —$Z^{201}$-$L^2$-$Z^{202}$ wherein
$Z^{201}$ is optionally substituted $(C_1-C_6)$alkylene, optionally substituted $(C_1-C_{10})$heteroarylene, optionally substituted $(C_1-C_{10})$heterocyclylene, or optionally substituted $(C_6-C_{10})$arylene;
$L^2$ is a bond, optionally substituted $(C_1-C_4)$alkylene, —$CH_2C(O)$, —C(O)—, —$C(O)CH_2$—, —$N(R^a)$—, —O—, -optionally substituted $(C_1-C_4)$alkylene-N$(R^a)C(O)$—, -optionally substituted $(C_1-C_4)$alkylene-$C(O)N(R^a)$—, —$C(O)N(R^a)$—, —$N(R^a)C(O)$—, —$C(O)N(R^a)S(O)_2$—, —$S(O)_2N(R^a)C(O)$—, —$C(O)N(R^a)$-optionally substituted $(C_1-C_4)$alkylene-, —$N(R^a)C(O)$-optionally substituted $(C_1-C_4)$alkylene-, -optionally substituted $(C_1-C_4)$alkylene-N$(R^a)C(O)$-optionally substituted $(C_1-C_4)$alkylene-, -optionally substituted $(C_1-C_4)$alkylene-C$(O)N(R^a)$-optionally substituted $(C_1-C_4)$alkylene-, -optionally substituted $(C_1-C_4)$alkylene-$N(R^a)S(O)_2$—, -optionally substituted $(C_1-C_4)$alkylene-$S(O)_2 N(R^a)$—, —$N(R^a)S(O)_2CH_2$—, —$S(O)_2N(R^a)$-optionally substituted $(C_1-C_4)$alkylene-, —$S(O)_2$—, —$S(O)_2N(R^a)$—, —$N(R^a)S(O)_2$—, —$(C_1-C_4)$alkylene-O—, or —O—$(C_1-C_4)$alkylene-;

$Z^{202}$ is H, —CN, —N(R$^a$)(R$^b$), —OR$^a$, optionally substituted (C$_1$-C$_6$)alkyl, optionally substituted (C$_1$-C$_4$) alkoxy, optionally substituted (C$_3$-C$_{10}$)cycloalkyl, optionally substituted (C$_6$-C$_{10}$)aryl, optionally substituted (C$_1$-C$_{10}$)heteroaryl, optionally substituted (C$_1$-C$_{10}$)heterocyclyl, optionally substituted bridged (C$_5$-C$_{12}$)cycloalkyl, or optionally substituted bridged (C$_2$-C$_{10}$)heterocyclyl;

R$^7$ is H, deuterium, optionally substituted-(CH$_2$)$_n$—P(=O)(OR$^a$)(OR$^a$), optionally substituted —(CH$_2$)$_n$—O—P(=O)(OR$^a$)(OR$^a$), optionally substituted-(CH$_2$)$_n$—P(=O)(OR$^a$)(R$^a$), or —CH=CH—P(=O)(OR$^a$)(OR$^a$);

R$^a$ and R$^b$ are each independently H, deuterium, an optionally substituted (C$_1$-C$_{10}$)alkyl, optionally substituted (C$_2$-C$_{10}$)alkenyl, optionally substituted (C$_2$-C$_{10}$)alkynyl, an optionally substituted (C$_1$-C$_{10}$)alkyl-O—(C$_1$-C$_{10}$)alkyl, optionally substituted (C$_3$-C$_{10}$)cycloalkyl, an optionally substituted (C$_6$-C$_{10}$)aryl, optionally substituted (C$_1$-C$_{10}$)heteroaryl, optionally substituted (C$_1$-C$_{10}$)heterocyclyl, optionally substituted —(C$_1$-C$_6$)alkylene-(C$_3$-C$_{10}$)cycloalkyl, an optionally substituted —(C$_1$-C$_6$)alkylene-(C$_6$-C$_{10}$)aryl, optionally substituted —(C$_1$-C$_6$)alkylene-(C$_1$-C$_{10}$)heteroaryl, or optionally substituted —(C$_1$-C$_6$)alkylene-(C$_1$-C$_{10}$)heterocyclyl;

n is 1, 2 or 3;

wherein the optional substituent is selected from the group consisting of: (C$_1$-C$_8$)alkyl groups, (C$_2$-C$_8$)alkenyl groups, (C$_2$-C$_8$)alkynyl groups, (C$_3$-C$_{10}$)cycloalkyl groups, halogen, halogenated (C$_1$-C$_8$)alkyl groups, —O—(C$_1$-C$_8$)alkyl groups, —OH, —S—(C$_1$-C$_8$)alkyl groups, —SH, —NH(C$_1$-C$_8$)alkyl groups, —N((C$_1$-C$_8$)alkyl)$_2$ groups, —NH$_2$, —C(O)NH$_2$, —C(O)NH(C$_1$-C$_8$)alkyl groups, —C(O)N((C$_1$-C$_8$)alkyl)$_2$, —NHC(O)H, —NHC(O)(C$_1$-C$_8$)alkyl groups, —NHC(O)(C$_3$-C$_8$)cycloalkyl groups, —N((C$_1$-C$_8$)alkyl)C(O)H, —N((C$_1$-C$_8$)alkyl)C(O)(C$_1$-C$_8$)alkyl groups, —NHC(O)NH$_2$, —NHC(O)NH(C$_1$-C$_8$)alkyl groups, —N((C$_1$-C$_8$)alkyl)C(O)NH$_2$ groups, —NHC(O)N((C$_1$-C$_8$)alkyl)$_2$ groups, —N((C$_1$-C$_8$)alkyl)C(O)N((C$_1$-C$_8$)alkyl)$_2$ groups, —N((C$_1$-C$_8$)alkyl)C(O)NH((C$_1$-C$_8$)alkyl), —C(O)H, —C(O)(C$_1$-C$_8$)alkyl groups, —CN, —NO$_2$, —S(O)(C$_1$-C$_8$)alkyl groups, —S(O)$_2$(C$_1$-C$_8$)alkyl groups, —S(O)$_2$N((C$_1$-C$_8$)alkyl)$_2$ groups, —S(O)$_2$NH(C$_1$-C$_8$)alkyl groups, —S(O)$_2$NH(C$_3$-C$_8$)cycloalkyl groups, —S(O)$_2$NH$_2$ groups, —NHS(O)$_2$(C$_1$-C$_8$)alkyl groups, —N((C$_1$-C$_8$)alkyl)S(O)$_2$(C$_1$-C$_8$)alkyl groups, —(C$_1$-C$_8$)alkyl-O—(C$_1$-C$_8$)alkyl groups, —O—(C$_1$-C$_8$)alkyl-O—(C$_1$-C$_8$)alkyl groups, —C(O)OH, —C(O)O(C$_1$-C$_8$) alkyl groups, NHOH, NHO(C$_1$-C$_8$)alkyl groups, —O-halogenated (C$_1$-C$_8$)alkyl groups —S(O)$_2$-halogenated (C$_1$-C$_8$)alkyl groups, —S-halogenated (C$_1$-C$_8$) alkyl groups, —(C$_1$-C$_6$) heterocyclyl, —(C$_1$-C$_6$) heteroaryl, -phenyl, —NHC(O)O—(C$_1$-C$_6$)alkyl groups, —N((C$_1$-C$_6$)alkyl)C(O)O—(C$_1$-C$_6$)alkyl groups, —C(=NH)—(C$_1$-C$_6$)alkyl groups, —C(=NOH)—(C$_1$-C$_6$)alkyl groups, and —C(=N—O—(C$_1$-C$_6$)alkyl)-(C$_1$-C$_6$)alkyl groups;

provided that R$^1$ and R$^6$ are not both H.

9. A compound selected from
2-(4-(1-methyl-1,6-dihydropyrazolo[3,4-d]pyrrolo[2,3-b]pyridin-7-yl)phenyl)propan-2-ol,
4-(3-(1-methyl-1,6-dihydropyrazolo[3,4-d]pyrrolo[2,3-b]pyridin-7-yl)benzyl)morpholine,
7-(5-fluoro-1-methyl-1H-indol-3-yl)-1-methyl-1,6-dihydropyrazolo[3,4-d]pyrrolo[2,3-b]pyridine,
7-(benzofuran-3-yl)-1-methyl-1,6-dihydropyrazolo[3,4-d]pyrrolo[2,3-b]pyridine,
7-(5-methoxy-1H-indol-3-yl)-1-methyl-1,6-dihydropyrazolo[3,4-d]pyrrolo[2,3-b]pyridine,
1-methyl-7-(1-methyl-1H-indol-3-yl)-1,6-dihydropyrazolo[3,4-d]pyrrolo[2,3-b]pyridine,
N-(3-(1-methyl-1,6-dihydropyrazolo[3,4-d]pyrrolo[2,3-b]pyridin-7-yl)benzyl)acetamide,
N-methyl-3-(1-methyl-1,6-dihydropyrazolo[3,4-d]pyrrolo[2,3-b]pyridin-7-yl)benzamide,
3-(1-methyl-1,6-dihydropyrazolo[3,4-d]pyrrolo[2,3-b]pyridin-7-yl)benzonitrile,
7-(3-fluorophenyl)-1-methyl-1,6-dihydropyrazolo[3,4-d]pyrrolo[2,3-b]pyridine,
2-(5-methoxy-3-(1-methyl-1,6-dihydropyrazolo[3,4-d]pyrrolo[2,3-b]pyridin-7-yl)-1H-indol-1-yl)-1-morpholinoethanone,
2-(5-methoxy-3-(1-methyl-1,6-dihydropyrazolo[3,4-d]pyrrolo[2,3-b]pyridin-7-yl)-1H-indol-1-yl)acetic acid,
4-(2-(5-methoxy-3-(1-methyl-1,6-dihydropyrazolo[3,4-d]pyrrolo[2,3-b]pyridin-7-yl)-1H-indol-1-yl)ethyl)morpholine,
2-(5-methoxy-3-(1-methyl-1,6-dihydropyrazolo[3,4-d]pyrrolo[2,3-b]pyridin-7-yl)-1H-indol-1-yl)ethanol,
(3-(1-methyl-1,6-dihydropyrazolo[3,4-d]pyrrolo[2,3-b]pyridin-7-yl)phenyl)methanamine,
2-(5-methoxy-3-(1-methyl-1,6-dihydropyrazolo[3,4-d]pyrrolo[2,3-b]pyridin-7-yl)-1H-indol-1-yl)-N,N-dimethylethanamine,
2-(dimethylamino)-N-(3-(1-methyl-1,6-dihydropyrazolo[3,4-d]pyrrolo[2,3-b]pyridin-7-yl)benzyl)acetamide,
3-(1-methyl-1,6-dihydropyrazolo[3,4-d]pyrrolo[2,3-b]pyridin-7-yl)-N-(2-morpholinoethyl)benzamide,
N-(3-methoxypropyl)-3-(1-methyl-1,6-dihydropyrazolo[3,4-d]pyrrolo[2,3-b]pyridin-7-yl)benzamide,
3-methoxy-N-(3-(1-methyl-1,6-dihydropyrazolo[3,4-d]pyrrolo[2,3-b]pyridin-7-yl)benzyl)propanamide,
N-(3-(1-methyl-1,6-dihydropyrazolo[3,4-d]pyrrolo[2,3-b]pyridin-7-yl)benzyl)methanesulfonamide,
(3-(1-methyl-1,6-dihydropyrazolo[3,4-d]pyrrolo[2,3-b]pyridin-7-yl)phenyl)(pyrrolidin-1-yl)methanone,
2-(5-methoxy-3-(1-methyl-1,6-dihydropyrazolo[3,4-d]pyrrolo[2,3-b]pyridin-7-yl)-1H-indol-1-yl)-1-(4-methylpiperazin-1-yl)ethanone,
N-(3-(1-methyl-1,6-dihydropyrazolo[3,4-d]pyrrolo[2,3-b]pyridin-7-yl)benzyl)-3-morpholinopropanamide,
7-(6,7-dihydro-5H-pyrrolo[1,2-a]imidazol-3-yl)-1-methyl-1,6-dihydropyrazolo[3,4-d]pyrrolo[2,3-b]pyridine,
N-methyl-2-(3-(1-methyl-1,6-dihydropyrazolo[3,4-d]pyrrolo[2,3-b]pyridin-7-yl)phenyl)acetamide,
N-(3-hydroxy-2,2-dimethylpropyl)-2-(3-(1-methyl-1,6-dihydropyrazolo[3,4-d]pyrrolo[2,3-b]pyridin-7-yl)phenyl)acetamide,
N-(3-(1-methyl-1,6-dihydropyrazolo[3,4-d]pyrrolo[2,3-b]pyridin-7-yl)benzyl)pentanamide,
1-(dimethylamino)-3-(5-methoxy-3-(1-methyl-1,6-dihydropyrazolo[3,4-d]pyrrolo[2,3-b]pyridin-7-yl)-1H-indol-1-yl)propan-2-ol,
N-(3-methoxypropyl)-2-(3-(1-methyl-1,6-dihydropyrazolo[3,4-d]pyrrolo[2,3-b]pyridin-7-yl)phenyl)acetamide,
2-(3-(1-methyl-1,6-dihydropyrazolo[3,4-d]pyrrolo[2,3-b]pyridin-7-yl)phenyl)-N-(2-(4-methylpiperazin-1-yl)ethyl)acetamide,
1-methyl-7-(pyridin-4-yl)-1,6-dihydropyrazolo[3,4-d]pyrrolo[2,3-b]pyridine, 1-methyl-7-(pyridin-3-yl)-1,6-dihydropyrazolo[3,4-d]pyrrolo[2,3-b]pyridine,
2-(5-methoxy-3-(1-methyl-1,6-dihydropyrazolo[3,4-d]pyrrolo[2,3-b]pyridin-7-yl)-1H-indol-1-yl)-N,N-dimethylacetamide,
2-(3-(1-methyl-1,6-dihydropyrazolo[3,4-d]pyrrolo[2,3-b]pyridin-7-yl)phenyl)-N-(2-morpholinoethyl)acetamide,
N,N-dimethyl-3-(1-methyl-1,6-dihydropyrazolo[3,4-d]pyrrolo[2,3-b]pyridin-7-yl)benzenesulfonamide,
2-(4-(8-ethyl-1-methyl-1,6-dihydropyrazolo[3,4-d]pyrrolo[2,3-b]pyridin-7-yl)phenyl)propan-2-ol,
8-ethyl-1-methyl-7-(3-(methylsulfonyl)phenyl)-1,6-dihydropyrazolo[3,4-d]pyrrolo[2,3-b]pyridine,
2-(5-methoxy-3-(1-methyl-1,6-dihydropyrazolo[3,4-d]pyrrolo[2,3-b]pyridin-7-yl)-1H-indol-1-yl)-N-(2-methoxyethyl)acetamide,
N-(2-(dimethylamino)ethyl)-2-(3-(1-methyl-1,6-dihydropyrazolo[3,4-d]pyrrolo[2,3-b]pyridin-7-yl)phenyl)acetamide,
N-methyl-3-(1-methyl-1,6-dihydropyrazolo[3,4-d]pyrrolo[2,3-b]pyridin-7-yl)benzenesulfonamide,
3-(1-methyl-1,6-dihydropyrazolo[3,4-d]pyrrolo[2,3-b]pyridin-7-yl)benzenesulfonamide,
N-(2-hydroxyethyl)-3-(1-methyl-1,6-dihydropyrazolo[3,4-d]pyrrolo[2,3-b]pyridin-7-yl)benzenesulfonamide,
7-(4-methoxyphenyl)-1-methyl-1,6-dihydropyrazolo[3,4-d]pyrrolo[2,3-b]pyridine,
3-(5-methoxy-3-(1-methyl-1,6-dihydropyrazolo[3,4-d]pyrrolo[2,3-b]pyridin-7-yl)-1H-indol-1-yl)propane-1,2-diol,
N,N-dimethyl-2-(4-(1-methyl-1,6-dihydropyrazolo[3,4-d]pyrrolo[2,3-b]pyridin-7-yl)phenoxy)ethanamine,
4-(2-(4-(1-methyl-1,6-dihydropyrazolo[3,4-d]pyrrolo[2,3-b]pyridin-7-yl)phenoxy)ethyl)morpholine,
4-(3-(4-(1-methyl-1,6-dihydropyrazolo[3,4-d]pyrrolo[2,3-b]pyridin-7-yl)phenoxy)propyl)morpholine,
1-methyl-7-(quinolin-5-yl)-1,6-dihydropyrazolo[3,4-d]pyrrolo[2,3-b]pyridine,
1-methyl-7-(quinolin-6-yl)-1,6-dihydropyrazolo[3,4-d]pyrrolo[2,3-b]pyridine,
1-methyl-7-(quinoxalin-6-yl)-1,6-dihydropyrazolo[3,4-d]pyrrolo[2,3-b]pyridine,
3-(8-ethyl-1-methyl-1,6-dihydropyrazolo[3,4-d]pyrrolo[2,3-b]pyridin-7-yl)-N-(2-morpholinoethyl)benzamide,
8-ethyl-1-methyl-7-(1-methyl-1H-indol-5-yl)-1,6-dihydropyrazolo[3,4-d]pyrrolo[2,3-b]pyridine,
8-ethyl-1-methyl-7-(1-methyl-1H-indol-4-yl)-1,6-dihydropyrazolo[3,4-d]pyrrolo[2,3-b]pyridine,
4-(4-(8-ethyl-1-methyl-1,6-dihydropyrazolo[3,4-d]pyrrolo[2,3-b]pyridin-7-yl)phenyl)morpholine,
7-(1,3-dimethyl-1H-pyrazol-4-yl)-8-ethyl-1-methyl-1,6-dihydropyrazolo[3,4-d]pyrrolo[2,3-b]pyridine,
7-(1,5-dimethyl-1H-pyrazol-4-yl)-8-ethyl-1-methyl-1,6-dihydropyrazolo[3,4-d]pyrrolo[2,3-b]pyridine,
8-ethyl-7-(5-methoxy-1-methyl-1H-indol-3-yl)-1-methyl-1,6-dihydropyrazolo[3,4-d]pyrrolo[2,3-b]pyridine,
4-(8-ethyl-1-methyl-1,6-dihydropyrazolo[3,4-d]pyrrolo[2,3-b]pyridin-7-yl)-N-(2-morpholinoethyl)benzamide,
3-(8-ethyl-1-methyl-1,6-dihydropyrazolo[3,4-d]pyrrolo[2,3-b]pyridin-7-yl)-N-propylbenzamide,
N,N-diethyl-3-(8-ethyl-1-methyl-1,6-dihydropyrazolo[3,4-d]pyrrolo[2,3-b]pyridin-7-yl)benzenesulfonamide,
3-(1-methyl-1,6-dihydropyrazolo[3,4-d]pyrrolo[2,3-b]pyridin-7-yl)-N-(2-morpholinoethyl)benzenesulfonamide,
N-(2-methoxyethyl)-3-(1-methyl-1,6-dihydropyrazolo[3,4-d]pyrrolo[2,3-b]pyridin-7-yl)benzenesulfonamide,
8-ethyl-7-(4-methoxyphenyl)-1-methyl-1,6-dihydropyrazolo[3,4-d]pyrrolo[2,3-b]pyridine,
8-ethyl-1-methyl-7-(1-methyl-1H-pyrazol-4-yl)-1,6-dihydropyrazolo[3,4-d]pyrrolo[2,3-b]pyridine,
4-(2-(4-(8-ethyl-1-methyl-1,6-dihydropyrazolo[3,4-d]pyrrolo[2,3-b]pyridin-7-yl)phenoxy)ethyl)morpholine,
8-ethyl-7-(4-(2-methoxyethoxy)phenyl)-1-methyl-1,6-dihydropyrazolo[3,4-d]pyrrolo[2,3-b]pyridine,
2-(4-(8-ethyl-1-methyl-1,6-dihydropyrazolo[3,4-d]pyrrolo[2,3-b]pyridin-7-yl)phenoxy)-N,N-dimethylethanamine,
1-methyl-7-(1-methyl-1H-indol-5-yl)-1,6-dihydropyrazolo[3,4-d]pyrrolo[2,3-b]pyridine,
2-(4-(8-ethyl-1-methyl-1,6-dihydropyrazolo[3,4-d]pyrrolo[2,3-b]pyridin-7-yl)phenyl)propan-2-amine,
7-(2,4-dimethylphenyl)-1-methyl-1,6-dihydropyrazolo[3,4-d]pyrrolo[2,3-b]pyridine,
7-(1-isopropyl-5-methoxy-1H-indol-3-yl)-1-methyl-1,6-dihydropyrazolo[3,4-d]pyrrolo[2,3-b]pyridine,
7-(1-isopropyl-1H-indol-3-yl)-1-methyl-1,6-dihydropyrazolo[3,4-d]pyrrolo[2,3-b]pyridine,
1-methyl-7-(1-methyl-1H-pyrrolo[3,2-c]pyridin-3-yl)-1,6-dihydropyrazolo[3,4-d]pyrrolo[2,3-b]pyridine,
7-(5-methoxy-1-methyl-1H-indazol-3-yl)-1-methyl-1,6-dihydropyrazolo[3,4-d]pyrrolo[2,3-b]pyridine,
2-(1-methyl-3-(1-methyl-1,6-dihydropyrazolo[3,4-d]pyrrolo[2,3-b]pyridin-7-yl)-1H-indol-5-yl)propan-2-ol,
1-methyl-7-(3-methyl-4-(4-methylpiperazin-1-yl)phenyl)-1,6-dihydropyrazolo[3,4-d]pyrrolo[2,3-b]pyridine,
1-methyl-3-(1-methyl-1,6-dihydropyrazolo[3,4-d]pyrrolo[2,3-b]pyridin-7-yl)-N-(2-morpholinoethyl)-1H-indole-5-carboxamide,
N-(1-hydroxy-2-methylpropan-2-yl)-1-methyl-3-(1-methyl-1,6-dihydropyrazolo[3,4-d]pyrrolo[2,3-b]pyridin-7-yl)-1H-indole-5-carboxamide,
1-methyl-3-(1-methyl-1,6-dihydropyrazolo[3,4-d]pyrrolo[2,3-b]pyridin-7-yl)-1H-indole-5-carboxylic acid,
N-(3-hydroxy-2,2-dimethylpropyl)-1-methyl-3-(1-methyl-1,6-dihydropyrazolo[3,4-d]pyrrolo[2,3-b]pyridin-7-yl)-1H-indole-5-carboxamide,
7-(1,5-dimethyl-1H-indol-3-yl)-1-methyl-1,6-dihydropyrazolo[3,4-d]pyrrolo[2,3-b]pyridine,
1-methyl-7-(1H-pyrrol-2-yl)-1,6-dihydropyrazolo[3,4-d]pyrrolo[2,3-b]pyridine,
1,6-dihydropyrazolo[3,4-d]pyrrolo[2,3-b]pyridin-7-yl)-1H-pyrrol-1-yl)-1-(4-methylpiperazin-1-yl)ethanone,
N-(3-ethoxypropyl)-2-(2-(1-methyl-1,6-dihydropyrazolo[3,4-d]pyrrolo[2,3-b]pyridin-7-yl)-1H-pyrrol-1-yl)acetamide,
2-(2-(1-methyl-1,6-dihydropyrazolo[3,4-d]pyrrolo[2,3-b]pyridin-7-yl)-1H-pyrrol-1-yl)-1-morpholinoethanone,
N-(2-hydroxyethyl)-1-methyl-3-(1-methyl-1,6-dihydropyrazolo[3,4-d]pyrrolo[2,3-b]pyridin-7-yl)-1H-indole-5-carboxamide,
2-(2-(1-methyl-1,6-dihydropyrazolo[3,4-d]pyrrolo[2,3-b]pyridin-7-yl)-1H-pyrrol-1-yl)acetic acid,
N-(2-(dimethylamino)ethyl)-1-methyl-3-(1-methyl-1,6-dihydropyrazolo[3,4-d]pyrrolo[2,3-b]pyridin-7-yl)-1H-indole-5-carboxamide, (4-(hydroxymethyl)piperidin-1-yl)(1-methyl-3-(1-methyl-1,6-dihydropyrazolo[3,4-d]pyrrolo[2,3-b]pyridin-7-yl)-1H-indol-5-yl)methanone, N,N,1-trimethyl-3-(1-methyl-1,6-dihydropyrazolo[3,4-d]pyrrolo[2,3-b]pyridin-7-yl)-1H-indole-5-carboxamide, N-(3-hydroxy-2,2-dimethylpropyl)-N,1-dimethyl-3-(1-methyl-1,6-dihydropyrazolo[3,4-d]pyrrolo[2,3-b]pyridin-7-yl)-1H-indole-5-carboxamide, 1-methyl-3-(1-methyl-1,6-dihydropyrazolo[3,4-d]pyrrolo[2,3-b]pyridin-7-yl)-1H-indole-6-carboxylic acid, 4-(2-(1-methyl-3-(1-methyl-1,6-dihydropyrazolo[3,4-d]pyrrolo[2,3-b]pyridin-7-yl)-1H-indol-5-yloxy)ethyl)morpholine, 1-methyl-3-(1-methyl-1,6-dihydropyrazolo[3,4-d]pyrrolo[2,3-b]pyridin-7-yl)-N-(2-(4-methylpiperazin-1-yl)-2-oxoethyl)-1H-indole-5-carboxamide, N,N,1-trimethyl-3-(1-methyl-1,6-dihydropyrazolo[3,4-d]pyrrolo[2,3-b]pyridin-7-yl)-1H-indole-6-carboxamide, N-(3-hydroxy-2,2-dimethylpropyl)-1-methyl-3-(1-methyl-1,6-dihydropyrazolo[3,4-d]pyrrolo[2,3-b]pyridin-7-yl)-1H-indole-6-carboxamide, N-(1-hydroxy-2-methylpropan-2-yl)-1-methyl-3-(1-methyl-1,6-dihydropyrazolo[3,4-d]pyrrolo[2,3-b]pyridin-7-yl)-1H-indole-6-carboxamide, 1-methyl-3-(1-methyl-1,6-dihydropyrazolo[3,4-d]pyrrolo[2,3-b]pyridin-7-yl)-N-(2-morpholinoethyl)-1H-indole-6-carboxamide, 1-methyl-3-(1-methyl-1,6-dihydropyrazolo[3,4-d]pyrrolo[2,3-b]pyridin-7-yl)-N-(methylsulfonyl)-1H-indole-5-carboxamide, 2-(4-(8-ethyl-1-methyl-1,6-dihydropyrazolo[3,4-d]pyrrolo[2,3-b]pyridin-3-yl)phenyl)propan-2-ol, 7-(5-methoxy-1-methyl-1H-pyrrolo[3,2-b]pyridin-3-yl)-1-methyl-1,6-dihydropyrazolo[3,4-d]pyrrolo[2,3-b]pyridine, 1-methyl-7-(5-methyl-5H-pyrrolo[2,3-b]pyrazin-7-yl)-1,6-dihydropyrazolo[3,4-d]pyrrolo[2,3-b]pyridine, 3-(4-methoxyphenyl)-1-methyl-1,6-dihydropyrazolo[3,4-d]pyrrolo[2,3-b]pyridine, 7-(5-methoxy-1-methyl-1H-pyrrolo[2,3-c]pyridin-3-yl)-1-methyl-1,6-dihydropyrazolo[3,4-d]pyrrolo[2,3-b]pyridine, 7-(5-methoxy-1-methyl-1H-pyrrolo[2,3-b]pyridin-3-yl)-1-methyl-1,6-dihydropyrazolo[3,4-d]pyrrolo[2,3-b]pyridine, 3-(4-methoxyphenyl)-1,6-dihydropyrazolo[3,4-d]pyrrolo[2,3-b]pyridine, 7-(4-(2-hydroxypropan-2-yl)phenyl)-1-methyl-1,6-dihydropyrazolo[3,4-d]pyrrolo[2,3-b]pyridine-8-carbonitrile, 1-methyl-3-(4-(methylthio)phenyl)-1,6-dihydropyrazolo[3,4-d]pyrrolo[2,3-b]pyridine, 8-bromo-3-(4-methoxyphenyl)-1-methyl-1,6-dihydropyrazolo[3,4-d]pyrrolo[2,3-b]pyridine, 1-methyl-3-(4-(methylsulfonyl)phenyl)-1,6-dihydropyrazolo[3,4-d]pyrrolo[2,3-b]pyridine, 1-(4-(1-methyl-1,6-dihydropyrazolo[3,4-d]pyrrolo[2,3-b]pyridin-3-yl)phenyl)ethanone, 2-(4-(1-methyl-1,6-dihydropyrazolo[3,4-d]pyrrolo[2,3-b]pyridin-3-yl)phenyl)propan-2-ol, 3-(4-methoxyphenyl)-1-methyl-1,6-dihydropyrazolo[3,4-d]pyrrolo[2,3-b]pyridine-8-carbonitrile, 8-ethyl-3-(3-fluoro-4-methoxyphenyl)-1-methyl-1,6-dihydropyrazolo[3,4-d]pyrrolo[2,3-b]pyridine, 8-ethyl-1-methyl-3-(quinoxalin-6-yl)-1,6-dihydropyrazolo[3,4-d]pyrrolo[2,3-b]pyridine, 8-ethyl-3-(4-isopropoxyphenyl)-1-methyl-1,6-dihydropyrazolo[3,4-d]pyrrolo[2,3-b]pyridine, N-cyclopropyl-4-(8-ethyl-1-methyl-1,6-dihydropyrazolo[3,4-d]pyrrolo[2,3-b]pyridin-3-yl)benzamide, (4-(8-ethyl-1-methyl-1,6-dihydropyrazolo[3,4-d]pyrrolo[2,3-b]pyridin-3-yl)phenyl)methanol, 4-(8-ethyl-1-methyl-1,6-dihydropyrazolo[3,4-d]pyrrolo[2,3-b]pyridin-3-yl)benzenesulfonamide, 8-ethyl-1-methyl-3-(thiophen-3-yl)-1,6-dihydropyrazolo[3,4-d]pyrrolo[2,3-b]pyridine, 8-ethyl-3-(4-methoxyphenyl)-1-methyl-1,6-dihydropyrazolo[3,4-d]pyrrolo[2,3-b]pyridine, 8-ethyl-1-methyl-3-(pyridin-3-yl)-1,6-dihydropyrazolo[3,4-d]pyrrolo[2,3-b]pyridine, 8-ethyl-1-methyl-3-(1-methyl-1H-pyrazol-4-yl)-1,6-dihydropyrazolo[3,4-d]pyrrolo[2,3-b]pyridine, 8-ethyl-1-methyl-3-(3,4,5-trimethoxyphenyl)-1,6-dihydropyrazolo[3,4-d]pyrrolo[2,3-b]pyridine, or pharmaceutically acceptable salts or stereoisomers thereof.

* * * * *